US011446287B2

(12) United States Patent
Spevak et al.

(10) Patent No.: US 11,446,287 B2
(45) Date of Patent: Sep. 20, 2022

(54) COMPOUNDS AND METHODS FOR EP300 OR CBP MODULATION AND INDICATIONS THEREFOR

(71) Applicant: Opna Immuno-Oncology SA, Epalinges (CH)

(72) Inventors: Wayne Spevak, Berkeley, CA (US); John Buell, San Francisco, CA (US); Zuojun Guo, Pasadena, CA (US); Hiroaki Inagaki, Edogawa-ku (JP); Yongil Jin, Emeryville, CA (US); Phuongly Pham, San Francisco, CA (US); Songyuan Shi, Fremont, CA (US); Jack Walleshauser, Berkeley, CA (US); Jeffrey Wu, Berkeley, CA (US); Guoxian Wu, Foster City, CA (US); Chao Zhang, Moraga, CA (US); Jiazhong Zhang, Foster City, CA (US); Ying Zhang, Fremont, CA (US)

(73) Assignee: Opna Immuno-Oncology SA, Epalinges (CH)

( * ) Notice: Subject to any disclaimer, the term of this patent is extended or adjusted under 35 U.S.C. 154(b) by 0 days.

(21) Appl. No.: 16/843,700

(22) Filed: Apr. 8, 2020

(65) Prior Publication Data

US 2021/0315872 A1 Oct. 14, 2021

Related U.S. Application Data

(60) Provisional application No. 62/831,622, filed on Apr. 9, 2019.

(51) Int. Cl.

| | |
|---|---|
| *A61K 31/444* | (2006.01) |
| *A61K 31/437* | (2006.01) |
| *A61K 31/497* | (2006.01) |
| *A61K 31/501* | (2006.01) |
| *A61K 31/506* | (2006.01) |
| *A61K 45/06* | (2006.01) |
| *C07D 471/04* | (2006.01) |

(52) U.S. Cl.

CPC .......... *A61K 31/444* (2013.01); *A61K 31/437* (2013.01); *A61K 31/497* (2013.01); *A61K 31/501* (2013.01); *A61K 31/506* (2013.01); *A61K 45/06* (2013.01); *C07D 471/04* (2013.01)

(58) Field of Classification Search

None

See application file for complete search history.

(56) References Cited

U.S. PATENT DOCUMENTS 7,202,266 B2 4/2007 Arnold et al.
7,348,338 B2 3/2008 Arnold et al.
7,432,375 B2 * 10/2008 Graczyk .................. A61P 7/02 546/113
7,476,746 B2 1/2009 Artis et al.
7,491,831 B2 2/2009 Artis et al.
7,504,509 B2 3/2009 Ibrahim et al.
7,517,970 B2 4/2009 West
7,572,806 B2 8/2009 Arnold et al.
7,585,859 B2 9/2009 Ibrahim et al.
7,605,168 B2 10/2009 Ibrahim et al.
7,723,374 B2 5/2010 Artis et al.
7,759,475 B2 7/2010 West
7,846,941 B2 12/2010 Zhang et al.
7,863,288 B2 1/2011 Ibrahim et al.
7,893,075 B2 2/2011 Zhang et al.
8,067,434 B2 11/2011 Ibrahim et al.
8,110,576 B2 2/2012 Ibrahim et al.
8,143,271 B2 3/2012 Ibrahim et al.
8,153,641 B2 4/2012 Ibrahim et al.
8,158,636 B2 4/2012 Ibrahim et al.
8,268,858 B2 9/2012 Wu et al.
8,367,828 B2 2/2013 Arnold et al.

(Continued)

FOREIGN PATENT DOCUMENTS

WO WO 2009/054941 A1 4/2009
WO WO 2012/129338 A1 9/2012

(Continued)

OTHER PUBLICATIONS

Silverman, R. "The Organic Chemistry of Drug Design and Drug Action," 2004, Elsevier, pp. 29-32.*

(Continued)

*Primary Examiner* — Heidi Reese

(74) *Attorney, Agent, or Firm* — Elmore Patent Law Group, P.C.; Carolyn S. Elmore; Joseph C. Zucchero

(57) ABSTRACT

Disclosed are compounds of Formula I:

I

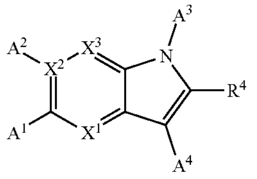

or a pharmaceutically acceptable salt, a solvate, a tautomer, a stereoisomer or a deuterated analog thereof, wherein $A^1$, $A^2$, $A^3$, $A^4$, $R^4$, $X^1$, $X^2$, and $X^3$ are as described in any of the embodiments described in this disclosure; compositions thereof; and uses thereof.

37 Claims, No Drawings

(56) References Cited

U.S. PATENT DOCUMENTS

| | | | |
|---|---|---|---|
| 8,404,700 | B2 | 3/2013 | Ibrahim et al. |
| 8,415,469 | B2 | 4/2013 | Ibrahim et al. |
| 8,461,169 | B2 | 6/2013 | Zhang et al. |
| 8,470,818 | B2 | 6/2013 | Ibrahim et al. |
| 8,470,821 | B2 | 6/2013 | Ibrahim et al. |
| 8,642,606 | B2 | 2/2014 | Ibrahim et al. |
| 8,673,928 | B2 | 3/2014 | Ibrahim et al. |
| 8,722,702 | B2 | 5/2014 | Zhang et al. |
| 8,865,735 | B2 | 10/2014 | Ibrahim et al. |
| 8,901,118 | B2 | 12/2014 | Zhang et al. |
| 8,901,301 | B2 | 12/2014 | Ibrahim et al. |
| 8,912,204 | B2 | 12/2014 | Ibrahim et al. |
| 9,096,593 | B2 | 8/2015 | Zhang et al. |
| 9,150,570 | B2 | 10/2015 | Ibrahim |
| 9,169,250 | B2 | 10/2015 | Zhang et al. |
| 9,260,437 | B2 | 2/2016 | Ibrahim et al. |
| 9,358,235 | B2 | 6/2016 | Bollag et al. |
| 9,440,969 | B2 | 9/2016 | Ibrahim et al. |
| 9,447,089 | B2 | 9/2016 | Desai et al. |
| 9,469,640 | B2 | 10/2016 | Wu et al. |
| 9,487,515 | B2 | 11/2016 | Zhang et al. |
| 9,550,768 | B2 | 1/2017 | Zhang et al. |
| 9,617,267 | B2 | 4/2017 | Ibrahim et al. |
| 9,624,213 | B2 | 4/2017 | Ibrahim et al. |
| 9,663,517 | B2 | 5/2017 | Desai et al. |
| 9,676,748 | B2 | 6/2017 | Wu et al. |
| 9,682,981 | B2 | 6/2017 | Zhang et al. |
| 9,695,169 | B2 | 7/2017 | Ibrahim |
| 9,718,847 | B2 | 8/2017 | Zhang et al. |
| 9,730,918 | B2 | 8/2017 | Bollag et al. |
| 9,745,298 | B2 | 8/2017 | Ibrahim et al. |
| 9,771,363 | B2 | 9/2017 | Ibrahim et al. |
| 9,771,369 | B2 | 9/2017 | Lin et al. |
| 9,776,998 | B2 | 10/2017 | Ibrahim et al. |
| 9,802,932 | B2 | 10/2017 | Ibrahim et al. |
| 9,814,714 | B2 | 11/2017 | Ibrahim et al. |
| 9,822,109 | B2 | 11/2017 | Zhang et al. |
| 9,844,539 | B2 | 12/2017 | Wu et al. |
| 9,856,259 | B2 | 1/2018 | Shi et al. |
| 9,873,700 | B2 | 1/2018 | Zhang et al. |
| 9,938,273 | B2 | 4/2018 | Wu et al. |
| 9,975,894 | B2 | 5/2018 | Ibrahim et al. |
| 9,994,567 | B2 | 6/2018 | Ibrahim et al. |
| 10,040,792 | B2 | 8/2018 | Ibrahim et al. |
| 10,123,998 | B2 | 11/2018 | Bollag et al. |
| 10,160,747 | B2 | 12/2018 | Lin et al. |
| 10,160,755 | B2 | 12/2018 | Lin et al. |
| 10,189,833 | B2 | 1/2019 | Ibrahim et al. |
| 10,227,357 | B2 | 3/2019 | Lin et al. |
| 10,301,280 | B2 | 5/2019 | Wu et al. |
| 10,316,032 | B2 | 6/2019 | Ibrahim et al. |
| 10,370,374 | B2 | 8/2019 | Ibrahim et al. |
| 10,399,975 | B2 | 9/2019 | Ibrahim et al. |
| 10,421,761 | B2 | 9/2019 | Zhang et al. |
| 10,426,760 | B2 | 10/2019 | Wu et al. |
| 10,428,067 | B2 | 10/2019 | Zhang et al. |
| 10,435,404 | B2 | 10/2019 | Ibrahim et al. |
| 10,501,460 | B2 | 12/2019 | Zhang et al. |
| 10,508,085 | B2 | 12/2019 | Zhang et al. |
| 10,519,177 | B2 | 12/2019 | Zhang et al. |
| 10,577,366 | B2 | 3/2020 | Lin et al. |
| 10,584,122 | B2 | 3/2020 | Ibrahim et al. |
| 10,647,716 | B2 | 5/2020 | Ibrahim et al. |
| 10,899,761 | B2 | 1/2021 | Ibrahim et al. |
| 2007/0032519 | A1 | 2/2007 | Zhang et al. |
| 2007/0049615 | A1 | 3/2007 | Ibrahim et al. |
| 2008/0188514 | A1 | 8/2008 | Wu et al. |
| 2009/0076046 | A1 | 3/2009 | Zhang et al. |
| 2009/0286783 | A1 | 11/2009 | Ibrahim et al. |
| 2009/0306086 | A1 | 12/2009 | Ibrahim et al. |
| 2009/0306087 | A1 | 12/2009 | Ibrahim et al. |
| 2010/0210036 | A1 | 8/2010 | Arnold et al. |
| 2010/0249118 | A1 | 9/2010 | Ibrahim et al. |
| 2010/0286178 | A1 | 11/2010 | Ibrahim et al. |
| 2010/0310659 | A1 | 12/2010 | Desai et al. |
| 2011/0152258 | A1 | 6/2011 | Ibrahim et al. |
| 2011/0230482 | A1 | 9/2011 | Zhang et al. |
| 2012/0309756 | A1 | 12/2012 | Zhang et al. |
| 2013/0274259 | A1 | 10/2013 | Zhang et al. |
| 2014/0037617 | A1 | 2/2014 | Bollag et al. |
| 2014/0039002 | A1 | 2/2014 | Diodone et al. |
| 2014/0045840 | A1 | 2/2014 | Zhang et al. |
| 2014/0094611 | A1 | 4/2014 | Ibrahim |
| 2014/0128390 | A1 | 5/2014 | Lin et al. |
| 2014/0213554 | A1 | 7/2014 | Wu et al. |
| 2014/0288070 | A1 | 9/2014 | Ibrahim et al. |
| 2014/0357612 | A1 | 12/2014 | Zhang et al. |
| 2015/0080372 | A1 | 3/2015 | Ibrahim et al. |
| 2015/0133400 | A1 | 5/2015 | Zhang et al. |
| 2015/0166547 | A1 | 6/2015 | Ibrahim et al. |
| 2015/0183793 | A1 | 7/2015 | Zhang et al. |
| 2015/0265586 | A1 | 9/2015 | Zhang et al. |
| 2015/0284397 | A1 | 10/2015 | Lin et al. |
| 2015/0368243 | A1 | 12/2015 | Ibrahim |
| 2016/0068528 | A1 | 3/2016 | Zhang et al. |
| 2016/0075712 | A1 | 3/2016 | Shi et al. |
| 2016/0168146 | A1 | 6/2016 | Wu et al. |
| 2016/0243092 | A1 | 8/2016 | Bollag et al. |
| 2016/0326162 | A1 | 11/2016 | Lin et al. |
| 2016/0326168 | A1 | 11/2016 | Ibrahim et al. |
| 2016/0326169 | A1 | 11/2016 | Ibrahim et al. |
| 2016/0339025 | A1 | 11/2016 | Ibrahim et al. |
| 2016/0340357 | A1 | 11/2016 | Ibrahim et al. |
| 2016/0340358 | A1 | 11/2016 | Ibrahim et al. |
| 2016/0355513 | A1 | 12/2016 | Desai et al. |
| 2017/0029413 | A1 | 2/2017 | Holladay et al. |
| 2017/0056382 | A1 | 3/2017 | Wu et al. |
| 2017/0081326 | A1 | 3/2017 | Ibrahim et al. |
| 2017/0157120 | A1 | 6/2017 | Ibrahim et al. |
| 2017/0267660 | A1 | 9/2017 | Lin et al. |
| 2017/0320899 | A1 | 11/2017 | Zhang et al. |
| 2017/0334909 | A1 | 11/2017 | Ibrahim et al. |
| 2017/0349572 | A1 | 12/2017 | Wu et al. |
| 2017/0362231 | A1 | 12/2017 | Ibrahim et al. |
| 2018/0002332 | A1 | 1/2018 | Ibrahim et al. |
| 2018/0030051 | A1 | 2/2018 | Ibrahim et al. |
| 2018/0055828 | A1 | 3/2018 | Bollag et al. |
| 2018/0072722 | A1 | 3/2018 | Zhang et al. |
| 2018/0099939 | A1 | 4/2018 | Zhang et al. |
| 2018/0099975 | A1 | 4/2018 | Zhang et al. |
| 2018/0215763 | A1 | 8/2018 | Wu et al. |
| 2018/0265508 | A1 | 9/2018 | Lin et al. |
| 2018/0305358 | A1 | 10/2018 | Ibrahim et al. |
| 2018/0327403 | A1 | 11/2018 | Ibrahim et al. |
| 2018/0354946 | A1 | 12/2018 | Zhang et al. |
| 2019/0031654 | A1 | 1/2019 | Ibrahim et al. |
| 2019/0119273 | A1 | 4/2019 | Ibrahim et al. |
| 2019/0125747 | A1 | 5/2019 | Rezaei et al. |
| 2019/0161484 | A1 | 5/2019 | Ibrahim et al. |
| 2019/0175567 | A1 | 6/2019 | Wu et al. |
| 2019/0300487 | A1 | 10/2019 | Zhang et al. |
| 2019/0337943 | A1 | 11/2019 | Ibrahim et al. |
| 2019/0337944 | A1 | 11/2019 | Ibrahim et al. |
| 2019/0367507 | A1 | 12/2019 | Ibrahim et al. |
| 2020/0010465 | A1 | 1/2020 | Ibrahim et al. |
| 2020/0299293 | A1 | 9/2020 | Ibrahim et al. |
| 2021/0198239 | A1 | 7/2021 | Vander Wal et al. |
| 2021/0315869 | A1 | 10/2021 | Albers et al. |
| 2021/0346358 | A1 | 11/2021 | Wu et al. |
| 2021/0353602 | A1 | 11/2021 | Wu et al. |

FOREIGN PATENT DOCUMENTS

| | | | |
|---|---|---|---|
| WO | WO 2013/075785 | A1 | 5/2013 |
| WO | WO 2014/053568 | A1 | 4/2014 |
| WO | WO 2014/145051 | A1 | 9/2014 |
| WO | WO 2014/154760 | A1 | 10/2014 |
| WO | WO 2017/053243 | A1 | 3/2017 |
| WO | WO 2018/175311 | A1 | 9/2018 |

(56) References Cited

FOREIGN PATENT DOCUMENTS

| | | | |
|---|---|---|---|
| WO | WO 2019/075243 | A1 | 4/2019 |
| WO | WO 2020/210366 | A1 | 10/2020 |

OTHER PUBLICATIONS

Search Report and Written Opinion for PCT/US2020/027282, dated Jul. 17, 2020, 14 pages.

Airaksinen et al, "Radiosynthesis and evaluation of new [alpha]1—adrenoceptor antagonists as PET radioligands for brain imaging", *Nuclear Medicine and Biology*, vol. 40, No. 6, Aug. 1, 2013, pp. 747-754, XP055712575.

Morten et al, "Discovery of novel [alpha]1—adrenoceptor ligands based on the antipsychotic sertindole suitable for labeling as PET ligands", Bioorganic & Medicinal Chemistry : A Tetrahedron Publication For The Rapid Dissemination of Full Original Research Papers and Critical Reviews on Biomolecular Chemistry, Medicinal Chemistry and Related Disciplines, vol. 21, No. 1, Nov. 15, 2012, pp. 196-204, XP028961411.

U.S. Appl. No. 16/684,198, filed Nov. 14, 2019, Desai et al.
U.S. Appl. No. 16/687,015, filed Nov. 18, 2019, Zhang et al.
U.S. Appl. No. 16/706,497, filed Dec. 6, 2019, Ibrahim et al.
U.S. Appl. No. 16/749,893, filed Jan. 22, 2020, Ibrahim et al.
U.S. Appl. No. 16/814,632, filed Mar. 10, 2020, Wu et al.
U.S. Appl. No. 16/838,383, filed Apr. 2, 2020, Ibrahim et al.
U.S. Appl. No. 16/854,646, filed Apr. 21, 2020, Zhang et al.
U.S. Appl. No. 16/894,683, filed Jun. 5, 2020, Ibrahim et al.
U.S. Appl. No. 17/238,076, filed Apr. 22, 2021, Ibrahim et al.
U.S. Appl. No. 17/238,121, filed Apr. 22, 2021, Shi et al.
U.S. Appl. No. 17/335,898, filed Jun. 1, 2021, Wu et al.
U.S. Appl. No. 17/368,582, filed Jul. 6, 2021, Ibrahim et al.
U.S. Appl. No. 17/379,837, filed Jul. 19, 2021, Rezaei et al.
U.S. Appl. No. 17/387,775, filed Jul. 28, 2021, Ibrahim et al.
U.S. Appl. No. 17/407,811, filed Aug. 20, 2021, Powell et al.
U.S. Appl. No. 17/477,240, filed Sep. 16, 2021, Zhang et al.
U.S. Appl. No. 17/478,148, filed Sep. 17, 2021, Desai et al.
U.S. Appl. No. 17/480,111, filed Sep. 20, 2021, Zhang et al.
U.S. Appl. No. 17/501,850, filed Oct. 14, 2021, Ibrahim et al.

* cited by examiner

COMPOUNDS AND METHODS FOR EP300 OR CBP MODULATION AND INDICATIONS THEREFOR

CROSS-REFERENCE TO RELATED APPLICATIONS

This application claims the benefit under 35 U.S.C. § 119(e) to U.S. Provisional Application Ser. No. 62/831,622, filed on Apr. 9, 2019 which is hereby incorporated by reference in its entirety.

FIELD

The present invention relates to organic compounds useful for therapy in mammals, and in particular for modulating EP300 or CBP for various diseases associated with the overexpression of EP300 or CBP.

BACKGROUND

Adenovirus E1A-associated 300 kDa protein (EP300, also referred to as P300 or KAT3B) and CREB-binding protein (CBP, also referred to as CREBBP or KAT3A) have homologous bromodomain-containing transcription coactivation factors, assembling with other proteins to cause the initiation of expression of specific genes. More specifically, EP300 and CBP are histone acetyltransferases (HATs) that acetylate both histone and non-histone proteins that play a role in gene expression regulation, transcription, and cell cycle regulation. The acetylation status of lysine residues in histone tails is one of a number of epigenetic post-translational modifications that alter DNA-templated processes, such as transcription, to facilitate malignant transformation. Protein acetylation also helps to block poly-ubiquitinylation, thereby preventing proteosomal degradation and cell death. (Giotopoulos et al. The epigenetic regulators CBP and p300 facilitate leukemogenesis and represent therapeutic targets in acute myeloid leukemia, Oncogene, 2016 Jan. 21; 35(3): 279-289.) Bromodomains, including BDR4, are the readers of the acetyl marks in histone tails that are written by EP300/CBP, and thus, bromodomains, EP300, and CBP all share the same pathway in the regulation of gene transcription (Perez-Salvia et al., Bromodomain inhibitors and cancer therapy: From structures to applications, Epigenetics & Chromatin, 2018, 11:30). These proteins interact with many others involved in transcription and cell cycle regulation, and products of oncogenes and fused genes (Giotopoulos et al., 2016).

It has been found that inhibition of CBP or EP300 has an inhibitory effect on the growth of acute myeloid leukemia cells, and EP300 and CPB are promising therapeutic targets across multiple subtypes of acute myeloid leukemia (AML) (Giotopoulos et al., 2016). It has further been reported that inactivating mutations of acetyltransferase genes in B-cell lymphoma. (Mullighan et al., CREBBP mutations in relapsed acute lymphoblastic leukemia, *Nature,* 2011; 471 (7337): 235-9.)

It has also been reported that CPB or EP300 inhibition abrogates the viability of multiple myeloma cell lines as a result of direct transcriptional suppression of the lymphocyte-specific transcription factor IRF4, which is necessary for the viability of myeloma cells, and that CBP/EP300 inhibition is a viable therapeutic strategy for targeting multiple myeloma and other lymphoid malignancies dependent on the IRF4 network (Conery et al, Bromodomain inhibition of the transcriptional coactivators CBP/EP300 as a therapeutic strategy to target the IRF4 network in multiple myeloma. https://doi.org/10.7554/eLife.10483.001).

EP300 inhibition can also stimulate autophagy to produce antiaging effect. For example, Spermidine is a polyamine agent that that delays age-related disease and death by acting as an EP300 inhibitor that stimulates autophagy to produce an anti-aging effect (Madeo et al., Spermidine delays ageing in humans, Aging, 2018, Vol. 10, No. 8).

It has also been shown that inhibition of CBP or EP300 can downregulate the expression of AR (androgen receptor) dependent cancer cells, and this has been demonstrated in AR-dependent prostate cancer cells lines and AR-dependent breast cancer tumors (Garcia-Carpizo et al., CREBBP/EP300 bromodomain inhibitors in breast cancer, Mol. Cancer Res., 17(3) March 2019).

Compounds that can inhibit EP300 or CBP, therefore, represent a new class of potential therapeutics capable of modulating histone acetyltransferases (HATs) which acetylate histone and non-histone proteins. As there are no EP300 or CBBP inhibitors that are currently approved for the treatment or prevention of diseases in humans, there is an unmet need for new compounds that are capable of modulating EP300 or CBP.

SUMMARY

One embodiment of the disclosure relates to novel compounds, as described in any of the embodiments herein, or a pharmaceutically acceptable salt, a solvate, a tautomer, a stereoisomer or a deuterated analog thereof, wherein these novel compounds can modulate EP300 or CBP.

Another embodiment of this disclosure relates to a compound of Formula I:

I

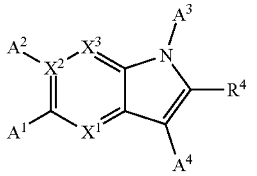

wherein $A^1$, $A^2$, $A^3$, $A^4$, $R^4$, $X^1$, $X^2$, or $X^3$ are as described in any of the embodiments described in this disclosure.

Other embodiments and sub-embodiments of Formula I are further described herein in this disclosure.

Another embodiment of the disclosure relates to a pharmaceutical composition comprising a compound according to Formula I or any embodiment and sub-embodiment of Formula I described herein in this disclosure, or a pharmaceutically acceptable salt, a solvate, a tautomer, a stereoisomer or a deuterated analog of any of these compounds, and a pharmaceutically acceptable carrier or excipient.

Another embodiment of the disclosure relates to a pharmaceutical composition comprising a compound according to Formula I, or any embodiment of Formula I described herein in this disclosure, or a pharmaceutically acceptable salt, a solvate, a tautomer, a stereoisomer or a deuterated analog of any of these compounds, and another therapeutic agent.

Another embodiment of this disclosure relates to a method for treating a subject with a disease or condition mediated by EP300 or CBP, said method comprising administering to the subject an effective amount of a compound according to Formula I, or any embodiment of Formula I described in this disclosure, or a pharmaceutically acceptable salt, a solvate, a tautomer, a stereoisomer or a deuterated analog of any of these compounds, or a pharmaceutical composition of any of the compounds as described in this disclosure, wherein the disease or condition comprises expression, aberrantly or otherwise, of EP300 or CBP, or activating mutations or translocations of any of the foregoing.

Additional embodiments are described are further described in the Detailed Description of this disclosure.

DETAILED DESCRIPTION

I. Definitions

As used herein the following definitions apply unless clearly indicated otherwise:

It is noted here that as used herein and the appended claims, the singular forms "a," "an," and "the" include plural reference unless the context clearly dictates otherwise.

Unless a point of attachment indicates otherwise, the chemical moieties listed in the definitions of the variables of Formula I of this disclosure, and all the embodiments thereof, are to be read from left to right, wherein the right hand side is directly attached to the parent structure as defined. However, if a point of attachment (e.g., a dash "-") is shown on the left hand side of the chemical moiety (e.g., -alkyloxy-($C_1$-$C_{25}$)alkyl), then the left hand side of this chemical moiety is attached directly to the parent moiety as defined.

It is assumed that when considering generic descriptions of compounds described herein for the purpose of constructing a compound, such construction results in the creation of a stable structure. That is, one of ordinary skill in the art would recognize that, theoretically, some constructs would not normally be considered as stable compounds (that is, sterically practical and/or synthetically feasible).

"Alkyl," by itself, or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, arylalkyl, cycloalkylalkyl, heterocycloalkylalkyl, heteroarylalkyl, etc.), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl refers to a straight or branched hydrocarbon having 1, 2, 3, 4, 5 or 6 carbon atoms and includes, but is not limited to, —$CH_3$, $C_2$ alkyl, $C_3$ alkyl, $C_4$ alkyl, $C_5$ alkyl, $C_6$ alkyl, $C_{1-2}$ alkyl, $C_2$ alkyl, $C_3$ alkyl, $C_{1-3}$ alkyl, $C_{1-4}$ alkyl, $C_{1-5}$ alkyl, $C_{1-6}$ alkyl, $C_{2-3}$ alkyl, $C_{2-4}$ alkyl, $C_{2-5}$ alkyl, $C_{2-6}$ alkyl, $C_{3-4}$ alkyl, $C_{3-5}$ alkyl, $C_{3-6}$ alkyl, $C_{4-5}$ alkyl, $C_{4-6}$ alkyl, $C_{5-6}$ alkyl and $C_6$ alkyl. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

"Alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—CH$(CH_3)CH_2$—, —$CH_2$—$C(CH_3)_2$—$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms, or 4 or fewer main chain carbon atoms, or 3 or fewer main chain carbon atoms, or 2 or fewer main chain carbon atoms, or 1 carbon atom.

"Alkenyl" refers to a linear monovalent hydrocarbon radical or a branched monovalent hydrocarbon radical having the number of carbon atoms indicated in the prefix and containing at least one double bond. For example, $C_2$-$C_6$ alkenyl is meant to include ethenyl, propenyl, and the like. "$C_2$-$C_6$alkenyl$C_1$-$C_6$alkylene" is a group —$C_1$-$C_6$alkylene-$C_2$-$C_6$alkenyl, where alkenyl and alkylene are as defined herein.

The term "alkenylene" refers to a linear divalent hydrocarbon radical or a branched divalent hydrocarbon radical containing at least one double bond and having the number of carbon atoms indicated in the prefix.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, e.g. —C≡$CCH_3$), and the like. When a prefix is not included to indicate the number of carbon atoms in an alkenyl or alkynyl portion, the alkenyl or alkynyl moiety or portion thereof will have 12 or fewer main chain carbon atoms or 8 or fewer main chain carbon atoms, 6 or fewer main chain carbon atoms or 4 or fewer main chain carbon atoms.

The term "alkynylene" refers to a linear divalent hydrocarbon radical or a branched divalent hydrocarbon radical containing at least one triple bond and having the number of carbon atoms indicated in the prefix. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

"Alkoxy" or "alkoxyl" refers to a —O-alkyl group, where alkyl is as defined herein. By way of example, "$C_1$-$C_6$alkoxy" refers to a —O—$C_1$-$C_6$alkyl group, where alkyl is as defined herein. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

The terms "alkoxyalkyl" and "alkoxyalkylene" refer to an alkyl group substituted with an alkoxy group. By way of example, "$C_1$-$C_6$alkoxy$C_1$-$C_6$alkyl" refers to $C_1$-$C_6$alkyl substituted with a $C_1$-$C_6$alkoxy where alkyl and alkoxy are as defined herein, while "$C_1$-$C_3$alkoxy$C_1$-$C_3$alkylene" refers to $C_1$-$C_3$alkyl substituted with a $C_1$-$C_3$alkoxy where alkylene and alkoxy are as defined herein.

"Alkylsulfonyl" refers to a group —$S(O)_2$-alkyl, for example, $C_1$-$C_6$alkylsulfonyl is a group —$S(O)_2$—$C_1$-$C_6$alkyl. "Alkylsulfonylalkylene" refers to a group alkylene-$S(O)_2$-alkyl, for example, $C_1$-$C_6$alkylsulfonyl$C_1$-$C_6$alkylene is —$C_1$-$C_6$alkylene-$S(O)_2$—$C_1$-$C_6$alkyl.

"Amino" or "amine" denotes the group —$NH_2$.

"Alkylamino" refers to a —NH-alkyl group, where alkyl is as defined herein. Exemplary alkylamino groups include $CH_3NH$—, ethylamino, and the like. By way of example, $C_1$-$C_6$alkylamino refers to —N(H)$C_1$-$C_6$alkyl.

The terms "aminoalkyl" and "aminoalkylene" refer to -alkylene-$NH_2$. Byway of example, $C_1$-$C_6$aminoalkyl refers to —$C_1$-$C_6$alkyl-$NH_2$. "Alkylaminoalkylene" refers to an -alkylene-NH-alkyl group, for example, $C_1$-$C_6$alkylamino$C_1$-$C_6$alkylene is a group —$C_1$-$C_6$alkylene-NH—$C_1$-$C_6$alkyl.

"Dialkylamino" refers to a —N(alkyl)(alkyl) group, where each alkyl is independently as defined herein. Exemplary dialkylamino groups include dimethylamino, diethylamino, ethylmethylamino, and the like. Di-$C_1$-$C_6$alkylamino refers to —N($C_1$-$C_6$alkyl)$_2$.

"Cycloalkyl" or "Carbocycle" or "Carbocyclic" by itself, or as part of another substituent, unless otherwise stated, refers to saturated or partially unsaturated, non-aromatic monocyclic ring, or fused rings, such as bicyclic or tricyclic carbon ring systems, or cubane, having the number of carbon atoms indicated in the prefix or if unspecified having 3-6, also 4-6, and also 5-6 ring members per ring, such as cyclopropyl, cyclopentyl, cyclohexyl, where one or two ring carbon atoms may optionally be replaced by a carbonyl. Further, the term cycloalkyl is intended to encompass ring systems fused to an aromatic ring (e.g., of an aryl or heteroaryl), regardless of the point of attachment to the remainder of the molecule. Cycloalkyl refers to hydrocarbon rings having the indicated number of ring atoms (e.g., $C_{3-6}$ cycloalkyl and 3-6 membered cycloalkyl both mean three to six ring carbon atoms). The term "cycloalkenyl" refers to a cycloalkyl having at least one unit of unsaturation. A substituent of a cycloalkyl or cycloalkenyl may be at the point of attachment of the cycloalkyl or cycloalkenyl group, forming a quaternary center.

"Cycloalkylalkyl" and "cycloalkylalkylene" refer to an -(alkylene)-cycloalkyl group where alkylene as defined herein has the indicated number of carbon atoms or if unspecified having six or fewer carbon atoms; and cycloalkyl is as defined herein has the indicated number of carbon atoms or if unspecified having 3-10, also 3-8, and also 3-6, ring members per ring. By way of example, 4-6 membered cycloalkyl-$C_1$-$C_6$alkyl refers to a cycloalkyl with 4-6 carbon atoms attached to an alkylene chain with 1-6 carbon atoms, wherein the alkylene chain is attached to the parent moiety. Other exemplary cycloalkylalkyl includes, e.g., cyclopropylmethylene, cyclobutylethylene, cyclobutylmethylene, and the like. "Cycloalkylalkynylene" refers to a -(alkynylene)-cycloalkyl group, for example, $C_3$-$C_6$cycloalkyl$C_2$-$C_6$alkynylene is a group —($C_2$-$C_6$alkynylene)-$C_3$-$C_6$cycloalkyl. "$C_3$-$C_6$cycloalkylethynylene" is a group —C≡C—$C_3$-$C_6$cycloalkyl.

"Cycloalkylalkoxy" refers to an -(alkoxy)-cycloalkyl group where alkoxy as defined herein has the indicated number of carbon atoms, or if unspecified has six or fewer carbon atoms; and cycloalkyl is as defined herein and has the indicated number of carbon atoms, or if unspecified has 3-10, also 3-8, or 3-6, ring members per ring. By way of example, $C_3$-$C_6$cycloalkylalkoxy refers to a cycloalkyl with 3-6 ring carbon atoms attached to an alkoxy having one to six carbon atoms, wherein the alkoxy chain is attached to the parent moiety. Other exemplary cycloalkylalkoxy include, e.g., cyclopropylmethoxy, cyclobutylethoxy, cyclobutylmethoxy, and the like.

The term "cyano" refers to the group —CN. The term "$C_1$-$C_6$cyanoalkyl" refers to a $C_1$-$C_6$alkyl, as defined herein, that is substituted with 1, 2 or 3 cyano groups. "$C_1$-$C_6$cyanoalkylethynylene" is a group —C≡C—$C_1$-$C_6$cyanoalkyl.

"Aryl" by itself, or as part of another substituent, unless otherwise stated, refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Aryl, however, does not encompass or overlap in any way with heteroaryl defined below. If one or more aryl rings are fused with a heteroaryl ring, the resulting ring system is heteroaryl. Non-limiting examples of unsubstituted aryl groups include phenyl, 1-naphthyl and 2-naphthyl. The term "arylene" refers to a divalent aryl, wherein the aryl is as defined herein.

"Arylalkyl" or "aralkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl, and the like. In another example, phenyl-$C_1$-$C_6$alkoxy refers to a phenyl group attached to $C_1$-$C_6$alkoxy group, wherein $C_1$-$C_6$alkoxy is as defined herein and is attached to the parent moiety.

The term "haloalkyl" refers to an alkyl substituted by one to seven halogen atoms. Haloalkyl includes monohaloalkyl or polyhaloalkyl. For example, the term "$C_1$-$C_6$haloalkyl" is meant to include trifluoromethyl, difluoromethyl, 2,2,2-trifluoroethyl, 4-chlorobutyl, 3-bromopropyl, and the like. Further, the term "haloalkylene" refers to an alkylene substituted by one to seven halogen atoms.

"Halogen" or "halo" refers to all halogens, that is, chloro (Cl), fluoro (F), bromo (Br), or iodo (I).

The term "haloalkoxy" refers to an alkoxy substituted by one to seven halogen atoms. Haloalkoxy includes monohaloalkoxy or polyhaloalkoxy. For example, the term "$C_1$-$C_6$haloalkoxy" is meant to include trifluoromethoxy, difluoromethoxy, 2,2,2-trifluoroethoxy, 4-chlorobutoxy, 3-bromopropoxy, and the like.

"Heteroatom" is meant to include oxygen (O), nitrogen (N), and sulfur (S).

"Heteroaryl" refers to a monocyclic or bicyclic aromatic ring radical containing 5-9 ring atoms (also referred to in this disclosure as a 5-9 membered heteroaryl), including monocyclic aromatic ring radicals containing 5 or 6 ring atoms (also referred to in this disclosure as a 5-6 membered heteroaryl), containing one or more, 1-4, 1-3, or 1-2, heteroatoms independently selected from the group consisting of O, S, and N. Any aromatic ring or ring system containing at least one heteroatom is a heteroaryl regardless of the point of attachment (i.e., through any one of the fused rings). Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalazinyl, benzotriazinyl, benzimidazolyl, benzopyrazolyl, benzotriazolyl, benzisoxazolyl, isobenzofuryl, isoindolyl, indolizinyl, benzotriazinyl, thienopyridyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein at least one of the ring heteroatoms is N.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein.

"Heterocycloalkyl" refers to a saturated or partially unsaturated non-aromatic cycloalkyl group that contains from one to five heteroatoms selected from N, O, S (including S(O) and $S(O)_2$), or P (including phosphine oxide) wherein the nitrogen, sulfur, and phosphorous atoms are optionally oxidized, and the nitrogen atom(s) are optionally quarternized, the remaining ring atoms being C, where one or two C atoms may optionally be present as a carbonyl. Further, the term heterocycloalkyl is intended to encompass any ring or ring system containing at least one heteroatom that is not a heteroaryl, regardless of the point of attachment to the remainder of the molecule. Heterocycloalkyl groups include those having a ring with a formally charge-separated aromatic resonance structure, for example, N-methylpyridonyl. The heterocycloalkyl may be substituted with one or two oxo groups, and can include sulfone and sulfoxide derivatives. The heterocycloalkyl may be a monocyclic, a fused bicyclic or a fused polycyclic ring system of 3 to 12, 4 to 10, 5 to 10, or 5 to 6 ring atoms in which one to five ring atoms are heteroatoms selected from —N═, —N—, —O—, —S—, —S(O)—, or —$S(O)_2$— and further wherein one or two ring atoms are optionally replaced by a —C(O)— group. As an example, a 4-6 membered heterocycloalkyl is a heterocycloalkyl with 4-6 ring members having at least one heteroatom. The heterocycloalkyl can also be a heterocyclic alkyl ring fused with a cycloalkyl. Non limiting examples of heterocycloalkyl groups include pyrrolidinyl, piperidinyl, morpholinyl, pyridonyl, and the like. A heterocycloalkyl group can be attached to the remainder of the molecule through a ring carbon or a heteroatom. The "heterocycloalkenyl" refers to a heterocycloalkyl having at least one unit of unsaturation. A substituent of a heterocycloalkyl or heterocycloalkenyl may be at the point of attachment of the heterocycloalkyl or heterocycloalkenyl group, forming a quaternary center.

"Heterocycloalkylalkyl" or "heterocyclylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein.

"Hydroxyl" or "hydroxy" refers to the group —OH. The term "hydroxyalkyl" or "hydroxyalkylene" refers to an alkyl group or alkylene group, respectively as defined herein, substituted with 1-5 hydroxy groups.

The term "$C_1$-$C_6$ haloalkoxy" refers to $C_1$-$C_6$ alkoxy as defined herein that is substituted with one or more halogen atoms.

The term "oxo" refers to C(═O) or (O). In some embodiments, two possible points of attachment on a carbon form an oxo group.

"Optional substituents" or "optionally substituted" as used throughout the disclosure means that the substitution on a compound may or may not occur, and that the description includes instances where the substitution occurs and instances in which the substitution does not. For example, the phrase "optionally substituted with 1-4 $J^1$ groups" means that the $J^1$ group may but need not be present. It is assumed in this disclosure that optional substitution on a compound occurs in a way that would result in a stable compound.

As used herein in connection with compounds of the disclosure, the term "synthesizing" and like terms means chemical synthesis from one or more precursor materials.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Such salts can be derived from pharmaceutically acceptable inorganic or organic bases and from pharmaceutically-acceptable inorganic or organic acids, depending on the particular substituents found on the compounds described herein.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

When compounds of the present disclosure contain relatively acidic functionalities, base addition salts can be obtained by contacting the neutral form of such compounds with a sufficient amount of the desired base (i.e. a primary, secondary, tertiary, quaternary, or cyclic amine; an alkali metal hydroxide; alkaline earth metal hydroxide; or the like), either neat or in a suitable inert solvent. The desired acid can be, for example, a pyranosidyl acid (such as glucuronic acid or galacturonic acid), an alpha-hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid), or the like. In some embodiments, salts can be derived from pharmaceutically acceptable acids such as acetic, trifluoroacetic, propionic, ascorbic, benzenesulfonic, benzoic, camphorsulfonic, citric, ethanesulfonic, fumaric, glycolic, gluconic, glucoronic, glutamic, hippuric, hydrobromic, hydrochloric, isethionic, lactic, lactobionic, maleic, malic, malonic, mandelic, oxalic, methanesulfonic, mucic, naphthalenesulfonic, nicotinic, nitric, pamoic, pantothenic, phosphoric, succinic, sulfuric, sulfamic, hydroiodic, carbonic, tartaric, p-toluenesulfonic, pyruvic, aspartic, benzoic, cinnamic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylsulfamic, cyclohexylaminosulfonic, quinic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The pharmaceutically acceptable salt of the different compounds may be present as a complex. Examples of complexes include 8-chlorotheophylline complex (analogous to, e.g., dimenhydrinate:diphenhydramine 8-chlorotheophylline (1:1) complex; Dramamine) and various cyclodextrin inclusion complexes.

The term "deuterated" as used herein alone or as part of a group, means substituted deuterium atoms. The term "deuterated analog" as used herein alone or as part of a group, means substituted deuterium atoms in place of hydrogen. The deuterated analog of the disclosure may be a fully or partially deuterium substituted derivative. In some embodiments, the deuterium substituted derivative of the disclosure holds a fully or partially deuterium substituted alkyl, aryl or heteroaryl group.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. All isotopic variations of the compounds of the present disclosure, whether radioactive or not, are intended to be encompassed within the scope of the present disclosure. Examples of isotopes that can be incorporated into compounds of the disclosure include isotopes of hydrogen, carbon, nitrogen, oxygen, phosphorous, fluorine, and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Unless otherwise stated, when a position is designated specifically as "H" or "hydrogen," the position is understood to have hydrogen at its natural abundance isotopic composition or its isotopes, such as deuterium (D) or tritium (3H). Certain isotopically-labeled compounds of the present disclosure (e.g., those labeled with $^{3}H$ and $^{14}C$) are useful in compound and/or substrate tissue distribution assays. Tritiated (i.e., $^{3}H$) and carbon-14 (i.e., $^{14}C$) and fluorine-18 ($^{18}F$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

"Prodrugs" means any compound which releases an active parent drug according to Formula I in vivo when such prodrug is administered to a subject. Prodrugs of a compound of Formula I are prepared by modifying functional groups present in the compound of Formula I in such a way, either in routine manipulation or in vivo, that the modifications may be cleaved in vivo to release the parent compound. Prodrugs may proceed from prodrug form to active form in a single step or may have one or more intermediate forms which may themselves have activity or may be inactive. Some prodrugs are activated enzymatically to yield the active compound, or a compound which, upon further chemical reaction, yields the active compound. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Other examples of prodrugs include, without limitation, carbonates, ureides, solvates, or hydrates of the active compound. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As described in The Practice of Medicinal Chemistry, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

(1) Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

(2) Reductive reactions: Reductive reactions are exemplified without limitation to reactions such as reduction of carbonyl functionalities, reduction of alcohol functionalities and carbon-carbon double bonds, reduction of nitrogen-containing functional groups, and other reduction reactions.

(3) Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols.

The term "carrier" is also meant to include microspheres, liposomes, micelles, nanoparticles (naturally-equipped nanocarriers, for example, exosomes), and the like. It is known that exosomes can be highly effective drug carriers, and there are various ways in which drugs can be loaded into exosomes, including those techniques described in J Control Release. 2015 Dec. 10; 219: 396-405, the contents of which are incorporated by reference in its entirety.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, J. Med. Chem., 40:2011-2016; Shan et al., 1997, J Pharm Sci 86(7):756-757; Bagshawe, 1995, Drug Dev. Res., 34:220-230.

"Tautomer" means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N═C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular Formulae but differ in the nature or sequence of bonding of their atoms or in the arrangement of their atoms in space. Isomers that differ in the arrangement of their atoms in space are termed "stereoisomers." "Stereoisomer" and "stereoisomers" refer to compounds that exist in different stereoisomeric forms, for example, if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, an atom such as carbon bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." As another example, stereoisomers include geometric isomers, such as cis- or trans-orientation of substituents on adjacent carbons of a double bond. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

"Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as those described herein. Generally a ligand or modulator will be a small molecule, where "small molecule refers to a compound with a molecular weight of 1500 Daltons or less, 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant ($K_D$) of 10 mM or less, 1,000 μM or less, 100 μM or less, 10 μM or less, 1 μM or less, 1,000 nM or less, 100 nM or less, 10 nM or less, or 1 nM or less. In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

The terms "modulate," "modulation," and the like refer to the ability of a compound to increase or decrease the function and/or expression of a target, such as EP300 or CBP, where such function may include transcription regulatory activity and/or binding. Modulation may occur in vitro or in vivo. Modulation, as described herein, includes the inhibition, antagonism, partial antagonism, activation, agonism or partial agonism of a function or characteristic associated with EP300 or CBP, either directly or indirectly, and/or the upregulation or downregulation of the expression EP300 or CBP, either directly or indirectly. In another embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction.

As used herein, the terms "treat," "treating," "therapy," "therapies," and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or requiring a disorder or condition or one or more of its attendant symptoms.

As used herein, the term "subject," "animal subject," and the like refers to a living organism including, but not limited to, human and non-human vertebrates, e.g. any mammal, such as a human, other primates, sports animals and animals of commercial interest such as cattle, horses, ovines, or porcines, rodents, or pets such as dogs and cats.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

The ability of a compound to inhibit the function of EP300 or CBP can be demonstrated in a biochemical assay, e.g., binding assay, or a cell-based assay.

As used herein, the term "EP300 or CBP mediated disease or condition" refers to a disease or condition in which the biological function of EP300, CBP, or both EP300 and CBP affect the development and/or course of the disease or condition, and/or in which modulation of EP300, CBP, or both EP300 and CBP alters the development, course, and/or symptoms. An EP300 or CBP mediated disease or condition includes a disease or condition for which EP300 inhibition, CBP inhibition, or both EP300 and CBP inhibition provides a therapeutic benefit, e.g. wherein treatment with EP300 or CBP inhibitors, including compounds described herein, provides a therapeutic benefit to the subject suffering from or at risk of the disease or condition. An EP300 or CBP mediated disease or condition is intended to include a cancer that harbors loss of function mutations in CBP or EP300, or a cancer where there is activation of EP300 or CBP. An EP300 or CBP mediated disease or condition is also intended to include a cancer that expresses the androgen receptor.

The term "EP300 mediated disease or disorder" includes a disease associated with or that implicates EP300 activity, for example, the overactivity of EP300, and conditions that accompany these diseases. The term "overactivity of EP300" refers to either: 1) EP300 expression in cells which normally do not express EP300; 2) increased EP300 expression leading to unwanted cell proliferation; or 3) mutations leading to constitutive activation of EP300. An EP300 mediated disease or disorder would include tumors with a CBP inactivating mutation, also known as synthetic lethality. Examples of an EP300 mediated diseases or disorders include a disorder resulting from abnormally high amount of EP300 activity. An EP300 mediated disease or condition is intended to include a cancer that harbors loss of a function mutation in CBP, or a cancer where there is activation of EP300. An EP300 mediated disease or condition is also intended to include a cancer that expresses the androgen receptor. It is known that overactivity of EP300 has been implicated in the pathogenesis of a number of diseases, including proliferative and non-proliferative disorders, including neoplastic disorders and cancers, inflammatory disorders, cognitive disorders and neurodegenerative diseases.

The term "CBP mediated disease or disorder" includes a disease associated with or that implicates CBP activity, for example, the overactivity of CBP, and conditions that accompany with these diseases. The term "overactivity of CBP" refers to either: 1) CBP expression in cells which normally do not express CBP; 2) increased CBP expression leading to unwanted cell proliferation; or 3) mutations leading to constitutive activation of CBP. Examples of CBP mediated diseases or disorders include a disorder resulting from abnormally high amount of CBP activity. A CBP mediated disease or condition is intended to include a cancer that harbors loss of a function mutation in EP300, or a cancer where there is activation of CBP. A CBP mediated disease or condition is also intended to include a cancer that expresses the androgen receptor. It is known that overactivity of CBP has been implicated in the pathogenesis of a number of diseases, including proliferative and non-proliferative disorders, including neoplastic disorders and cancers, inflammatory disorders, cognitive disorders and neurodegenerative diseases.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of EP300, CBP or even other epigenetic targets. In particular embodiments, the greater specificity is at least 2, 3, 4, 5, 8, 10, 50, 100, 200, 400, 500, or 1000-fold greater specificity.

As used herein in connection with binding compounds or ligands, the term "specific for EP300," and terms of like import mean that a particular compound binds to EP300 to a statistically greater extent than to other epigenetic targets that may be present in a particular sample. Also, where biological activity other than binding is indicated, the term "specific for EP300" indicates that a particular compound has greater biological effect associated with binding EP300 than to other enzymes, e.g., enzyme activity inhibition. The specificity is also with respect to other biomolecules (not limited to EP300) that may be present in a particular sample.

As used herein in connection with binding compounds or ligands, the term "specific for CBP," and terms of like import mean that a particular compound binds to CBP to a statistically greater extent than to other epigenetic targets that may be present in a particular sample. Also, where biological activity other than binding is indicated, the term "specific for CBP" indicates that a particular compound has greater biological effect associated with binding CBP than to other enzymes, e.g., enzyme activity inhibition. The specificity is also with respect to other biomolecules (not limited to CBP) that may be present in a particular sample.

The term "first line cancer therapy" refers to therapy administered to a subject as an initial regimen to reduce the number of cancer cells. First line therapy is also referred to as induction therapy, primary therapy and primary treatment. First-line therapy can be an administered combination with one or more agents. A summary of currently accepted approaches to first line treatment for certain disease can be found in the NCI guidelines for such diseases.

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy." A summary of the currently accepted approaches to second line treatment for certain diseases is described in the NCI guidelines for such diseases.

The term "refractory" refers to circumstances wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of, or following, a particular therapy.

In addition, abbreviations as used herein have respective meanings as follows:

| | |
|---|---|
| ° C. | Degree Celsius |
| Ac | Acetyl |
| BOC | tert-Butoxycarbonyl |
| DBU | 1,8-Diazabicyclo[5.4.0]undec-7-ene |
| DCM | Dichloromethane |
| DEAE | Diethylaminoethyl |
| DMAP | Dimethylaminopyridine |
| DMEM | Dulbecco's Modified Eagle's Medium |
| DME | Dimethoxyethane |
| DMF | Dimethylformamide |
| DMSO | Dimethylsulfoxide |
| ESI | Electrospray ionization |
| FBS | Fetal bovine serum |
| HPLC | High Performance Liquid Chromatography |
| LCMS | Liquid Chromatography Mass Spectrometry |
| [M + H+ ]+ or (MH)+ | Mass peak plus hydrogen |
| [M − H−]− or (MH)− | Mass peak minus hydrogen |
| mCPBA | Meta-chloroperoxybenzoic acid |
| Me | Methyl |
| MeOH | Methanol |
| MS | Mass spectrometry |
| PBS | Phosphate buffered saline |
| RT | Room temperature |
| S-Phos | 2-Dicyclohexylphosphino-2',6'-dimethoxybiphenyl |
| TBAF | Tetrabutylammonium fluoride |
| TLC | Thin-layer chromatography |
| THF | Tetrahydrofuran |
| n-Bu | n-Butyl |
| N | Normal |
| $IC_{50}$ | Half maximal (50%) inhibitory concentration |
| RP | Reverse phase |
| X-Phos | 2-Dicyclohexylphosphino-2',4',6'-triisopropylbiphenyl |

II. Compounds

Embodiment 1 of this disclosure relates to a compound of I:

1. A compound of Formula I:

I

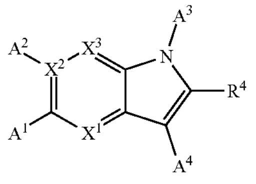

or a pharmaceutically acceptable salt, a solvate, a tautomer, a stereoisomer, or a deuterated analog thereof, wherein:

$A^1$ is $R^6$, $A^2$ is $R^7$, $A^3$ is $-L-R^1$, $A^4$ is $R^5$, X is CH, $X^2$ is C, and $X^3$ is N; or $A^1$ is $R^6$, $A^2$ is $R^7$, $A^3$ is $-L-R^1$, $A^4$ is $R^5$, X is CH, $X^2$ is C, and $X^3$ is CH; or $A^1$ is $R^6$, $A^2$ is absent, $A^3$ is $-L-R^1$, $A^4$ is $R^5$, $X^1$ is CH, $X^2$ is N, and $X^3$ is CH; or $A^1$ is $R^7$, $A^2$ is $R^6$, $A^3$ is $-L-R^1$, $A^4$ is $R^5$, $X^1$ is N, $X^2$ is C, and $X^3$ is CH; or $A^1$ is $R^7$, $A^2$ is $R^6$, $A^3$ is $R^5$, $A^4$ is $-L-R^1$, $X^1$ is N, $X^2$ is C, and $X^3$ is CH;

$L^2$ is a bond, $-CH_2-CH_2-$, $-(CH_2)_{1-2}-CH{=}CH-(CH_2)_{0-1}-$, $-CR^2R^3-$, $-C(O)-$, or $-S(O)_2-$;

$L^2$ is a bond or $-C(R^{13})_2-$;

$R^1$ is phenyl, 5-9 membered heteroaryl, $C_3$-$C_6$cycloalkyl, $C_5$-$C_6$cycloalkenyl, 4-9 membered heterocycloalkyl, or 5-6 membered heterocycloalkenyl, wherein $R^1$ is optionally substituted with 1 $G^1$ group and 1-3 $G^2$ groups;

$R^2$ is H, $C_1$-$C_6$alkyl, or OH;

$R^3$ is H, $C_1$-$C_6$alkyl, $C_1$-$C_6$cyanoalkyl, $C_1$-$C_6$haloalkyl, $C_3$-$C_6$cycloalkyl, or 5-6 membered heteroaryl;

$R^4$ is H, OH, $C_1$-$C_6$alkyl, or $C_1$-$C_6$haloalkyl;

$R^5$, when attached to carbon, is 4-6 membered cycloalkyl, 5-6 membered cycloalkenyl, phenyl, 5-9 membered heteroaryl, 5-6-membered heterocycloalkyl, 4-6 membered cycloalkyl-$C_1$-$C_6$alkyl,

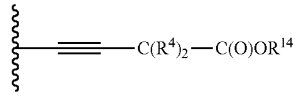

, or

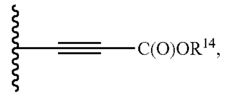

wherein the 4-6 membered cycloalkyl, 5-6 membered cycloalkenyl, phenyl, 5-9-membered heteroaryl, or 4-6 membered cycloalkyl-$C_1$-$C_6$alkyl are each optionally substituted with one $-L^2-J^1$ group and 0-4 $J^2$ groups, provided that $J^1$ is directly bonded to a carbon atom;

or $R^5$, when attached to nitrogen, is 4-6 membered cycloalkyl, 5-6 membered cycloalkenyl, phenyl, 5-9 membered heteroaryl, or 4-6 membered cycloalkyl-$C_1$-$C_6$alkyl, wherein the 4-6 membered cycloalkyl, 5-6 membered cycloalkenyl, phenyl, 5-9-membered heteroaryl, or 4-6 membered cycloalkyl-$C_1$-$C_6$alkyl are each optionally substituted with $1-L^2-J^1$ group and 1-4 $J^2$ groups, provided that $J^1$ is directly bonded to a carbon atom;

$R^6$ is a five membered heteroaryl containing at least one nitrogen atom, wherein the 5-membered heteroaryl is optionally substituted with 0-2 $R^8$ groups;

$R^7$ is H, halo or $C_1$-$C_6$alkyl;

$R^8$ is $C_1$-$C_6$alkyl or $C_1$-$C_3$alkoxy$C_1$-$C_3$alkylene;

each $R^{10}$ is independently H, $C_1$-$C_6$alkyl, $C_1$-$C_6$haloalkyl or cyclopropyl;

each $R^{11}$ is independently H, $C_1$-$C_6$alkyl, or $C_1$-$C_6$haloalkyl, or two $R^{11}$ groups, together with the carbon atom to which both $R^{11}$ groups are attached, join to form a cyclopropyl group;

each $R^{12}$ is independently H, $C_1$-$C_6$alkyl, $C_1$-$C_6$hydroxyalkyl or $C_1$-$C_6$haloalkyl;

each $R^{13}$ is independently H, $CH_3$, or F, or each $R^{13}$ join, together with the carbon atom to which they are both attached, to form a $C_3$-$C_6$ cycloalkyl group;

$R^{14}$ is H, $C_1$-$C_6$alkyl or $C_1$-$C_3$alkoxy$C_1$-$C_3$alkylene;

$G^1$ is cyano, $C_2$-$C_6$ alkenyl, $C_1$-$C_6$cyanoalkyl, $C_1$-$C_6$cyanoalkylethynylene, $C_2$-$C_6$alkenyl$C_1$-$C_6$alkylene, $C_1$-$C_6$alkylsulfonyl, $C_1$-$C_6$alkylsulfonyl$C_1$-$C_6$alkylene, $-N(R^{10})_2$, di-$C_1$-$C_6$alkylamino$C_1$-$C_6$alkylene, $C_1$-$C_6$alkylamino$C_1$-$C_6$alkylene, amino$C_1$-$C_6$alkylene, $-C(O)-$ $C_1$-$C_6$alkyl, $-C(O)-C_1$-$C_6$hydroxyalkyl, $-C(O)-C_1$-$C_6$haloalkyl, $-C(O)OR^2$, $-C_1$-$C_3$alkylene-C(O)OR$^2$, $-C(O)-N(H)-C_3$-$C_6$cycloalkyl, $C_3$-$C_6$cycloalkyl, $C_3$-$C_6$cycloalkyl$C_1$-$C_6$alkylene, $C_3$-$C_6$cycloalkyl$C_2$-$C_6$alkynylene, 4-6 membered heterocycloalkyl, $-C(O)-N(R^{10})_2$, $-C_1$-$C_6$alkylene-C(O)—N$(R^{10})_2$ or phenyl-$C_1$-$C_6$alkoxy, provided that when $G^1$ is attached to a nitrogen atom, $G^1$ is not cyano;

each $G^2$ is independently halo, $C_1$-$C_6$alkyl, $C_1$-$C_6$haloalkyl, $C_1$-$C_6$alkoxy, $C_1$-$C_6$haloalkoxy, OH, oxo, $C_1$-$C_6$hydroxyalkyl, provided that when $G^2$ is attached to a nitrogen atom, $G^2$ is not halo, $C_1$-$C_6$alkoxy, $C_1$-$C_6$haloalkoxy, or OH;

$J^1$ is —$C(R^{11})_2$—C(O)OH, —C(O)OH, —C(O)O—$C_1$-$C_6$alkyl, $CH_2$—C(O)O—$C_1$-$C_6$alkyl, —C(O)N$(R^{10})_2$, —C(O)N(H)—CN, —C(O)N(H)OH, —C(O)N(H)—$SO_2$—$C_1$-$C_6$alkyl, —N(H)—$SO_2$—$C_1$-$C_6$alkyl, $C_1$-$C_6$alkylsulfonyl, tetrazolyl, or —$S(O)_2$—N$(R^{10})_2$; and each $J^2$ is independently 4-6 membered heterocycloalkyl, —O-(4-6 membered heterocycloalkyl), —O—$C_3$-$C_6$cycloalkyl, $C_3$-$C_6$cycloalkylalkoxy, phenyl-$C_1$-$C_6$alkoxy, $C_1$-$C_6$alkyl, $C_1$-$C_6$alkoxy, halo, $C_1$-$C_6$haloalkyl, $C_1$-$C_6$haloalkoxy, OH, $C_1$-$C_6$hydroxyalkyl, CN, $C_1$-$C_6$cyanoalkyl, $C_2$-$C_6$alkynyl, $C_3$-$C_6$cycloalkylethynylene, $C_3$-$C_6$cycloalkyl, 4-6 membered heterocycloalkyl, $NO_2$, or —N$(R^{10})_2$, provided that when $J^2$ is attached to nitrogen, $J^2$ is not —O-(4-6 membered heterocycloalkyl), —O—$C_3$-$C_6$cycloalkyl, $C_3$-$C_6$cycloalkylalkoxy, phenyl-$C_1$-$C_6$alkoxy, $C_1$-$C_6$alkoxy, halo, $C_1$-$C_6$haloalkoxy, OH, CN, $C_2$-$C_6$alkynyl, $C_3$-$C_6$cycloalkylethynylene, or —N$(R^{10})_2$.

The phrase "wherein $R^1$ is optionally substituted with 1 $G^1$ group and 1-3 $G^2$ groups" is intended to include instances where $R^1$ is optionally substituted with 1 $G^1$ Group; $R^1$ is optionally substituted with 1-3 $G^2$ groups, and $R^1$ is optionally substituted with both 1 $G^1$ Group and 1-3 $G^2$ groups. This interpretation applies to all variables described in this disclosure (such as $R^1$, and $J^1$ and $J^2$ with respect to R) which can be optionally substituted with more than one additional variable (such as $G^1$ and $G^2$ or $J^1$ and $J^2$).

Subembodiments of Embodiment 1

Embodiment 1(a1) of this disclosure relates to Embodiment 1, wherein: L is a bond, —$CH_2$—$CH_2$—, —$(CH_2)_{1-2}$—CH═CH—$(CH_2)_{0-1}$—, —$CR^2R^3$—, —C(O)—, or —$S(O)_2$—; provided that when $A^1$ is $R^7$, $A^2$ is $R^6$, $A^3$ is -L-$R^1$, $A^4$ is $R^5$, $X^1$ is N, $X^2$ is C, and $X^3$ is C, then L is a bond.

Embodiment 1(a2) of this disclosure relates to Embodiment 1, wherein $R^5$, when attached to carbon, is 4-6 membered cycloalkyl, 5-6 membered cycloalkenyl, phenyl, 5-9 membered heteroaryl, 5-6-membered heterocycloalkyl

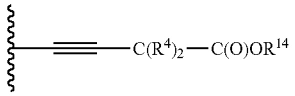

, or

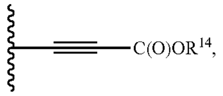

wherein the 4-6 membered cycloalkyl, 5-6 membered cycloalkenyl, phenyl, or 5-9-membered heteroaryl are each optionally substituted with one -$L^2$-$J^1$ group and 0-4 $J^2$ groups, provided that $J^1$ is directly bonded to a carbon atom;

or $R^5$, when attached to nitrogen, is 4-6 membered cycloalkyl, 5-6 membered cycloalkenyl, phenyl, or 5-9 membered heteroaryl wherein the 4-6 membered cycloalkyl, 5-6 membered cycloalkenyl, phenyl, or 5-9-membered heteroaryl are each optionally substituted with 1-$L^2$-$J^1$ group and 1-4 $J^2$ groups, provided that $J^1$ is directly bonded to a carbon atom.

Embodiment 1(a) of this disclosure relates to Embodiment 1, wherein:

$A^1$ is $R^6$, $A^2$ is $R^7$, $A^3$ is -L-$R^1$, $A^4$ is $R^5$, $X^1$ is C, $X^2$ is C, and $X^3$ is N; or $A^1$ is $R^7$, $A^2$ is $R^6$, $A^3$ is -L-$R^1$, $A^4$ is $R^5$, $X^1$ is N, $X^2$ is C, and $X^3$ is C; or $A^1$ is $R^7$, $A^2$ is $R^6$, $A^3$ is $R^5$, $A^4$ is -L-$R^1$, $X^1$ is N, $X^2$ is C, and $X^3$ is C.

Embodiment 1(b) of this disclosure relates to Embodiment 1, wherein:

$A^1$ is $R^7$, $A^2$ is $R^6$, $A^3$ is -L-$R^1$, $A^4$ is $R^5$, $X^1$ is N, $X^2$ is C, and $X^3$ is C; or $A^1$ is $R^7$, $A^2$ is $R^6$, $A^3$ is $R^5$, $A^4$ is -L-$R^1$, X is N, $X^2$ is C, and $X^3$ is C.

Embodiment 1(c) of this disclosure relates to Embodiment 1, wherein:

$A^1$ is $R^6$, $A^2$ is $R^7$, $A^3$ is -L-$R^1$, $A^4$ is $R^5$, $X^1$ is C, $X^2$ is C, and $X^3$ is N.

Embodiment 1(d) of this disclosure relates to Embodiment 1, wherein:

$A^1$ is $R^6$, $A^2$ is $R^7$, $A^3$ is -L-$R^1$, $A^4$ is $R^5$, $X^1$ is C, $X^2$ is C, and $X^3$ is C.

Embodiment 1(e) of this disclosure relates to Embodiment 1, wherein:

$A^1$ is $R^6$, $A^2$ is absent, $A^3$ is -L-$R^1$, $A^4$ is $R^5$, $X^1$ is C, $X^2$ is N, and $X^3$ is C.

Embodiment 1(f) of this disclosure relates to Embodiment 1, wherein:

$A^1$ is $R^7$, $A^2$ is $R^6$, $A^3$ is -L-$R^1$, $A^4$ is $R^5$, $X^1$ is N, $X^2$ is C, and $X^3$ is C.

Embodiment 1(g) of this disclosure relates to Embodiment 1, wherein:

$A^1$ is $R^7$, $A^2$ is $R^6$, $A^3$ is $R^5$, $A^4$ is -L-$R^1$, $X^1$ is N, $X^2$ is C, and $X^3$ is C.

Embodiment 1(h) of this disclosure relates to Embodiment 1, 1(a1), 1(a2), 1(a), 1(b), 1(c), 1(d), 1(e), 1(f), or 1(g), wherein L is a bond.

Embodiment 1(i) of this disclosure relates to Embodiment 1, 1(a1), 1(a2), 1(a), 1(b), 1(c), 1(d), 1(e), 1(f), or 1(g), wherein L is a bond, or —$CR^2R^3$—.

Embodiment 1(j) of this disclosure relates to Embodiment 1, 1(a1), 1(a2), 1(a), 1(b), 1(c), 1(d), 1(e), 1(f), or 1(g), wherein L is —$CR^2R^3$—.

Embodiment 1(j) of this disclosure relates to Embodiment 1, 1(a1), 1(a2), 1(a), 1(b), 1(c), 1(d), 1(e), 1(f), or 1(g), wherein L —$(CH_2)_{1-2}$—CH═CH—$(CH_2)_{0-1}$—.

Embodiment 1(k) of this disclosure relates to Embodiment 1, 1(a1), 1(a2), 1(a), 1(b), 1(c), 1(d), 1(e), 1(f), or 1(g), wherein L is —C(O)—.

Embodiment 1(l) of this disclosure relates to Embodiment 1, 1(a1), 1(a2), 1(a), 1(b), 1(c), 1(d), 1(e), 1(f), or 1(g), wherein L is —$S(O)_2$—.

Embodiment 1(m) of this disclosure relates to Embodiment 1, 1(a1), 1(a2), 1(a), 1(b), 1(c), 1(d), 1(e), 1(f), 1(g), 1(h), 1(i), 1(j), 1(k), or 1(l) wherein $R^1$ is phenyl or a 5-9 membered heteroaryl, wherein $R^1$ is optionally substituted with 1 G group and 1-3 $G^2$ groups.

Embodiment 1(o) of this disclosure relates to Embodiment 1, 1(a1), 1(a2), 1(a), 1(b), 1(c), 1(d), 1(e), 1(f), 1(g), 1(h), 1(i), 1(j), 1(k), or 1(l), wherein $R^1$ is phenyl optionally substituted with 1 $G^1$ group and 1-3 $G^2$ groups.

Embodiment 1(p) of this disclosure relates to Embodiment 1, 1(a1), 1(a2), 1(a), 1(b), 1(c), 1(d), 1(e), 1(f), 1(g), 1(h), 1(i), 1(j), 1(k), or 1(l), wherein $R^1$ is a 5-9 membered heteroaryl, optionally substituted with 1 $G^1$ group and 1-3 $G^2$ groups.

Embodiment 1(q) of this disclosure relates to Embodiment 1, 1(a1), 1(a2), 1(a), 1(b), 1(c), 1(d), 1(e), 1(f), 1(g), 1(h), 1(i), 1(j), 1(k), or 1(l), wherein $R^1$ is $C_3$-$C_6$cycloalkyl or $C_5$-$C_6$cycloalkenyl, wherein $R^1$ is optionally substituted with 1 $G^1$ group and 1-3 $G^2$ groups.

Embodiment 1(r) of this disclosure relates to Embodiment 1, 1(a1), 1(a2), 1(a), 1(b), 1(c), 1(d), 1(e), 1(f), 1(g), 1(h), 1(i), 1(j), 1(k), or 1(l), wherein $R^1$ is 4-9 membered heterocycloalkyl, or 5-6 membered heterocycloalkenyl, wherein $R^1$ is optionally substituted with 1 $G^1$ group and 1-3 $G^2$ groups.

Embodiment 1(s) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q) or 1(r), wherein $R^5$ is attached to carbon and is 4-6 membered cycloalkyl, 5-6 membered cycloalkenyl, phenyl, 5-9 membered heteroaryl, 5-6-membered heterocycloalkyl,

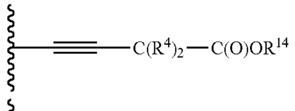

, or

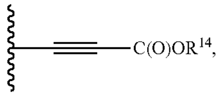

wherein the 4-6 membered cycloalkyl, 5-6 membered cycloalkenyl, phenyl, or 5-9-membered heteroaryl are each optionally substituted with one -$L^2$-$J^1$ group and 0-4 $J^2$ groups, provided that $J^1$ is directly bonded to a carbon atom.

Embodiment 1(t) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q) or 1(r), wherein or $R^5$ is attached to nitrogen and is 4-6 membered cycloalkyl, 5-6 cycloalkenyl, phenyl, or 5-9 membered heteroaryl, wherein the 4-6 membered cycloalkyl, 5-6 membered cycloalkenyl, phenyl, or 5-9-membered heteroaryl are each optionally substituted with 1-$L^2$-$J^1$ group and 1-4 $J^2$ groups, provided that $J^1$ is directly bonded to a carbon atom.

Embodiment 1(u) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s) or 1(t), wherein $J^1$ is —C(O)OH or —C(O)O—$C_1$-$C_6$alkyl.

Embodiment 1(v) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s) or 1(t), wherein $J^1$ is —C(O)OH.

Embodiment 1(w) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s) or 1(t), wherein $J^1$ is —C(O)O—$C_1$-$C_6$alkyl or $CH_2$—C(O)O—$C_1$-$C_6$alkyl.

Embodiment 1(x) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s) or 1(t), wherein $J^1$ is —C(O)N($R^{10}$)$_2$, —C(O)N(H)—CN or —C(O)N(H)OH.

Embodiment 1(y) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s) or 1(t), wherein $J^1$ is —C(O)N(H)—$SO_2$—$C_1$-$C_6$alkyl, —N(H)—$SO_2$—$C_1$-$C_6$alkyl, $C_1$-$C_6$alkylsulfonyl or —S(O)$_2$—N($R^{10}$)$_2$.

Embodiment 1(z) of this disclosure relates to Embodiment 1, 1(a1), 1(a2), 1(a), 1(b), 1(c), 1(d), 1(e), 1(f), 1(g), 1(h), 1(i), 1(j), 1(k), 1(l), 1(m), 1(n), 1(o), 1(p), 1(q), 1(r), 1(s) or 1(t), wherein $J^1$ is tetrazolyl.

Tetrazolyl within the definition of $J^1$ is a carboxylic acid isostere, and other carboxylic acid isosteres can be used in its place, such as those described in FIG. 25 in Meanwell, Synopsis of Some Recent Tactical Application of Bioisosteres in Drug Design, Journal of Medicinal Chemistry, dx.doi.org/10.1021/jm1013693, which is incorporated by reference in its entirety.

In another embodiment of Embodiment 1, $J^1$ can be a carboxylic acid isostere as described in Meanwell.

Embodiment 2 of this disclosure relates to a compound according to Embodiment 1 or Embodiment 1(a1), wherein:

$R^1$ is phenyl, 5-6 membered heteroaryl, $C_3$-$C_6$cycloalkyl, $C_5$-$C_6$cycloalkenyl, 4-6 membered heterocycloalkyl, or 5-6 membered heterocycloalkenyl, wherein $R^1$ is optionally substituted with 1 $G^1$ group and 1-3 $G^2$ groups;

$R^3$ is H, $C_1$-$C_6$alkyl, $C_1$-$C_6$cyanoalkyl, $C_1$-$C_6$haloalkyl, $C_3$-$C_6$cycloalkyl, or 5-6 membered heteroaryl;

$R^4$ is H, OH, $C_1$-$C_2$alkyl, or $C_1$-$C_2$haloalkyl;

$R^5$, when attached to carbon, is 4-6 membered cycloalkyl, cyclohexenyl, phenyl, 5-6 membered heteroaryl, 5-6-membered heterocycloalkyl,

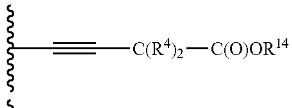

, or

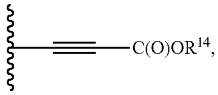

wherein the 4-6 membered cycloalkyl, cyclohexenyl, phenyl, 5-6-membered heteroaryl, or 5-6-membered heterocycloalkyl are each optionally substituted with one $J^1$ group and 0-4 $J^2$ groups, provided that J is directly bonded to a carbon atom;

or $R^5$, when attached to nitrogen, is 4-6 membered cycloalkyl, cyclohexenyl, phenyl, or 5-6 membered heteroaryl, wherein the 4-6 membered cycloalkyl, cyclohexenyl, phenyl, or 5-6-membered heteroaryl are each optionally substituted with 1-$L^2$-$J^1$ group and 1-4 $J^2$ groups, provided that $J^1$ is directly bonded to a carbon atom;

$R^6$ is a five membered heteroaryl containing at least one nitrogen atom, wherein the heteroaryl is optionally substituted with 1-2 $R^8$ groups;

$R^7$ is H, halo or $C_1$-$C_5$alkyl;

$R^8$ is $C_1$-$C_4$alkyl or $C_1$-$C_2$alkoxy$C_1$-$C_2$alkylene;

each $R^{10}$ is independently H, $C_1$-$C_5$alkyl, $C_1$-$C_5$haloalkyl or cyclopropyl;

each $R^{11}$ is independently H, $C_1$-$C_5$alkyl, or $C_1$-$C_5$haloalkyl, or two $R^{11}$ groups, together with the carbon atom to which both $R^{11}$ groups are attached, join to form a cyclopropyl group;

each $R^{12}$ is H;

$G^1$ is CN, $C_1$-$C_6$cyanoalkyl, $C_1$-$C_5$cyanoalkylethynylene, $C_2$-$C_5$alkenyl$C_1$-$C_5$alkylene, $C_1$-$C_5$alkylsulfonyl, $C_1$-$C_5$alkylsulfonyl$C_1$-$C_5$alkylene, —N($R^{10}$)$_2$, di-$C_1$-$C_5$alkylamino-$C_1$-$C_5$alkylene, $C_1$-$C_5$alkylamino-$C_1$-$C_5$alkylene, amino$C_1$-$C_5$alkylene, —C(O)—$C_1$-$C_5$alkyl, —C(O)—$C_1$-$C_5$hydroxyalkyl, —C(O)—$C_1$-$C_5$haloalkyl, —C(O)O$R^{12}$, —$C_1$-$C_3$alkylene-C(O)O$R^2$, —C(O)—N(H)—$C_3$-$C_6$cycloalkyl, $C_3$-$C_6$cycloalkyl, $C_3$-$C_6$cycloalkyl$C_1$-$C_5$alkylene, $C_3$-$C_6$cycloalkyl$C_2$-$C_5$alkynylene, 4-6 membered heterocycloalkyl, —C(O)—N $(R^{10})_2$, $—C_1$-$C_5$alkylene-C(O)—$N(R^{10})_2$ or phenyl-$C_1$-$C_5$alkoxy, provided that when $G^1$ is attached to a nitrogen atom, $G^1$ is not CN;

each $G^2$ is independently CN, halo, $C_1$-$C_5$alkyl, $C_1$-$C_5$haloalkyl, $C_1$-$C_5$alkoxy, $C_1$-$C_5$haloalkoxy, OH, oxo, $C_1$-$C_5$hydroxyalkyl, provided that when $G^2$ is attached to a nitrogen atom, $G^2$ is not CN, halo, $C_1$-$C_5$alkoxy, $C_1$-$C_5$haloalkoxy, or OH;

$J^1$ is $—C(R^{11})_2$—C(O)OH, —C(O)OH, —C(O)O—$C_1$-$C_5$alkyl, $CH_2$—C(O)O—$C_1$-$C_5$alkyl, —C(O)$N(R^{10})_2$, —C(O)N(H)—CN, —C(O)N(H)OH, —C(O)N(H)—$SO_2$—$C_1$-$C_5$alkyl, —N(H)—$SO_2$—$C_1$-$C_5$alkyl, $C_1$-$C_5$alkylsulfonyl, tetrazolyl, or $—S(O)_2—N(R^{10})_2$; and each $J^2$ is independently 4-6 membered heterocycloalkyl, —O-(4-6 membered heterocycloalkyl), —O—$C_3$-$C_6$cycloalkyl, $C_3$-$C_6$cycloalkylalkoxy, phenyl-$C_1$-$C_5$alkoxy, $C_1$-$C_5$alkyl, $C_1$-$C_5$alkoxy, halo, $C_1$-$C_5$haloalkyl, $C_1$-$C_5$haloalkoxy, OH, $C_1$-$C_5$hydroxyalkyl, CN, $C_1$-$C_5$cyanoalkyl, $C_2$-$C_5$alkynyl, $C_3$-$C_6$cycloalkylethynylene, $C_3$-$C_6$cycloalkyl, 4-6 membered heterocycloalkyl, or $—N(R^{10})_2$, provided that when $J^2$ is attached to nitrogen, $J^2$ is not —O-(4-6 membered heterocycloalkyl), —O—$C_3$-$C_6$cycloalkyl, $C_3$-$C_6$cycloalkylalkoxy, phenyl-$C_1$-$C_5$alkoxy, $C_1$-$C_5$alkoxy, halo, $C_1$-$C_5$haloalkoxy, OH, CN, $C_2$-$C_6$alkynyl, $C_3$-$C_6$cycloalkylethynylene, or $—N(R^{10})_2$.

Subembodiments of Embodiment 2

Embodiment 2(a) of this disclosure relates to Embodiment 2, wherein:

$A^1$ is $R^6$, $A^2$ is $R^7$, $A^3$ is -L-$R^1$, $A^4$ is $R^5$, X is C, $X^2$ is C, and $X^3$ is N; or $A^1$ is $R^7$, $A^2$ is $R^6$, $A^3$ is -L-$R^1$, $A^4$ is $R^5$, X is N, $X^2$ is C, and $X^3$ is C; or $A^1$ is $R^7$, $A^2$ is $R^6$, $A^3$ is $R^5$, $A^4$ is -L-$R^1$, $X^1$ is N, $X^2$ is C, and $X^3$ is C.

Embodiment 2(b) of this disclosure relates to Embodiment 2, wherein:

$A^1$ is $R^7$, $A^2$ is $R^6$, $A^3$ is -L-$R^1$, $A^4$ is $R^5$, $X^1$ is N, $X^2$ is C, and $X^3$ is C; or $A^1$ is $R^7$, $A^2$ is $R^6$, $A^3$ is $R^5$, $A^4$ is -L-$R^1$, $X^1$ is N, $X^2$ is C, and $X^3$ is C.

Embodiment 2(c) of this disclosure relates to Embodiment 2, wherein:

$A^1$ is $R^6$, $A^2$ is $R^7$, $A^3$ is -L-$R^1$, $A^4$ is $R^1$, $X^1$ is C, $X^2$ is C, and $X^3$ is N.

Embodiment 2(d) of this disclosure relates to Embodiment 2, wherein:

$A^1$ is $R^6$, $A^2$ is $R^7$, $A^3$ is -L-$R^1$, $A^4$ is $R^5$, $X^1$ is C, $X^2$ is C, and $X^3$ is C.

Embodiment 2(e) of this disclosure relates to Embodiment 2, wherein:

$A^1$ is $R^6$, $A^2$ is absent, $A^3$ is -L-$R^1$, $A^4$ is $R^5$, $X^1$ is C, $X^2$ is N, and $X^3$ is C.

Embodiment 2(f) of this disclosure relates to Embodiment 2, wherein:

$A^1$ is $R^7$, $A^2$ is $R^6$, $A^3$ is -L-$R^1$, $A^4$ is $R^5$, $X^1$ is N, $X^2$ is C, and $X^3$ is C.

Embodiment 2(g) of this disclosure relates to Embodiment 2, wherein:

$A^1$ is $R^7$, $A^2$ is $R^6$, $A^3$ is $R^5$, $A^4$ is -L-$R^1$, $X^1$ is N, $X^2$ is C, and $X^3$ is C.

Embodiment 2(h) of this disclosure relates to Embodiment 2, 2(a), 2(b), 2(c), 2(d), 2(e), 2(f), or 2(g), wherein L is a bond.

Embodiment 2(i) of this disclosure relates to Embodiment 2, 2(a), 2(b), 2(c), 2(d), 2(e), 2(f), or 2(g), wherein L is a bond, or $—CR^2R^3—$.

Embodiment 2(j) of this disclosure relates to Embodiment 2, 2(a), 2(b), 2(c), 2(d), 2(e), 2(f), or 2(g), wherein L is $—CR^2R^3—$.

Embodiment 2(j) of this disclosure relates to Embodiment 2, 2(a), 2(b), 2(c), 2(d), 2(e), 2(f), or 2(g), wherein L $—(CH_2)_{1-2}—CH{=}CH—(CH_2)_{0-1}—$.

Embodiment 2(k) of this disclosure relates to Embodiment 2, 2(a), 2(b), 2(c), 2(d), 2(e), 2(f), or 2(g), wherein L is —C(O)—.

Embodiment 2(l) of this disclosure relates to Embodiment 2, 2(a), 2(b), 2(c), 2(d), 2(e), 2(f), or 2(g), wherein L is $—S(O)_2—$.

Embodiment 2(m) of this disclosure relates to Embodiment 2, 2(a), 2(b), 2(c), 2(d), 2(e), 2(f), 2(g), 2(h), 2(i), 2(j), 2(k), or 2(l), wherein $R^1$ is phenyl or a 5-6 membered heteroaryl, wherein $R^1$ is optionally substituted with 1 $G^1$ group and 1-3 $G^2$ groups.

Embodiment 2(o) of this disclosure relates to Embodiment 2, 2(a), 2(b), 2(c), 2(d), 2(e), 2(f), 2(g), 2(h), 2(i), 2(j), 2(k), or 2(l), wherein $R^1$ is phenyl optionally substituted with 1 G group and 1-3 $G^2$ groups.

Embodiment 2(p) of this disclosure relates to Embodiment 2, 2(a), 2(b), 2(c), 2(d), 2(e), 2(f), 2(g), 2(h), 2(i), 2(j), 2(k), or 2(l), wherein $R^1$ is a 5-6 membered heteroaryl, optionally substituted with 1 $G^1$ group and 1-3 $G^2$ groups.

Embodiment 2(q) of this disclosure relates to Embodiment 2, 2(a), 2(b), 2(c), 2(d), 2(e), 2(f), 2(g), 2(h), 2(i), 2(j), 2(k), or 2(l), wherein $R^1$ is $C_3$-$C_6$cycloalkyl or $C_5$-$C_6$cycloalkenyl, wherein $R^1$ is optionally substituted with 1 $G^1$ group and 1-3 $G^2$ groups.

Embodiment 2(r) of this disclosure relates to Embodiment 2, 2(a), 2(b), 2(c), 2(d), 2(e), 2(f), 2(g), 2(h), 2(i), 2(j), 2(k), or 2(l), wherein $R^1$ is 4-9 membered heterocycloalkyl, or 5-6 membered heterocycloalkenyl, wherein $R^1$ is optionally substituted with 1 $G^1$ group and 1-3 $G^2$ groups.

Embodiment 2(s) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q) or 2(r), wherein $R^5$ is attached to carbon and is 4-6 membered cycloalkyl, cyclohexenyl, phenyl, 5-6 membered heteroaryl, 5-6-membered heterocycloalkyl,

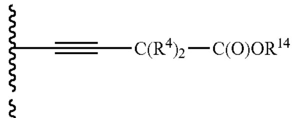

, or

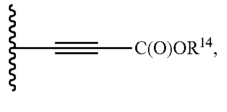

wherein the 4-6 membered cycloalkyl, cyclohexenyl, phenyl, 5-6-membered heteroaryl, or 5-6-membered heterocycloalkyl are each optionally substituted with one -$L^2$-$J^1$ group and 0-4 $J^2$ groups, provided that $J^1$ is directly bonded to a carbon atom.

Embodiment 2(t) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q) or 2(r), wherein or $R^5$ is attached to nitrogen and is 4-6 membered cycloalkyl, cyclohexenyl, phenyl, or 5-6 membered heteroaryl, wherein the 4-6 membered cycloalkyl, cyclohexenyl, phenyl, or 5-6- membered heteroaryl are each optionally substituted with 1-$L^2$-$J^1$ group and 1-4 $J^2$ groups, provided that $J^1$ is directly bonded to a carbon atom.

Embodiment 2(u) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q), 2(r), 2(s) or 2(t), wherein $J^1$ is —C(O)OH or —C(O)O—$C_1$-$C_5$alkyl.

Embodiment 2(v) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q), 2(r), 2(s) or 2(t), wherein $J^1$ is —C(O)OH.

Embodiment 2(w) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q), 2(r), 2(s) or 2(t), wherein $J^1$ is —C(O)O—$C_1$-$C_5$alkyl or —$CH_2$—C(O)O—$C_1$-$C_5$alkyl.

Embodiment 2(x) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q), 2(r), 2(s) or 2(t), wherein $J^1$ is —C(O)N($R^{10}$)$_2$, —C(O)N(H)—CN or —C(O)N(H)OH.

Embodiment 2(y) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q), 2(r), 2(s) or 2(t), wherein $J^1$ is —C(O)N(H)—$SO_2$—$C_1$-$C_5$alkyl, —N(H)—$SO_2$—$C_1$-$C_5$alkyl, $C_1$-$C_5$alkylsulfonyl or —S(O)$_2$—N($R^{10}$)$_2$.

Embodiment 2(z) of this disclosure relates to Embodiment 2, 2(a), 2(b), 2(c), 2(d), 2(e), 2(f), 2(g), 2(h), 2(i), 2(j), 2(k), 2(l), 2(m), 2(n), 2(o), 2(p), 2(q), 2(r), 2(s) or 2(t), wherein $J^1$ is tetrazolyl.

Embodiment 3 of this disclosure relates to a compound according to Embodiment 1 or 2 having Formula II(a), II(b) or II(c)

II(a)

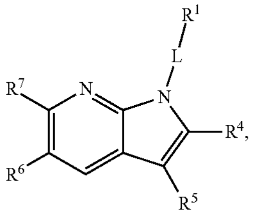

II(b)

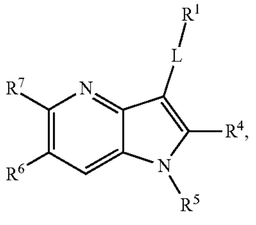

II(c)

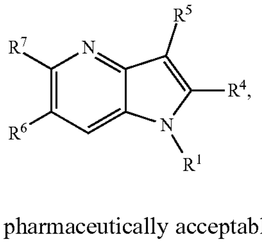

or a pharmaceutically acceptable salt, a solvate, a tautomer, a stereoisomer, or a deuterated analog thereof.

Subembodiments of Embodiment 3

Embodiment 3(a1) of this disclosure relates to Embodiment 3 having Formula II(a) or II(b).

Embodiment 3(a) of this disclosure relates to Embodiment 3 having Formula II(a).

Embodiment 3(b) of this disclosure relates to Embodiment 3 having Formula II(b).

Embodiment 3(c) of this disclosure relates to Embodiment 3 having Formula II(c).

Embodiment 3(d) of this disclosure relates to Embodiment 3, 3(a1), 3(a), 3(b), or 3(c), wherein L is a bond.

Embodiment 3(e) of this disclosure relates to Embodiment 3, 3(a1), 3(a), 3(b), or 3(c), wherein L is a bond, or —$CR^2R^3$—.

Embodiment 3(f) of this disclosure relates to Embodiment 3, 3(a1), 3(a), 3(b), or 3(c), wherein L is —$CR^2R^3$—.

Embodiment 3(g) of this disclosure relates to Embodiment 3, 3(a1), 3(a), 3(b), 3(c), 3(d), 3(e), or 3(f), wherein $R^1$ is phenyl or a 5-6 membered heteroaryl, wherein $R^1$ is optionally substituted with 1 $G^1$ group and 1-3 $G^2$ groups.

Embodiment 3(h) of this disclosure relates to Embodiment 3, 3(a1), 3(a), 3(b), 3(c), 3(d), 3(e), or 3(f), wherein $R^1$ is phenyl optionally substituted with 1 $G^1$ group and 1-3 $G^2$ groups.

Embodiment 3(i) of this disclosure relates to Embodiment 3, 3(a1), 3(a), 3(b), 3(c), 3(d), 3(e), or 3(f), wherein $R^1$ is a 5-6 membered heteroaryl, optionally substituted with 1 $G^1$ group and 1-3 $G^2$ groups.

Embodiment 3(j) of this disclosure relates to Embodiment 3, 3(a1), 3(a), 3(b), 3(c), 3(d), 3(e), or 3(f), wherein $R^1$ is $C_3$-$C_6$cycloalkyl or $C_5$-$C_6$cycloalkenyl, wherein $R^1$ is optionally substituted with 1 $G^1$ group and 1-3 $G^2$ groups.

Embodiment 3(k) of this disclosure relates to Embodiment 3, 3(a1), 3(a), 3(b), 3(c), 3(d), 3(e), or 3(f), wherein $R^1$ is 4-9 membered heterocycloalkyl, or 5-6 membered heterocycloalkenyl, wherein $R^1$ is optionally substituted with 1 $G^1$ group and 1-3 $G^2$ groups.

Embodiment 3(l) of this disclosure relates to Embodiment 3, 3(a1), 3(a), 3(b), 3(c), 3(d), 3(e), 3(f), 3(g), 3(h), 3(i), 3(j), or 3(k), wherein $R^5$ is attached to carbon and is 4-6 membered cycloalkyl, cyclohexenyl, phenyl, 5-6 membered heteroaryl, 5-6-membered heterocycloalkyl,

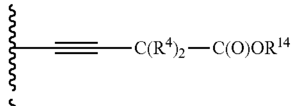

, or

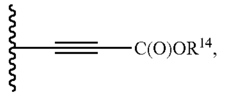

wherein the 4-6 membered cycloalkyl, cyclohexenyl, phenyl, 5-6-membered heteroaryl, or 5-6-membered heterocycloalkyl are each optionally substituted with one -$L^2$-$J^1$ group and 0-4 $J^2$ groups, provided that $J^1$ is directly bonded to a carbon atom.

Embodiment 3(m) of this disclosure relates to Embodiment 3, 3(a1), 3(a), 3(b), 3(c), 3(d), 3(e), 3(f), 3(g), 3(h), 3(i), 3(j), or 3(k), wherein or $R^5$ is attached to nitrogen and is 4-6 membered cycloalkyl, cyclohexenyl, phenyl, or 5-6 membered heteroaryl, wherein the 4-6 membered cycloalkyl, cyclohexenyl, phenyl, or 5-6-membered heteroaryl are each optionally substituted with 1-$L^2$-$J^1$ group and 1-4 $J^2$ groups, provided that $J^1$ is directly bonded to a carbon atom.

Embodiment 3(n) of this disclosure relates to 3, 3(a1), 3(a), 3(b), 3(c), 3(d), 3(e), 3(f), 3(g), 3(h), 3(i), 3(j), 3(k), 3(l), or 3(m), wherein $J^1$ is —C(O)OH or —C(O)O—$C_1$-$C_5$alkyl.

Embodiment 3(o) of this disclosure relates to Embodiment 3, 3(a1), 3(a), 3(b), 3(c), 3(d), 3(e), 3(f), 3(g), 3(h), 3(i), 3(j), 3(k), 3(l), or 3(m), wherein $J^1$ is —C(O)OH.

Embodiment 3(p) of this disclosure relates to Embodiment 3, 3(a1), 3(a), 3(b), 3(c), 3(d), 3(e), 3(f), 3(g), 3(h), 3(i), 3(j), 3(k), 3(l), or 3(m), wherein $J^1$ is —C(O)O—$C_1$-$C_5$alkyl or —$CH_2$—C(O)O—$C_1$-$C_5$alkyl.

Embodiment 3(q) of this disclosure relates to Embodiment 3, 3(a1), 3(a), 3(b), 3(c), 3(d), 3(e), 3(f), 3(g), 3(h), 3(i), 3(j), 3(k), 3(l), or 3(m), wherein $J^1$ is —C(O)N($R^{10}$)$_2$, —C(O)N(H)—CN or —C(O)N(H)OH.

Embodiment 3(r) of this disclosure relates to Embodiment 3, 3(a1), 3(a), 3(b), 3(c), 3(d), 3(e), 3(f), 3(g), 3(h), 3(i), 3(j), 3(k), 3(l), or 3(m), wherein $J^1$ is —C(O)N(H)—$SO_2$—$C_1$-$C_5$alkyl, —N(H)—$SO_2$—$C_1$-$C_5$alkyl, $C_1$-$C_5$alkylsulfonyl or —$S(O)_2$—N($R^{10}$)$_2$.

Embodiment 3(s) of this disclosure relates to Embodiment 3, 3(a1), 3(a), 3(b), 3(c), 3(d), 3(e), 3(f), 3(g), 3(h), 3(i), 3(j), 3(k), 3(l), or 3(m), wherein $J^1$ is tetrazolyl.

Embodiment 4 of this disclosure relates to a compound according to anyone of Embodiments 1-3, including any subembodiments thereof, having any one of Formulae III (a)-III(f):

III(a)

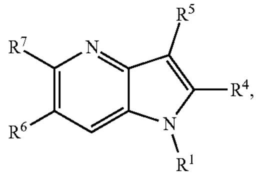

III(b)

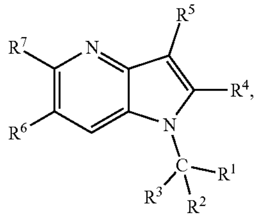

III(c)

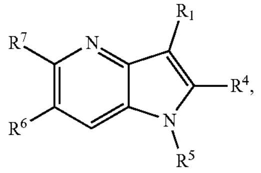

III(d)

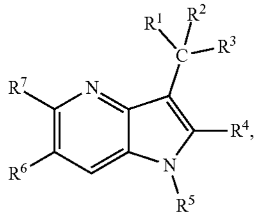

III(e)

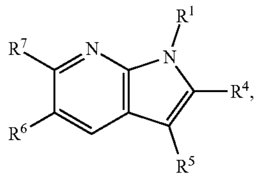

-continued

III(f)

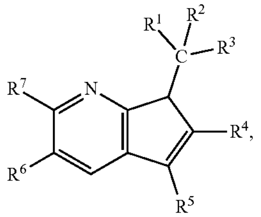

or a pharmaceutically acceptable salt, a solvate, a tautomer, a stereoisomer, or a deuterated analog thereof.

Subembodiments of Embodiment 4

Embodiment 4(a1) of this disclosure relates to Embodiment 4 having any one of formulae III(a), III(c), III(d), III(e) or III(f).

Embodiment 4(a2) of this disclosure relates to Embodiment 4 having anyone of formulae III(a), III(c) or III(d).

Embodiment 4(a) of this disclosure relates to Embodiment 4 having any one of formulae III(a), III(b), III(c) or III(d).

Embodiment 4(b) of this disclosure relates to Embodiment 4 having any one of formulae III(e) or III(f).

Embodiment 4(c) of this disclosure relates to Embodiment 4 having formula III(a).

Embodiment 4(d) of this disclosure relates to Embodiment 4 having formula III(b).

Embodiment 4(e) of this disclosure relates to Embodiment 4 having formula III(c).

Embodiment 4(f) of this disclosure relates to Embodiment 4 having formula III(d).

Embodiment 4(g) of this disclosure relates to Embodiment 4 having formula III(e).

Embodiment 4(h) of this disclosure relates to Embodiment 4 having formula III(f).

Embodiment 4(i) of this disclosure relates to Embodiment 4, 4(a1), 4(a2), 4(a), 4(b), 4(c), 4(d), 4(e), 4(f), 4(g), or 4(h) wherein $R^1$ is phenyl or a 5-6 membered heteroaryl, wherein $R^1$ is optionally substituted with 1 $G^1$ group and 1-3 $G^2$ groups.

Embodiment 4(j) of this disclosure relates to Embodiment 4, 4(a1), 4(a2), 4(a), 4(b), 4(c), 4(d), 4(e), 4(f), 4(g), or 4(h), wherein $R^1$ is phenyl optionally substituted with 1 $G^1$ group and 1-3 $G^2$ groups.

Embodiment 4(k) of this disclosure relates to Embodiment 4, 4(a1), 4(a2), 4(a), 4(b), 4(c), 4(d), 4(e), 4(f), 4(g), or 4(h), wherein $R^1$ is a 5-6 membered heteroaryl, optionally substituted with 1 $G^1$ group and 1-3 $G^2$ groups.

Embodiment 4(l) of this disclosure relates to Embodiment 4, 4(a1), 4(a2), 4(a), 4(b), 4(c), 4(d), 4(e), 4(f), 4(g), or 4(h), wherein $R^1$ is $C_3$-$C_6$cycloalkyl or $C_5$-$C_6$cycloalkenyl, wherein $R^1$ is optionally substituted with 1 $G^1$ group and 1-3 $G^2$ groups.

Embodiment 4(m) of this disclosure relates to Embodiment 4, 4(a1), 4(a2), 4(a), 4(b), 4(c), 4(d), 4(e), 4(f), 4(g), or 4(h), wherein $R^1$ is 4-9 membered heterocycloalkyl, or 5-6 membered heterocycloalkenyl, wherein $R^1$ is optionally substituted with 1 $G^1$ group and 1-3 $G^2$ groups.

Embodiment 4(n) of this disclosure relates to Embodiment 4, 4(a1), 4(a2), 4(a), 4(b), 4(c), 4(d), 4(e), 4(f), 4(g), 4(h), 4(i), 4(j), 4(k), 4(l), or 4(m), wherein $R^5$ is attached to carbon and is 4-6 membered cycloalkyl, cyclohexenyl, phenyl, 5-6 membered heteroaryl, 5-6-membered heterocycloalkyl,

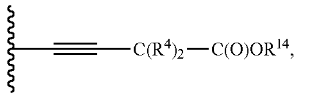
or

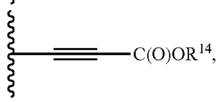

wherein the 4-6 membered cycloalkyl, cyclohexenyl, phenyl, 5-6-membered heteroaryl, or 5-6-membered heterocycloalkyl are each optionally substituted with one -$L^2$-$J^1$ group and 0-4 $J^2$ groups, provided that $J^1$ is directly bonded to a carbon atom.

Embodiment 4(o) of this disclosure relates to Embodiment 4, 4(a1), 4(a2), 4(a), 4(b), 4(c), 4(d), 4(e), 4(f), 4(g), 4(h), 4(i), 4(j), 4(k), 4(l), or 4(m), wherein or $R^5$ is attached to nitrogen and is 4-6 membered cycloalkyl, cyclohexenyl, phenyl, or 5-6 membered heteroaryl, wherein the 4-6 membered cycloalkyl, cyclohexenyl, phenyl, or 5-6-membered heteroaryl are each optionally substituted with 1-$L^2$ $J^1$ group and 1-4 $J^2$ groups, provided that $J^1$ is directly bonded to a carbon atom.

Embodiment 4(p) of this disclosure relates to Embodiment 4, 4(a1), 4(a2), 4(a), 4(b), 4(c), 4(d), 4(e), 4(f), 4(g), 4(h), 4(i), 4(j), 4(k), 4(l), 4(m), 4(n), or 4(o), wherein $J^1$ is —C(O)OH or —C(O)O—$C_1$-$C_5$alkyl.

Embodiment 4(q) of this disclosure relates to Embodiment 4, 4(a1), 4(a2), 4(a), 4(b), 4(c), 4(d), 4(e), 4(f), 4(g), 4(h), 4(i), 4(j), 4(k), 4(l), 4(m), 4(n), or 4(o), wherein $J^1$ is —C(O)OH.

Embodiment 4(r) of this disclosure relates to Embodiment 4, 4(a1), 4(a), 4(b), 4(c), 4(d), 4(e), 4(f), 4(g), 4(h), 4(i), 4(j), 4(k), 4(l), 4(m), 4(n), or 4(o), wherein $J^1$ is —C(O)O—$C_1$-$C_5$alkyl or —$CH_2$—C(O)O—$C_1$-$C_5$alkyl.

Embodiment 4(s) of this disclosure relates to Embodiment 4, 4(a1), 4(a2), 4(a), 4(b), 4(c), 4(d), 4(e), 4(f), 4(g), 4(h), 4(i), 4(j), 4(k), 4(l), 4(m), 4(n), or 4(o), wherein $J^1$ is —C(O)N($R^{10}$)$_2$, —C(O)N(H)—CN or —C(O)N(H)OH.

Embodiment 4(t) of this disclosure relates to Embodiment 4, 4(a1), 4(a2), 4(a), 4(b), 4(c), 4(d), 4(e), 4(f), 4(g), 4(h), 4(i), 4(j), 4(k), 4(l), 4(m), 4(n), or 4(o), wherein $J^1$ is —C(O)N(H)—$SO_2$—$C_1$-$C_5$alkyl, —N(H)—$SO_2$—$C_1$-$C_5$alkyl, $C_1$-$C_5$alkylsulfonyl or —S(O)$_2$—N($R^{10}$)$_2$.

Embodiment 4(u) of this disclosure relates to Embodiment 4, 4(a1), 4(a2), 4(a), 4(b), 4(c), 4(d), 4(e), 4(f), 4(g), 4(h), 4(i), 4(j), 4(k), 4(l), 4(m), 4(n), or 4(o), wherein $J^1$ is tetrazolyl.

Embodiment 5 of this disclosure relates to a compound according to any one of Embodiments 1-4, including any subembodiments thereof, wherein $R^6$ is:

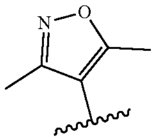
,
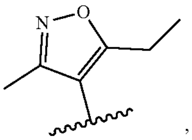
,
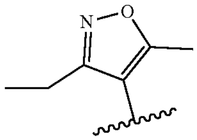
,
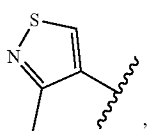
,
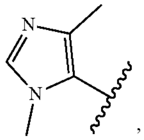
,

-continued

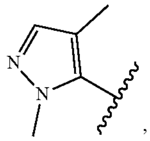
,
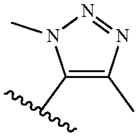
,
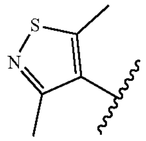
or
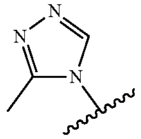
.

Embodiment 6 of this disclosure relates to a compound according to any one of Embodiments 1-5, including any subembodiments thereof, wherein $R^6$ is:

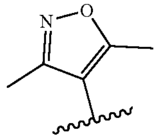
,
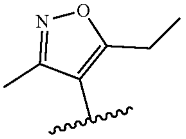
or
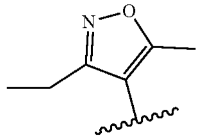
.

Subembodiments of Embodiment 6

Embodiment 6(a) of this disclosure relates to Embodiment 6, wherein $R^6$ is:

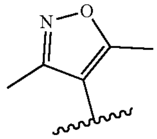
.

Embodiment 6(b) of this disclosure relates to Embodiment 6, wherein $R^6$ is:

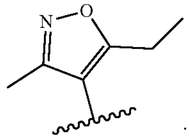 [SMILES: *c1c(C)noc1CC]
.

Embodiment 6(c) of this disclosure relates to Embodiment 6, wherein $R^6$ is:

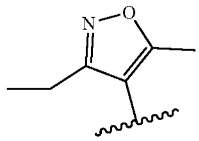
.

Embodiment 7 of this disclosure relates to a compound according to any one of Embodiments 1-6, including any subembodiments thereof, wherein $R^4$ is H, OH, $CF_3$, or $CH_3$.

Subembodiments of Embodiment 7

Embodiment 7(a) of this disclosure relates to Embodiment 7 wherein $R^4$ is H, $CF_3$, or $CH_3$.

Embodiment 7(b) of this disclosure relates to Embodiment 7 wherein $R^4$ is H.

Embodiment 7(c) of this disclosure relates to Embodiment 7 wherein $R^4$ is $CF_3$, or $CH_3$.

Embodiment 7(d) of this disclosure relates to Embodiment 7 wherein $R^4$ is $CH_3$.

Embodiment 8 of this disclosure relates to a compound according to any one of Embodiments 1, 2, 3, 5, 6, or 7, including any subembodiments thereof where applicable, wherein L is a bond, —$CH_2$—, —$(CH_2)_2$—, $CH(CH_3)$—, $CH(CH_2CH_3)$—, —C(O)—, —CH($C_3$-$C_6$cycloalkyl)-, —CH(pyridyl)-, —C($CH_3$)(pyridyl)-, —$S(O)_2$—, or —C(H)($CH_2$CN)—.

The term "where applicable" as used in the Embodiments and Subembodiments of this disclosure is meant to exclude inapplicable instances where a previous subembodiment is narrower in scope than the later embodiment. For example, Embodiment 8 is broader in scope than embodiments 2(h)-2(l), so Embodiment 8 cannot be applied to Subembodiments 2(h)-2(l). This interpretation of the Embodiment and Subembodiments in this disclosure applies to all instances whether or not the term "where applicable" is used.

Subembodiments of Embodiment 8

Embodiment 8(a) of this disclosure relates to Embodiment 8 wherein Lisa bond.

Embodiment 8(b) of this disclosure relates to Embodiment 8 wherein L is —$CH_2$—, —$(CH_2)_2$—, $CH(CH_3)$—, or $CH(CH_2CH_3)$—.

Embodiment 8(c) of this disclosure relates to Embodiment 8 wherein L is —C(O)— or —$S(O)_2$—.

Embodiment 8(d) of this disclosure relates to Embodiment 8 wherein L is —CH($C_3$-$C_6$cycloalkyl)-.

Embodiment 8(e) of this disclosure relates to Embodiment 8 wherein L is —CH(pyridyl)-or —C($CH_3$)(pyridyl)-.

Embodiment 8(f) of this disclosure relates to Embodiment 8 wherein L is —C(H)($CH_2$CN)—.

Embodiment 9 of this disclosure relates to a compound according to any one of Embodiments 1-8, including any subembodiments thereof where applicable, wherein $R^1$ is phenyl, pyridyl, pyrimidinyl, pyridazinyl, pyrazolyl, $C_3$-$C_6$ cycloalkyl, cyclohexenyl, morpholinyl, piperazinyl, piperidinyl, pyrrolidinyl, tetrahydro-2H-furanyl, oxetanyl, azetidine, tetrahydro-2H-pyranyl, tetrahydro-2H-thiopyranyl 1,1-dioxide, tetrahydro-2H-thiopyranyl 1-oxide, tetrahydro-2H-thiopyranyl, tetrahydrothienyl, or thienyl, wherein $R^1$ is optionally substituted with 1 $G^1$ group and 1-3 $G^2$ groups.

Subembodiments of Embodiment 9

Embodiment 9(a) of this disclosure relates to Embodiment 9 wherein $R^1$ is phenyl, pyridyl, or pyrimidinyl, wherein $R^1$ is optionally substituted with 1 $G^1$ group and 1-3 $G^2$ groups.

Embodiment 9(b) of this disclosure relates to Embodiment 9 wherein $R^1$ is $C_3$-$C_6$ cycloalkyl or cyclohexynyl, wherein $R^1$ is optionally substituted with 1 $G^1$ group and 1-3 $G^2$ groups.

Embodiment 9(c) of this disclosure relates to Embodiment 9 wherein $R^1$ is morpholinyl, piperazinyl, piperidinyl, pyrrolidinyl, tetrahydro-2H-furanyl, tetrahydro-2H-pyranyl, tetrahydro-2H-thiopyranyl 1,1-dioxide, tetrahydro-2H-thiopyranyl 1-oxide, tetrahydro-2H-thiopyranyl, or tetrahydrothiophenyl, wherein $R^1$ is optionally substituted with 1 $G^1$ group and 1-3 $G^2$ groups.

Embodiment 9(d) of this disclosure relates to Embodiment 9 wherein $R^1$ is phenyl optionally substituted with 1 $G^1$ group and 1-3 $G^2$ groups.

Embodiment 9(f) of this disclosure relates to Embodiment 9 wherein $R^1$ is pyridyl, optionally substituted with 1 $G^1$ group and 1-3 $G^2$ groups.

Embodiment 9(g) of this disclosure relates to Embodiment 9 wherein $R^1$ is pyrimidinyl, optionally substituted with 1 $G^1$ group and 1-3 $G^2$ groups.

Embodiment 9(h) of this disclosure relates to Embodiment 9 wherein $R^1$ is $C_3$-$C_6$ cycloalkyl optionally substituted with 1 $G^1$ group and 1-3 $G^2$ groups.

Embodiment 9(j) of this disclosure relates to Embodiment 9 wherein $R^1$ is morpholinyl optionally substituted with 1 $G^1$ group and 1-3 $G^2$ groups.

Embodiment 9(k) of this disclosure relates to Embodiment 9 wherein $R^1$ is piperazinyl optionally substituted with 1 $G^1$ group and 1-3 $G^2$ groups.

Embodiment 9(l) of this disclosure relates to Embodiment 9 wherein $R^1$ is piperidinyl optionally substituted with 1 $G^1$ group and 1-3 $G^2$ groups.

Embodiment 9(m) of this disclosure relates to Embodiment 9 wherein $R^1$ is pyrrolidinyl optionally substituted with 1 $G^1$ group and 1-3 $G^2$ groups.

Embodiment 9(n) of this disclosure relates to Embodiment 9 wherein $R^1$ is tetrahydro-2H-furanyl optionally substituted with 1 $G^1$ group and 1-3 $G^2$ groups.

Embodiment 9(o) of this disclosure relates to Embodiment 9 wherein $R^1$ is tetrahydro-2H-pyranyl optionally substituted with 1 $G^1$ group and 1-3 $G^2$ groups.

Embodiment 9(p) of this disclosure relates to Embodiment 9 wherein $R^1$ is tetrahydro-2H-thiopyranyl optionally substituted with 1 $G^1$ group and 1-3 $G^2$ groups.

Embodiment 10 of this disclosure relates to a compound according to any one of Embodiments 1-9, including any subembodiments thereof where applicable, wherein:

$R^1$ is one of (a), (b), (c), (d), (e), (f), (g), (h), (i), (j), (k), (l), or (m):

(a) $C_3$-$C_6$ cycloalkyl optionally substituted with 1-3 $G^2$ groups, wherein $G^2$ is F, cyano, or —$CH_2$CN;

(b) phenyl optionally substituted with 1 $G^1$ group and 1-3 $G^2$ groups, wherein $G^1$ is benzyloxy, —C(=$CH_2$)$CH_3$, —C(O)OH, —C(O)$NH_2$, —C(O)N(H)-cyclopropyl, cyclopropyl, cyano, or —$SO_2CH_3$; and each $G^2$ is independently —$OCHF_2$, Cl, F, —$OCH_3$, —$OCF_3$, $CH_3$, $CF_3$, and —C$(CH_3)_2$—OH;

(c) pyridyl optionally substituted with 1 $G^1$ group and 1-2 $G^2$ groups, wherein $G^1$ is —C(O)OH, —C(O)$NH_2$, cyclopropyl, or cyclopropylalkynylene; and each $G^2$ is independently F, CN, $OCH_3$, $CF_3$, $CH_3$, OH, —CH$(CH_3)_2$, and Cl;

(d) pyrazolyl optionally substituted with 1 $G^1$ group and 1-2 $G^2$ groups, provided that L is a bond when $R^1$ is pyrazolyl, wherein $G^1$, which can substitute a hydrogen atom of —NH— or =CH—, is —$CH_2$—$SO_2$—$CH_3$, —$(CH_2)_2$—N$(CH_3)_2$, cyclopropyl, —$CH_2$-cyclopropyl, —$(CH_2)_2$—CN, or —$CH_2$C(O)N$(CH_3)_2$; and each $G^2$, which can substitute a hydrogen atom of —NH— or =CH—, is independently $C_1$-$C_6$alkyl, $C_1$-$C_6$haloalkyl, and hydroxy$C_1$-$C_6$alkyl;

(e) pyrimidinyl optionally substituted with —$NH_2$, —N$(CH_3)_2$, $OCH_3$, n-azetdinyl or cyclopropyl;

(f) pyridazinyl;

(g) tetrahydro-2H-pyranyl optionally substituted with 1-2 groups each independently $C_1$-$C_6$alkyl, $C_1$-$C_6$haloalkyl, hydroxy$C_1$-$C_6$alkyl, Cl and F;

(h) tetrahydro-2H-furanyl optionally substituted with 1-2 groups each independently $C_1$-$C_6$alkyl, $C_1$-$C_6$haloalkyl, hydroxy$C_1$-$C_6$alkyl, Cl and F;

(i) morpholinyl optionally substituted with 1-2 groups each independently $C_1$-$C_6$alkyl, $C_1$-$C_6$haloalkyl, and hydroxy$C_1$-$C_6$alkyl;

(j) oxetanyl;

(k) piperidinyl optionally substituted with 1-2 groups each independently $C_1$-$C_6$alkyl, $C_1$-$C_6$haloalkyl, and hydroxy$C_1$-$C_6$alkyl;

(l) cyclohexenyl optionally substituted with 1-2 groups each independently $C_1$-$C_6$alkyl, $C_1$-$C_6$haloalkyl, hydroxy$C_1$-$C_6$alkyl, Cl and F; or (m) thienyl.

Subembodiments of Embodiment 10

Embodiment 11 of this disclosure relates to a compound according to anyone of Embodiments 1-7, including any subembodiments thereof where applicable, wherein -L-$R^1$ is:

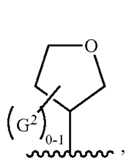 , 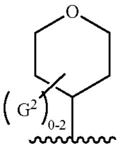 , 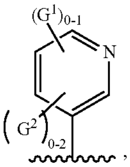 ,

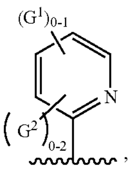 , 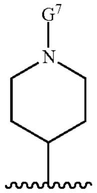 , 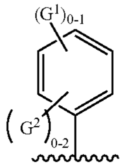 ,

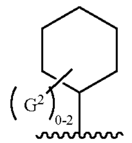 , 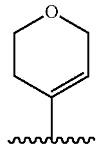 , 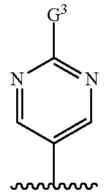 ,

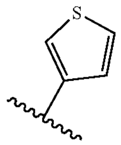 , 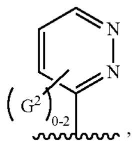 , 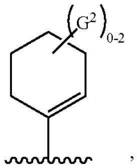 ,

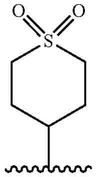 , 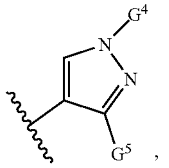 , 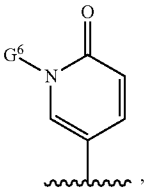 ,

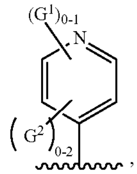 , 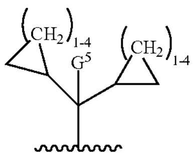 ,

-continued

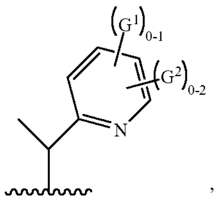 , 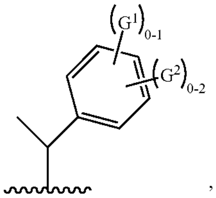 ,

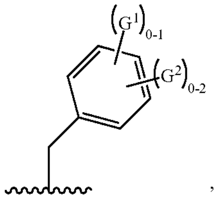 , 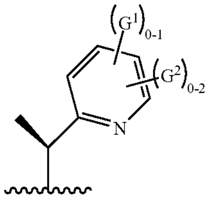 ,

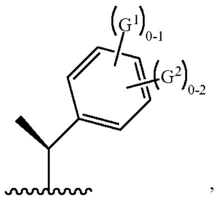 , 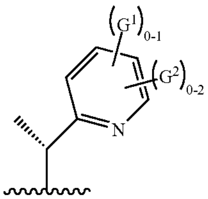 ,

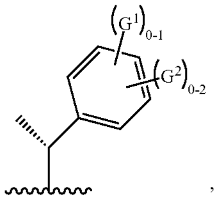 , 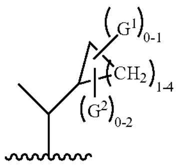 ,

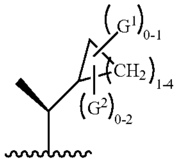 , 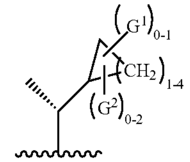 ,

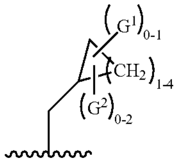 , 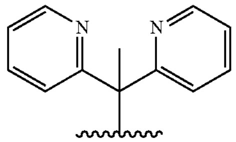 ,

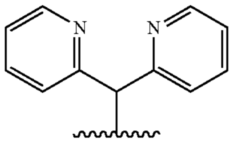 , 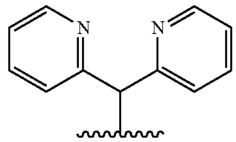 ,

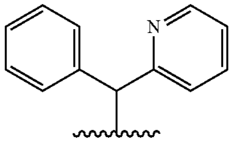 , 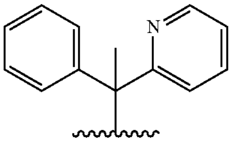 ,

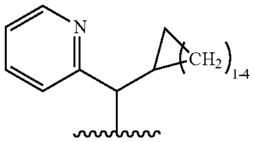 , 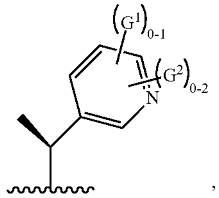 ,

-continued

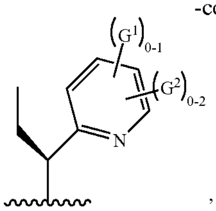

,

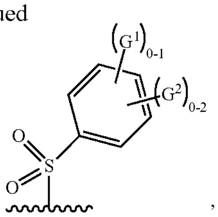

,

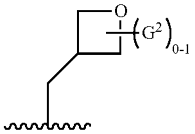

,

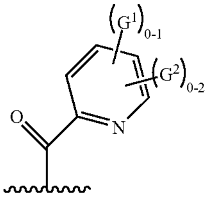

,

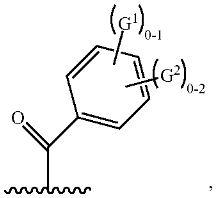

,

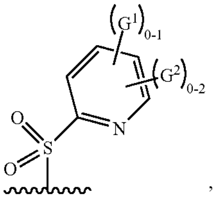

,

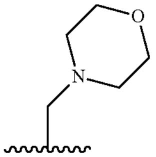

,

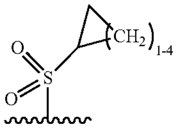

,

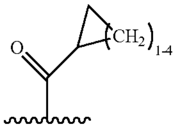

,

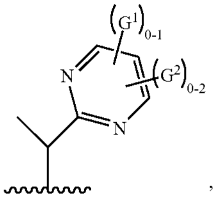

,

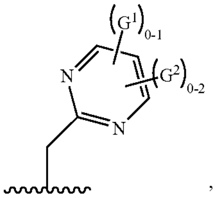

,

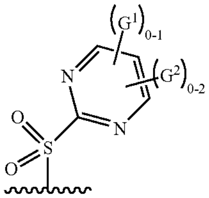

,

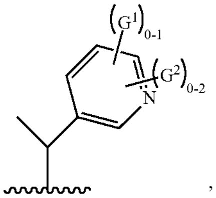

,

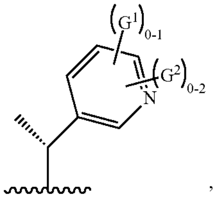

,

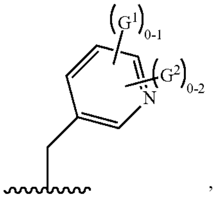

, or

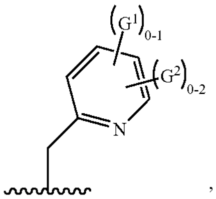

, wherein:

$G^3$ is H, $OCH_3$, N-azetidinyl, $NH_2$, $—N(CH_3)_2$, cyclopropyl;

$G^4$ is H, $CH_3$, $—CH_2CH_3$, $—(CH_2)N(CH_3)_2$, $—CH_2—SO_2—CH_3$, $—CH(CH_3)_2$, $—CH_2C(CH_3)_2(OH)$, cyclopropyl, $—CH_2$-cyclopropyl, $—(CH_2)_2—CN$, or $—CH_2C(O)N(CH_3)_2$;

$G^5$ is H or OH;

$G^6$ is H or $CH_3$; and $G^7$ is H, $CH_3$, $—(CH_2)N(CH_3)_2$, $—SO_2—CH_3$, $—CH_2—SO_2—CH_3$, $—CH(CH_3)_2$, $—CH_2C(CH_3)_2(OH)$, cyclopropyl, $—CH_2$-cyclopropyl, $—(CH_2)_2—CN$, $—CH_2C(O)N(CH_3)_2$, $—C(O)OC(CH_3)_3$, $—C(O)CH_3$, or $—C(O)C(CH_3)_3$.

Subembodiments of Embodiment 11

Embodiment 11(a) of this disclosure relates to Embodiment 11 wherein -L-$R^1$ is:

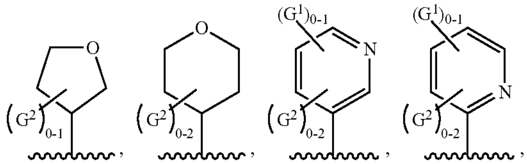

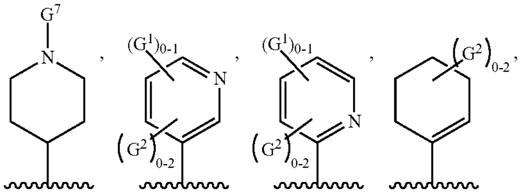

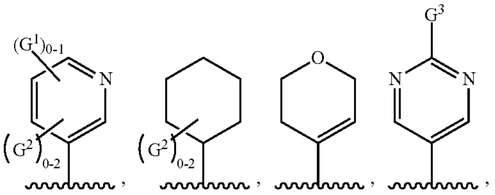

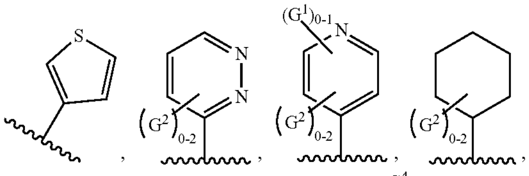

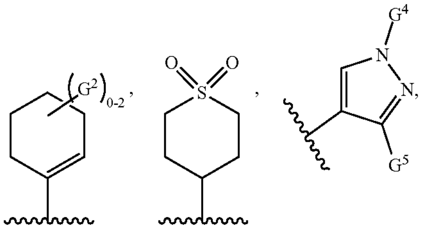

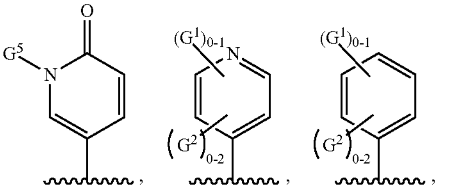

or

-continued

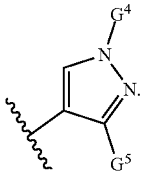

Embodiment 11(b) of this disclosure relates to Embodiment 11 wherein -L-$R^1$ is:

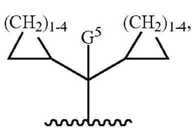

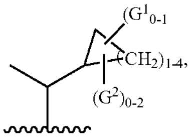

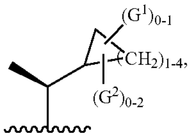

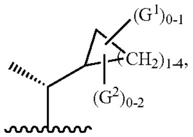

or

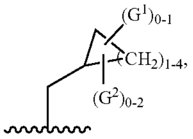

Embodiment 11(c) of this disclosure relates to Embodiment 11 wherein -L-$R^1$ is:

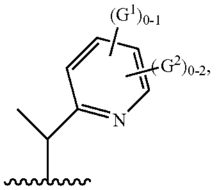

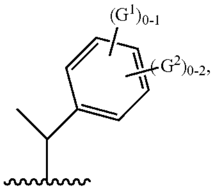

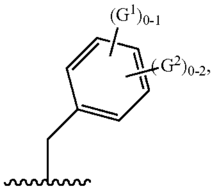

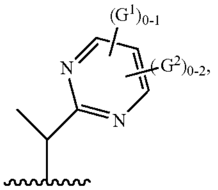

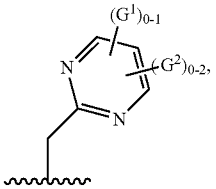

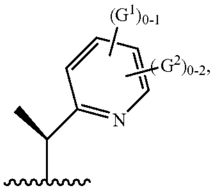

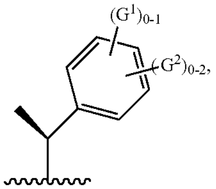

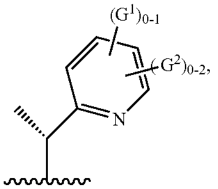

-continued

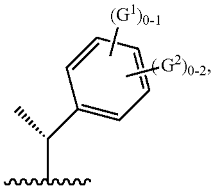

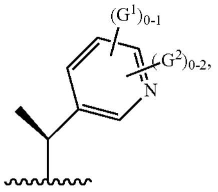

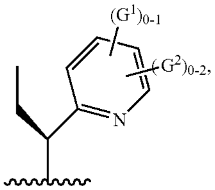

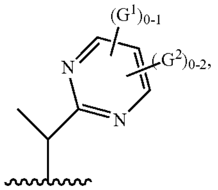

or

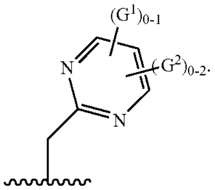

Embodiment 11(d) of this disclosure relates to Embodiment 11, wherein -L-$R^1$ is:

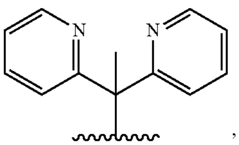

,

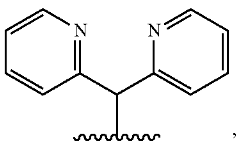

,

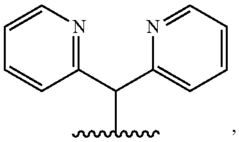

,

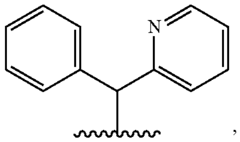

,

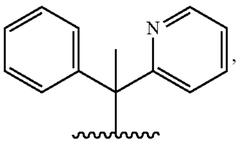

, or

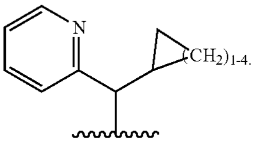

Embodiment 12 of this disclosure relates to a compound according to Embodiment 11, including any subembodiments thereof where applicable, wherein:

$G^1$ is benzyloxy, —C(=$CH_2$)$CH_3$, —C(O)OH, —C(O)$NH_2$, —C(O)N(H)-cyclopropyl, cyclopropyl, —$CH_2$-cyclopropyl, cyclopropylalkynylene, —$CH_2$—$SO_2$—$CH_3$, —$SO_2$—$CH_3$, —($CH_2$)N($CH_3$)$_2$, —($CH_2$)$_2$—N($CH_3$)$_2$, —$CH_2$-cyclopropyl, —($CH_2$)$_2$—CN, —C(O)OC($CH_3$)$_3$, —C(O)$CH_3$, and —C(O)C($CH_3$)$_3$, —$CH_2$C(O)N($CH_3$)$_2$, cyano, or —$SO_2CH_3$; and each $G^2$ is independently —$OCHF_2$, —$OCH_2F$, Cl, F, —$OCH_3$, OH, —$OCF_3$, $CH_3$, —CH($CH_3$)$_2$, $CF_3$, —$CH_2$CN, $CH_2$C($CH_3$)$_2$(OH), and —C($CH_3$)$_2$—OH.

Embodiment 13 of this disclosure relates to a compound according to Embodiment 11, wherein -L-$R^1$ is:

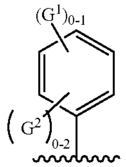,
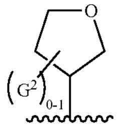,
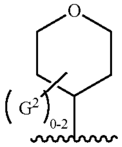,
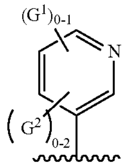,
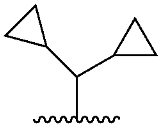,
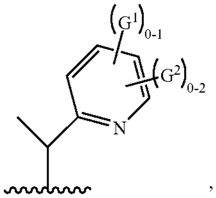,
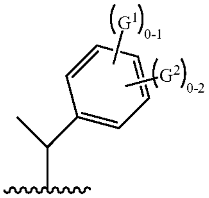,
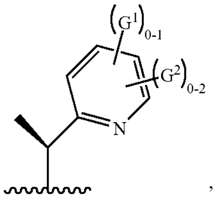,
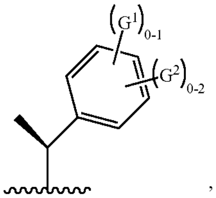,
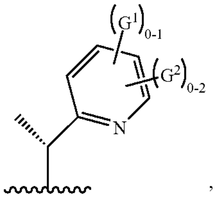,
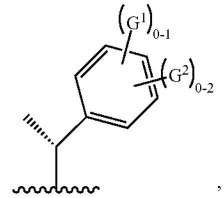,
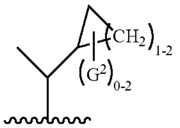,
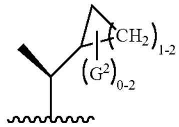,
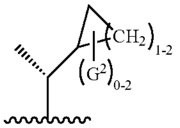,
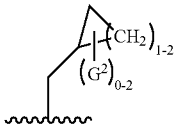,
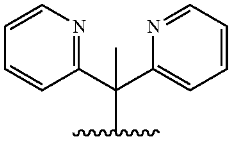,
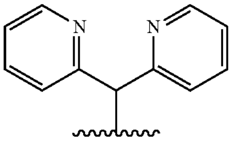,
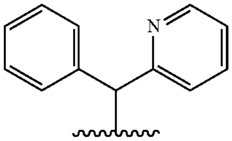,
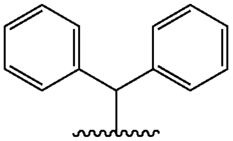,
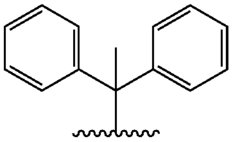
or -continued

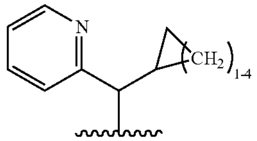
.

Embodiment 14 of this disclosure relates to a compound according to Embodiment 13, wherein $G^1$ is benzyloxy, $-C(=CH_2)CH_3$, $-C(O)OH$, $-C(O)NH_2$, $-C(O)N(H)$-cyclopropyl, cyclopropyl, $-CH_2$-cyclopropyl, cyclopropylalkynylene, $-CH_2-SO_2-CH_3$, $-SO_2-CH_3$, $-(CH_2)N(CH_3)_2$, $-(CH_2)_2-N(CH_3)_2$, $-CH_2-$ cyclopropyl, $-(CH_2)_2-CN$, $-C(O)OC(CH_3)_3$, $-C(O)CH_3$, $-C(O)C(CH_3)_3$, $-CH_2C(O)N(CH_3)_2$, cyano, or $SO_2CH_3$; and each $G^2$ is independently $-OCHF_2$, $-OCH_2F$, Cl, F, $-OCH_3$, OH, $-OCF_3$, $CH_3$, $-CH(CH_3)_2$, $CF_3$, $-CH_2CN$, $CH_2C(CH_3)_2(OH)$, and $-C(CH_3)_2-OH$.

Embodiment 15 of this disclosure relates to a compound according to any one of Embodiments 1-14, including any subembodiments thereof where applicable, wherein $R^5$, when attached to carbon, is:

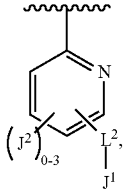
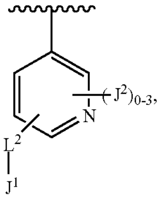
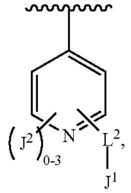
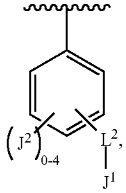
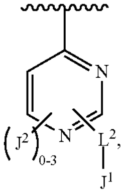
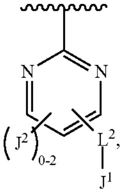
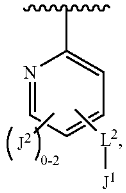
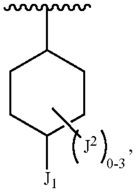
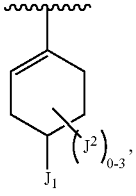
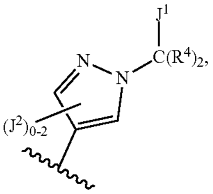
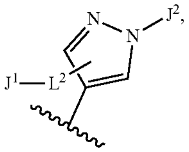
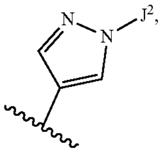
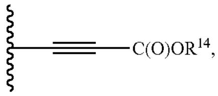

-continued

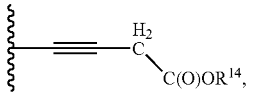

or

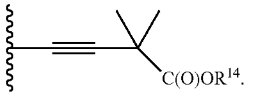

Subembodiments of Embodiment 15

Embodiment 15(a) of this disclosure relates to Embodiment 15, wherein $R^5$ is:

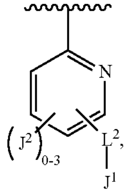

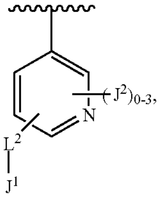

or

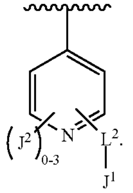

Embodiment 15(b) of this disclosure relates to Embodiment 15, wherein $R^5$ is:

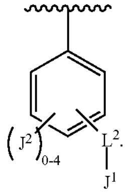

Embodiment 15(c) of this disclosure relates to Embodiment 15, wherein $R^5$ is:

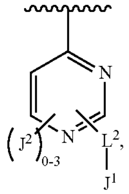

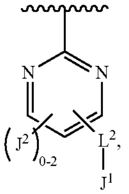

or

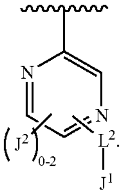

Embodiment 15(d) of this disclosure relates to Embodiment 15, wherein $R^5$ is:

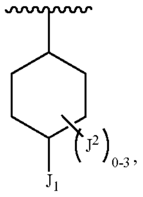

or

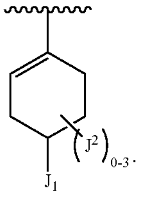

Embodiment 15(d) of this disclosure relates to Embodiment 15, wherein $R^5$ is:

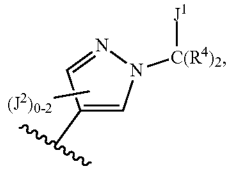

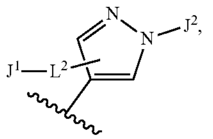

or

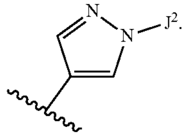

Embodiment 15(e) of this disclosure relates to Embodiment 15, wherein $R^5$ is:

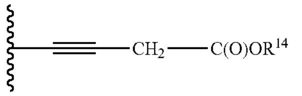

or

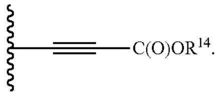

Embodiment 16 of this disclosure relates to a compound according to any one of Embodiments 1-14, including any subembodiments thereof where applicable, wherein $R^5$, is:

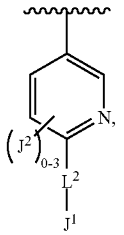

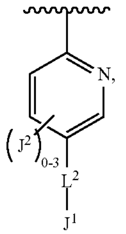

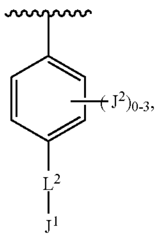

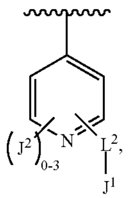

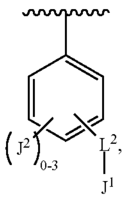

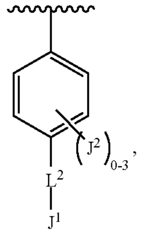

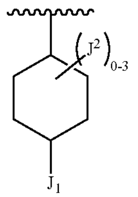

or

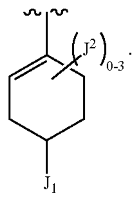

Subembodiments of Embodiment 16

Embodiment 16(a) of this disclosure relates to Embodiment 16, wherein $R^5$ is:

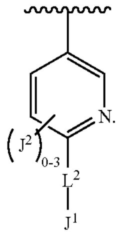

Embodiment 16(b) of this disclosure relates to Embodiment 16, wherein $R^5$ is:

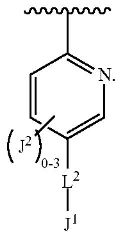

Embodiment 16(c) of this disclosure relates to Embodiment 16, wherein $R^5$ is:

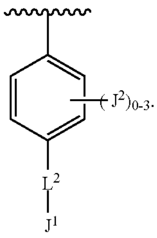

Embodiment 16(d) of this disclosure relates to Embodiment 16, wherein $R^5$ is:

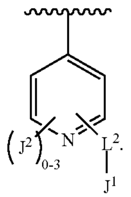

Embodiment 16(e) of this disclosure relates to Embodiment 16, wherein $R^5$ is:

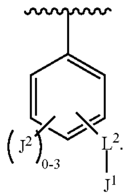

Embodiment 16(f) of this disclosure relates to Embodiment 16, wherein $R^5$ is:

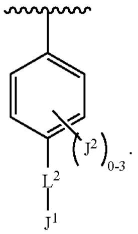

Embodiment 16(g) of this disclosure relates to Embodiment 16, wherein $R^5$ is:

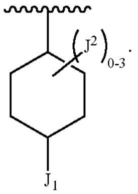

Embodiment 16(h) of this disclosure relates to Embodiment 16, wherein $R^5$ is:

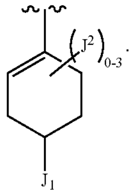

Embodiment 17 of this disclosure relates to a compound according to any one of Embodiments 1-14, including any subembodiments thereof where applicable, wherein $R^5$ is:

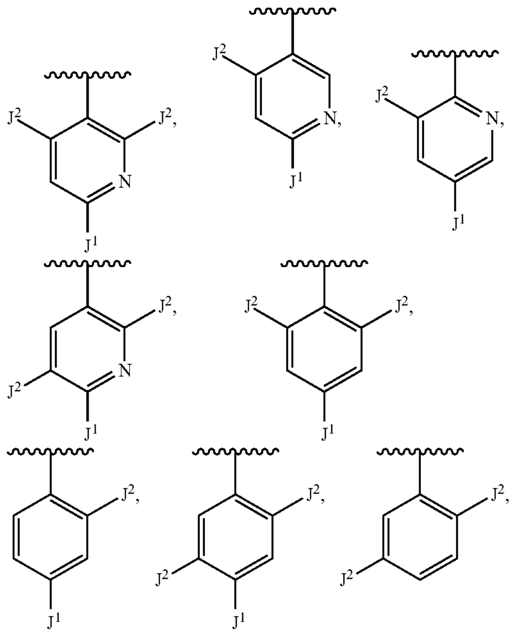

-continued

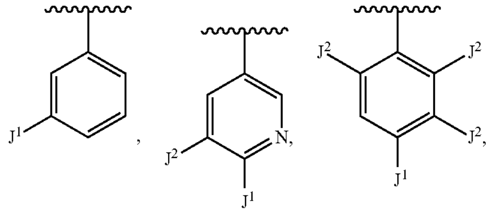

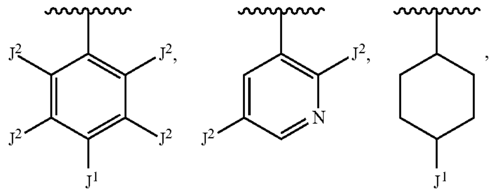

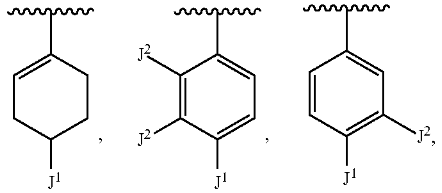

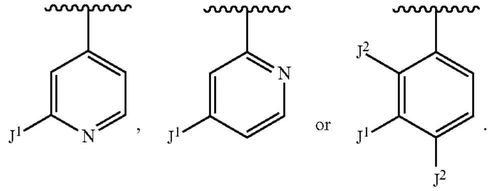

Embodiment 18 of this disclosure relates to a compound according to any one of Embodiments 1-14, including any subembodiments thereof where applicable, wherein $R^5$ is:

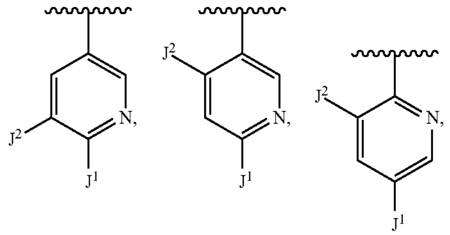

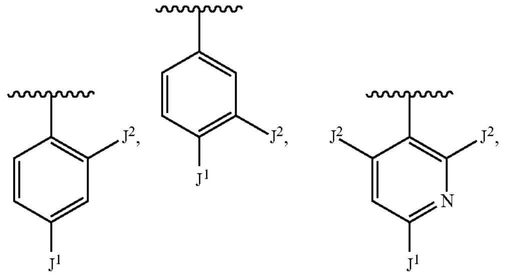

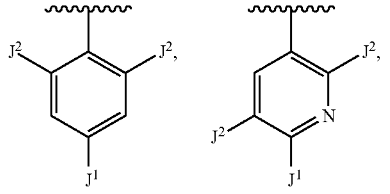

-continued

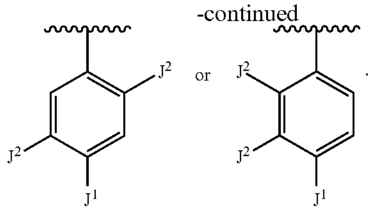

Subembodiments of Embodiment 18

Embodiment 18(a) of this disclosure relates to Embodiment 18, wherein $R^5$ is:

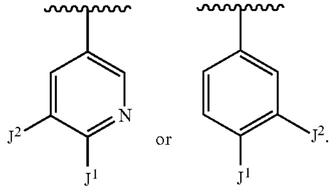

Embodiment 18(b) of this disclosure relates to Embodiment 18 wherein $R^5$ is:

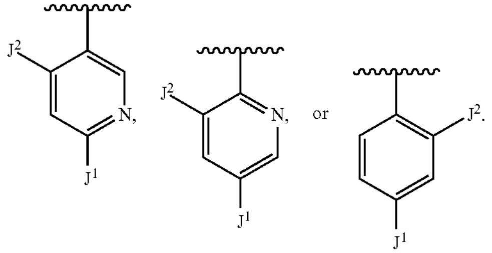

Embodiment 18(c) of this disclosure relates to Embodiment 18, wherein $R^5$ is:

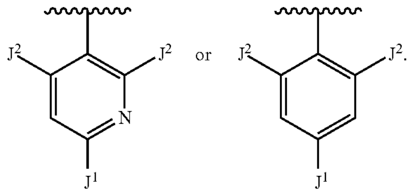

Embodiment 18(d) of this disclosure relates to Embodiment 18, wherein $R^5$ is:

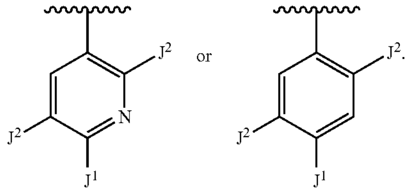

Embodiment 18(e) of this disclosure relates to Embodiment 18, wherein $R^5$ is:

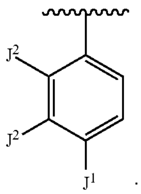

Embodiment 19 of this disclosure relates to a compound according to any one of Embodiments 15-18, including any subembodiments thereof where applicable, wherein $R^5$ is:

$J^1$ is —C(O)OH, —C(O)$OCH_3$, —$CH_2$C(O)OH, —C(O)N(H)$CH_3$, —C(O)$NH_2$, tetrazolyl, —$SO_2CH_3$, —C(O)N(H)CN, C(O)N(H)OH, —$SO_2NH_2$, —$SO_2$NH-cyclopropyl, —C(O)N(H)$SO_2CH_3$; and each $J^2$ is independently —O-cyclobutyl, —$OCH_2$-phenyl, —O-cyclopropyl, —O—$CH_2$-cyclopropyl, cyclopropylethynylene, CN, OH, cyclopropyl, F, Cl, —$OCH_3$, —$OCHF_2$, $OCF_3$, —$OCH_2CF_3$, —$OCH_2CHF_2$, —OCH$(CH_3)_2$, —$CH_2CH_3$, —$OCH_2CH_3$, —$OCH_2CH_2CH_3$, and $CH_3$.

Embodiment 20 of this disclosure relates to a compound according to Embodiment 19, wherein:

$J^1$ is —C(O)OH or —C(O)$OCH_3$; and each $J^2$ is independently F, Cl, —$OCH_3$, —$OCHF_2$, $OCF_3$, —$OCH_2CF_3$, —$OCH_2CHF_2$, —OCH$(CH_3)_2$, —$CH_2CH_3$, —$OCH_2CH_3$, —$OCH_2CH_2CH_3$, and $CH_3$.

Embodiment 21 of this disclosure relates to a compound according to Embodiment 1 having any one of Formulae IV(a)-IV(c):

IV(a)

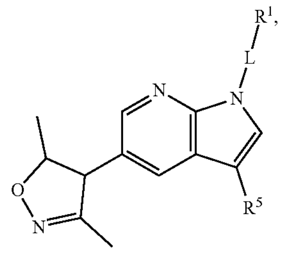

IV(b)

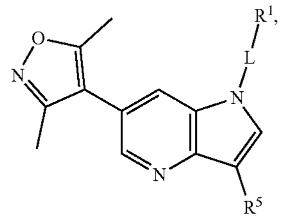

or

IV(c)

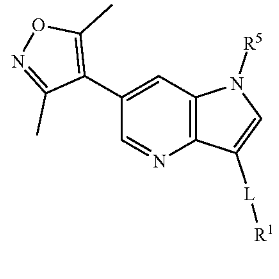

or a pharmaceutically acceptable salt, a solvate, a tautomer, a stereoisomer, or a deuterated analog thereof, wherein:

$R^5$ is:

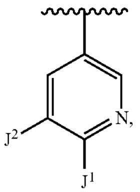 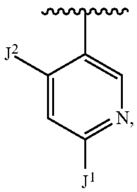 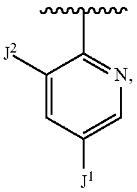

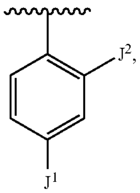 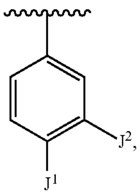 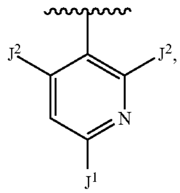

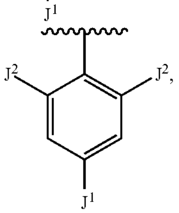 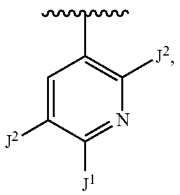

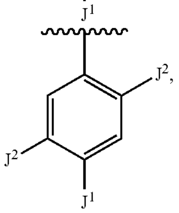 or 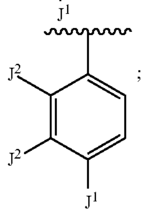 ;

$J^1$ is —C(O)OH or —C(O)$OCH_3$;

each $J^2$ is independently F, Cl, —$OCH_3$, —$OCHF_2$, $OCF_3$, —$OCH_2CF_3$, —$OCH_2CHF_2$, —OCH$(CH_3)_2$, —$CH_2CH_3$, —$OCH_2CH_3$, —$OCH_2CH_2CH_3$, and $CH_3$;

-L-$R^1$ is

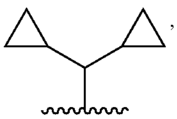 , 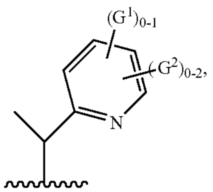

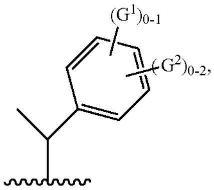 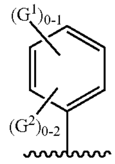 ,

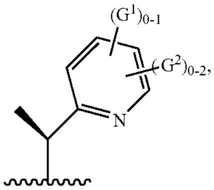 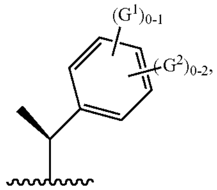

-continued

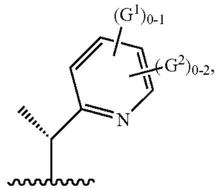

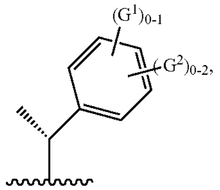

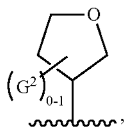

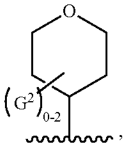

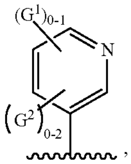

or

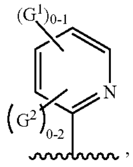

wherein $G^1$ is benzyloxy, $-C(=CH_2)CH_3$, $-C(O)OH$, $-C(O)NH_2$, $-C(O)N(H)$-cyclopropyl, cyclopropyl, $-CH_2$-cyclopropyl, cyclopropylalkynylene, $-CH_2-SO_2-CH_3$, $-SO_2-CH_3$, $-(CH_2)N(CH_3)_2$, $-(CH_2)_2-N(CH_3)_2$, $-CH_2$-cyclopropyl, $-(CH_2)_2-CN$, $-C(O)OC(CH_3)_3$, $-C(O)CH_3$, $-C(O)C(CH_3)_3$, $-CH_2C(O)N(CH_3)_2$, CN, or $-SO_2CH_3$; and each $G^2$ is independently $-OCHF_2$, $-OCH_2F$, Cl, F, $-OCH_3$, OH, $-OCF_3$, $CH_3$, $-CH(CH_3)_2$, $CF_3$, CN, $-CH_2CN$, $CH_2C(CH_3)_2(OH)$, and $-C(CH_3)_2-OH$.

Subembodiments of Embodiment 21

Embodiment 21(a1) of this disclosure relates to Embodiment 21 having Formula IV(a) or Formula IV(c).

Embodiment 21(a) of this disclosure relates to Embodiment 21 having Formula IV(a).

Embodiment 21(b) of this disclosure relates to Embodiment 21 having Formula IV(b).

Embodiment 21(c) of this disclosure relates to Embodiment 21 having Formula IV(c).

Embodiment 21(d) of this disclosure relates to anyone of Embodiments 21, 21(a1), 21(a), 21(b), or 21(c), wherein $R^5$ is:

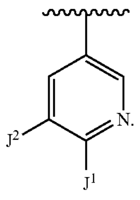

Embodiment 21(e) of this disclosure relates to anyone of Embodiments 21, 21(a1), 21(a), 21(b), or 21(c), wherein $R^5$ is:

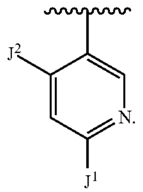

Embodiment 21(f) of this disclosure relates to any one of Embodiments 21, 21(a1), 21(a), 21(b), or 21(c), wherein $R^5$ is:

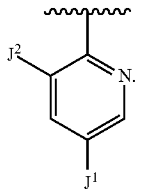

Embodiment 21(g) of this disclosure relates to anyone of Embodiments 21, 21(a1), 21(a), 21(b), or 21(c), wherein $R^5$ is:

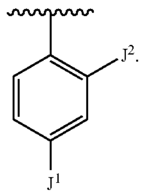

Embodiment 21(g) of this disclosure relates to anyone of Embodiments 21, 21(a1), 21(a), 21(b), or 21(c), wherein $R^5$ is:

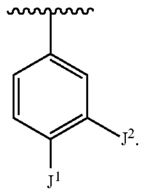

Embodiment 21(h) of this disclosure relates to anyone of Embodiments 21, 21(a1), 21(a), 21(b), or 21(c), wherein $R^5$ is:

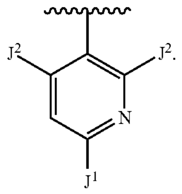

Embodiment 21(i) of this disclosure relates to anyone of Embodiments 21, 21(a1), 21(a), 21(b), or 21(c), wherein $R^5$ is:

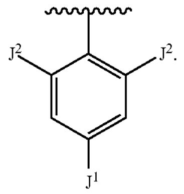

Embodiment 21(j) of this disclosure relates to anyone of Embodiments 21, 21(a1), 21(a), 21(b), or 21(c), wherein $R^5$ is:

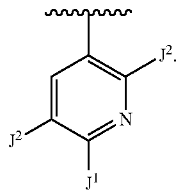

Embodiment 21(k) of this disclosure relates to anyone of Embodiments 21, 21(a1), 21(a), 21(b), or 21(c), wherein $R^5$ is:

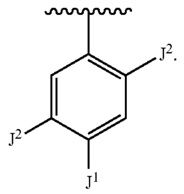

Embodiment 21(l) of this disclosure relates to anyone of Embodiments 21, 21(a1), 21(a), 21(b), or 21(c), wherein $R^5$ is:

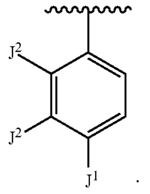

Embodiment 21(m) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein $-L-R^1$ is:

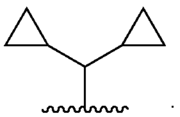 [SMILES: *C(C1CC1)C1CC1]

Embodiment 21(n) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein $-L-R^1$ is:

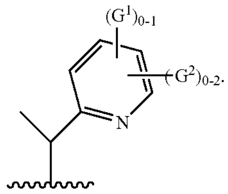

Embodiment 21(o) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein $-L-R^1$ is:

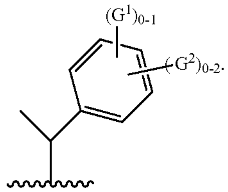

Embodiment 21(p) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein $-L-R^1$ is:

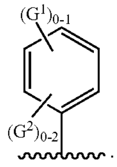

Embodiment 21(q) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein $-L-R^1$ is:

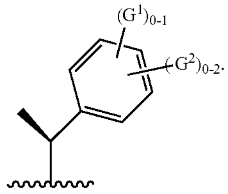

Embodiment 21(r) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein $-L-R^1$ is:

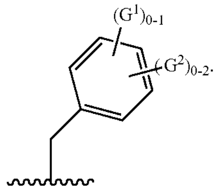

Embodiment 21(s) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein -L-$R^1$ is:

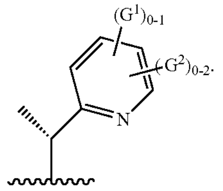

Embodiment 21(t) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein -L-$R^1$ is:

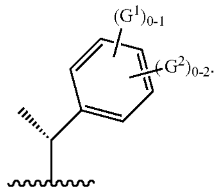

Embodiment 21(u) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein -L-$R^1$ is:

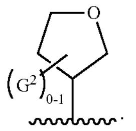

Embodiment 21(v) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein -L-$R^1$ is:

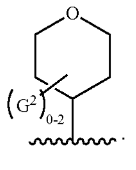

Embodiment 21(w) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein -L-$R^1$ is:

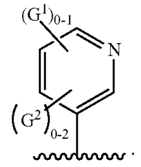

Embodiment 21(x) of this disclosure relates to anyone of Embodiments 21, 21(a1), 21(a), 21(b), or 21(c), 21(d), 21(e), 21(f), 21(g), 21(h), 21(i), 21(j), 21(k), or 21(l), wherein -L-$R^1$ is:

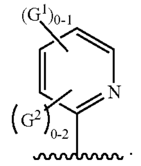

Embodiment 22 relates to a compound according to Embodiment 1 of this disclosure that is selected from Table 1 of this disclosure, or a pharmaceutically acceptable salt thereof.

Compounds contemplated herein are described with reference to both generic formulae and specific compounds. In addition, the compounds described herein may exist in a number of different forms or derivatives, all within the scope of the present disclosure. These include, for example, tautomers, stereoisomers, racemic mixtures, regioisomers, salts, prodrugs (e.g. carboxylic acid esters), solvated forms, and active metabolites.

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers as defined herein. All such single stereoisomers, racemates and mixtures thereof are intended to be within the scope of the present disclosure. Unless specified to the contrary, all such stereoisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present disclosure includes both such regioisomers.

In addition to the present formulae and compounds described herein, the disclosure also includes prodrugs (generally pharmaceutically acceptable prodrugs), active metabolic derivatives (active metabolites), and their pharmaceutically acceptable salts.

Unless specified to the contrary, specification of a compound herein includes pharmaceutically acceptable salts of such compound.

In some embodiments, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

III. Formulations and Administration

Embodiment 23 of this disclosure relates to a pharmaceutical composition comprising a compound in one of Embodiments of this disclosure relates to a compound according to any one of Embodiments 1-22, including any subembodiments thereof, wherein, and a pharmaceutically acceptable carrier.

Embodiment 24 of this disclosure relates to a pharmaceutical composition of Embodiment 23, further comprising a second pharmaceutical agent.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, $21^{st}$ edition, Lippincott, Williams and Wilkins, Philadelphia, Pa., 2005 (hereby incorporated by reference herein).

Compounds of the present disclosure (i.e. any of the compounds described in Embodiments 1-22, including any of the subembodiments thereof) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, the compounds can be administered by oral administration. For oral administration, for example, the compounds can be formulated into conventional oral dosage forms such as capsules, tablets, and liquid preparations such as syrups, elixirs, and concentrated drops.

For inhalants, compounds of the disclosure may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the disclosure are formulated in sterile liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

IV. Methods of Use

The methods and compounds will typically be used in therapy for human subjects. However, they may also be used to treat similar or identical indications in other animal subjects.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500 mg per day. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day or more. In certain embodiments, the compound is administered continuously.

In certain embodiments, provided herein is a method for treating a diseases or condition mediated by EP300 or CBP by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of any of the compounds described in a compound in one of Embodiments 1-22, or a pharmaceutically acceptable salt, deuterated analog, a tautomer or a stereoisomer thereof, and wherein the compound is administered on an empty stomach.

Embodiment 25 of this disclosure relates to a method for treating a subject with a disease or condition mediated by EP300 or CBP, said method comprising administering to the subject an effective amount of a compound in one of Embodiments 1-22, or a pharmaceutically acceptable salt, deuterated analog, a tautomer or a stereoisomer thereof, or a pharmaceutical composition in one of Embodiments 23-24.

Embodiment 26 of this disclosure relates to the method for treating a subject with a disease or condition according to Embodiment 25, wherein the disease or condition is a cancer that harbors inactivating mutations in CBP or EP300, or a cancer where there is activation of EP300 or CBP.

Embodiment 27 of this disclosure relates to the method for treating a subject with a disease or condition according to Embodiment 25, wherein the disease or condition is a cancer that expresses the androgen receptor.

Embodiment 28 of this disclosure relates to the method for treating a subject with a disease or condition according to Embodiment 25, wherein the disease or condition is a neoplastic disorder, a cancer, an inflammatory disorder, an age-related disease, a cognitive disorder and or a neurodegenerative disease.

Embodiment 29 of this disclosure relates to the method for treating a subject with a disease or condition according to Embodiment 25, wherein the disease or condition is acral lentiginous melanoma, acute eosinophilic leukemia, acute erythroid leukemia, acute lymphoblastic leukemia, acute megakaryoblastic leukemia, acute monocytic leukemia, acute promyelocytic leukemia, bladder cancer, adenocarcinoma, adult T-cell leukemia/lymphoma, aggressive NK-cell leukemia, AIDS-related lymphoma, anaplastic large cell lymphoma, angioimmunoblastic T-cell lymphoma, B-cell chronic lymphocytic leukemia, B-cell prolymphocytic leukemia, B-cell lymphoma, bone cancer, Burkitt's lymphoma, cutaneous T-cell lymphoma, colorectal cancer, diffuse large B-cell lymphoma, enteropathy-associated T-cell lymphoma, follicular lymphoma, glioblastoma multiforme, glioma, gastric cancer, hepatosplenic T-cell lymphoma, Hodgkin's lymphoma, non-Hodgkin's lymphoma, leukemia, lymphoma, acute lymphocytic leukemia, acute myeloid leukemia, chronic lymphocytic leukemia, small cell lung cancer, non-small cell lung cancer, MALT lymphoma, malignant peripheral nerve sheath tumor, mantle cell lymphoma, marginal zone B-cell lymphoma, mast cell leukemia, breast cancer, medulloblastoma, melanoma, merkel cell cancer, mesothelioma, multiple myeloma, neuroblastoma, neurofibroma, nodular melanoma, osteosarcoma, ovarian cancer, precursor T-lymphoblastic lymphoma, primary central nervous system lymphoma, primary effusion lymphoma, prostate cancer, pancreatic cancer, skin cancer, T-cell lymphoma, uveal melanoma, Alzheimer's disease, Parkinson's disease, or colorectal cancer.

Embodiment 29(a) of this disclosure relates to the method for treating a subject with a disease or condition according to Embodiment 29, wherein the disease or condition is acute myeloid leukemia.

Embodiment 29(b) of this disclosure relates to the method for treating a subject with a disease or condition according to Embodiment 29, wherein the disease or condition is multible myeloma.

Embodiment 29(c) of this disclosure relates to the method for treating a subject with a disease or condition according to Embodiment 29, wherein the disease or condition is prostate cancer.

Embodiment 29(d) of this disclosure relates to the method for treating a subject with a disease or condition according to Embodiment 29, wherein the disease or condition is prostate cancer.

Embodiment 30 of this disclosure relates to the method for treating a subject with a disease or condition according to Embodiment 29, wherein the disease or condition is small-cell lung cancer, non-small cell lung cancer, bladder cancer, non-Hodgkin's lymphoma, acute myeloid leukemia, multiple myeloma, diffuse large B-cell lymphoma, breast cancer or prostate cancer.

Embodiment 31 of this disclosure relates to the method for treating a subject with a disease or condition according to Embodiment 29, wherein the disease or condition is Alzheimer's disease or Parkinson's disease.

V. Combination Therapy

EP300 and CBP modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In another embodiment, the present disclosure provides methods for treating a disease or condition mediated by EP300 or CBP by administering to the subject an effective amount of a composition including any one or more compound(s) as described herein in combination with one or more other suitable therapies for treating the disease.

Embodiment 32 of this disclosure relates to the method according to any one of Embodiments 25-31, or any subembodiments thereof, further comprising administering one or more additional therapeutic agents.

Embodiment 33 of this disclosure relates to the method according Embodiment 32, wherein the one or more additional therapeutic agents is one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immunotherapy agent (including PD-1 or PD-L1 inhibitors) selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, a PD-1 inhibitor, or xx) an epigenetic modulator.

Embodiment 33(a) of this disclosure relates to the method according Embodiment 32, wherein the one or more additional therapeutic agents is one or more of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immunotherapy agent selected from a PD-1 or PD-L1 inhibitor; v) a hormone or hormone antagonist selected from the group consisting of enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, a PD-1 inhibitor, or xx) an epigenetic modulator.

Embodiment 34 of this disclosure relates to the method according Embodiment 33, wherein the one or more additional therapeutic agents is an epigenetic modulator selected from the group consisting of:

(a) a DNA methyltransferase;

(b) a histone or protein methyltransferase;

(c) a histone demethylase;

(d) a histone deacetylase inhibitor;

(f) other chromatin remodelers; and (g) a BRD4 inhibitor.

Embodiment 35 of this disclosure relates to the method according to Embodiment 34, wherein the epigenetic modulator is a histone deacetylase inhibitor selected from the group consisting of vornostat, romidepsin, chidamide, panobinostat, belinostat, valproic acid, mocetinostat, abexinostat, entinostat, resminostat, givinostat, and quisinostat.

Embodiment 36 of this disclosure relates to the method according to Embodiment 34, wherein the epigenetic modulator is a BRD4 inhibitor.

Embodiment 37 of this disclosure relates to the method according to Embodiment 33, wherein the one or more additional therapeutic agents is a PD-1 inhibitor, quizartinib, enzalutamide, abiraterone, or a BRD4 inhibitor.

Embodiment 38 of this disclosure relates to the method according to Embodiment 33, wherein the one or more additional therapeutic agent is enzalutamide and the disease is prostate cancer including, but not limited to, castrate resistant prostate cancer.

Embodiment 39 of this disclosure relates to the method according to Embodiment 33, wherein the one or more additional therapeutic agent is abiraterone and the disease is prostate cancer including, but not limited to, castrate resistant prostate cancer.

Bromodomains (e.g., BET proteins, such as BRD2, BRD3, BRD4, and/or BRDT), and e.g., diseases related to abnormal expression of bromodomains, include cell proliferative disorders, cancers, chronic autoimmune, and inflammatory conditions, among others. Non-limiting examples of BET inhibitors include PLX1107, GSK1210151A and GSK525762.

The histone deacetylase inhibitors (HDAC inhibitors) are cytostatic agents that inhibit the proliferation of tumor cells in culture and in vivo by inducing cell cycle arrest, differentiation and/or apoptosis. HDAC inhibitors exert their anti-tumor effects via the induction of expression changes of oncogenes or tumour suppressor, through modulating that the acetylation/deactylation of histones and/or non-histone proteins such as transcription factors. Histone acetylation and deacetylation play important roles in the modulation of chromatin topology and the regulation of gene transcription. Non-limiting examples of HDAC inhibitors include vorinostat, romidepsin, chidamide, panobinostat, belinostat, valproic acid, mocetinostat, abexinostat, entinostat, resminostat, givinostat, and quisinostat. HDAC inhibitors have been used extensively in psychiatry and neurology as mood stabilzers and anti-epileptics. One example of this is valproic acid, marketed as a drug under the trade names Depakene, Depakote, and Divalproex. HDAC inhibitors are also being used as a mitigator for neurodegenerative diseases such as Alzheimer's disease and Huntington's disease.

In another embodiment, the present disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, .gamma.-ray, or electron, proton, neutron, or alpha. particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, or bone marrow and stem cell transplantation.

VI. Kits

In another aspect, the present disclosure provides kits that include one or more compounds as described in any one of a compound in one of Embodiments 1-22, or a pharmaceutically acceptable salt, deuterated analog, a tautomer or a stereoisomer thereof, or a pharmaceutical composition in one of Embodiments 23-24. In some embodiments, the compound or composition is packaged, e.g., in a vial, bottle, flask, which may be further packaged, e.g., within a box, envelope, or bag. The compound or composition may be approved by the U.S. Food and Drug Administration or similar regulatory agency for administration to a mammal, e.g., a human. The compound or composition may be approved for administration to a mammal, e.g., a human, for an EP300 or CBP mediated disease or condition. The kits described herein may include written instructions for use and/or other indication that the compound or composition is suitable or approved for administration to a mammal, e.g., a human, for an EP300 or CBP mediated disease or condition. The compound or composition may be packaged in unit dose or single dose form, e.g., single dose pills, capsules, or the like.

VII. Binding Assays

The methods of the present disclosure can involve assays that are able to detect the binding of compounds to a target molecule. Such binding is at a statistically significant level, with a confidence level of at least 90%, or at least 95, 97, 98, 99% or greater confidence level that the assay signal represents binding to the target molecule, i.e., is distinguished from background. In some embodiments, controls are used to distinguish target binding from non-specific binding. A large variety of assays indicative of binding are known for different target types and can be used for this disclosure.

Binding compounds can be characterized by their effect on the activity of the target molecule. Thus, a "low activity" compound has an inhibitory concentration ($IC_{50}$) or effective concentration ($EC_{50}$) of greater than 1 μM under standard conditions. By "very low activity" is meant an $IC_{50}$ or $EC_{50}$ of above 100 μM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 μM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121:313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3): 310-8; Malmqvist., (1999) BIACORE: an affinity biosensor system for characterization of biomolecular interactions, Biochemical Society Transactions 27:335-40; Alfthan, (1998) Surface plasmon resonance biosensors as atool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra-high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) The Chemist's Companion: A Handbook Of Practical Data, Techniques, And References, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well-known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

General Synthesis

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

The compounds of this disclosure may contain one or more asymmetric or chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromathography, chiral seed crystals, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

It will also be appreciated that in each of the schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

Compounds of the present disclosure may be synthesized in accordance with the general reaction schemes and/or examples described below. The general schemes may be altered by substitution of the starting materials with other materials having similar structures to result in corresponding products. The structure of the desired product will generally make apparent to a person of skill in the art the required starting materials.

Schemes 1 and 2 provide exemplary synthetic routes for the synthesis of compounds provided herein (e.g., compounds of Formula I). The compounds of Formula I, or other formulas or compounds disclosed herein, are typically prepared by first providing the core Formula X(a) or X(d) and then attaching the desired substituents using suitable conditions (e.g., coupling).

In some embodiments, synthesis of a compound of Formula I proceeds according to Scheme 1.

Scheme 1

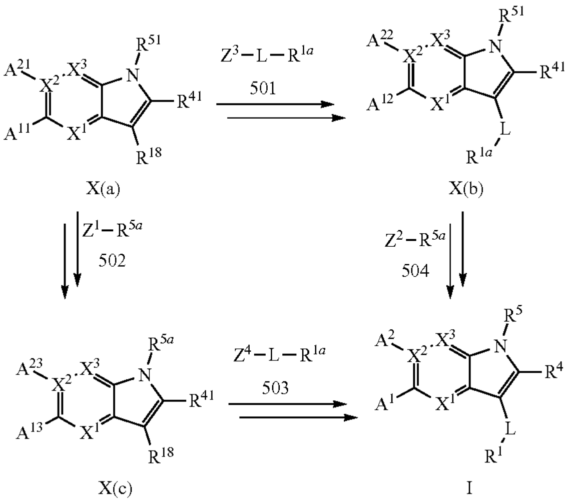

In Scheme 1, $A^1$, $A^2$, L, $R^1$, $R^4$, $R^5$, X, $X^2$, and $X^3$ are as defined in Formula I. In Scheme 1, a compound of Formula X(a) is converted into a compound of Formula X(b) or of Formula X(c). The compound of Formula X(b) or Formula X(c), respectively, may then be converted into a compound of Formula I.

In Scheme 1, Each of $Z^1$, $Z^2$, $Z^3$, and $Z^4$ is independently a suitable leaving group, e.g., a halide or hydroxide (e.g., in the presence of triphenylphosphine and a dialkylazodicarboxylate), a suitable coupling partner, e.g., a halide, a boronic acid, a boronate or hydrogen (e.g., of a terminal alkyne), or a suitable electrophile, e.g., an aldehyde or ketone.

In Scheme 1, $R^{51}$ is $R^{5a}$, hydrogen or a suitable leaving group, e.g., a halide or hydroxide (e.g., in the presence of triphenylphosphine and a dialkylazodicarboxylate), or a suitable coupling partner, e.g., a halide, a boronic acid, a boronate. $R^{5a}$ is $R^5$ or a suitable precursor, for example, where $R^5$ comprises a carboxylic acid, $R^{5a}$ may comprise an ester. Where $R^5$ comprises a carboxylic acid, conversion of Formula X(b) to Formula I, or conversion of Formula X(a) to Formula X(c), may comprise the step of hydrolyzing an ester. $R^{18}$ is -L-$R^1$, hydrogen or a suitable leaving group, e.g., a halide or hydroxide (e.g., in the presence of triphenylphosphine and a dialkylazodicarboxylate), a suitable coupling partner, e.g., a halide, a boronic acid, a boronate, or a suitable electrophile, e.g., an aldehyde or ketone. $R^{41}$ is $R^4$. Each of $A^{11}$, $A^{12}$, and $A^{13}$ is A. Each of $A^{21}$, $A^{22}$, and $A^{23}$ is either $A^2$ or a suitable moiety for appending $A^2$, e.g., a suitable coupling partner such as a halide, a boronic acid, a boronate or hydrogen.

A person of skill in the art will appreciate that any of a compound of Formula X(a), X(b), or X(c) may be available from a commercial supplier for a particular embodiment. Alternative synthesis of a compound of Formula X(a), X(b), or X(c) may be as described herein or as known to those of skill in the art.

In some embodiments, synthesis of a compound of Formula I proceeds according to Scheme 2.

Scheme 2

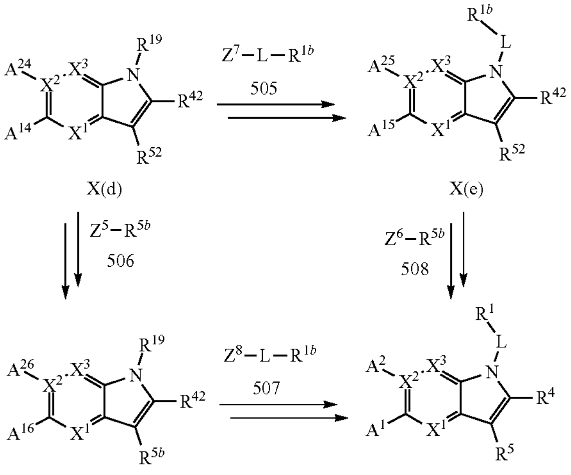

X(d) X(e) X(f) I

In Scheme 2, $A^1$, $A^2$, L, $R^1$, $R^4$, $R^5$, $X^1$, $X^2$, and $X^3$ are as defined in Formula I. In Scheme 1, a compound of Formula X(d) is converted into a compound of Formula X(e) or of Formula X(f). The compound of Formula X(e) or Formula X(f), respectively, may then be converted into a compound of Formula I.

In Scheme 2, Each of $Z^5$, $Z^6$, $Z^7$, and $Z^8$ is independently a suitable leaving group, e.g., a halide or hydroxide (e.g., in the presence of triphenylphosphine and a dialkylazodicarboxylate), a suitable coupling partner, e.g., a halide, a boronic acid, a boronate or hydrogen (e.g., of a terminal alkyne), or a suitable electrophile, e.g., an aldehyde or ketone.

In Scheme 2, $R^{52}$ is $R^{5b}$, hydrogen or a suitable leaving group, e.g., a halide or hydroxide (e.g., in the presence of triphenylphosphine and a dialkylazodicarboxylate), or a suitable coupling partner, e.g., a halide, a boronic acid, a boronate. $R^{5b}$ is $R^5$ or a suitable precursor, for example, where R comprises a carboxylic acid, $R^{5b}$ may comprise an ester. Where $R^5$ comprises a carboxylic acid, conversion of Formula X(e) to Formula I, or conversion of Formula X(d) to Formula X(f), may comprise the step of hydrolyzing an ester. $R^{19}$ is -L-$R^1$, hydrogen or a suitable leaving group, e.g., a halide or hydroxide (e.g., in the presence of triphenylphosphine and a dialkylazodicarboxylate), a suitable coupling partner, e.g., a halide, a boronic acid, a boronate, or a suitable electrophile, e.g., an aldehyde, ketone, or nitrile, or an α-,β-unsaturated derivative thereof, or an N-protecting group, e.g., a p-toluenesulfonyl or tert-butoxycarbonyl. $R^{42}$ is either $R^4$ or a suitable moiety for appending $R^4$, e.g., a hydrogen. Each of $A^{14}$, $A^{15}$, and $A^{16}$ is either $A^1$ or a suitable moiety for appending $A^1$, e.g., a suitable coupling partner such as a halide, a boronic acid, a boronate or hydrogen. Each of $A^{24}$, $A^{25}$, and $A^{26}$ is $A^2$.

A person of skill in the art will appreciate that any of a compound of Formula X(d), X(e), or X(f) may be available from a commercial supplier for a particular embodiment. Alternative synthesis of a compound of Formula X(d), X(e), or X(f) may be as described herein or as known to those of skill in the art.

Palladium Coupling Conditions

Where appropriate, where an (hetero)aryl carbon-(hetero)aryl carbon bond is formed, Formula X(a), X(b), X(c), X(d), X(e), or X(f) is coupled with compound 501, 502, 503, 504, 505, 506, 507, or 508 in which $Z^1$, $Z^2$, $Z^3$, $Z^4$, $Z^5$, $Z^6$, $Z^7$, or $Z^8$ is a suitable coupling partner, for example, a halide (e.g., bromide or iodide) or boronic acid, or ester thereof, under standard metal-catalyzed cross coupling conditions (e.g., using a palladium catalyst) in a suitable solvent (e.g., dioxane, acetonitrile, water, etc.), optionally under an inert atmosphere. The cross coupling reaction is carried out in an inert solvent, for example aqueous 1,4-dioxane or aqueous N,N-dimethylformamide, in the presence of a mild base, for example potassium acetate, potassium carbonate, sodium carbonate, or sodium bicarbonate. The reaction is typically conducted in the presence of a metal catalyst with an appropriate ligand, for example dichlorobis(triphenylphosphine) palladium(II) or dichloro 1,1'-bis(diphenylphosphino)ferrocene palladium(II), at a temperature of about 60 to 150° C., for about 10 minutes to about 12 hours. When the reaction is substantially complete, the product is isolated by conventional means.

Copper ("Buchwald") Coupling Conditions

Where appropriate, for example, where an (hetero)aryl carbon-nitrogen bond is formed, Formula X(a), X(b), X(c), X(d), X(e), or X(f) is coupled with compound 501, 502, 503, 504, 505, 506, 507, or 508 in which $Z^1$, $Z^2$, $Z^3$, $Z^4$, $Z^5$, $Z^6$, $Z^7$, or $Z^8$ is a suitable coupling partner, for example, a halide (e.g., bromide or iodide), under copper-catalyzed coupling conditions (e.g., using a copper catalyst), in a suitable solvent (e.g., toluene, DMF, etc.), optionally under an inert atmosphere. The coupling reaction is carried out in an inert solvent, for example toluene or N,N-dimethylformamide, in the presence of a mild base, for example potassium carbonate, or potassium phosphate tribasic. The reaction is typically conducted in the presence of a metal catalyst, for example, copper(I) iodide, copper(I) bromide or copper(II) acetate monohydrate, with an appropriate ligand, for example trans N,N'-dimethylcyclohexane-1,2-diamine, at a temperature of about 60 to 150° C., for about 10 minutes to about 7 days. When the reaction is substantially complete, the product is isolated by conventional means.

Aryl Nucleophilic Displacement Conditions

Where appropriate, for example, where an (hetero)aryl carbon-nitrogen bond is formed, Formula X(a), X(b), X(c), X(d), X(e), or X(f) is coupled with compound 501, 502, 503, 504, 505, 506, 507, or 508 in which Z, $Z^2$, $Z^3$, $Z^4$, $Z^5$, $Z^6$, $Z^7$, or $Z^8$ is a suitable leaving group, for example, a fluoride, under nucleophilic substitution-aromatic ("$SN_{Ar}$") conditions, in a suitable solvent (e.g., DMSO, DMF, etc.), optionally under an inert atmosphere. The reaction is carried out in an inert solvent, for example DMSO, in the presence of a mild base, for example potassium carbonate or cesium carbonate. The reaction is typically conducted at a temperature of about 60 to 150° C., for about 1 hour to about 7 days. When the reaction is substantially complete, the product is isolated by conventional means.

Alkyne Coupling Conditions

Where appropriate, for example, where a alkynyl carbon-nitrogen bond is formed, Formula X(a), X(b), X(c), X(d), X(e), or X(f) is coupled with compound 501, 502, 503, 504, 505, 506, 507, or 508 in which $Z^1$, $Z^2$, $Z^3$, $Z^4$, $Z^5$, $Z^6$, $Z^7$, or $Z^8$ is a hydrogen or trialkylsilane, under copper-catalyzed coupling conditions (e.g., using a palladium catalyst and/or a copper catalyst), in a suitable solvent (e.g., toluene, DMF, etc.), optionally under an inert atmosphere. The coupling reaction is carried out in an inert solvent, for example toluene or N,N-dimethylformamide, in the presence of a mild base, for example triethylamine. The reaction is typically conducted in the presence of a metal catalyst, for example, bis(triphenylphosphine) palladium(II) dichloride, copper(I) iodide or copper(I) bromide, optionally with an appropriate ligand, for example trans N,N'-dimethylcyclohexane-1,2-diamine, at a temperature of about 60 to 150° C., for about 10 minutes to about 1 day. When the reaction is substantially complete, the product is isolated by conventional means.

Ester Hydrolysis Conditions

Where appropriate, for example, where a carboxylic ester is cleaved in $R^{1a}$ or $R^{5a}$ to form a carboxylic acid in $R^1$ or $R^5$ respectively, Formula X(a), X(b), X(c), X(d), X(e), or X(f) is subjected to ester hydrolysis conditions. Ester hydrolysis conditions may comprise, for example, using a base such as an alkali metal alkoxide (e.g., sodium methoxide or sodium ethoxide) or an alkali metal hydroxide (e.g., sodium hydroxide or lithium hydroxide) in a suitable solvent (e.g., water, dioxane, an alcohol and/or THF), at a temperature of about 0 to 100° C., for about 10 minutes to about 24 hours. When the reaction is substantially complete, the product is isolated by conventional means.

EXAMPLES

The examples below depict the general synthetic procedure for the compounds described herein. Synthesis of the compounds described herein is not limited by these examples and schemes. One skilled in the art will know that other procedures can be used to synthesize the compounds described herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. Unless otherwise specified, intermediate compounds in the examples below, that do not contain a description of how they are made, are either commercially available to one skilled in the art, or can otherwise be synthesized by the skilled artisan using commercially available precursor molecules and synthetic methods known in the art.

The following Schemes and synthetic examples are intended to be illustrative and are not limiting or restrictive to the scope of the disclosure.

Example 1

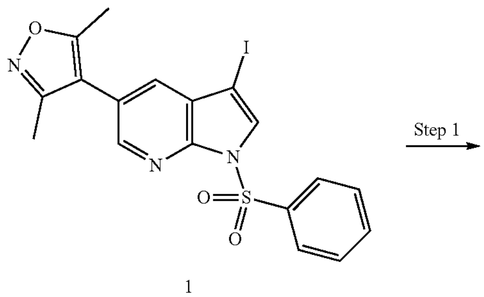

1

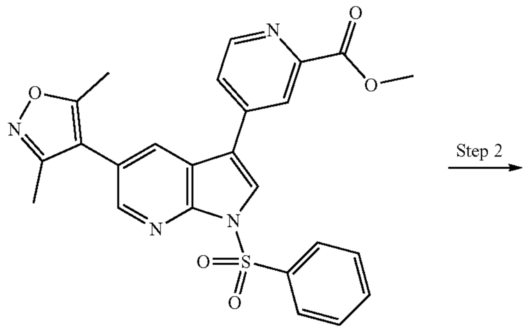

2

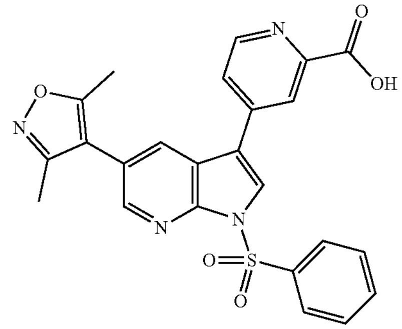

P-0055

Step 1: Preparation of methyl 4-(5-(3,5-dimethylisoxazol-4-yl)-1-(phenylsulfonyl)-1H-pyrrolo[2,3-b]pyridin-3-yl)picolinate 2

To a microwave pressure vial charged with 4-[1-(benzenesulfonyl)-3-iodo-pyrrolo[2,3-b]pyridin-5-yl]-3,5-dimethyl-isoxazole (1, 150 mg, 0.313 mmol), methyl 4-(4,4,5,5-tetramethyl-1,3,2-dioxaborolan-2-yl)pyridine-2-carboxylate (167 mg, 0.635 mmol), 1,1'-bis(diphenylphosphino)ferrocene-palladium(II) dichloride dichloromethane complex (26.6 mg, 0.033 mmol) was added 1,4-dioxane (3 ml). The flask was flushed with argon and then 2.5M aqueous potassium carbonate (0.376 ml) was added. The vial was sealed and allowed to stir in an oil bath at 120° C. for 2 hours. The reaction was allowed to cool to room temperature and the biphasic mixture was filtered through Celite washing with THF and ethyl acetate. The filtrate was concentrated under reduced pressure and the material was purified by silica gel flash column chromatography eluting with a gradient from 0-100% ethyl acetate in hexane. This provided methyl 4-(5-(3,5-dimethylisoxazol- 4-yl)-1-(phenylsulfonyl)-1H-pyrrolo[2,3-b]pyridin-3-yl)picolinate (2). MS (ESI) $[M+H^+]^+$=489.0.

Step 2: Preparation of 4-(5-(3,5-dimethylisoxazol-4-yl)-1-(phenylsulfonyl)-1H-pyrrolo[2,3-b]pyridin-3-yl)picolinic acid P-0055

A solution of methyl 4-(5-(3,5-dimethylisoxazol-4-yl)-1-(phenylsulfonyl)-1H-pyrrolo[2,3-b]pyridin-3-yl)picolinate (2, 78.5 mg, 0.16 mmol) dissolved in dioxane (6 ml) was cooled in an ice bath. Then, 3 ml of 1M LiOH (aqueous) was added. After 30 min, the reaction was quenched with 1 M HCl (aqueous) to a pH of 1 and then extracted with ethyl acetate. The layers were separated and the aqueous layer was extracted with ethyl acetate. The combined organic layers were washed with brine, dried over anhydrous sodium sulfate and filtered. The volatiles were removed by rotary evaporation and the resulting residue was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 4-(5-(3,5-dimethylisoxazol-4-yl)-1-(phenylsulfonyl)-1H-pyrrolo[2,3-b]pyridin-3-yl)picolinic acid (P-0055). MS (ESI) $[M+H^+]^+$=474.9.

Example 2

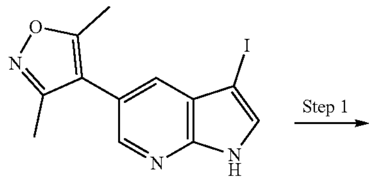

3

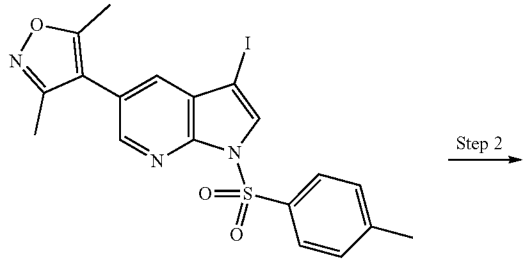

4

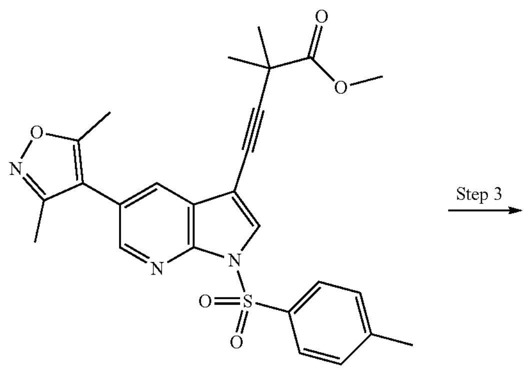

5

-continued

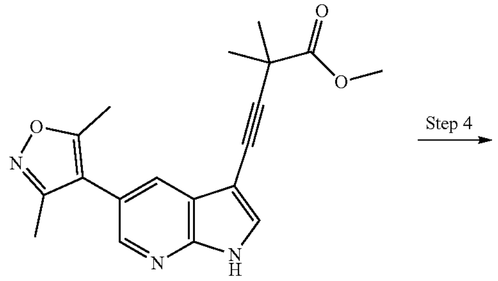

6

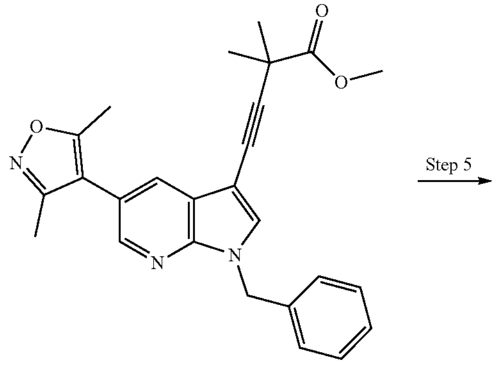

7

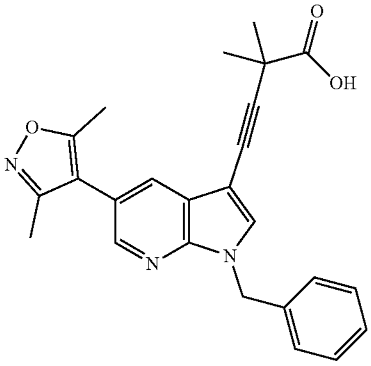

P-0051

Step 1: Preparation of 4-(3-iodo-1-tosyl-1H-pyrrolo[2,3-b]pyridin-5-yl)-3,5-dimethylisoxazole 4

In a round flask charged with 4-(3-iodo-1H-pyrrolo[2,3-b]pyridin-5-yl)-3,5-dimethyl-isoxazole (3, 10 g, 29.5 mmol) and anhydrous THF (150 ml) was added sodium hydride (60%, 1.65 g, 41.3 mmol). The reaction was allowed to stir at room temperature for 1 hour followed by the addition of 4-methylbenzenesulfonyl chloride (6.80 g, 35.7 mmol). The reaction mixture was stirred at room temperature overnight. The reaction mixture was quenched with brine (160 mL) and diluted with ethyl acetate (160 mL). The organic layer was separated, dried over anhydrous sodium sulfate, filtered and concentrated under reduced pressure. The residue was dry-loaded onto silica gel and purified by silica gel flash column chromatography eluting with 0-20% ethyl acetate in hexane to give 4-(3-iodo-1-tosyl-1H-pyrrolo[2,3-b]pyridin-5-yl)-3,5-dimethylisoxazole (4). MS (ESI) $[M+H^+]^+$=493.9.

Step 2: Preparation of methyl 4-(5-(3,5-dimethylisoxazol-4-yl)-1-tosyl-1H-pyrrolo[2,3-b]pyridin-3-yl)-2,2-dimethylbut-3-ynoate 5

A mixture of 4-(3-iodo-1-tosyl-H-pyrrolo[2,3-b]pyridin-5-yl)-3,5-dimethylisoxazole (4, 104 mg, 0.21 mmol), bis(triphenylphosphine) palladium(II) dichloride (4.42 mg, 6.3 umol) and copper(I) iodide (1.2 mg, 6.3 umol) in (1:3) triethylamine in acetonitrile (2.0 ml) was purged with nitrogen gas, then methyl 2,2-dimethylbut-3-ynoate (53 mg, 0.42 mmol) was added. The mixture was heated at 90° C. for 2 hours. The mixture was concentrated down under reduced pressure and purified by flash chromatography eluting with 20% ethyl acetate in hexane to provide methyl 4-(5-(3,5-dimethylisoxazol-4-yl)-1-tosyl-1H-pyrrolo[2,3-b]pyridin-3-yl)-2,2-dimethylbut-3-ynoate (5). MS (ESI) $[M+H^+]^+=492.2$.

Step 3: Preparation of methyl 4-(5-(3,5-dimethylisoxazol-4-yl)-1H-pyrrolo[2,3-b]pyridin-3-yl)-2,2-dimethylbut-3-ynoate 6

To a mixture of methyl 4-(5-(3,5-dimethylisoxazol-4-yl)-1-tosyl-1H-pyrrolo[2,3-b]pyridin-3-yl)-2,2-dimethylbut-3-ynoate (5, 88 mg, 0.18 mmol) in THF (2 ml) was added 1M TBAF in THF (0.400 ml). The mixture was allowed to stir at 70° C. for 15 hours. The reaction was diluted with ethyl acetate which was washed with saturated sodium bicarbonate (aqueous), water and then brine. The layers were separated and the organic layer was dried over anhydrous magnesium sulfate, filtered and concentrated under reduced pressure and was triturated with 5% ethyl acetate in hexane to provide methyl 4-(5-(3,5-dimethylisoxazol-4-yl)-1H-pyrrolo[2,3-b]pyridin-3-yl)-2,2-dimethylbut-3-ynoate (6). MS (ESI) $[M+H^+]^+=338.6$.

Step 4: Preparation of methyl 4-(1-benzyl-5-(3,5-dimethylisoxazol-4-yl)-1H-pyrrolo[2,3-b]pyridin-3-yl)-2,2-dimethylbut-3-ynoate 7

To a mixture of methyl 4-(5-(3,5-dimethylisoxazol-4-yl)-1H-pyrrolo[2,3-b]pyridin-3-yl)-2,2-dimethylbut-3-ynoate (6, 28.6 mg) in DMF (1 ml) was added 60% NaH in mineral oil (60%, 4.07 mg, 0.1 mmol). The mixture was allowed to stir for 2 minutes and then bromomethylbenzene (21.75 mg, 0.13 mmol) was added. The resulting mixture was stirred at 60° C. for 2 hours. The mixture was diluted with water, extracted with ethyl acetate and the organic layer was washed with water, followed by brine. The layers were separated and the organic layer was dried over anhydrous magnesium sulfate, filtered and concentrated under reduced pressure. The material was purified by flash chromatography eluting with 50% ethyl acetate in hexane to provide methyl 4-(1-benzyl-5-(3,5-dimethylisoxazol-4-yl)-1H-pyrrolo[2,3-b]pyridin-3-yl)-2,2-dimethylbut-3-ynoate (7). MS (ESI) $[M+H^+]^+=428.6$.

Step 5: Preparation of 4-(1-benzyl-5-(3,5-dimethylisoxazol-4-yl)-1H-pyrrolo[2,3-b]pyridin-3-yl)-2,2-dimethylbut-3-ynoic acid P-0051

To a mixture of methyl 4-(1-benzyl-5-(3,5-dimethylisoxazol-4-yl)-1H-pyrrolo[2,3-b]pyridin-3-yl)-2,2-dimethylbut-3-ynoate (7, 22.6 mg, 0.05 mmol) in (1:1) THF/MeOH (0.5 ml) was added 4.18 M LiOH (0.030 ml). The mixture was stirred at 70° C. for 3 hours. The reaction was acidified with 3N HCl in MeOH and concentrated under reduced pressure. The material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 4-(1-benzyl-5-(3,5-dimethylisoxazol-4-yl)-1H-pyrrolo[2,3-b]pyridin-3-yl)-2,2-dimethylbut-3-ynoic acid (P-0051). MS (ESI) $[M+H^+]^+=414.5$.

Example 3

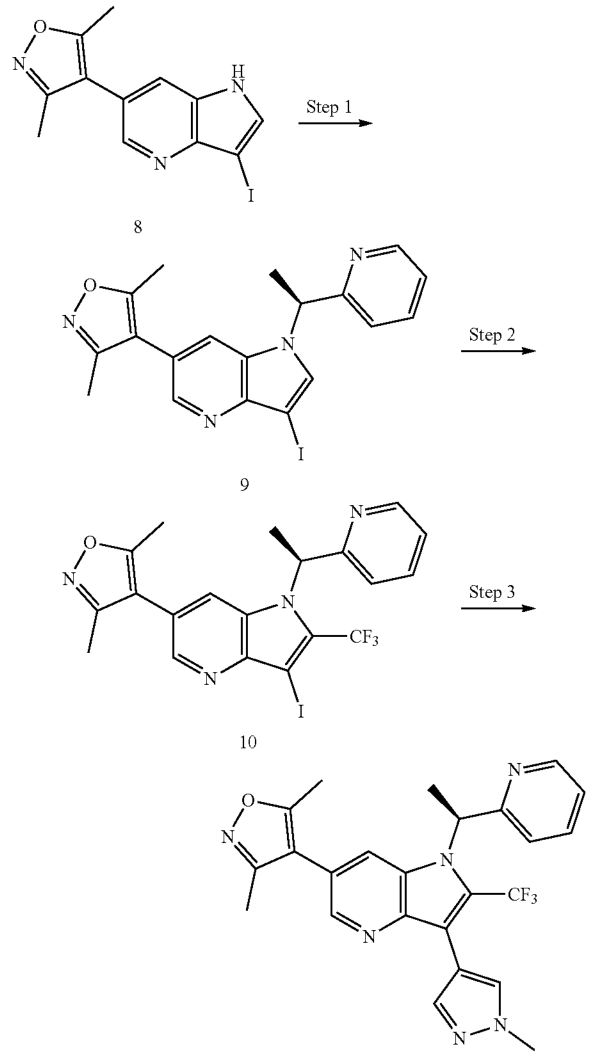

8

9

10

P-0160

Step 1: Preparation of (S)-4-(3-iodo-1-(1-(pyridin-2-yl)ethyl)-1H-pyrrolo[3,2-b]pyridin-6-yl)-3,5-dimethylisoxazole 9

To 4-(3-iodo-H-pyrrolo[3,2-b]pyridin-6-yl)-3,5-dimethylisoxazole (8, 0.92 g, 2.71 mmol) in THF (20 ml) was added (1R)-1-(2-pyridyl)ethanol (0.38 g, 3.09 mmol) followed by triphenylphosphine (0.957 g, 3.65 mmol). The reaction was cooled to 0° C. in an ice water bath, followed by the dropwise addition of diisopropyl azodicarboxylate (0.738 g, 3.65 mmol). After 1 hour, the reaction was removed from the ice bath and allowed to warm to room temperature for 1 hour. The reaction was concentrated under reduced pressure and purified with silica gel column chromatography eluting with 20% to 100% ethyl acetate in hexane to give (S)-4-(3-iodo-1-(1-(pyridin-2-yl)ethyl)-1H-pyrrolo[3,2-b]pyridin-6-yl)-3,5-dimethylisoxazole (9).

Step 2: Preparation of (S)-4-(3-iodo-1-(1-(pyridin-2-yl)ethyl)-2-(trifluoromethyl)-1H-pyrrolo[3,2-b]pyridin-6-yl)-3,5-dimethylisoxazole 10

To (S)-4-(3-iodo-1-(1-(pyridin-2-yl)ethyl)-1H-pyrrolo[3,2-b]pyridin-6-yl)-3,5-dimethylisoxazole (9, 0.91 g, 2.05 mmol) and zinc trifluoromethanesulfinate (1.36 g, 4.10 mmol) was added DMSO (10 ml) followed by water (4 ml). The reaction was cooled in an ice bath and tert-Butyl hydroperoxide (0.86 ml, 6.8 mmol) was added dropwise. The reaction was removed from the ice bath and allowed to warm to ambient temperature and then placed in an oil bath at 50° C. and allowed to stir overnight. After 22 hours, LCMS indicated -10% product formation. An additional 1.27 g of zinc trifluoromethanesulfinate was added, followed by 1 ml of tert-Butyl hydroperoxide. The reaction was allowed to continue for an additional 17 hours at 50° C. The reaction was extracted with saturated sodium bicarbonate and ethyl acetate. The organic layer was separated and the aqueous layer was extracted 3 more times with 5 mL portions of ethyl acetate. The organic layers were combined and volatiles removed by rotary evaporation to provide the crude product that was purified by silica gel column chromatography (10-60% ethyl acetate in hexanes). This provided (S)-4-(3-iodo-1-(1-(pyridin-2-yl)ethyl)-2-(trifluoromethyl)-1H-pyrrolo[3,2-b]pyridin-6-yl)-3,5-dimethylisoxazole (10). MS (ESI) $[M+H^+]^+$=512.1.

Step 3: Preparation of (S)-3,5-dimethyl-4-(3-(1-methyl-1H-pyrazol-4-yl)-1-(1-(pyridin-2-yl)ethyl)-2-(trifluoromethyl)-1H-pyrrolo[3,2-b]pyridin-6-yl)isoxazole P-160

To a reaction vial charged with (S)-4-(3-iodo-1-(1-(pyridin-2-yl)ethyl)-2-(trifluoromethyl)-1H-pyrrolo[3,2-b]pyridin-6-yl)-3,5-dimethylisoxazole (10, 61.47 mg, 0.12 mmol), 1-methyl-4-(4,4,5,5-tetramethyl-1,3,2-dioxaborolan-2-yl)pyrazole (49.94 mg, 0.24 mmol) and 1,1'-bis(diphenylphosphino)ferrocene-palladium(II) dichloride dichloromethane complex (9.8 mg, 0.012 mmol) in dioxane (2 ml) and purged with nitrogen gas, was added 2.5M aqueous $K_2CO_3$ (0.144 ml). The mixture was heated at 110° C. for 15 hours. The sample was diluted with ethyl acetate which was dried over anhydrous magnesium sulfate; filtered, concentrated down and purified by flash chromatography eluting with 100% ethyl acetate, followed by reversed chromatography to provide (S)-3,5-dimethyl-4-(3-(1-methyl-1H-pyrazol-4-yl)-1-(1-(pyridin-2-yl)ethyl)-2-(trifluoromethyl)-1H-pyrrolo[3,2-b]pyridin-6-yl)isoxazole (P-0160). MS (ESI) $[M+H^+]^+$=467.6

Example 4

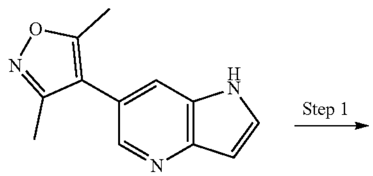

11

-continued

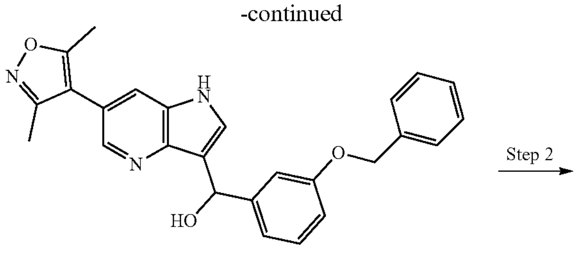

12

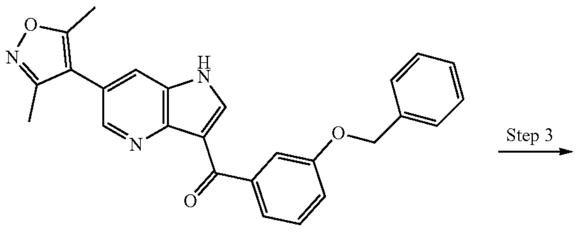

13

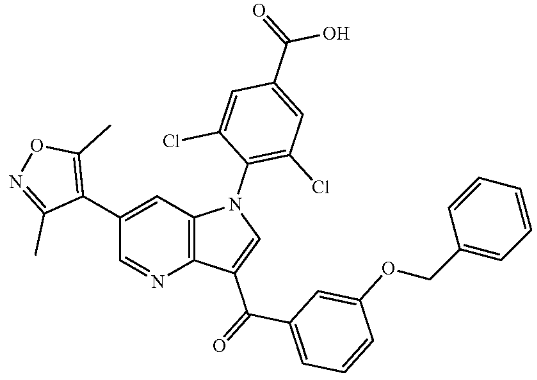

P-0133

Step 1: Preparation of (3-(benzyloxy)phenyl)(6-(3,5-dimethylisoxazol-4-yl)-1H-pyrrolo[3,2-b]pyridin-3-yl)methanol 12

To 3,5-dimethyl-4-(1H-pyrrolo[3,2-b]pyridin-6-yl)isoxazole (11, 0.24 g, 1.11 mmol) in methanol (5 ml) was added by potassium hydroxide (0.177 g, 3.15 mmol) and 3-benzyloxybenzaldehyde (0.26 g, 1.23 mmol). The mixture was stirred at room temperature for 4 hours. The reaction mixture was extracted with ethyl acetate and water with 1N citric acid. The organic layer was washed with water and brine, then dried over magnesium sulfate and filtered. The volatiles were removed under reduced pressure and the material was purified by silica gel column chromatography (0-60% ethyl acetate in hexanes). This provided (3-(benzyloxy) phenyl)(6-(3,5-dimethylisoxazol-4-yl)-1H-pyrrolo[3,2-b]pyridin-3-yl)methanol (12). MS (ESI) $[M+H^+]^+$=426.5.

Step 2: Preparation of (3-(benzyloxy)phenyl)(6-(3,5-dimethylisoxazol-4-yl)-1H-pyrrolo[3,2-b]pyridin-3-yl)methanone 13

To provided (3-(benzyloxy) phenyl)(6-(3,5-dimethylisoxazol-4-yl)-1H-pyrrolo[3,2-b]pyridin-3-yl)methanol (12, 34 mg, 0.080 mmol) in tetrahydrofuran (10 ml) was added by Dess-Martin periodinane (0.07 g, 0.16 mmol). The mixture was stirred at room temperature for 1 hour. The reaction mixture was diluted with water and extracted with ethyl acetate. The organic layer was washed with water and brine, then dried over magnesium sulfate and filtered. The volatiles were removed under reduced pressure and the material was purified by silica gel column chromatography (0-100% ethyl acetate in dichloromethane) to provide (3-(benzyloxy)phenyl)(6-(3,5-dimethylisoxazol-4-yl)-1H-pyrrolo[3,2-b]pyridin-3-yl)methanone (13). MS (ESI) $[M+H^+]^+$=424.1.

Step 3: Preparation of 4-(3-(3-(benzyloxy)benzoyl)-6-(3,5-dimethylisoxazol-4-yl)-1H-pyrrolo[3,2-b]pyridin-1-yl)-3,5-dichlorobenzoic acid P-0133

To a mixture of (3-(benzyloxy)phenyl)(6-(3,5-dimethylisoxazol-4-yl)-1H-pyrrolo[3,2-b]pyridin-3-yl)methanone (13, 29 mg, 0.068 mmol), 3,5-dichloro-4-fluoro-benzoic acid (40 mg, 0.19 mmol), and cesium carbonate (120 mg, 0.37 mmol) was added DMSO (3 ml). The reaction mixture was heated at 90° C. for 3 days. The reaction mixture was diluted with water and extracted with ethyl acetate. The organic layer was washed with water and brine, then dried over magnesium sulfate and filtered. The volatiles were removed under reduced pressure and the crude material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 4-(3-(3-(benzyloxy)benzoyl)-6-(3,5-dimethylisoxazol-4-yl)-1H-pyrrolo[3,2-b]pyridin-1-yl)-3,5-dichlorobenzoic acid (P-0133). MS (ESI) $[M+H^+]^+$=612.0.

Example 5

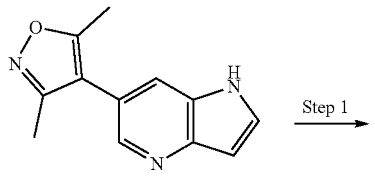

11

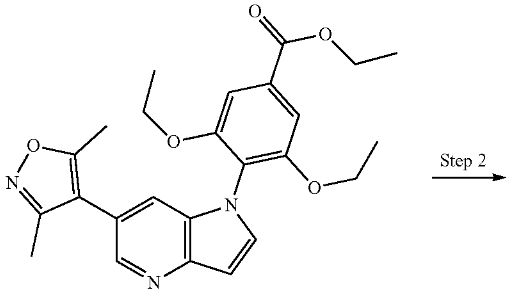

14

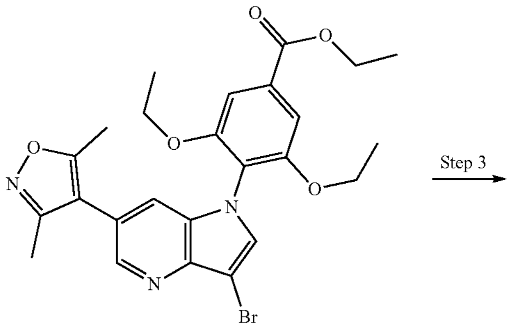

15

-continued

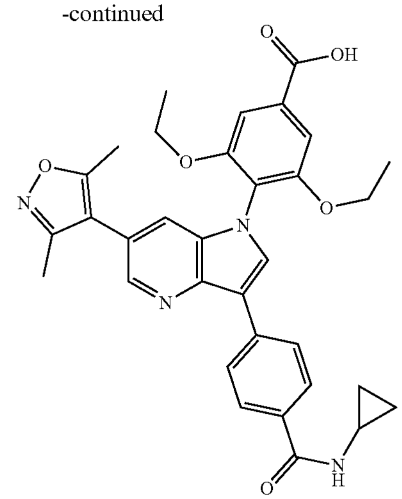

P-0218

Step 1: Preparation of ethyl 4-(6-(3,5-dimethylisoxazol-4-yl)-1H-pyrrolo[3,2-b]pyridin-1-yl)-3,5-diethoxybenzoate 14

3,5-dimethyl-4-(1H-pyrrolo[3,2-b]pyridin-6-yl)isoxazole (11, 0.60 g, 2.81 mmol), ethyl 4-bromo-3,5-diethoxybenzoate (1.34 g, 4.21 mmol), potassium phosphate tribasic (1.25 g, 5.91 mmol), copper (I) iodide (0.11 g, 0.56 mmol), trans N,N'-dimethylcyclohexane-1,2-diamine (0.80 g, 5.6 mmol) were combined in toluene (6 ml) and flushed with argon. Then the reaction mixture was allowed to stir at 110° C. overnight. The reaction mixture was cooled to ambient temperature, diluted with 2 mL of ethyl acetate and filtered through a pad of Celite with ethyl acetate. This material was purified by silica gel column chromatography (0-50% ethyl acetate in hexane) to provide ethyl 4-(6-(3,5-dimethylisoxazol-4-yl)-1H-pyrrolo[3,2-b]pyridin-1-yl)-3,5-diethoxybenzoate (14).

Step 2: Preparation of ethyl 4-(3-bromo-6-(3,5-dimethylisoxazol-4-yl)-1H-pyrrolo[3,2-b]pyridin-1-yl)-3,5-diethoxybenzoate 15

To a 100 mL round bottom flask was added ethyl 4-(6-(3,5-dimethylisoxazol-4-yl)-1H-pyrrolo[3,2-b]pyridin-1-yl)-3,5-diethoxybenzoate (14, 620 mg, 1.38 mmol) and acetonitrile (14 mL). The reaction flask was placed under $N_2$ and cooled to 0° C., followed by the slow addition of N-bromosuccinimide (246 mg, 1.38 mmol). The reaction mixture was stirred at 0° C. and allowed to warm to room temperature for 2 hours. The reaction was diluted with ethyl acetate and partitioned between water and ethyl acetate. The extracted organic fraction was washed with brine and dried over magnesium sulfate and filtered. The filtrate was concentrated under reduced pressure and was purified by silica gel column chromatography (0-60% ethyl acetate in hexane) to provide ethyl 4-(3-bromo-6-(3,5-dimethylisoxazol-4-yl)-1H-pyrrolo[3,2-b]pyridin-1-yl)-3,5-diethoxybenzoate (15).

Step 3: Preparation of 4-(3-(4-(cyclopropylcarbamoyl)phenyl)-6-(3,5-dimethylisoxazol-4-yl)-1H-pyrrolo[3,2-b]pyridin-1-yl)-3,5-diethoxybenzoic acid P-0218

Ethyl 4-(3-bromo-6-(3,5-dimethylisoxazol-4-yl)-1H-pyrrolo[3,2-b]pyridin-1-yl)-3,5-diethoxybenzoate (15, 40 mg, 0.08 mmol), (4-(cyclopropylcarbamoyl)phenyl)boronic acid (31 mg, 0.15 mmol), 1,1'-bis(diphenylphosphino)ferrocene-palladium(II) dichloride dichloromethane complex (8.7 mg, 0.011 mmol), and 2.5M aqueous $K_2CO_3$ (0.09 ml) were combined in dioxane/acetonitrile (0.5 ml each) and heated to 100° C. for 8 hrs. The reaction was then cooled, filtered through celite, and purified by silica gel column chromatography (0-10% methanol in dichloromethane) to provide 4-(3-(4-(cyclopropylcarbamoyl)phenyl)-6-(3,5-dimethylisoxazol-4-yl)-1H-pyrrolo[3,2-b]pyridin-1-yl)-3,5-diethoxybenzoic acid (P-0218). MS (ESI) $[M+H^+]^+$=581.2.

Example 6

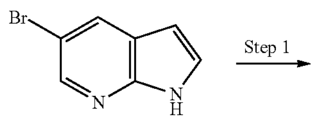

16

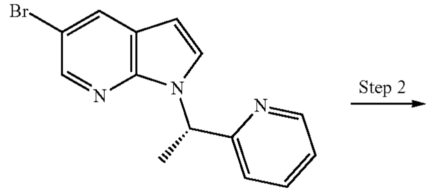

17

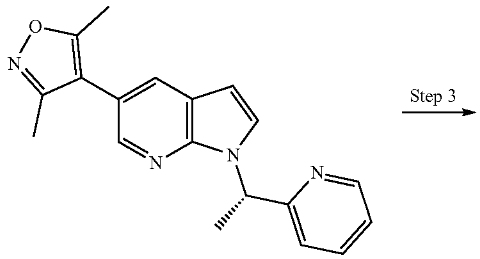

18

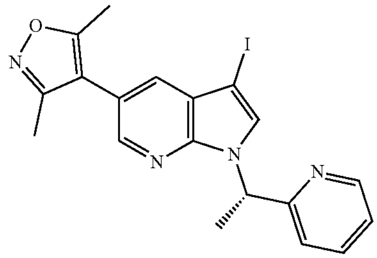

19

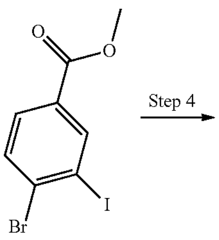

20

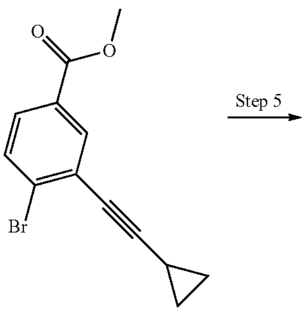

21

-continued

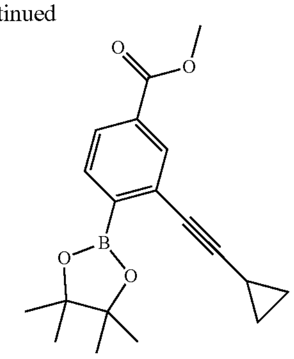

22

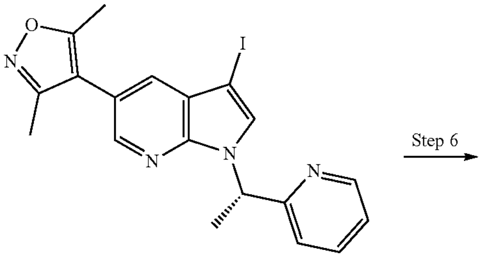

19

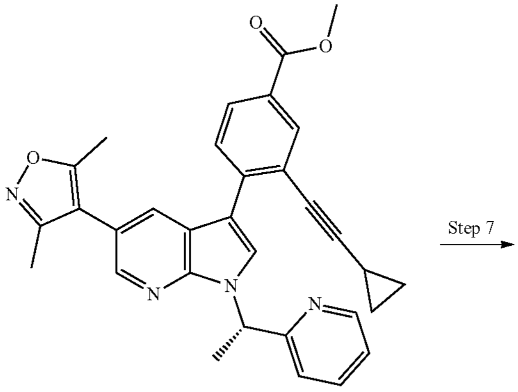

23

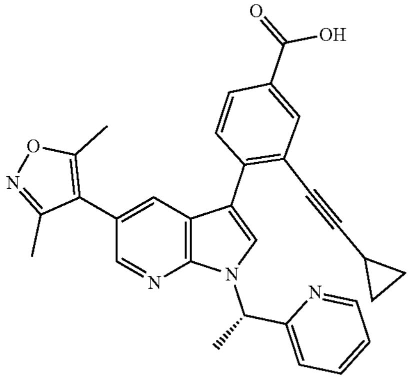

P-0178

Step 1: Preparation of (S)-5-bromo-1-(1-(pyridin-2-yl)ethyl)-1H-pyrrolo[2,3-b]pyridine 17

To an ice cold solution of 5-bromo-H-pyrrolo[2,3-b]pyridine (16, 689 mg, 3.5 mmol), (1R)-1-(2-pyridyl)ethanol (646 mg, 5.25 mmol) and triphenylphosphine (1377 mg, 5.25 mmol) in THF (35 ml) under nitrogen gas was added slowly diisopropylazodicarboxylate (1.04 ml, 5.25 mmol). The mixture was stirred and allowed to reach room temperature for 15 hours. The mixture was concentrated down under reduced pressure and was purified by silica gel column chromatography eluting with 20% ethyl acetate in hexane to provide (S)-5-bromo-1-(1-(pyridin-2-yl)ethyl)-1H-pyrrolo[2,3-b]pyridine (17). MS (ESI) $[M+H^+]^+$=303.9.

Step 2: Preparation of (S)-3,5-dimethyl-4-(1-(1-(pyridin-2-yl)ethyl)-1H-pyrrolo[2,3-b]pyridin-5-yl) isoxazole 18

A mixture of (S)-5-bromo-1-(1-(pyridin-2-yl)ethyl)-1H-pyrrolo[2,3-b]pyridine (17, 618 mg, 2.05 mmol), 3,5-dimethyl-4-(4,4,5,5-tetramethyl-1,3,2-dioxaborolan-2-yl)isoxazole (502 mg, 2.25 mmol) and 1,1'-bis(diphenylphosphino) ferrocene-palladium(II) dichloride dichloromethane complex (149 mg, 0.182 mmol) in dioxane (20 ml) was purged with nitrogen gas, then 2.5M $K_2CO_3$ (2.5 ml) was added. The mixture was heated at 100° C. for 4 hours. The sample was diluted with ethyl acetate and dried over anhydrous magnesium sulfate, filtered and concentrated under reduced pressure. The material was purified by silica gel column chromatography eluting with 40% ethyl acetate in hexane to provide (S)-3,5-dimethyl-4-(1-(1-(pyridin-2-yl) ethyl)-1H-pyrrolo[2,3-b]pyridin-5-yl)isoxazole (18). MS (ESI) $[M+H^+]^+$=319.5.

Step 3: Preparation of (S)-4-(3-iodo-1-(1-(pyridin-2-yl)ethyl)-1H-pyrrolo[2,3-b]pyridin-5-yl)-3,5-dimethylisoxazole 19

To an ice cold solution of (S)-3,5-dimethyl-4-(1-(1-(pyridin-2-yl)ethyl)-1H-pyrrolo[2,3-b]pyridin-5-yl)isoxazole (18, 620 mg, 1.56 mmol) in acetonitrile (20 ml) was added N-iodosuccinimide (420 mg, 1.87 mmol). The mixture was stirred to reach room temperature for 2 hrs. The mixture was diluted with saturated aqueous $Na_2S_2O_3$ solution, extracted with ethyl acetate and the organic layer was washed with water followed by brine. The organic layer was dried over anhydrous magnesium sulfate, filtered and concentrated under reduced pressure. The material was purified by silica gel column chromatography eluting with 40% ethyl acetate in hexane to provide (S)-4-(3-iodo-1-(1-(pyridin-2-yl) ethyl)-1H-pyrrolo[2,3-b]pyridin-5-yl)-3,5-dimethylisoxazole (19). MS (ESI) $[M+H^+]^+$=445.0.

Step 4: Preparation of methyl 4-bromo-3-(cyclopropylethynyl)benzoate 21

A mixture of methyl 4-bromo-3-iodo-benzoate (20, 1022 mg, 3 mmol), bis(triphenylphosphine) palladium(II) dichloride (63 mg, 0.09 mmol) and copper(I) iodide (17 mg, 0.09 mmol) in (1:3) triethylamine in acetonitrile (20.0 ml) was purged with nitrogen gas, then ethynylcyclopropane (238 mg, 3.6 mmol) was added. The mixture was heated at 60° C. for 5 hours. The mixture was concentrated down under reduced pressure and purified by silica gel column chromatography eluting with 30% dichloromethane in hexane to provide methyl 4-bromo-3-(cyclopropylethynyl)benzoate (21). MS (ESI) $[M+H^+]^+$=280.9.

Step 5: Preparation of methyl 3-(cyclopropylethynyl)-4-(4,4,5,5-tetramethyl-1,3,2-dioxaborolan-2-yl) benzoate 22

A mixture of methyl 4-bromo-3-(cyclopropylethynyl) benzoate (21, 307 mg, 1.1 mmol), bis(pinacolato)diboron (419 mg, 1.65 mmol), 1,1'-bis(diphenylphosphino)ferrocene-palladium(II) dichloride dichloromethane complex (89.83 mg, 0.104 mmol) and potassium acetate (323 mg, 3.3 mmol) in dioxane (10 ml) was heated at 100° C. for 15 hrs. The mixture was diluted with ethyl acetate which was washed with water, brine and dried over anhydrous magnesium sulfate. The organic layer was filtered and concentrated under reduced pressure. The sample was purified by silica gel column chromatography eluting with 10% ethyl acetate in hexane to provide methyl 3-(cyclopropylethynyl)-4-(4,4,5,5-tetramethyl-1,3,2-dioxaborolan-2-yl)benzoate (22). MS (ESI) $[M+H^+]^+$=327.1.

Step 6: Preparation of methyl (S)-3-(cyclopropylethynyl)-4-(5-(3,5-dimethylisoxazol-4-yl)-1-(1-(pyridin-2-yl)ethyl)-1H-pyrrolo[2,3-b]pyridin-3-yl) benzoate 23

To (S)-4-(3-iodo-1-(1-(pyridin-2-yl)ethyl)-1H-pyrrolo[2,3-b]pyridin-5-yl)-3,5-dimethylisoxazole (19, 62 mg, 0.14 mmol), methyl 3-(2-cyclopropylethynyl)-4-(4,4,5,5-tetramethyl-1,3,2-dioxaborolan-2-yl)benzoate (22, 150 mg, 0.46 mmol) and 1,1'-bis(diphenylphosphino)ferrocene-palladium (II) dichloride dichloromethane complex (11.43 mg, 0.013 mmol) in dioxane (2 ml) was added 2.5M $K_2CO_3$ (0.170 ml). The mixture was heated at 100° C. for 4 hours. The sample was diluted with ethyl acetate which was washed with water, then brine and dried over anhydrous magnesium sulfate. The organic layer was filtered and concentrated under reduced pressure. The material was purified by silica gel column chromatography eluting with 50% ethyl acetate in hexane to provide methyl (S)-3-(cyclopropylethynyl)-4-(5-(3,5-dimethylisoxazol-4-yl)-1-(1-(pyridin-2-yl)ethyl)-1H-pyrrolo[2,3-b]pyridin-3-yl)benzoate (23). MS (ESI) $[M+H^+]^+$=517.2.

Step 7: Preparation of (S)-3-(cyclopropylethynyl)-4-(5-(3,5-dimethylisoxazol-4-yl)-1-(1-(pyridin-2-yl) ethyl)-1H-pyrrolo[2,3-b]pyridin-3-yl)benzoic acid P-0178

To a mixture of methyl (S)-3-(cyclopropylethynyl)-4-(5-(3,5-dimethylisoxazol-4-yl)-1-(1-(pyridin-2-yl)ethyl)-1H-pyrrolo[2,3-b]pyridin-3-yl)benzoate (23.12 mg, 0.02 mmol) in (1:1) THF/MeOH (1 ml) was added aqueous 4.18 M LiOH (0.020 ml). The mixture was stirred at 70° C. for 3 hrs. The mixture was acidified with 3M HCl/MeOH, diluted with ethyl acetate and concentrated down under reduced pressure. The material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide (S)-3-(cyclopropylethynyl)-4-(5-(3,5-dimethylisoxazol-4-yl)-1-(1-(pyridin-2-yl)ethyl)-1H-pyrrolo[2,3-b]pyridin-3-yl)benzoic acid (P-0178). MS (ESI) $[M+H^+]^+$=503.2.

Example 7

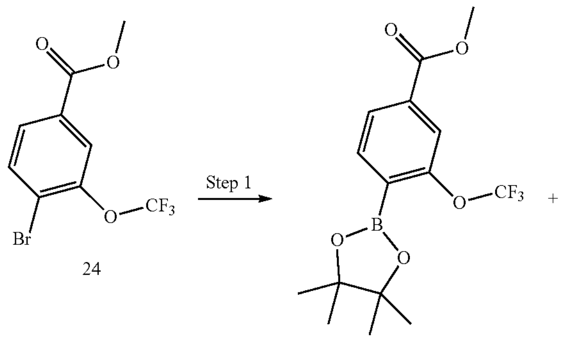

24

25

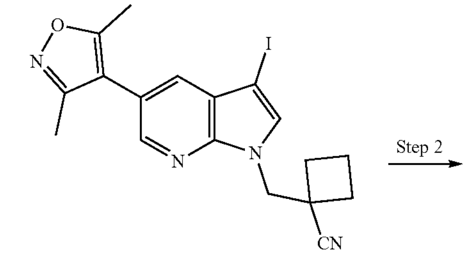

26

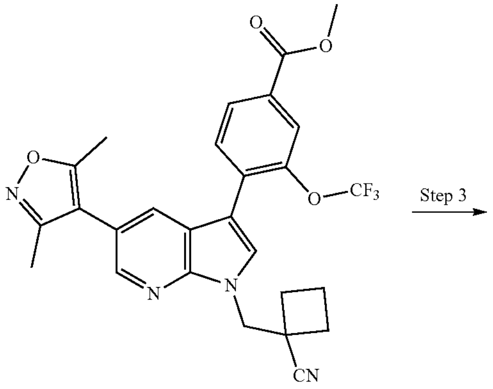

27

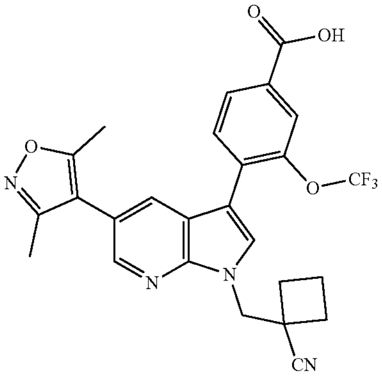

P-0364

Step 1: Preparation of methyl 4-(4,4,5,5-tetramethyl-1,3,2-dioxaborolan-2-yl)-3-(trifluoromethoxy)benzoate 25

A mixture of methyl 4-bromo-3-(trifluoromethoxy)benzoate (344 mg, 1.15 mmol), bis(pinacolato)diboron (24, 584 mg, 2.3 mmol), and 1,1'-bis(diphenylphosphino)ferrocene-palladium(II) dichloride dichloromethane complex (94 mg, 0.115 mmol) and potassium acetate (339 mg, 3.45 mmol) in dioxane (12 ml) was heated at 100° C. for 15 hrs. The mixture was diluted with ethyl acetate which was washed with water and brine, then dried over anhydrous magnesium sulfate. The organic layer was filtered and concentrated down under reduced pressure. The material was purified by silica gel column chromatography eluting with 10% ethyl acetate in hexane to provide methyl 4-(4,4,5,5-tetramethyl-1,3,2-dioxaborolan-2-yl)-3-(trifluoromethoxy)benzoate (25). MS (ESI) $[M+H^+]^+=347.1$.

Step 2: Preparation of methyl 4-(1-((1-cyanocyclobutyl)methyl)-5-(3,5-dimethylisoxazol-4-yl)-1H-pyrrolo[2,3-b]pyridin-3-yl)-3-(trifluoromethoxy)benzoate 27

To a mixture of 1-((5-(3,5-dimethylisoxazol-4-yl)-3-iodo-1H-pyrrolo[2,3-b]pyridin-1-yl)methyl)cyclobutane-1-carbonitrile (26.52 mg, 0.12 mmol, prepared in a manner similar to compound 19), methyl 4-(4,4,5,5-tetramethyl-1,3,2-dioxaborolan-2-yl)-3-(trifluoromethoxy)benzoate (25, 54 mg, 0.16 mmol) and 1,1'-bis(diphenylphosphino)ferrocene-palladium(II) dichloride dichloromethane complex (9.8 mg, 0.012 mmol) in dioxane (2 ml), purged with nitrogen gas, was added aqueous 2.5M potassium carbonate (0.150 ml). The mixture was heated at 110° C. for 3 hours. The sample was diluted with ethyl acetate and dried over anhydrous magnesium sulfate, filtered and concentrated under reduced pressure. The material was purified by silica gel column chromatography eluting with 40% ethyl acetate in hexane to provide methyl 4-(1-((1-cyanocyclobutyl)methyl)-5-(3,5-dimethylisoxazol-4-yl)-1H-pyrrolo[2,3-b]pyridin-3-yl)-3-(trifluoromethoxy)benzoate (27). MS (ESI) $[M+H^+]^+=525.1$.

Step 3: Preparation of 4-(1-((1-cyanocyclobutyl)methyl)-5-(3,5-dimethylisoxazol-4-yl)-1H-pyrrolo[2,3-b]pyridin-3-yl)-3-(trifluoromethoxy)benzoic acid P-0364

To methyl 4-(1-((1-cyanocyclobutyl)methyl)-5-(3,5-dimethylisoxazol-4-yl)-1H-pyrrolo[2,3-b]pyridin-3-yl)-3-(trifluoromethoxy)benzoate (27, 31 mg, 0.06 mmol) in (1:1) THF/MeOH (2.0 ml) was added aqueous 4.18 M LiOH (0.050 ml). The mixture was stirred at 70° C. for 2 hrs. The mixture was diluted with ethyl acetate, acidified with 1N HCl in MeOH and concentrated under reduced pressure. The material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 4-(1-((1-cyanocyclobutyl)methyl)-5-(3,5-dimethylisoxazol-4-yl)-1H-pyrrolo[2,3-b]pyridin-3-yl)-3-(trifluoromethoxy)benzoic acid (P-0364). MS (ESI) $[M+H^+]^+=511.2$.

Example 8

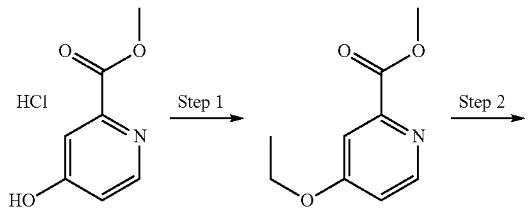

28 29

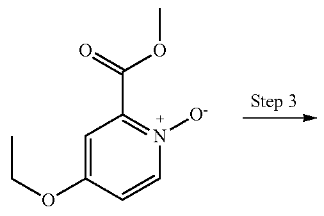

30

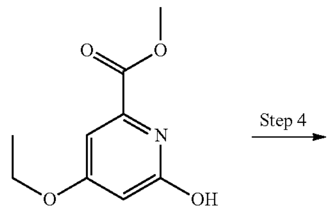

31

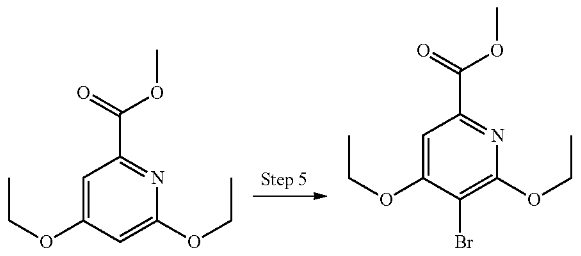

32 33

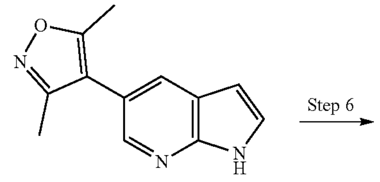

34

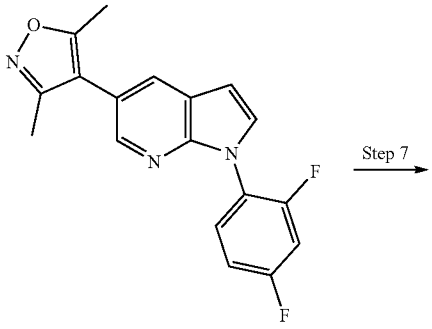

35

-continued

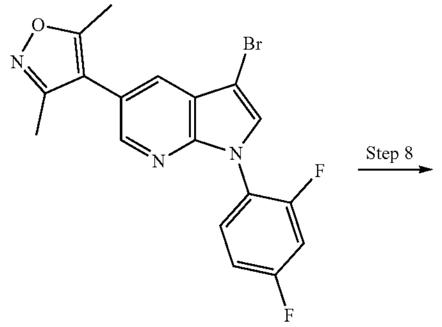

36

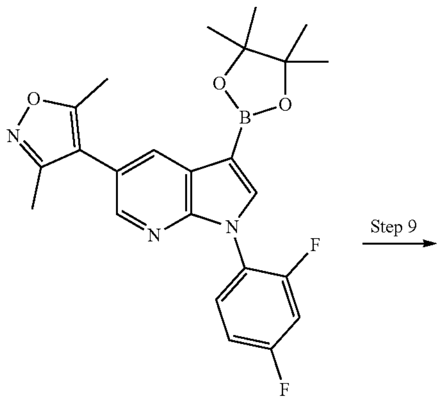

37

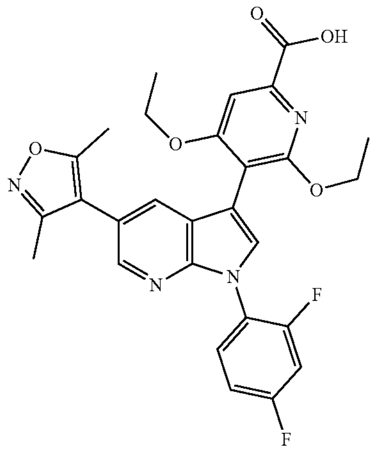

P-0329

Step 1: Preparation of methyl 4-ethoxypicolinate 29

A mixture of methyl 4-hydroxypyridine-2-carboxylate hydrochloride (28, 3.79 g, 20.00 mmol), iodoethane (2.41 ml, 30.00 mmol), potassium carbonate (8.29 g, 60.00 mmol) and N,N-dimethylformamide (60 mL) was stirred at room temperature overnight. The reaction mixture was poured into water (200 mL) and extracted with ethyl acetate/hexane=1/1 (600 mL). The organic layer was isolated, washed with water (2×100 mL), brine (100 mL), dried over anhydrous sodium sulfate, filtered through a short silica gel pad and concentrated under reduced pressure. This provided methyl 4-ethoxypicolinate (29).

Step 2: Preparation of 4-ethoxy-2-(methoxycarbonyl)pyridine 1-oxide 30

To a solution of methyl 4-ethoxypicolinate (29, 2.53 g, 13.96 mmol) in ethyl acetate (40.0 mL) was added mCPBA (77%, 3.755 g, 16.76 mmol) portionwise at 0° C. and stirred at room temperature for 22 hrs. Additional mCPBA (77%, 1.876 g, 8.38 mmol) was added and the mixture was stirred for another 5 hrs. The reaction was diluted with ethyl acetate (200 mL) and washed with saturated aqueous sodium bicarbonate (50 mL). The separated aqueous phase was extracted with DCM/MeOH=9/1 (5×50 mL) and the combined organic layers were dried over anhydrous sodium sulfate, filtered and concentrated under reduced pressure. The resultant material was purified by silica gel column chromatography (0-10% methanol in dichloromethane) to provide 4-ethoxy-2-(methoxycarbonyl)pyridine 1-oxide (30).

Step 3: Preparation of methyl 4-ethoxy-6-hydroxypicolinate 31

To a solution of 4-ethoxy-2-(methoxycarbonyl)pyridine 1-oxide (30, 740 mg, 3.75 mmol) and triethylamine (1.57 mL, 11.26 mmol) in THF (20.0 mL) was added trifluoroacetic anhydride (1.57 mL, 11.86 mmol) dropwise over 5 min at 0° C. The mixture was stirred for another 4 hours at 0° C. The reaction was diluted with dichloromethane (200 mL) and extracted with a mixed solution of saturated aqueous sodium bicarbonate (10 mL) and brine (50 mL). The organic layer was separated and dried over anhydrous sodium sulfate, filtered and concentrated under reduced pressure. The resultant crude material was purified by silica gel column chromatography (0-10% methanol in dichloromethane) to provide methyl 4-ethoxy-6-hydroxypicolinate (31). MS (ESI) $[M+H^+]^+$=198.1.

Step 4: Preparation of methyl 4,6-diethoxypicolinate 32

To a mixture of methyl 4-ethoxy-6-hydroxypicolinate (31, 313 mg, 1.59 mmol), potassium carbonate (329 mg, 2.38 mmol) in DMF (8 mL) was added iodoethane (0.255 mL, 3.18 mmol) and the mixture was stirred overnight at room temperature. The reaction was diluted with ethyl acetate/hexane (1/1, 150 ml) and was extracted with water (50 ml, 3×) and brine (30 ml). The organic layer was dried over anhydrous sodium sulfate, filtered through short silica gel pad and concentrated under reduced pressure. The resultant material was purified with silica gel column chromatography (0-20% ethyl acetate in hexane) to provide methyl 4,6-diethoxypicolinate (32).

Step 5: Preparation of methyl 5-bromo-4,6-diethoxypicolinate 33

To a solution of methyl 4,6-diethoxypicolinate (32, 95 mg, 0.42 mmol) in DMF (1.5 ml) was added N-bromosuccinimide (76 mg, 0.43 mmol) and the mixture was stirred at 50° C. overnight. An additional 2 equivalents of N-bromosuccinimide (15 mg, 0.18 mmol) was added and stirred for another 1 hour. LC/MS showed reaction incomplete, so another 2 equivalents of N-bromosuccinimide (15 mg, 0.18 mmol) was added and stirred for another 1 hour. LC/MS showed that all starting material was consumed and conversion was complete. The reaction was diluted with ethyl acetate/hexane (1/1, 20 mL) and was extracted with 5% aqueous sodium sodium thiosulfate (3 mL), water (5 mL) and brine (5 mL). The organic layer was dried over anhydrous sodium sulfate and concentrated under reduced pressure. The material was purified by silica gel column chromatography (0-15% ethyl acetate in hexane) to provide methyl 5-bromo-4,6-diethoxypicolinate (33).

Step 6: Preparation of 4-(1-(2,4-difluorophenyl)-1H-pyrrolo[2,3-b]pyridin-5-yl)-3,5-dimethylisoxazole 35

A mixture of 3,5-dimethyl-4-(1H-pyrrolo[2,3-b]pyridin-5-yl)isoxazole (34, 2.13 g, 10.00 mmol), 2,4-difluorobromobenzene (3.39 mL, 30.00 mmol), potassium carbonate (6.91 g, 50.00 mmol), CuI (571 mg, 3.00 mmol), trans N,N'-dimethylcyclohexane-1,2-diamine (0.473 mL, 3.00 mmol) in toluene (100 mL) was stirred at 110° C. for 7 hours. Additional 2,4-difluorobromobenzene (2.26 mL, 20.00 mmol) was added and the reaction was continued overnight. The reaction mixture was filtered through Celite, washing with ethyl acetate. The filtrate was concentrated under reduced pressure and purified by silica gel column chromatography (0-50% ethyl acetate in hexane) to provide 4-(1-(2,4-difluorophenyl)-1H-pyrrolo[2,3-b]pyridin-5-yl)-3,5-dimethylisoxazole (35).

Step 7: Preparation of 4-(3-bromo-1-(2,4-difluorophenyl)-1H-pyrrolo[2,3-b]pyridin-5-yl)-3,5-dimethylisoxazole 36

To a solution of 4-(1-(2,4-difluorophenyl)-1H-pyrrolo[2,3-b]pyridin-5-yl)-3,5-dimethylisoxazole (35, 2.47 g, 7.59 mmol) in acetonitrile (75 ml) at 0° C. was added N-bromosuccinimide (1.49 g, 8.35 mmol). The reaction was stirred for 30 min at 0° C. and then for 20 min at room temperature followed by the addition of aqueous 5% sodium thiosulfate (20 ml). The reaction was concentrated under reduced pressure to remove acetonitrile and then saturated aqueous sodium bicarbonate was added and the mixture was extracted with ethyl acetate. The organic layer was washed with brine (50 ml), dried over anhydrous sodium sulfate, filtered and concentrated under reduced pressure. The material was purified by silica gel column chromatography (0-20% ethyl acetate in hexane) to provide 4-(3-bromo-1-(2,4-difluorophenyl)-1H-pyrrolo[2,3-b]pyridin-5-yl)-3,5-dimethylisoxazole (36).

Step 8: Preparation of 4-(1-(2,4-difluorophenyl)-3-(4,4,5,5-tetramethyl-1,3,2-dioxaborolan-2-yl)-1H-pyrrolo[2,3-b]pyridin-5-yl)-3,5-dimethylisoxazole 37

A mixture of 4-(3-bromo-1-(2,4-difluorophenyl)-1H-pyrrolo[2,3-b]pyridin-5-yl)-3,5-dimethylisoxazole (36, 1.68 g, 4.15 mmol), bis(pinacolato)diboron (2.11 g, 8.30 mmol), X-Phos (119 mg, 0.249 mmol), Pd2dba3 (114 mg, 0.125 mmol), potassium acetate (1631 mg, 16.62 mmol) and toluene (40 mL) was allowed to stir at 95° C. for 8 hours under a nitrogen atmosphere. The reaction was filtered through Celite and concentrated under reduced pressure. The mixture was purified by silica gel column chromatography (0-10% ethyl acetate in dichloromethane) to provide 4-(1-(2,4-difluorophenyl)-3-(4,4,5,5-tetramethyl-1,3,2-dioxaborolan-2-yl)-1H-pyrrolo[2,3-b]pyridin-5-yl)-3,5-dimethylisoxazole (37).

Step 9: Preparation of 5-(1-(2,4-difluorophenyl)-5-(3,5-dimethylisoxazol-4-yl)-1H-pyrrolo[2,3-b]pyridin-3-yl)-4,6-diethoxypicolinic acid P-0329

4-(1-(2,4-difluorophenyl)-3-(4,4,5,5-tetramethyl-1,3,2-dioxaborolan-2-yl)-1H-pyrrolo[2,3-b]pyridin-5-yl)-3,5-dimethylisoxazole (37, 57 mg, 0.095 mmol), methyl 5-bromo-4,6-diethoxypicolinate (33, 29 mg, 0.095 mmol), $Pd(OAc)_2$ (1.1 mg, 0.005 mmol), S-Phos (2.0 mg, 0.005 mmol), potassium phosphate (61 mg, 0.286 mmol), 1,4-dioxane (1 ml), and water (0.2 ml) was allowed to stir for 4 hours at 95° C. Then, aqueous 1 N HCl (1 ml) was added and the mixture was diluted with dichloromethane/methanol (10/1, 20 ml) and filtered through Celite. The mother liquor was dried over anhydrous sodium sulfate, filtered and concentrated under reduced pressure. The resultant crude material was purified by silica gel column chromatography (0-10% methanol in dichloromethane) to give the methyl ester of P-0329 (85 mg). This material was dissolved in THF (0.75 ml) and methanol (0.25 ml) and aqueous 2N LiOH aq. (0.25 ml) was added to the solution and the resultant mixture was stirred for 2 hours at room temperature. After the addition of aqueous 1 N HCl (0.25 ml), the mixture was concentrated under reduced pressure and purified by silica gel column chromatography (0-10% methanol in dichloromethane) to provide 5-(1-(2,4-difluorophenyl)-5-(3,5-dimethylisoxazol-4-yl)-1H-pyrrolo[2,3-b]pyridin-3-yl)-4,6-diethoxypicolinic acid (P-0329). MS (ESI) $[M+H^+]^+$=535.2.

Example 9

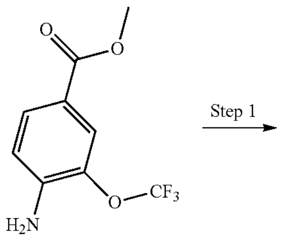

38

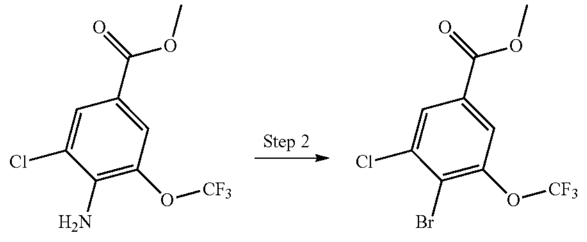

39 40

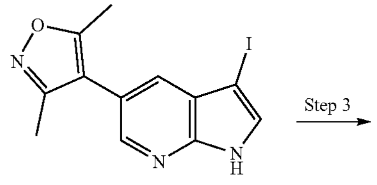

3

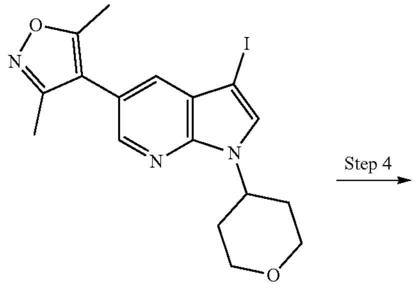

41

-continued

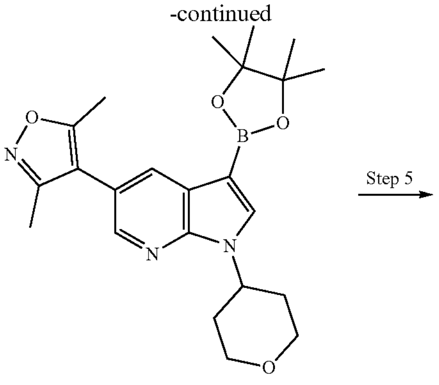

42

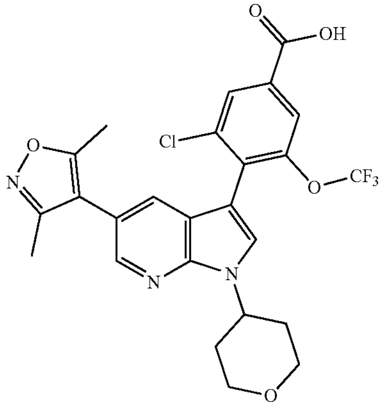

P-0355

Step 1: Preparation of methyl 4-amino-3-chloro-5-(trifluoromethoxy)benzoate 39

To a solution of methyl 4-amino-3-(trifluoromethoxy) benzoate (38, 1.06 g, 4.5 mmol) in acetonitrile (40 ml) was added N-chlorosuccinimide (631 mg, 4.73 mmol). The mixture was heated at 80° C. for 3 hours. The reaction was diluted with saturated aqueous sodium thiosulfate and extracted with ethyl acetate which was washed with water followed by brine. The organic layer was dried over anhydrous magnesium sulfate, filtered and concentrated under reduced pressure to provide methyl 4-amino-3-chloro-5-(trifluoromethoxy)benzoate (39). MS (ESI) $[M+H^+]^+$ =270.0.

Step 2: Preparation of methyl 4-bromo-3-chloro-5-(trifluoromethoxy)benzoate 40

To a mixture of methyl 4-amino-3-chloro-5-(trifluoromethoxy)benzoate (39, 502 mg, 1.86 mmol) in aqueous HBr (10 ml) at 0° C. was added slowly sodium nitrite (193 mg, 2.79 mmol). The mixture was stirred at 0° C. for 10 minutes, then copper (I) bromide (294 mg, 2.05 mmol) was added. The mixture was allowed to warm to room temperature over 3 hours. The reaction mixture was poured in to ice water and extracted with ethyl acetate. The organic layer was washed with water followed by brine, dried over anhydrous magnesium sulfate, filtered and concentrated under reduced pressure. The material was purified by silica gel column chromatography (20% dichloromethane in hexane) to provide methyl 4-bromo-3-chloro-5-(trifluoromethoxy)benzoate (40).

Step 3: Preparation of 4-(3-iodo-1-(tetrahydro-2H-pyran-4-yl)-1H-pyrrolo[2,3-b]pyridin-5-yl)-3,5-dimethylisoxazole 41

1M diisopropyl azodicarboxylate in THF (19.46 mL, 19.46 mmol, 1.5 equiv) was added dropwise to a solution of 4-(3-iodo-H-pyrrolo[2,3-b]pyridin-5-yl)-3,5-dimethylisoxazole (3, 4.4 g, 12.97 mmol, 1 equiv), tetrahydro-2H-pyran-4-ol (1.99 g, 19.5 mmol, 1.5 equiv) and triphenylphosphine (5.10 g, 19.46 mmol, 1.5 equiv) in THF (65 mL) at −20° C. The reaction was allowed to warm to room temperature and stirred overnight. The volatiles were removed under reduced pressure and the residue was triturated with toluene (100 mL) and filtered to give 4-(3-iodo-1-(tetrahydro-2H-pyran-4-yl)-1H-pyrrolo[2,3-b]pyridin-5-yl)-3,5-dimethylisoxazole (41).

Step 4: Preparation of 3,5-dimethyl-4-(1-(tetrahydro-2H-pyran-4-yl)-3-(4,4,5,5-tetramethyl-1,3,2-dioxaborolan-2-yl)-1H-pyrrolo[2,3-b]pyridin-5-yl)isoxazole 42

2M i-propylmagnesiumchloride (9.1 mL, 18.15 mmol, 2.4 equiv) in THF was added to a slurry of 4-(3-iodo-1-(tetrahydro-2H-pyran-4-yl)-1H-pyrrolo[2,3-b]pyridin-5-yl)-3,5-dimethylisoxazole (41, 3.2 g, 7.56 mmol, 1 equiv) in THF (76 mL) at 0° C. The reaction was warmed to room temperature and stirred for 30 minutes resulting in dissolution, at which point metal/halogen exchange was determined to be complete by 1H NMR. The solution was cooled to 0° C. and pinacolborane (3.29 mL, 22.68 mmol, 3 equiv) was added. The reaction was warmed to room temperature and stirred overnight. The reaction was poured into saturated ammonium chloride (200 mL) and extracted with ethyl acetate (200 mL). The organic layer was washed with saturated brine (200 mL) and concentrated under reduced pressure. The residue was purified on by silica gel column chromatography (0 to 100% ethyl acetate in heptanes). This provided 3,5-dimethyl-4-(1-(tetrahydro-2H-pyran-4-yl)-3-(4,4,5,5-tetramethyl-1,3,2-dioxaborolan-2-yl)-1H-pyrrolo[2,3-b]pyridin-5-yl)isoxazole (42).

Step 5: Preparation of 3-chloro-4-(5-(3,5-dimethylisoxazol-4-yl)-1-(tetrahydro-2H-pyran-4-yl)-1H-pyrrolo[2,3-b]pyridin-3-yl)-5-(trifluoromethoxy)benzoic acid P-0355

To a mixture of 3,5-dimethyl-4-(1-(tetrahydro-2H-pyran-4-yl)-3-(4,4,5,5-tetramethyl-1,3,2-dioxaborolan-2-yl)-1H-pyrrolo[2,3-b]pyridin-5-yl)isoxazole (42, 0.1 g, 0.24 mmol), methyl 4-bromo-3-chloro-5-(trifluoromethoxy)benzoate (40, 0.12 g, 0.35 mmol) and 1,1'-bis(diphenylphosphino)ferrocene-palladium(II) dichloride dichloromethane complex (20 mg, 0.025 mmol) in dioxane (3 ml) was added aqueous 1M potassium carbonate (0.47 ml). The reaction was allowed to stir at 100° C. for 3 hours. The reaction was allowed to cool and then was diluted with ethyl acetate and evaporated on to silica. The methyl ester intermediate was purified by silica gel column chromatography (0-100% ethyl acetate in hexanes). The resulting methyl ester of P-0355 was dissolved in methanol/THF (1:1, 4 ml) and aqueous 1M lithium hydroxide (1.18 ml) was added. The mixture was allowed to stir at room temperature for 3 hours. The reaction was quenched with solid extracted sodium sulfate, filtered, and the filtrate was concentrated under reduced pressure. The material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 3-chloro-4-(5-(3,5-dimethylisoxazol-4-yl)-1-(tetrahydro-2H-pyran-4-yl)-1H-pyrrolo[2,3-b]pyridin-3-yl)-5-(trifluoromethoxy)benzoic acid (P-0355). MS (ESI) $[M+H^+]^+$=536.0.

Example 10

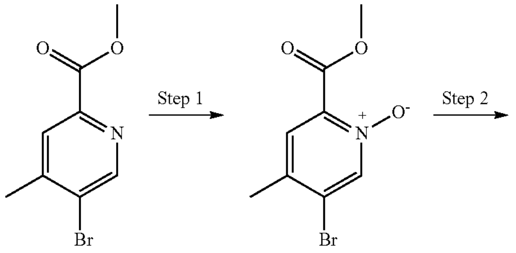

43 44

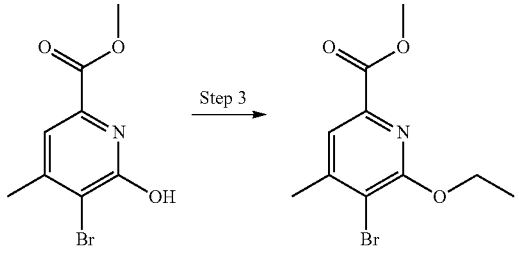

45 46

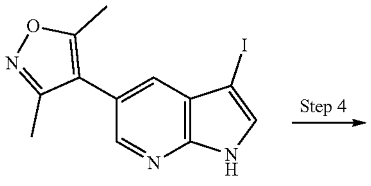

3

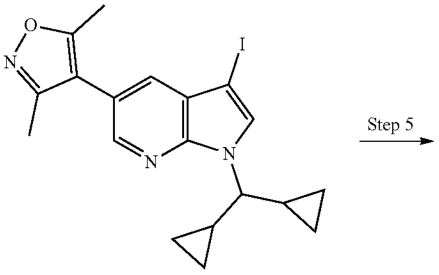

47

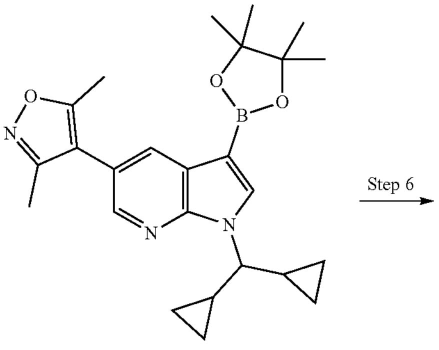

48

-continued

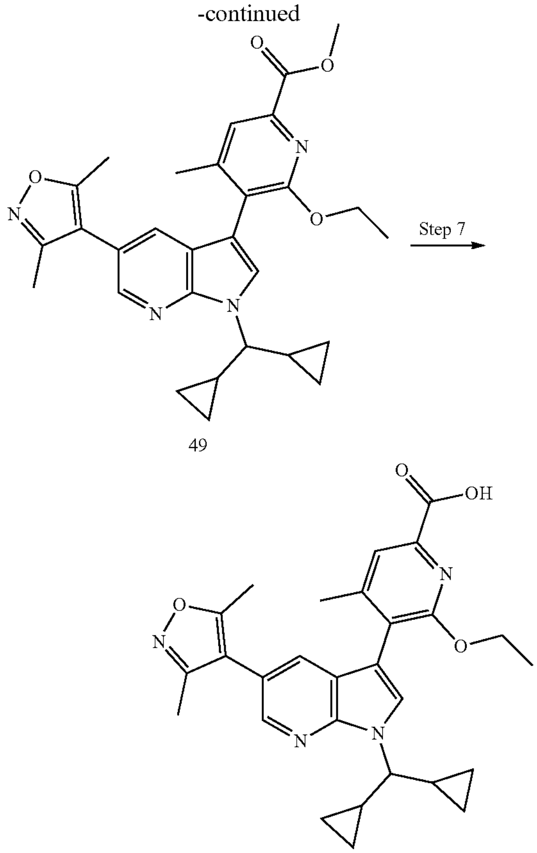

49

P-0417

Step 1: Preparation of 5-bromo-2-(methoxycarbonyl)-4-methylpyridine 1-oxide 44

To methyl 5-bromo-4-methylpicolinate (43, 1.00 g, 4.35 mmol) in 1,2-dichloroethane (10 ml) was added mCPBA (77%, 3.00 g, 13.39 mmol) in one portion. The reaction mixture was allowed to stir at room temperature for 16 hours. The reaction was filtered and the filtrate was concentrated under reduced pressure. The material was purified by silica gel column chromatography (0-100% ethyl acetate in hexane). This provided 5-bromo-2-(methoxycarbonyl)-4-methylpyridine 1-oxide (44). MS (ESI) [M+H]+=246.0.

Step 2: Preparation of methyl 5-bromo-6-hydroxy-4-methylpicolinate 45

To a solution of 5-bromo-2-(methoxycarbonyl)-4-methylpyridine 1-oxide (44, 480 mg, 1.95 mmol) in dichloromethane (5 ml) and triethylamine (0.8 ml, 5.74 mmol) under argon gas and cooled to 0° C. was added trifluoroacetic anhydride (0.7 ml, 5.04 mmol). The reaction mixture was allowed to warm to room temperature and then quenched by the addition of water (5 ml). The reaction mixture was extracted with ethyl acetate and water. The organic layer was washed with water and then brine, dried over anhydrous magnesium sulfate and filtered. The filtrate was concentrated under reduced pressure and was purified by silica gel column chromatography (0-75% ethyl acetate in hexane). This provided methyl 5-bromo-6-hydroxy-4-methylpicolinate (45). MS (ESI) $[M+H^+]^+$=246.0.

Step 3: Preparation of methyl 5-bromo-6-ethoxy-4-methylpicolinate 46

A mixture of methyl 5-bromo-6-hydroxy-4-methylpicolinate (45, 50 mg, 0.2 mmol) and cesium carbonate (150 mg, 0.46 mmol) in N,N-dimethylformamide (2 ml) was heated to 90° C. for 10 minutes. Then, iodoethane (0.5 ml, 5.18 mmol) was added and the reaction allowed to stir at 90° C. for 4 hours. The reaction mixture was diluted with THF (20 ml) and filtered. The filtrate was concentrated under reduced pressure purified by silica gel column chromatography (0-70% ethyl acetate in hexane). This provided methyl 5-bromo-6-ethoxy-4-methylpicolinate (46). MS (ESI) $[M+H^+]^+$=274.0 and 276.0.

Step 4: Preparation of 4-(1-(dicyclopropylmethyl)-3-iodo-1H-pyrrolo[2,3-b]pyridin-5-yl)-3,5-dimethylisoxazole 47

Diisopropyl azodicarboxylate (26.1 ml, 133 mmol, 2.5 equiv) was added dropwise to a solution of 4-(3-iodo-1H-pyrrolo[2,3-b]pyridin-5-yl)-3,5-dimethylisoxazole (3, 18 g, 53.1 mmol, 1 equiv), compound 10 (8.93 g, 80 mmol, 1.5 equiv) and triphenylphosphine (34.8 g, 133 mmol, 2.5 equiv) in THF (185 ml) at 0° C. The reaction was allowed to warm to room temperature and stirred overnight. The reaction was poured into saturated sodium bicarbonate (500 ml) and extracted with ethyl acetate (300 ml). The organic layer was washed with saturated brine (500 ml) and concentrated under reduced pressure. The crude product was purified by silica gel column chromatography (0-50% ethyl acetate in heptanes). The product was triturated with a -1 to 1 mixture of MTBE and heptanes (~50 ml) to give 4-(1-(dicyclopropylmethyl)-3-iodo-1H-pyrrolo[2,3-b]pyridin-5-yl)-3,5-dimethylisoxazole (47).

Step 5: Preparation of 4-(1-(dicyclopropylmethyl)-3-(4,4,5,5-tetramethyl-1,3,2-dioxaborolan-2-yl)-1H-pyrrolo[2,3-b]pyridin-5-yl)-3,5-dimethylisoxazole 48

2M i-propylmagnesium chloride (11.1 ml, 22.16 mmol, 2.4 equiv) in THF was added to a solution of 4-(1-(dicyclopropylmethyl)-3-iodo-1H-pyrrolo[2,3-b]pyridin-5-yl)-3,5-dimethylisoxazole (47, 4 g, 9.23 mmol, 1 equiv) in THF (90 ml) at 0° C. After stirring for 30 minutes, metal/halogen exchange was determined to be complete by 1H NMR. i-Propylpinacolborate (11.3 ml, 55.4 mmol, 6 equiv) was added and the reaction was allowed to warm to room temperature and stirred overnight. The reaction was poured into water (200 ml), the pH was adjusted to 6 with 10% aqueous acetic acid (40 ml). The mixture was extracted with ethyl acetate (200 ml). The organic layer was washed with saturated brine (200 ml) and concentrated under reduced pressure. The residue was purified by silica gel column chromatography (0-100% ethyl acetate in heptanes) to provide 4-(1-(dicyclopropylmethyl)-3-(4,4,5,5-tetramethyl-1,3,2-dioxaborolan-2-yl)-1H-pyrrolo[2,3-b]pyridin-5-yl)-3,5-dimethylisoxazole (48).

Step 6: Preparation of methyl 5-(1-(dicyclopropylmethyl)-5-(3,5-dimethylisoxazol-4-yl)-1H-pyrrolo[2,3-b]pyridin-3-yl)-6-ethoxy-4-methylpicolinate 49

To 4-(1-(dicyclopropylmethyl)-3-(4,4,5,5-tetramethyl-1,3,2-dioxaborolan-2-yl)-1H-pyrrolo[2,3-b]pyridin-5-yl)-3,5-dimethylisoxazole (48, 55 mg, 0.127 mmol), methyl 5-bromo-6-ethoxy-4-methylpicolinate (46, 17 mg, 0 mol) and 1,1'-bis(diphenylphosphino)ferrocene-palladium(II) dichloride dichloromethane complex (14 mg, 0.017 mmol) in 1,4-dioxane (2 ml) was added aqueous 1M potassium carbonate (1 ml). The reaction mixture was allowed to stir at 90° C. for 15 minutes. The reaction mixture was poured into water and extracted with ethyl acetate. The organic layer was washed with water followed by brine, then dried over anhydrous magnesium sulfate. The volatiles were removed under reduced pressure. The material was purified by silica gel column chromatography (0-75% ethyl acetate in hexane). This provided methyl 5-(1-(dicyclopropylmethyl)-5-(3,5-dimethylisoxazol-4-yl)-1H-pyrrolo[2,3-b]pyridin-3-yl)-6-ethoxy-4-methylpicolinate (49). MS (ESI) $[M+H^+]^+$=501.2.

Step 7: Preparation of 5-(1-(dicyclopropylmethyl)-5-(3,5-dimethylisoxazol-4-yl)-1H-pyrrolo[2,3-b]pyridin-3-yl)-6-ethoxy-4-methylpicolinic acid P-0417

To methyl 5-(1-(dicyclopropylmethyl)-5-(3,5-dimethylisoxazol-4-yl)-1H-pyrrolo[2,3-b]pyridin-3-yl)-6-ethoxy-4-methylpicolinate (49, 27 mg, 0.05 mmol) in THF (10 ml) was added aqueous 1M lithium hydroxide (5 ml). The reaction mixture was allowed to stir at room temperature for 5 hours. The organic layer of the reaction mixture was separated after adding aqueous formic acid, and was concentrated under reduced pressure. The material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 5-(1-(dicyclopropylmethyl)-5-(3,5-dimethylisoxazol-4-yl)-1H-pyrrolo[2,3-b]pyridin-3-yl)-6-ethoxy-4-methylpicolinic acid (P-0417). MS (ESI) $[M+H^+]^+$=487.2.

Example 11

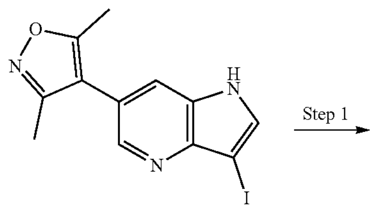

8

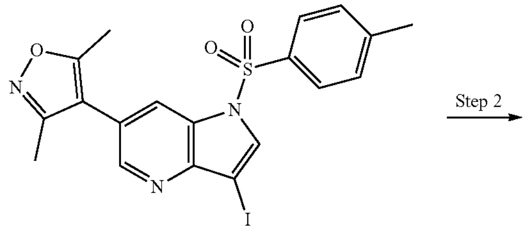

50

-continued

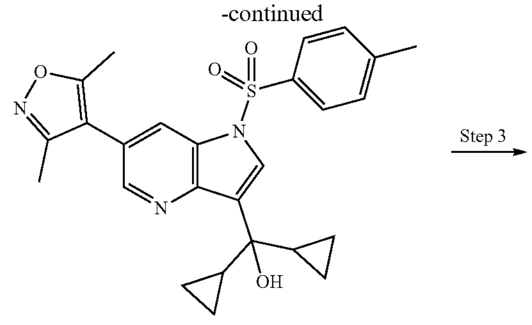

51

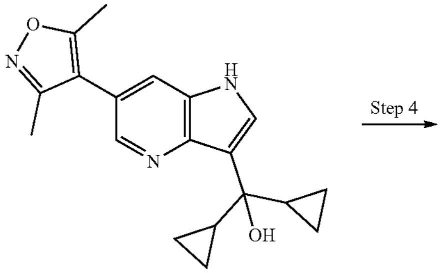

52

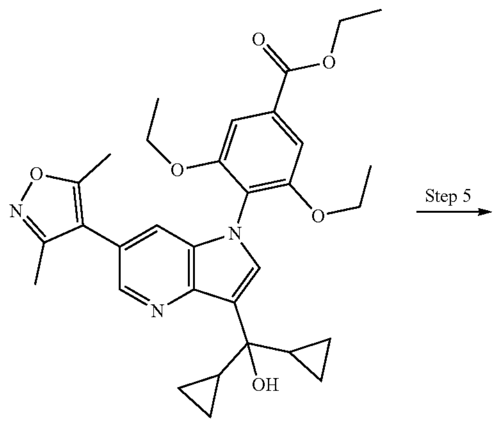

53

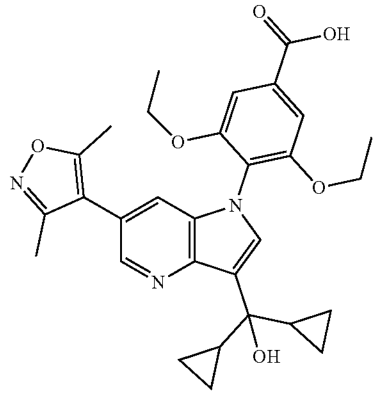

P-0165

Step 1: Preparation of 4-(3-odo-1-tosyl-1H-pyrrolo[3,2-b]pyridin-6-yl)-3,5-dimethylisoxazole 50

To 4-(3-iodo-1H-pyrrolo[3,2-b]pyridin-6-yl)-3,5-dimethylisoxazole (8, 1.2 g, 3.54 mmol) in THF (50 ml) was added sodium hydride (60%, 0.17 mg, 4.25 mmol). The mixture was allowed to stir at room temperature for 30 minutes. Then, 4-methylbenzenesulfonyl chloride (1.01 g, 5.31 mmol) was added and the reaction was allowed to stir for 3 hours. The reaction mixture was diluted with water and extracted with ethyl acetate. The organic layer was washed with water followed by brine, then dried over anhydrous magnesium sulfate and filtered. The filtrate was concentrated under reduced pressure. The material was purified by silica gel column chromatography (0-45% ethyl acetate in hexanes). This provided 4-(3-iodo-1-tosyl-1H-pyrrolo[3,2-b]pyridin-6-yl)-3,5-dimethylisoxazole (50). MS (ESI) $[M+H^+]^+=494.1$.

Step 2: Preparation of dicyclopropyl(6-(3,5-dimethylisoxazol-4-yl)-1-tosyl-1H-pyrrolo[3,2-b]pyridin-3-yl)methanol 51

To a solution of 4-(3-iodo-1-tosyl-1H-pyrrolo[3,2-b]pyridin-6-yl)-3,5-dimethylisoxazole (50, 866 mg, 1.76 mmol) in THF (5 ml) cooled to −55° C. was added a THF solution of 2M isopropylmagnesium chloride (1.5 ml). The reaction mixture was allowed to slowly warm to 0° C. for about 1 hour. The reaction mixture was cooled to −55° C. followed by the addition of dicyclopropylmethanone (0.35 ml, 3.05 mmol). The reaction mixture was allowed to slowly warm to room temperature over 1-2 hours and kept at room temperature for 90 minutes. The reaction was quenched with aqueous 1 N HCl (3 ml). The reaction mixture was diluted with water and extracted with ethyl acetate. The organic layer was washed with water followed by brine, then dried over anhydrous magnesium sulfate and filtered. The filtrate was concentrated under reduced pressure. The material was purified by silica gel column chromatography (0-80% ethyl acetate in hexane). This provided dicyclopropyl(6-(3,5-dimethylisoxazol-4-yl)-1-tosyl-1H-pyrrolo[3,2-b]pyridin-3-yl)methanol (51). MS (ESI) $[M+H^+]^+=478.1$.

Step 3: Preparation of dicyclopropyl(6-(3,5-dimethylisoxazol-4-yl)-1H-pyrrolo[3,2-b]pyridin-3-yl)methanol 52

To dicyclopropyl(6-(3,5-dimethylisoxazol-4-yl)-1-tosyl-H-pyrrolo[3,2-b]pyridin-3-yl)methanol (51, 390 mg, 0.817 mmol) in was added a solution of 1M potassium hydroxide in methanol (10 ml). The reaction mixture was allowed to stir at room temperature for 2 hours. The reaction mixture was diluted with water and extracted with ethyl acetate. The organic layer was washed with water followed by brine, and then dried over anhydrous magnesium sulfate and filtered. The filtrate was concentrated under reduced pressure to provide dicyclopropyl(6-(3,5-dimethylisoxazol-4-yl)-1H-pyrrolo[3,2-b]pyridin-3-yl)methanol (52).

Step 4: Preparation of ethyl 4-(3-(dicyclopropyl(hydroxy)methyl)-6-(3,5-dimethylisoxazol-4-yl)-1H-pyrrolo[3,2-b]pyridin-1-yl)-3,5-diethoxybenzoate 53

To dicyclopropyl(6-(3,5-dimethylisoxazol-4-yl)-1H-pyrrolo[3,2-b]pyridin-3-yl)methanol (52, 100 mg, 0.309 mmol), potassium phosphate tribasic (140 mg, 0.660 mmol), copper (I) iodide (13 mg, 0.068 mmol), trans N,N'-dimethylcyclohexane-1,2-diamine (100 mg, 0.703 mmol), and ethyl 4-bromo-3,5-diethoxy-benzoate (160 mg, 0.504 mmol) was added toluene (2 ml). The reaction mixture was heated to 110° C. for 16 hours. The reaction mixture was filtered and the filtrate was concentrated to dryness under reduced pressure. The material was purified by silica gel column chromatography (0-8% methanol in dichloromethane). This provided of ethyl 4-(3-(dicyclopropyl(hydroxy)methyl)-6-(3,5-dimethylisoxazol-4-yl)-1H-pyrrolo[3,2-b]pyridin-1-yl)-3,5-diethoxybenzoate (53). MS (ESI) $[M+H^+]^+=560.6$.

Step 5: Preparation of 4-(3-(dicyclopropyl(hydroxy)methyl)-6-(3,5-dimethylisoxazol-4-yl)-1H-pyrrolo[3,2-b]pyridin-1-yl)-3,5-diethoxybenzoic acid P-0165

To ethyl 4-(3-(dicyclopropyl(hydroxy)methyl)-6-(3,5-dimethylisoxazol-4-yl)-1H-pyrrolo[3,2-b]pyridin-1-yl)-3,5-diethoxybenzoate (53, 17 mg, 0.030 mmol) in THF (10 ml) was added aqueous 1M lithium hydroxide (5 ml). The reaction mixture was allowed to stir at room temperature for 20 hours. The organic layer of the reaction mixture was collected and concentrated under reduced pressure. The material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 4-(3-(dicyclopropyl(hydroxy)methyl)-6-(3,5-dimethylisoxazol-4-yl)-1H-pyrrolo[3,2-b]pyridin-1-yl)-3,5-diethoxybenzoic acid (P-0165). MS (ESI) $[M+H^+]^+=532.15$.

Example 12

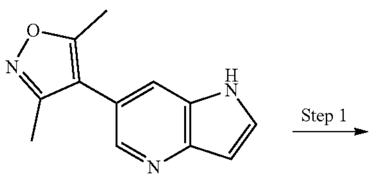

11

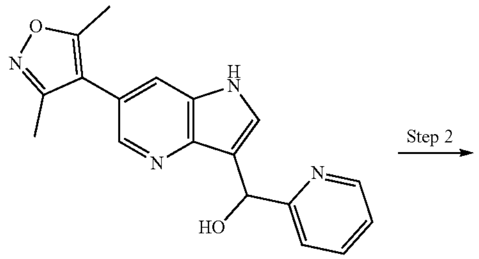

54

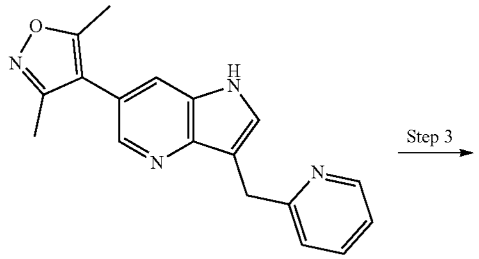

55

-continued

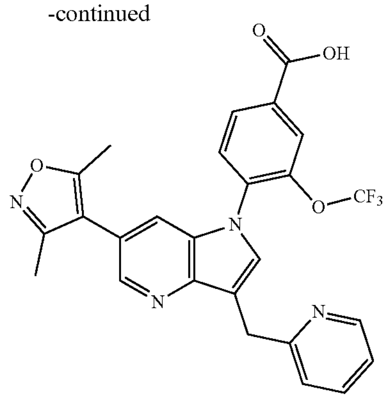

P-0159

Step 1: Preparation of (6-(3,5-dimethylisoxazol-4-yl)-1H-pyrrolo[3,2-b]pyridin-3-yl)(pyridin-2-yl) methanol 54

A mixture of 3,5-dimethyl-4-(1H-pyrrolo[3,2-b]pyridin-6-yl)isoxazole (11, 213 mg, 1.00 mmol), pyridine-2-carbaldehyde (161 mg, 1.50 mmol) and potassium hydroxide (281 mg, 5.00 mmol) in methanol (10 ml) was allowed to stir at room temperature for 15 hours. The mixture was diluted with water and extracted with ethyl acetate. The organic layer was washed with water followed by brine, dried over anhydrous magnesium sulfate and filtered. The filtrate was concentrated under reduced pressure and purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide (6-(3,5-dimethylisoxazol-4-yl)-1H-pyrrolo[3,2-b]pyridin-3-yl)(pyridin-2-yl)methanol (54). MS (ESI) $[M+H^+]^+$=321.1.

Step 2: Preparation of 3,5-dimethyl-4-(3-(pyridin-2-ylmethyl)-1H-pyrrolo[3,2-b]pyridin-6-yl)isoxazole 55

To a mixture of (6-(3,5-dimethylisoxazol-4-yl)-1H-pyrrolo[3,2-b]pyridin-3-yl)(pyridin-2-yl)methanol (54, 210 mg, 0.656 mmol) in dichloroethane (6 ml) was added triethylsilane (0.52 ml, 3.28 mmol) and trifluoroacetic acid (0.25 ml, 3.28 mmol). The mixture was allowed to stir at 80° C. for 2 hours. The reaction was quenched with saturated aqueous potassium carbonate and extracted with ethyl acetate. The organic layer was washed with water followed by brine, dried over anhydrous magnesium sulfate and filtered. The filtrate was concentrated under reduced pressure to provide 3,5-dimethyl-4-(3-(pyridin-2-ylmethyl)-1H-pyrrolo[3,2-b]pyridin-6-yl)isoxazole (55). MS (ESI) $[M+H^+]^+$=305.1.

Step 3: Preparation of 4-(6-(3,5-dimethylisoxazol-4-yl)-3-(pyridin-2-ylmethyl)-1H-pyrrolo[3,2-b]pyridin-1-yl)-3-(trifluoromethoxy)benzoic acid P-0159

To 3,5-dimethyl-4-(3-(pyridin-2-ylmethyl)-1H-pyrrolo[3,2-b]pyridin-6-yl)isoxazole (55, 33 mg, 0.108 mmol) and copper(I) bromide (10 mg, 0.070 mmol) in N,N-dimethylformamide (2 ml) was added methyl 4-bromo-3-(trifluoromethoxy)benzoate (50 mg, 0.167 mmol) and potassium carbonate (50 mg, 0.362 mmol). The mixture was heated to 100° C. for 10 minutes. Then, sodium hydroxide (100 mg, 2.50 mmol) and copper(II) acetate monohydrate (10 mg, 0.050 mmol) were added to the reaction mixture. The reaction mixture was heated to 110° C. for 6 days. The reaction was cooled to room temperature and filtered. The filtrate was concentrated to dryness under reduced pressure. The resulting residue was extracted with water (+1N citric acid) and ethyl acetate.

The organic layer was washed with water followed by brine, then dried over anhydrous magnesium sulfate and filtered. The filtrate was concentrated under reduced pressure and the material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 4-(6-(3,5-dimethylisoxazol-4-yl)-3-(pyridin-2-ylmethyl)-1H-pyrrolo[3,2-b]pyridin-1-yl)-3-(trifluoromethoxy)benzoic acid (P-0159). MS (ESI) $[M+H^+]^+$=509.5.

Example 13

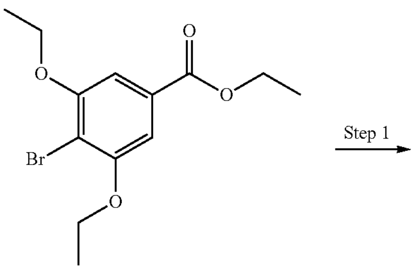

56

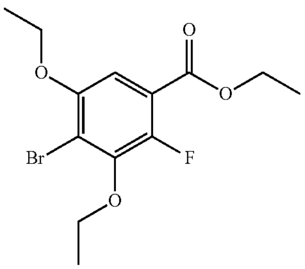

57

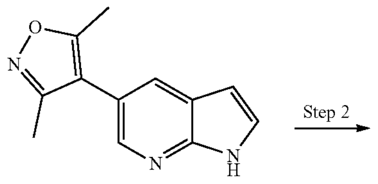

3a

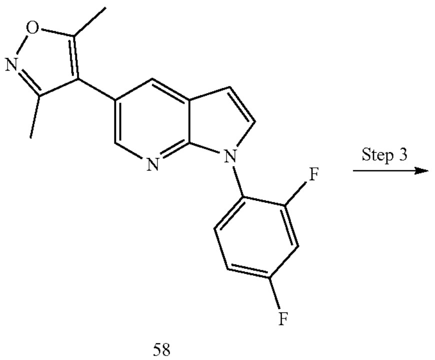

58

-continued

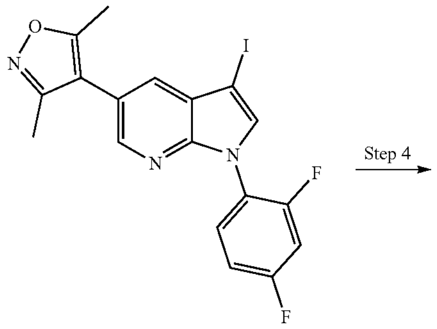

59

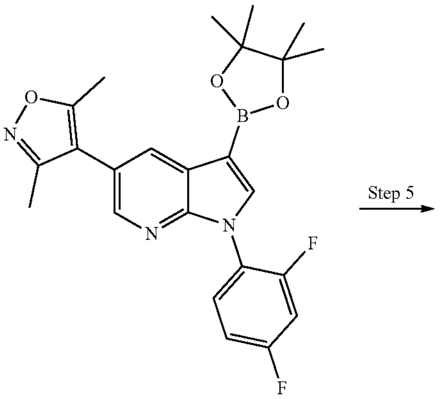

60

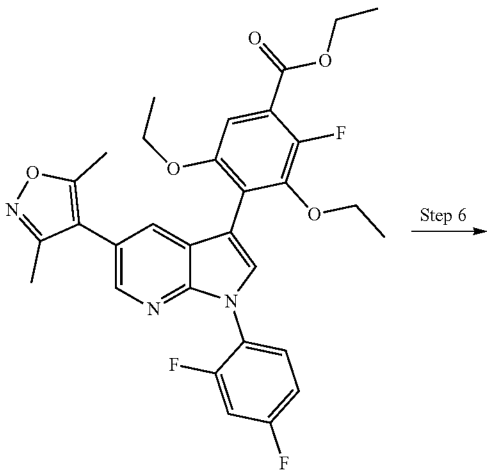

61

-continued

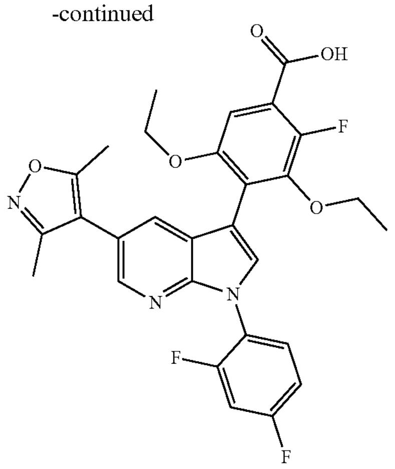

P-0297

Step 1: Preparation of ethyl 4-bromo-3,5-diethoxy-2-fluorobenzoate 57

To ethyl 4-bromo-3,5-diethoxybenzoate (56, 1.02 g, 3.20 mmol) in acetonitrile (20 ml) was added 1-(chloromethyl)-4-fluoro-1,4-diazoniabicyclo[2.2.2]octane ditetrafluoroborate (2.08 g, 5.87 mmol). The reaction mixture was immediately heated at 60° C. After 18 hours the reaction mixture was diluted with ethyl acetate and extracted with water (+HCl). The organic layer was washed with saturated aqueous sodium bicarbonate followed by brine. The organic layer was dried over anhydrous magnesium sulfate, filtered and concentrated under reduced pressure. This material was purified by silica gel flash column chromatography (0 to 20% ethyl acetate/DCM 40/60 in hexane). The front running mixed fractions were combined and purified with a second column. The back running mixed fractions were combined and purified with a third column. This provided the mono-F product ethyl 4-bromo-3,5-diethoxy-2-fluorobenzoate (57). MS (ESI) $[M+H^+]^+=334.9$.

Step 2: Preparation of 4-(1-(2,4-difluorophenyl)-1H-pyrrolo[2,3-b]pyridin-5-yl)-3,5-dimethylisoxazole 58

In an pressure vessel with a magnetic stir bar was added 3,5-dimethyl-4-(1H-pyrrolo[2,3-b]pyridin-5-yl)isoxazole (3a, 1.91 g, 8.97 mmol), 1-bromo-2,4-difluoro-benzene (4.71 g, 24.4 mmol), copper(I) iodide (521 mg, 2.74 mmol), potassium hydroxide (0.884 g, 15.8 mmol) and 1,4-dioxane (50 ml). Then, (1R,2R)—N1,N2-dimethylcyclohexane-1,2-diamine (0.524 g, 3.68 mmol) was added and the reaction was purged with argon, sealed and was allowed to stir in an oil bath at 120° C. After 17 hours, the reaction was filtered through celite, washing with ethyl acetate. The filtrate was extracted with 1M aqueous HCl (2×) and brine (1×). The organic layer was dried over anhydrous magnesium sulfate, filtered and concentrated and the resulting residue purified by silica gel flash column chromatography eluting with a gradient of 20 to 50% ethyl acetate in hexane to provide 4-(1-(2,4-difluorophenyl)-1H-pyrrolo[2,3-b]pyridin-5-yl)-3,5-dimethylisoxazole (58). MS (ESI) $[M+H^+]^+=326.4$.

Step 3: Preparation of 4-(1-(2,4-difluorophenyl)-3-iodo-1H-pyrrolo[2,3-b]pyridin-5-yl)-3,5-dimethylisoxazole 59

To a solution of 4-(1-(2,4-difluorophenyl)-1H-pyrrolo[2,3-b]pyridin-5-yl)-3,5-dimethylisoxazole (58, 825 mg, 2.54 mmol) in acetonitrile (20 ml) was added N-iodosuccinimide (857 mg, 3.81 mmol). The reaction was allowed to stir at room temperature for 22 hours. TLC indicated all starting material had been consumed. The reaction was poured into ethyl acetate and saturated aqueous sodium thiosulfate and the layers were separated. The organic layer was washed with additional saturated aqueous sodium thiosulfate and then brine, dried over anhydrous magnesium sulfate and filtered. The volatiles were removed by rotary evaporation and the resulting residue was purified by silica gel flash column chromatography eluting with 0-20% ethyl acetate in hexane. This provided 4-(1-(2,4-difluorophenyl)-3-iodo-1H-pyrrolo[2,3-b]pyridin-5-yl)-3,5-dimethylisoxazole (59). MS (ESI) $[M+H^+]^+=451.9$.

Step 4: Preparation of 4-(1-(2,4-difluorophenyl)-3-(4,4,5,5-tetramethyl-1,3,2-dioxaborolan-2-yl)-1H-pyrrolo[2,3-b]pyridin-5-yl)-3,5-dimethylisoxazole 60

In round bottom flask charged with 4-(1-(2,4-difluorophenyl)-3-iodo-1H-pyrrolo[2,3-b]pyridin-5-yl)-3,5-dimethylisoxazole (59, 956 mg, 2.12 mmol), Pd X-Phos G1 (152 mg, 0.206 mmol) and pinacolborane (1.23 ml, 8.48 mmol) was added 1,4-dioxane (16 ml). The stirred solution was purged with argon and then triethylamine (1.48 ml, 10.6 mmol) was added and the reaction placed in an oil bath at 60° C. under an argon atmosphere for 1.5 hrs. TLC indicated the starting iodide was consumed. The cooled reaction was diluted with ethyl acetate (25 ml) and brine (25 ml), allowed to stir for 30 min and filtered through celite washing with ethyl acetate. The layers were separated and the organic layer was dried over anhydrous sodium sulfate and filtered. The volatiles were removed by rotary evaporation and the resulting residue was purified by silica gel flash column chromatography eluting with 0-20% ethyl acetate in hexane to provide 4-(1-(2,4-difluorophenyl)-3-(4,4,5,5-tetramethyl-1,3,2-dioxaborolan-2-yl)-1H-pyrrolo[2,3-b]pyridin-5-yl)-3,5-dimethylisoxazole (60). MS (ESI) $[M+H^+]^+=452.0$.

Step 5: Preparation of ethyl 4-(1-(2,4-difluorophenyl)-5-(3,5-dimethylisoxazol-4-yl)-1H-pyrrolo[2,3-b]pyridin-3-yl)-3,5-diethoxy-2-fluorobenzoate 61

In a pressure vessel with a magnetic stir bar was added 4-(1-(2,4-difluorophenyl)-3-(4,4,5,5-tetramethyl-1,3,2-dioxaborolan-2-yl)-1H-pyrrolo[2,3-b]pyridin-5-yl)-3,5-dimethylisoxazole (60, 662 mg, 1.47 mmol), ethyl 4-bromo-3,5-diethoxy-2-fluoro-benzoate (57, 485 mg, 1.45 mmol), dichloro[1,1'-bis(diphenylphosphino)ferrocene]palladium (II) dichloromethane adduct (239 mg, 0.293 mmol) and 1,4-dioxane (7 ml). Then, 2.5M potassium carbonate in water (2.32 ml) was added and the reaction was purged with argon, sealed and immediately heated at 120° C. in an oil bath for 15 min. The reaction mixture was allowed to cool and was poured into water (20 ml) and ethyl acetate (20 ml) and was filtered through celite. The organic layer was washed with 1M aqueous HCl which produced dark, solid material which was removed by filtration through celite. The organic layer was washed with brine, then dried over anhydrous magnesium sulfate and filtered. The filtrate was concentrated under reduced pressure and purified by silica gel column chromatography eluting with a gradient of 20-50% ethyl acetate in hexane to provide ethyl 4-(1-(2,4-difluorophenyl)-5-(3,5-dimethylisoxazol-4-yl)-1H-pyrrolo[2,3-b]pyridin-3-yl)-3,5-diethoxy-2-fluorobenzoate (61). MS (ESI) $[M+H^+]^+=580.4$.

Step 6: Preparation of 4-(1-(2,4-difluorophenyl)-5-(3,5-dimethylisoxazol-4-yl)-1H-pyrrolo[2,3-b]pyridin-3-yl)-3,5-diethoxy-2-fluorobenzoic acid P-0297

To ethyl 4-(1-(2,4-difluorophenyl)-5-(3,5-dimethylisoxazol-4-yl)-1H-pyrrolo[2,3-b]pyridin-3-yl)-3,5-diethoxy-2-fluorobenzoate (61, 142 mg, 0.25 mmol) dissolved in THF (8.7 ml) was added aqueous 1M lithium hydroxide (4.6 ml) and the biphasic mixture was allowed to stir at room temperature for 5 hours. The reaction was quenched with aqueous 2N HCl (3 ml) and diluted with ethyl acetate (20 ml). The organic layer was washed with brine and then dried over anhydrous magnesium sulfate and filtered. The filtrate was concentrated under reduced pressure and this material was purified by silica gel flash column chromatography (0 to 10% methanol in dichloromethane) to provide 4-(1-(2,4-difluorophenyl)-5-(3,5-dimethylisoxazol-4-yl)-1H-pyrrolo[2,3-b]pyridin-3-yl)-3,5-diethoxy-2-fluorobenzoic acid (P-0297). MS (ESI) $[M+H^+]^+=552.1$.

Example 14

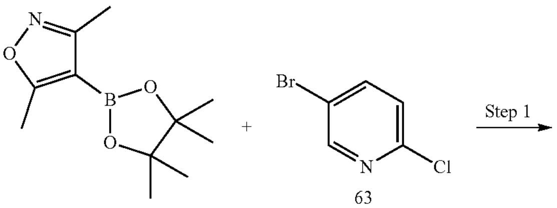

62 63

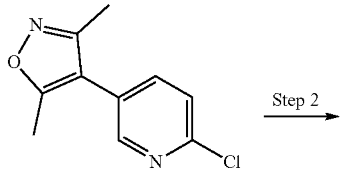

64

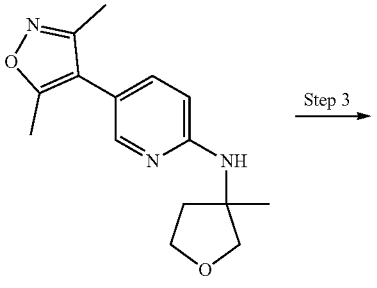

65

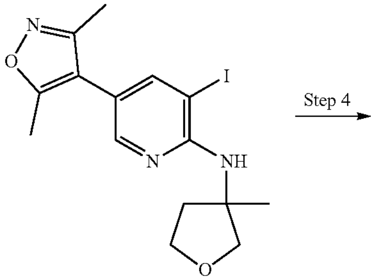

66

-continued

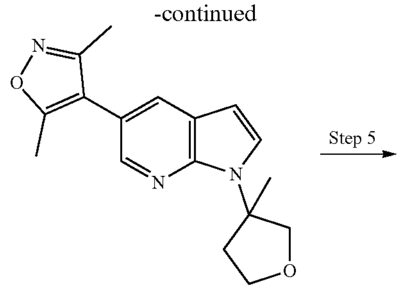

67

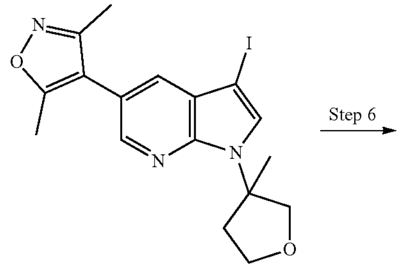

68

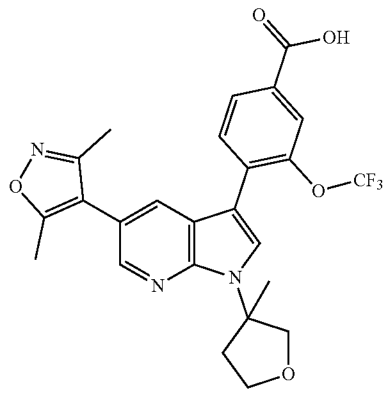

P-0383

Step 1:Preparation of 4-(6-chloropyridin-3-yl)-3,5-dimethylisoxazole 64

To 5-bromo-2-chloro-pyridine (63, 2.00 g, 10.4 mmol) was added 3,5-dimethyl-4-(4,4,5,5-tetramethyl-1,3,2-dioxaborolan-2-yl)isoxazole (62, 2.55 g, 11.4 mol), aqueous 1M potassium carbonate (15.59 ml), 1,1'-bis(diphenylphosphino)ferrocene-palladium(II) dichloride dichloromethane complex (0.76 g, 0.93 mmol) and dioxane (10 ml). The reaction was heated to 60° C. for 2 hours. The reaction was poured into brine and extracted with ethyl acetate. The organic layer was dried over sodium sulfate, filtered then evaporated onto silica. The product was isolated by silica gel flash column chromatography (0 to 100% ethyl acetate in hexane) to provide 4-(6-chloropyridin-3-yl)-3,5-dimethylisoxazole (64). MS (ESI) $[M+H^+]^+$=209.1.

Step 2: Preparation of 5-(3,5-dimethylisoxazol-4-yl)-N-(3-methyltetrahydrofuran-3-yl)pyridin-2-amine 65

4-(6-chloropyridin-3-yl)-3,5-dimethylisoxazole (64, 0.5 g, 2.4 mmol) was dissolved in DME (2 ml) in a 20 mL microwave vial. Then, 3-methyloxolan-3-amine (0.3 ml, 2.88 mmol), sodium tert-butoxide (345 mg, 3.59 mmol), and RuPhos (196 mg, 0.24 mmol) were added and the vial was sealed and heated to 120° C. in an oil bath for 18 hours under a nitrogen atmosphere. The reaction mixture was filtered through Celite, then evaporated on to silica. The material was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 5-(3,5-dimethylisoxazol-4-yl)-N-(3-methyltetrahydrofuran-3-yl)pyridin-2-amine (65). MS (ESI) $[M+H^+]^+$=274.2.

Step 3: Preparation of 5-(3,5-dimethylisoxazol-4-yl)-3-iodo-N-(3-methyltetrahydrofuran-3-yl)pyridin-2-amine 66

5-(3,5-dimethylisoxazol-4-yl)-N-(3-methyltetrahydrofuran-3-yl)pyridin-2-amine (65, 515 mg, 1.88 mmol) was dissolved in DMF (8 ml) in a 20 ml microwave vial. Trifluoroacetic acid (0.42 ml, 5.65 mmol) and N-iodosuccinimide (636 mg, 2.83 mmol) were added and the vial was sealed and heated to 80° C. for 4 hours. The reaction mixture was poured over sodium thiosulfate, filtered, and then evaporated on to silica gel. The product was isolated silica gel flash column chromatography (0 to 100% ethyl acetate in hexane) to provide 5-(3,5-dimethylisoxazol-4-yl)-3-iodo-N-(3-methyltetrahydrofuran-3-yl)pyridin-2-amine (66). MS (ESI) $[M+H^+]^+$=399.9.

Step 4: Preparation of 3,5-dimethyl-4-(1-(3-methyltetrahydrofuran-3-yl)-1H-pyrrolo[2,3-b]pyridin-5-yl)isoxazole 67

5-(3,5-dimethylisoxazol-4-yl)-3-iodo-N-(3-methyltetrahydrofuran-3-yl)pyridin-2-amine (66, 0.5 g, 1.25 mmol) and (E)-1-ethoxyethene-2-boronic acid pinacol ester (0.413 ml, 1.88 mmol) were dissolved in DMF (3 ml) in a 5 ml microwave vial. Then, 1,1'-bis(diphenylphosphino)ferrocene-palladium(II) dichloride dichloromethane complex (92 mg, 0.11 mmol) and lithium hydroxide (90 mg, 3.76 mmol) were added and the vial was sealed and heated to 80° C. for 6 hours in an oil bath under nitrogen atmosphere. The reaction was then cooled to 50° C. and 25% HCl aq. (0.37 ml, 2.5 mmol) was added via syringe and the reaction was stirred for 2 hours. The reaction was poured into saturated aqueous sodium bicarbonate and extracted with ethyl acetate. The organic layer was evaporated onto silica gel and purified by silica gel flash column chromatography (0 to 10% methanol in dichloromethane) to provide 3,5-dimethyl-4-(1-(3-methyltetrahydrofuran-3-yl)-1H-pyrrolo[2,3-b]pyridin-5-yl)isoxazole (67). MS (ESI) $[M+H^+]^+$=298.1.

Step 5: Preparation of 4-(3-iodo-1-(3-methyltetrahydrofuran-3-yl)-1H-pyrrolo[2,3-b]pyridin-5-yl)-3,5-dimethylisoxazole 68

3,5-dimethyl-4-(1-(3-methyltetrahydrofuran-3-yl)-1H-pyrrolo[2,3-b]pyridin-5-yl)isoxazole (67, 340 mg, 1.14 mmol) was dissolved in DMF (3 ml) and was cooled to 0° C. Then, a solution of N-iodosuccinimide (309 mg, 1.37 mmol) in DMF (2 mL) was added. The reaction was allowed to stir for 2 hours while warming to room temperature. The reaction was poured into saturated aqueous sodium thiosulfate and extracted with ethyl acetate. The organic layer was evaporated on to silica and purified by silica gel flash column chromatography (0 to 100% ethyl acetate in hexane) to provide 4-(3-iodo-1-(3-methyltetrahydrofuran-3-yl)-1H-pyrrolo[2,3-b]pyridin-5-yl)-3,5-dimethylisoxazole (68).

Step 6: Preparation of 4-(5-(3,5-dimethylisoxazol-4-yl)-1-(3-methyltetrahydrofuran-3-yl)-1H-pyrrolo[2,3-b]pyridin-3-yl)-3-(trifluoromethoxy)benzoic acid P-0383

4-(3-iodo-1-(3-methyltetrahydrofuran-3-yl)-1H-pyrrolo[2,3-b]pyridin-5-yl)-3,5-dimethylisoxazole (68, 50 mg, 0.12 mmol) and methyl 4-(4,4,5,5-tetramethyl-1,3,2-dioxaborolan-2-yl)-3-(trifluoromethoxy)benzoate (25, 61 mg, 0.18 mmol) were dissolved in dioxane (3 ml) followed by the addition of aqueous 1M potassium carbonate (0.24 ml) and 1,1'-bis(diphenylphosphino)ferrocene-palladium(II) dichloride dichloromethane complex (9 mg, 0.01 mmol). The reaction was allowed to stir at 110° C. for 4 hours. The reaction was diluted with ethyl acetate and evaporated onto silica gel. The methyl ester intermediate was isolated by silica gel flash column chromatography (0 to 100% ethyl acetate in hexane). The isolated product was dissolved in MeOH/THF (4 ml) and aqueous 1M lithium hydroxide (0.59 ml) and allowed to stir at room temperature for 4 hours. The reaction was poured into saturated aqueous ammonium chloride and extracted with ethyl acetate. The organic layer was evaporated onto silica gel and purified by reverse phase silica gel flash column chromatography (0-100% B; A: 5% $CH_3CN$, 95% $H_2O$, 0.1% $HCO_2H$; B: 95% $CH_3CN$, 5% $H_2O$, 0.1% $HCO_2H$) to provide 4-(5-(3,5-dimethylisoxazol-4-yl)-1-(3-methyltetrahydrofuran-3-yl)-1H-pyrrolo[2,3-b]pyridin-3-yl)-3-(trifluoromethoxy)benzoic acid (P-0383). MS (ESI) $[M+H^+]^+$=502.0.

Example 15

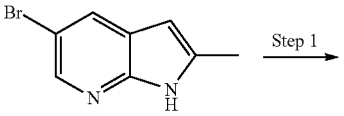

69

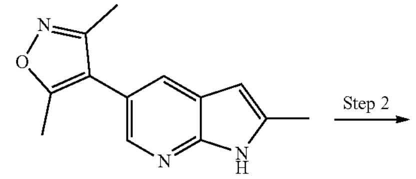

70

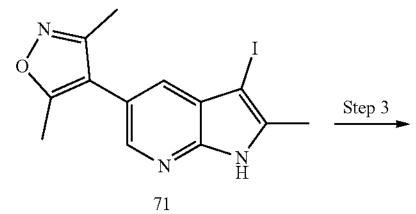

71

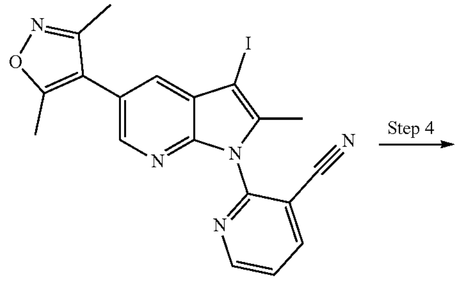

72

-continued

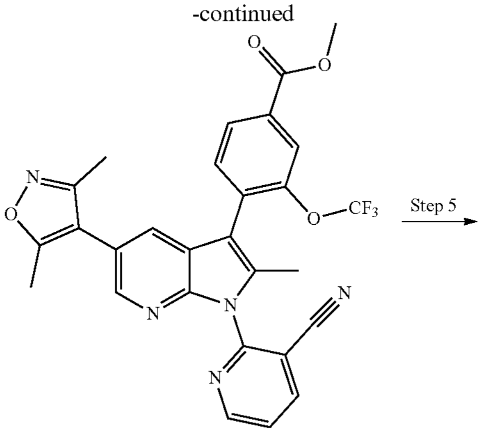

73

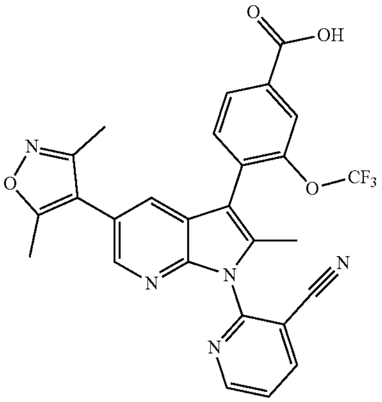

P-0345

Step 1: Preparation of 3,5-dimethyl-4-(2-methyl-1H-pyrrolo[2,3-b]pyridin-5-yl)isoxazole 70

To a mixture of 5-bromo-2-methyl-1H-pyrrolo[2,3-b]pyridine (69, 2.01 g, 9.5 mmol), 3,5-dimethyl-4-(4,4,5,5-tetramethyl-1,3,2-dioxaborolan-2-yl)isoxazole (4.24 g, 19 mmol) and 1,1'-bis(diphenylphosphino)ferrocene-palladium (II) dichloride dichloromethane complex (695 mg, 0.852 mmol) in dioxane (60 ml) purged with nitrogen gas, was added aqueous 2.5M potassium carbonate (12 ml). The mixture was heated at 110° C. for 3 hours. The reaction was cooled and diluted with water and extracted with ethyl acetate. The organic layer was washed with brine, dried over anhydrous magnesium sulfate, and filtered. The filtrate was concentrated under reduced pressure and purified by silica gel flash column chromatography (40% ethyl acetate in hexane) to provide 3,5-dimethyl-4-(2-methyl-1H-pyrrolo[2,3-b]pyridin-5-yl)isoxazole (70). MS (ESI) $[M+H^+]^+$=228.1.

Step 2: Preparation of 4-(3-iodo-2-methyl-1H-pyrrolo[2,3-b]pyridin-5-yl)-3,5-dimethylisoxazole 71

To an ice cold solution of 3,5-dimethyl-4-(2-methyl-1H-pyrrolo[2,3-b]pyridin-5-yl)isoxazole (70, 1.00 g, 4.4 mmol) in acetonitrile (40 ml) was added N-iodosuccinimide (1.09 g, 4.84 mmol). The mixture was stirred at 0° C. for 2 hours. The reaction was diluted with saturated aqueous sodium thiosulfate and extracted with ethyl acetate. The organic layer was washed with water followed by brine, dried over anhydrous magnesium sulfate and filtered. The filtrate was concentrated under reduced pressure and the material was purified by silica gel flash column chromatography (50% ethyl acetate in hexane) to provide 4-(3-iodo-2-methyl-1H-pyrrolo[2,3-b]pyridin-5-yl)-3,5-dimethylisoxazole (71). MS (ESI) $[M+H^+]^+$=354.0.

Step 3: Preparation of 2-(5-(3,5-dimethylisoxazol-4-yl)-3-iodo-2-methyl-1H-pyrrolo[2,3-b]pyridin-1-yl) nicotinonitrile 72

A mixture of 4-(3-iodo-2-methyl-1H-pyrrolo[2,3-b]pyridin-5-yl)-3,5-dimethylisoxazole (71, 353 mg, 1.00 mmol), potassium carbonate (276 mg, 2.00 mmol) and 2-fluoropyridine-3-carbonitrile (244 mg, 2.00 mmol) in DMF (5 ml) was allowed to stir at 100° C. for 3 hours. The reaction was allowed to cool and was diluted with water and extracted with ethyl acetate. The filtrate was washed with brine, dried over anhydrous magnesium sulfate and filtered. The filtrate was concentrated under reduced pressure and was purified by silica gel flash column chromatography (70% ethyl acetate in hexane) to provide 2-(5-(3,5-dimethylisoxazol-4-yl)-3-iodo-2-methyl-1H-pyrrolo[2,3-b]pyridin-1-yl)nicotinonitrile (72). MS (ESI) $[M+H^+]^+$=456.0.

Step 4: Preparation of methyl 4-(1-(3-cyanopyridin-2-yl)-5-(3,5-dimethylisoxazol-4-yl)-2-methyl-1H-pyrrolo[2,3-b]pyridin-3-yl)-3-(trifluoromethoxy) benzoate 73

To a mixture of 2-(5-(3,5-dimethylisoxazol-4-yl)-3-iodo-2-methyl-1H-pyrrolo[2,3-b]pyridin-1-yl)nicotinonitrile (72, 100 mg, 0.22 mmol), methyl 4-(4,4,5,5-tetramethyl-1,3,2-dioxaborolan-2-yl)-3-(trifluoromethoxy)benzoate (25, 99 mg, 0.29 mmol) and 1,1'-bis(diphenylphosphino)ferrocene-palladium(II) dichloride dichloromethane complex (18 mg, 0.022 mmol) in dioxane (2 ml) purged with nitrogen gas, was added 2.5M aqueous potassium carbonate (0.270 ml). The reaction was heated at 110° C. for 3 hours. The reaction was cooled to room temperature and diluted with ethyl acetate, dried over anhydrous magnesium sulfate and filtered. The filtrate was concentrated down and purified by silica gel flash column chromatography (70% ethyl acetate in hexane) to provide methyl 4-(1-(3-cyanopyridin-2-yl)-5-(3,5-dimethylisoxazol-4-yl)-2-methyl-1H-pyrrolo[2,3-b]pyridin-3-yl)-3-(trifluoromethoxy)benzoate (73). MS (ESI) $[M+H^+]^+$=548.2.

Step 5: Preparation of 4-(1-(3-cyanopyridin-2-yl)-5-(3,5-dimethylisoxazol-4-yl)-2-methyl-1H-pyrrolo[2,3-b]pyridin-3-yl)-3-(trifluoromethoxy)benzoic acid P-0345

To a mixture of methyl 4-(1-(3-cyanopyridin-2-yl)-5-(3,5-dimethylisoxazol-4-yl)-2-methyl-1H-pyrrolo[2,3-b]pyridin-3-yl)-3-(trifluoromethoxy)benzoate (73, 116 mg, 0.21 mmol) in (1:1) THF/MeOH (2.0 ml) was added aqueous 4.18 M lithium hydroxide (0.150 ml). The mixture was allowed to stir at 70° C. for 2 hours. The reaction was diluted with ethyl acetate, acidified with 1N HCl in MeOH and concentrated under reduced pressure. The material was purified by reverse phase silica gel flash column chromatography (0-100% B; A: 5% $CH_3CN$, 95% $H_2O$, 0.1% $HCO_2H$; B: 95% $CH_3CN$, 5% $H_2O$, 0.1% $HCO_2H$) to provide 4-(1-(3-cyanopyridin-2-yl)-5-(3,5-dimethylisoxazol-4-yl)-2-methyl-1H-pyrrolo[2,3-b]pyridin-3-yl)-3-(trifluoromethoxy)benzoic acid (P-0345). MS (ESI) $[M+H^+]^+$=534.0.

Example 16

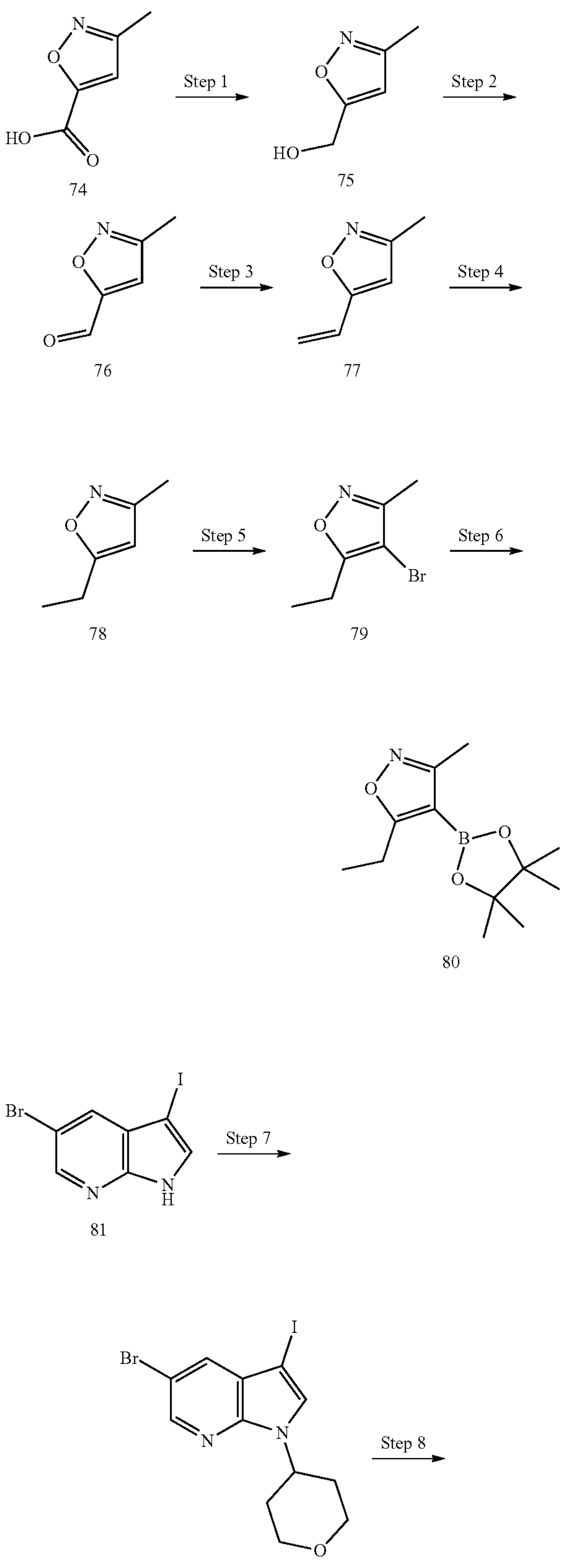

-continued

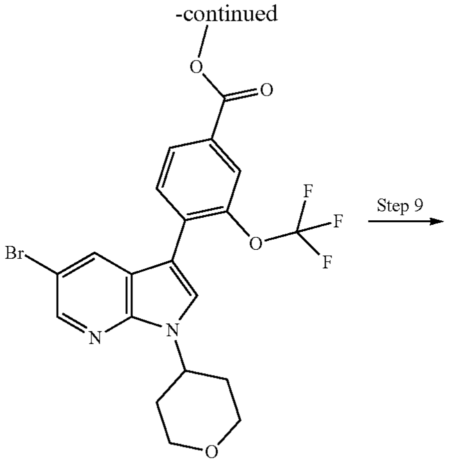

83

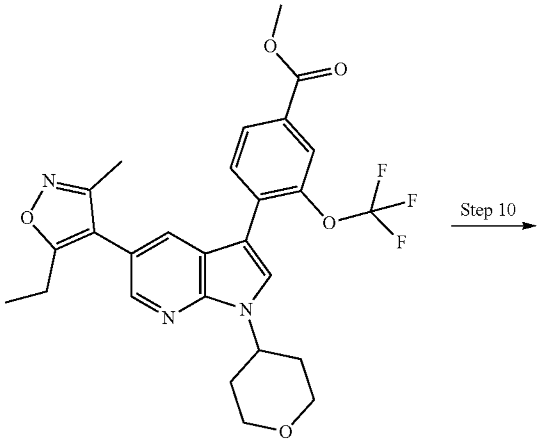

84

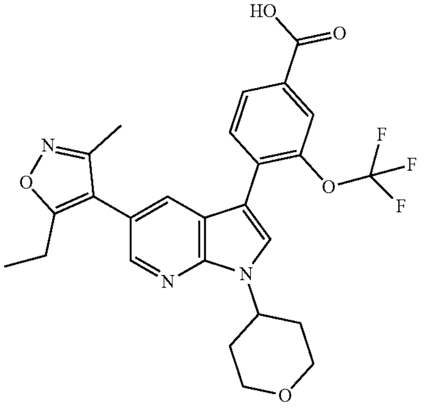

P-0401

Step 1: Preparation of (3-methylisoxazol-5-yl)methanol 75

To a solution of 3-methylisoxazole-5-carboxylic acid (74, 6.36 g, 50 mmol) and TEA (8.36 mL, 60 mmol) in THF (150 mL) was added isobutyl carbonochloridate (7.13 mL, 55 mmol) dropwise over 5 min at 0° C. Then the mixture was stirred at 0° C. for 5 min, and at room temperature for 10 min. The precipitate was removed by filtration and the precipitate was rinsed with THF (50 mL), then the mother liquor and rinsed solution were combined and cooled down to 0° C. Water (5 ml) was added to the solution at 0° C. and then sodium borohydride (3.78 g, 100 mmol) was slowly added to the solution over 15 min at 0° C. Then water (35 mL) was also added carefully. The resultant mixture was stirred for 1 hour at 0° C., and then 30 min at room temperature. After cooling down the reaction mixture to 0° C., aqueous 4 N sulfuric acid (80 mL) was slowly added to the solution, and the mixture was extracted with ethyl acetate (400 mL). The extract was washed with water (50 mL) and brine (50 mL), dried over anhydrous sodium sulfate, filtered and the filtrate was concentrated under reduced pressure. This provided (3-methylisoxazol-5-yl) methanol (75).

Step 2: Preparation of 3-methylisoxazole-5-carbaldehyde 76

To a solution of (3-methylisoxazol-5-yl)methanol (75, 3.50 g, 27 mmol) in dichloromethane (140 mL) was added Dess-Martin periodinane (13.9 g, 32.7 mmol) at 0° C. and the mixture was allowed to stir at room temperature for 6.5 hours. The mixture was diluted with dichloromethane (500 mL) and was washed with aqueous 5% sodium thiosulfate (150 mL), and aqueous saturated sodium bicarbonate (150 mL). The organic layer was dried over anhydrous sodium sulfate, filtered and concentrated under reduced pressure. This material was purified by silica gel flash column chromatography (0 to 40% ethyl acetate in hexane) to provide 3-methylisoxazole-5-carbaldehyde (76).

Step 3: Preparation of 3-methyl-5-vinylisoxazole 77

To a solution of 3-methylisoxazole-5-carbaldehyde (76, 1.91 g, 17.19 mmol) in THF (25 mL) was added ((trimethylsilyl)methyl)magnesium chloride solution (1.0 M in THF, 25.8 mL, 25.8 mmol) at 0° C. dropwise over 5 min. After stirring for 1 hour at 0° C., the solution was allowed to warm to room temperature and stirred for 6.5 hours. At 0° C., aqueous 1N sulfuric acid (25 mL) was added and the reaction was extracted with ethyl acetate (100 mL). The organic layer was washed with aqueous saturated sodium bicarbonate (25 mL) and brine (25 mL), dried over anhydrous sodium sulfate and concentrated under reduced pressure. The resulting TMS-$CH_2$ adduct was dissolved in diethyl ether (60 mL), and concentrated sulfuric acid (3.41 mL) was added dropwise at 0° C. over 5 min. Then the mixture was stirred at RT for 2 hours. The mixture was poured into ice-cooled aqueous saturated sodium bicarbonate (40 mL) and the resultant mixture was extracted with diethyl ether (160 mL). After the organic layer was washed with brine (30 mL), the solution was dried over anhydrous sodium sulfate and concentrated under reduced pressure to provide 3-methyl-5-vinylisoxazole (77).

Step 4: Preparation of 5-ethyl-3-methylisoxazole 78

To a solution of crude 3-methyl-5-vinylisoxazole (77, 2.31 g, 17.2 mmol) in MeOH (120 mL) was add 10% Pd/C (50% wet, 730 mg) and stirred vigorously under hydrogen at room temperature for 1 hour. After removing the catalyst by filtration through Celite, the mixture was concentrated under reduced pressure to provide 5-ethyl-3-methylisoxazole (78).

Step 5: Preparation of 4-bromo-5-ethyl-3-methylisoxazole 79

To a solution of 5-ethyl-3-methylisoxazole (78, 1.63 g, 14.7 mmol) in DMF (30 mL) was added N-bromosuccinimide (3.13 g, 17.6 mmol) and the mixture was stirred at room temperature overnight. After adding additional N-bromosuccinimide (522 mg, 2.93 mmol), the mixture was allowed to stir at room temperature for an additional 5 hours. The reaction was diluted with ethyl acetate and hexane (1/1, 300 mL) and was washed with aqueous 5% sodium thiosulfate (90 mL), aqueous 1N NaOH (60 mL), water (60 mL) and brine (60 mL). The filtrate was dried with anhydrous sodium sulfate, filtered and concentrated under reduced pressure. This material was purified by silica gel flash column chromatography (0 to 10% ethyl acetate in hexane) to provide to give 4-bromo-5-ethyl-3-methylisoxazole (79).

Step 6: Preparation of 5-ethyl-3-methyl-4-(4,4,5,5-tetramethyl-1,3,2-dioxaborolan-2-yl)isoxazole 80

To a solution of 4-bromo-5-ethyl-3-methylisoxazole (79, 161 mg, 0.847 mmol) in THF (4.5 mL) was added n-BuLi solution (2.5 M in hexane, 0.54 mL, 1.36 mmol) dropwise at −78° C. After stirring the mixture for 20 min at −78° C., 2-isopropoxy-4,4,5,5-tetramethyl-1,3,2-dioxaborolane (0.31 mL, 1.53 mmol) was added and the mixture was stirred for another 2 hours at −78° C. The reaction was quenched with aqueous saturated ammonium chloride (1 mL), diluted with ethyl acetate (50 mL) and washed with water (30 mL) and brine (50 mL). The organic layer was dried over anhydrous sodium sulfate, filtered and concentrated under reduced pressure. This material was purified by silica gel flash column chromatography (0 to 10% ethyl acetate in hexane) to provide 5-ethyl-3-methyl-4-(4,4,5,5-tetramethyl-1,3,2-dioxaborolan-2-yl)isoxazole (80).

Step 7: Preparation of 5-bromo-3-iodo-1-(tetrahydro-2H-pyran-4-yl)-1H-pyrrolo[2,3-b]pyridine 82

To a solution of 5-bromo-3-iodo-1H-pyrrolo[2,3-b]pyridine (81, 3.23 g, 10.0 mmol), tetrahydro-2H-pyran-4-ol (1.02 mg, 10.0 mmol) and triphenylphosphane (3.93 g, 15.0 mmol) in THF (50 mL) was added diisopropyl azodicarboxylate (2.95 mL, 15.0 mmol) dropwise at 0° C. over 5 min, and the mixture was allowed to stir at room temperature for 2 days. The reaction was concentrated under reduced pressure and the material was purified by silica gel flash column chromatography (0 to 35% ethyl acetate in hexane). Impure fractions were further re-purified by chromatography or suspension of solid product in ethyl acetate/hexanes (1/3 ratio) followed by filtration. This provided 5-bromo-3-iodo-1-(tetrahydro-2H-pyran-4-yl)-1H-pyrrolo [2,3-b]pyridine (82).

Step 8: Preparation of methyl 4-(5-bromo-1-(tetrahydro-2H-pyran-4-yl)-1H-pyrrolo[2,3-b]pyridin-3-yl)-3-(trifluoromethoxy)benzoate 83

A mixture of 5-bromo-3-iodo-1-(tetrahydro-2H-pyran-4-yl)-1H-pyrrolo [2,3-b]pyridine (82, 330 mg, 0.811 mmol), methyl 4-(4,4,5,5-tetramethyl-1,3,2-dioxaborolan-2-yl)-3-(trifluoromethoxy)benzoate (25, 281 mg, 0.811 mmol), $PdC_2(Ph_3P)_2$ (28.5 mg, 0.041 mmol), sodium carbonate (258 mg, 2.432 mmol), 1,4-dioxane (6.4 mL), and water (1.6 mL) was allowed to stir overnight at 60° C. The reaction was concentrated under reduced pressure and then partitioned between ethyl acetate (50 mL) and water (10 mL). The organic layer was isolated and washed with brine (10 ml), dried over anhydrous sodium sulfate, filtered and concentrated under reduced pressure. The resultant crude was purified by silica gel flash column chromatography (0 to 30% ethyl acetate in hexane) to provide methyl 4-(5-bromo-1-(tetrahydro-2H-pyran-4-yl)-1H-pyrrolo[2,3-b]pyridin-3-yl)-3-(trifluoromethoxy)benzoate (83).

Step 9: Preparation of methyl 4-(5-(5-ethyl-3-methylisoxazol-4-yl)-1-(tetrahydro-2H-pyran-4-yl)-1H-pyrrolo[2,3-b]pyridin-3-yl)-3-(trifluoromethoxy) benzoate 84

A mixture of 5-ethyl-3-methyl-4-(4,4,5,5-tetramethyl-1,3,2-dioxaborolan-2-yl)isoxazole (80, 26 mg, 0.110 mmol), methyl 4-(5-bromo-1-(tetrahydro-2H-pyran-4-yl)-1H-pyrrolo[2,3-b]pyridin-3-yl)-3-(trifluoromethoxy)benzoate (83, 55 mg, 0.110 mmol), $Pd(OAc)_2$ (1.2 mg, 0.006 mmol), S-Phos (2.3 mg, 0.006 mol) and $K_3PO_4$ (58 mg, 0.275 mmol) in dioxane (1.0 mL) and water (0.25 mL) was allowed to stir at 105° C. for 15 hours. The reaction was incomplete, so additional 5-ethyl-3-methyl-4-(4,4,5,5-tetramethyl-1,3,2-dioxaborolan-2-yl)isoxazole (80, 26 mg, 0.110 mmol), $Pd(OAc)_2$ (1.2 mg, 0.006 mmol), S-Phos (2.3 mg, 0.006 mol) and $K_3PO_4$ (58 mg, 0.275 mmol) were added and the mixture was allowed to stir at 105° C. for 6 more hours. The reaction was cooled, filtered through Celite and the filtrate was concentrated under reduced pressure. The resulting mixture of compounds 84 and P-0401 was dissolved in DMF (0.5 mL), and potassium carbonate (30 mg, 0.220 mmol) and methyl iodide (0.014 mL, 0.220 mmol) were added and the mixture was allowed to stir overnight at room temperature. The reaction was diluted with ethyl acetate (50 mL) and the solution was washed with aqueous 0.2 N HCl (5 mL), water (2×5 mL) and brine (5 mL), dried over anhydrous sodium sulfate, filtered and concentrated under reduced pressure. This material was purified by silica gel flash column chromatography (0 to 50% ethyl acetate in hexane) to provide methyl 4-(5-(5-ethyl-3-methylisoxazol-4-yl)-1-(tetrahydro-2H-pyran-4-yl)-1H-pyrrolo[2,3-b]pyridin-3-yl)-3-(trifluoromethoxy)benzoate (84). MS (ESI) $[M+H^+]^+$=530.2.

Step 10: Preparation of 4-(5-(5-ethyl-3-methylisoxazol-4-yl)-1-(tetrahydro-2H-pyran-4-yl)-1H-pyrrolo[2,3-b]pyridin-3-yl)-3-(trifluoromethoxy) benzoic acid P-0401

To methyl 4-(5-(5-ethyl-3-methylisoxazol-4-yl)-1-(tetrahydro-2H-pyran-4-yl)-1H-pyrrolo[2,3-b]pyridin-3-yl)-3-(trifluoromethoxy)benzoate (84, 31 mg) dissolved in THF (0.75 mL) and MeOH (0.25 mL) was added aqueous 2N lithium hydroxide (0.25 mL, 0.500 mmol) and the reaction was allowed to stir at room temperature for 3 hours. The reaction was quenched with the addition of aqueous 1N HCl (0.5 mL), the mixture was concentrated under reduced pressure. This material was purified by silica gel flash column chromatography (0 to 10% methanol in dichloromethane to provide 4-(5-(5-ethyl-3-methylisoxazol-4-yl)-1-(tetrahydro-2H-pyran-4-yl)-1H-pyrrolo[2,3-b]pyridin-3-yl)-3-(trifluoromethoxy)benzoic acid (P-0401). MS (ESI) $[M+H^+]^+$=516.1.

Example 17

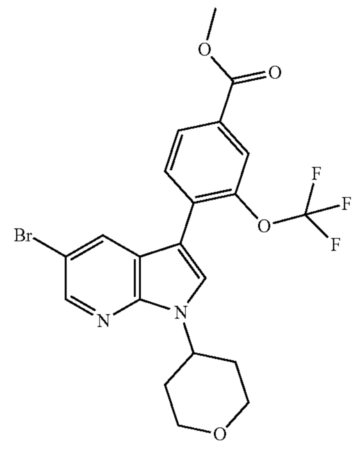

+

83

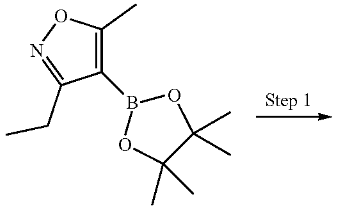

84

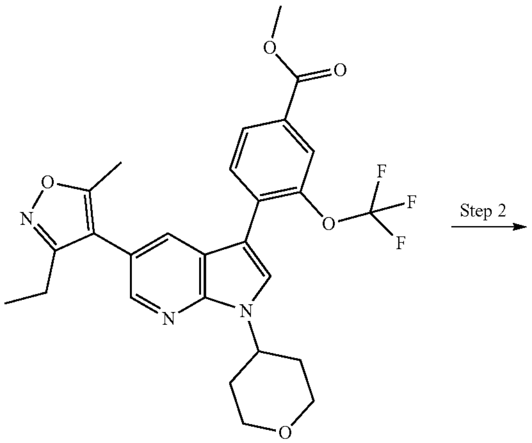

85

-continued

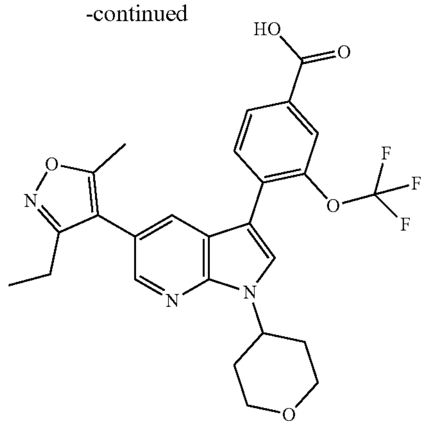

P-0400

Step 1: Preparation of methyl 4-(5-(3-ethyl-5-methylisoxazol-4-yl)-1-(tetrahydro-2H-pyran-4-yl)-1H-pyrrolo[2,3-b]pyridin-3-yl)-3-(trifluoromethoxy) benzoate 85

A mixture of 3-ethyl-5-methyl-4-(4,4,5,5-tetramethyl-1,3,2-dioxaborolan-2-yl)isoxazole (84, 26 mg, 0.110 mmol, prepared in 6 steps from 5-methylisoxazole-3-carboxylic acid in a manner analogous to compound 80 as depicted in example 16), methyl 4-(5-bromo-1-tetrahydropyran-4-yl-pyrrolo[2,3-b]pyridin-3-yl)-3-(trifluoromethoxy)benzoate (83, 55 mg, 0.110 mmol), $Pd(OAc)_2$(1.2 mg, 0.006 mmol), S-Phos (2.3 mg, 0.006 mol) and potassium phosphate (58 mg, 0.275 mmol) in dioxane (1.0 mL) and water (0.25 mL) was allowed to stir at 105° C. overnight. Additional 3-ethyl-5-methyl-4-(4,4,5,5-tetramethyl-1,3,2-dioxaborolan-2-yl) isoxazole (84, 26 mg, 0.110 mmol), $Pd(OAc)_2$(1.2 mg, 0.006 mmol), S-Phos (2.3 mg, 0.006 mol) and potassium phosphate (58 mg, 0.275 mmol) was added and the reaction continued at 105° C. for 6 more hours. Then, the reaction was allowed to cool and was filtered through Celite. The filtrate was concentrated under reduced pressure. The resulting mixture of compounds 85 and P-0400 was dissolved with DMF (0.5 mL) and potassium carbonate (30 mg, 0.220 mmol) and methyl iodide (0.014 mL, 0.220 mmol) were added. The reaction was allowed to stir overnight at room temperature. The reaction was diluted with ethyl acetate (50 mL) and the solution was washed with aqueous 0.2 N HCl (5 mL), water (2×5 mL) and brine (5 mL), dried over anhydrous sodium sulfate, filtered and concentrated under reduced pressure. This material was purified by silica gel flash column chromatography (0 to 50% ethyl acetate in hexane) to provide methyl 4-(5-(3-ethyl-5-methylisoxazol-4-yl)-1-(tetrahydro-2H-pyran-4-yl)-1H-pyrrolo[2,3-b]pyridin-3-yl)-3-(trifluoromethoxy)benzoate (85). MS (ESI) $[M+H^+]^+=530.2$.

Step 2: Preparation of 4-(5-(3-ethyl-5-methylisoxazol-4-yl)-1-(tetrahydro-2H-pyran-4-yl)-1H-pyrrolo [2,3-b]pyridin-3-yl)-3-(trifluoromethoxy)benzoic acid P-0400

To methyl 4-(5-(3-ethyl-5-methylisoxazol-4-yl)-1-(tetrahydro-2H-pyran-4-yl)-1H-pyrrolo[2,3-b]pyridin-3-yl)-3-(trifluoromethoxy)benzoate (85, 47 mg) dissolved in THF (0.75 mL) and MeOH (0.25 mL) was added aqueous 2N LiOH (0.25 mL, 0.500 mmol) and was stirred at room temperature for 2.5 hours. Then, aqueous 1N HCl (0.5 mL) was added and the mixture was concentrated under reduced pressure. This material was purified by silica gel flash column chromatography (0 to 10% methanol in dichloromethane) to provide 4-(5-(3-ethyl-5-methylisoxazol-4-yl)-1-(tetrahydro-2H-pyran-4-yl)-1H-pyrrolo[2,3-b]pyridin-3-yl)-3-(trifluoromethoxy)benzoic acid (P-0400). MS (ESI) $[M+H^+]^+=516.1$.

Example 18

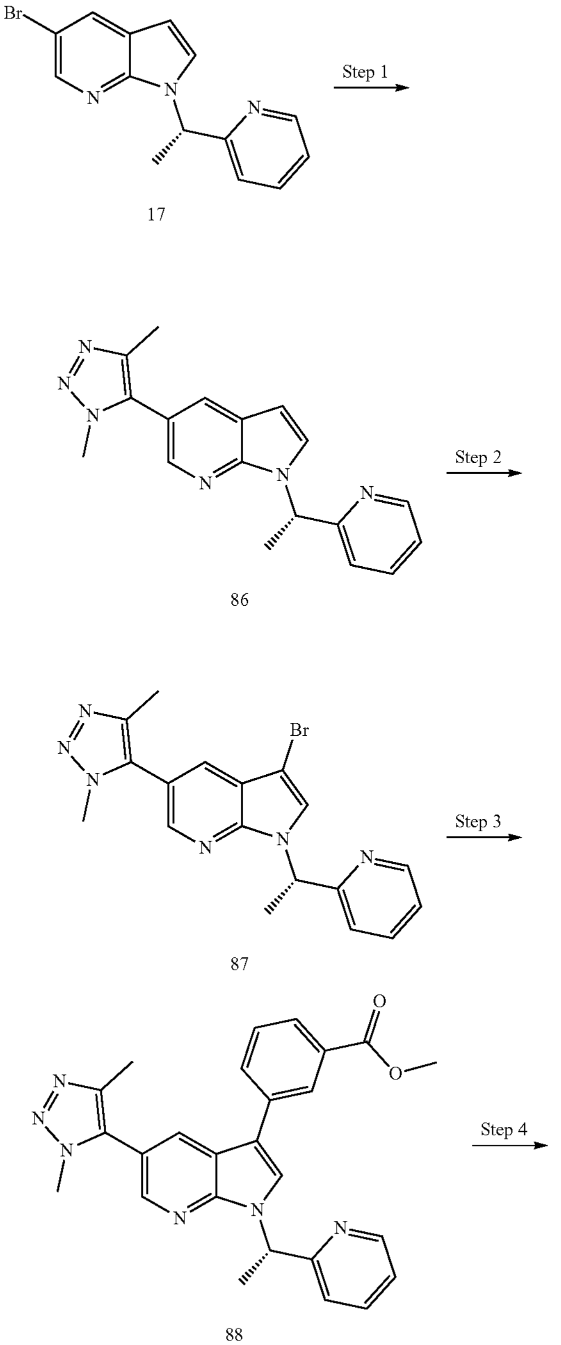

17

86

87

88

-continued

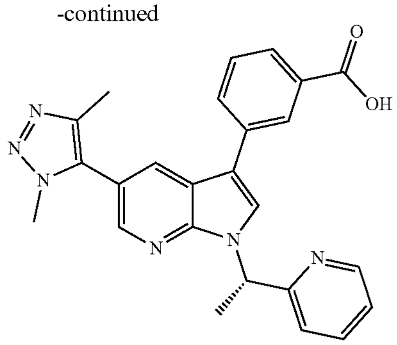

P-0449

Step 1: Preparation of (S)-5-(1,4-dimethyl-1H-1,2,3-triazol-5-yl)-1-(1-(pyridin-2-yl)ethyl)-1H-pyrrolo[2,3-b]pyridine 86

A mixture (S)-5-bromo-1-(1-(pyridin-2-yl)ethyl)-1H-pyrrolo[2,3-b]pyridine (17, 199 mg, 0.66 mmol), 1,4-dimethyl-5-(4,4,5,5-tetramethyl-1,3,2-dioxaborolan-2-yl)triazole (177 mg, 0.79 mmol) and 1,1'-bis(diphenylphosphino)ferrocene-palladium(II) dichloride dichloromethane complex (48 mg, 0.059 mmol) in dioxane (6.0 ml) was purged with nitrogen gas, and then aqueous 2.5M potassium carbonate (0.80 ml) was added. The reaction vial was sealed and heated at 140° C. for 2 hours. The reaction was diluted with ethyl acetate, dried over anhydrous magnesium sulfate, filtered and concentrated under reduced pressure. This material was purified by silica gel flash column chromatography (100% ethyl acetate) to provide (S)-5-(1,4-dimethyl-1H-1,2,3-triazol-5-yl)-1-(1-(pyridin-2-yl)ethyl)-1H-pyrrolo[2,3-b]pyridine (86). MS (ESI) $[M+H^+]^+=319.9$.

Step 2: Preparation of (S)-3-bromo-5-(1,4-dimethyl-1H-1,2,3-triazol-5-yl)-1-(1-(pyridin-2-yl)ethyl)-1H-pyrrolo[2,3-b]pyridine 87

To a solution of (S)-5-(1,4-dimethyl-1H-1,2,3-triazol-5-yl)-1-(1-(pyridin-2-yl)ethyl)-1H-pyrrolo[2,3-b]pyridine (86, 50 mg, 0.16 mmol) in acetonitrile (2 ml) was added N-bromosuccinimide (29 mg, 0.16 mmol). The mixture was allowed to stir and to warm to room temperature for 2 hours. The reaction was diluted with saturated aqueous sodium thiosulfate and extracted with ethyl acetate. The organic layer was washed with water, brine, dried over anhydrous magnesium sulfate, filtered and concentrated under reduced pressure to provide (S)-3-bromo-5-(1,4-dimethyl-1H-1,2,3-triazol-5-yl)-1-(1-(pyridin-2-yl)ethyl)-1H-pyrrolo[2,3-b]pyridine (87). MS (ESI) $[M+H^+]^+=399.0$.

Step 3: Preparation of methyl (S)-3-(5-(1,4-dimethyl-1H-1,2,3-triazol-5-yl)-1-(1-(pyridin-2-yl)ethyl)-1H-pyrrolo[2,3-b]pyridin-3-yl)benzoate 88

A mixture of (S)-3-bromo-5-(1,4-dimethyl-1H-1,2,3-triazol-5-yl)-1-(1-(pyridin-2-yl)ethyl)-1H-pyrrolo[2,3-b]pyridine (87, 39 mg, 0.10 mmol), methyl 3-(4,4,5,5-tetramethyl-1,3,2-dioxaborolan-2-yl)benzoate (39 mg, 0.15 mmol) and 1,1'-bis(diphenylphosphino)ferrocene-palladium(II) dichloride dichloromethane complex (8 mg, 0.009 mmol) in dioxane (1 ml) was purged with nitrogen gas, and then aqueous 2.5M potassium carbonate (0.120 ml) was added. The reaction vial was sealed and heated at 130° C. for 2 days. The reaction was cooled and diluted with ethyl acetate, dried over anhydrous magnesium sulfate, filtered and concentrated under reduced pressure. This material was purified by silica gel flash column chromatography (30% ethyl acetate) to provide methyl (S)-3-(5-(1,4-dimethyl-1H-1,2,3-triazol-5-yl)-1-(1-(pyridin-2-yl)ethyl)-1H-pyrrolo[2,3-b]pyridin-3-yl)benzoate (88). MS (ESI) $[M+H^+]^+=453.2$.

Step 4: Preparation of (S)-3-(5-(1,4-dimethyl-1H-1,2,3-triazol-5-yl)-1-(1-(pyridin-2-yl)ethyl)-1H-pyrrolo[2,3-b]pyridin-3-yl)benzoic acid P-0449

To a solution of methyl (S)-3-(5-(1,4-dimethyl-1H-1,2,3-triazol-5-yl)-1-(1-(pyridin-2-yl)ethyl)-1H-pyrrolo[2,3-b]pyridin-3-yl)benzoate (88, 20 mg, 0.04 mmol) in THF/MeOH (1:1, 1.0 ml) was added aqueous 4.18 M lithium hydroxide (0.020 ml). The reaction was allowed to stir at 70° C. for 2 hours. The reaction was acidified with aqueous 1N HCl, concentrated down under reduced pressure, and the material was purified by reverse phase silica gel flash column chromatography (0-100% B; A: 5% $CH_3CN$, 95% $H_2O$, 0.1% $HCO_2H$; B: 95% $CH_3CN$, 5% $H_2O$, 0.1% $HCO_2H$) to provide (S)-3-(5-(1,4-dimethyl-1H-1,2,3-triazol-5-yl)-1-(1-(pyridin-2-yl)ethyl)-1H-pyrrolo[2,3-b]pyridin-3-yl)benzoic acid (P-0449). MS (ESI) $[M+H^+]^+=439.1$.

Example 19

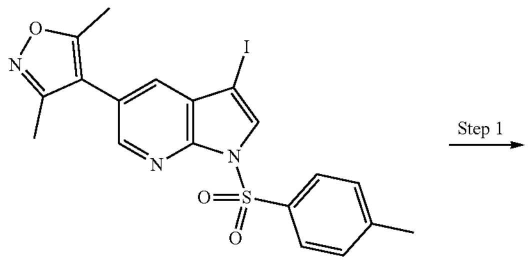

4

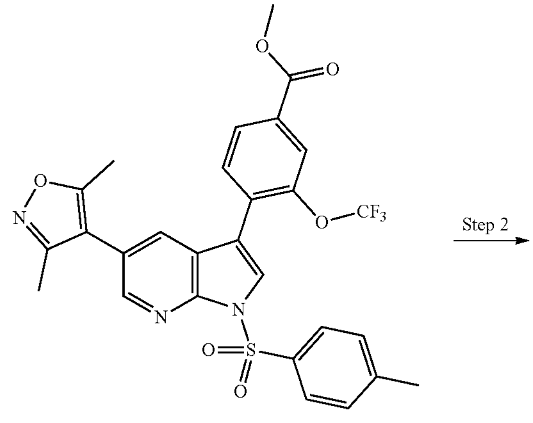

89

-continued

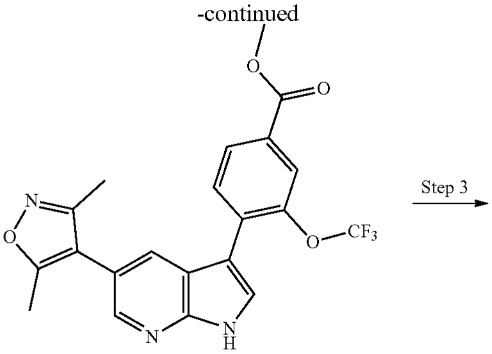

90

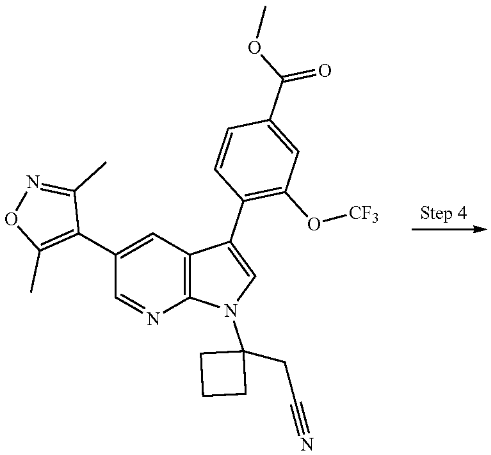

91

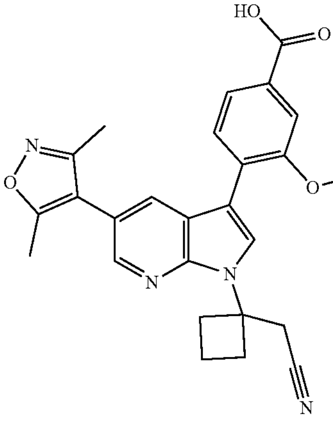

P-0335

Step 1: Preparation of methyl 4-(5-(3,5-dimethylisoxazol-4-yl)-1-tosyl-1H-pyrrolo[2,3-b]pyridin-3-yl)-3-(trifluoromethoxy)benzoate 89

To a mixture of 4-(3-iodo-1-tosyl-1H-pyrrolo[2,3-b]pyridin-5-yl)-3,5-dimethylisoxazole (4, 1.01 g, 2.05 mmol), methyl 4-(4,4,5,5-tetramethyl-1,3,2-dioxaborolan-2-yl)-3-(trifluoromethoxy)benzoate (25, 1.06 g, 3.08 mmol) and 1,1'-bis(diphenylphosphino)ferrocene-palladium(II) dichloride dichloromethane complex (167 mg, 0.205 mmol) in dioxane (20 ml), purged with nitrogen gas, was added aqueous 2.5M potassium carbonate (2.5 ml). The reaction vial was sealed and heated at 110° C. for 3 hours. The reaction was cooled and diluted with ethyl acetate, dried over anhydrous magnesium sulfate, filtered and concentrated down. This material was purified by silica gel flash column chromatography (30% ethyl acetate) to provide methyl 4-(5-(3,5-dimethylisoxazol-4-yl)-1-tosyl-1H-pyrrolo[2,3-b]pyridin-3-yl)-3-(trifluoromethoxy)benzoate (89). MS (ESI) $[M+H^+]^+$=586.5.

Step 2: Preparation of methyl 4-(5-(3,5-dimethylisoxazol-4-yl)-1H-pyrrolo[2,3-b]pyridin-3-yl)-3-(trifluoromethoxy)benzoate 90

To a solution of methyl 4-(5-(3,5-dimethylisoxazol-4-yl)-1-tosyl-1H-pyrrolo[2,3-b]pyridin-3-yl)-3-(trifluoromethoxy)benzoate (89, 865.8 mg, 1.48 mmol) dissolved in THF (15 ml) was added 1M tetra-n-butylammonium fluoride in THF (1.8 ml). The reaction was allowed to stir at 70° C. for 15 hours. The reaction was diluted with ethyl acetate, washed with saturated aqueous sodium bicarbonate, water and brine and dried over magnesium sulfate. After filtration, the filtrate was concentrated under reduced pressure and the resulting solid was triturated with dichloromethane/hexane to provide methyl 4-(5-(3,5-dimethylisoxazol-4-yl)-1H-pyrrolo[2,3-b]pyridin-3-yl)-3-(trifluoromethoxy)benzoate (90). MS (ESI) $[M+H^+]^+$=432.5.

Step 3: Preparation of methyl 4-(1-(1-(cyanomethyl)cyclobutyl)-5-(3,5-dimethylisoxazol-4-yl)-1H-pyrrolo[2,3-b]pyridin-3-yl)-3-(trifluoromethoxy)benzoate 91

A mixture of methyl 4-(5-(3,5-dimethylisoxazol-4-yl)-1H-pyrrolo[2,3-b]pyridin-3-yl)-3-(trifluoromethoxy)benzoate (90, 52 mg, 0.12 mmol), DBU (0.06 ml, 0.48 mmol) and 2-cyclobutylideneacetonitrile (45 mg, 0.48 mmol) in acetonitrile (1 ml) was allowed to stir at 80° C. for 15 hours. The reaction was concentrated down under reduced pressure and purified by silica gel flash column chromatography (50% ethyl acetate) to provide methyl 4-(1-(1-(cyanomethyl)cyclobutyl)-5-(3,5-dimethylisoxazol-4-yl)-1H-pyrrolo[2,3-b]pyridin-3-yl)-3-(trifluoromethoxy)benzoate (91). MS (ESI) $[M+H^+]^+$=525.1.

Step 4: Preparation of 4-(1-(1-(cyanomethyl)cyclobutyl)-5-(3,5-dimethylisoxazol-4-yl)-1H-pyrrolo[2,3-b]pyridin-3-yl)-3-(trifluoromethoxy)benzoic acid P-0335

To a solution of methyl 4-(1-(1-(cyanomethyl)cyclobutyl)-5-(3,5-dimethylisoxazol-4-yl)-1H-pyrrolo[2,3-b]pyridin-3-yl)-3-(trifluoromethoxy)benzoate (91, 55 mg, 0.1 mmol) in THF/MeOH (1:1, 1 ml), was added aqueous 4.18 M lithium hydroxide (0.050 ml). The reaction was allowed to stir at 70° C. for 3 hours. The reaction was diluted with ethyl acetate, acidified with 1N HCl in MeOH and concentrated under reduced pressure. The material was purified by reverse phase silica gel flash column chromatography (0-100% B; A: 5% $CH_3CN$, 95% $H_2O$, 0.1% $HCO_2H$; B: 95% $CH_3CN$, 5% $H_2O$, 0.1% $HCO_2H$) to provide 4-(1-(1-(cyanomethyl)cyclobutyl)-5-(3,5-dimethylisoxazol-4-yl)-1H-pyrrolo[2,3-b]pyridin-3-yl)-3-(trifluoromethoxy)benzoic acid (P-0335). MS (ESI) $[M+H^+]^+$=511.0.

Example 20

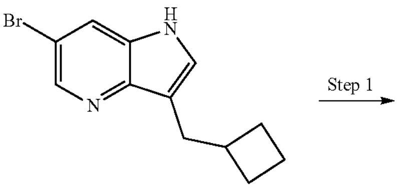

92

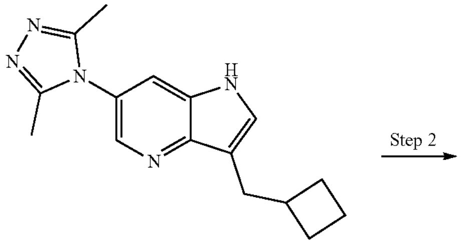

93

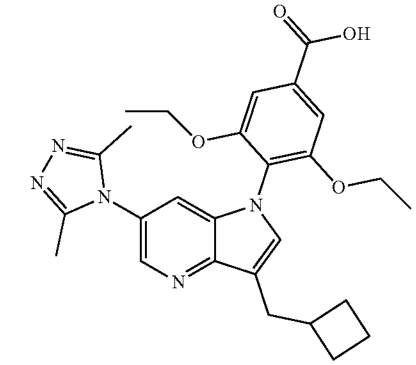

P-0270

Step 1: Preparation of 3-(cyclobutylmethyl)-6-(3,5-dimethyl-4H-1,2,4-triazol-4-yl)-1H-pyrrolo[3,2-b]pyridine 93

A mixture of 3,5-dimethyl-4H-1,2,4-triazole (0.50 g, 5.2 mmol), 6-bromo-3-(cyclobutylmethyl)-1H-pyrrolo[3,2-b]pyridine (92, 1.0 g, 3.8 mmol, prepared in 2 steps from 6-bromo-1H-pyrrolo[3,2-b]pyridine and cyclobutanecarbaldehyde in a manner analogous to compound 55 as depicted in example 12), trans N,N'-dimethylcyclohexane-1,2-diamine (1.1 mL, 7.0 mmol), and cesium carbonate (2.5 g, 7.67 mmol) in toluene (5 mL) and DMF (5 ML) was purged with nitrogen and allowed to stir at 130° C. for 3 days. The reaction mixture was poured into water and extracted with ethyl acetate. The organic layer was collected, washed with brine, and dried over sodium sulfate. After removal of drying agent and solvent, the residue was purified silica gel flash column chromatography to provide 3-(cyclobutylmethyl)-6-(3,5-dimethyl-4H-1,2,4-triazol-4-yl)-1H-pyrrolo[3,2-b]pyridine (93). MS (ESI) $[M+H^+]^+$=282.1.

Step 2: Preparation of 4-(3-(cyclobutylmethyl)-6-(3,5-dimethyl-4H-1,2,4-triazol-4-yl)-1H-pyrrolo[3,2-b]pyridin-1-yl)-3,5-diethoxybenzoic acid P-0270

A mixture of 3-(cyclobutylmethyl)-6-(3,5-dimethyl-4H-1,2,4-triazol-4-yl)-1H-pyrrolo[3,2-b]pyridine (93, 200 mg, 0.71 mmol), methyl 4-bromo-3,5-diethoxybenzoate (300 mg, 0.99 mmol), copper (I) iodide (30 mg, 1.58 mmol) and trans N,N'-dimethylcyclohexane-1,2-diamine (300 ul, 1.9 mmol) in toluene (5 ml) and DMF (5 ml) was purged with nitrogen and allowed to stir at 120° C. overnight. The reaction mixture was filtered and the filtrate was purified by reverse phase HPLC (C18; 0-100% B; A: 5% $CH_3CN$, 95% $H_2O$, 0.1% $HCO_2H$; B: 95% $CH_3CN$, 5% $H_2O$, 0.1% $HCO_2H$) to provide 4-(3-(cyclobutylmethyl)-6-(3,5-dimethyl-4H-1,2,4-triazol-4-yl)-1H-pyrrolo[3,2-b]pyridin-1-yl)-3,5-diethoxybenzoic acid (P-0270). MS (ESI) $[M+H^+]^+$=490.1.

Example 21

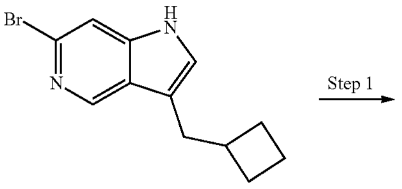

94

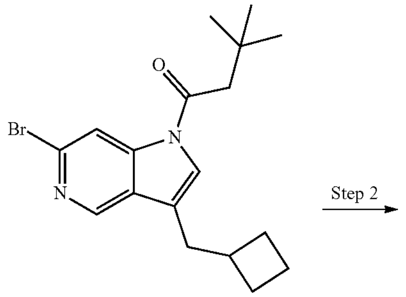

95

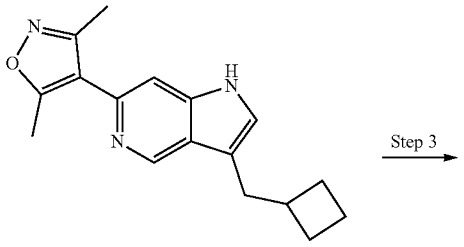

96

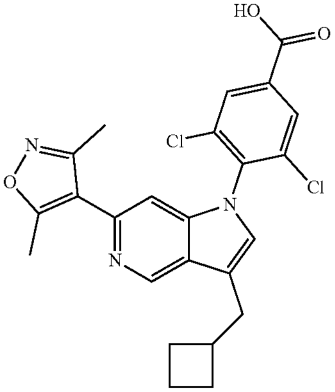

P-0149

Step 1: Preparation of tert-butyl 6-bromo-3-(cyclobutylmethyl)-1H-pyrrolo[3,2-c]pyridine-1-carboxylate 95

6-bromo-3-(cyclobutylmethyl)-1H-pyrrolo[3,2-c]pyridine (94, 300 mg, 1.13 mmol, prepared in 2 steps from 6-bromo-H-pyrrolo[3,2-c]pyridine and cyclobutanecarbaldehyde in a manner analogous to compound 55 as depicted in example 12), di-tert-butyl dicarbonate (370 mg, 1.70 mmol), DMAP (14 mg, 0.11 mmol), and trimethylamine (0.79 ml, 5.66 mmol) were dissolved in THF and allowed to stir at room temperature for 3 hours. The reaction was then partitioned between ethyl acetate and aqueous ammonium chloride solution. The organic layer was washed with brine, dried over anhydrous magnesium sulfate, filtered and then loaded onto silica gel. The material was purified by silica gel flash column chromatography (0 to 50% ethyl acetate in hexane) to provide tert-butyl 6-bromo-3-(cyclobutylmethyl)-1H-pyrrolo[3,2-c]pyridine-1-carboxylate (95).

Step 2: Preparation of 4-(3-(cyclobutylmethyl)-1H-pyrrolo[3,2-c]pyridin-6-yl)-3,5-dimethylisoxazole 96 tert-butyl 6-bromo-3-(cyclobutylmethyl)-1H-pyrrolo[3,2-c]pyridine-1-carboxylate (95, 250 mg, 0.68 mmol), 3,5-dimethyl-4-(4,4,5,5-tetramethyl-1,3,2-dioxaborolan-2-yl) isoxazole (343 mg, 1.54 mmol), aqueous 2.5M potassium carbonate (0.55 ml), and 1,1'-bis(diphenylphosphino)ferrocene-palladium(II) dichloride dichloromethane complex (50 mg, 0.061 mmol) were combined in acetonitrile and dioxane, then flushed with argon and irradiated in amicrowave reactor to 125° C. for 1 hour. The reaction was then filtered through Celite and partitioned between ethyl acetate and aqueous ammonium chloride. The organic layer was dried over magnesium sulfate, filtered and concentrated. This material was dissolved in DCM (3 ml) and trifluoroacetic acid (0.53 ml, 6.84 mmol). The reaction was allowed to stir for 2 hours, then concentrated under reduced pressure. The resulting material was dissolved in ethyl acetate and washed with aqueous sodium bicarbonate solution. The organic layer was further washed with brine, then dried over anhydrous magnesium sulfate and filtered. The filtrate was concentrated under reduced pressure and the material was purified by silica gel flash column chromatography (0 to 5% methanol in DCM) to provide 4-(3-(cyclobutylmethyl)-1H-pyrrolo[3,2-c]pyridin-6-yl)-3,5-dimethylisoxazole (96).

Step 3: Preparation of 3,5-dichloro-4-(3-(cyclobutylmethyl)-6-(3,5-dimethylisoxazol-4-yl)-1H-pyrrolo[3,2-c]pyridin-1-yl)benzoic acid P-0149

4-(3-(cyclobutylmethyl)-1H-pyrrolo[3,2-c]pyridin-6-yl)-3,5-dimethylisoxazole (96, 20 mg, 0.071 mmol) 3,5-dichloro-4-fluorobenzoic acid (22 mg, 0.107 mmol), and cesium carbonate (51 mg, 0.16 mmol) were combined in DMSO (0.8 ml) and allowed to stir at 85° C. for 5 hours. The reaction was then filtered through cotton wool and partitioned between ethyl acetate and aqueous ammonium chloride. The organic layer was washed with water, then brine, dried over anhydrous magnesium sulfate and filtered. The filtrate was concentrated under reduced pressure and the material was purified by silica gel flash column chromatography (0 to 10% methanol in DCM) to provide partially pure material that was further purified by reverse phase HPLC (C18; 0-100% B; A: 5% $CH_3CN$, 95% $H_2O$, 0.100$HCO_2H$; B: 95% $CH_3CN$, 5% $H_2O$, 0.1% $HCO_2H$) to provide 3,5-dichloro-4-(3-(cyclobutylmethyl)-6-(3,5-dimethylisoxazol-4-yl)-1H-pyrrolo[3,2-c]pyridin-1-yl)benzoic acid(P-0149). MS (ESI) $[M+H^+]^+$=471.0.

All compounds in Table 1 listed below can be made according to the synthetic examples described in this disclosure, and by making any necessary substitutions of starting materials that the skilled artisan would be able to obtain either commercially or otherwise.

TABLE 1

| P# | Structure | Name | (MH)+ |
|---|---|---|---|
| P-0001 | 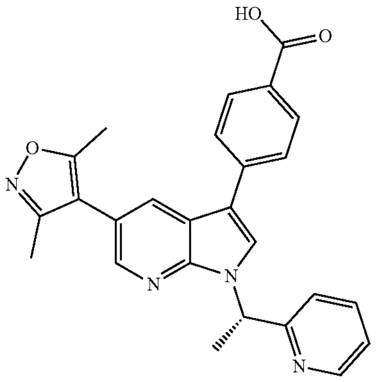 [SMILES: Cc1noc(C)c1-c1cnc2c(c1)c(-c1ccc(C(=O)O)cc1)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)benzoic acid | 439.6 |
| P-0002 | 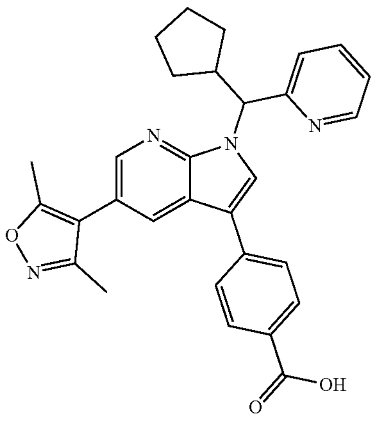 [SMILES: Cc1noc(C)c1-c1cnc2c(c1)c(-c1ccc(C(=O)O)cc1)cn2C(c1ccccn1)C1CCCC1] | 4-(1-(cyclopentyl(pyridin-2-yl)methyl)-5-(3,5-dimethylisoxazol-4-yl)-1H-pyrrolo[2,3-b]pyridin-3-yl)benzoic acid | 493.6 |
| P-0003 | 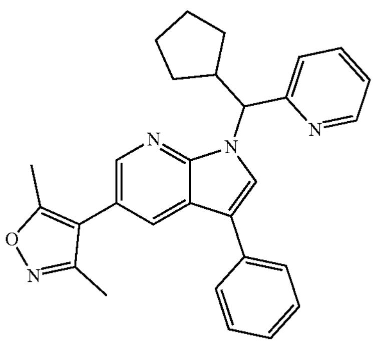 [SMILES: Cc1noc(C)c1-c1cnc2c(c1)c(-c1ccccc1)cn2C(c1ccccn1)C1CCCC1] | 4-(1-(cyclopentyl(pyridin-2-yl)methyl)-3-phenyl-1H-pyrrolo[2,3-b]pyridin-5-yl)-3,5-dimethylisoxazole | 449.20 |

TABLE 1-continued
| P# | Structure | Name | (MH)+ |
|---|---|---|---|
| P-0004 | 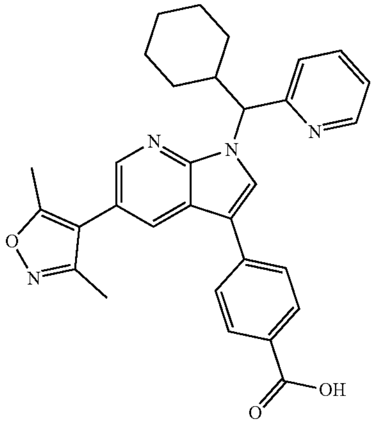 [SMILES: Cc1noc(C)c1-c1cnc2c(c1)c(-c1ccc(C(=O)O)cc1)cn2C(c1ccccn1)C1CCCCC1] | 4-(1-(cyclohexyl(pyridin-2-yl)methyl)-5-(3,5-dimethylisoxazol-4-yl)-1H-pyrrolo[2,3-b]pyridin-3-yl)benzoic acid | 507.2 |
| P-0005 | 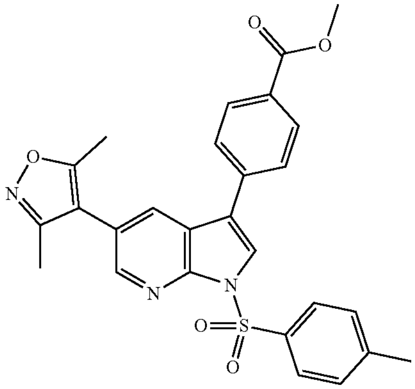 [SMILES: COC(=O)c1ccc(-c2cn(S(=O)(=O)c3ccc(C)cc3)c3ncc(-c4c(C)noc4C)cc23)cc1] | methyl 4-(5-(3,5-dimethylisoxazol-4-yl)-1-tosyl-1H-pyrrolo[2,3-b]pyridin-3-yl)benzoate | 502.1 |
| P-0006 | 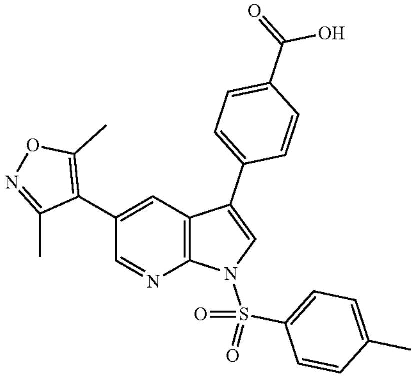 [SMILES: Cc1ccc(S(=O)(=O)n2cc(-c3ccc(C(=O)O)cc3)c3cc(-c4c(C)noc4C)cnc32)cc1] | 4-(5-(3,5-dimethylisoxazol-4-yl)-1-tosyl-1H-pyrrolo[2,3-b]pyridin-3-yl)benzoic acid | 488.1 |
| P-0007 | 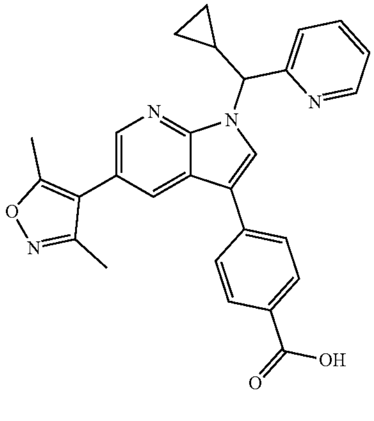 [SMILES: Cc1noc(C)c1-c1cnc2c(c1)c(-c1ccc(C(=O)O)cc1)cn2C(c1ccccn1)C1CC1] | 4-(1-(cyclopropyl(pyridin-2-yl)methyl)-5-(3,5-dimethylisoxazol-4-yl)-1H-pyrrolo[2,3-b]pyridin-3-yl)benzoic acid | 465.55 |

TABLE 1-continued

| P# | Structure | Name | (MH)+ |
|---|---|---|---|
| P-0008 | 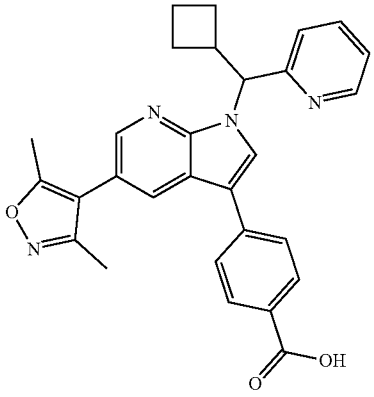 [SMILES: Cc1noc(C)c1-c1cnc2c(c1)c(-c1ccc(C(=O)O)cc1)cn2C(c1ccccn1)C1CCC1] | 4-(1-(cyclobutyl(pyridin-2-yl)methyl)-5-(3,5-dimethylisoxazol-4-yl)-1H-pyrrolo[2,3-b]pyridin-3-yl)benzoic acid | 479.1 |
| P-0009 | 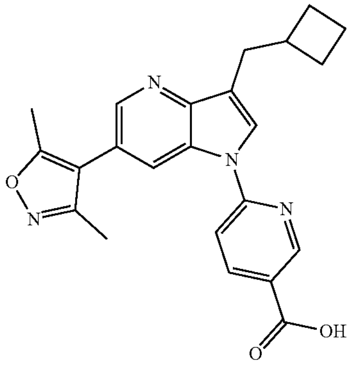 [SMILES: Cc1noc(C)c1-c1cnc2c(CC3CCC3)cn(-c3ccc(C(=O)O)cn3)c2c1] | 6-(3-(cyclobutylmethyl)-6-(3,5-dimethylisoxazol-4-yl)-1H-pyrrolo[3,2-b]pyridin-1-yl)nicotinic acid | 403.1 |
| P-0010 | 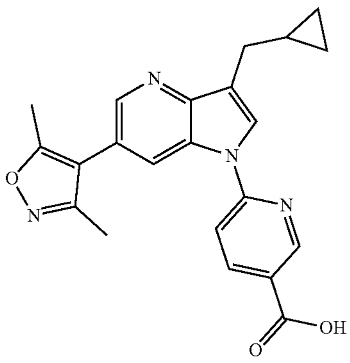 [SMILES: Cc1noc(C)c1-c1cnc2c(CC3CC3)cn(-c3ccc(C(=O)O)cn3)c2c1] | 6-(3-(cyclopropylmethyl)-6-(3,5-dimethylisoxazol-4-yl)-1H-pyrrolo[3,2-b]pyridin-1-yl)nicotinic acid | 388.4 |
| P-0011 | 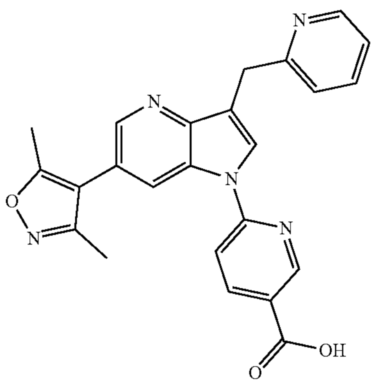 [SMILES: Cc1noc(C)c1-c1cnc2c(Cc3ccccn3)cn(-c3ccc(C(=O)O)cn3)c2c1] | 6-(6-(3,5-dimethylisoxazol-4-yl)-3-(pyridin-2-ylmethyl)-1H-pyrrolo[3,2-b]pyridin-1-yl)nicotinic acid | 425.4 |

TABLE 1-continued

| P# | Structure | Name | (MH)+ |
|---|---|---|---|
| P-0012 | 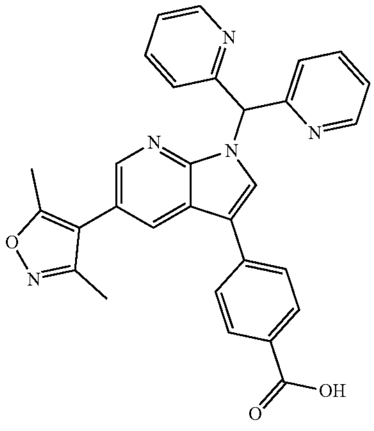 [SMILES: Cc1noc(C)c1-c1cnc2c(c1)c(-c1ccc(C(=O)O)cc1)cn2C(c1ccccn1)c1ccccn1] | 4-(1-(di(pyridin-2-yl)methyl)-5-(3,5-dimethylisoxazol-4-yl)-1H-pyrrolo[2,3-b]pyridin-3-yl)benzoic acid | 501.5 |
| P-0013 | 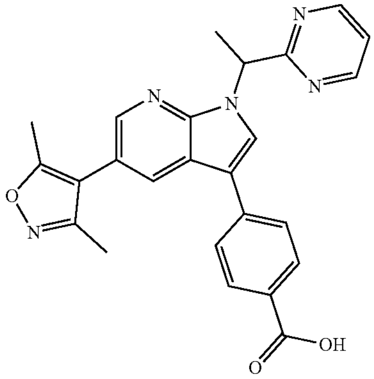 [SMILES: Cc1noc(C)c1-c1cnc2c(c1)c(-c1ccc(C(=O)O)cc1)cn2C(C)c1ncccn1] | 4-(5-(3,5-dimethylisoxazol-4-yl)-1-(1-(pyrimidin-2-yl)ethyl)-1H-pyrrolo[2,3-b]pyridin-3-yl)benzoic acid | 439.5 |
| P-0014 | 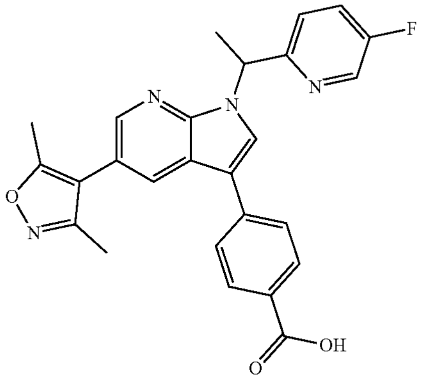 [SMILES: Cc1noc(C)c1-c1cnc2c(c1)c(-c1ccc(C(=O)O)cc1)cn2C(C)c1ccc(F)cn1] | 4-(5-(3,5-dimethylisoxazol-4-yl)-1-(1-(5-fluoropyridin-2-yl)ethyl)-1H-pyrrolo[2,3-b]pyridin-3-yl)benzoic acid | 456.5 |
| P-0015 | 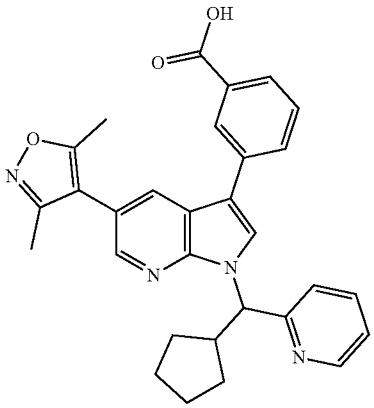 [SMILES: Cc1noc(C)c1-c1cnc2c(c1)c(-c1cccc(C(=O)O)c1)cn2C(c1ccccn1)C1CCCC1] | 3-(1-(cyclopentyl(pyridin-2-yl)methyl)-5-(3,5-dimethylisoxazol-4-yl)-1H-pyrrolo[2,3-b]pyridin-3-yl)benzoic acid | 492.6 |

TABLE 1-continued

| P# | Structure | Name | (MH)+ |
|---|---|---|---|
| P-0016 | 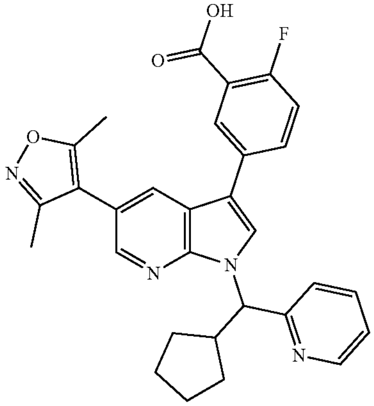 [SMILES: Cc1noc(C)c1-c1cnc2c(c1)c(-c1ccc(F)c(C(=O)O)c1)cn2C(c1ccccn1)C1CCCC1] | 5-(1-(cyclopentyl(pyridin-2-yl)methyl)-5-(3,5-dimethylisoxazol-4-yl)-1H-pyrrolo[2,3-b]pyridin-3-yl)-2-fluorobenzoic acid | 510.6 |
| P-0017 | 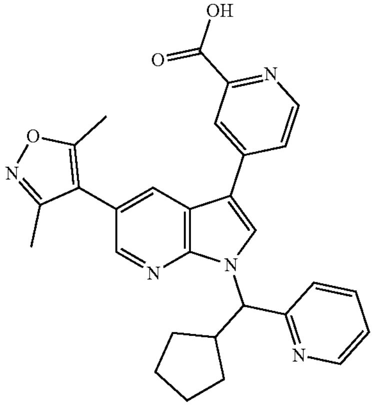 | 4-(1-(cyclopentyl(pyridin-2-yl)methyl)-5-(3,5-dimethylisoxazol-4-yl)-1H-pyrrolo[2,3-b]pyridin-3-yl)picolinic acid | 493.6 |
| P-0018 | 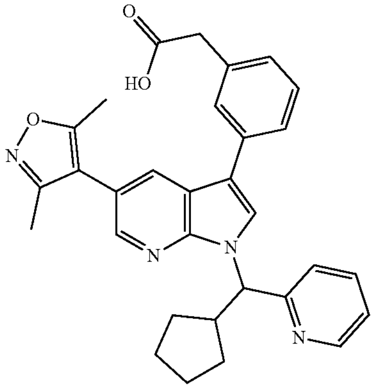 [SMILES: Cc1noc(C)c1-c1cnc2c(c1)c(-c1cccc(CC(=O)O)c1)cn2C(c1ccccn1)C1CCCC1] | 2-(3-(1-(cyclopentyl(pyridin-2-yl)methyl)-5-(3,5-dimethylisoxazol-4-yl)-1H-pyrrolo[2,3-b]pyridin-3-yl)phenyl)acetic acid | 507.1 |
| P-0019 | 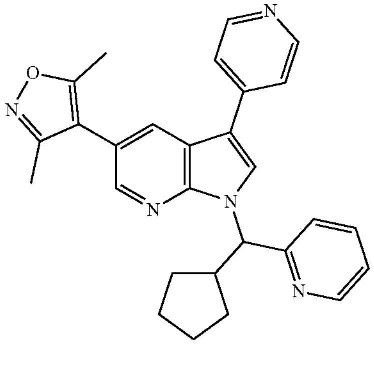 [SMILES: Cc1noc(C)c1-c1cnc2c(c1)c(-c1ccncc1)cn2C(c1ccccn1)C1CCCC1] | 4-(1-(cyclopentyl(pyridin-2-yl)methyl)-3-(pyridin-4-yl)-1H-pyrrolo[2,3-b]pyridin-5-yl)-3,5-dimethylisoxazole | 449.5 |

TABLE 1-continued
| P# | Structure | Name | (MH)+ |
|---|---|---|---|
| P-0020 | 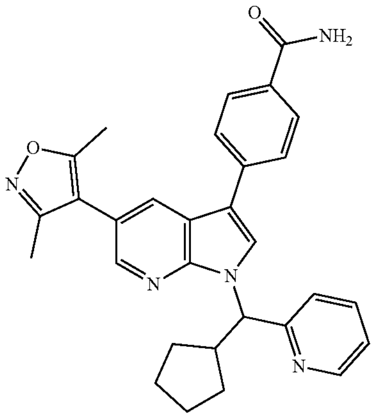 [SMILES: Cc1noc(C)c1-c1cnc2c(c1)c(-c1ccc(C(N)=O)cc1)cn2C(c1ccccn1)C1CCCC1] | 4-(1-(cyclopentyl(pyridin-2-yl)methyl)-5-(3,5-dimethylisoxazol-4-yl)-1H-pyrrolo[2,3-b]pyridin-3-yl)benzamide | 491.6 |
| P-0021 | 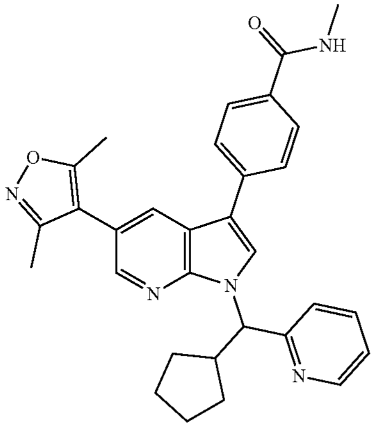 [SMILES: CNC(=O)c1ccc(-c2cn(C(c3ccccn3)C3CCCC3)c3ncc(-c4c(C)noc4C)cc23)cc1] | 4-(1-(cyclopentyl(pyridin-2-yl)methyl)-5-(3,5-dimethylisoxazol-4-yl)-1H-pyrrolo[2,3-b]pyridin-3-yl)-N-methylbenzamide | 506.2 |
| P-0022 | 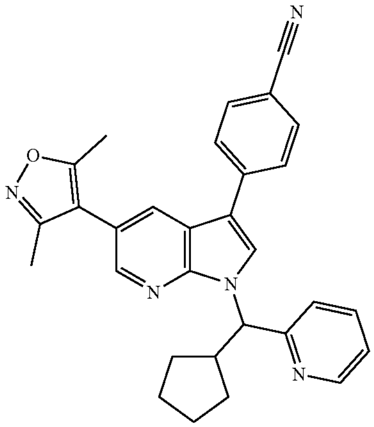 [SMILES: Cc1noc(C)c1-c1cnc2c(c1)c(-c1ccc(C#N)cc1)cn2C(c1ccccn1)C1CCCC1] | 4-(1-(cyclopentyl(pyridin-2-yl)methyl)-5-(3,5-dimethylisoxazol-4-yl)-1H-pyrrolo[2,3-b]pyridin-3-yl)benzonitrile | 474.1 |

TABLE 1-continued
| P# | Structure | Name | (MH)+ |
|---|---|---|---|
| P-0023 | 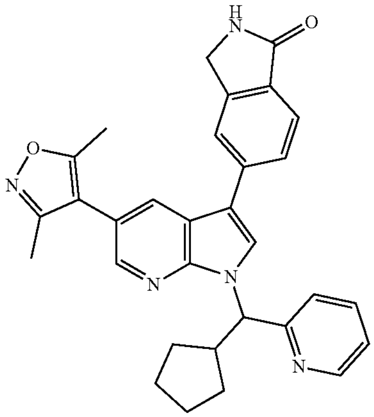 [SMILES: Cc1noc(C)c1-c1cnc2c(c1)c(-c1ccc3c(c1)CNC3=O)cn2C(c1ccccn1)C1CCCC1] | 5-(1-(cyclopentyl(pyridin-2-yl)methyl)-5-(3,5-dimethylisoxazol-4-yl)-1H-pyrrolo[2,3-b]pyridin-3-yl)isoindolin-1-one | 503.6 |
| P-0024 | 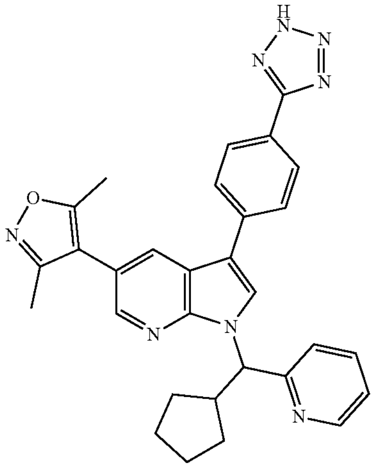 [SMILES: Cc1noc(C)c1-c1cnc2c(c1)c(-c1ccc(-c3nn[nH]n3)cc1)cn2C(c1ccccn1)C1CCCC1] | 4-(3-(4-(2H-tetrazol-5-yl)phenyl)-1-(cyclopentyl(pyridin-2-yl)methyl)-1H-pyrrolo[2,3-b]pyridin-5-yl)-3,5-dimethylisoxazole | 517.3 |
| P-0025 | 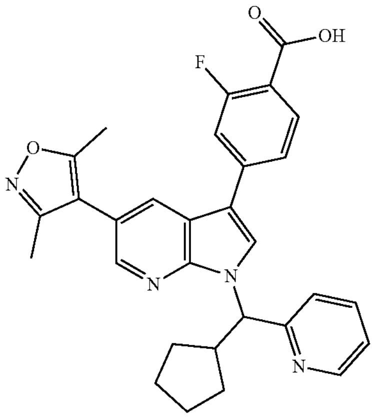 [SMILES: Cc1noc(C)c1-c1cnc2c(c1)c(-c1ccc(C(=O)O)c(F)c1)cn2C(c1ccccn1)C1CCCC1] | 4-(1-(cyclopentyl(pyridin-2-yl)methyl)-5-(3,5-dimethylisoxazol-4-yl)-1H-pyrrolo[2,3-b]pyridin-3-yl)-2-fluorobenzoic acid | 511.3 |

TABLE 1-continued
| P# | Structure | Name | (MH)+ |
|---|---|---|---|
| P-0026 | 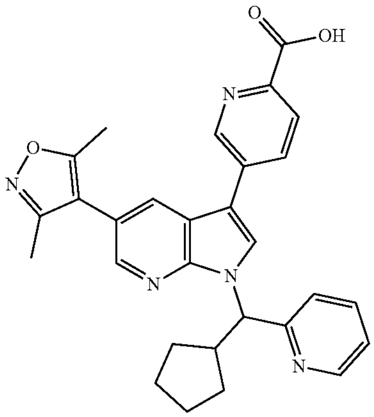 [SMILES: Cc1noc(C)c1-c1cnc2c(c1)c(-c1ccc(C(=O)O)nc1)cn2C(c1ccccn1)C1CCCC1] | 5-(1-(cyclopentyl(pyridin-2-yl)methyl)-5-(3,5-dimethylisoxazol-4-yl)-1H-pyrrolo[2,3-b]pyridin-3-yl)picolinic acid | 494.2 |
| P-0027 | 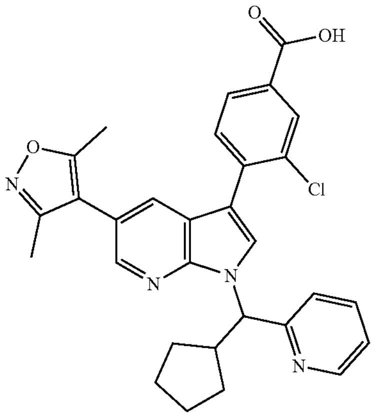 [SMILES: Cc1noc(C)c1-c1cnc2c(c1)c(-c1ccc(C(=O)O)cc1Cl)cn2C(c1ccccn1)C1CCCC1] | 3-chloro-4-(1-(cyclopentyl(pyridin-2-yl)methyl)-5-(3,5-dimethylisoxazol-4-yl)-1H-pyrrolo[2,3-b]pyridin-3-yl)benzoic acid | 527.2 |
| P-0028 | 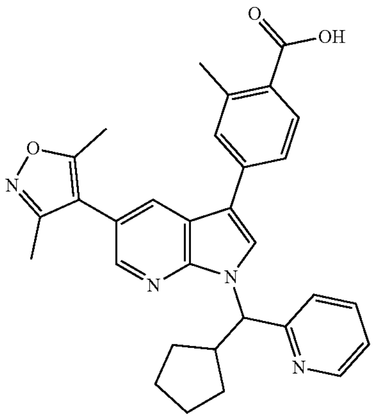 [SMILES: Cc1cc(-c2cn(C(c3ccccn3)C3CCCC3)c3ncc(-c4c(C)noc4C)cc23)ccc1C(=O)O] | 4-(1-(cyclopentyl(pyridin-2-yl)methyl)-5-(3,5-dimethylisoxazol-4-yl)-1H-pyrrolo[2,3-b]pyridin-3-yl)-2-methylbenzoic acid | 507.1 |

TABLE 1-continued
| P# | Structure | Name | (MH)+ |
|---|---|---|---|
| P-0029 | 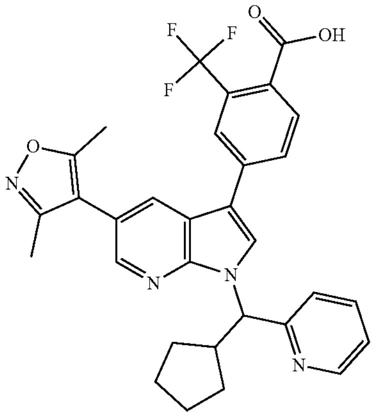 [SMILES: Cc1noc(C)c1-c1cnc2c(c1)c(-c1ccc(C(=O)O)c(C(F)(F)F)c1)cn2C(c1ccccn1)C1CCCC1] | 4-(1-(cyclopentyl(pyridin-2-yl)methyl)-5-(3,5-dimethylisoxazol-4-yl)-1H-pyrrolo[2,3-b]pyridin-3-yl)-2-(trifluoromethyl)benzoic acid | 561.1 |
| P-0030 | 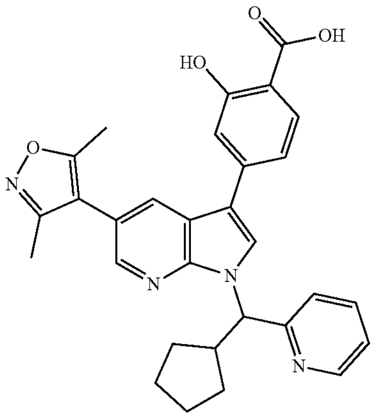 [SMILES: Cc1noc(C)c1-c1cnc2c(c1)c(-c1ccc(C(=O)O)c(O)c1)cn2C(c1ccccn1)C1CCCC1] | 4-(1-(cyclopentyl(pyridin-2-yl)methyl)-5-(3,5-dimethylisoxazol-4-yl)-1H-pyrrolo[2,3-b]pyridin-3-yl)-2-hydroxybenzoic acid | 509.2 |
| P-0031 | 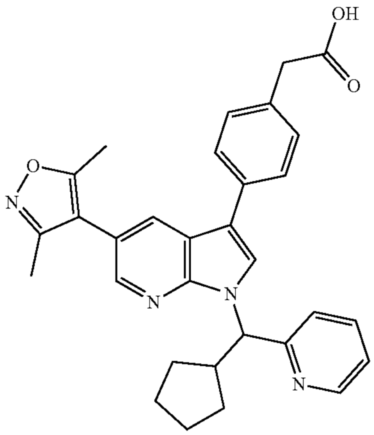 [SMILES: Cc1noc(C)c1-c1cnc2c(c1)c(-c1ccc(CC(=O)O)cc1)cn2C(c1ccccn1)C1CCCC1] | 2-(4-(1-(cyclopentyl(pyridin-2-yl)methyl)-5-(3,5-dimethylisoxazol-4-yl)-1H-pyrrolo[2,3-b]pyridin-3-yl)phenyl)acetic acid | 507.1 |

TABLE 1-continued

| P# | Structure | Name | (MH)+ |
|---|---|---|---|
| P-0032 | 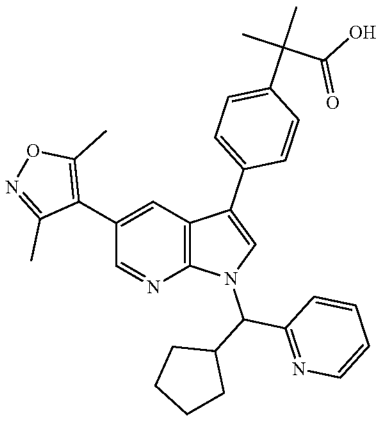 [SMILES: Cc1noc(C)c1-c1cnc2c(c1)c(-c1ccc(C(C)(C)C(=O)O)cc1)cn2C(c1ccccn1)C1CCCC1] | 2-(4-(1-(cyclopentyl(pyridin-2-yl)methyl)-5-(3,5-dimethylisoxazol-4-yl)-1H-pyrrolo[2,3-b]pyridin-3-yl)phenyl)-2-methylpropanoic acid | 535.3 |
| P-0033 | 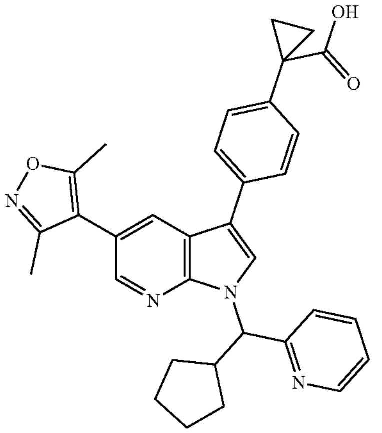 [SMILES: Cc1noc(C)c1-c1cnc2c(c1)c(-c1ccc(C3(C(=O)O)CC3)cc1)cn2C(c1ccccn1)C1CCCC1] | 1-(4-(1-(cyclopentyl(pyridin-2-yl)methyl)-5-(3,5-dimethylisoxazol-4-yl)-1H-pyrrolo[2,3-b]pyridin-3-yl)phenyl)cyclopropane-1-carboxylic acid | 533.2 |
| P-0034 | 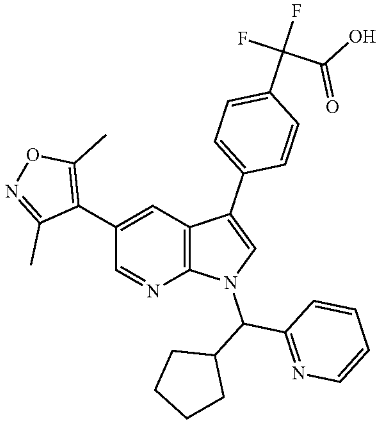 [SMILES: Cc1noc(C)c1-c1cnc2c(c1)c(-c1ccc(C(F)(F)C(=O)O)cc1)cn2C(c1ccccn1)C1CCCC1] | 2-(4-(1-(cyclopentyl(pyridin-2-yl)methyl)-5-(3,5-dimethylisoxazol-4-yl)-1H-pyrrolo[2,3-b]pyridin-3-yl)phenyl)-2,2-difluoroacetic acid | 543.1 |

TABLE 1-continued
| P# | Structure | Name | (MH)+ |
|---|---|---|---|
| P-0035 | 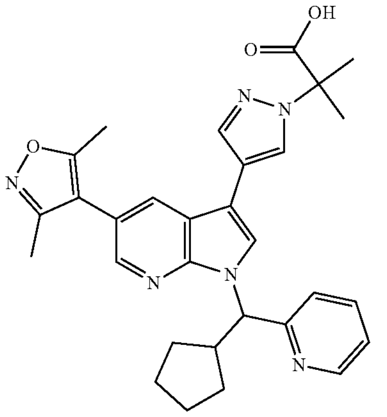 [SMILES: Cc1noc(C)c1-c1cnc2c(c1)c(-c1cnn(C(C)(C)C(=O)O)c1)cn2C(c1ccccn1)C1CCCC1] | 2-(4-(1-(cyclopentyl(pyridin-2-yl)methyl)-5-(3,5-dimethylisoxazol-4-yl)-1H-pyrrolo[2,3-b]pyridin-3-yl)-1H-pyrazol-1-yl)-2-methylpropanoic acid | 525.4 |
| P-0036 | 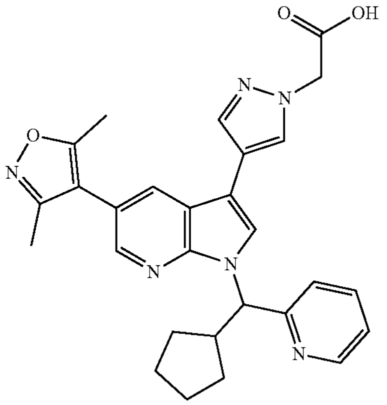 [SMILES: Cc1noc(C)c1-c1cnc2c(c1)c(-c1cnn(CC(=O)O)c1)cn2C(c1ccccn1)C1CCCC1] | 2-(4-(1-(cyclopentyl(pyridin-2-yl)methyl)-5-(3,5-dimethylisoxazol-4-yl)-1H-pyrrolo[2,3-b]pyridin-3-yl)-1H-pyrazol-1-yl)acetic acid | 497.2 |
| P-0037 | 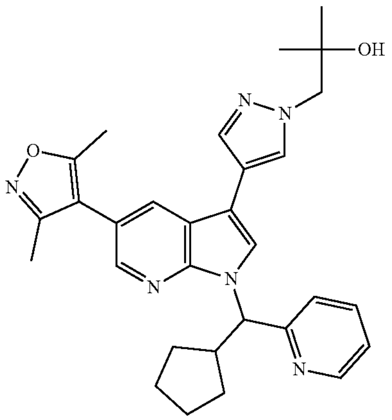 [SMILES: Cc1noc(C)c1-c1cnc2c(c1)c(-c1cnn(CC(C)(C)O)c1)cn2C(c1ccccn1)C1CCCC1] | 1-(4-(1-(cyclopentyl(pyridin-2-yl)methyl)-5-(3,5-dimethylisoxazol-4-yl)-1H-pyrrolo[2,3-b]pyridin-3-yl)-1H-pyrazol-1-yl)-2-methylpropan-2-ol | 511.3 |

TABLE 1-continued

| P# | Structure | Name | (MH)+ |
|---|---|---|---|
| P-0038 | 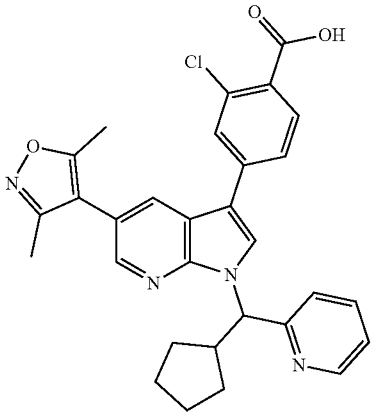 [SMILES: Cc1noc(C)c1-c1cnc2c(c1)c(-c1ccc(C(=O)O)c(Cl)c1)cn2C(c1ccccn1)C1CCCC1] | 2-chloro-4-(1-(cyclopentyl(pyridin-2-yl)methyl)-5-(3,5-dimethylisoxazol-4-yl)-1H-pyrrolo[2,3-b]pyridin-3-yl)benzoic acid | 527.2 |
| P-0040 | 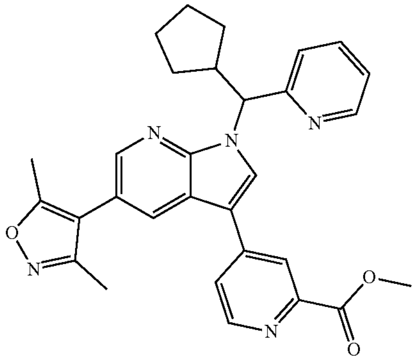 [SMILES: COC(=O)c1cc(-c2cn(C(c3ccccn3)C3CCCC3)c3ncc(-c4c(C)noc4C)cc23)ccn1] | methyl 4-(1-(cyclopentyl(pyridin-2-yl)methyl)-5-(3,5-dimethylisoxazol-4-yl)-1H-pyrrolo[2,3-b]pyridin-3-yl)picolinate | 508.2 |
| P-0041 | 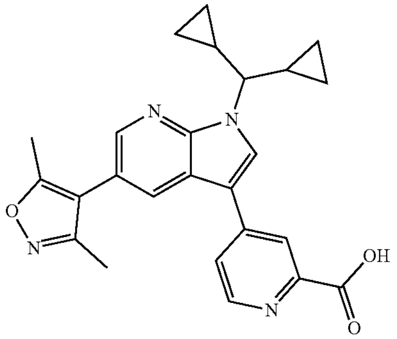 [SMILES: Cc1noc(C)c1-c1cnc2c(c1)c(-c1ccnc(C(=O)O)c1)cn2C(C1CC1)C1CC1] | 4-(1-(dicyclopropylmethyl)-5-(3,5-dimethylisoxazol-4-yl)-1H-pyrrolo[2,3-b]pyridin-3-yl)picolinic acid | 429.1 |
| P-0042 | 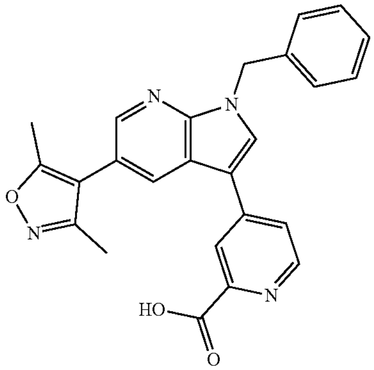 [SMILES: Cc1noc(C)c1-c1cnc2c(c1)c(-c1ccnc(C(=O)O)c1)cn2Cc1ccccc1] | 4-(1-benzyl-5-(3,5-dimethylisoxazol-4-yl)-1H-pyrrolo[2,3-b]pyridin-3-yl)picolinic acid | 425.2 |

TABLE 1-continued

| P# | Structure | Name | (MH)+ |
|---|---|---|---|
| P-0043 | 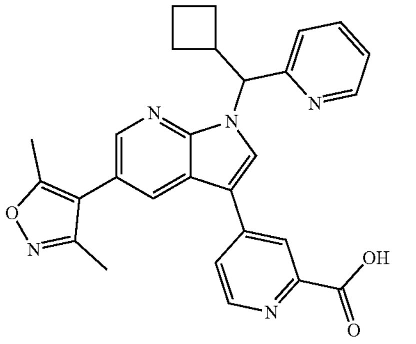 [SMILES: Cc1noc(C)c1-c1cnc2c(c1)c(-c1ccnc(C(=O)O)c1)cn2C(c1ccccn1)C1CCC1] | 4-(1-(cyclobutyl(pyridin-2-yl)methyl)-5-(3,5-dimethylisoxazol-4-yl)-1H-pyrrolo[2,3-b]pyridin-3-yl)picolinic acid | 480.0 |
| P-0044 | 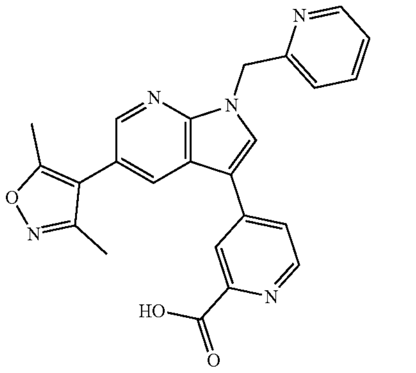 [SMILES: Cc1noc(C)c1-c1cnc2c(c1)c(-c1ccnc(C(=O)O)c1)cn2Cc1ccccn1] | 4-(5-(3,5-dimethylisoxazol-4-yl)-1-(pyridin-2-ylmethyl)-1H-pyrrolo[2,3-b]pyridin-3-yl)picolinic acid | 426.2 |
| P-0045 | 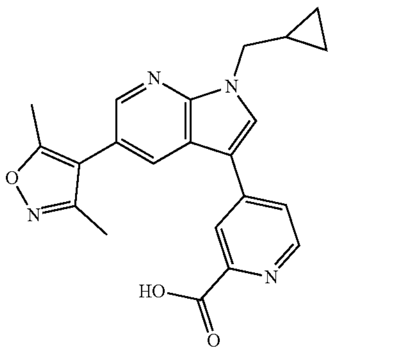 [SMILES: Cc1noc(C)c1-c1cnc2c(c1)c(-c1ccnc(C(=O)O)c1)cn2CC1CC1] | 4-(1-(cyclopropylmethyl)-5-(3,5-dimethylisoxazol-4-yl)-1H-pyrrolo[2,3-b]pyridin-3-yl)picolinic acid | 389.2 |
| P-0046 | 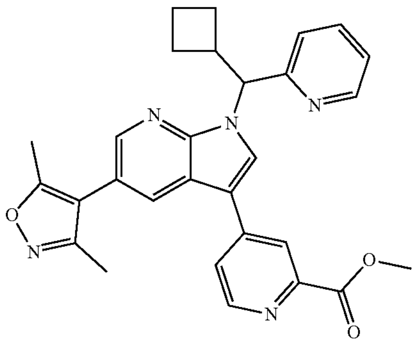 [SMILES: COC(=O)c1cc(-c2cn(C(c3ccccn3)C3CCC3)c3ncc(-c4c(C)noc4C)cc23)ccn1] | methyl 4-(1-(cyclobutyl(pyridin-2-yl)methyl)-5-(3,5-dimethylisoxazol-4-yl)-1H-pyrrolo[2,3-b]pyridin-3-yl)picolinate | 494.2 |

TABLE 1-continued
| P# | Structure | Name | (MH)+ |
|---|---|---|---|
| P-0047 | 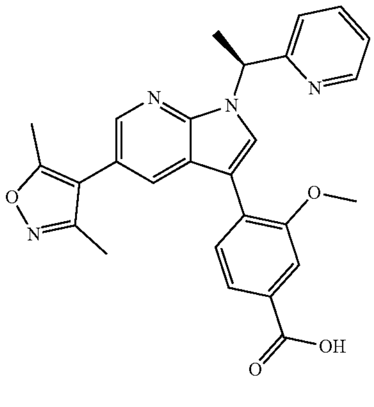 [SMILES: COc1cc(C(=O)O)ccc1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3-methoxybenzoic acid | 469.6 |
| P-0048 | 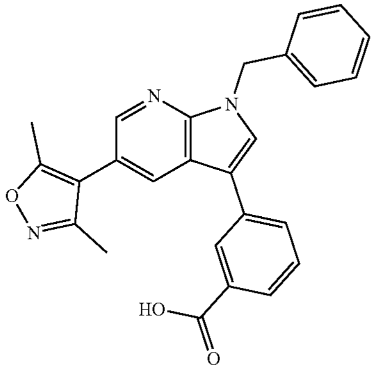 [SMILES: Cc1noc(C)c1-c1cnc2c(c1)c(-c1cccc(C(=O)O)c1)cn2Cc1ccccc1] | 3-(1-benzyl-5-(3,5-dimethylisoxazol-4-yl)-1H-pyrrolo[2,3-b]pyridin-3-yl)benzoic acid | 424.2 |
| P-0049 | 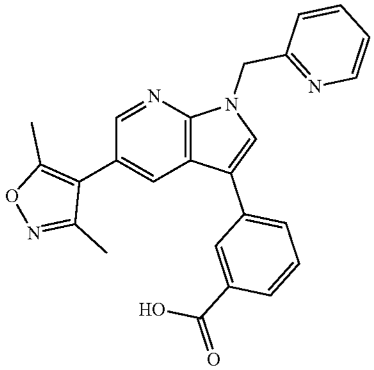 [SMILES: Cc1noc(C)c1-c1cnc2c(c1)c(-c1cccc(C(=O)O)c1)cn2Cc1ccccn1] | 3-(5-(3,5-dimethylisoxazol-4-yl)-1-(pyridin-2-ylmethyl)-1H-pyrrolo[2,3-b]pyridin-3-yl)benzoic acid | 425.2 |
| P-0050 | 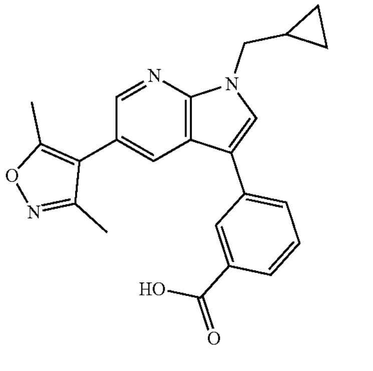 [SMILES: Cc1noc(C)c1-c1cnc2c(c1)c(-c1cccc(C(=O)O)c1)cn2CC1CC1] | 3-(1-(cyclopropylmethyl)-5-(3,5-dimethylisoxazol-4-yl)-1H-pyrrolo[2,3-b]pyridin-3-yl)benzoic acid | 387.4 |

TABLE 1-continued
| P# | Structure | Name | (MH)+ |
|---|---|---|---|
| P-0051 | 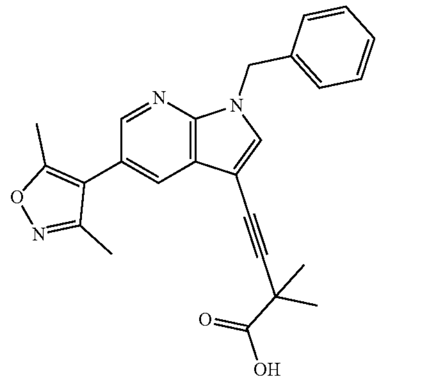 [SMILES: Cc1noc(C)c1-c1cnc2c(c1)c(C#CC(C)(C)C(=O)O)cn2Cc1ccccc1] | 4-(1-benzyl-5-(3,5-dimethylisoxazol-4-yl)-1H-pyrrolo[2,3-b]pyridin-3-yl)-2,2-dimethylbut-3-ynoic acid | 414.6 |
| P-0052 | 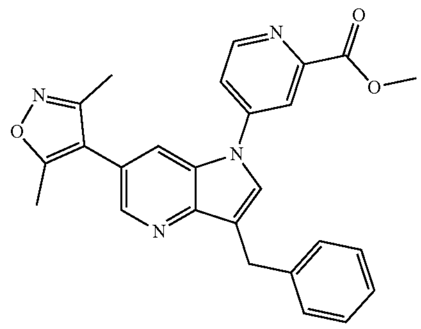 [SMILES: COC(=O)c1cc(-n2cc(Cc3ccccc3)c3ncc(-c4c(C)noc4C)cc32)ccn1] | methyl 4-(3-benzyl-6-(3,5-dimethylisoxazol-4-yl)-1H-pyrrolo[3,2-b]pyridin-1-yl)picolinate | 439.5 |
| P-0053 | 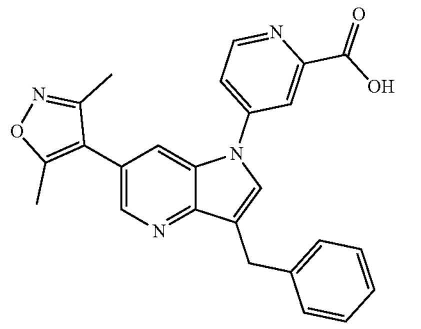 [SMILES: Cc1noc(C)c1-c1cnc2c(Cc3ccccc3)cn(-c3ccnc(C(=O)O)c3)c2c1] | 4-(3-benzyl-6-(3,5-dimethylisoxazol-4-yl)-1H-pyrrolo[3,2-b]pyridin-1-yl)picolinic acid | 425.0 |
| P-0054 | 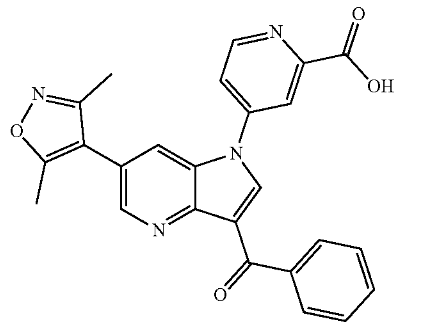 [SMILES: Cc1noc(C)c1-c1cnc2c(C(=O)c3ccccc3)cn(-c3ccnc(C(=O)O)c3)c2c1] | 4-(3-benzoyl-6-(3,5-dimethylisoxazol-4-yl)-1H-pyrrolo[3,2-b]pyridin-1-yl)picolinic acid | 439.0 |

TABLE 1-continued
| P# | Structure | Name | (MH)+ |
|---|---|---|---|
| P-0055 | 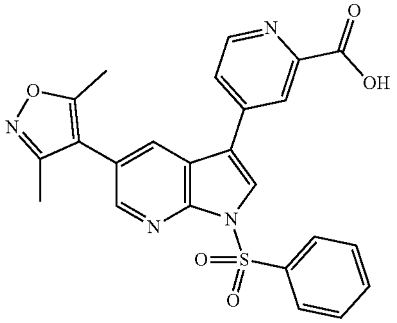 [SMILES: Cc1noc(C)c1-c1cnc2c(c1)c(-c1ccnc(C(=O)O)c1)cn2S(=O)(=O)c1ccccc1] | 4-(5-(3,5-dimethylisoxazol-4-yl)-1-(phenylsulfonyl)-1H-pyrrolo[2,3-b]pyridin-3-yl)picolinic acid | 474.9 |
| P-0056 | 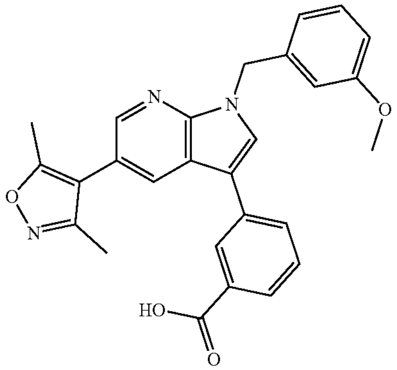 [SMILES: COc1cccc(Cn2cc(-c3cccc(C(=O)O)c3)c3cc(-c4c(C)noc4C)cnc32)c1] | 3-(5-(3,5-dimethylisoxazol-4-yl)-1-(3-methoxybenzyl)-1H-pyrrolo[2,3-]pyridin-3-yl)benzoic acid | 454.2 |
| P-0057 | 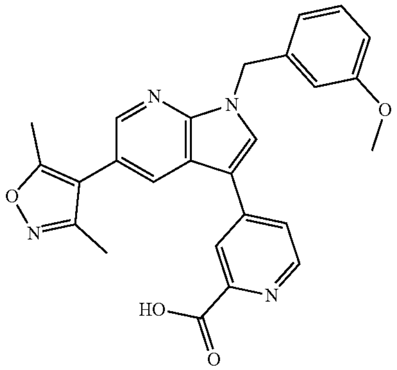 [SMILES: COc1cccc(Cn2cc(-c3ccnc(C(=O)O)c3)c3cc(-c4c(C)noc4C)cnc32)c1] | 4-(5-(3,5-dimethylisoxazol-4-yl)-1-(3-methoxybenzyl)-1H-pyrrolo[2,3-b]pyridin-3-yl)picolinic acid | 455.2 |
| P-0058 | 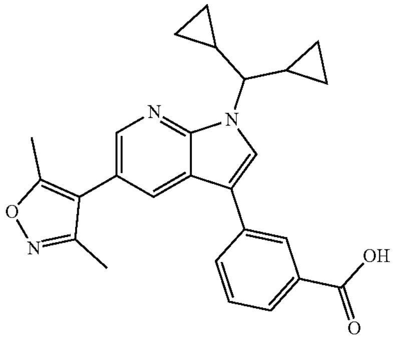 [SMILES: Cc1noc(C)c1-c1cnc2c(c1)c(-c1cccc(C(=O)O)c1)cn2C(C1CC1)C1CC1] | 3-(1-(dicyclopropylmethyl)-5-(3,5-dimethylisoxazol-4-yl)-1H-pyrrolo[2,3-b]pyridin-3-yl)benzoic acid | 428.2 |

TABLE 1-continued
| P# | Structure | Name | (MH)+ |
|---|---|---|---|
| P-0059 | 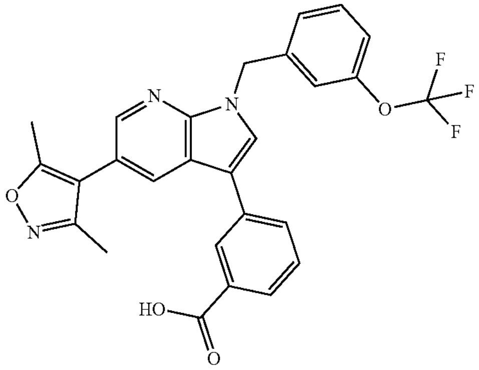 [SMILES: Cc1noc(C)c1-c1cnc2c(c1)c(-c1cccc(C(=O)O)c1)cn2Cc1cccc(OC(F)(F)F)c1] | 3-(5-(3,5-dimethylisoxazol-4-yl)-1-(3-(trifluoromethoxy)benzyl)-1H-pyrrolo[2,3-b]pyridin-3-yl)benzoic acid | 508.2 |
| P-0060 | 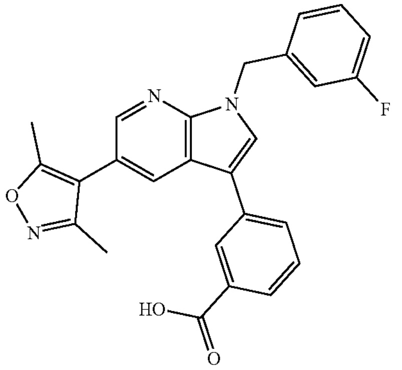 [SMILES: Cc1noc(C)c1-c1cnc2c(c1)c(-c1cccc(C(=O)O)c1)cn2Cc1cccc(F)c1] | 3-(5-(3,5-dimethylisoxazol-4-yl)-1-(3-fluorobenzyl)-1H-pyrrolo[2,3-b]pyridin-3-yl)benzoic acid | 442.2 |
| P-0061 | 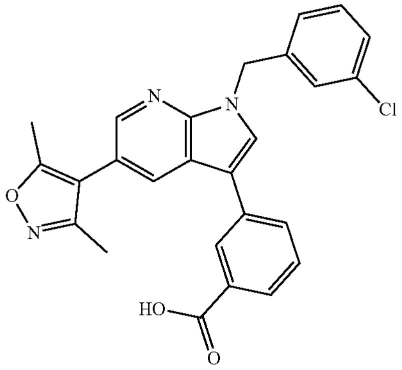 [SMILES: Cc1noc(C)c1-c1cnc2c(c1)c(-c1cccc(C(=O)O)c1)cn2Cc1cccc(Cl)c1] | 3-(1-(3-chlorobenzyl)-5-(3,5-dimethylisoxazol-4-yl)-1H-pyrrolo[2,3-b]pyridin-3-yl)benzoic acid | 458.1 |
| P-0062 | 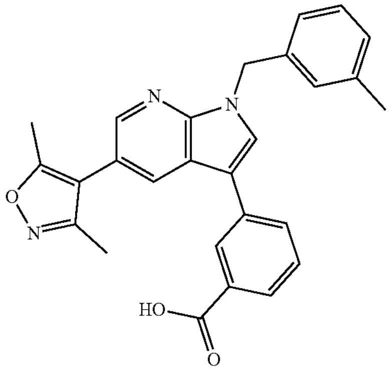 [SMILES: Cc1cccc(Cn2cc(-c3cccc(C(=O)O)c3)c3cc(-c4c(C)noc4C)cnc32)c1] | 3-(5-(3,5-dimethylisoxazol-4-yl)-1-(3-methylbenzyl)-1H-pyrrolo[2,3-b]pyridin-3-yl)benzoic acid | 438.2 |

TABLE 1-continued

| P# | Structure | Name | (MH)+ |
|---|---|---|---|
| P-0063 | 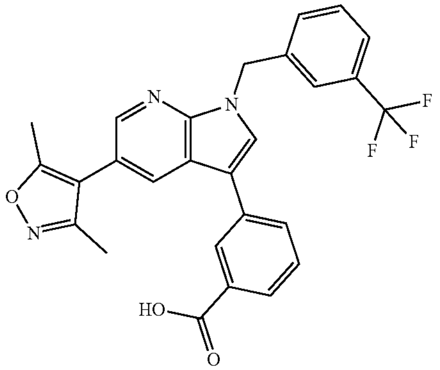 [SMILES: Cc1noc(C)c1-c1cnc2c(c1)c(-c1cccc(C(=O)O)c1)cn2Cc1cccc(C(F)(F)F)c1] | 3-(5-(3,5-dimethylisoxazol-4-yl)-1-(3-(trifluoromethyl)benzyl)-1H-pyrrolo[2,3-b]pyridin-3-yl)benzoic acid | 492.1 |
| P-0064 | 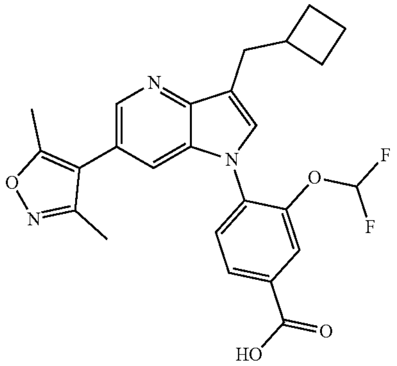 [SMILES: Cc1noc(C)c1-c1cnc2c(CC3CCC3)cn(-c3ccc(C(=O)O)cc3OC(F)F)c2c1] | 4-(3-(cyclobutylmethyl)-6-(3,5-dimethylisoxazol-4-yl)-1H-pyrrolo[3,2-b]pyridin-1-yl)-3-(difluoromethoxy)benzoic acid | 468.1 |
| P-0065 | 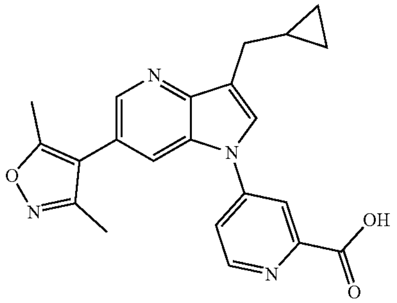 [SMILES: Cc1noc(C)c1-c1cnc2c(CC3CC3)cn(-c3ccnc(C(=O)O)c3)c2c1] | 4-(3-(cyclopropylmethyl)-6-(3,5-dimethylisoxazol-4-yl)-1H-pyrrolo[3,2-b]pyridin-1-yl)picolinic acid | 389.6 |
| P-0066 | 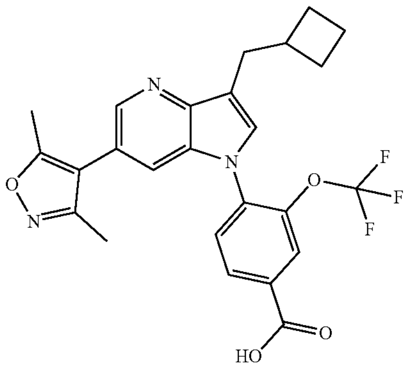 [SMILES: Cc1noc(C)c1-c1cnc2c(CC3CCC3)cn(-c3ccc(C(=O)O)cc3OC(F)(F)F)c2c1] | 4-(3-(cyclobutylmethyl)-6-(3,5-dimethylisoxazol-4-yl)-1H-pyrrolo[3,2-b]pyridin-1-yl)-3-(trifluoromethoxy)benzoic acid | 486.5 |

TABLE 1-continued

| P# | Structure | Name | (MH)+ |
|---|---|---|---|
| P-0067 | 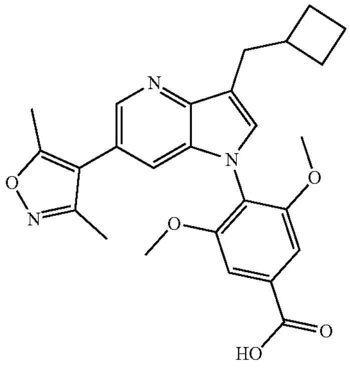 [SMILES: COc1cc(C(=O)O)cc(OC)c1-n1cc(CC2CCC2)c2ncc(-c3c(C)noc3C)cc21] | 4-(3-(cyclobutylmethyl)-6-(3,5-dimethylisoxazol-4-yl)-1H-pyrrolo[3,2-b]pyridin-1-yl)-3,5-dimethoxybenzoic acid | 462.1 |
| P-0068 | 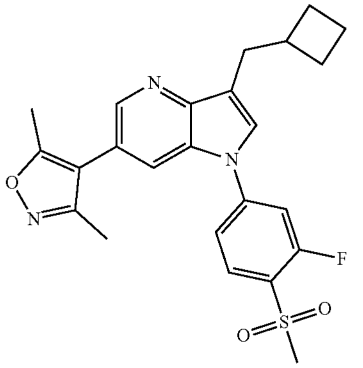 [SMILES: Cc1noc(C)c1-c1cnc2c(CC3CCC3)cn(-c3ccc(S(C)(=O)=O)c(F)c3)c2c1] | 4-(3-(cyclobutylmethyl)-1-(3-fluoro-4-(methylsulfonyl)phenyl)-1H-pyrrolo[3,2-b]pyridin-6-yl)-3,5-dimethylisoxazole | 454.2 |
| P-0069 | 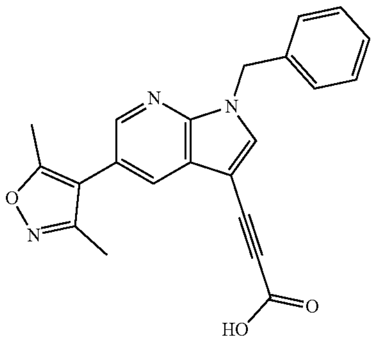 [SMILES: Cc1noc(C)c1-c1cnc2c(c1)c(C#CC(=O)O)cn2Cc1ccccc1] | 3-(1-benzyl-5-(3,5-dimethylisoxazol-4-yl)-1H-pyrrolo[2,3-b]pyridin-3-yl)propiolic acid | 372.1 |
| P-0070 | 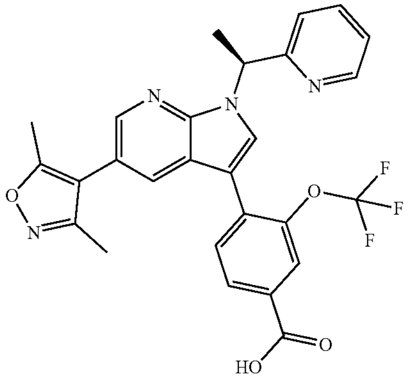 [SMILES: Cc1noc(C)c1-c1cnc2c(c1)c(-c1ccc(C(=O)O)cc1OC(F)(F)F)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)-3-(trifluoromethoxy)benzoic acid | 523.5 |

TABLE 1-continued

| P# | Structure | Name | (MH)+ |
|---|---|---|---|
| P-0071 | 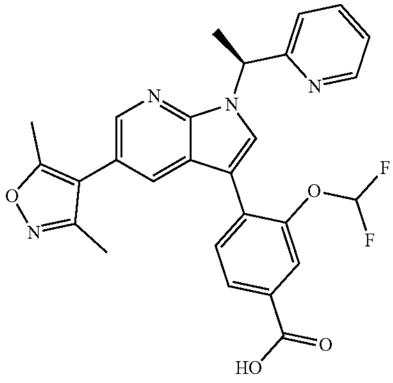 [SMILES: Cc1noc(C)c1-c1cnc2c(c1)c(-c1ccc(C(=O)O)cc1OC(F)F)cn2[C@@H](C)c1ccccn1] | (S)-3-(difluoromethoxy)-4-(5-(3,5-dimethylisoxazol-4-yl)-1-(1-(pyridin-2-yl)ethyl)-1H-pyrrolo[2,3-b]pyridin-3-yl)benzoic acid | 505.5 |
| P-0072 | 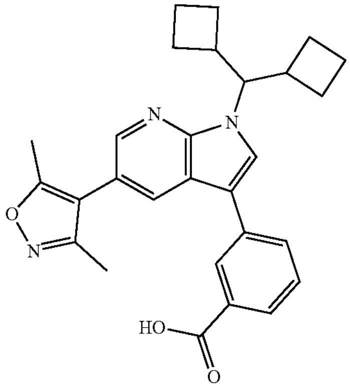 [SMILES: Cc1noc(C)c1-c1cnc2c(c1)c(-c1cccc(C(=O)O)c1)cn2C(C1CCC1)C1CCC1] | 3-(1-(dicyclobutylmethyl)-5-(3,5-dimethylisoxazol-4-yl)-1H-pyrrolo[2,3-b]pyridin-3-yl)benzoic acid | 456.2 |
| P-0073 | 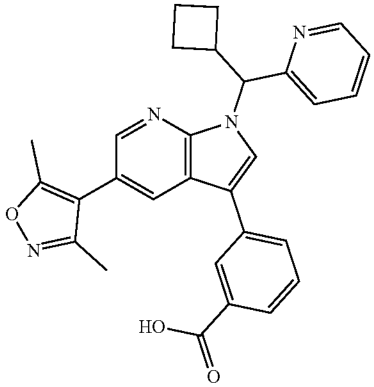 [SMILES: Cc1noc(C)c1-c1cnc2c(c1)c(-c1cccc(C(=O)O)c1)cn2C(c1ccccn1)C1CCC1] | 3-(1-(cyclobutyl(pyridin-2-yl)methyl)-5-(3,5-dimethylisoxazol-4-yl)-1H-pyrrolo[2,3-b]pyridin-3-yl)benzoic acid | 479.6 |
| P-0074 | 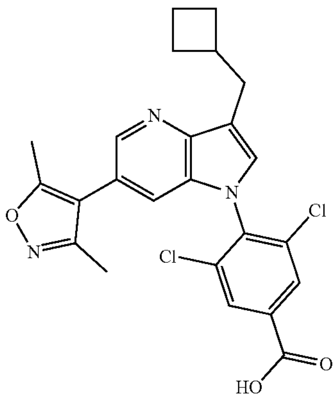 [SMILES: Cc1noc(C)c1-c1cnc2c(CC3CCC3)cn(-c3c(Cl)cc(C(=O)O)cc3Cl)c2c1] | 3,5-dichloro-4-(3-(cyclobutylmethyl)-6-(3,5-dimethylisoxazol-4-yl)-1H-pyrrolo[3,2-b]pyridin-1-yl)benzoic acid | 471.7 |

TABLE 1-continued
| P# | Structure | Name | (MH)+ |
|---|---|---|---|
| P-0075 | 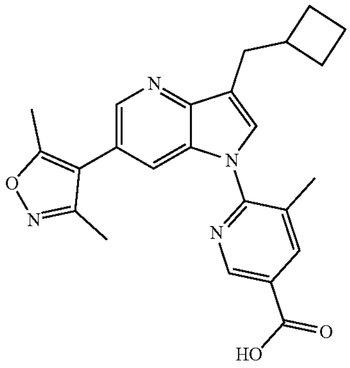 [SMILES: Cc1cc(C(=O)O)cnc1-n1cc(CC2CCC2)c2ncc(-c3c(C)noc3C)cc21] | 6-(3-(cyclobutylmethyl)-6-(3,5-dimethylisoxazol-4-yl)-1H-pyrrolo[3,2-b]pyridin-1-yl)-5-methylnicotinic acid | 417.1 |
| P-0076 | 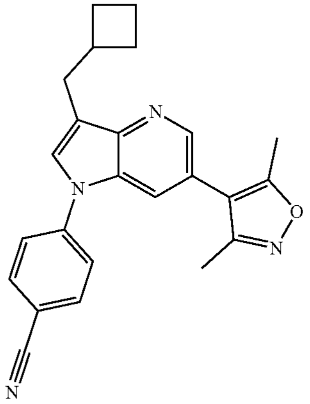 [SMILES: Cc1noc(C)c1-c1cnc2c(CC3CCC3)cn(-c3ccc(C#N)cc3)c2c1] | 4-(3-(cyclobutylmethyl)-6-(3,5-dimethylisoxazol-4-yl)-1H-pyrrolo[3,2-b]pyridin-1-yl)benzonitrile | 383.0 |
| P-0077 | 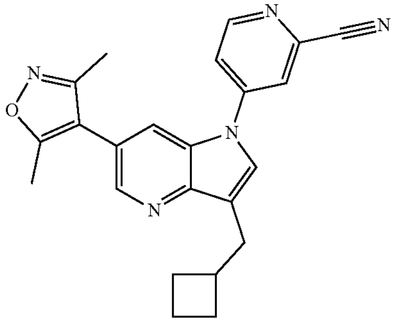 [SMILES: Cc1noc(C)c1-c1cnc2c(CC3CCC3)cn(-c3ccnc(C#N)c3)c2c1] | 4-(3-(cyclobutylmethyl)-6-(3,5-dimethylisoxazol-4-yl)-1H-pyrrolo[3,2-b]pyridin-1-yl)picolinonitrile | 384.0 |
| P-0078 | 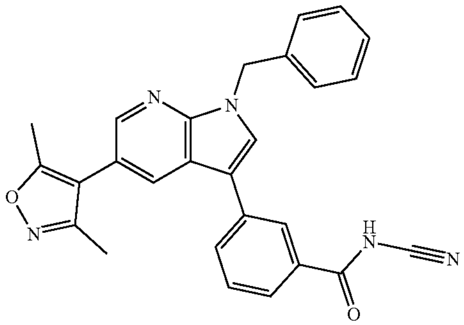 [SMILES: Cc1noc(C)c1-c1cnc2c(c1)c(-c1cccc(C(=O)NC#N)c1)cn2Cc1ccccc1] | 3-(1-benzyl-5-(3,5-dimethylisoxazol-4-yl)-1H-pyrrolo[2,3-b]pyridin-3-yl)-N-cyanobenzamide | 448.0 |

TABLE 1-continued
| P# | Structure | Name | (MH)+ |
|---|---|---|---|
| P-0079 | 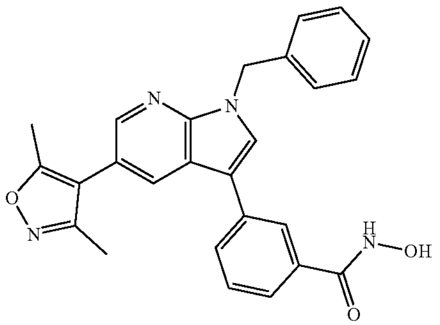 [SMILES: Cc1noc(C)c1-c1cnc2c(c1)c(-c1cccc(C(=O)NO)c1)cn2Cc1ccccc1] | 3-(1-benzyl-5-(3,5-dimethylisoxazol-4-yl)-1H-pyrrolo[2,3-b]pyridin-3-yl)-N-hydroxybenzamide | 439.0 |
| P-0080 | 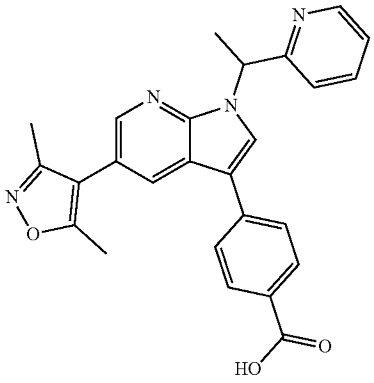 [SMILES: Cc1noc(C)c1-c1cnc2c(c1)c(-c1ccc(C(=O)O)cc1)cn2C(C)c1ccccn1] | 4-(5-(3,5-dimethylisoxazol-4-yl)-1-(1-(pyridin-2-yl)ethyl)-1H-pyrrolo[2,3-b]pyridin-3-yl)benzoic acid | 439.0 |
| P-0081 | 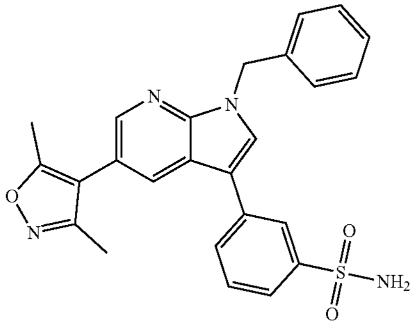 [SMILES: Cc1noc(C)c1-c1cnc2c(c1)c(-c1cccc(S(N)(=O)=O)c1)cn2Cc1ccccc1] | 3-(1-benzyl-5-(3,5-dimethylisoxazol-4-yl)-1H-pyrrolo[2,3-b]pyridin-3-yl)benzenesulfonamide | 459.0 |
| P-0082 | 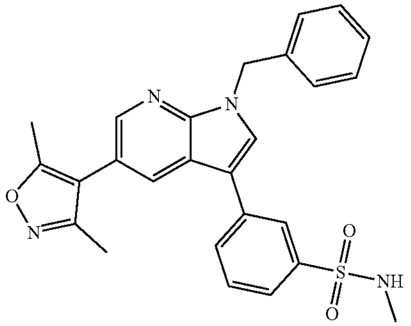 [SMILES: CNS(=O)(=O)c1cccc(-c2cn(Cc3ccccc3)c3ncc(-c4c(C)noc4C)cc23)c1] | 3-(1-benzyl-5-(3,5-dimethylisoxazol-4-yl)-1H-pyrrolo[2,3-b]pyridin-3-yl)-N-methylbenzenesulfonamide | 473.0 |

TABLE 1-continued

| P# | Structure | Name | (MH)+ |
|---|---|---|---|
| P-0083 | 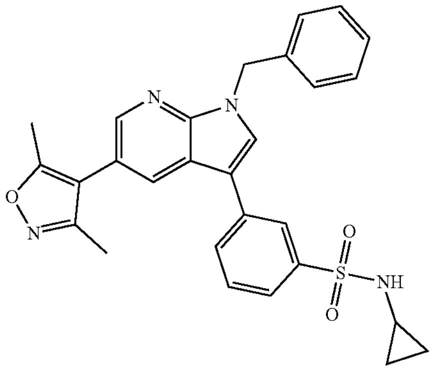 [SMILES: Cc1noc(C)c1-c1cnc2c(c1)c(-c1cccc(S(=O)(=O)NC3CC3)c1)cn2Cc1ccccc1] | 3-(1-benzyl-5-(3,5-dimethylisoxazol-4-yl)-1H-pyrrolo[2,3-b]pyridin-3-yl)-N-cyclopropylbenzenesulfonamide | 499.0 |
| P-0084 | 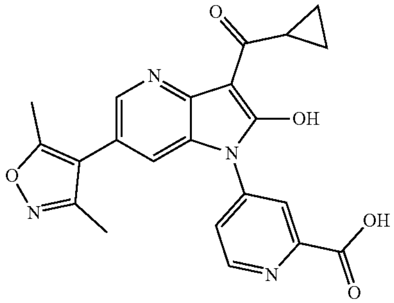 [SMILES: Cc1noc(C)c1-c1cnc2c(C(=O)C3CC3)c(O)n(-c3ccnc(C(=O)O)c3)c2c1] | 4-(3-(cyclopropanecarbonyl)-6-(3,5-dimethylisoxazol-4-yl)-2-hydroxy-1H-pyrrolo[3,2-b]pyridin-1-yl)picolinic acid | 419.0 |
| P-0085 | 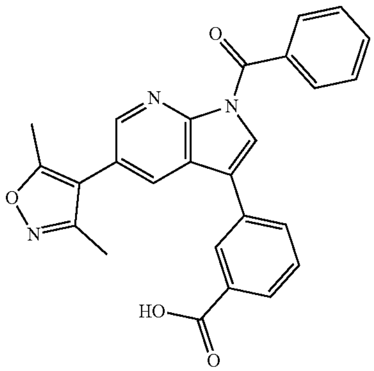 [SMILES: Cc1noc(C)c1-c1cnc2c(c1)c(-c1cccc(C(=O)O)c1)cn2C(=O)c1ccccc1] | 3-(1-benzoyl-5-(3,5-dimethylisoxazol-4-yl)-1H-pyrrolo[2,3-b]pyridin-3-yl)benzoic acid | 438.0 |
| P-0086 | 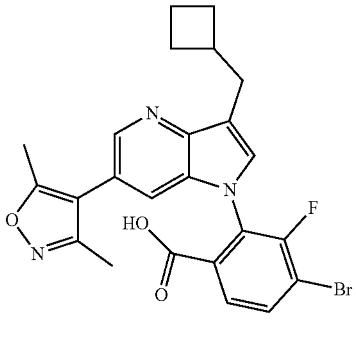 [SMILES: Cc1noc(C)c1-c1cnc2c(CC3CCC3)cn(-c3c(C(=O)O)ccc(Br)c3F)c2c1] | 4-bromo-2-(3-(cyclobutylmethyl)-6-(3,5-dimethylisoxazol-4-yl)-1H-pyrrolo[3,2-b]pyridin-1-yl)-3-fluorobenzoic acid | 499.9 |

TABLE 1-continued
| P# | Structure | Name | (MH)+ |
|---|---|---|---|
| P-0087 | 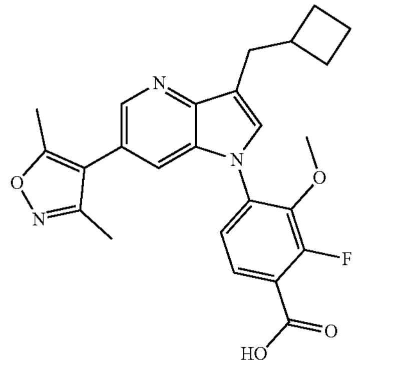 [SMILES: COc1c(-n2cc(CC3CCC3)c3ncc(-c4c(C)noc4C)cc32)ccc(C(=O)O)c1F] | 4-(3-(cyclobutylmethyl)-6-(3,5-dimethylisoxazol-4-yl)-1H-pyrrolo[3,2-b]pyridin-1-yl)-2-fluoro-3-methoxybenzoic acid | 450.1 |
| P-0088 | 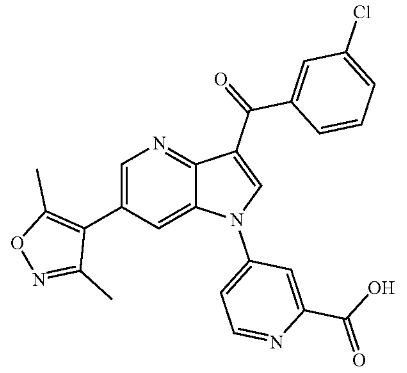 [SMILES: Cc1noc(C)c1-c1cnc2c(C(=O)c3cccc(Cl)c3)cn(-c3ccnc(C(=O)O)c3)c2c1] | 4-(3-(3-chlorobenzoyl)-6-(3,5-dimethylisoxazol-4-yl)-1H-pyrrolo[3,2-b]pyridin-1-yl)picolinic acid | 472.9 |
| P-0089 | 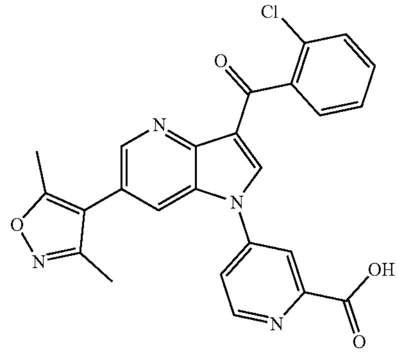 [SMILES: Cc1noc(C)c1-c1cnc2c(C(=O)c3ccccc3Cl)cn(-c3ccnc(C(=O)O)c3)c2c1] | 4-(3-(2-chlorobenzoyl)-6-(3,5-dimethylisoxazol-4-yl)-1H-pyrrolo[3,2-b]pyridin-1-yl)picolinic acid | 473.4 |
| P-0090 | 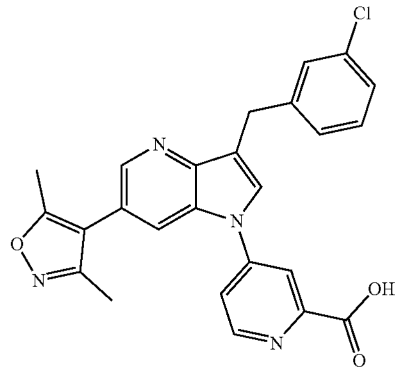 [SMILES: Cc1noc(C)c1-c1cnc2c(Cc3cccc(Cl)c3)cn(-c3ccnc(C(=O)O)c3)c2c1] | 4-(3-(3-chlorobenzyl)-6-(3,5-dimethylisoxazol-4-yl)-1H-pyrrolo[3,2-b]pyridin-1-yl)picolinic acid | 459.0 |

TABLE 1-continued
| P# | Structure | Name | (MH)+ |
|---|---|---|---|
| P-0091 | 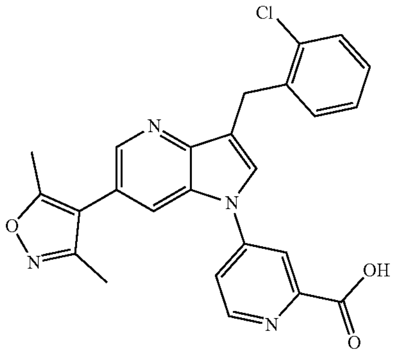 [SMILES: Cc1noc(C)c1-c1cnc2c(Cc3ccccc3Cl)cn(-c3ccnc(C(=O)O)c3)c2c1] | 4-(3-(2-chlorobenzyl)-6-(3,5-dimethylisoxazol-4-yl)-1H-pyrrolo[3,2-b]pyridin-1-yl)picolinic acid | 459.1 |
| P-0092 | 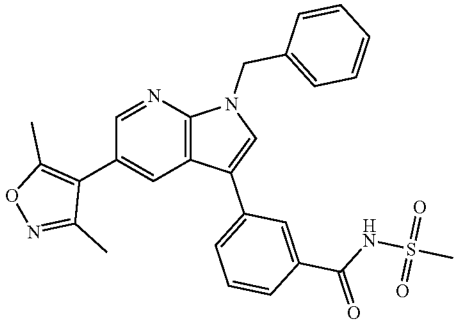 [SMILES: Cc1noc(C)c1-c1cnc2c(c1)c(-c1cccc(C(=O)NS(C)(=O)=O)c1)cn2Cc1ccccc1] | 3-(1-benzyl-5-(3,5-dimethylisoxazol-4-yl)-1H-pyrrolo[2,3-b]pyridin-3-yl)-N-(methylsulfonyl)benzamide | 501.1 |
| P-0093 | 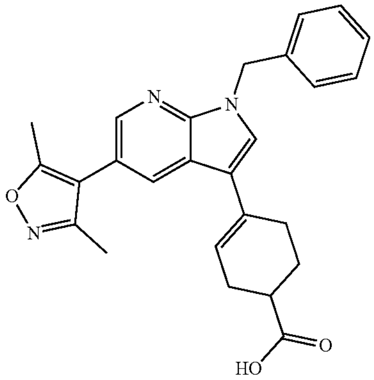 [SMILES: Cc1noc(C)c1-c1cnc2c(c1)c(C1=CCC(C(=O)O)CC1)cn2Cc1ccccc1] | 4-(1-benzyl-5-(3,5-dimethylisoxazol-4-yl)-1H-pyrrolo[2,3-b]pyridin-3-yl)cyclohex-3-ene-1-carboxylic acid | 428.1 |
| P-0094 | 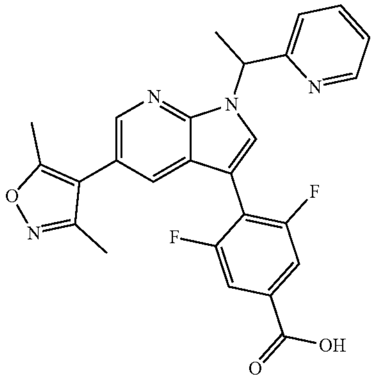 [SMILES: Cc1noc(C)c1-c1cnc2c(c1)c(-c1c(F)cc(C(=O)O)cc1F)cn2C(C)c1ccccn1] | 4-(5-(3,5-dimethylisoxazol-4-yl)-1-(1-(pyridin-2-yl)ethyl)-1H-pyrrolo[2,3-b]pyridin-3-yl)-3,5-difluorobenzoic acid | 475.5 |

TABLE 1-continued

| P# | Structure | Name | (MH)+ |
|---|---|---|---|
| P-0095 | 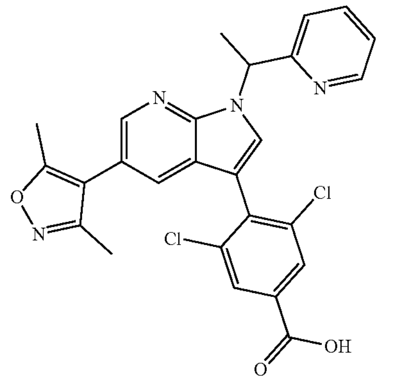 [SMILES: Cc1noc(C)c1-c1cnc2c(c1)c(-c1c(Cl)cc(C(=O)O)cc1Cl)cn2C(C)c1ccccn1] | 3,5-dichloro-4-(5-(3,5-dimethylisoxazol-4-yl)-1-(1-(pyridin-2-yl)ethyl)-1H-pyrrolo[2,3-b]pyridin-3-yl)benzoic acid | 507.1 (MH)– |
| P-0096 | 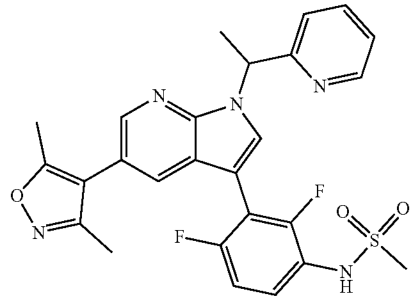 [SMILES: Cc1noc(C)c1-c1cnc2c(c1)c(-c1c(F)ccc(NS(C)(=O)=O)c1F)cn2C(C)c1ccccn1] | N-(3-(5-(3,5-dimethylisoxazol-4-yl)-1-(1-(pyridin-2-yl)ethyl)-1H-pyrrolo[2,3-b]pyridin-3-yl)-2,4-difluorophenyl)methanesulfonamide | 524.5 |
| P-0097 | 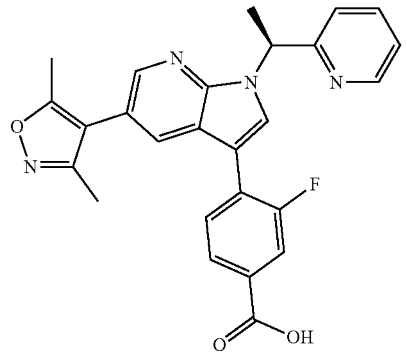 [SMILES: Cc1noc(C)c1-c1cnc2c(c1)c(-c1ccc(C(=O)O)cc1F)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)-3-fluorobenzoic acid | 457.3 |
| P-0098 | 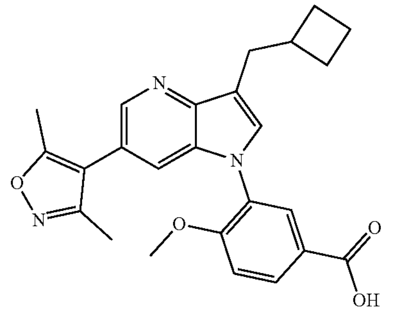 [SMILES: COc1ccc(C(=O)O)cc1-n1cc(CC2CCC2)c2ncc(-c3c(C)noc3C)cc21] | 3-(3-(cyclobutylmethyl)-6-(3,5-dimethylisoxazol-4-yl)-1H-pyrrolo[3,2-b]pyridin-1-yl)-4-methoxybenzoic acid | 432.1 |

TABLE 1-continued

| P# | Structure | Name | (MH)+ |
|---|---|---|---|
| P-0099 | 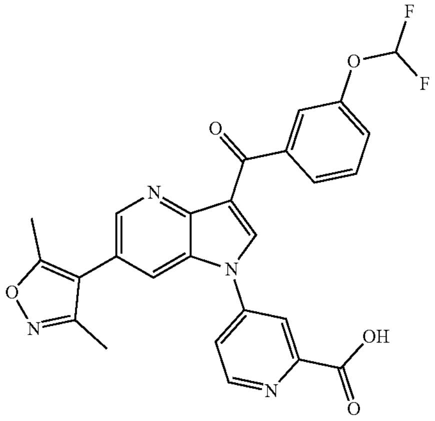 [SMILES: Cc1noc(C)c1-c1cnc2c(C(=O)c3cccc(OC(F)F)c3)cn(-c3ccnc(C(=O)O)c3)c2c1] | 4-(3-(3-(difluoromethoxy)benzoyl)-6-(3,5-dimethylisoxazol-4-yl)-1H-pyrrolo[3,2-b]pyridin-1-yl)picolinic acid | 505.1 |
| P-0100 | 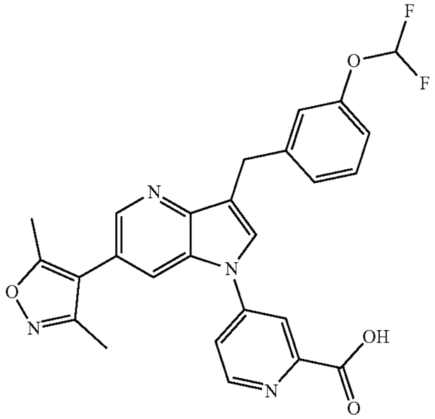 [SMILES: Cc1noc(C)c1-c1cnc2c(Cc3cccc(OC(F)F)c3)cn(-c3ccnc(C(=O)O)c3)c2c1] | 4-(3-(3-(difluoromethoxy)benzyl)-6-(3,5-dimethylisoxazol-4-yl)-1H-pyrrolo[3,2-b]pyridin-1-yl)picolinic acid | 491.0 |
| P-0101 | 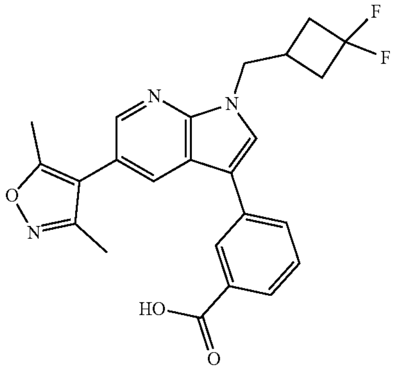 [SMILES: Cc1noc(C)c1-c1cnc2c(c1)c(-c1cccc(C(=O)O)c1)cn2CC1CC(F)(F)C1] | 3-(1-((3,3-difluorocyclobutyl)methyl)-5-(3,5-dimethylisoxazol-4-yl)-1H-pyrrolo[2,3-b]pyridin-3-yl)benzoic acid | 438.1 |
| P-0102 | 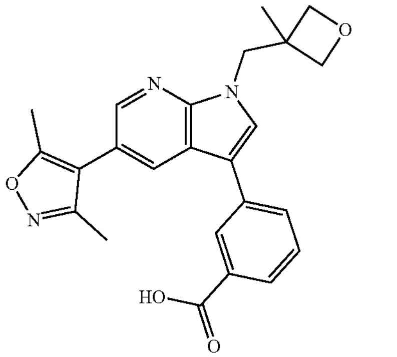 [SMILES: Cc1noc(C)c1-c1cnc2c(c1)c(-c1cccc(C(=O)O)c1)cn2CC1(C)COC1] | 3-(5-(3,5-dimethylisoxazol-4-yl)-1-((3-methyloxetan-3-yl)methyl)-1H-pyrrolo[2,3-b]pyridin-3-yl)benzoic acid | 418.1 |

TABLE 1-continued

| P# | Structure | Name | (MH)+ |
|---|---|---|---|
| P-0103 | 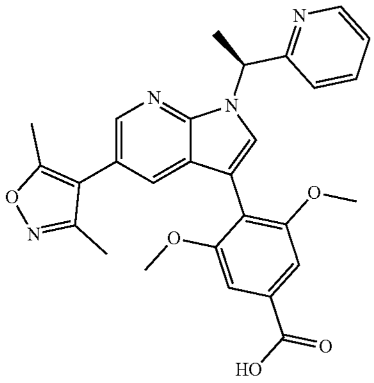 [SMILES: COc1cc(C(=O)O)cc(OC)c1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3,5-dimethoxybenzoic acid | 499.1 |
| P-0104 | 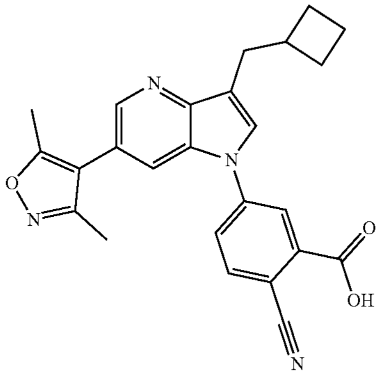 [SMILES: Cc1noc(C)c1-c1cnc2c(CC3CCC3)cn(-c3ccc(C#N)c(C(=O)O)c3)c2c1] | 2-cyano-5-(3-(cyclobutylmethyl)-6-(3,5-dimethylisoxazol-4-yl)-1H-pyrrolo[3,2-b]pyridin-1-yl)benzoic acid | 427.1 |
| P-0105 | 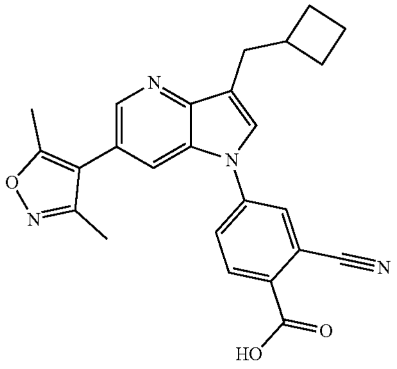 [SMILES: Cc1noc(C)c1-c1cnc2c(CC3CCC3)cn(-c3ccc(C(=O)O)c(C#N)c3)c2c1] | 2-cyano-4-(3-(cyclobutylmethyl)-6-(3,5-dimethylisoxazol-4-yl)-1H-pyrrolo[3,2-b]pyridin-1-yl)benzoic acid | 427.1 |
| P-0106 | 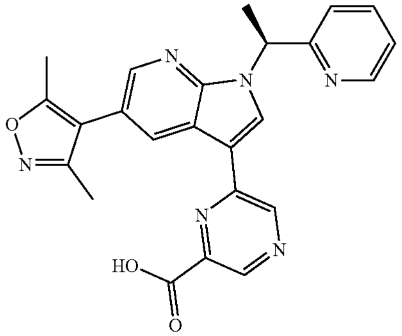 [SMILES: Cc1noc(C)c1-c1cnc2c(c1)c(-c1cncc(C(=O)O)n1)cn2[C@@H](C)c1ccccn1] | (S)-6-(5-(3,5-dimethylisoxazol-4-yl)-1-(1-(pyridin-2-yl)ethyl)-1H-pyrrolo[2,3-b]pyridin-3-yl)pyrazine-2-carboxylic acid | 441.1 |

TABLE 1-continued

| P# | Structure | Name | (MH)+ |
|---|---|---|---|
| P-0107 | 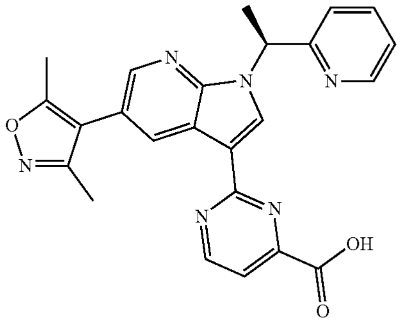 [SMILES: Cc1noc(C)c1-c1cnc2c(c1)c(-c1nccc(C(=O)O)n1)cn2[C@@H](C)c1ccccn1] | (S)-2-(5-(3,5-dimethylisoxazol-4-yl)-1-(1-(pyridin-2-yl)ethyl)-1H-pyrrolo[2,3-b]pyridin-3-yl)pyrimidine-4-carboxylic acid | 441.1 |
| P-0108 | 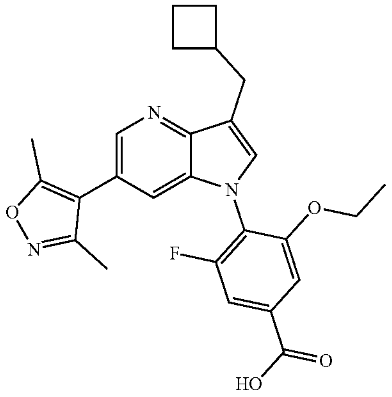 [SMILES: CCOc1cc(C(=O)O)cc(F)c1-n1cc(CC2CCC2)c2ncc(-c3c(C)noc3C)cc21] | 4-(3-(cyclobutylmethyl)-6-(3,5-dimethylisoxazol-4-yl)-1H-pyrrolo[3,2-b]pyridin-1-yl)-3-ethoxy-5-fluorobenzoic acid | 464.6 |
| P-0109 | 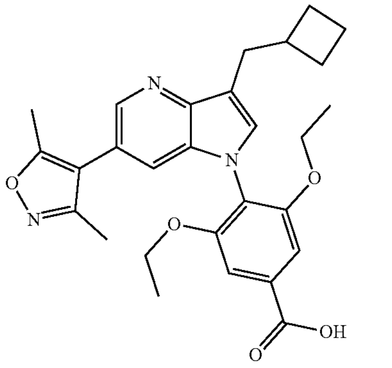 [SMILES: CCOc1cc(C(=O)O)cc(OCC)c1-n1cc(CC2CCC2)c2ncc(-c3c(C)noc3C)cc21] | 4-(3-(cyclobutylmethyl)-6-(3,5-dimethylisoxazol-4-yl)-1H-pyrrolo[3,2-b]pyridin-1-yl)-3,5-diethoxybenzoic acid | 490.2 |
| P-0110 | 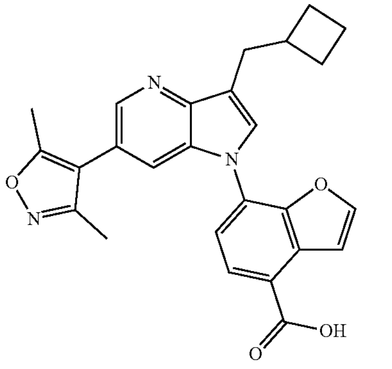 [SMILES: Cc1noc(C)c1-c1cnc2c(CC3CCC3)cn(-c3ccc(C(=O)O)c4ccoc34)c2c1] | 7-(3-(cyclobutylmethyl)-6-(3,5-dimethylisoxazol-4-yl)-1H-pyrrolo[3,2-b]pyridin-1-yl)benzofuran-4-carboxylic acid | 442.1 |

TABLE 1-continued

| P# | Structure | Name | (MH)+ |
|---|---|---|---|
| P-0111 | 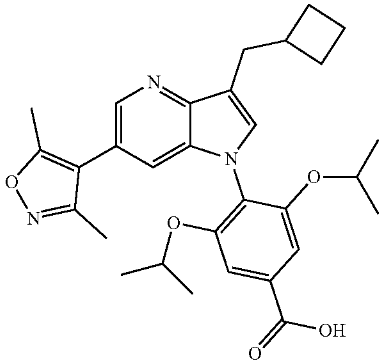 [SMILES: Cc1noc(C)c1-c1cnc2c(CC3CCC3)cn(-c3c(OC(C)C)cc(C(=O)O)cc3OC(C)C)c2c1] | 4-(3-(cyclobutylmethyl)-6-(3,5-dimethylisoxazol-4-yl)-1H-pyrrolo[3,2-b]pyridin-1-yl)-3,5-diisopropoxybenzoic acid | 518.2 |
| P-0112 | 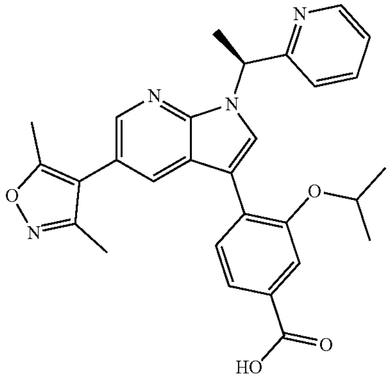 [SMILES: Cc1noc(C)c1-c1cnc2c(c1)c(-c1ccc(C(=O)O)cc1OC(C)C)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)-3-isopropoxybenzoic acid | 497.1 |
| P-0113 | 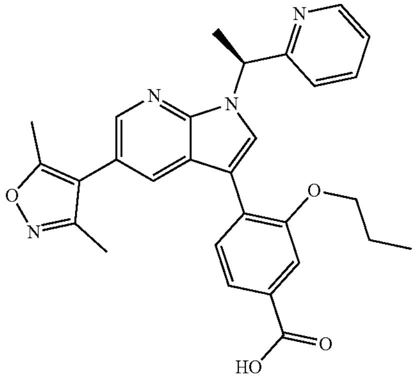 [SMILES: CCCOc1cc(C(=O)O)ccc1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3-propoxybenzoic acid | 497.1 |
| P-0114 | 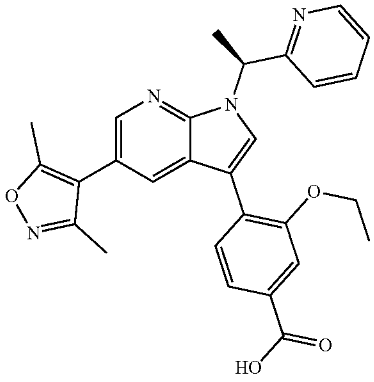 [SMILES: CCOc1cc(C(=O)O)ccc1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3-ethoxybenzoic acid | 483.1 |

TABLE 1-continued

| P# | Structure | Name | (MH)+ |
| --- | --- | --- | --- |
| P-0115 | 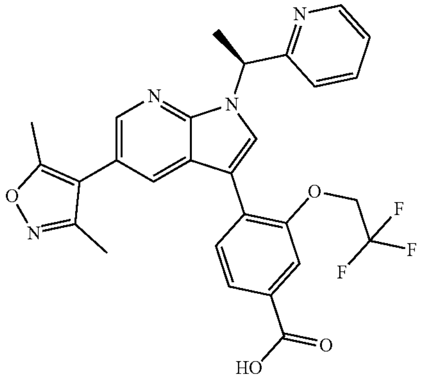 [SMILES: Cc1noc(C)c1-c1cnc2c(c1)c(-c1ccc(C(=O)O)cc1OCC(F)(F)F)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)-3-(2,2,2-trifluoroethoxy)benzoic acid | 537.6 |
| P-0116 | 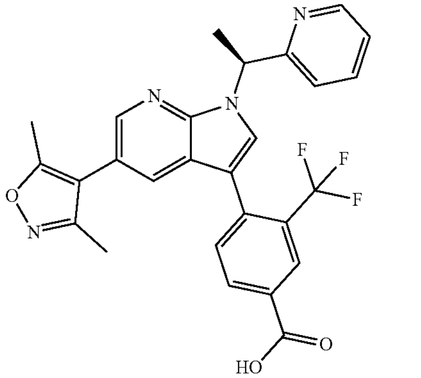 [SMILES: Cc1noc(C)c1-c1cnc2c(c1)c(-c1ccc(C(=O)O)cc1C(F)(F)F)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)-3-(trifluoromethyl)benzoic acid | 507.5 |
| P-0117 | 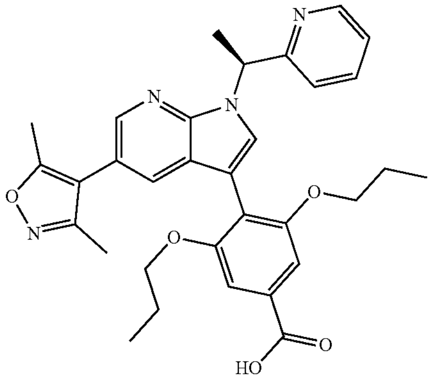 [SMILES: CCCOc1cc(C(=O)O)cc(OCCC)c1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3,5-dipropoxybenzoic acid | 555.6 |
| P-0118 | 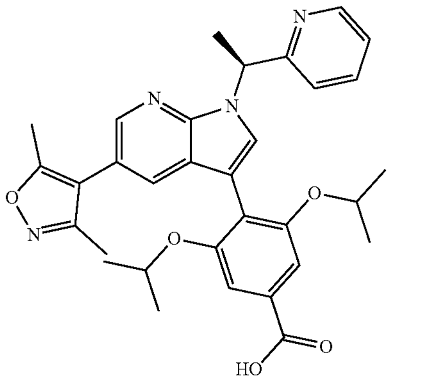 [SMILES: Cc1noc(C)c1-c1cnc2c(c1)c(-c1c(OC(C)C)cc(C(=O)O)cc1OC(C)C)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)-3,5-diisopropoxybenzoic acid | 555.6 |

TABLE 1-continued
| P# | Structure | Name | (MH)+ |
|---|---|---|---|
| P-0119 | 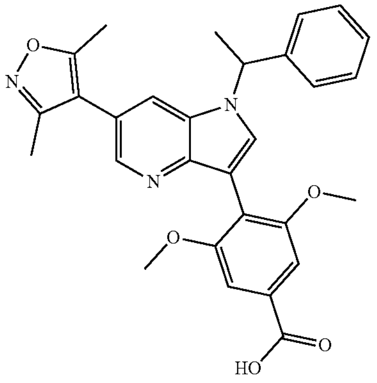 [SMILES: COc1cc(C(=O)O)cc(OC)c1-c1cn(C(C)c2ccccc2)c2cc(-c3c(C)noc3C)cnc12] | 4-(6-(3,5-dimethylisoxazol-4-yl)-1-(1-phenylethyl)-1H-pyrrolo[3,2-b]pyridin-3-yl)-3,5-dimethoxybenzoic acid | 498.6 |
| P-0120 | 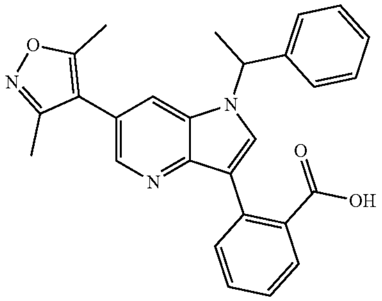 [SMILES: Cc1noc(C)c1-c1cnc2c(-c3ccccc3C(=O)O)cn(C(C)c3ccccc3)c2c1] | 2-(6-(3,5-dimethylisoxazol-4-yl)-1-(1-phenylethyl)-1H-pyrrolo[3,2-b]pyridin-3-yl)benzoic acid | 438.6 |
| P-0121 | 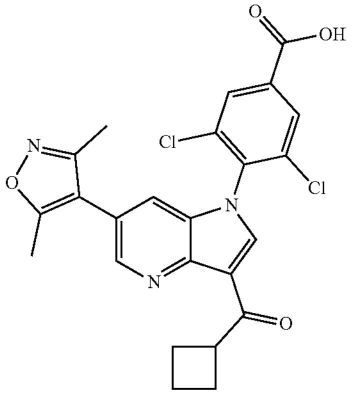 [SMILES: Cc1noc(C)c1-c1cnc2c(C(=O)C3CCC3)cn(-c3c(Cl)cc(C(=O)O)cc3Cl)c2c1] | 3,5-dichloro-4-(3-(cyclobutanecarbonyl)-6-(3,5-dimethylisoxazol-4-yl)-1H-pyrrolo[3,2-b]pyridin-1-yl)benzoic acid | 485.0 |
| P-0122 | 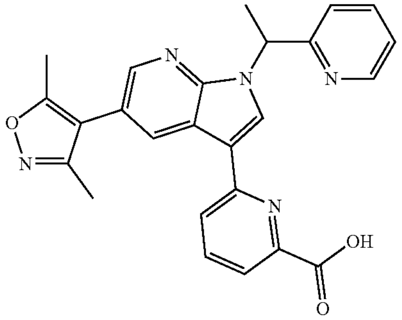 [SMILES: Cc1noc(C)c1-c1cnc2c(c1)c(-c1cccc(C(=O)O)n1)cn2C(C)c1ccccn1] | 6-(5-(3,5-dimethylisoxazol-4-yl)-1-(1-(pyridin-2-yl)ethyl)-1H-pyrrolo[2,3-b]pyridin-3-yl)picolinic acid | 440.2 |

TABLE 1-continued

| P# | Structure | Name | (MH)+ |
|---|---|---|---|
| P-0123 | 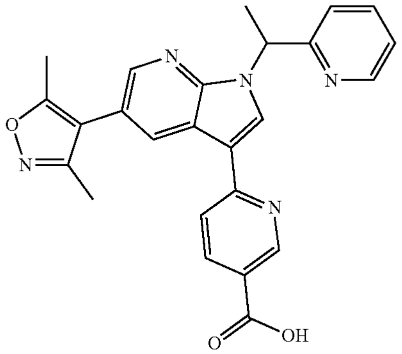 [SMILES: Cc1noc(C)c1-c1cnc2c(c1)c(-c1ccc(C(=O)O)cn1)cn2C(C)c1ccccn1] | 6-(5-(3,5-dimethylisoxazol-4-yl)-1-(1-(pyridin-2-yl)ethyl)-1H-pyrrolo[2,3-b]pyridin-3-yl)nicotinic acid | 439.5 |
| P-0124 | 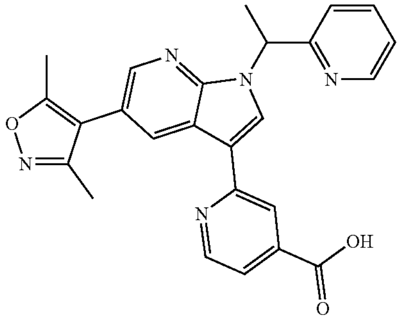 [SMILES: Cc1noc(C)c1-c1cnc2c(c1)c(-c1cc(C(=O)O)ccn1)cn2C(C)c1ccccn1] | 2-(5-(3,5-dimethylisoxazol-4-yl)-1-(1-(pyridin-2-yl)ethyl)-1H-pyrrolo[2,3-b]pyridin-3-yl)isonicotinic acid | 440.2 |
| P-0125 | 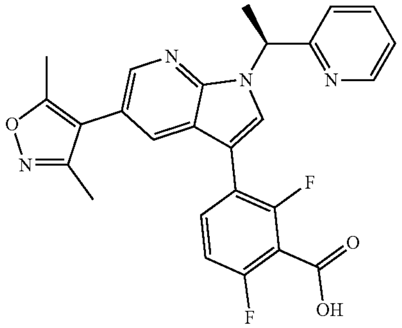 [SMILES: Cc1noc(C)c1-c1cnc2c(c1)c(-c1ccc(F)c(C(=O)O)c1F)cn2[C@@H](C)c1ccccn1] | (S)-3-(5-(3,5-dimethylisoxazol-4-yl)-1-(1-(pyridin-2-yl)ethyl)-1H-pyrrolo[2,3-b]pyridin-3-yl)-2,6-difluorobenzoic acid | 475.3 |
| P-0126 | 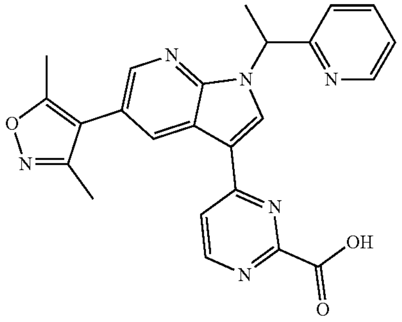 [SMILES: Cc1noc(C)c1-c1cnc2c(c1)c(-c1ccnc(C(=O)O)n1)cn2C(C)c1ccccn1] | 4-(5-(3,5-dimethylisoxazol-4-yl)-1-(1-(pyridin-2-yl)ethyl)-1H-pyrrolo[2,3-b]pyridin-3-yl)pyrimidine-2-carboxylic acid | 441.1 |

TABLE 1-continued
| P# | Structure | Name | (MH)+ |
|---|---|---|---|
| P-0127 | 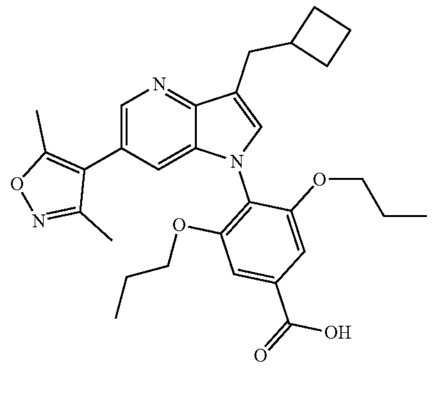 [SMILES: CCCOc1cc(C(=O)O)cc(OCCC)c1-n1cc(CC2CCC2)c2ncc(-c3c(C)noc3C)cc21] | 4-(3-(cyclobutylmethyl)-6-(3,5-dimethylisoxazol-4-yl)-1H-pyrrolo[3,2-b]pyridin-1-yl)-3,5-dipropoxybenzoic acid | 518.2 |
| P-0128 | 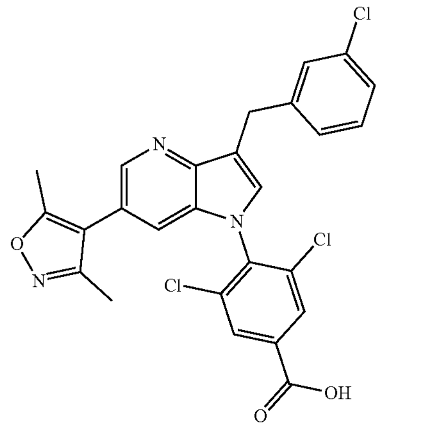 [SMILES: Cc1noc(C)c1-c1cnc2c(Cc3cccc(Cl)c3)cn(-c3c(Cl)cc(C(=O)O)cc3Cl)c2c1] | 3,5-dichloro-4-(3-(3-chlorobenzyl)-6-(3,5-dimethylisoxazol-4-yl)-1H-pyrrolo[3,2-b]pyridin-1-yl)benzoic acid | 525.9 (MH)− |
| P-0129 | 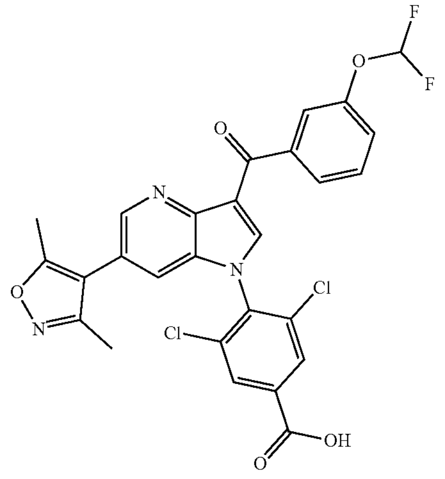 [SMILES: Cc1noc(C)c1-c1cnc2c(C(=O)c3cccc(OC(F)F)c3)cn(-c3c(Cl)cc(C(=O)O)cc3Cl)c2c1] | 3,5-dichloro-4-(3-(3-(difluoromethoxy)benzoyl)-6-(3,5-dimethylisoxazol-4-yl)-1H-pyrrolo[3,2-b]pyridin-1-yl)benzoic acid | 572.1 (MH)− |

TABLE 1-continued
| P# | Structure | Name | (MH)+ |
|---|---|---|---|
| P-0130 | 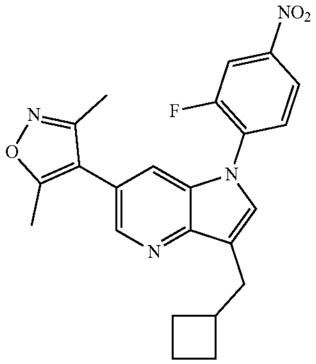 [SMILES: Cc1noc(C)c1-c1cnc2c(CC3CCC3)cn(-c3ccc([N+](=O)[O-])cc3F)c2c1] | 4-(3-(cyclobutylmethyl)-1-(2-fluoro-4-nitrophenyl)-1H-pyrrolo[3,2-b]pyridin-6-yl)-3,5-dimethylisoxazole | 421.3 |
| P-0131 | 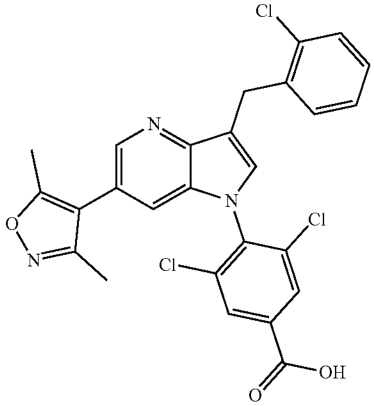 [SMILES: Cc1noc(C)c1-c1cnc2c(Cc3ccccc3Cl)cn(-c3c(Cl)cc(C(=O)O)cc3Cl)c2c1] | 3,5-dichloro-4-(3-(2-chlorobenzyl)-6-(3,5-dimethylisoxazol-4-yl)-1H-pyrrolo[3,2-b]pyridin-1-yl)benzoic acid | 526.0 (MH)− |
| P-0132 | 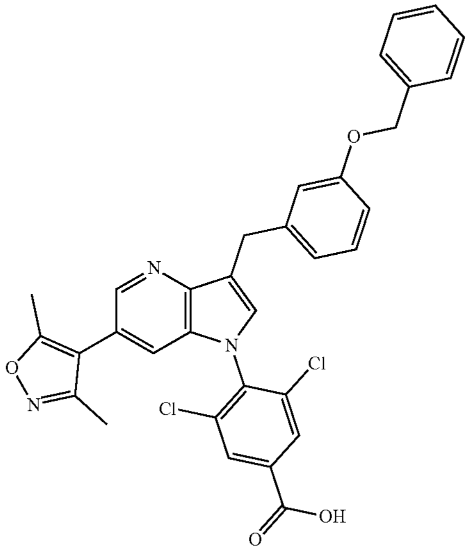 [SMILES: Cc1noc(C)c1-c1cnc2c(Cc3cccc(OCc4ccccc4)c3)cn(-c3c(Cl)cc(C(=O)O)cc3Cl)c2c1] | 4-(3-(3-(benzyloxy)benzyl)-6-(3,5-dimethylisoxazol-4-yl)-1H-pyrrolo[3,2-b]pyridin-1-yl)-3,5-dichlorobenzoic acid | 598.1 (MH)− |

TABLE 1-continued

| P# | Structure | Name | (MH)+ |
|---|---|---|---|
| P-0133 | 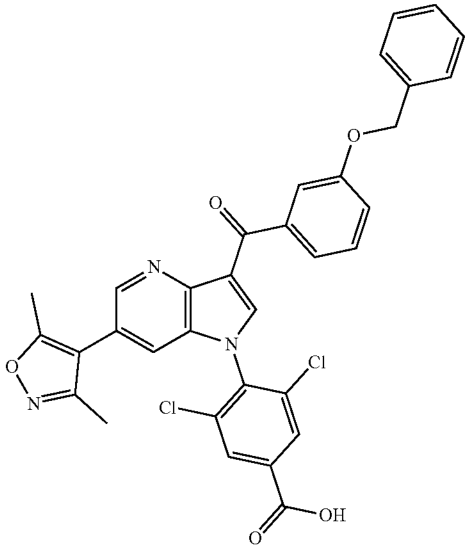 [SMILES: Cc1noc(C)c1-c1cnc2c(C(=O)c3cccc(OCc4ccccc4)c3)cn(-c3c(Cl)cc(C(=O)O)cc3Cl)c2c1] | 4-(3-(3-(benzyloxy)benzoyl)-6-(3,5-dimethylisoxazol-4-yl)-1H-pyrrolo[3,2-b]pyridin-1-yl)-3,5-dichlorobenzoic acid | 612.0 (MH)− |
| P-0134 | 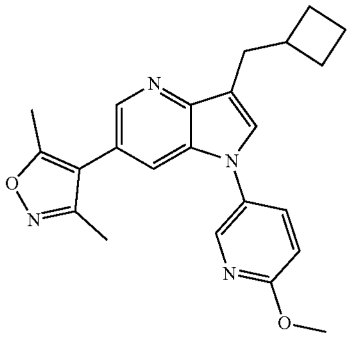 [SMILES: COc1ccc(-n2cc(CC3CCC3)c3ncc(-c4c(C)noc4C)cc32)cn1] | 4-(3-(cyclobutylmethyl)-1-(6-methoxypyridin-3-yl)-1H-pyrrolo[3,2-b]pyridin-6-yl)-3,5-dimethylisoxazole | 389.6 |
| P-0135 | 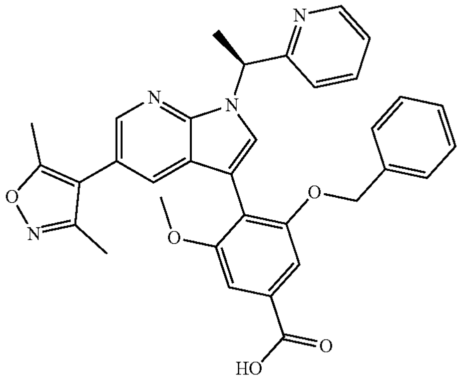 [SMILES: COc1cc(C(=O)O)cc(OCc2ccccc2)c1-c1cn([C@@H](C)c2ccccn2)c2ncc(-c3c(C)noc3C)cc12] | (S)-3-(benzyloxy)-4-(5-(3,5-dimethylisoxazol-4-yl)-1-(1-(pyridin-2-yl)ethyl)-1H-pyrrolo[2,3-b]pyridin-3-yl)-5-methoxybenzoic acid | 575.1 |
| P-0136 | 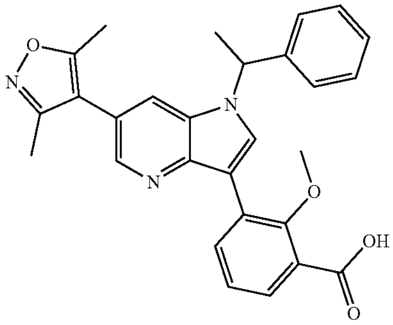 [SMILES: COc1c(C(=O)O)cccc1-c1cn(C(C)c2ccccc2)c2cc(-c3c(C)noc3C)cnc12] | 3-(6-(3,5-dimethylisoxazol-4-yl)-1-(1-phenylethyl)-1H-pyrrolo[3,2-b]pyridin-3-yl)-2-methoxybenzoic acid | 468.6 |

TABLE 1-continued

| P# | Structure | Name | (MH)+ |
|---|---|---|---|
| P-0137 | 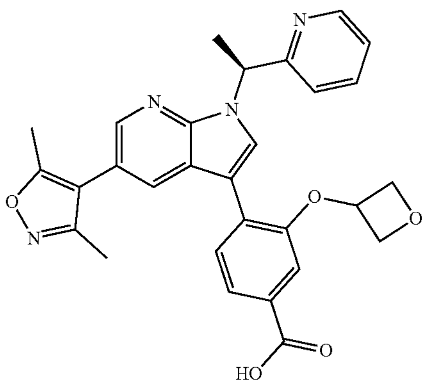 [SMILES: Cc1noc(C)c1-c1cnc2c(c1)c(-c1ccc(C(=O)O)cc1OC1COC1)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)-3-(oxetan-3-yloxy)benzoic acid | 511.5 |
| P-0138 | 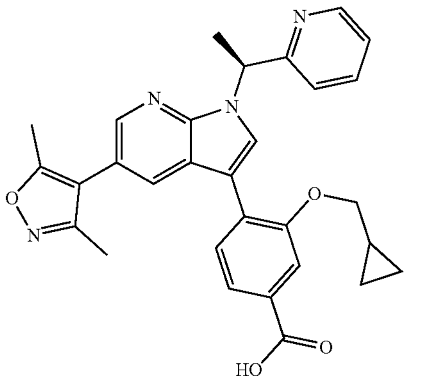 [SMILES: Cc1noc(C)c1-c1cnc2c(c1)c(-c1ccc(C(=O)O)cc1OCC1CC1)cn2[C@@H](C)c1ccccn1] | (S)-3-(cyclopropylmethoxy)-4-(5-(3,5-dimethylisoxazol-4-yl)-1-(1-(pyridin-2-yl)ethyl)-1H-pyrrolo[2,3-b]pyridin-3-yl)benzoic acid | 509.6 |
| P-0139 | 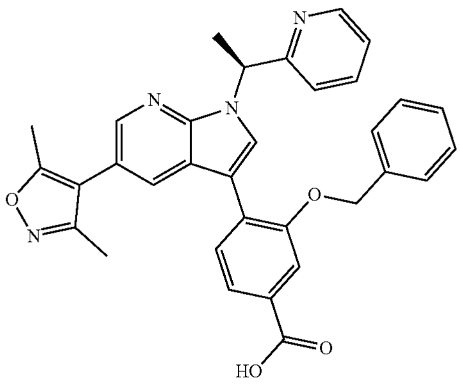 [SMILES: Cc1noc(C)c1-c1cnc2c(c1)c(-c1ccc(C(=O)O)cc1OCc1ccccc1)cn2[C@@H](C)c1ccccn1] | (S)-3-(benzyloxy)-4-(5-(3,5-dimethylisoxazol-4-yl)-1-(1-(pyridin-2-yl)ethyl)-1H-pyrrolo[2,3-b]pyridin-3-yl)benzoic acid | 545.5 |
| P-0140 | 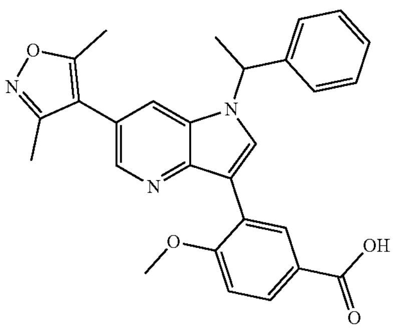 [SMILES: COc1ccc(C(=O)O)cc1-c1cn(C(C)c2ccccc2)c2cc(-c3c(C)noc3C)cnc12] | 3-(6-(3,5-dimethylisoxazol-4-yl)-1-(1-phenylethyl)-1H-pyrrolo[3,2-b]pyridin-3-yl)-4-methoxybenzoic acid | 468.6 |

TABLE 1-continued

| P# | Structure | Name | (MH)+ |
|---|---|---|---|
| P-0141 | 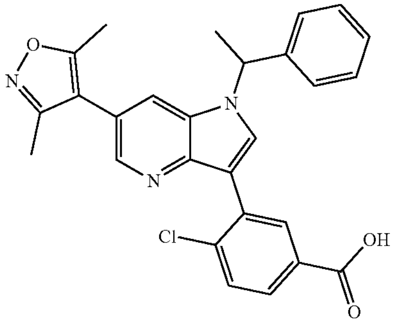 [SMILES: Cc1noc(C)c1-c1cnc2c(-c3cc(C(=O)O)ccc3Cl)cn(C(C)c3ccccc3)c2c1] | 4-chloro-3-(6-(3,5-dimethylisoxazol-4-yl)-1-(1-phenylethyl)-1H-pyrrolo[3,2-b]pyridin-3-yl)benzoic acid | 473.0 |
| P-0142 | 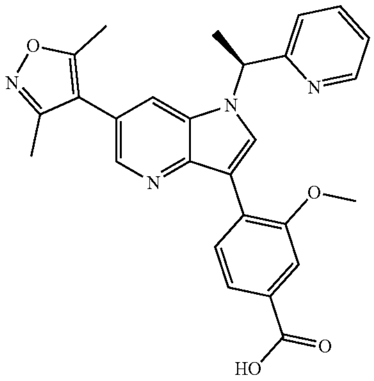 [SMILES: COc1cc(C(=O)O)ccc1-c1cn([C@@H](C)c2ccccn2)c2cc(-c3c(C)noc3C)cnc12] | (S)-4-(6-(3,5-dimethylisoxazol-4-yl)-1-(1-(pyridin-2-yl)ethyl)-1H-pyrrolo[3,2-b]pyridin-3-yl)-3-methoxybenzoic acid | 469.6 |
| P-0143 | 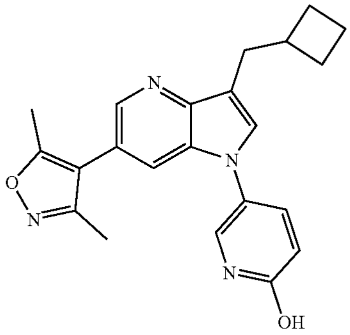 [SMILES: Cc1noc(C)c1-c1cnc2c(CC3CCC3)cn(-c3ccc(O)nc3)c2c1] | 5-(3-(cyclobutylmethyl)-6-(3,5-dimethylisoxazol-4-yl)-1H-pyrrolo[3,2-b]pyridin-1-yl)pyridin-2-ol | 375.2 |
| P-0144 | 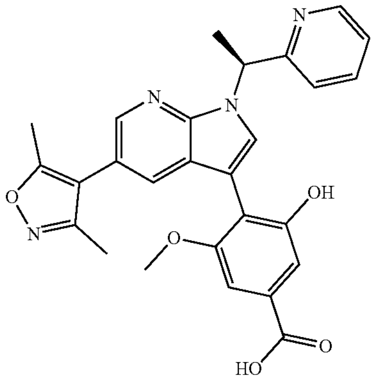 [SMILES: COc1cc(C(=O)O)cc(O)c1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3-hydroxy-5-methoxybenzoic acid | 485.6 |

TABLE 1-continued

| P# | Structure | Name | (MH)+ |
|---|---|---|---|
| P-0145 | 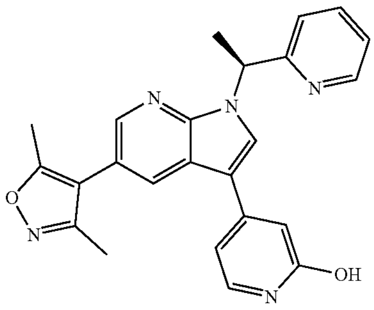 [SMILES: Cc1noc(C)c1-c1cnc2c(c1)c(-c1ccnc(O)c1)cn2[C@@H](C)c1ccccn1] | (S)-4-(5-(3,5-dimethylisoxazol-4-yl)-1-(1-(pyridin-2-yl)ethyl)-1H-pyrrolo[2,3-b]pyridin-3-yl)pyridin-2-ol | 412.2 |
| P-0146 | 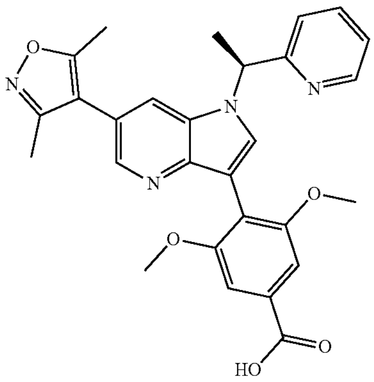 [SMILES: COc1cc(C(=O)O)cc(OC)c1-c1cn([C@@H](C)c2ccccn2)c2cc(-c3c(C)noc3C)cnc12] | (S)-4-(6-(3,5-dimethylisoxazol-4-yl)-1-(1-(pyridin-2-yl)ethyl)-1H-pyrrolo[3,2-b]pyridin-3-yl)-3,5-dimethoxybenzoic acid | 499.6 |
| P-0147 | 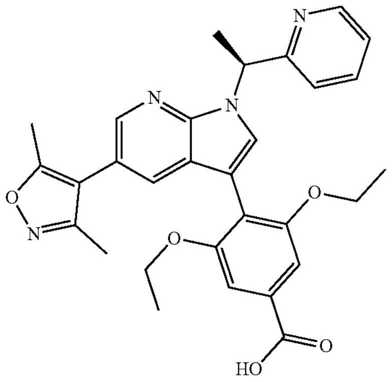 [SMILES: CCOc1cc(C(=O)O)cc(OCC)c1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3,5-diethoxybenzoic acid | 527.6 |
| P-0148 | 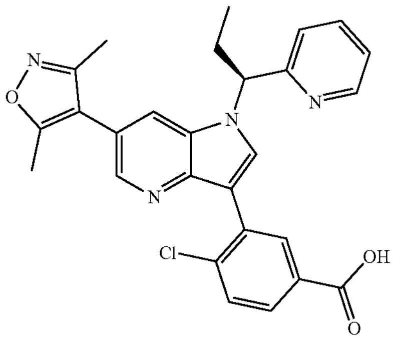 [SMILES: CC[C@@H](c1ccccn1)n1cc(-c2cc(C(=O)O)ccc2Cl)c2ncc(-c3c(C)noc3C)cc21] | (S)-4-chloro-3-(6-(3,5-dimethylisoxazol-4-yl)-1-(1-(pyridin-2-yl)propyl)-1H-pyrrolo[3,2-b]pyridin-3-yl)benzoic acid | 487.5 |

TABLE 1-continued

| P# | Structure | Name | (MH)+ |
|---|---|---|---|
| P-0149 | 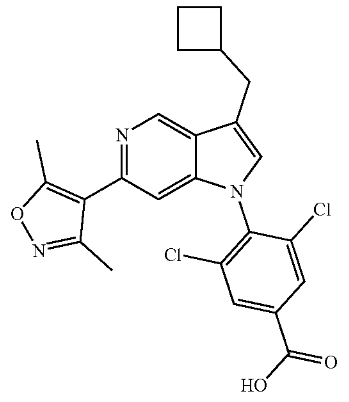 [SMILES: Cc1noc(C)c1-c1cc2c(cn1)c(CC1CCC1)cn2-c1c(Cl)cc(C(=O)O)cc1Cl] | 3,5-dichloro-4-(3-(cyclobutylmethyl)-6-(3,5-dimethylisoxazol-4-yl)-1H-pyrrolo[3,2-c]pyridin-1-yl)benzoic acid | 471.0 |
| P-0150 | 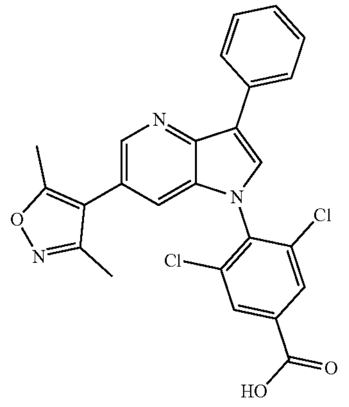 [SMILES: Cc1noc(C)c1-c1cnc2c(-c3ccccc3)cn(-c3c(Cl)cc(C(=O)O)cc3Cl)c2c1] | 3,5-dichloro-4-(6-(3,5-dimethylisoxazol-4-yl)-3-phenyl-1H-pyrrolo[3,2-b]pyridin-1-yl)benzoic acid | 478.0 |
| P-0151 | 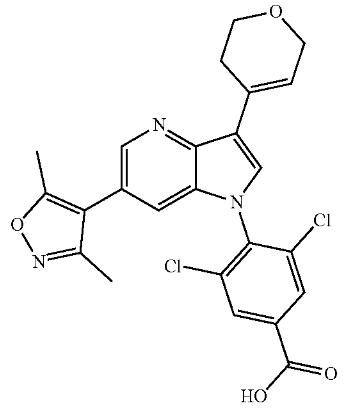 [SMILES: Cc1noc(C)c1-c1cnc2c(C3=CCOCC3)cn(-c3c(Cl)cc(C(=O)O)cc3Cl)c2c1] | 3,5-dichloro-4-(3-(3,6-dihydro-2H-pyran-4-yl)-6-(3,5-dimethylisoxazol-4-yl)-1H-pyrrolo[3,2-b]pyridin-1-yl)benzoic acid | 485.7 |
| P-0152 | 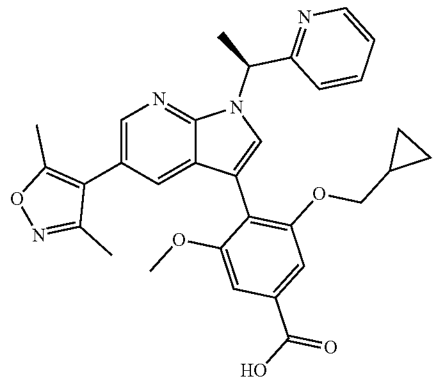 [SMILES: COc1cc(C(=O)O)cc(OCC2CC2)c1-c1cn([C@@H](C)c2ccccn2)c2ncc(-c3c(C)noc3C)cc12] | (S)-3-(cyclopropylmethoxy)-4-(5-(3,5-dimethylisoxazol-4-yl)-1-(1-(pyridin-2-yl)ethyl)-1H-pyrrolo[2,3-b]pyridin-3-yl)-5-methoxybenzoic acid | 539.6 |

TABLE 1-continued

| P# | Structure | Name | (MH)+ |
|---|---|---|---|
| P-0153 | 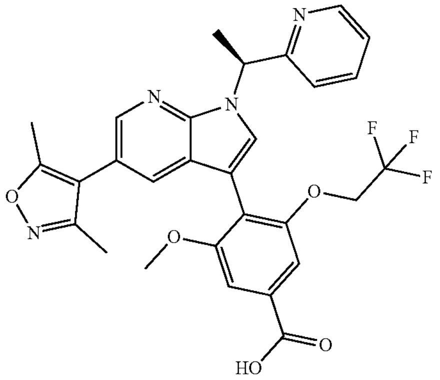 [SMILES: COc1cc(C(=O)O)cc(OCC(F)(F)F)c1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3-methoxy-5-(2,2,2-trifluoroethoxy)benzoic acid | 566.5 |
| P-0154 | 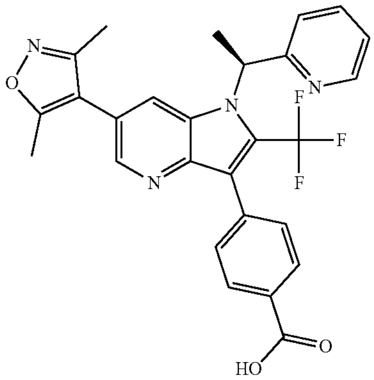 [SMILES: Cc1noc(C)c1-c1cnc2c(-c3ccc(C(=O)O)cc3)c(C(F)(F)F)n([C@@H](C)c3ccccn3)c2c1] | (S)-4-(6-(3,5-dimethylisoxazol-4-yl)-1-(1-(pyridin-2-yl)ethyl)-2-(trifluoromethyl)-1H-pyrrolo[3,2-b]pyridin-3-yl)benzoic acid | 507.1 |
| P-0155 | 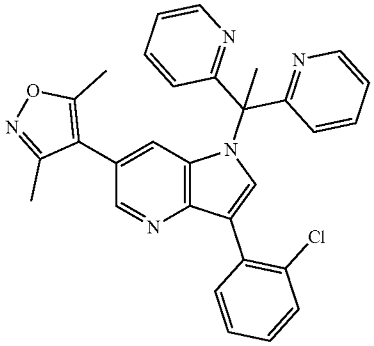 [SMILES: Cc1noc(C)c1-c1cnc2c(-c3ccccc3Cl)cn(C(C)(c3ccccn3)c3ccccn3)c2c1] | 4-(3-(2-chlorophenyl)-1-(1,1-di(pyridin-2-yl)ethyl)-1H-pyrrolo[3,2-b]pyridin-6-yl)-3,5-dimethylisoxazole | 506.1 |
| P-0156 | 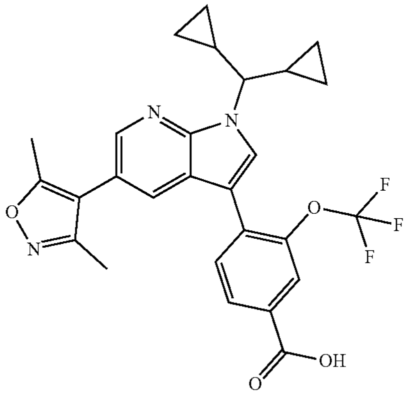 [SMILES: Cc1noc(C)c1-c1cnc2c(c1)c(-c1ccc(C(=O)O)cc1OC(F)(F)F)cn2C(C1CC1)C1CC1] | 4-(1-(dicyclopropylmethyl)-5-(3,5-dimethylisoxazol-4-yl)-1H-pyrrolo[2,3-b]pyridin-3-yl)-3-(trifluoromethoxy)benzoic acid | 512.1 |

TABLE 1-continued

| P# | Structure | Name | (MH)+ |
|---|---|---|---|
| P-0157 | 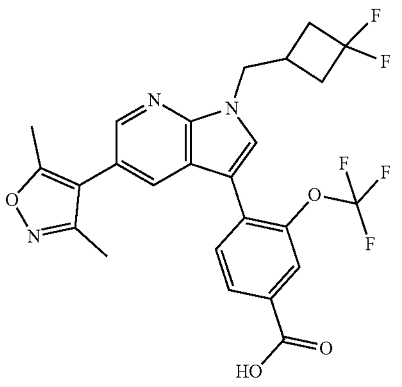 [SMILES: Cc1noc(C)c1-c1cnc2c(c1)c(-c1ccc(C(=O)O)cc1OC(F)(F)F)cn2CC1CC(F)(F)C1] | 4-(1-((3,3-difluorocyclobutyl)methyl)-5-(3,5-dimethylisoxazol-4-yl)-1H-pyrrolo[2,3-b]pyridin-3-yl)-3-(trifluoromethoxy)benzoic acid | 522.5 |
| P-0158 | 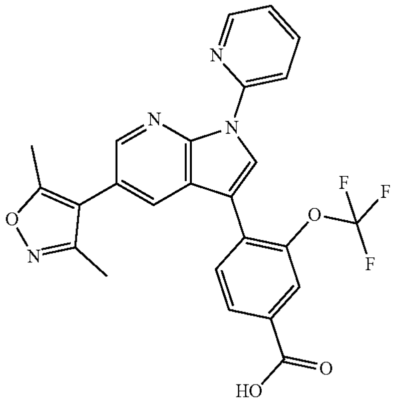 [SMILES: Cc1noc(C)c1-c1cnc2c(c1)c(-c1ccc(C(=O)O)cc1OC(F)(F)F)cn2-c1ccccn1] | 4-(5-(3,5-dimethylisoxazol-4-yl)-1-(pyridin-2-yl)-1H-pyrrolo[2,3-b]pyridin-3-yl)-3-(trifluoromethoxy)benzoic acid | 495.5 |
| P-0159 | 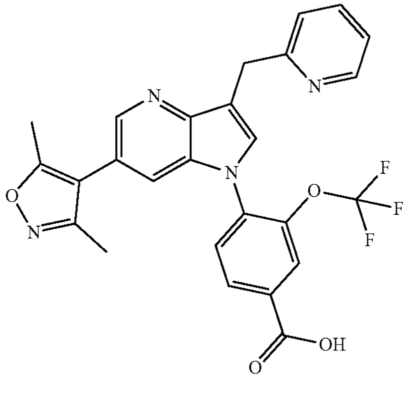 [SMILES: Cc1noc(C)c1-c1cnc2c(Cc3ccccn3)cn(-c3ccc(C(=O)O)cc3OC(F)(F)F)c2c1] | 4-(6-(3,5-dimethylisoxazol-4-yl)-3-(pyridin-2-ylmethyl)-1H-pyrrolo[3,2-b]pyridin-1-yl)-3-(trifluoromethoxy)benzoic acid | 509.5 |
| P-0160 | 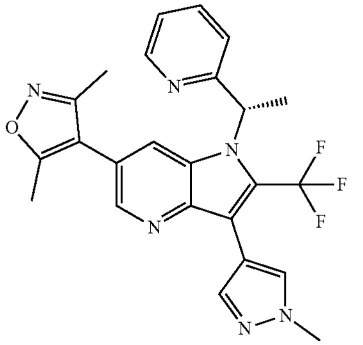 [SMILES: Cc1noc(C)c1-c1cnc2c(-c3cnn(C)c3)c(C(F)(F)F)n([C@@H](C)c3ccccn3)c2c1] | (S)-3,5-dimethyl-4-(3-(1-methyl-1H-pyrazol-4-yl)-1-(1-(pyridin-2-yl)ethyl)-2-(trifluoromethyl)-1H-pyrrolo[3,2-b]pyridin-6-yl)isoxazole | 467.6 |

TABLE 1-continued

| P# | Structure | Name | (MH)+ |
| --- | --- | --- | --- |
| P-0161 | 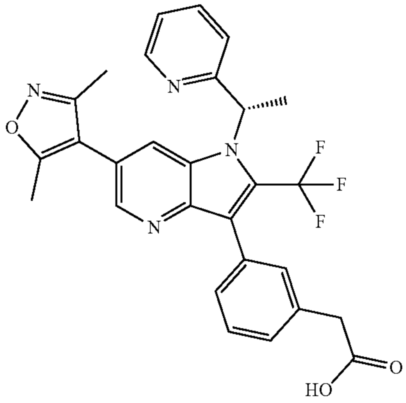 [SMILES: Cc1noc(C)c1-c1cnc2c(-c3cccc(CC(=O)O)c3)c(C(F)(F)F)n([C@@H](C)c3ccccn3)c2c1] | (S)-2-(3-(6-(3,5-dimethylisoxazol-4-yl)-1-(1-(pyridin-2-yl)ethyl)-2-(trifluoromethyl)-1H-pyrrolo[3,2-b]pyridin-3-yl)phenyl)acetic acid | 521.6 |
| P-0162 | 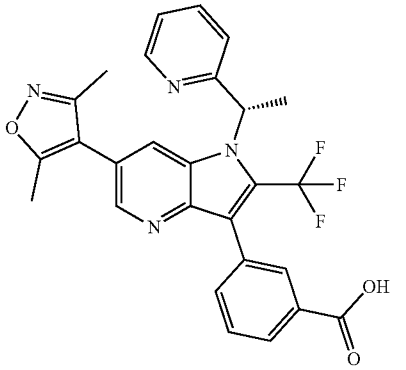 [SMILES: Cc1noc(C)c1-c1cnc2c(-c3cccc(C(=O)O)c3)c(C(F)(F)F)n([C@@H](C)c3ccccn3)c2c1] | (S)-3-(6-(3,5-dimethylisoxazol-4-yl)-1-(1-(pyridin-2-yl)ethyl)-2-(trifluoromethyl)-1H-pyrrolo[3,2-b]pyridin-3-yl)benzoic acid | 507.5 |
| P-0163 | 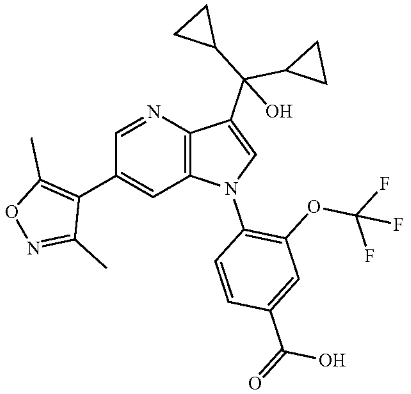 [SMILES: Cc1noc(C)c1-c1cnc2c(C(O)(C3CC3)C3CC3)cn(-c3ccc(C(=O)O)cc3OC(F)(F)F)c2c1] | 4-(3-(dicyclopropyl(hydroxy)methyl)-6-(3,5-dimethylisoxazol-4-yl)-1H-pyrrolo[3,2-b]pyridin-1-yl)-3-(trifluoromethoxy)benzoic acid | 528.1 |
| P-0164 | 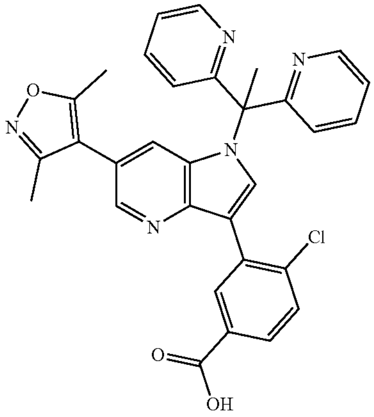 [SMILES: Cc1noc(C)c1-c1cnc2c(-c3cc(C(=O)O)ccc3Cl)cn(C(C)(c3ccccn3)c3ccccn3)c2c1] | 4-chloro-3-(1-(1,1-di(pyridin-2-yl)ethyl)-6-(3,5-dimethylisoxazol-4-yl)-1H-pyrrolo[3,2-b]pyridin-3-yl)benzoic acid | 550.1 |

TABLE 1-continued

| P# | Structure | Name | (MH)+ |
|---|---|---|---|
| P-0165 | 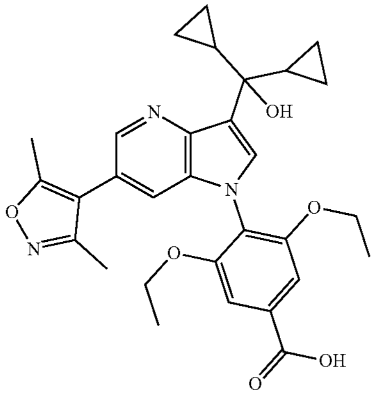 [SMILES: CCOc1cc(C(=O)O)cc(OCC)c1-n1cc(C(O)(C2CC2)C2CC2)c2ncc(-c3c(C)noc3C)cc21] | 4-(3-(dicyclopropyl(hydroxy)methyl)-6-(3,5-dimethylisoxazol-4-yl)-1H-pyrrolo[3,2-b]pyridin-1-yl)-3,5-diethoxybenzoic acid | 532.2 |
| P-0166 | 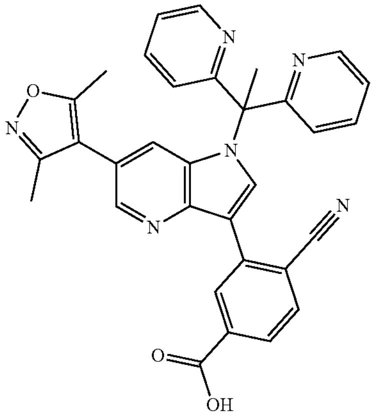 [SMILES: Cc1noc(C)c1-c1cnc2c(-c3cc(C(=O)O)ccc3C#N)cn(C(C)(c3ccccn3)c3ccccn3)c2c1] | 4-cyano-3-(1-(1,1-di(pyridin-2-yl)ethyl)-6-(3,5-dimethylisoxazol-4-yl)-1H-pyrrolo[3,2-b]pyridin-3-yl)benzoic acid | 541.1 |
| P-0167 | 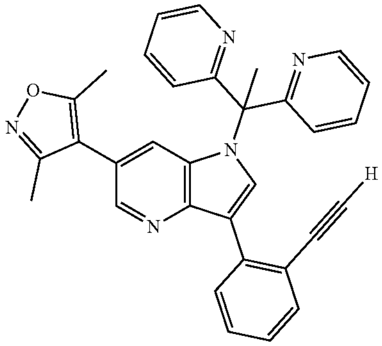 [SMILES: C#Cc1ccccc1-c1cn(C(C)(c2ccccn2)c2ccccn2)c2cc(-c3c(C)noc3C)cnc12] | 4-(1-(1,1-di(pyridin-2-yl)ethyl)-3-(2-ethynylphenyl)-1H-pyrrolo[3,2-b]pyridin-6-yl)-3,5-dimethylisoxazole | 496.6 |
| P-0168 | 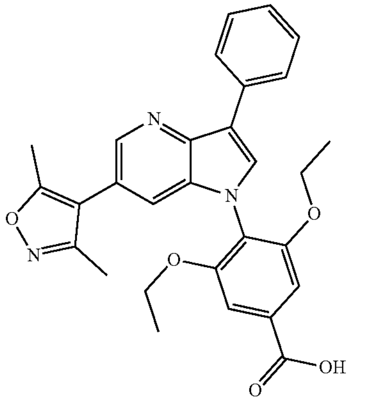 [SMILES: CCOc1cc(C(=O)O)cc(OCC)c1-n1cc(-c2ccccc2)c2ncc(-c3c(C)noc3C)cc21] | 4-(6-(3,5-dimethylisoxazol-4-yl)-3-phenyl-1H-pyrrolo[3,2-b]pyridin-1-yl)-3,5-diethoxybenzoic acid | 498.6 |

TABLE 1-continued

| P# | Structure | Name | (MH)+ |
|---|---|---|---|
| P-0169 | 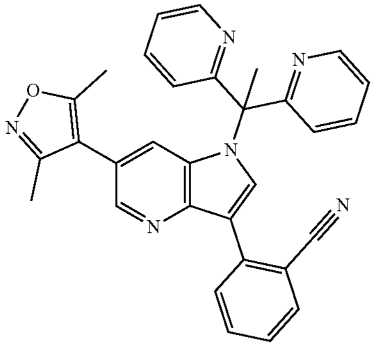 [SMILES: Cc1noc(C)c1-c1cnc2c(-c3ccccc3C#N)cn(C(C)(c3ccccn3)c3ccccn3)c2c1] | 2-(1-(1,1-di(pyridin-2-yl)ethyl)-6-(3,5-dimethylisoxazol-4-yl)-1H-pyrrolo[3,2-b]pyridin-3-yl)benzonitrile | 497.1 |
| P-0170 | 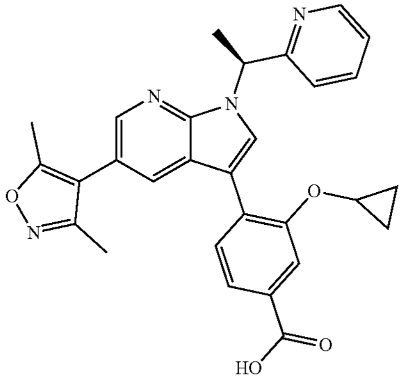 [SMILES: Cc1noc(C)c1-c1cnc2c(c1)c(-c1ccc(C(=O)O)cc1OC1CC1)cn2[C@@H](C)c1ccccn1] | (S)-3-cyclopropoxy-4-(5-(3,5-dimethylisoxazol-4-yl)-1-(1-(pyridin-2-yl)ethyl)-1H-pyrrolo[2,3-b]pyridin-3-yl)benzoic acid | 495.6 |
| P-0171 | 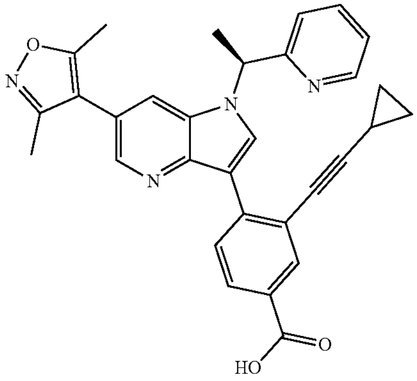 [SMILES: Cc1noc(C)c1-c1cnc2c(-c3ccc(C(=O)O)cc3C#CC3CC3)cn([C@@H](C)c3ccccn3)c2c1] | (S)-3-(cyclopropylethynyl)-4-(6-(3,5-dimethylisoxazol-4-yl)-1-(1-(pyridin-2-yl)ethyl)-1H-pyrrolo[3,2-b]pyridin-3-yl)benzoic acid | 503.6 |
| P-0172 | 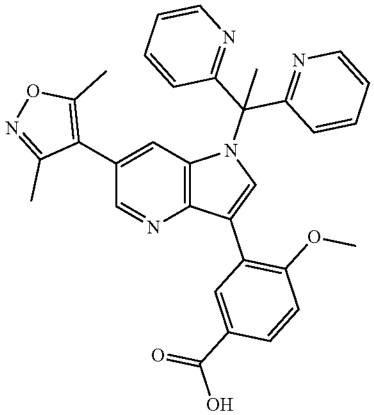 [SMILES: COc1ccc(C(=O)O)cc1-c1cn(C(C)(c2ccccn2)c2ccccn2)c2cc(-c3c(C)noc3C)cnc12] | 3-(1-(1,1-di(pyridin-2-yl)ethyl)-6-(3,5-dimethylisoxazol-4-yl)-1H-pyrrolo[3,2-b]pyridin-3-yl)-4-methoxybenzoic acid | 546.6 |

TABLE 1-continued

| P# | Structure | Name | (MH)+ |
| --- | --- | --- | --- |
| P-0173 | 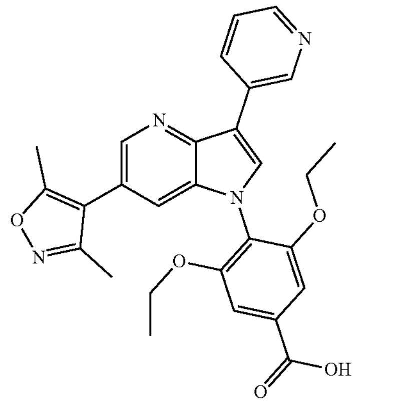 [SMILES: CCOc1cc(C(=O)O)cc(OCC)c1-n1cc(-c2cccnc2)c2ncc(-c3c(C)noc3C)cc21] | 4-(6-(3,5-dimethylisoxazol-4-yl)-3-(pyridin-3-yl)-1H-pyrrolo[3,2-b]pyridin-1-yl)-3,5-diethoxybenzoic acid | 499.1 |
| P-0174 | 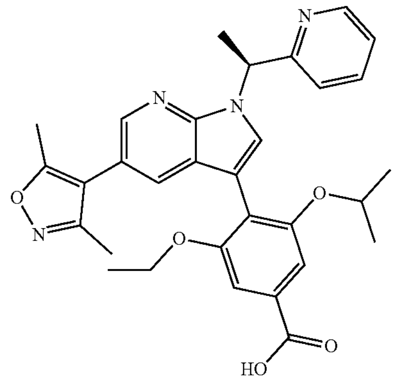 [SMILES: CCOc1cc(C(=O)O)cc(OC(C)C)c1-c1cn([C@@H](C)c2ccccn2)c2ncc(-c3c(C)noc3C)cc12] | (S)-4-(5-(3,5-dimethylisoxazol-4-yl)-1-(1-(pyridin-2-yl)ethyl)-1H-pyrrolo[2,3-b]pyridin-3-yl)-3-ethoxy-5-isopropoxybenzoic acid | |
| P-0175 | 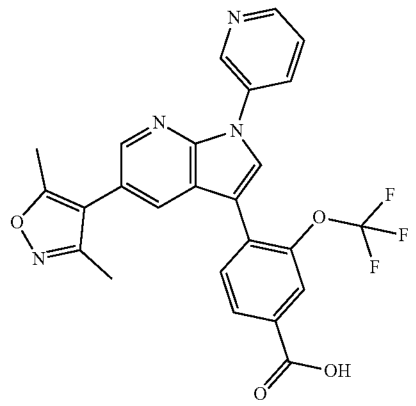 [SMILES: Cc1noc(C)c1-c1cnc2c(c1)c(-c1ccc(C(=O)O)cc1OC(F)(F)F)cn2-c1cccnc1] | 4-(5-(3,5-dimethylisoxazol-4-yl)-1-(pyridin-3-yl)-1H-pyrrolo[2,3-b]pyridin-3-yl)-3-(trifluoromethoxy)benzoic acid | 495.0 |
| P-0176 | 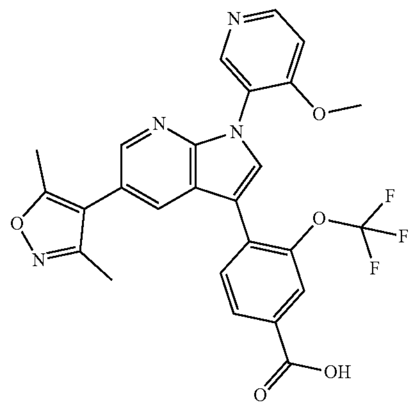 [SMILES: COc1ccncc1-n1cc(-c2ccc(C(=O)O)cc2OC(F)(F)F)c2cc(-c3c(C)noc3C)cnc21] | 4-(5-(3,5-dimethylisoxazol-4-yl)-1-(4-methoxypyridin-3-yl)-1H-pyrrolo[2,3-b]pyridin-3-yl)-3-(trifluoromethoxy)benzoic acid | 525.0 |

TABLE 1-continued

| P# | Structure | Name | (MH)+ |
|---|---|---|---|
| P-0177 | 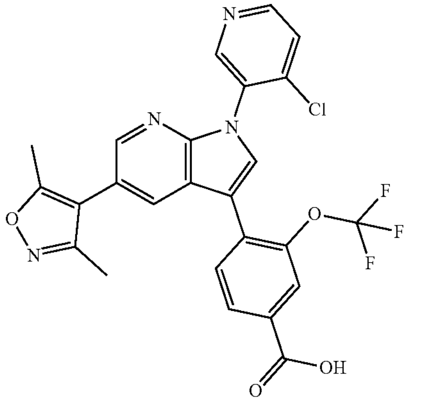 | 4-(1-(4-chloropyridin-3-yl)-5-(3,5-dimethylisoxazol-4-yl)-1H-pyrrolo[2,3-b]pyridin-3-yl)-3-(trifluoromethoxy)benzoic acid | 529.0 |
| P-0178 | 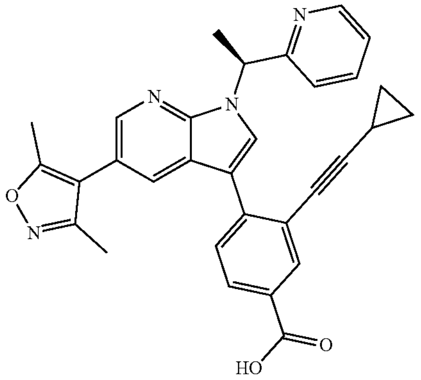 [SMILES: Cc1noc(C)c1-c1cnc2c(c1)c(-c1ccc(C(=O)O)cc1C#CC1CC1)cn2[C@@H](C)c1ccccn1] | (S)-3-(cyclopropylethynyl)-4-(5-(3,5-dimethylisoxazol-4-yl)-1-(1-(pyridin-2-yl)ethyl)-1H-pyrrolo[2,3-b]pyridin-3-yl)benzoic acid | 503.2 |
| P-0179 | 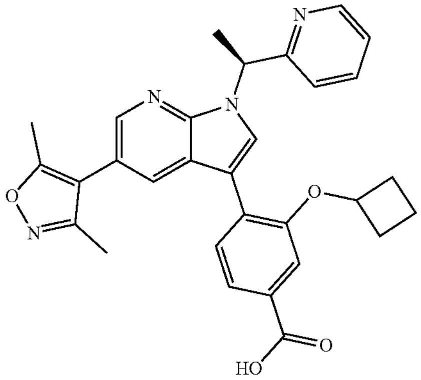 [SMILES: Cc1noc(C)c1-c1cnc2c(c1)c(-c1ccc(C(=O)O)cc1OC1CCC1)cn2[C@@H](C)c1ccccn1] | (S)-3-cyclobutoxy-4-(5-(3,5-dimethylisoxazol-4-yl)-1-(1-(pyridin-2-yl)ethyl)-1H-pyrrolo[2,3-b]pyridin-3-yl)benzoic acid | 509.1 |
| P-0180 | 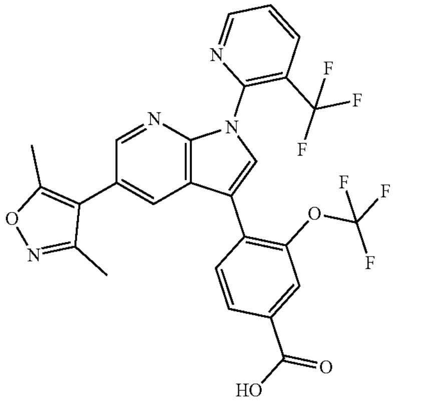 [SMILES: Cc1noc(C)c1-c1cnc2c(c1)c(-c1ccc(C(=O)O)cc1OC(F)(F)F)cn2-c1ncccc1C(F)(F)F] | 4-(5-(3,5-dimethylisoxazol-4-yl)-1-(3-(trifluoromethyl)pyridin-2-yl)-1H-pyrrolo[2,3-b]pyridin-3-yl)-3-(trifluoromethoxy)benzoic acid | 563.1 |

TABLE 1-continued
| P# | Structure | Name | (MH)+ |
|---|---|---|---|
| P-0181 | 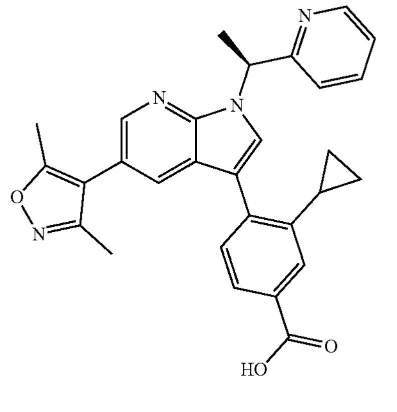 [SMILES: Cc1noc(C)c1-c1cnc2c(c1)c(-c1ccc(C(=O)O)cc1C1CC1)cn2[C@@H](C)c1ccccn1] | (S)-3-cyclopropyl-4-(5-(3,5-dimethylisoxazol-4-yl)-1-(1-(pyridin-2-yl)ethyl)-1H-pyrrolo[2,3-b]pyridin-3-yl)benzoic acid | 479.1 |
| P-0182 | 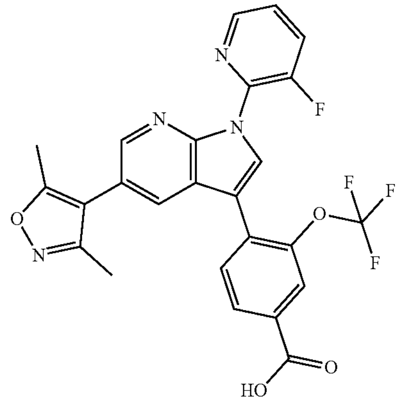 [SMILES: Cc1noc(C)c1-c1cnc2c(c1)c(-c1ccc(C(=O)O)cc1OC(F)(F)F)cn2-c1ncccc1F] | 4-(5-(3,5-dimethylisoxazol-4-yl)-1-(3-fluoropyridin-2-yl)-1H-pyrrolo[2,3-b]pyridin-3-yl)-3-(trifluoromethoxy)benzoic acid | 513.1 |
| P-0183 | 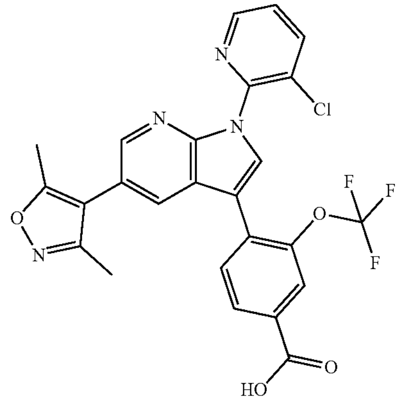 [SMILES: Cc1noc(C)c1-c1cnc2c(c1)c(-c1ccc(C(=O)O)cc1OC(F)(F)F)cn2-c1ncccc1Cl] | 4-(1-(3-chloropyridin-2-yl)-5-(3,5-dimethylisoxazol-4-yl)-1H-pyrrolo[2,3-b]pyridin-3-yl)-3-(trifluoromethoxy)benzoic acid | 529.5 |

TABLE 1-continued
| P# | Structure | Name | (MH)+ |
|---|---|---|---|
| P-0184 | 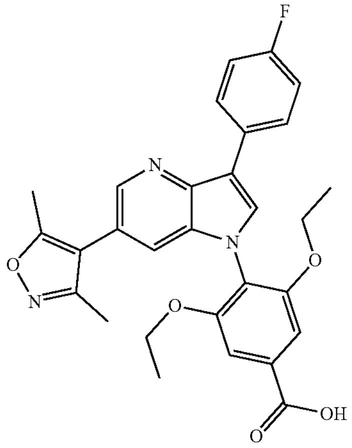 [SMILES: CCOc1cc(C(=O)O)cc(OCC)c1-n1cc(-c2ccc(F)cc2)c2ncc(-c3c(C)noc3C)cc21] | 4-(6-(3,5-dimethylisoxazol-4-yl)-3-(4-fluorophenyl)-1H-pyrrolo[3,2-b]pyridin-1-yl)-3,5-diethoxybenzoic acid | 516.1 |
| P-0185 | 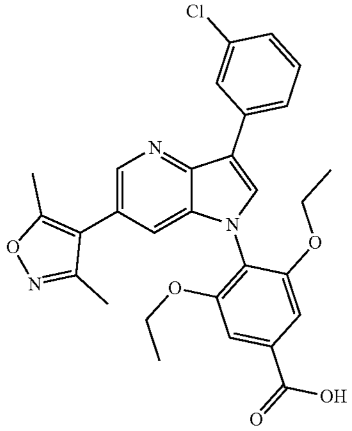 [SMILES: CCOc1cc(C(=O)O)cc(OCC)c1-n1cc(-c2cccc(Cl)c2)c2ncc(-c3c(C)noc3C)cc21] | 4-(3-(3-chlorophenyl)-6-(3,5-dimethylisoxazol-4-yl)-1H-pyrrolo[3,2-b]pyridin-1-yl)-3,5-diethoxybenzoic acid | 532.1 |
| P-0186 | 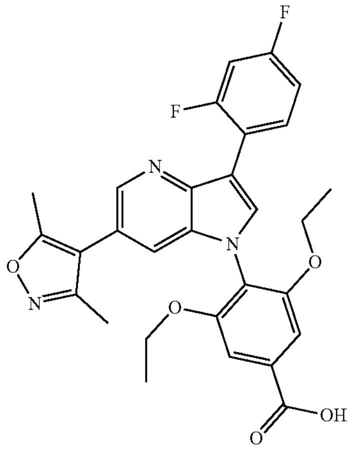 [SMILES: CCOc1cc(C(=O)O)cc(OCC)c1-n1cc(-c2ccc(F)cc2F)c2ncc(-c3c(C)noc3C)cc21] | 4-(3-(2,4-difluorophenyl)-6-(3,5-dimethylisoxazol-4-yl)-1H-pyrrolo[3,2-b]pyridin-1-yl)-3,5-diethoxybenzoic acid | 534.1 |

TABLE 1-continued

| P# | Structure | Name | (MH)+ |
|---|---|---|---|
| P-0187 | 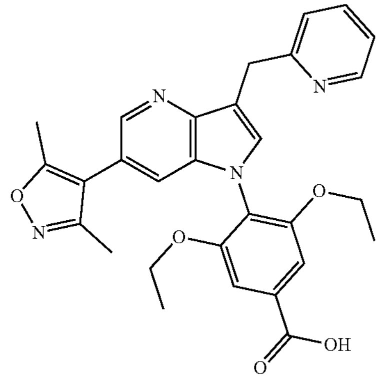 [SMILES: CCOc1cc(C(=O)O)cc(OCC)c1-n1cc(Cc2ccccn2)c2ncc(-c3c(C)noc3C)cc21] | 4-(6-(3,5-dimethylisoxazol-4-yl)-3-(pyridin-2-ylmethyl)-1H-pyrrolo[3,2-b]pyridin-1-yl)-3,5-diethoxybenzoic acid | 513.2 |
| P-0188 | 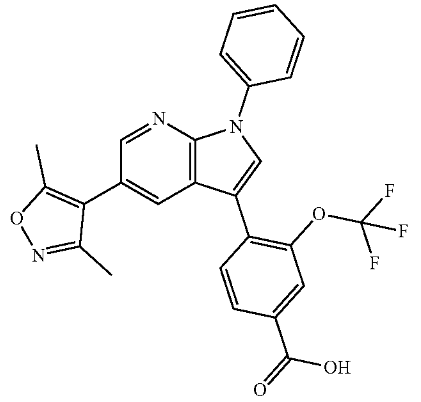 [SMILES: Cc1noc(C)c1-c1cnc2c(c1)c(-c1ccc(C(=O)O)cc1OC(F)(F)F)cn2-c1ccccc1] | 4-(5-(3,5-dimethylisoxazol-4-yl)-1-phenyl-1H-pyrrolo[2,3-b]pyridin-3-yl)-3-(trifluoromethoxy)benzoic acid | 494.1 |
| P-0189 | 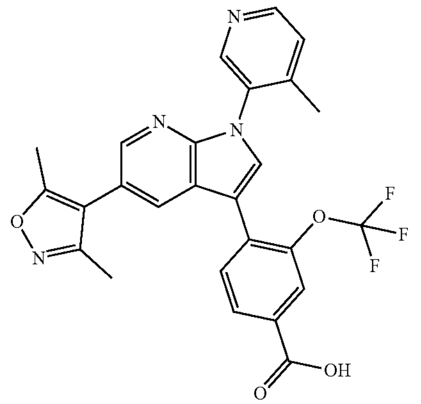 [SMILES: Cc1ccncc1-n1cc(-c2ccc(C(=O)O)cc2OC(F)(F)F)c2cc(-c3c(C)noc3C)cnc21] | 4-(5-(3,5-dimethylisoxazol-4-yl)-1-(4-methylpyridin-3-yl)-1H-pyrrolo[2,3-b]pyridin-3-yl)-3-(trifluoromethoxy)benzoic acid | 509.5 |
| P-0190 | 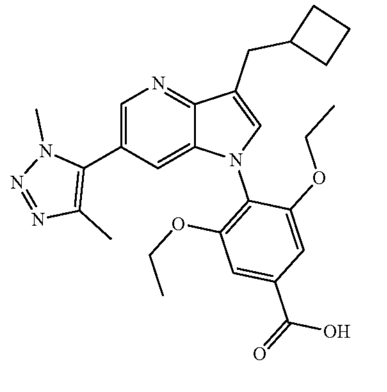 [SMILES: CCOc1cc(C(=O)O)cc(OCC)c1-n1cc(CC2CCC2)c2ncc(-c3c(C)nnn3C)cc21] | 4-(3-(cyclobutylmethyl)-6-(1,4-dimethyl-1H-1,2,3-triazol-5-yl)-1H-pyrrolo[3,2-b]pyridin-1-yl)-3,5-diethoxybenzoic acid | 490.1 |

TABLE 1-continued
| P# | Structure | Name | (MH)+ |
|---|---|---|---|
| P-0191 | 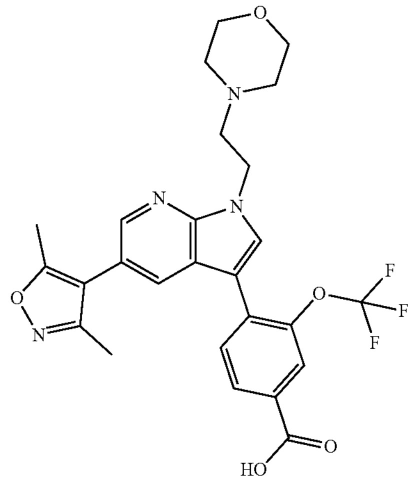 [SMILES: Cc1noc(C)c1-c1cnc2c(c1)c(-c1ccc(C(=O)O)cc1OC(F)(F)F)cn2CCN1CCOCC1] | 4-(5-(3,5-dimethylisoxazol-4-yl)-1-(2-morpholinoethyl)-1H-pyrrolo[2,3-b]pyridin-3-yl)-3-(trifluoromethoxy)benzoic acid | 531.5 |
| P-0192 | 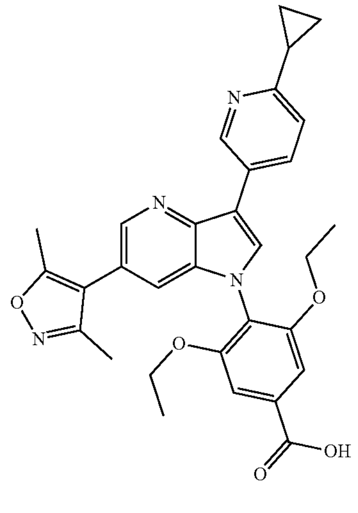 [SMILES: CCOc1cc(C(=O)O)cc(OCC)c1-n1cc(-c2ccc(C3CC3)nc2)c2ncc(-c3c(C)noc3C)cc21] | 4-(3-(6-cyclopropylpyridin-3-yl)-6-(3,5-dimethylisoxazol-4-yl)-1H-pyrrolo[3,2-b]pyridin-1-yl)-3,5-diethoxybenzoic acid | 539.6 |
| P-0193 | 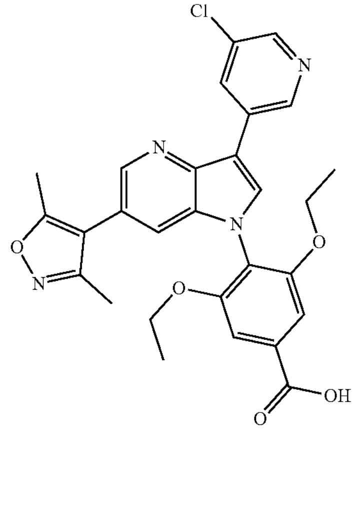 [SMILES: CCOc1cc(C(=O)O)cc(OCC)c1-n1cc(-c2cncc(Cl)c2)c2ncc(-c3c(C)noc3C)cc21] | 4-(3-(5-chloropyridin-3-yl)-6-(3,5-dimethylisoxazol-4-yl)-1H-pyrrolo[3,2-b]pyridin-1-yl)-3,5-diethoxybenzoic acid | 533.1 |

TABLE 1-continued
| P# | Structure | Name | (MH)+ |
|---|---|---|---|
| P-0194 | 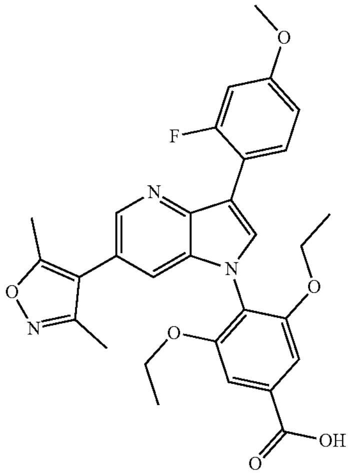 [SMILES: CCOc1cc(C(=O)O)cc(OCC)c1-n1cc(-c2ccc(OC)cc2F)c2ncc(-c3c(C)noc3C)cc21] | 4-(6-(3,5-dimethylisoxazol-4-yl)-3-(2-fluoro-4-methoxyphenyl)-1H-pyrrolo[3,2-b]pyridin-1-yl)-3,5-diethoxybenzoic acid | |
| P-0195 | 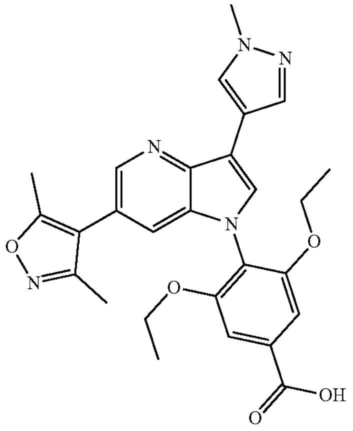 [SMILES: CCOc1cc(C(=O)O)cc(OCC)c1-n1cc(-c2cnn(C)c2)c2ncc(-c3c(C)noc3C)cc21] | 4-(6-(3,5-dimethylisoxazol-4-yl)-3-(1-methyl-1H-pyrazol-4-yl)-1H-pyrrolo[3,2-b]pyridin-1-yl)-3,5-diethoxybenzoic acid | 502.6 |
| P-0196 | 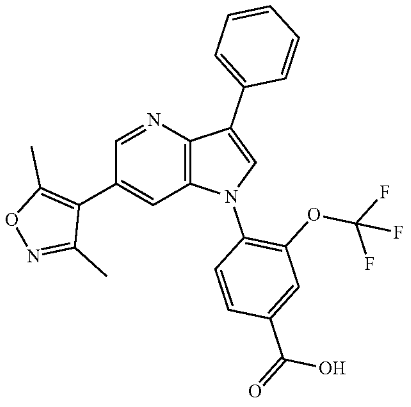 [SMILES: Cc1noc(C)c1-c1cnc2c(-c3ccccc3)cn(-c3ccc(C(=O)O)cc3OC(F)(F)F)c2c1] | 4-(6-(3,5-dimethylisoxazol-4-yl)-3-phenyl-1H-pyrrolo[3,2-b]pyridin-1-yl)-3-(trifluoromethoxy)benzoic acid | 494.0 |

TABLE 1-continued
| P# | Structure | Name | (MH)+ |
|---|---|---|---|
| P-0197 | 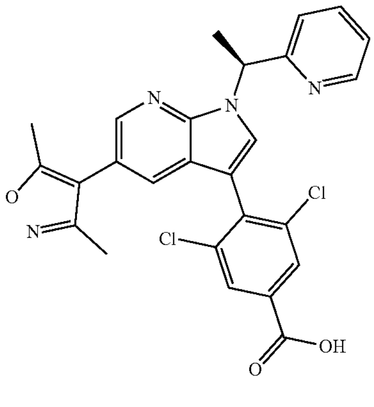 [SMILES: CC(=N)/C(=C(/C)O)c1cnc2c(c1)c(-c1c(Cl)cc(C(=O)O)cc1Cl)cn2[C@@H](C)c1ccccn1] | (S)-3,5-dichloro-4-(5-(3,5-dimethylisoxazol-4-yl)-1-(1-(pyridin-2-yl)ethyl)-1H-pyrrolo[2,3-b]pyridin-3-yl)benzoic acid | 507.1 |
| P-0198 | 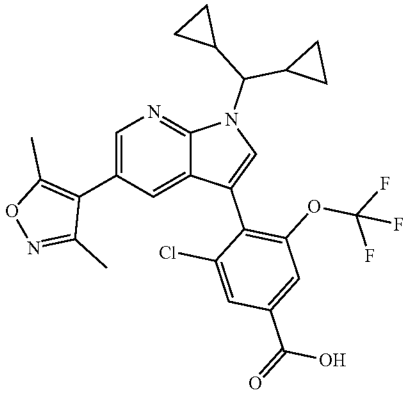 [SMILES: Cc1noc(C)c1-c1cnc2c(c1)c(-c1c(Cl)cc(C(=O)O)cc1OC(F)(F)F)cn2C(C1CC1)C1CC1] | 3-chloro-4-(1-(dicyclopropylmethyl)-5-(3,5-dimethylisoxazol-4-yl)-1H-pyrrolo[2,3-b]pyridin-3-yl)-5-(trifluoromethoxy)benzoic acid | 546.1 |
| P-0199 | 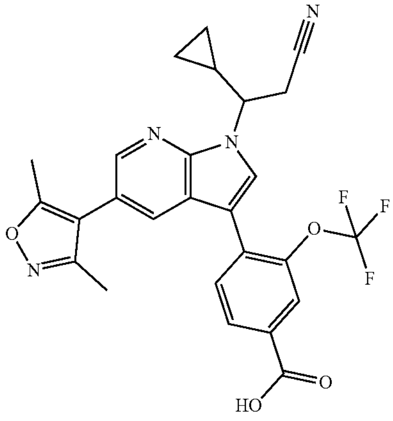 [SMILES: Cc1noc(C)c1-c1cnc2c(c1)c(-c1ccc(C(=O)O)cc1OC(F)(F)F)cn2C(CC#N)C1CC1] | 4-(1-(2-cyano-1-cyclopropylethyl)-5-(3,5-dimethylisoxazol-4-yl)-1H-pyrrolo[2,3-b]pyridin-3-yl)-3-(trifluoromethoxy)benzoic acid | 511.1 |

TABLE 1-continued
| P# | Structure | Name | (MH)+ |
|---|---|---|---|
| P-0200 | 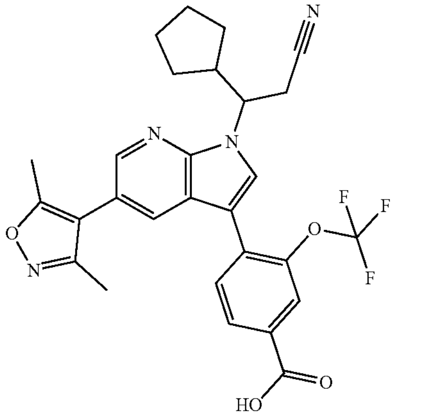 [SMILES: Cc1noc(C)c1-c1cnc2c(c1)c(-c1ccc(C(=O)O)cc1OC(F)(F)F)cn2C(CC#N)C1CCCC1] | 4-(1-(2-cyano-1-cyclopentylethyl)-5-(3,5-dimethylisoxazol-4-yl)-1H-pyrrolo[2,3-b]pyridin-3-yl)-3-(trifluoromethoxy)benzoic acid | 539.1 |
| P-0201 | 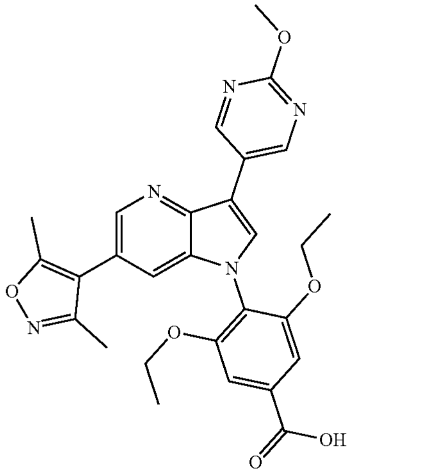 [SMILES: CCOc1cc(C(=O)O)cc(OCC)c1-n1cc(-c2cnc(OC)nc2)c2ncc(-c3c(C)noc3C)cc21] | 4-(6-(3,5-dimethylisoxazol-4-yl)-3-(2-methoxypyrimidin-5-yl)-1H-pyrrolo[3,2-b]pyridin-1-yl)-3,5-diethoxybenzoic acid | 530.2 |
| P-0202 | 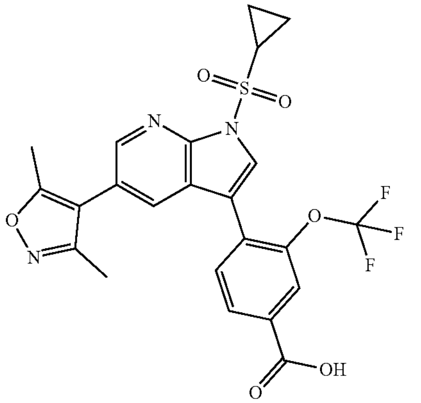 [SMILES: Cc1noc(C)c1-c1cnc2c(c1)c(-c1ccc(C(=O)O)cc1OC(F)(F)F)cn2S(=O)(=O)C1CC1] | 4-(1-(cyclopropylsulfonyl)-5-(3,5-dimethylisoxazol-4-yl)-1H-pyrrolo[2,3-b]pyridin-3-yl)-3-(trifluoromethoxy)benzoic acid | 522.0 |

TABLE 1-continued

| P# | Structure | Name | (MH)+ |
|---|---|---|---|
| P-0203 | 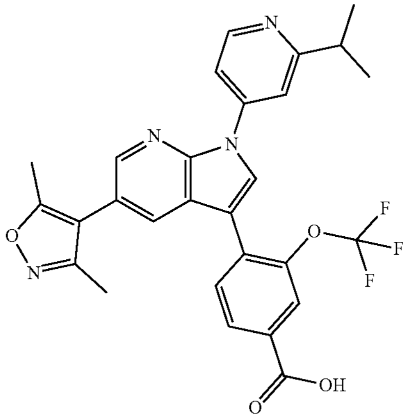 [SMILES: Cc1noc(C)c1-c1cnc2c(c1)c(-c1ccc(C(=O)O)cc1OC(F)(F)F)cn2-c1ccnc(C(C)C)c1] | 4-(5-(3,5-dimethylisoxazol-4-yl)-1-(2-isopropylpyridin-4-yl)-1H-pyrrolo[2,3-b]pyridin-3-yl)-3-(trifluoromethoxy)benzoic acid | 537.5 |
| P-0204 | 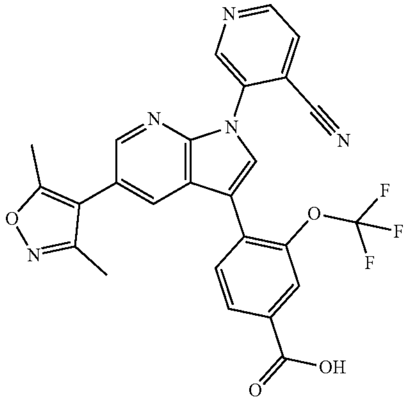 [SMILES: Cc1noc(C)c1-c1cnc2c(c1)c(-c1ccc(C(=O)O)cc1OC(F)(F)F)cn2-c1cnccc1C#N] | 4-(1-(4-cyanopyridin-3-yl)-5-(3,5-dimethylisoxazol-4-yl)-1H-pyrrolo[2,3-b]pyridin-3-yl)-3-(trifluoromethoxy)benzoic acid | 520.1 |
| P-0205 | 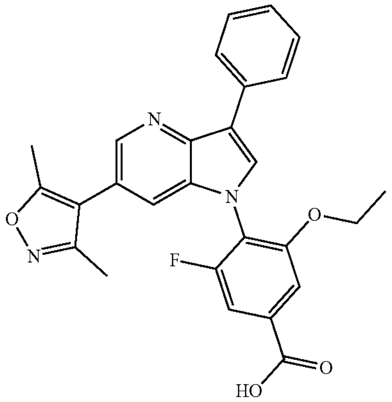 [SMILES: CCOc1cc(C(=O)O)cc(F)c1-n1cc(-c2ccccc2)c2ncc(-c3c(C)noc3C)cc21] | 4-(6-(3,5-dimethylisoxazol-4-yl)-3-phenyl-1H-pyrrolo[3,2-b]pyridin-1-yl)-3-ethoxy-5-fluorobenzoic acid | 472.1 |
| P-0206 | 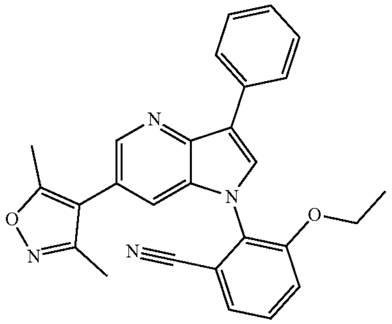 [SMILES: CCOc1cccc(C#N)c1-n1cc(-c2ccccc2)c2ncc(-c3c(C)noc3C)cc21] | 2-(6-(3,5-dimethylisoxazol-4-yl)-3-phenyl-1H-pyrrolo[3,2-b]pyridin-1-yl)-3-ethoxybenzonitrile | 435.1 |

TABLE 1-continued

| P# | Structure | Name | (MH)+ |
|---|---|---|---|
| P-0207 | 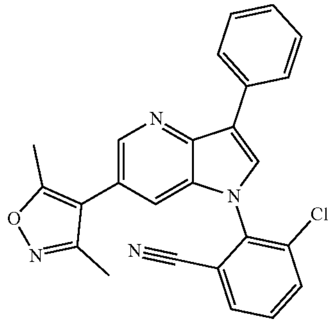 [SMILES: Cc1noc(C)c1-c1cnc2c(-c3ccccc3)cn(-c3c(Cl)cccc3C#N)c2c1] | 3-chloro-2-(6-(3,5-dimethylisoxazol-4-yl)-3-phenyl-1H-pyrrolo[3,2-b]pyridin-1-yl)benzonitrile | 425.0 |
| P-0208 | 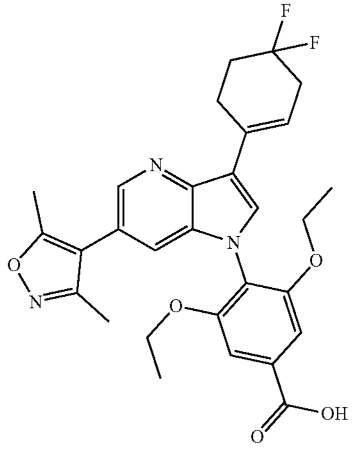 [SMILES: CCOc1cc(C(=O)O)cc(OCC)c1-n1cc(C2=CCC(F)(F)CC2)c2ncc(-c3c(C)noc3C)cc21] | 4-(3-(4,4-difluorocyclohex-1-en-1-yl)-6-(3,5-dimethylisoxazol-4-yl)-1H-pyrrolo[3,2-b]pyridin-1-yl)-3,5-diethoxybenzoic acid | 538.6 |
| P-0209 | 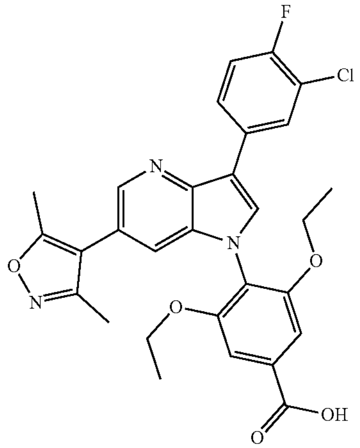 [SMILES: CCOc1cc(C(=O)O)cc(OCC)c1-n1cc(-c2ccc(F)c(Cl)c2)c2ncc(-c3c(C)noc3C)cc21] | 4-(3-(3-chloro-4-fluorophenyl)-6-(3,5-dimethylisoxazol-4-yl)-1H-pyrrolo[3,2-b]pyridin-1-yl)-3,5-diethoxybenzoic acid | 550.1 |
| P-0210 | 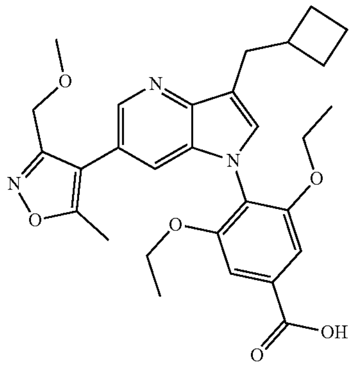 [SMILES: CCOc1cc(C(=O)O)cc(OCC)c1-n1cc(CC2CCC2)c2ncc(-c3c(COC)noc3C)cc21] | 4-(3-(cyclobutylmethyl)-6-(3-(methoxymethyl)-5-methylisoxazol-4-yl)-1H-pyrrolo[3,2-b]pyridin-1-yl)-3,5-diethoxybenzoic acid | 520.1 |

TABLE 1-continued
| P# | Structure | Name | (MH)+ |
|---|---|---|---|
| P-0211 | 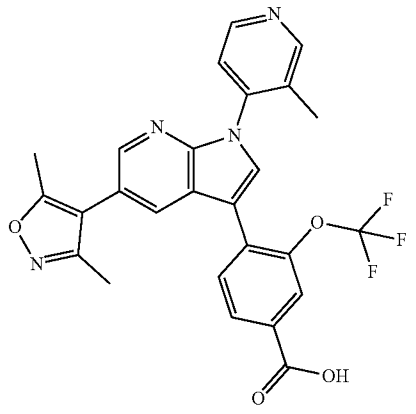 [SMILES: Cc1cnccc1-n1cc(-c2ccc(C(=O)O)cc2OC(F)(F)F)c2cc(-c3c(C)noc3C)cnc21] | 4-(5-(3,5-dimethylisoxazol-4-yl)-1-(3-methylpyridin-4-yl)-1H-pyrrolo[2,3-b]pyridin-3-yl)-3-(trifluoromethoxy)benzoic acid | 509.1 |
| P-0212 | 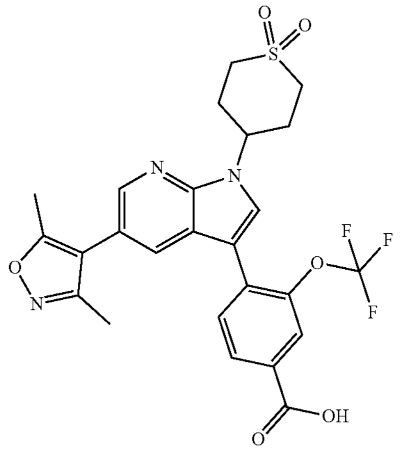 [SMILES: Cc1noc(C)c1-c1cnc2c(c1)c(-c1ccc(C(=O)O)cc1OC(F)(F)F)cn2C1CCS(=O)(=O)CC1] | 4-(5-(3,5-dimethylisoxazol-4-yl)-1-(1,1-dioxidotetrahydro-2H-thiopyran-4-yl)-1H-pyrrolo[2,3-b]pyridin-3-yl)-3-(trifluoromethoxy)benzoic acid | 550.1 |
| P-0213 | 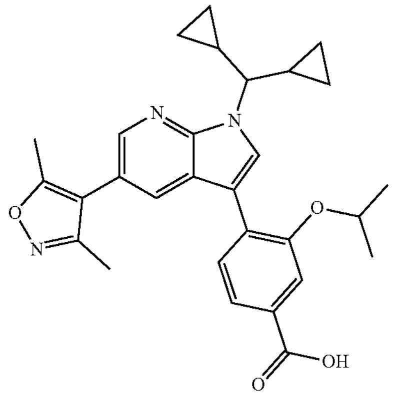 [SMILES: Cc1noc(C)c1-c1cnc2c(c1)c(-c1ccc(C(=O)O)cc1OC(C)C)cn2C(C1CC1)C1CC1] | 4-(1-(dicyclopropylmethyl)-5-(3,5-dimethylisoxazol-4-yl)-1H-pyrrolo[2,3-b]pyridin-3-yl)-3-isopropoxybenzoic acid | 486.2 |

TABLE 1-continued
| P# | Structure | Name | (MH)+ |
|---|---|---|---|
| P-0214 | 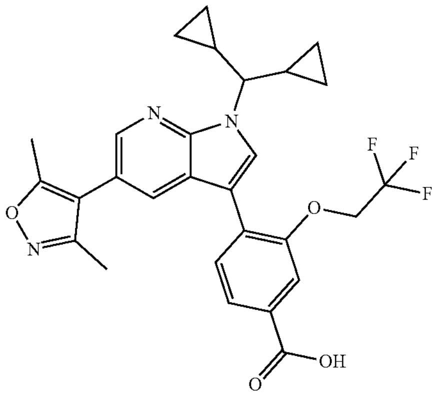 [SMILES: Cc1noc(C)c1-c1cnc2c(c1)c(-c1ccc(C(=O)O)cc1OCC(F)(F)F)cn2C(C1CC1)C1CC1] | 4-(1-(dicyclopropylmethyl)-5-(3,5-dimethylisoxazol-4-yl)-1H-pyrrolo[2,3-b]pyridin-3-yl)-3-(2,2,2-trifluoroethoxy)benzoic acid | 526.1 |
| P-0215 | 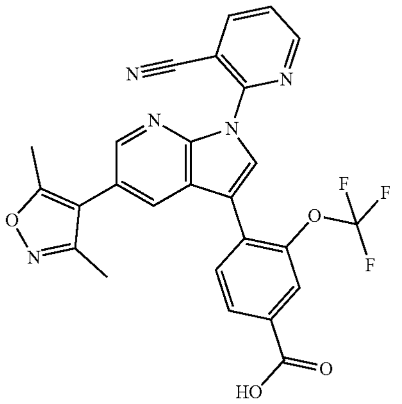 [SMILES: Cc1noc(C)c1-c1cnc2c(c1)c(-c1ccc(C(=O)O)cc1OC(F)(F)F)cn2-c1ncccc1C#N] | 4-(1-(3-cyanopyridin-2-yl)-5-(3,5-dimethylisoxazol-4-yl)-1H-pyrrolo[2,3-b]pyridin-3-yl)-3-(trifluoromethoxy)benzoic acid | 520.1 |
| P-0216 | 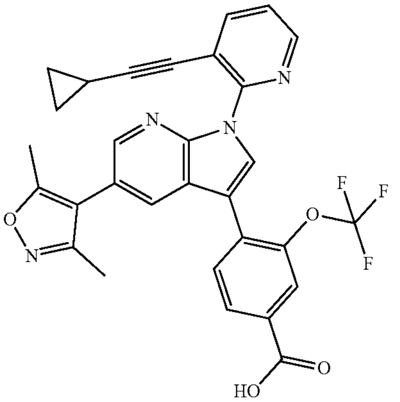 [SMILES: Cc1noc(C)c1-c1cnc2c(c1)c(-c1ccc(C(=O)O)cc1OC(F)(F)F)cn2-c1ncccc1C#CC1CC1] | 4-(1-(3-(cyclopropylethynyl)pyridin-2-yl)-5-(3,5-dimethylisoxazol-4-yl)-1H-pyrrolo[2,3-b]pyridin-3-yl)-3-(trifluoromethoxy)benzoic acid | 559.1 |

TABLE 1-continued
| P# | Structure | Name | (MH)+ |
|---|---|---|---|
| P-0217 | 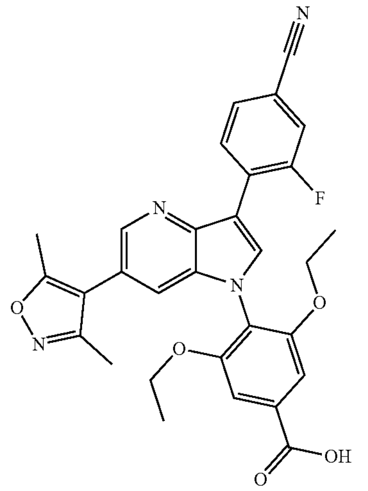 [SMILES: CCOc1cc(C(=O)O)cc(OCC)c1-n1cc(-c2ccc(C#N)cc2F)c2ncc(-c3c(C)noc3C)cc21] | 4-(3-(4-cyano-2-fluorophenyl)-6-(3,5-dimethylisoxazol-4-yl)-1H-pyrrolo[3,2-b]pyridin-1-yl)-3,5-diethoxybenzoic acid | 541.2 |
| P-0218 | 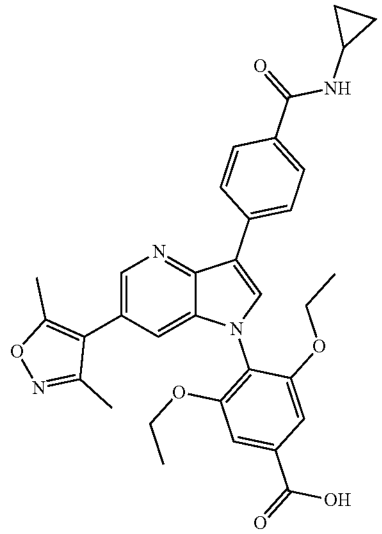 [SMILES: CCOc1cc(C(=O)O)cc(OCC)c1-n1cc(-c2ccc(C(=O)NC3CC3)cc2)c2ncc(-c3c(C)noc3C)cc21] | 4-(3-(4-(cyclopropylcarbamoyl)phenyl)-6-(3,5-dimethylisoxazol-4-yl)-1H-pyrrolo[3,2-b]pyridin-1-yl)-3,5-diethoxybenzoic acid | 581.2 |
| P-0219 | 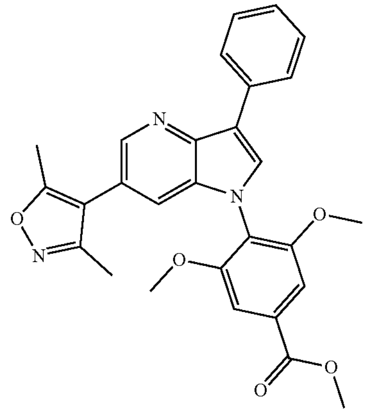 [SMILES: COC(=O)c1cc(OC)c(-n2cc(-c3ccccc3)c3ncc(-c4c(C)noc4C)cc32)c(OC)c1] | methyl 4-(6-(3,5-dimethylisoxazol-4-yl)-3-phenyl-1H-pyrrolo[3,2-b]pyridin-1-yl)-3,5-dimethoxybenzoate | 484.1 |

TABLE 1-continued
| P# | Structure | Name | (MH)+ |
| --- | --- | --- | --- |
| P-0220 | 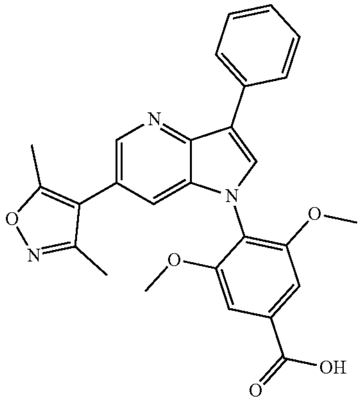 [SMILES: COc1cc(C(=O)O)cc(OC)c1-n1cc(-c2ccccc2)c2ncc(-c3c(C)noc3C)cc21] | 4-(6-(3,5-dimethylisoxazol-4-yl)-3-phenyl-1H-pyrrolo[3,2-b]pyridin-1-yl)-3,5-dimethoxybenzoic acid | 470.1 |
| P-0221 | 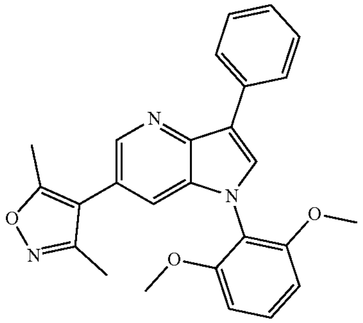 [SMILES: COc1cccc(OC)c1-n1cc(-c2ccccc2)c2ncc(-c3c(C)noc3C)cc21] | 4-(1-(2,6-dimethoxyphenyl)-3-phenyl-1H-pyrrolo[3,2-b]pyridin-6-yl)-3,5-dimethylisoxazole | 426.6 |
| P-0222 | 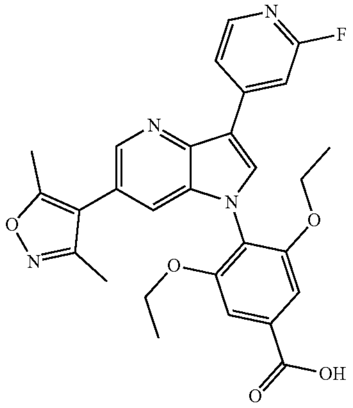 [SMILES: CCOc1cc(C(=O)O)cc(OCC)c1-n1cc(-c2ccnc(F)c2)c2ncc(-c3c(C)noc3C)cc21] | 4-(6-(3,5-dimethylisoxazol-4-yl)-3-(2-fluoropyridin-4-yl)-1H-pyrrolo[3,2-b]pyridin-1-yl)-3,5-diethoxybenzoic acid | 517.1 |
| P-0223 | 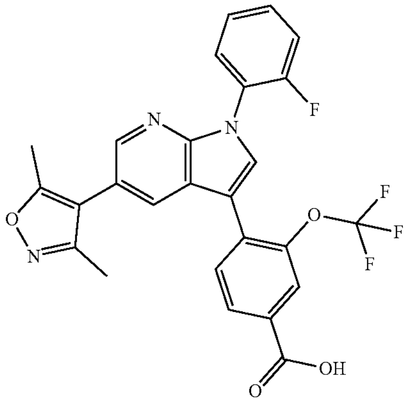 [SMILES: Cc1noc(C)c1-c1cnc2c(c1)c(-c1ccc(C(=O)O)cc1OC(F)(F)F)cn2-c1ccccc1F] | 4-(5-(3,5-dimethylisoxazol-4-yl)-1-(2-fluorophenyl)-1H-pyrrolo[2,3-b]pyridin-3-yl)-3-(trifluoromethoxy)benzoic acid | 512.1 |

TABLE 1-continued

| P# | Structure | Name | (MH)+ |
|---|---|---|---|
| P-0224 | 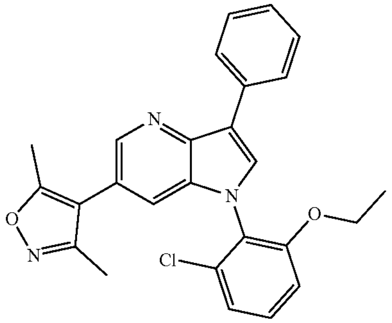 [SMILES: CCOc1cccc(Cl)c1-n1cc(-c2ccccc2)c2ncc(-c3c(C)noc3C)cc21] | 4-(1-(2-chloro-6-ethoxyphenyl)-3-phenyl-1H-pyrrolo[3,2-b]pyridin-6-yl)-3,5-dimethylisoxazole | 444.0 |
| P-0225 | 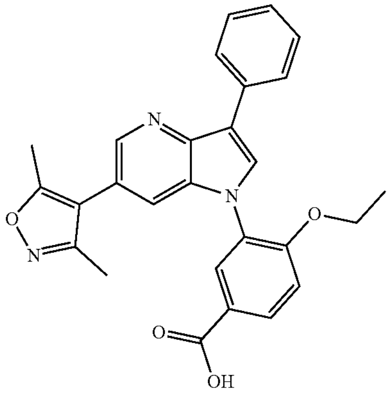 [SMILES: CCOc1ccc(C(=O)O)cc1-n1cc(-c2ccccc2)c2ncc(-c3c(C)noc3C)cc21] | 3-(6-(3,5-dimethylisoxazol-4-yl)-3-phenyl-1H-pyrrolo[3,2-b]pyridin-1-yl)-4-ethoxybenzoic acid | 454.1 |
| P-0226 | 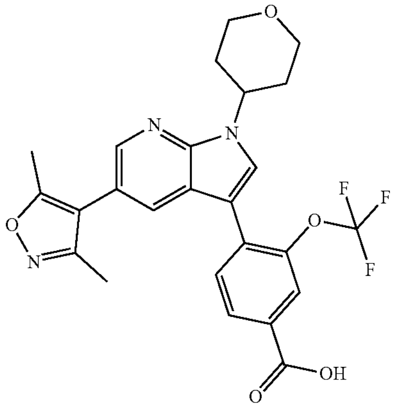 [SMILES: Cc1noc(C)c1-c1cnc2c(c1)c(-c1ccc(C(=O)O)cc1OC(F)(F)F)cn2C1CCOCC1] | 4-(5-(3,5-dimethylisoxazol-4-yl)-1-(tetrahydro-2H-pyran-4-yl)-1H-pyrrolo[2,3-b]pyridin-3-yl)-3-(trifluoromethoxy)benzoic acid | 502.1 |
| P-0227 | 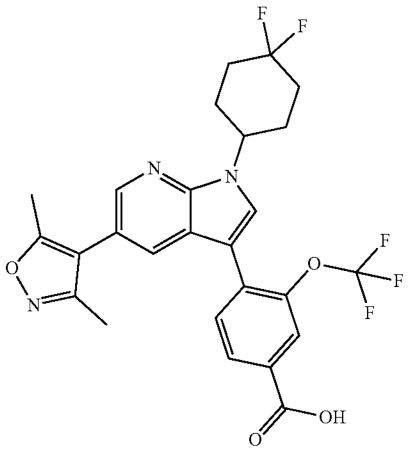 [SMILES: Cc1noc(C)c1-c1cnc2c(c1)c(-c1ccc(C(=O)O)cc1OC(F)(F)F)cn2C1CCC(F)(F)CC1] | 4-(1-(4,4-difluorocyclohexyl)-5-(3,5-dimethylisoxazol-4-yl)-1H-pyrrolo[2,3-b]pyridin-3-yl)-3-(trifluoromethoxy)benzoic acid | 536.1 |

TABLE 1-continued
| P# | Structure | Name | (MH)+ |
|---|---|---|---|
| P-0228 | 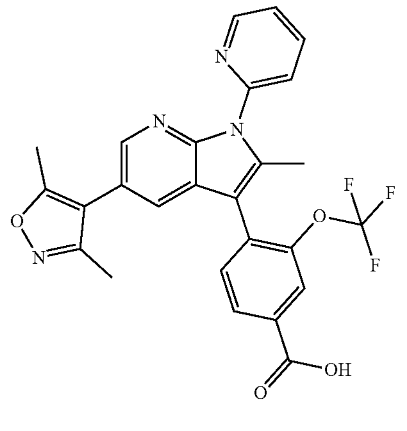 [SMILES: Cc1noc(C)c1-c1cnc2c(c1)c(-c1ccc(C(=O)O)cc1OC(F)(F)F)c(C)n2-c1ccccn1] | 4-(5-(3,5-dimethylisoxazol-4-yl)-2-methyl-1-(pyridin-2-yl)-1H-pyrrolo[2,3-b]pyridin-3-yl)-3-(trifluoromethoxy)benzoic acid | 509.1 |
| P-0229 | 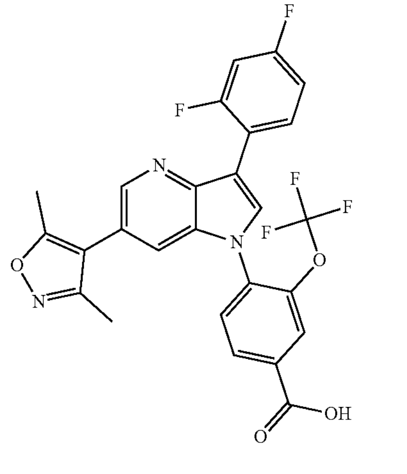 [SMILES: Cc1noc(C)c1-c1cnc2c(-c3ccc(F)cc3F)cn(-c3ccc(C(=O)O)cc3OC(F)(F)F)c2c1] | 4-(3-(2,4-difluorophenyl)-6-(3,5-dimethylisoxazol-4-yl)-1H-pyrrolo[3,2-b]pyridin-1-yl)-3-(trifluoromethoxy)benzoic acid | 530.1 |
| P-0230 | 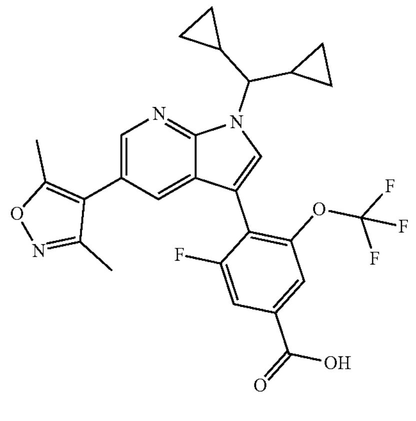 [SMILES: Cc1noc(C)c1-c1cnc2c(c1)c(-c1c(F)cc(C(=O)O)cc1OC(F)(F)F)cn2C(C1CC1)C1CC1] | 4-(1-(dicyclopropylmethyl)-5-(3,5-dimethylisoxazol-4-yl)-1H-pyrrolo[2,3-b]pyridin-3-yl)-3-fluoro-5-(trifluoromethoxy)benzoic acid | 530.1 |

TABLE 1-continued
| P# | Structure | Name | (MH)+ |
|---|---|---|---|
| P-0231 | 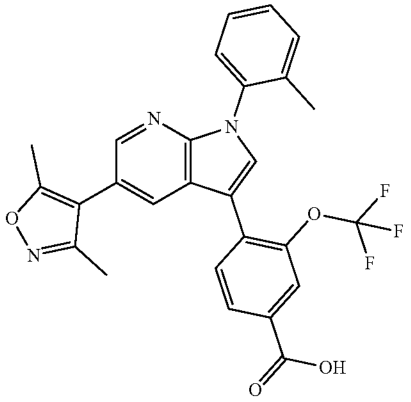 [SMILES: Cc1ccccc1-n1cc(-c2ccc(C(=O)O)cc2OC(F)(F)F)c2cc(-c3c(C)noc3C)cnc21] | 4-(5-(3,5-dimethylisoxazol-4-yl)-1-(o-tolyl)-1H-pyrrolo[2,3-b]pyridin-3-yl)-3-(trifluoromethoxy)benzoic acid | 508.1 |
| P-0232 | 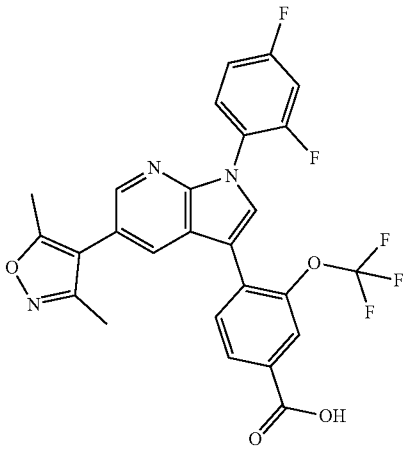 [SMILES: Cc1noc(C)c1-c1cnc2c(c1)c(-c1ccc(C(=O)O)cc1OC(F)(F)F)cn2-c1ccc(F)cc1F] | 4-(1-(2,4-difluorophenyl)-5-(3,5-dimethylisoxazol-4-yl)-1H-pyrrolo[2,3-b]pyridin-3-yl)-3-(trifluoromethoxy)benzoic acid | 530.1 |
| P-0233 | 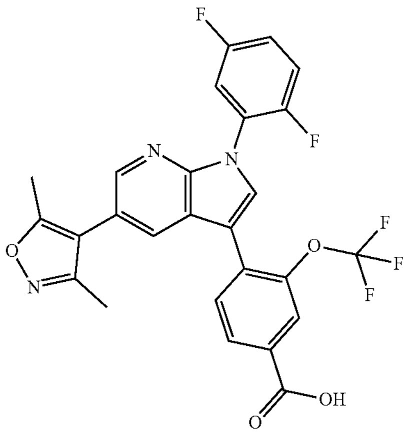 [SMILES: Cc1noc(C)c1-c1cnc2c(c1)c(-c1ccc(C(=O)O)cc1OC(F)(F)F)cn2-c1cc(F)ccc1F] | 4-(1-(2,5-difluorophenyl)-5-(3,5-dimethylisoxazol-4-yl)-1H-pyrrolo[2,3-b]pyridin-3-yl)-3-(trifluoromethoxy)benzoic acid | 530.0 |

TABLE 1-continued

| P# | Structure | Name | (MH)+ |
|---|---|---|---|
| P-0234 | 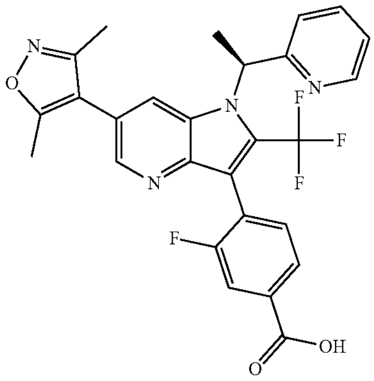 [SMILES: Cc1noc(C)c1-c1cnc2c(-c3ccc(C(=O)O)cc3F)c(C(F)(F)F)n([C@@H](C)c3ccccn3)c2c1] | (S)-4-(6-(3,5-dimethylisoxazol-4-yl)-1-(1-(pyridin-2-yl)ethyl)-2-(trifluoromethyl)-1H-pyrrolo[3,2-b]pyridin-3-yl)-3-fluorobenzoic acid | 525.4 |
| P-0235 | 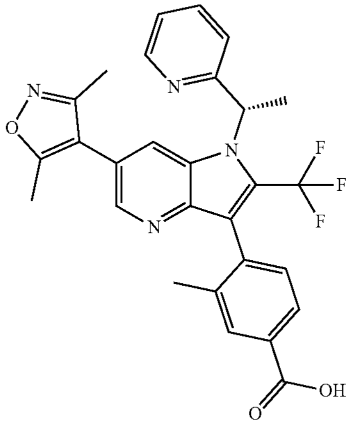 [SMILES: Cc1cc(C(=O)O)ccc1-c1c(C(F)(F)F)n([C@@H](C)c2ccccn2)c2cc(-c3c(C)noc3C)cnc12] | (S)-4-(6-(3,5-dimethylisoxazol-4-yl)-1-(1-(pyridin-2-yl)ethyl)-2-(trifluoromethyl)-1H-pyrrolo[3,2-b]pyridin-3-yl)-3-methylbenzoic acid | 521.2 |
| P-0236 | 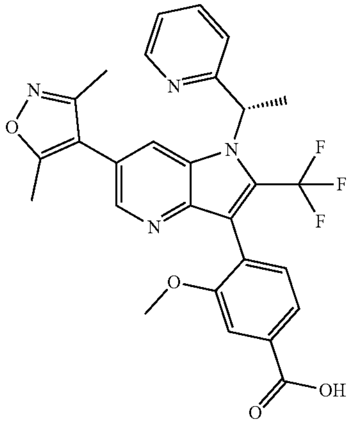 [SMILES: COc1cc(C(=O)O)ccc1-c1c(C(F)(F)F)n([C@@H](C)c2ccccn2)c2cc(-c3c(C)noc3C)cnc12] | (S)-4-(6-(3,5-dimethylisoxazol-4-yl)-1-(1-(pyridin-2-yl)ethyl)-2-(trifluoromethyl)-1H-pyrrolo[3,2-b]pyridin-3-yl)-3-methoxybenzoic acid | 537.4 |
| P-0237 | 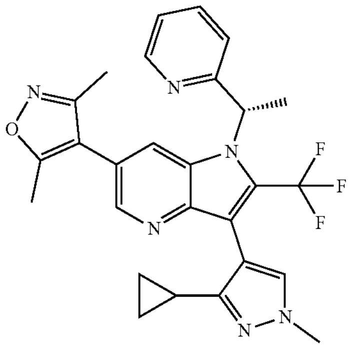 [SMILES: Cc1noc(C)c1-c1cnc2c(-c3cn(C)nc3C3CC3)c(C(F)(F)F)n([C@@H](C)c3ccccn3)c2c1] | (S)-4-(3-(3-cyclopropyl-1-methyl-1H-pyrazol-4-yl)-1-(1-(pyridin-2-yl)ethyl)-2-(trifluoromethyl)-1H-pyrrolo[3,2-b]pyridin-6-yl)-3,5-dimethylisoxazole | 507.1 |

TABLE 1-continued

| P# | Structure | Name | (MH)+ |
|---|---|---|---|
| P-0238 | 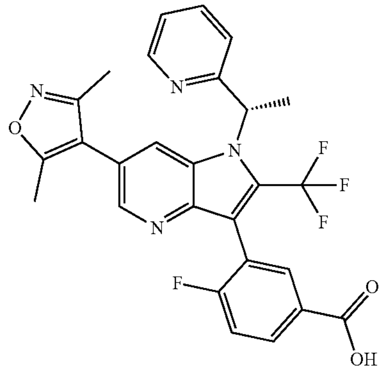 [SMILES: Cc1noc(C)c1-c1cnc2c(-c3cc(C(=O)O)ccc3F)c(C(F)(F)F)n([C@@H](C)c3ccccn3)c2c1] | (S)-3-(6-(3,5-dimethylisoxazol-4-yl)-1-(1-(pyridin-2-yl)ethyl)-2-(trifluoromethyl)-1H-pyrrolo[3,2-b]pyridin-3-yl)-4-fluorobenzoic acid | 525.4 |
| P-0239 | 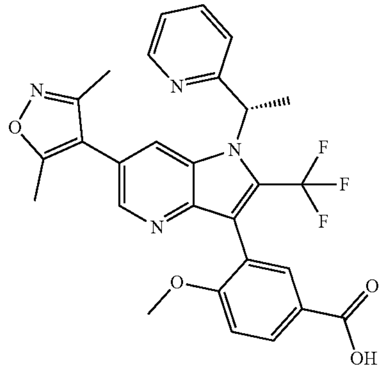 [SMILES: COc1ccc(C(=O)O)cc1-c1c(C(F)(F)F)n([C@@H](C)c2ccccn2)c2cc(-c3c(C)noc3C)cnc12] | (S)-3-(6-(3,5-dimethylisoxazol-4-yl)-1-(1-(pyridin-2-yl)ethyl)-2-(trifluoromethyl)-1H-pyrrolo[3,2-b]pyridin-3-yl)-4-methoxybenzoic acid | 537.4 |
| P-0240 | 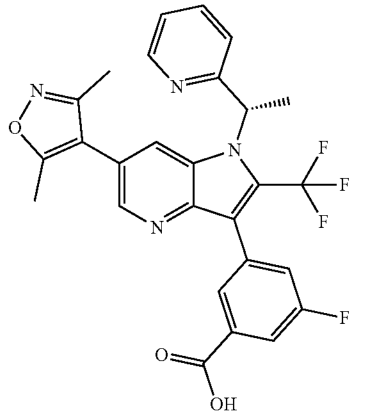 [SMILES: Cc1noc(C)c1-c1cnc2c(-c3cc(F)cc(C(=O)O)c3)c(C(F)(F)F)n([C@@H](C)c3ccccn3)c2c1] | (S)-3-(6-(3,5-dimethylisoxazol-4-yl)-1-(1-(pyridin-2-yl)ethyl)-2-(trifluoromethyl)-1H-pyrrolo[3,2-b]pyridin-3-yl)-5-fluorobenzoic acid | 525.4 |
| P-0241 | 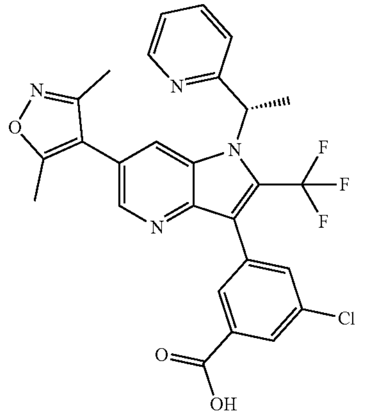 [SMILES: Cc1noc(C)c1-c1cnc2c(-c3cc(Cl)cc(C(=O)O)c3)c(C(F)(F)F)n([C@@H](C)c3ccccn3)c2c1] | (S)-3-chloro-5-(6-(3,5-dimethylisoxazol-4-yl)-1-(1-(pyridin-2-yl)ethyl)-2-(trifluoromethyl)-1H-pyrrolo[3,2-b]pyridin-3-yl)benzoic acid | 541.3 |

TABLE 1-continued
| P# | Structure | Name | (MH)+ |
|---|---|---|---|
| P-0242 | 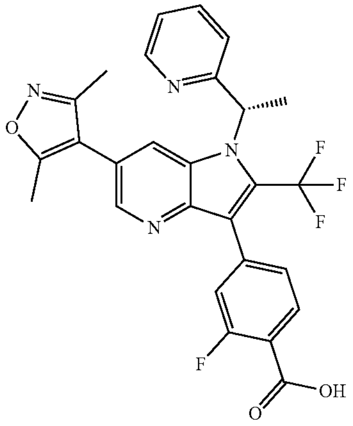 | (S)-4-(6-(3,5-dimethylisoxazol-4-yl)-1-(1-(pyridin-2-yl)ethyl)-2-(trifluoromethyl)-1H-pyrrolo[3,2-b]pyridin-3-yl)-2-fluorobenzoic acid | 521.2 |
| P-0243 | 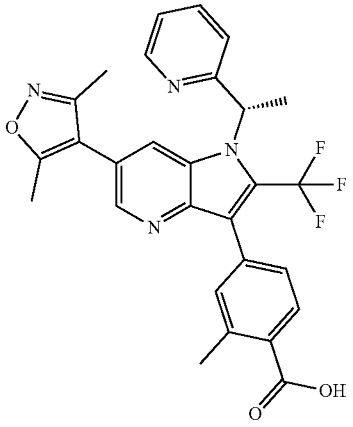 [SMILES: Cc1cc(-c2c(C(F)(F)F)n([C@@H](C)c3ccccn3)c3cc(-c4c(C)noc4C)cnc23)ccc1C(=O)O] | (S)-4-(6-(3,5-dimethylisoxazol-4-yl)-1-(1-(pyridin-2-yl)ethyl)-2-(trifluoromethyl)-1H-pyrrolo[3,2-b]pyridin-3-yl)-2-methylbenzoic acid | 521.2 |
| P-0244 | 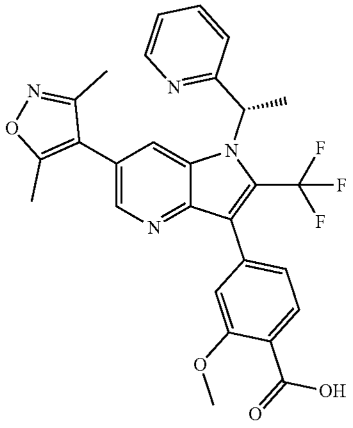 [SMILES: COc1cc(-c2c(C(F)(F)F)n([C@@H](C)c3ccccn3)c3cc(-c4c(C)noc4C)cnc23)ccc1C(=O)O] | (S)-4-(6-(3,5-dimethylisoxazol-4-yl)-1-(1-(pyridin-2-yl)ethyl)-2-(trifluoromethyl)-1H-pyrrolo[3,2-b]pyridin-3-yl)-2-methoxybenzoic acid | 537.4 |

TABLE 1-continued

| P# | Structure | Name | (MH)+ |
|---|---|---|---|
| P-0245 | 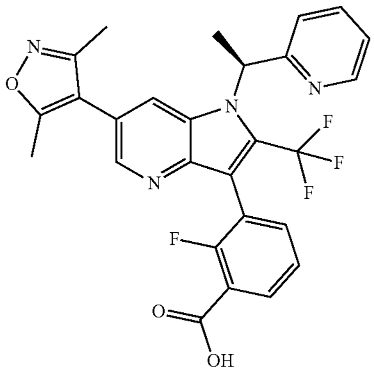 [SMILES: Cc1noc(C)c1-c1cnc2c(-c3cccc(C(=O)O)c3F)c(C(F)(F)F)n([C@@H](C)c3ccccn3)c2c1] | (S)-3-(6-(3,5-dimethylisoxazol-4-yl)-1-(1-(pyridin-2-yl)ethyl)-2-(trifluoromethyl)-1H-pyrrolo[3,2-b]pyridin-3-yl)-2-fluorobenzoic acid | 525.4 |
| P-0246 | 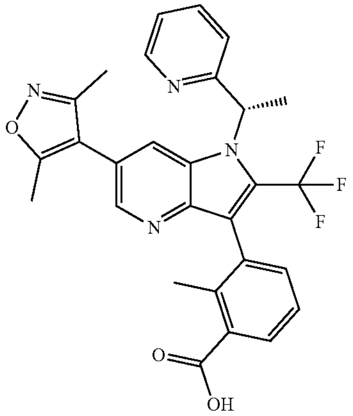 [SMILES: Cc1noc(C)c1-c1cnc2c(-c3cccc(C(=O)O)c3C)c(C(F)(F)F)n([C@@H](C)c3ccccn3)c2c1] | (S)-3-(6-(3,5-dimethylisoxazol-4-yl)-1-(1-(pyridin-2-yl)ethyl)-2-(trifluoromethyl)-1H-pyrrolo[3,2-b]pyridin-3-yl)-2-methylbenzoic acid | 521.2 |
| P-0247 | 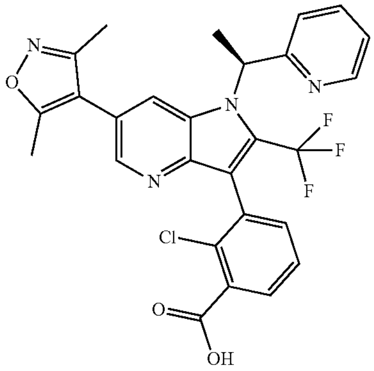 [SMILES: Cc1noc(C)c1-c1cnc2c(-c3cccc(C(=O)O)c3Cl)c(C(F)(F)F)n([C@@H](C)c3ccccn3)c2c1] | (S)-2-chloro-3-(6-(3,5-dimethylisoxazol-4-yl)-1-(1-(pyridin-2-yl)ethyl)-2-(trifluoromethyl)-1H-pyrrolo[3,2-b]pyridin-3-yl)benzoic acid | 541.3 |
| P-0248 | 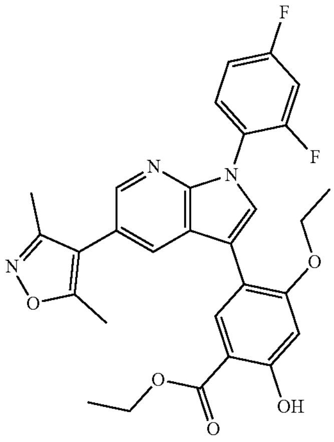 [SMILES: CCOC(=O)c1cc(-c2cn(-c3ccc(F)cc3F)c3ncc(-c4c(C)noc4C)cc23)c(OCC)cc1O] | ethyl 5-(1-(2,4-difluorophenyl)-5-(3,5-dimethylisoxazol-4-yl)-1H-pyrrolo[2,3-b]pyridin-3-yl)-4-ethoxy-2-hydroxybenzoate | 534.2 |

TABLE 1-continued
| P# | Structure | Name | (MH)+ |
|---|---|---|---|
| P-0249 | 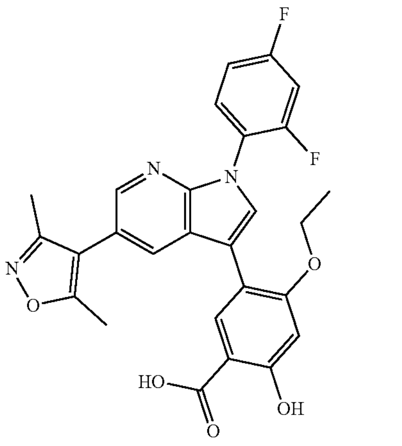 [SMILES: CCOc1cc(O)c(C(=O)O)cc1-c1cn(-c2ccc(F)cc2F)c2ncc(-c3c(C)noc3C)cc12] | 5-(1-(2,4-difluorophenyl)-5-(3,5-dimethylisoxazol-4-yl)-1H-pyrrolo[2,3-b]pyridin-3-yl)-4-ethoxy-2-hydroxybenzoic acid | 506.1 |
| P-0250 | 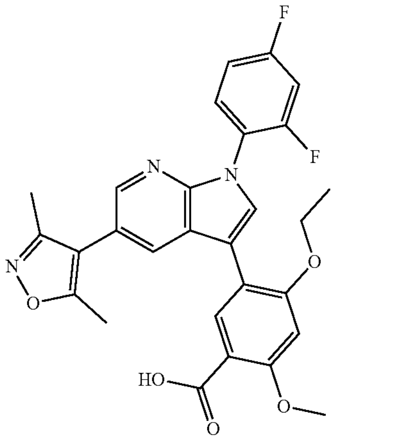 [SMILES: CCOc1cc(OC)c(C(=O)O)cc1-c1cn(-c2ccc(F)cc2F)c2ncc(-c3c(C)noc3C)cc12] | 5-(1-(2,4-difluorophenyl)-5-(3,5-dimethylisoxazol-4-yl)-1H-pyrrolo[2,3-b]pyridin-3-yl)-4-ethoxy-2-methoxybenzoic acid | 520.1 |
| P-0251 | 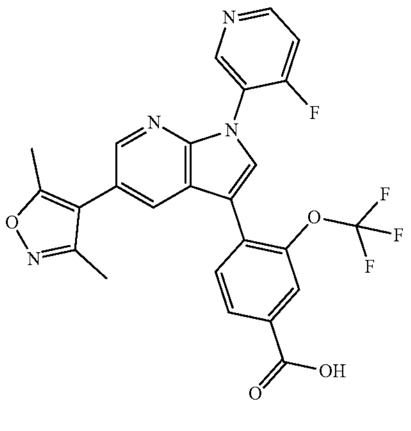 [SMILES: Cc1noc(C)c1-c1cnc2c(c1)c(-c1ccc(C(=O)O)cc1OC(F)(F)F)cn2-c1cnccc1F] | 4-(5-(3,5-dimethylisoxazol-4-yl)-1-(4-fluoropyridin-3-yl)-1H-pyrrolo[2,3-b]pyridin-3-yl)-3-(trifluoromethoxy)benzoic acid | 513.1 |

TABLE 1-continued
| P# | Structure | Name | (MH)+ |
|---|---|---|---|
| P-0252 | 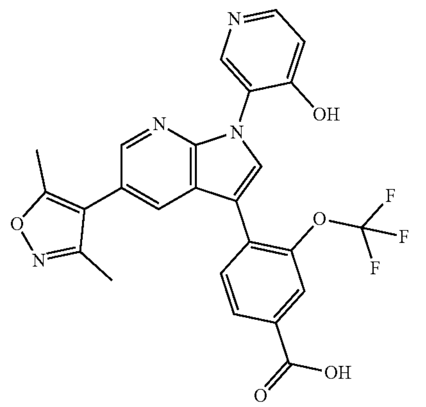 [SMILES: Cc1noc(C)c1-c1cnc2c(c1)c(-c1ccc(C(=O)O)cc1OC(F)(F)F)cn2-c1cnccc1O] | 4-(5-(3,5-dimethylisoxazol-4-yl)-1-(4-hydroxypyridin-3-yl)-1H-pyrrolo[2,3-b]pyridin-3-yl)-3-(trifluoromethoxy)benzoic acid | 511.1 |
| P-0253 | 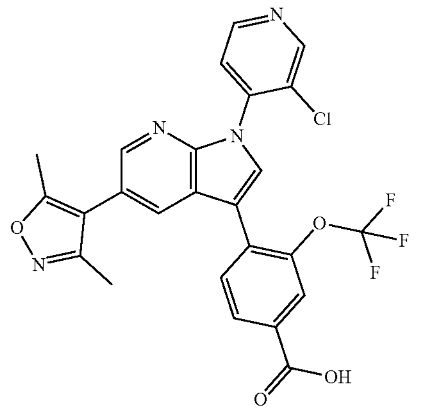 [SMILES: Cc1noc(C)c1-c1cnc2c(c1)c(-c1ccc(C(=O)O)cc1OC(F)(F)F)cn2-c1ccncc1Cl] | 4-(1-(3-chloropyridin-4-yl)-5-(3,5-dimethylisoxazol-4-yl)-1H-pyrrolo[2,3-b]pyridin-3-yl)-3-(trifluoromethoxy)benzoic acid | 529.0 |
| P-0254 | 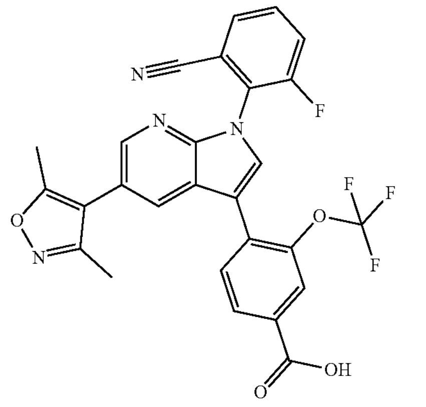 [SMILES: Cc1noc(C)c1-c1cnc2c(c1)c(-c1ccc(C(=O)O)cc1OC(F)(F)F)cn2-c1c(F)cccc1C#N] | 4-(1-(2-cyano-6-fluorophenyl)-5-(3,5-dimethylisoxazol-4-yl)-1H-pyrrolo[2,3-b]pyridin-3-yl)-3-(trifluoromethoxy)benzoic acid | 537.1 |

TABLE 1-continued
| P# | Structure | Name | (MH)+ |
|---|---|---|---|
| P-0255 | 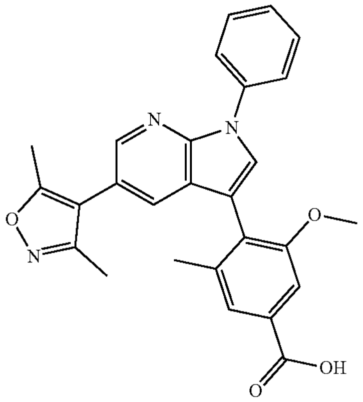 [SMILES: COc1cc(C(=O)O)cc(C)c1-c1cn(-c2ccccc2)c2ncc(-c3c(C)noc3C)cc12] | 4-(5-(3,5-dimethylisoxazol-4-yl)-1-phenyl-1H-pyrrolo[2,3-b]pyridin-3-yl)-3-methoxy-5-methylbenzoic acid | 454.1 |
| P-0256 | 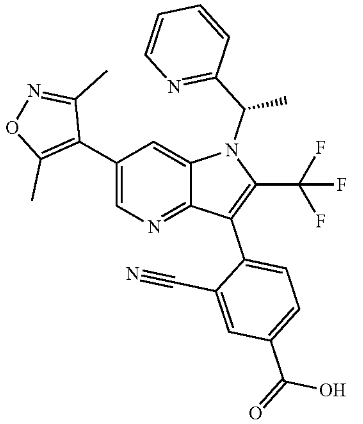 [SMILES: Cc1noc(C)c1-c1cnc2c(-c3ccc(C(=O)O)cc3C#N)c(C(F)(F)F)n([C@@H](C)c3ccccn3)c2c1] | (S)-3-cyano-4-(6-(3,5-dimethylisoxazol-4-yl)-1-(1-(pyridin-2-yl)ethyl)-2-(trifluoromethyl)-1H-pyrrolo[3,2-b]pyridin-3-yl)benzoic acid | 532.3 |
| P-0257 | 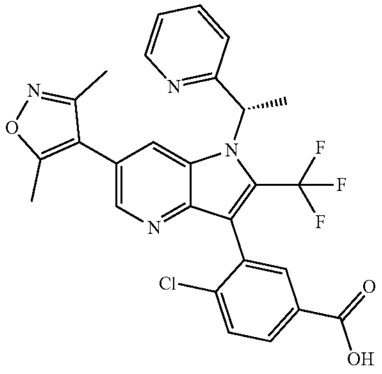 [SMILES: Cc1noc(C)c1-c1cnc2c(-c3cc(C(=O)O)ccc3Cl)c(C(F)(F)F)n([C@@H](C)c3ccccn3)c2c1] | (S)-4-chloro-3-(6-(3,5-dimethylisoxazol-4-yl)-1-(1-(pyridin-2-yl)ethyl)-2-(trifluoromethyl)-1H-pyrrolo[3,2-b]pyridin-3-yl)benzoic acid | 541.3 |

TABLE 1-continued
| P# | Structure | Name | (MH)+ |
|---|---|---|---|
| P-0258 | 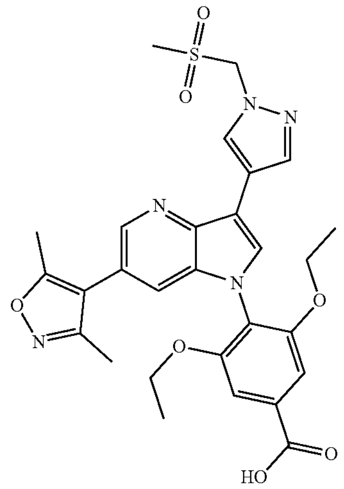 [SMILES: CCOc1cc(C(=O)O)cc(OCC)c1-n1cc(-c2cnn(CS(C)(=O)=O)c2)c2ncc(-c3c(C)noc3C)cc21] | 4-(6-(3,5-dimethylisoxazol-4-yl)-3-(1-((methylsulfonyl)methyl)-1H-pyrazol-4-yl)-1H-pyrrolo[3,2-b]pyridin-1-yl)-3,5-diethoxybenzoic acid | 580.3 |
| P-0259 | 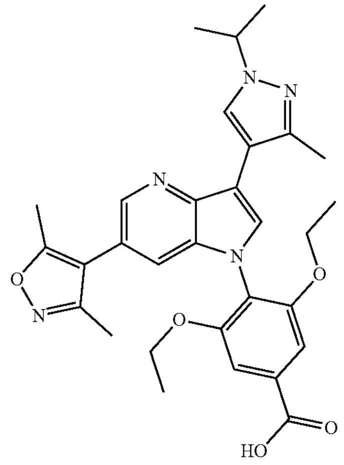 [SMILES: CCOc1cc(C(=O)O)cc(OCC)c1-n1cc(-c2cn(C(C)C)nc2C)c2ncc(-c3c(C)noc3C)cc21] | 4-(6-(3,5-dimethylisoxazol-4-yl)-3-(1-isopropyl-3-methyl-1H-pyrazol-4-yl)-1H-pyrrolo[3,2-b]pyridin-1-yl)-3,5-diethoxybenzoic acid | 544.3 |
| P-0260 | 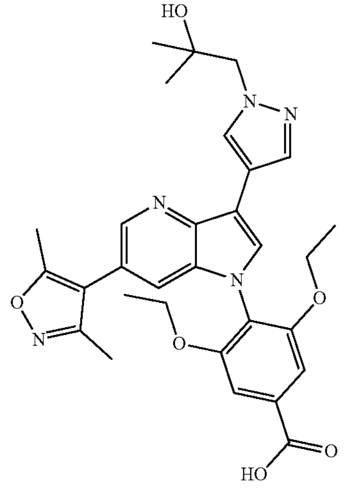 [SMILES: CCOc1cc(C(=O)O)cc(OCC)c1-n1cc(-c2cnn(CC(C)(C)O)c2)c2ncc(-c3c(C)noc3C)cc21] | 4-(6-(3,5-dimethylisoxazol-4-yl)-3-(1-(2-hydroxy-2-methylpropyl)-1H-pyrazol-4-yl)-1H-pyrrolo[3,2-b]pyridin-1-yl)-3,5-diethoxybenzoic acid | 560.2 |

TABLE 1-continued
| P# | Structure | Name | (MH)+ |
|---|---|---|---|
| P-0261 | 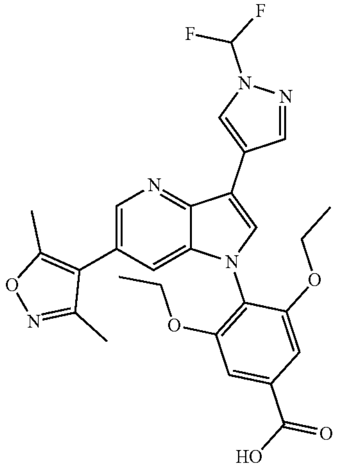 [SMILES: CCOc1cc(C(=O)O)cc(OCC)c1-n1cc(-c2cnn(C(F)F)c2)c2ncc(-c3c(C)noc3C)cc21] | 4-(3-(1-(difluoromethyl)-1H-pyrazol-4-yl)-6-(3,5-dimethylisoxazol-4-yl)-1H-pyrrolo[3,2-b]pyridin-1-yl)-3,5-diethoxybenzoic acid | 538.6 |
| P-0262 | 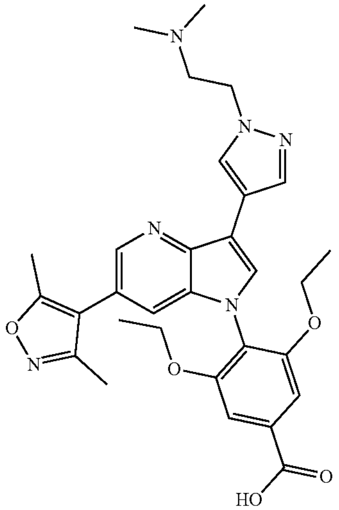 [SMILES: CCOc1cc(C(=O)O)cc(OCC)c1-n1cc(-c2cnn(CCN(C)C)c2)c2ncc(-c3c(C)noc3C)cc21] | 4-(3-(1-(2-(dimethylamino)ethyl)-1H-pyrazol-4-yl)-6-(3,5-dimethylisoxazol-4-yl)-1H-pyrrolo[3,2-b]pyridin-1-yl)-3,5-diethoxybenzoic acid | 559.3 |
| P-0263 | 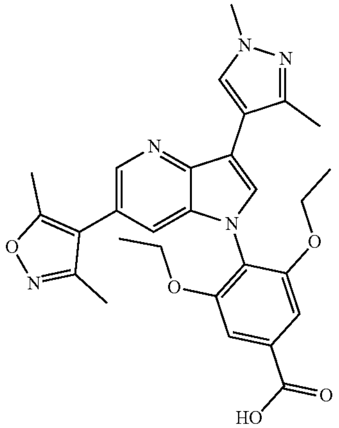 [SMILES: CCOc1cc(C(=O)O)cc(OCC)c1-n1cc(-c2cn(C)nc2C)c2ncc(-c3c(C)noc3C)cc21] | 4-(3-(1,3-dimethyl-1H-pyrazol-4-yl)-6-(3,5-dimethylisoxazol-4-yl)-1H-pyrrolo[3,2-b]pyridin-1-yl)-3,5-diethoxybenzoic acid | 516.4 |

TABLE 1-continued
| P# | Structure | Name | (MH)+ |
|---|---|---|---|
| P-0264 | 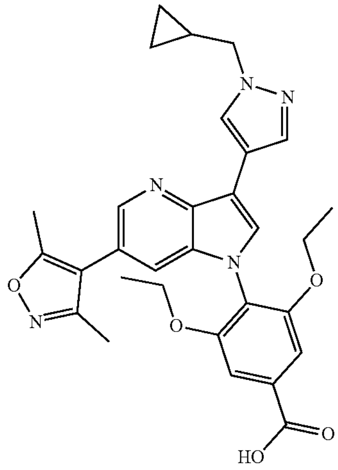 [SMILES: CCOc1cc(C(=O)O)cc(OCC)c1-n1cc(-c2cnn(CC3CC3)c2)c2ncc(-c3c(C)noc3C)cc21] | 4-(3-(1-(cyclopropylmethyl)-1H-pyrazol-4-yl)-6-(3,5-dimethylisoxazol-4-yl)-1H-pyrrolo[3,2-b]pyridin-1-yl)-3,5-diethoxybenzoic acid | 542.5 |
| P-0265 | 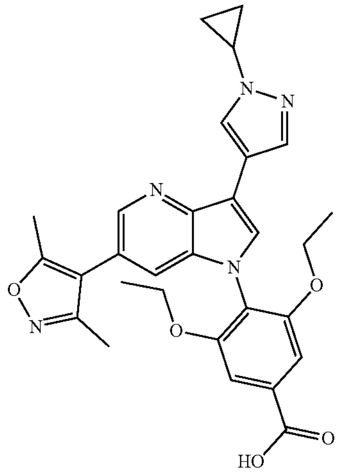 [SMILES: CCOc1cc(C(=O)O)cc(OCC)c1-n1cc(-c2cnn(C3CC3)c2)c2ncc(-c3c(C)noc3C)cc21] | 4-(3-(1-cyclopropyl-1H-pyrazol-4-yl)-6-(3,5-dimethylisoxazol-4-yl)-1H-pyrrolo[3,2-b]pyridin-1-yl)-3,5-diethoxybenzoic acid | 528.4 |
| P-0266 | 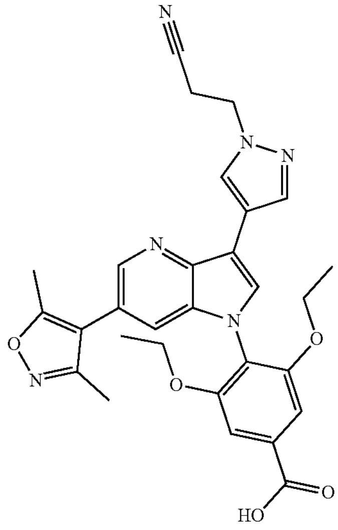 [SMILES: CCOc1cc(C(=O)O)cc(OCC)c1-n1cc(-c2cnn(CCC#N)c2)c2ncc(-c3c(C)noc3C)cc21] | 4-(3-(1-(2-cyanoethyl)-1H-pyrazol-4-yl)-6-(3,5-dimethylisoxazol-4-yl)-1H-pyrrolo[3,2-b]pyridin-1-yl)-3,5-diethoxybenzoic acid | 541.3 |

TABLE 1-continued
| P# | Structure | Name | (MH)+ |
|---|---|---|---|
| P-0267 | 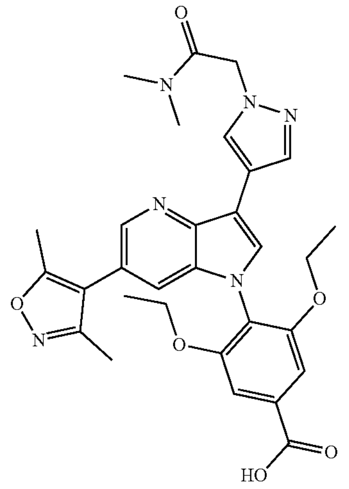 [SMILES: CCOc1cc(C(=O)O)cc(OCC)c1-n1cc(-c2cnn(CC(=O)N(C)C)c2)c2ncc(-c3c(C)noc3C)cc21] | 4-(3-(1-(2-(dimethylamino)-2-oxoethyl)-1H-pyrazol-4-yl)-6-(3,5-dimethylisoxazol-4-yl)-1H-pyrrolo[3,2-b]pyridin-1-yl)-3,5-diethoxybenzoic acid | 573.4 |
| P-0268 | 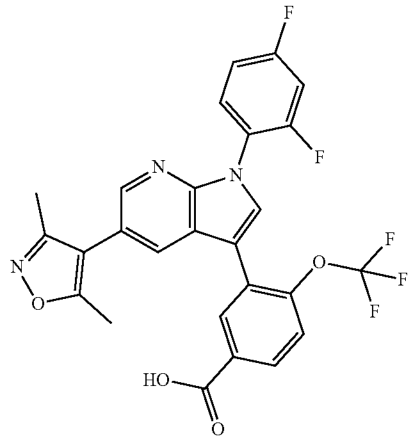 [SMILES: Cc1noc(C)c1-c1cnc2c(c1)c(-c1cc(C(=O)O)ccc1OC(F)(F)F)cn2-c1ccc(F)cc1F] | 3-(1-(2,4-difluorophenyl)-5-(3,5-dimethylisoxazol-4-yl)-1H-pyrrolo[2,3-b]pyridin-3-yl)-4-(trifluoromethoxy)benzoic acid | 530.1 |
| P-0269 | 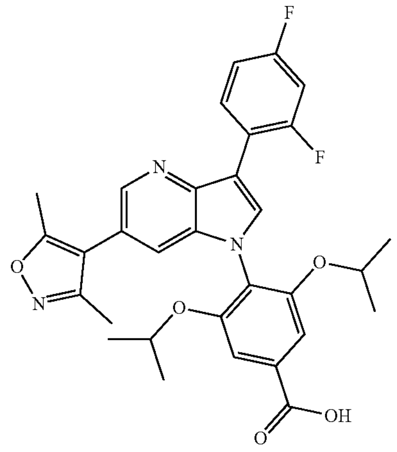 [SMILES: Cc1noc(C)c1-c1cnc2c(-c3ccc(F)cc3F)cn(-c3c(OC(C)C)cc(C(=O)O)cc3OC(C)C)c2c1] | 4-(3-(2,4-difluorophenyl)-6-(3,5-dimethylisoxazol-4-yl)-1H-pyrrolo[3,2-b]pyridin-1-yl)-3,5-diisopropoxybenzoic acid | 562.1 |

TABLE 1-continued
| P# | Structure | Name | (MH)+ |
|---|---|---|---|
| P-0270 | 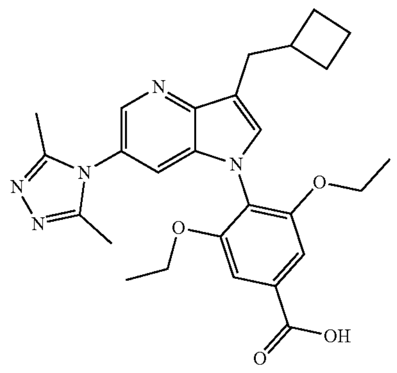 [SMILES: CCOc1cc(C(=O)O)cc(OCC)c1-n1cc(CC2CCC2)c2ncc(-n3c(C)nnc3C)cc21] | 4-(3-(cyclobutylmethyl)-6-(3,5-dimethyl-4H-1,2,4-triazol-4-yl)-1H-pyrrolo[3,2-b]pyridin-1-yl)-3,5-diethoxybenzoic acid | 490.1 |
| P-0271 | 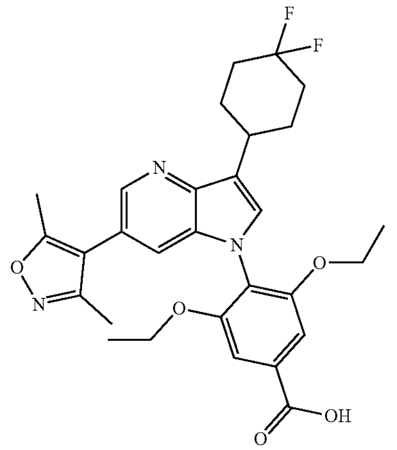 [SMILES: CCOc1cc(C(=O)O)cc(OCC)c1-n1cc(C2CCC(F)(F)CC2)c2ncc(-c3c(C)noc3C)cc21] | 4-(3-(4,4-difluorocyclohexyl)-6-(3,5-dimethylisoxazol-4-yl)-1H-pyrrolo[3,2-b]pyridin-1-yl)-3,5-diethoxybenzoic acid | 540.1 |
| P-0272 | 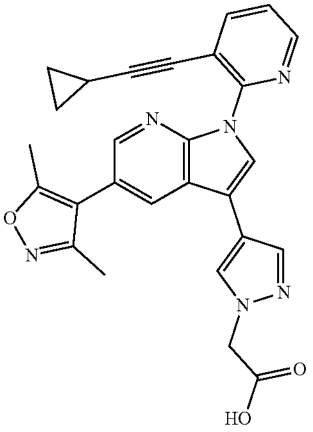 [SMILES: Cc1noc(C)c1-c1cnc2c(c1)c(-c1cnn(CC(=O)O)c1)cn2-c1ncccc1C#CC1CC1] | 2-(4-(1-(3-(cyclopropylethynyl)pyridin-2-yl)-5-(3,5-dimethylisoxazol-4-yl)-1H-pyrrolo[2,3-b]pyridin-3-yl)-1H-pyrazol-1-yl)acetic acid | 479.2 |

TABLE 1-continued
| P# | Structure | Name | (MH)+ |
|---|---|---|---|
| P-0273 | 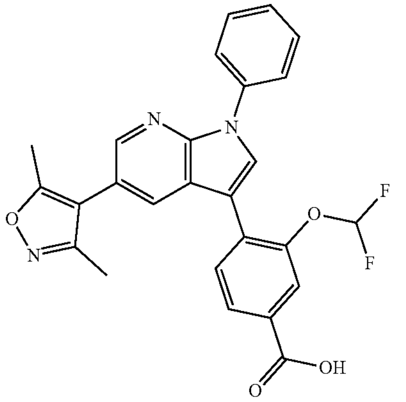 [SMILES: Cc1noc(C)c1-c1cnc2c(c1)c(-c1ccc(C(=O)O)cc1OC(F)F)cn2-c1ccccc1] | 3-(difluoromethoxy)-4-(5-(3,5-dimethylisoxazol-4-yl)-1-phenyl-1H-pyrrolo[2,3-b]pyridin-3-yl)benzoic acid | 476.1 |
| P-0274 | 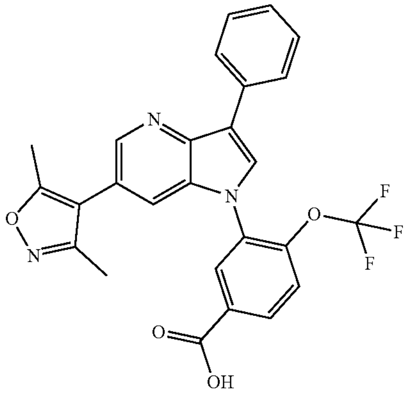 [SMILES: Cc1noc(C)c1-c1cnc2c(-c3ccccc3)cn(-c3cc(C(=O)O)ccc3OC(F)(F)F)c2c1] | 3-(6-(3,5-dimethylisoxazol-4-yl)-3-phenyl-1H-pyrrolo[3,2-b]pyridin-1-yl)-4-(trifluoromethoxy)benzoic acid | 494.0 |
| P-0275 | 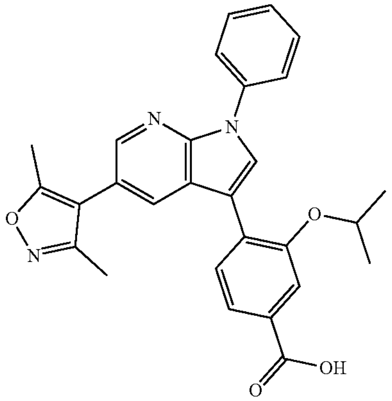 [SMILES: Cc1noc(C)c1-c1cnc2c(c1)c(-c1ccc(C(=O)O)cc1OC(C)C)cn2-c1ccccc1] | 4-(5-(3,5-dimethylisoxazol-4-yl)-1-phenyl-1H-pyrrolo[2,3-b]pyridin-3-yl)-3-isopropoxybenzoic acid | 468.1 |
| P-0276 | 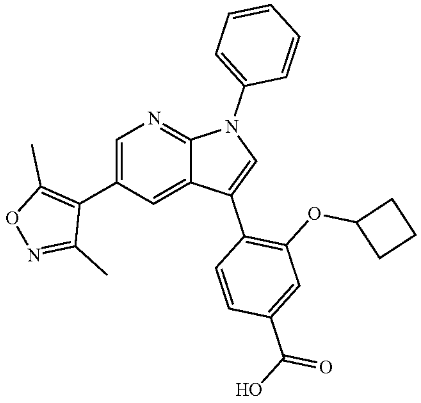 [SMILES: Cc1noc(C)c1-c1cnc2c(c1)c(-c1ccc(C(=O)O)cc1OC1CCC1)cn2-c1ccccc1] | 3-cyclobutoxy-4-(5-(3,5-dimethylisoxazol-4-yl)-1-phenyl-1H-pyrrolo[2,3-b]pyridin-3-yl)benzoic acid | 480.1 |

TABLE 1-continued
| P# | Structure | Name | (MH)+ |
|---|---|---|---|
| P-0277 | 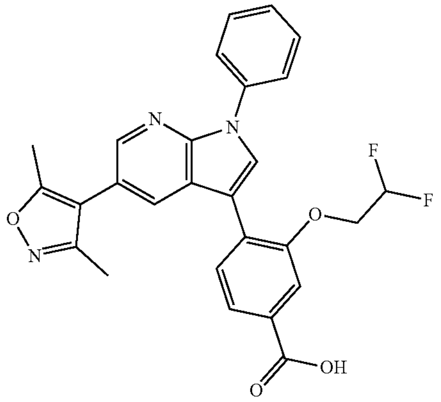 [SMILES: Cc1noc(C)c1-c1cnc2c(c1)c(-c1ccc(C(=O)O)cc1OCC(F)F)cn2-c1ccccc1] | 3-(2,2-difluoroethoxy)-4-(5-(3,5-dimethylisoxazol-4-yl)-1-phenyl-1H-pyrrolo[2,3-b]pyridin-3-yl)benzoic acid | 490.1 |
| P-0278 | 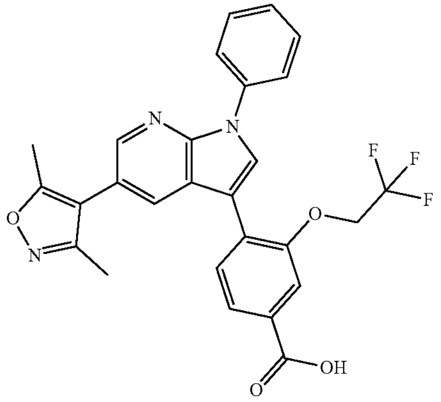 [SMILES: Cc1noc(C)c1-c1cnc2c(c1)c(-c1ccc(C(=O)O)cc1OCC(F)(F)F)cn2-c1ccccc1] | 4-(5-(3,5-dimethylisoxazol-4-yl)-1-phenyl-1H-pyrrolo[2,3-b]pyridin-3-yl)-3-(2,2,2-trifluoroethoxy)benzoic acid | 508.1 |
| P-0279 | 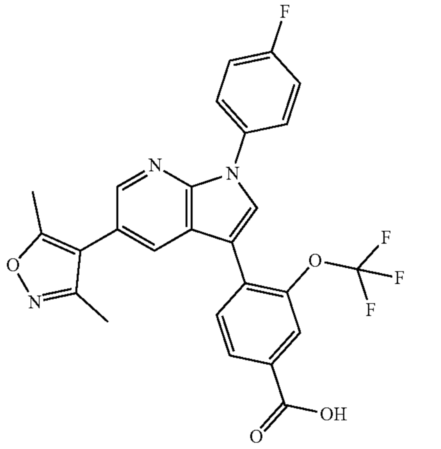 [SMILES: Cc1noc(C)c1-c1cnc2c(c1)c(-c1ccc(C(=O)O)cc1OC(F)(F)F)cn2-c1ccc(F)cc1] | 4-(5-(3,5-dimethylisoxazol-4-yl)-1-(4-fluorophenyl)-1H-pyrrolo[2,3-b]pyridin-3-yl)-3-(trifluoromethoxy)benzoic acid | 512.0 |

TABLE 1-continued
| P# | Structure | Name | (MH)+ |
|---|---|---|---|
| P-0280 | 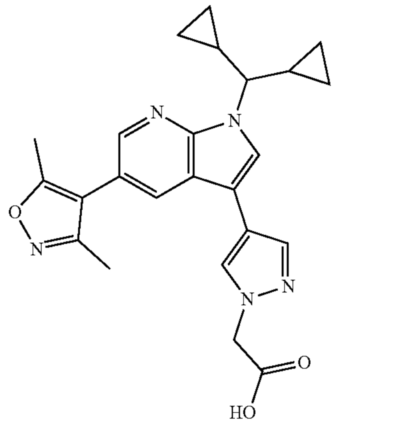 [SMILES: Cc1noc(C)c1-c1cnc2c(c1)c(-c1cnn(CC(=O)O)c1)cn2C(C1CC1)C1CC1] | 2-(4-(1-(dicyclopropylmethyl)-5-(3,5-dimethylisoxazol-4-yl)-1H-pyrrolo[2,3-b]pyridin-3-yl)-1H-pyrazol-1-yl)acetic acid | 432.2 |
| P-0281 | 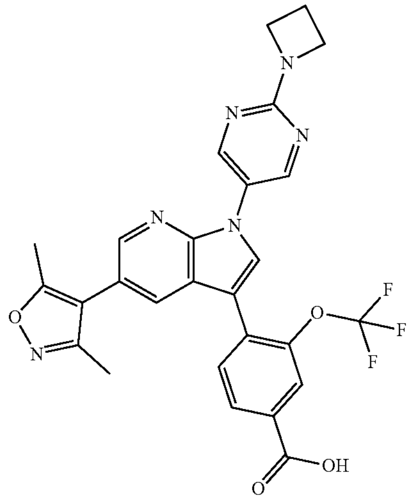 [SMILES: Cc1noc(C)c1-c1cnc2c(c1)c(-c1ccc(C(=O)O)cc1OC(F)(F)F)cn2-c1cnc(N2CCC2)nc1] | 4-(1-(2-(azetidin-1-yl)pyrimidin-5-yl)-5-(3,5-dimethylisoxazol-4-yl)-1H-pyrrolo[2,3-b]pyridin-3-yl)-3-(trifluoromethoxy)benzoic acid | 551.1 |
| P-0282 | 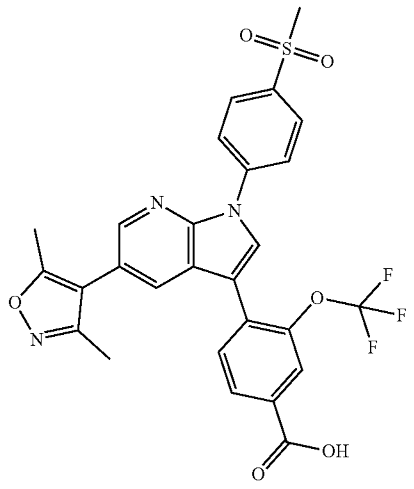 [SMILES: Cc1noc(C)c1-c1cnc2c(c1)c(-c1ccc(C(=O)O)cc1OC(F)(F)F)cn2-c1ccc(S(C)(=O)=O)cc1] | 4-(5-(3,5-dimethylisoxazol-4-yl)-1-(4-(methylsulfonyl)phenyl)-1H-pyrrolo[2,3-b]pyridin-3-yl)-3-(trifluoromethoxy)benzoic acid | 572.0 |

TABLE 1-continued

| P# | Structure | Name | (MH)+ |
| --- | --- | --- | --- |
| P-0283 | 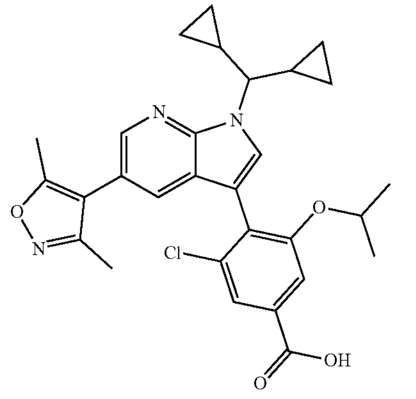 [SMILES: Cc1noc(C)c1-c1cnc2c(c1)c(-c1c(Cl)cc(C(=O)O)cc1OC(C)C)cn2C(C1CC1)C1CC1] | 3-chloro-4-(1-(dicyclopropylmethyl)-5-(3,5-dimethylisoxazol-4-yl)-1H-pyrrolo[2,3-b]pyridin-3-yl)-5-isopropoxybenzoic acid | 520.2 |
| P-0284 | 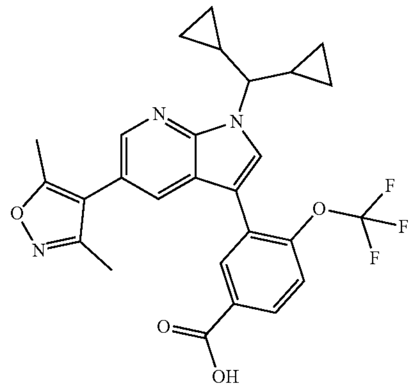 [SMILES: Cc1noc(C)c1-c1cnc2c(c1)c(-c1cc(C(=O)O)ccc1OC(F)(F)F)cn2C(C1CC1)C1CC1] | 3-(1-(dicyclopropylmethyl)-5-(3,5-dimethylisoxazol-4-yl)-1H-pyrrolo[2,3-b]pyridin-3-yl)-4-(trifluoromethoxy)benzoic acid | 512.1 |
| P-0285 | 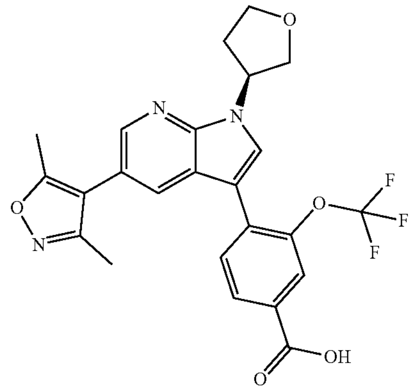 [SMILES: Cc1noc(C)c1-c1cnc2c(c1)c(-c1ccc(C(=O)O)cc1OC(F)(F)F)cn2[C@H]1CCOC1] | (S)-4-(5-(3,5-dimethylisoxazol-4-yl)-1-(tetrahydrofuran-3-yl)-1H-pyrrolo[2,3-b]pyridin-3-yl)-3-(trifluoromethoxy)benzoic acid | 488.1 |
| P-0286 | 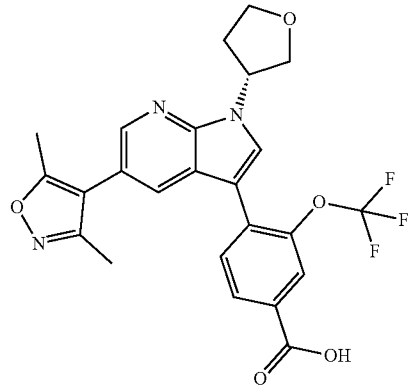 [SMILES: Cc1noc(C)c1-c1cnc2c(c1)c(-c1ccc(C(=O)O)cc1OC(F)(F)F)cn2[C@@H]1CCOC1] | (R)-4-(5-(3,5-dimethylisoxazol-4-yl)-1-(tetrahydrofuran-3-yl)-1H-pyrrolo[2,3-b]pyridin-3-yl)-3-(trifluoromethoxy)benzoic acid | 488.1 |

TABLE 1-continued

| P# | Structure | Name | (MH)+ |
|---|---|---|---|
| P-0287 | 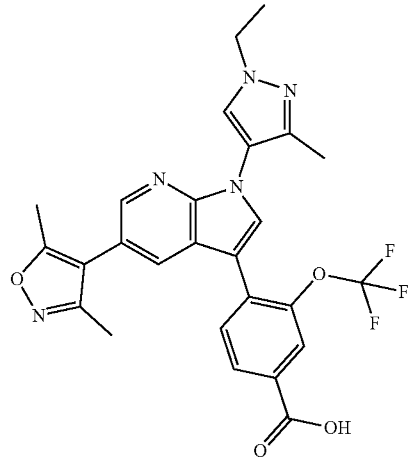 [SMILES: CCn1cc(-n2cc(-c3ccc(C(=O)O)cc3OC(F)(F)F)c3cc(-c4c(C)noc4C)cnc32)c(C)n1] | 4-(5-(3,5-dimethylisoxazol-4-yl)-1-(1-ethyl-3-methyl-1H-pyrazol-4-yl)-1H-pyrrolo[2,3-b]pyridin-3-yl)-3-(trifluoromethoxy)benzoic acid | 526.1 |
| P-0288 | 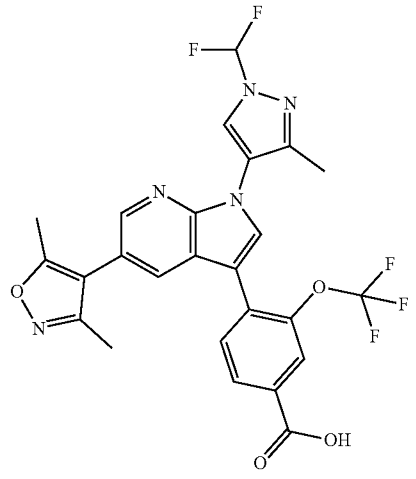 [SMILES: Cc1nn(C(F)F)cc1-n1cc(-c2ccc(C(=O)O)cc2OC(F)(F)F)c2cc(-c3c(C)noc3C)cnc21] | 4-(1-(1-(difluoromethyl)-3-methyl-1H-pyrazol-4-yl)-5-(3,5-dimethylisoxazol-4-yl)-1H-pyrrolo[2,3-b]pyridin-3-yl)-3-(trifluoromethoxy)benzoic acid | 548.1 |
| P-0289 | 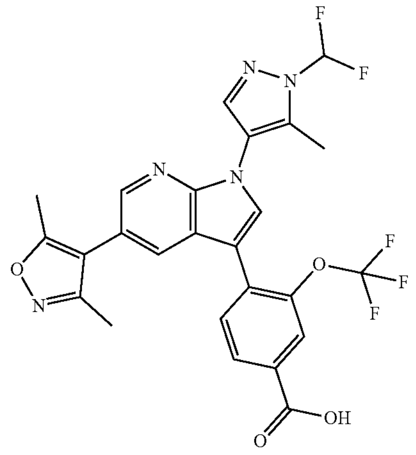 [SMILES: Cc1noc(C)c1-c1cnc2c(c1)c(-c1ccc(C(=O)O)cc1OC(F)(F)F)cn2-c1cnn(C(F)F)c1C] | 4-(1-(1-(difluoromethyl)-5-methyl-1H-pyrazol-4-yl)-5-(3,5-dimethylisoxazol-4-yl)-1H-pyrrolo[2,3-b]pyridin-3-yl)-3-(trifluoromethoxy)benzoic acid | 548.1 |

TABLE 1-continued
| P# | Structure | Name | (MH)+ |
|---|---|---|---|
| P-0290 | 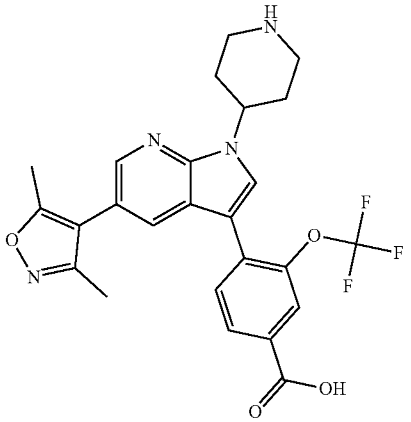 [SMILES: Cc1noc(C)c1-c1cnc2c(c1)c(-c1ccc(C(=O)O)cc1OC(F)(F)F)cn2C1CCNCC1] | 4-(5-(3,5-dimethylisoxazol-4-yl)-1-(piperidin-4-yl)-1H-pyrrolo[2,3-b]pyridin-3-yl)-3-(trifluoromethoxy)benzoic acid | 501.1 |
| P-0291 | 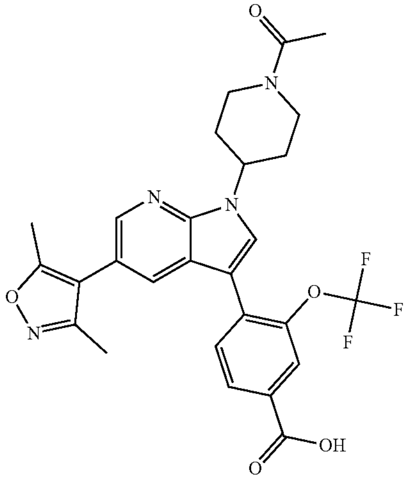 [SMILES: CC(=O)N1CCC(n2cc(-c3ccc(C(=O)O)cc3OC(F)(F)F)c3cc(-c4c(C)noc4C)cnc32)CC1] | 4-(1-(1-acetylpiperidin-4-yl)-5-(3,5-dimethylisoxazol-4-yl)-1H-pyrrolo[2,3-b]pyridin-3-yl)-3-(trifluoromethoxy)benzoic acid | 543.1 |
| P-0292 | 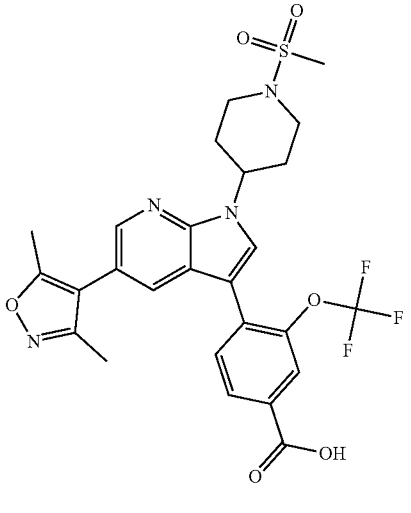 [SMILES: Cc1noc(C)c1-c1cnc2c(c1)c(-c1ccc(C(=O)O)cc1OC(F)(F)F)cn2C1CCN(S(C)(=O)=O)CC1] | 4-(5-(3,5-dimethylisoxazol-4-yl)-1-(1-(methylsulfonyl)piperidin-4-yl)-1H-pyrrolo[2,3-b]pyridin-3-yl)-3-(trifluoromethoxy)benzoic acid | 579.1 |

TABLE 1-continued
| P# | Structure | Name | (MH)+ |
|---|---|---|---|
| P-0293 | 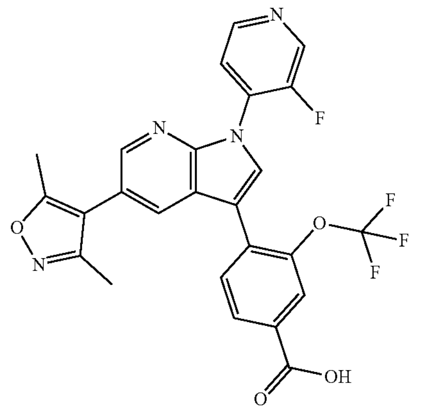 [SMILES: Cc1noc(C)c1-c1cnc2c(c1)c(-c1ccc(C(=O)O)cc1OC(F)(F)F)cn2-c1ccncc1F] | 4-(5-(3,5-dimethylisoxazol-4-yl)-1-(3-fluoropyridin-4-yl)-1H-pyrrolo[2,3-b]pyridin-3-yl)-3-(trifluoromethoxy)benzoic acid | 513.1 |
| P-0294 | 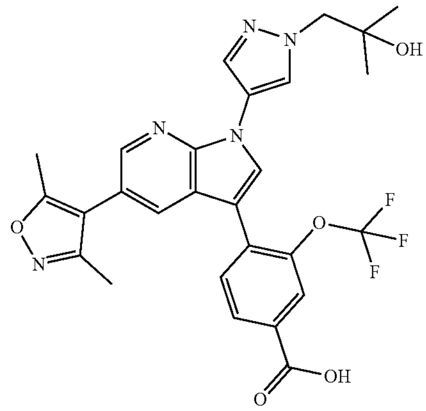 [SMILES: Cc1noc(C)c1-c1cnc2c(c1)c(-c1ccc(C(=O)O)cc1OC(F)(F)F)cn2-c1cnn(CC(C)(C)O)c1] | 4-(5-(3,5-dimethylisoxazol-4-yl)-1-(1-(2-hydroxy-2-methylpropyl)-1H-pyrazol-4-yl)-1H-pyrrolo[2,3-b]pyridin-3-yl)-3-(trifluoromethoxy)benzoic acid | 556.1 |
| P-0295 | 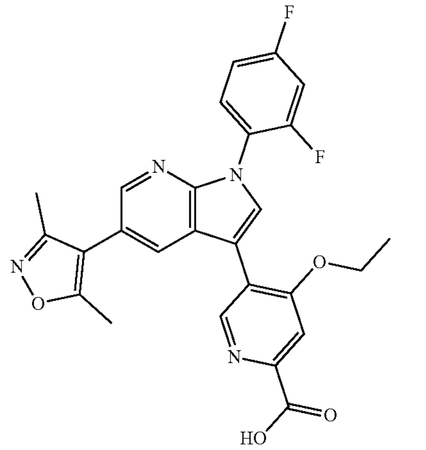 [SMILES: CCOc1cc(C(=O)O)ncc1-c1cn(-c2ccc(F)cc2F)c2ncc(-c3c(C)noc3C)cc12] | 5-(1-(2,4-difluorophenyl)-5-(3,5-dimethylisoxazol-4-yl)-1H-pyrrolo[2,3-b]pyridin-3-yl)-4-ethoxypicolinic acid | 491.1 |

TABLE 1-continued
| P# | Structure | Name | (MH)+ |
|---|---|---|---|
| P-0296 | 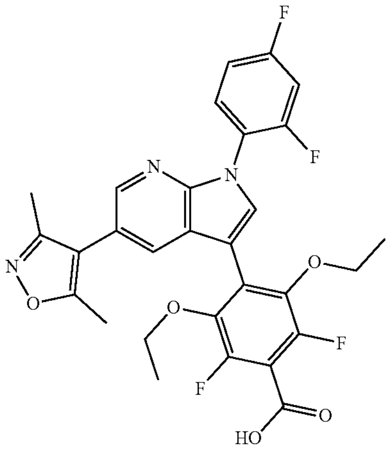 [SMILES: CCOc1c(F)c(C(=O)O)c(F)c(OCC)c1-c1cn(-c2ccc(F)cc2F)c2ncc(-c3c(C)noc3C)cc12] | 4-(1-(2,4-difluorophenyl)-5-(3,5-dimethylisoxazol-4-yl)-1H-pyrrolo[2,3-b]pyridin-3-yl)-3,5-diethoxy-2,6-difluorobenzoic acid | 570.1 |
| P-0297 | 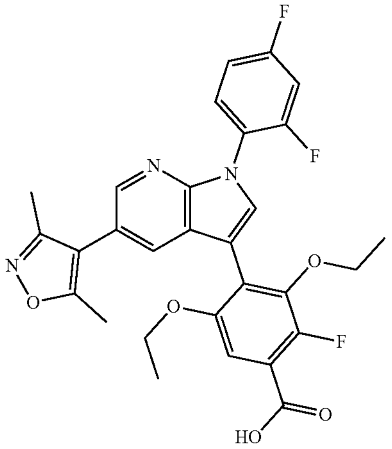 [SMILES: CCOc1cc(C(=O)O)c(F)c(OCC)c1-c1cn(-c2ccc(F)cc2F)c2ncc(-c3c(C)noc3C)cc12] | 4-(1-(2,4-difluorophenyl)-5-(3,5-dimethylisoxazol-4-yl)-1H-pyrrolo[2,3-b]pyridin-3-yl)-3,5-diethoxy-2-fluorobenzoic acid | 552.1 |
| P-0298 | 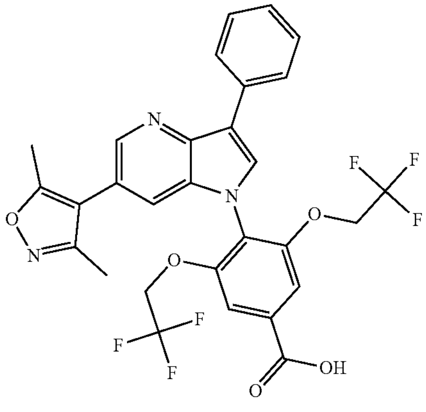 [SMILES: Cc1noc(C)c1-c1cnc2c(-c3ccccc3)cn(-c3c(OCC(F)(F)F)cc(C(=O)O)cc3OCC(F)(F)F)c2c1] | 4-(6-(3,5-dimethylisoxazol-4-yl)-3-phenyl-1H-pyrrolo[3,2-b]pyridin-1-yl)-3,5-bis(2,2,2-trifluoroethoxy)benzoic acid | 606.1 |

TABLE 1-continued
| P# | Structure | Name | (MH)+ |
|---|---|---|---|
| P-0299 | 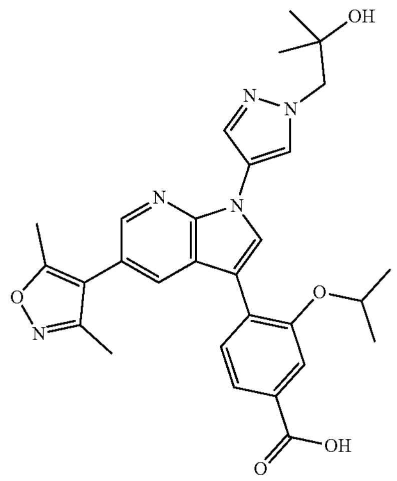 [SMILES: Cc1noc(C)c1-c1cnc2c(c1)c(-c1ccc(C(=O)O)cc1OC(C)C)cn2-c1cnn(CC(C)(C)O)c1] | 4-(5-(3,5-dimethylisoxazol-4-yl)-1-(1-(2-hydroxy-2-methylpropyl)-1H-pyrazol-4-yl)-1H-pyrrolo[2,3-b]pyridin-3-yl)-3-isopropoxybenzoic acid | 530.2 |
| P-0300 | 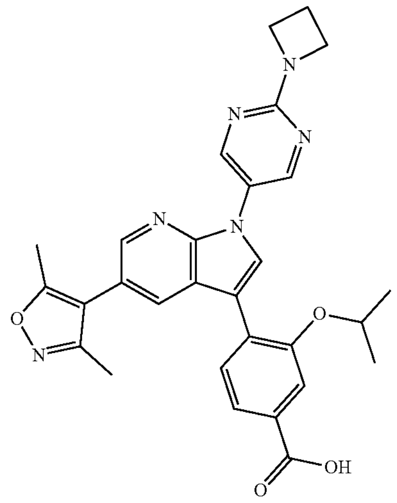 [SMILES: Cc1noc(C)c1-c1cnc2c(c1)c(-c1ccc(C(=O)O)cc1OC(C)C)cn2-c1cnc(N2CCC2)nc1] | 4-(1-(2-(azetidin-1-yl)pyrimidin-5-yl)-5-(3,5-dimethylisoxazol-4-yl)-1H-pyrrolo[2,3-b]pyridin-3-yl)-3-isopropoxybenzoic acid | 525.1 |
| P-0301 | 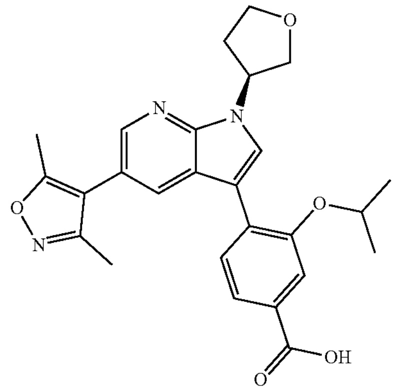 [SMILES: Cc1noc(C)c1-c1cnc2c(c1)c(-c1ccc(C(=O)O)cc1OC(C)C)cn2[C@H]1CCOC1] | (S)-4-(5-(3,5-dimethylisoxazol-4-yl)-1-(tetrahydrofuran-3-yl)-1H-pyrrolo[2,3-b]pyridin-3-yl)-3-isopropoxybenzoic acid | 462.1 |

TABLE 1-continued
| P# | Structure | Name | (MH)+ |
|---|---|---|---|
| P-0302 | 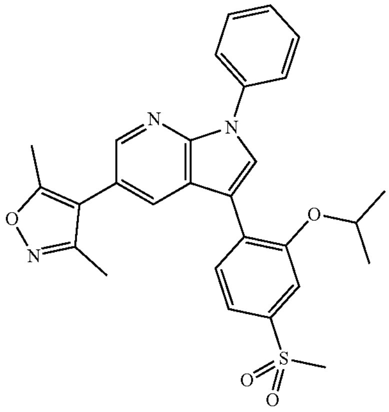 [SMILES: Cc1noc(C)c1-c1cnc2c(c1)c(-c1ccc(S(C)(=O)=O)cc1OC(C)C)cn2-c1ccccc1] | 4-(3-(2-isopropoxy-4-(methylsulfonyl)phenyl)-1-phenyl-1H-pyrrolo[2,3-b]pyridin-5-yl)-3,5-dimethylisoxazole | 502.1 |
| P-0303 | 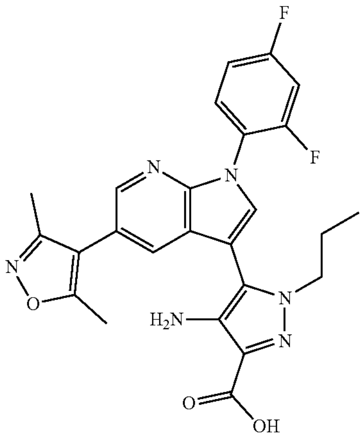 [SMILES: CCCn1nc(C(=O)O)c(N)c1-c1cn(-c2ccc(F)cc2F)c2ncc(-c3c(C)noc3C)cc12] | 4-amino-5-(1-(2,4-difluorophenyl)-5-(3,5-dimethylisoxazol-4-yl)-1H-pyrrolo[2,3-b]pyridin-3-yl)-1-propyl-1H-pyrazole-3-carboxylic acid | 493.1 |
| P-0304 | 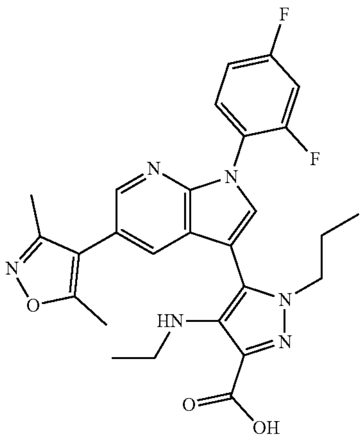 [SMILES: CCCn1nc(C(=O)O)c(NCC)c1-c1cn(-c2ccc(F)cc2F)c2ncc(-c3c(C)noc3C)cc12] | 5-(1-(2,4-difluorophenyl)-5-(3,5-dimethylisoxazol-4-yl)-1H-pyrrolo[2,3-b]pyridin-3-yl)-4-(ethylamino)-1-propyl-1H-pyrazole-3-carboxylic acid | 521.2 |

TABLE 1-continued
| P# | Structure | Name | (MH)+ |
|---|---|---|---|
| P-0305 | 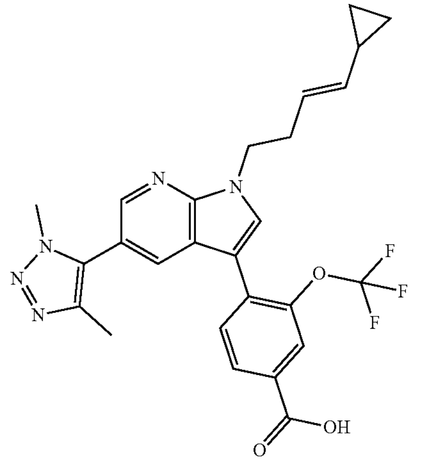 [SMILES: Cc1nnn(C)c1-c1cnc2c(c1)c(-c1ccc(C(=O)O)cc1OC(F)(F)F)cn2CC/C=C/C1CC1] | (E)-4-(1-(4-cyclopropylbut-3-en-1-yl)-5-(1,4-dimethyl-1H-1,2,3-triazol-5-yl)-1H-pyrrolo[2,3-b]pyridin-3-yl)-3-(trifluoromethoxy)benzoic acid | 512.1 |
| P-0306 | 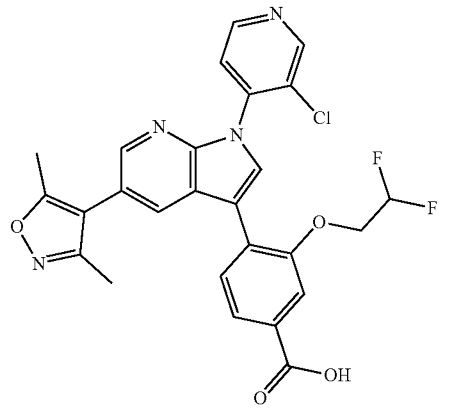 [SMILES: Cc1noc(C)c1-c1cnc2c(c1)c(-c1ccc(C(=O)O)cc1OCC(F)F)cn2-c1ccncc1Cl] | 4-(1-(3-chloropyridin-4-yl)-5-(3,5-dimethylisoxazol-4-yl)-1H-pyrrolo[2,3-b]pyridin-3-yl)-3-(2,2-difluoroethoxy)benzoic acid | 525.1 |
| P-0307 | 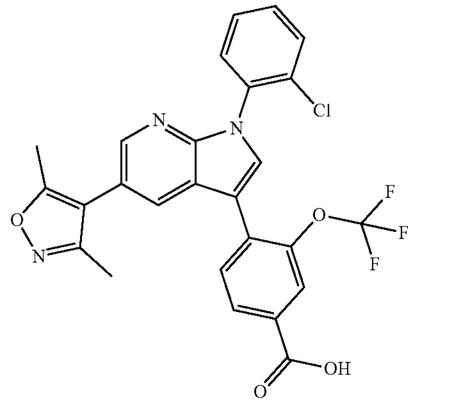 [SMILES: Cc1noc(C)c1-c1cnc2c(c1)c(-c1ccc(C(=O)O)cc1OC(F)(F)F)cn2-c1ccccc1Cl] | 4-(1-(2-chlorophenyl)-5-(3,5-dimethylisoxazol-4-yl)-1H-pyrrolo[2,3-b]pyridin-3-yl)-3-(trifluoromethoxy)benzoic acid | 528.1 |

TABLE 1-continued
| P# | Structure | Name | (MH)+ |
|---|---|---|---|
| P-0308 | 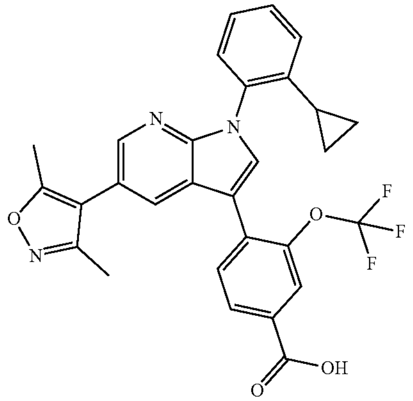 [SMILES: Cc1noc(C)c1-c1cnc2c(c1)c(-c1ccc(C(=O)O)cc1OC(F)(F)F)cn2-c1ccccc1C1CC1] | 4-(1-(2-cyclopropylphenyl)-5-(3,5-dimethylisoxazol-4-yl)-1H-pyrrolo[2,3-b]pyridin-3-yl)-3-(trifluoromethoxy)benzoic acid | 534.1 |
| P-0309 | 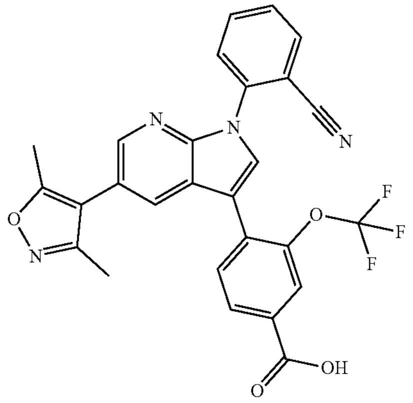 [SMILES: Cc1noc(C)c1-c1cnc2c(c1)c(-c1ccc(C(=O)O)cc1OC(F)(F)F)cn2-c1ccccc1C#N] | 4-(1-(2-cyanophenyl)-5-(3,5-dimethylisoxazol-4-yl)-1H-pyrrolo[2,3-b]pyridin-3-yl)-3-(trifluoromethoxy)benzoic acid | 519.4 |
| P-0310 | 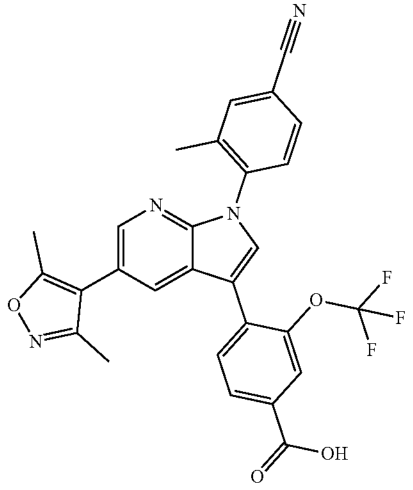 [SMILES: Cc1cc(C#N)ccc1-n1cc(-c2ccc(C(=O)O)cc2OC(F)(F)F)c2cc(-c3c(C)noc3C)cnc21] | 4-(1-(4-cyano-2-methylphenyl)-5-(3,5-dimethylisoxazol-4-yl)-1H-pyrrolo[2,3-b]pyridin-3-yl)-3-(trifluoromethoxy)benzoic acid | 533.2 |

TABLE 1-continued
| P# | Structure | Name | (MH)+ |
|---|---|---|---|
| P-0311 | 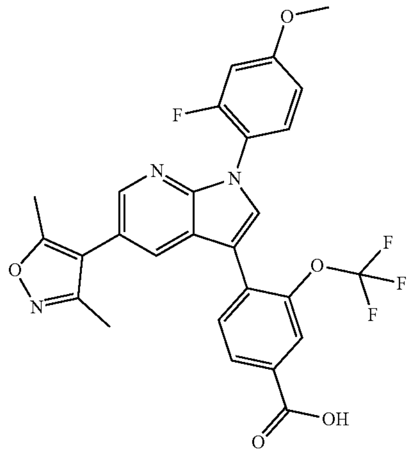 [SMILES: COc1ccc(-n2cc(-c3ccc(C(=O)O)cc3OC(F)(F)F)c3cc(-c4c(C)noc4C)cnc32)c(F)c1] | 4-(5-(3,5-dimethylisoxazol-4-yl)-1-(2-fluoro-4-methoxyphenyl)-1H-pyrrolo[2,3-b]pyridin-3-yl)-3-(trifluoromethoxy)benzoic acid | 542.2 |
| P-0312 | 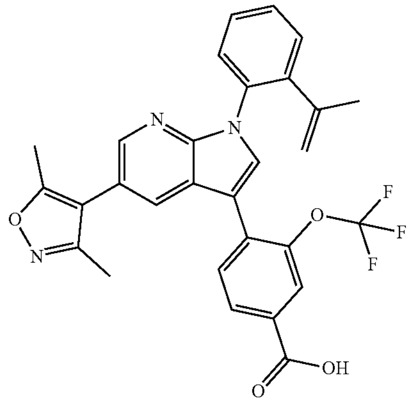 [SMILES: C=C(C)c1ccccc1-n1cc(-c2ccc(C(=O)O)cc2OC(F)(F)F)c2cc(-c3c(C)noc3C)cnc21] | 4-(5-(3,5-dimethylisoxazol-4-yl)-1-(2-(prop-1-en-2-yl)phenyl)-1H-pyrrolo[2,3-b]pyridin-3-yl)-3-(trifluoromethoxy)benzoic acid | 534.1 |
| P-0313 | 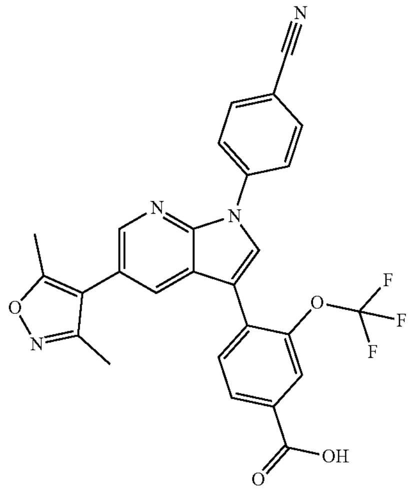 [SMILES: Cc1noc(C)c1-c1cnc2c(c1)c(-c1ccc(C(=O)O)cc1OC(F)(F)F)cn2-c1ccc(C#N)cc1] | 4-(1-(4-cyanophenyl)-5-(3,5-dimethylisoxazol-4-yl)-1H-pyrrolo[2,3-b]pyridin-3-yl)-3-(trifluoromethoxy)benzoic acid | 519.1 |

TABLE 1-continued
| P# | Structure | Name | (MH)+ |
|---|---|---|---|
| P-0314 | 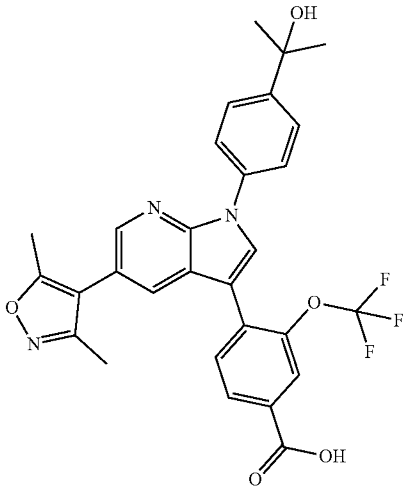 [SMILES: Cc1noc(C)c1-c1cnc2c(c1)c(-c1ccc(C(=O)O)cc1OC(F)(F)F)cn2-c1ccc(C(C)(C)O)cc1] | 4-(5-(3,5-dimethylisoxazol-4-yl)-1-(4-(2-hydroxypropan-2-yl)phenyl)-1H-pyrrolo[2,3-b]pyridin-3-yl)-3-(trifluoromethoxy)benzoic acid | 552.4 |
| P-0315 | 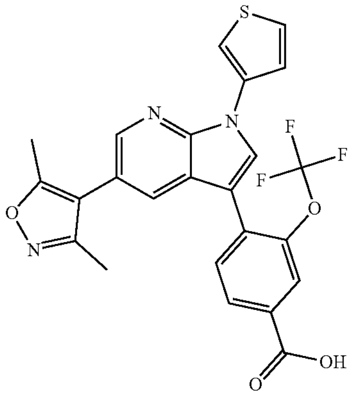 [SMILES: Cc1noc(C)c1-c1cnc2c(c1)c(-c1ccc(C(=O)O)cc1OC(F)(F)F)cn2-c1ccsc1] | 4-(5-(3,5-dimethylisoxazol-4-yl)-1-(thiophen-3-yl)-1H-pyrrolo[2,3-b]pyridin-3-yl)-3-(trifluoromethoxy)benzoic acid | 500.2 |
| P-0316 | 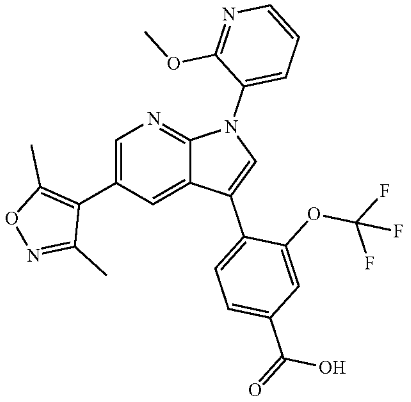 [SMILES: COc1ncccc1-n1cc(-c2ccc(C(=O)O)cc2OC(F)(F)F)c2cc(-c3c(C)noc3C)cnc21] | 4-(5-(3,5-dimethylisoxazol-4-yl)-1-(2-methoxypyridin-3-yl)-1H-pyrrolo[2,3-b]pyridin-3-yl)-3-(trifluoromethoxy)benzoic acid | 525.4 |

TABLE 1-continued
| P# | Structure | Name | (MH)+ |
|---|---|---|---|
| P-0317 | 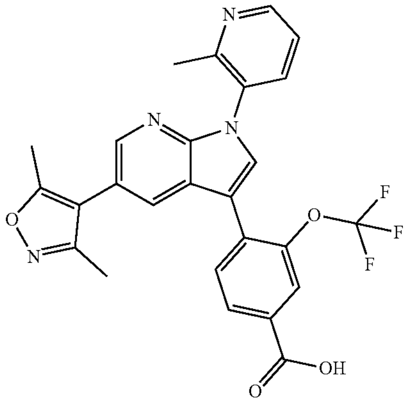 [SMILES: Cc1ncccc1-n1cc(-c2ccc(C(=O)O)cc2OC(F)(F)F)c2cc(-c3c(C)noc3C)cnc21] | 4-(5-(3,5-dimethylisoxazol-4-yl)-1-(2-methylpyridin-3-yl)-1H-pyrrolo[2,3-b]pyridin-3-yl)-3-(trifluoromethoxy)benzoic acid | 509.2 |
| P-0318 | 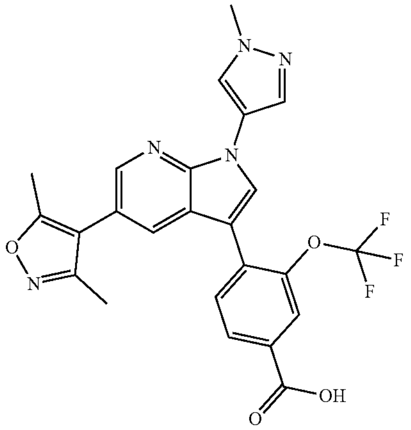 [SMILES: Cc1noc(C)c1-c1cnc2c(c1)c(-c1ccc(C(=O)O)cc1OC(F)(F)F)cn2-c1cnn(C)c1] | 4-(5-(3,5-dimethylisoxazol-4-yl)-1-(1-methyl-1H-pyrazol-4-yl)-1H-pyrrolo[2,3-b]pyridin-3-yl)-3-(trifluoromethoxy)benzoic acid | 498.4 |
| P-0319 | 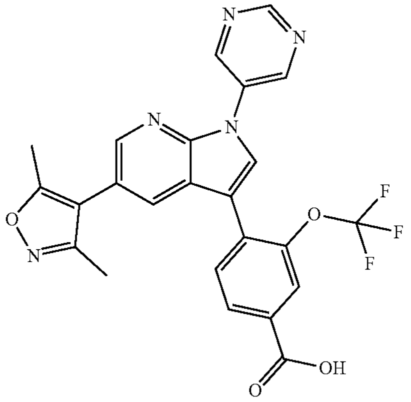 [SMILES: Cc1noc(C)c1-c1cnc2c(c1)c(-c1ccc(C(=O)O)cc1OC(F)(F)F)cn2-c1cncnc1] | 4-(5-(3,5-dimethylisoxazol-4-yl)-1-(pyrimidin-5-yl)-1H-pyrrolo[2,3-b]pyridin-3-yl)-3-(trifluoromethoxy)benzoic acid | 496.3 |

TABLE 1-continued
| P# | Structure | Name | (MH)+ |
|---|---|---|---|
| P-0320 | 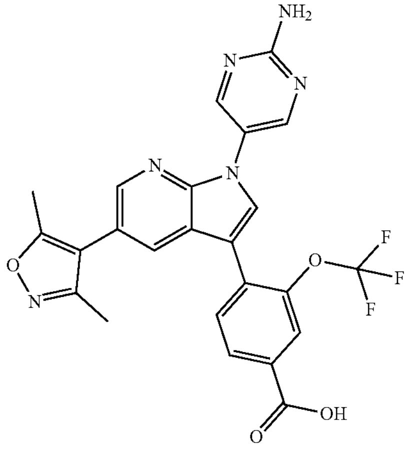 [SMILES: Cc1noc(C)c1-c1cnc2c(c1)c(-c1ccc(C(=O)O)cc1OC(F)(F)F)cn2-c1cnc(N)nc1] | 4-(1-(2-aminopyrimidin-5-yl)-5-(3,5-dimethylisoxazol-4-yl)-1H-pyrrolo[2,3-b]pyridin-3-yl)-3-(trifluoromethoxy)benzoic acid | 511.3 |
| P-0321 | 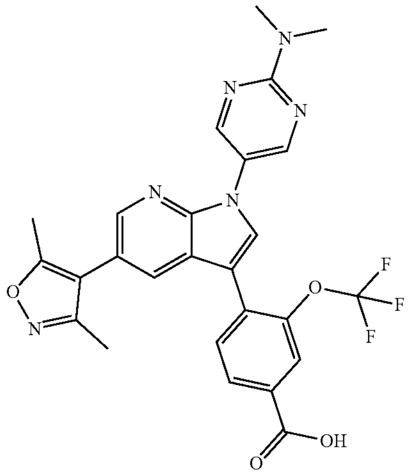 [SMILES: Cc1noc(C)c1-c1cnc2c(c1)c(-c1ccc(C(=O)O)cc1OC(F)(F)F)cn2-c1cnc(N(C)C)nc1] | 4-(1-(2-(dimethylamino)pyrimidin-5-yl)-1H-pyrrolo[2,3-b]pyridin-3-yl)-3-(trifluoromethoxy)benzoic acid | 539.5 |
| P-0322 | 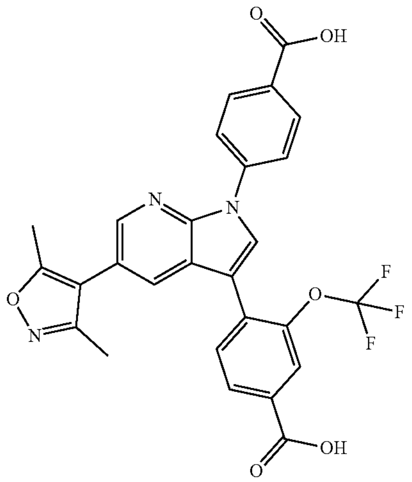 [SMILES: Cc1noc(C)c1-c1cnc2c(c1)c(-c1ccc(C(=O)O)cc1OC(F)(F)F)cn2-c1ccc(C(=O)O)cc1] | 4-(1-(4-carboxyphenyl)-5-(3,5-dimethylisoxazol-4-yl)-1H-pyrrolo[2,3-b]pyridin-3-yl)-3-(trifluoromethoxy)benzoic acid | 538.3 |

TABLE 1-continued
| P# | Structure | Name | (MH)+ |
| --- | --- | --- | --- |
| P-0323 | 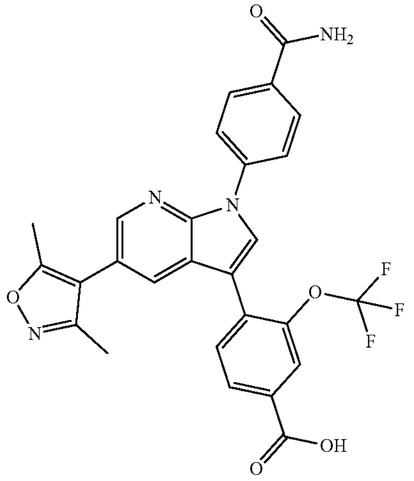 [SMILES: Cc1noc(C)c1-c1cnc2c(c1)c(-c1ccc(C(=O)O)cc1OC(F)(F)F)cn2-c1ccc(C(N)=O)cc1] | 4-(1-(4-carbamoylphenyl)-5-(3,5-dimethylisoxazol-4-yl)-1H-pyrrolo[2,3-b]pyridin-3-yl)-3-(trifluoromethoxy)benzoic acid | 537.4 |
| P-0324 | 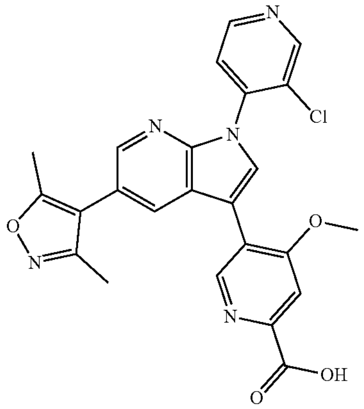 [SMILES: COc1cc(C(=O)O)ncc1-c1cn(-c2ccncc2Cl)c2ncc(-c3c(C)noc3C)cc12] | 5-(1-(3-chloropyridin-4-yl)-5-(3,5-dimethylisoxazol-4-yl)-1H-pyrrolo[2,3-b]pyridin-3-yl)-4-methoxypicolinic acid | 476.0 |
| P-0325 | 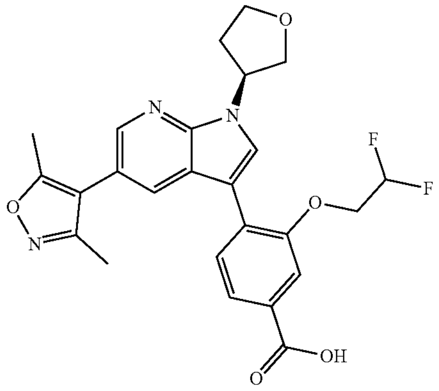 [SMILES: Cc1noc(C)c1-c1cnc2c(c1)c(-c1ccc(C(=O)O)cc1OCC(F)F)cn2[C@H]1CCOC1] | (S)-3-(2,2-difluoroethoxy)-4-(5-(3,5-dimethylisoxazol-4-yl)-1-(tetrahydrofuran-3-yl)-1H-pyrrolo[2,3-b]pyridin-3-yl)benzoic acid | 484.0 |

TABLE 1-continued
| P# | Structure | Name | (MH)+ |
|---|---|---|---|
| P-0326 | 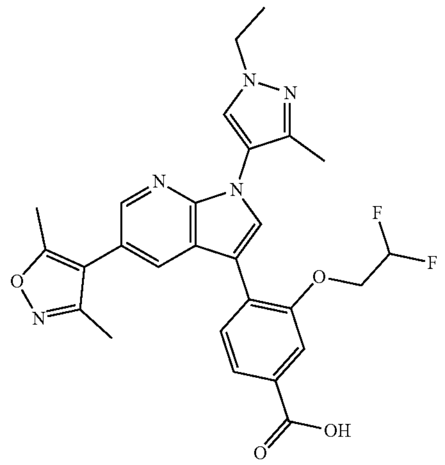 [SMILES: CCn1cc(-n2cc(-c3ccc(C(=O)O)cc3OCC(F)F)c3cc(-c4c(C)noc4C)cnc32)c(C)n1] | 3-(2,2-difluoroethoxy)-4-(5-(3,5-dimethylisoxazol-4-yl)-1-(1-ethyl-3-methyl-1H-pyrazol-4-yl)-1H-pyrrolo[2,3-b]pyridin-3-yl)benzoic acid | 522.1 |
| P-0327 | 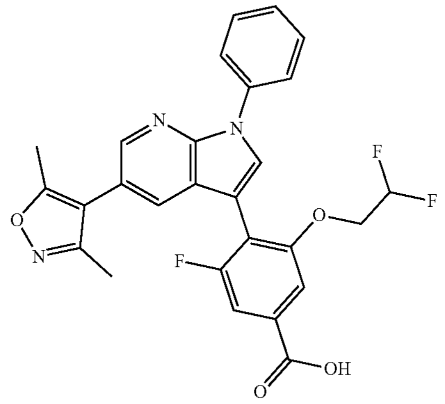 [SMILES: Cc1noc(C)c1-c1cnc2c(c1)c(-c1c(F)cc(C(=O)O)cc1OCC(F)F)cn2-c1ccccc1] | 3-(2,2-difluoroethoxy)-4-(5-(3,5-dimethylisoxazol-4-yl)-1-phenyl-1H-pyrrolo[2,3-b]pyridin-3-yl)-5-fluorobenzoic acid | 508.1 |
| P-0328 | 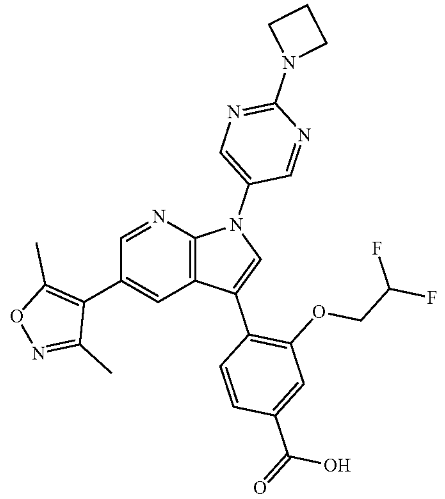 [SMILES: Cc1noc(C)c1-c1cnc2c(c1)c(-c1ccc(C(=O)O)cc1OCC(F)F)cn2-c1cnc(N2CCC2)nc1] | 4-(1-(2-(azetidin-1-yl)pyrimidin-5-yl)-5-(3,5-dimethylisoxazol-4-yl)-1H-pyrrolo[2,3-b]pyridin-3-yl)-3-(2,2-difluoroethoxy)benzoic acid | 547.2 |

TABLE 1-continued
| P# | Structure | Name | (MH)+ |
|---|---|---|---|
| P-0329 | 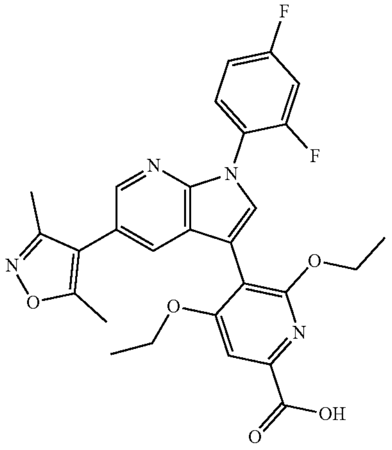 [SMILES: CCOc1cc(C(=O)O)nc(OCC)c1-c1cn(-c2ccc(F)cc2F)c2ncc(-c3c(C)noc3C)cc12] | 5-(1-(2,4-difluorophenyl)-5-(3,5-dimethylisoxazol-4-yl)-1H-pyrrolo[2,3-b]pyridin-3-yl)-4,6-diethoxypicolinic acid | 535.2 |
| P-0330 | 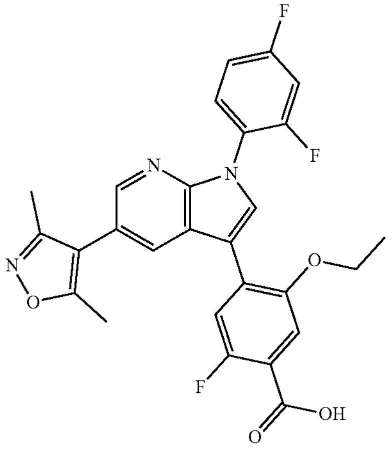 [SMILES: CCOc1cc(C(=O)O)c(F)cc1-c1cn(-c2ccc(F)cc2F)c2ncc(-c3c(C)noc3C)cc12] | 4-(1-(2,4-difluorophenyl)-5-(3,5-dimethylisoxazol-4-yl)-1H-pyrrolo[2,3-b]pyridin-3-yl)-5-ethoxy-2-fluorobenzoic acid | 508.1 |
| P-0331 | 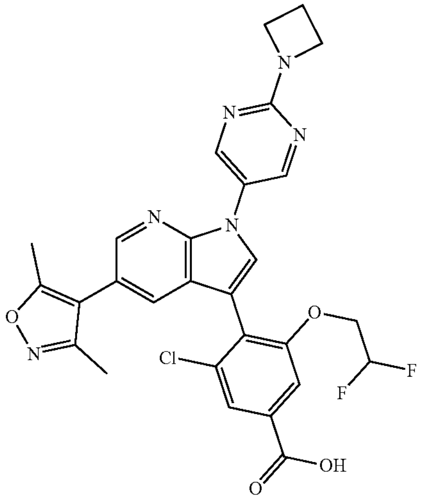 [SMILES: Cc1noc(C)c1-c1cnc2c(c1)c(-c1c(Cl)cc(C(=O)O)cc1OCC(F)F)cn2-c1cnc(N2CCC2)nc1] | 4-(1-(2-(azetidin-1-yl)pyrimidin-5-yl)-5-(3,5-dimethylisoxazol-4-yl)-1H-pyrrolo[2,3-b]pyridin-3-yl)-3-chloro-5-(2,2-difluoroethoxy)benzoic acid | 581.1 |

TABLE 1-continued
| P# | Structure | Name | (MH)+ |
|---|---|---|---|
| P-0332 | 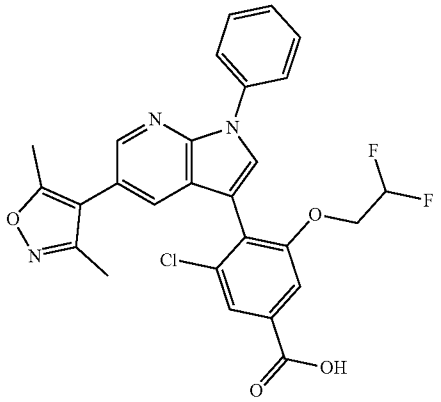 [SMILES: Cc1noc(C)c1-c1cnc2c(c1)c(-c1c(Cl)cc(C(=O)O)cc1OCC(F)F)cn2-c1ccccc1] | 3-chloro-5-(2,2-difluoroethoxy)-4-(5-(3,5-dimethylisoxazol-4-yl)-1-phenyl-1H-pyrrolo[2,3-b]pyridin-3-yl)benzoic acid | 524.0 |
| P-0333 | 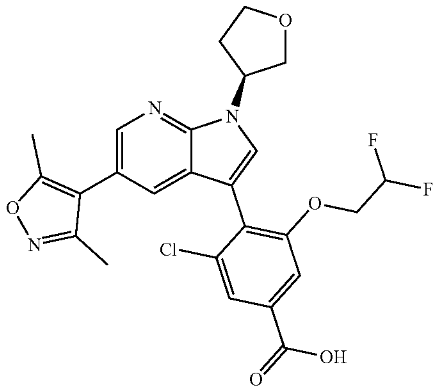 [SMILES: Cc1noc(C)c1-c1cnc2c(c1)c(-c1c(Cl)cc(C(=O)O)cc1OCC(F)F)cn2[C@H]1CCOC1] | (S)-3-chloro-5-(2,2-difluoroethoxy)-4-(5-(3,5-dimethylisoxazol-4-yl)-1-(tetrahydrofuran-3-yl)-1H-pyrrolo[2,3-b]pyridin-3-yl)benzoic acid | 518.1 |
| P-0334 | 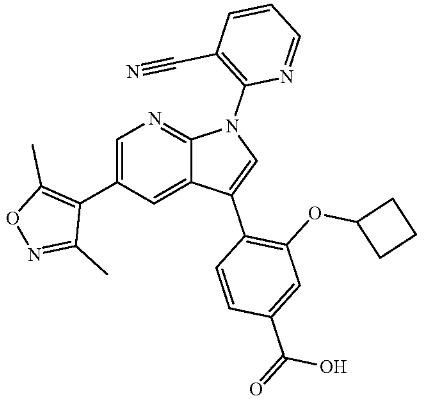 [SMILES: Cc1noc(C)c1-c1cnc2c(c1)c(-c1ccc(C(=O)O)cc1OC1CCC1)cn2-c1ncccc1C#N] | 4-(1-(3-cyanopyridin-2-yl)-5-(3,5-dimethylisoxazol-4-yl)-1H-pyrrolo[2,3-b]pyridin-3-yl)-3-cyclobutoxybenzoic acid | 506.2 |

TABLE 1-continued
| P# | Structure | Name | (MH)+ |
|---|---|---|---|
| P-0335 | 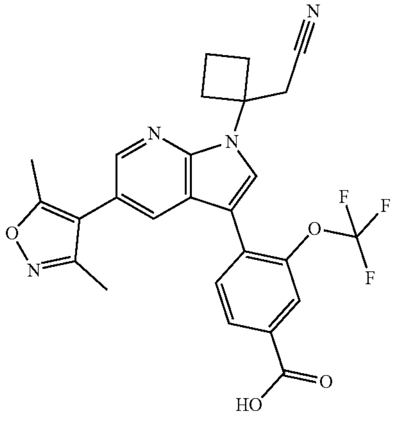 [SMILES: Cc1noc(C)c1-c1cnc2c(c1)c(-c1ccc(C(=O)O)cc1OC(F)(F)F)cn2C1(CC#N)CCC1] | 4-(1-(1-(cyanomethyl)cyclobutyl)-5-(3,5-dimethylisoxazol-4-yl)-1H-pyrrolo[2,3-b]pyridin-3-yl)-3-(trifluoromethoxy)benzoic acid | 511.0 |
| P-0336 | 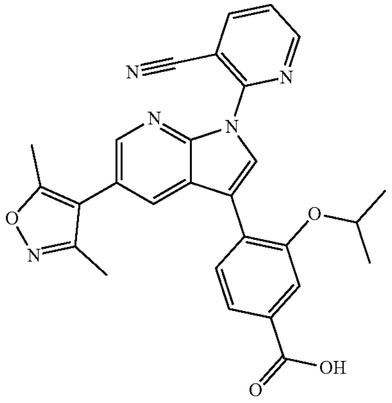 [SMILES: Cc1noc(C)c1-c1cnc2c(c1)c(-c1ccc(C(=O)O)cc1OC(C)C)cn2-c1ncccc1C#N] | 4-(1-(3-cyanopyridin-2-yl)-5-(3,5-dimethylisoxazol-4-yl)-1H-pyrrolo[2,3-b]pyridin-3-yl)-3-isopropoxybenzoic acid | 494.0 |
| P-0337 | 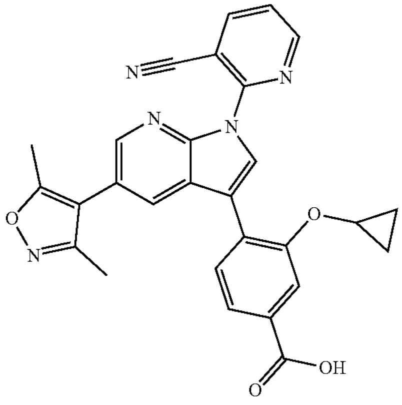 [SMILES: Cc1noc(C)c1-c1cnc2c(c1)c(-c1ccc(C(=O)O)cc1OC1CC1)cn2-c1ncccc1C#N] | 4-(1-(3-cyanopyridin-2-yl)-5-(3,5-dimethylisoxazol-4-yl)-1H-pyrrolo[2,3-b]pyridin-3-yl)-3-cyclopropoxybenzoic acid | 492.0 |

TABLE 1-continued

| P# | Structure | Name | (MH)+ |
|---|---|---|---|
| P-0338 | 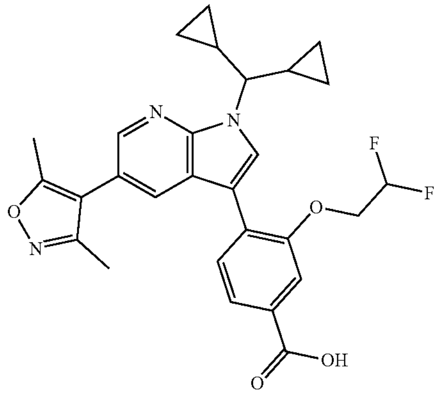 [SMILES: Cc1noc(C)c1-c1cnc2c(c1)c(-c1ccc(C(=O)O)cc1OCC(F)F)cn2C(C1CC1)C1CC1] | 4-(1-(dicyclopropylmethyl)-5-(3,5-dimethylisoxazol-4-yl)-1H-pyrrolo[2,3-b]pyridin-3-yl)-3-(2,2-difluoroethoxy)benzoic acid | 508.2 |
| P-0339 | 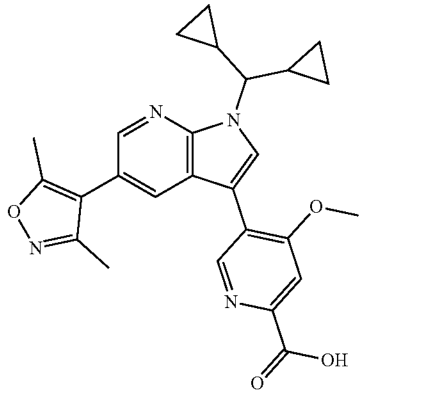 [SMILES: COc1cc(C(=O)O)ncc1-c1cn(C(C2CC2)C2CC2)c2ncc(-c3c(C)noc3C)cc12] | 5-(1-(dicyclopropylmethyl)-5-(3,5-dimethylisoxazol-4-yl)-1H-pyrrolo[2,3-b]pyridin-3-yl)-4-methoxypicolinic acid | 459.2 |
| P-0340 | 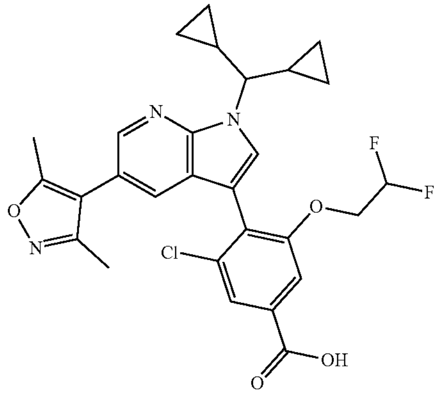 [SMILES: Cc1noc(C)c1-c1cnc2c(c1)c(-c1c(Cl)cc(C(=O)O)cc1OCC(F)F)cn2C(C1CC1)C1CC1] | 3-chloro-4-(1-(dicyclopropylmethyl)-5-(3,5-dimethylisoxazol-4-yl)-1H-pyrrolo[2,3-b]pyridin-3-yl)-5-(2,2-difluoroethoxy)benzoic acid | 542.1 |
| P-0341 | 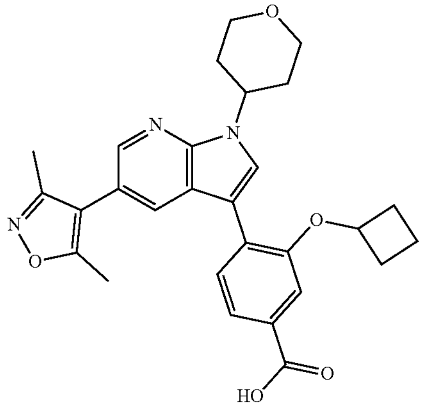 [SMILES: Cc1noc(C)c1-c1cnc2c(c1)c(-c1ccc(C(=O)O)cc1OC1CCC1)cn2C1CCOCC1] | 3-cyclobutoxy-4-(5-(3,5-dimethylisoxazol-4-yl)-1-(tetrahydro-2H-pyran-4-yl)-1H-pyrrolo[2,3-b]pyridin-3-yl)benzoic acid | 488.2 |

TABLE 1-continued
| P# | Structure | Name | (MH)+ |
|---|---|---|---|
| P-0342 | 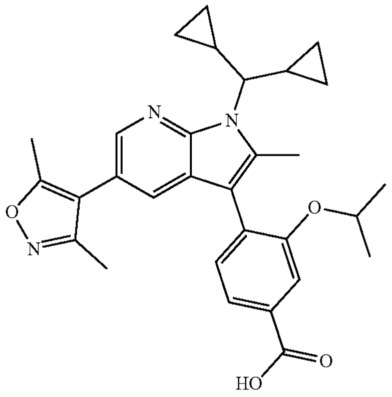 [SMILES: Cc1noc(C)c1-c1cnc2c(c1)c(-c1ccc(C(=O)O)cc1OC(C)C)c(C)n2C(C1CC1)C1CC1] | 4-(1-(dicyclopropylmethyl)-5-(3,5-dimethylisoxazol-4-yl)-2-methyl-1H-pyrrolo[2,3-b]pyridin-3-yl)-3-isopropoxybenzoic acid | 500.2 |
| P-0343 | 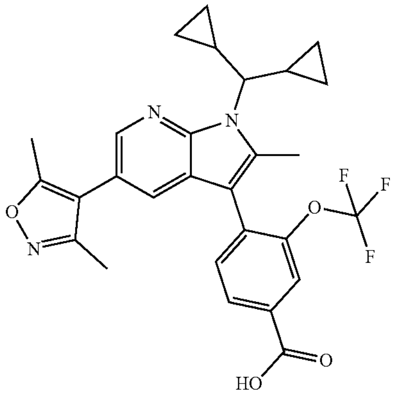 [SMILES: Cc1noc(C)c1-c1cnc2c(c1)c(-c1ccc(C(=O)O)cc1OC(F)(F)F)c(C)n2C(C1CC1)C1CC1] | 4-(1-(dicyclopropylmethyl)-5-(3,5-dimethylisoxazol-4-yl)-2-methyl-1H-pyrrolo[2,3-b]pyridin-3-yl)-3-(trifluoromethoxy)benzoic acid | 526.1 |
| P-0344 | 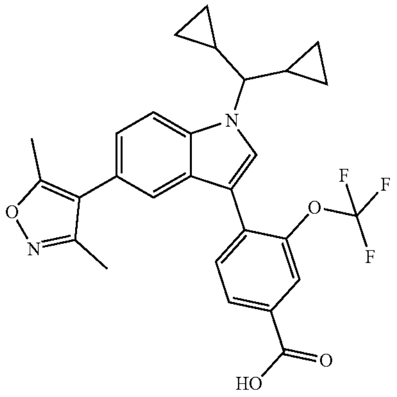 [SMILES: Cc1noc(C)c1-c1ccc2c(c1)c(-c1ccc(C(=O)O)cc1OC(F)(F)F)cn2C(C1CC1)C1CC1] | 4-(1-(dicyclopropylmethyl)-5-(3,5-dimethylisoxazol-4-yl)-1H-indol-3-yl)-3-(trifluoromethoxy)benzoic acid | 511.1 |

TABLE 1-continued
| P# | Structure | Name | (MH)+ |
| --- | --- | --- | --- |
| P-0345 | 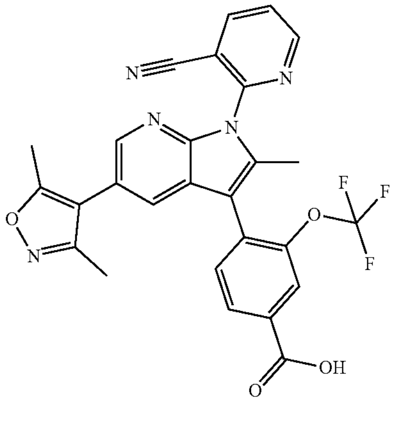 [SMILES: Cc1noc(C)c1-c1cnc2c(c1)c(-c1ccc(C(=O)O)cc1OC(F)(F)F)c(C)n2-c1ncccc1C#N] | 4-(1-(3-cyanopyridin-2-yl)-5-(3,5-dimethylisoxazol-4-yl)-2-methyl-1H-pyrrolo[2,3-b]pyridin-3-yl)-3-(trifluoromethoxy)benzoic acid | 534.0 |
| P-0346 | 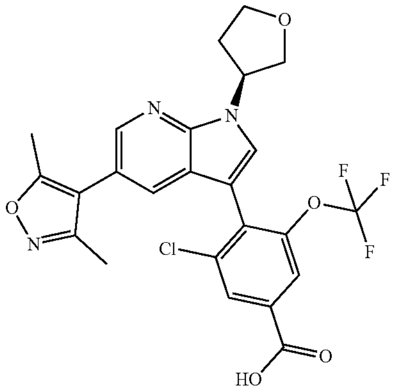 [SMILES: Cc1noc(C)c1-c1cnc2c(c1)c(-c1c(Cl)cc(C(=O)O)cc1OC(F)(F)F)cn2[C@H]1CCOC1] | (S)-3-chloro-4-(5-(3,5-dimethylisoxazol-4-yl)-1-(tetrahydrofuran-3-yl)-1H-pyrrolo[2,3-b]pyridin-3-yl)-5-(trifluoromethoxy)benzoic acid | 522.1 |
| P-0347 | 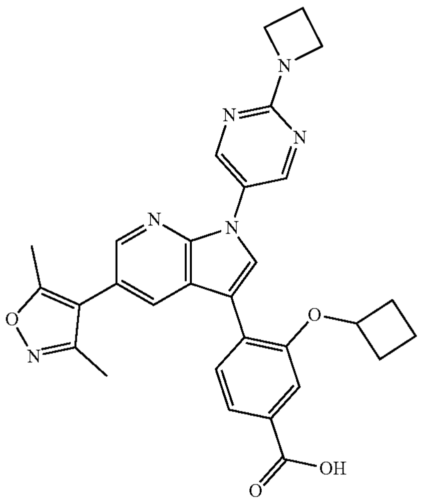 [SMILES: Cc1noc(C)c1-c1cnc2c(c1)c(-c1ccc(C(=O)O)cc1OC1CCC1)cn2-c1cnc(N2CCC2)nc1] | 4-(1-(2-(azetidin-1-yl)pyrimidin-5-yl)-5-(3,5-dimethylisoxazol-4-yl)-1H-pyrrolo[2,3-b]pyridin-3-yl)-3-cyclobutoxybenzoic acid | 537.1 |

TABLE 1-continued
| P# | Structure | Name | (MH)+ |
|---|---|---|---|
| P-0348 | 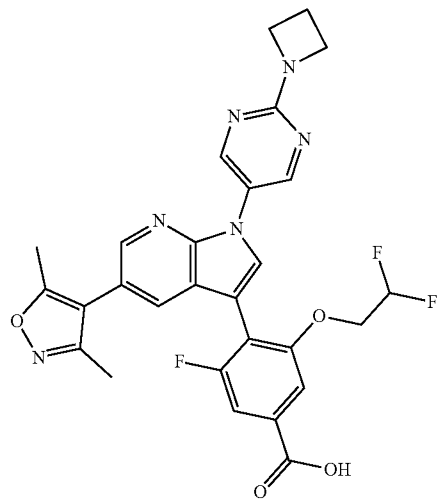 [SMILES: Cc1noc(C)c1-c1cnc2c(c1)c(-c1c(F)cc(C(=O)O)cc1OCC(F)F)cn2-c1cnc(N2CCC2)nc1] | 4-(1-(2-(azetidin-1-yl)pyrimidin-5-yl)-5-(3,5-dimethylisoxazol-4-yl)-1H-pyrrolo[2,3-b]pyridin-3-yl)-3-(2,2-difluoroethoxy)-5-fluorobenzoic acid | 565.1 |
| P-0349 | 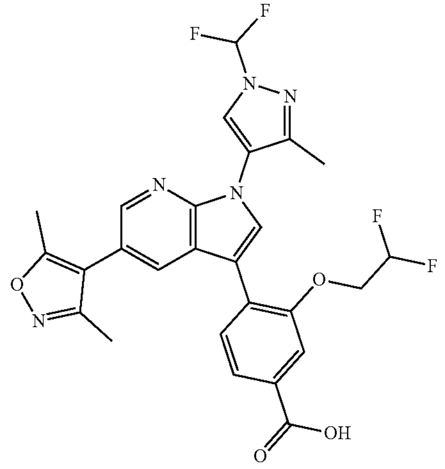 [SMILES: Cc1nn(C(F)F)cc1-n1cc(-c2ccc(C(=O)O)cc2OCC(F)F)c2cc(-c3c(C)noc3C)cnc21] | 3-(2,2-difluoroethoxy)-4-(1-(1-(difluoromethyl)-3-methyl-1H-pyrazol-4-yl)-5-(3,5-dimethylisoxazol-4-yl)-1H-pyrrolo[2,3-b]pyridin-3-yl)benzoic acid | 544.0 |
| P-0350 | 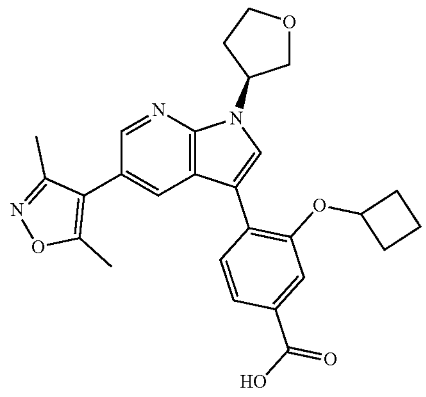 [SMILES: Cc1noc(C)c1-c1cnc2c(c1)c(-c1ccc(C(=O)O)cc1OC1CCC1)cn2[C@H]1CCOC1] | (S)-3-cyclobutoxy-4-(5-(3,5-dimethylisoxazol-4-yl)-1-(tetrahydrofuran-3-yl)-1H-pyrrolo[2,3-b]pyridin-3-yl)benzoic acid | 474.2 |

TABLE 1-continued

| P# | Structure | Name | (MH)+ |
|---|---|---|---|
| P-0351 | 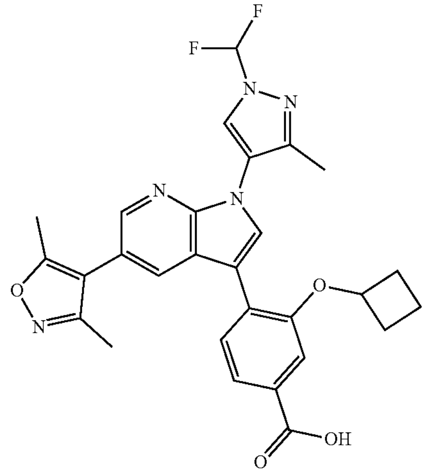 [SMILES: Cc1nn(C(F)F)cc1-n1cc(-c2ccc(C(=O)O)cc2OC2CCC2)c2cc(-c3c(C)noc3C)cnc21] | 3-cyclobutoxy-4-(1-(1-(difluoromethyl)-3-methyl-1H-pyrazol-4-yl)-5-(3,5-dimethylisoxazol-4-yl)-1H-pyrrolo[2,3-b]pyridin-3-yl)benzoic acid | 534.1 |
| P-0352 | 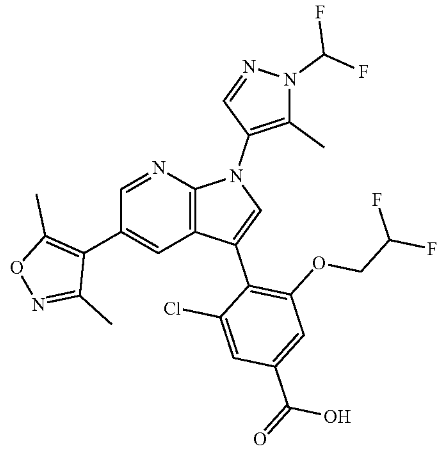 [SMILES: Cc1noc(C)c1-c1cnc2c(c1)c(-c1c(Cl)cc(C(=O)O)cc1OCC(F)F)cn2-c1cnn(C(F)F)c1C] | 3-chloro-5-(2,2-difluoroethoxy)-4-(1-(1-(difluoromethyl)-5-methyl-1H-pyrazol-4-yl)-5-(3,5-dimethylisoxazol-4-yl)-1H-pyrrolo[2,3-b]pyridin-3-yl)benzoic acid | 578.0 |
| P-0353 | 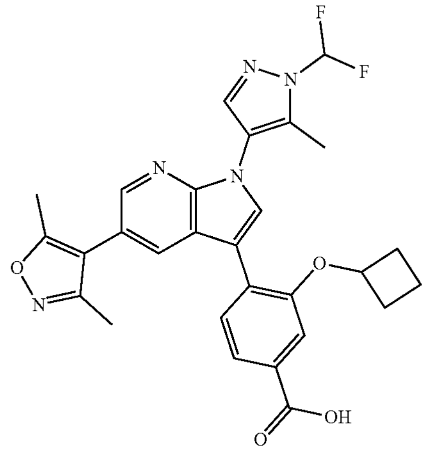 [SMILES: Cc1noc(C)c1-c1cnc2c(c1)c(-c1ccc(C(=O)O)cc1OC1CCC1)cn2-c1cnn(C(F)F)c1C] | 3-cyclobutoxy-4-(1-(1-(difluoromethyl)-5-methyl-1H-pyrazol-4-yl)-5-(3,5-dimethylisoxazol-4-yl)-1H-pyrrolo[2,3-b]pyridin-3-yl)benzoic acid | 534.1 |

TABLE 1-continued
| P# | Structure | Name | (MH)+ |
|---|---|---|---|
| P-0354 | 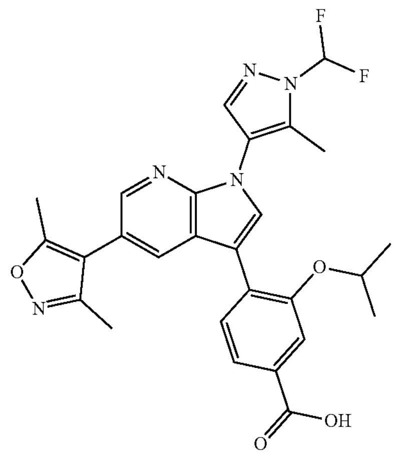 [SMILES: Cc1noc(C)c1-c1cnc2c(c1)c(-c1ccc(C(=O)O)cc1OC(C)C)cn2-c1cnn(C(F)F)c1C] | 4-(1-(1-(difluoromethyl)-5-methyl-1H-pyrazol-4-yl)-5-(3,5-dimethylisoxazol-4-yl)-1H-pyrrolo[2,3-b]pyridin-3-yl)-3-isopropoxybenzoic acid | 520.0 |
| P-0355 | 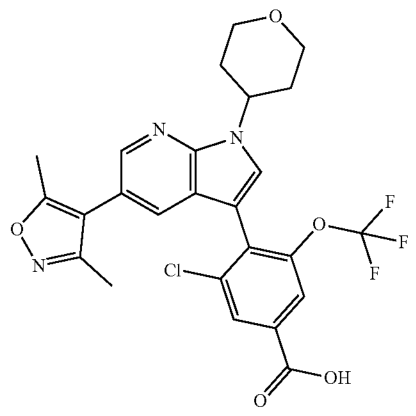 [SMILES: Cc1noc(C)c1-c1cnc2c(c1)c(-c1c(Cl)cc(C(=O)O)cc1OC(F)(F)F)cn2C1CCOCC1] | 3-chloro-4-(5-(3,5-dimethylisoxazol-4-yl)-1-(tetrahydro-2H-pyran-4-yl)-1H-pyrrolo[2,3-b]pyridin-3-yl)-5-(trifluoromethoxy)benzoic acid | 536.1 |
| P-0356 | 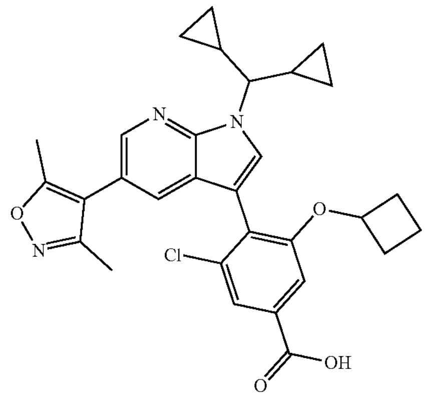 [SMILES: Cc1noc(C)c1-c1cnc2c(c1)c(-c1c(Cl)cc(C(=O)O)cc1OC1CCC1)cn2C(C1CC1)C1CC1] | 3-chloro-5-cyclobutoxy-4-(1-(dicyclopropylmethyl)-5-(3,5-dimethylisoxazol-4-yl)-1H-pyrrolo[2,3-b]pyridin-3-yl)benzoic acid | 532.2 |

TABLE 1-continued
| P# | Structure | Name | (MH)+ |
|---|---|---|---|
| P-0357 | 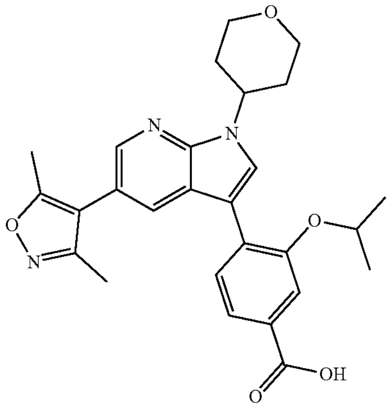 [SMILES: Cc1noc(C)c1-c1cnc2c(c1)c(-c1ccc(C(=O)O)cc1OC(C)C)cn2C1CCOCC1] | 4-(5-(3,5-dimethylisoxazol-4-yl)-1-(tetrahydro-2H-pyran-4-yl)-1H-pyrrolo[2,3-b]pyridin-3-yl)-3-isopropoxybenzoic acid | 476.2 |
| P-0358 | 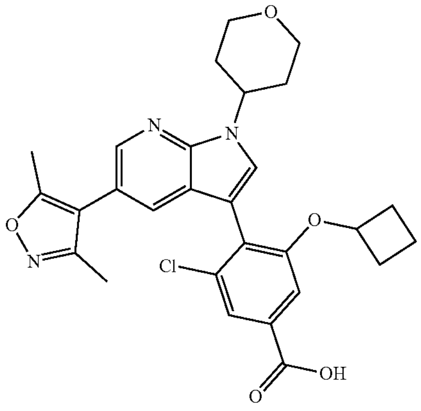 [SMILES: Cc1noc(C)c1-c1cnc2c(c1)c(-c1c(Cl)cc(C(=O)O)cc1OC1CCC1)cn2C1CCOCC1] | 3-chloro-5-cyclobutoxy-4-(5-(3,5-dimethylisoxazol-4-yl)-1-(tetrahydro-2H-pyran-4-yl)-1H-pyrrolo[2,3-b]pyridin-3-yl)benzoic acid | 522.1 |
| P-0359 | 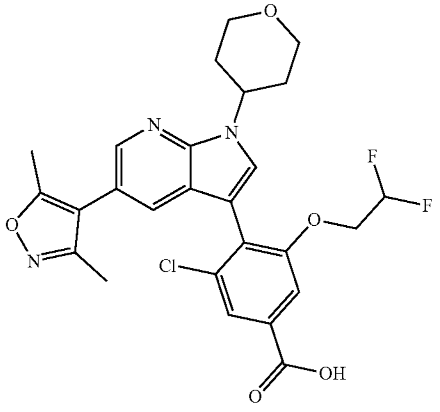 [SMILES: Cc1noc(C)c1-c1cnc2c(c1)c(-c1c(Cl)cc(C(=O)O)cc1OCC(F)F)cn2C1CCOCC1] | 3-chloro-5-(2,2-difluoroethoxy)-4-(5-(3,5-dimethylisoxazol-4-yl)-1-(tetrahydro-2H-pyran-4-yl)-1H-pyrrolo[2,3-b]pyridin-3-yl)benzoic acid | 532.0 |

TABLE 1-continued

| P# | Structure | Name | (MH)+ |
|---|---|---|---|
| P-0360 | 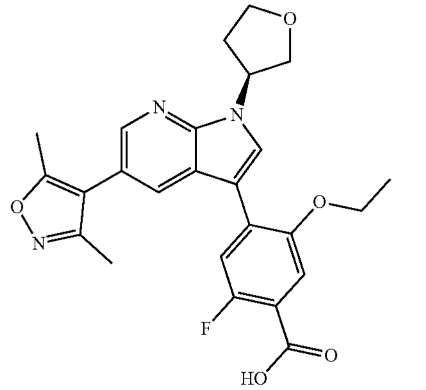 [SMILES: CCOc1cc(C(=O)O)c(F)cc1-c1cn([C@H]2CCOC2)c2ncc(-c3c(C)noc3C)cc12] | (S)-4-(5-(3,5-dimethylisoxazol-4-yl)-1-(tetrahydrofuran-3-yl)-1H-pyrrolo[2,3-b]pyridin-3-yl)-5-ethoxy-2-fluorobenzoic acid | 466.1 |
| P-0361 | 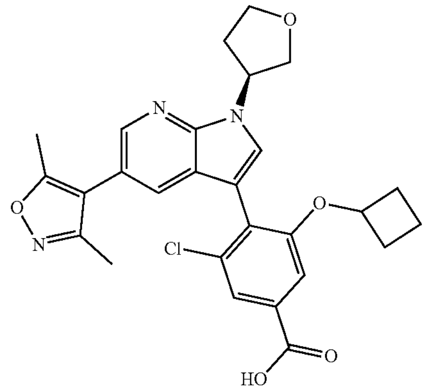 [SMILES: Cc1noc(C)c1-c1cnc2c(c1)c(-c1c(Cl)cc(C(=O)O)cc1OC1CCC1)cn2[C@H]1CCOC1] | (S)-3-chloro-5-cyclobutoxy-4-(5-(3,5-dimethylisoxazol-4-yl)-1-(tetrahydrofuran-3-yl)-1H-pyrrolo[2,3-b]pyridin-3-yl)benzoic acid | 508.1 |
| P-0362 | 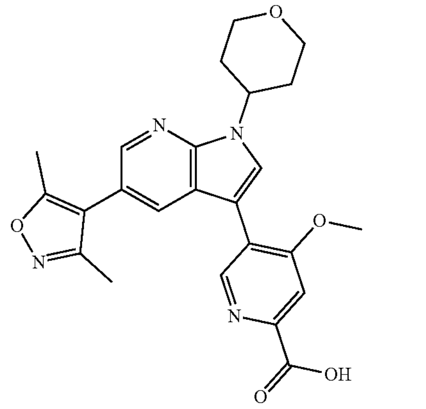 [SMILES: COc1cc(C(=O)O)ncc1-c1cn(C2CCOCC2)c2ncc(-c3c(C)noc3C)cc12] | 5-(5-(3,5-dimethylisoxazol-4-yl)-1-(tetrahydro-2H-pyran-4-yl)-1H-pyrrolo[2,3-b]pyridin-3-yl)-4-methoxypicolinic acid | 449.2 |
| P-0363 | 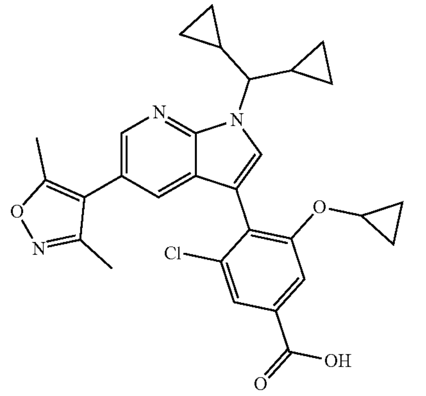 [SMILES: Cc1noc(C)c1-c1cnc2c(c1)c(-c1c(Cl)cc(C(=O)O)cc1OC1CC1)cn2C(C1CC1)C1CC1] | 3-chloro-5-cyclopropoxy-4-(1-(dicyclopropylmethyl)-5-(3,5-dimethylisoxazol-4-yl)-1H-pyrrolo[2,3-b]pyridin-3-yl)benzoic acid | 518.1 |

TABLE 1-continued

| P# | Structure | Name | (MH)+ |
|---|---|---|---|
| P-0364 | 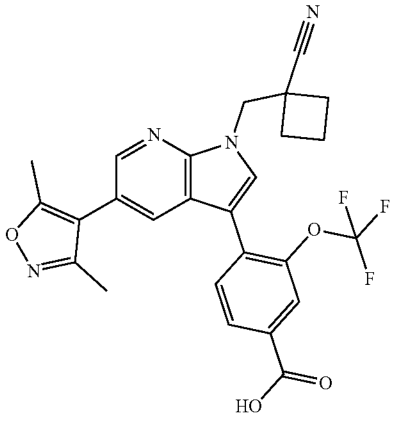 [SMILES: Cc1noc(C)c1-c1cnc2c(c1)c(-c1ccc(C(=O)O)cc1OC(F)(F)F)cn2CC1(C#N)CCC1] | 4-(1-((1-cyanocyclobutyl)methyl)-5-(3,5-dimethylisoxazol-4-yl)-1H-pyrrolo[2,3-b]pyridin-3-yl)-3-(trifluoromethoxy)benzoic acid | 511.2 |
| P-0365 | 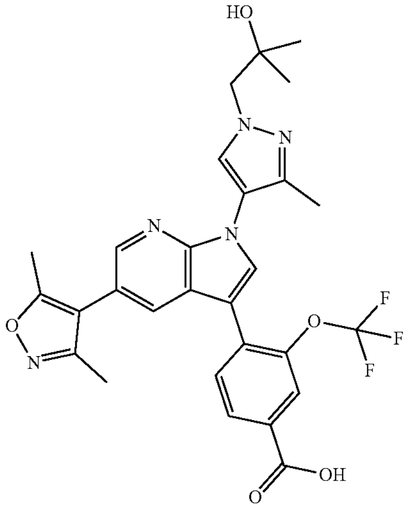 [SMILES: Cc1nn(CC(C)(C)O)cc1-n1cc(-c2ccc(C(=O)O)cc2OC(F)(F)F)c2cc(-c3c(C)noc3C)cnc21] | 4-(5-(3,5-dimethylisoxazol-4-yl)-1-(1-(2-hydroxy-2-methylpropyl)-3-methyl-1H-pyrazol-4-yl)-1H-pyrrolo[2,3-b]pyridin-3-yl)-3-(trifluoromethoxy)benzoic acid | 570.2 |
| P-0366 | 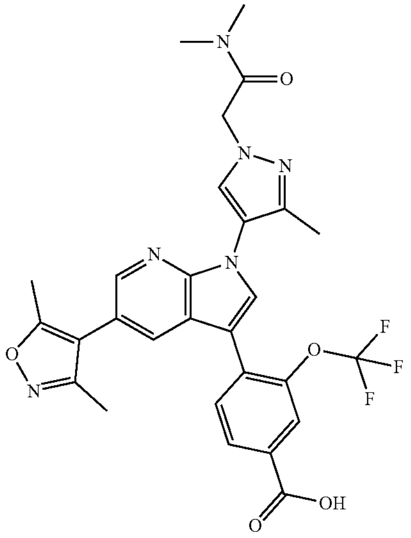 [SMILES: Cc1nn(CC(=O)N(C)C)cc1-n1cc(-c2ccc(C(=O)O)cc2OC(F)(F)F)c2cc(-c3c(C)noc3C)cnc21] | 4-(1-(1-(2-(dimethylamino)-2-oxoethyl)-3-methyl-1H-pyrazol-4-yl)-5-(3,5-dimethylisoxazol-4-yl)-1H-pyrrolo[2,3-b]pyridin-3-yl)-3-(trifluoromethoxy)benzoic acid | 583.2 |

TABLE 1-continued

| P# | Structure | Name | (MH)+ |
| --- | --- | --- | --- |
| P-0367 | 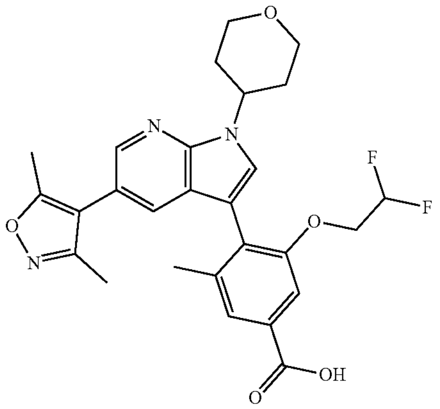 [SMILES: Cc1cc(C(=O)O)cc(OCC(F)F)c1-c1cn(C2CCOCC2)c2ncc(-c3c(C)noc3C)cc12] | 3-(2,2-difluoroethoxy)-4-(5-(3,5-dimethylisoxazol-4-yl)-1-(tetrahydro-2H-pyran-4-yl)-1H-pyrrolo[2,3-b]pyridin-3-yl)-5-methylbenzoic acid | 512.1 |
| P-0368 | 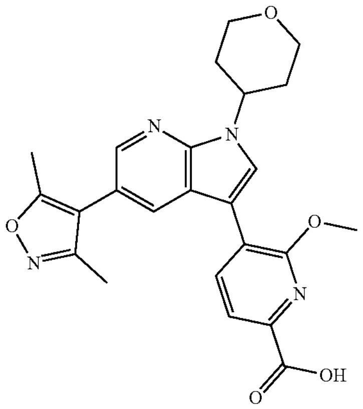 [SMILES: COc1nc(C(=O)O)ccc1-c1cn(C2CCOCC2)c2ncc(-c3c(C)noc3C)cc12] | 5-(5-(3,5-dimethylisoxazol-4-yl)-1-(tetrahydro-2H-pyran-4-yl)-1H-pyrrolo[2,3-b]pyridin-3-yl)-6-methoxypicolinic acid | 449.2 |
| P-0369 | 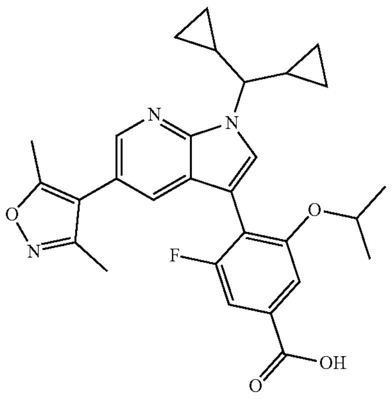 [SMILES: Cc1noc(C)c1-c1cnc2c(c1)c(-c1c(F)cc(C(=O)O)cc1OC(C)C)cn2C(C1CC1)C1CC1] | 4-(1-(dicyclopropylmethyl)-5-(3,5-dimethylisoxazol-4-yl)-1H-pyrrolo[2,3-b]pyridin-3-yl)-3-fluoro-5-isopropoxybenzoic acid | 504.2 |
| P-0370 | 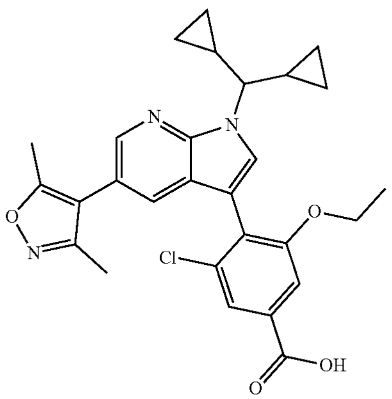 [SMILES: CCOc1cc(C(=O)O)cc(Cl)c1-c1cn(C(C2CC2)C2CC2)c2ncc(-c3c(C)noc3C)cc12] | 3-chloro-4-(1-(dicyclopropylmethyl)-5-(3,5-dimethylisoxazol-4-yl)-1H-pyrrolo[2,3-b]pyridin-3-yl)-5-ethoxybenzoic acid | 506.2 |

TABLE 1-continued
| P# | Structure | Name | (MH)+ |
|---|---|---|---|
| P-0371 | 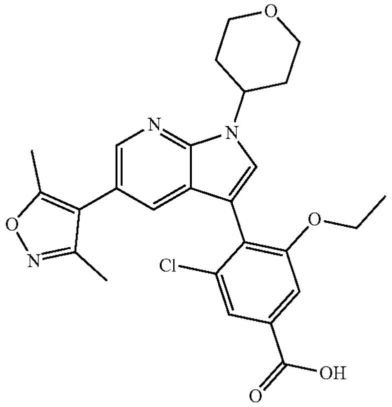 [SMILES: CCOc1cc(C(=O)O)cc(Cl)c1-c1cn(C2CCOCC2)c2ncc(-c3c(C)noc3C)cc12] | 3-chloro-4-(5-(3,5-dimethylisoxazol-4-yl)-1-(tetrahydro-2H-pyran-4-yl)-1H-pyrrolo[2,3-b]pyridin-3-yl)-5-ethoxybenzoic acid | 496.2 |
| P-0372 | 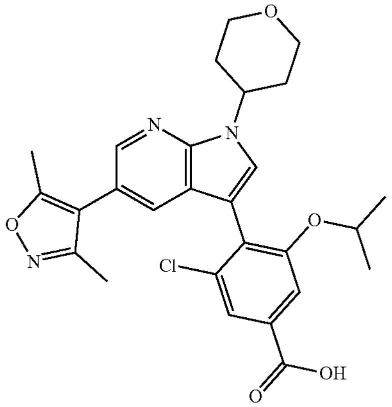 [SMILES: Cc1noc(C)c1-c1cnc2c(c1)c(-c1c(Cl)cc(C(=O)O)cc1OC(C)C)cn2C1CCOCC1] | 3-chloro-4-(5-(3,5-dimethylisoxazol-4-yl)-1-(tetrahydro-2H-pyran-4-yl)-1H-pyrrolo[2,3-b]pyridin-3-yl)-5-isopropoxybenzoic acid | 510.2 |
| P-0373 | 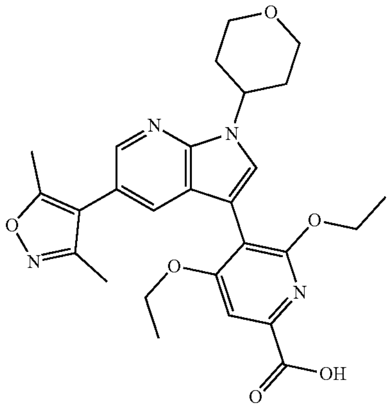 [SMILES: CCOc1cc(C(=O)O)nc(OCC)c1-c1cn(C2CCOCC2)c2ncc(-c3c(C)noc3C)cc12] | 5-(5-(3,5-dimethylisoxazol-4-yl)-1-(tetrahydro-2H-pyran-4-yl)-1H-pyrrolo[2,3-b]pyridin-3-yl)-4,6-diethoxypicolinic acid | 507.2 |

TABLE 1-continued
| P# | Structure | Name | (MH)+ |
|---|---|---|---|
| P-0374 | 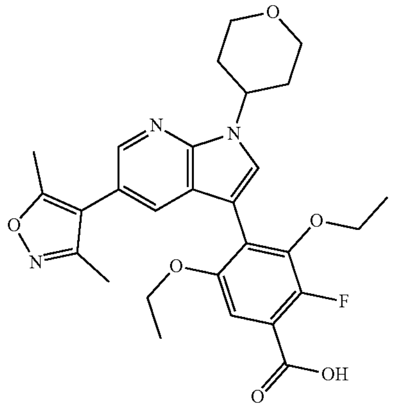 [SMILES: CCOc1cc(C(=O)O)c(F)c(OCC)c1-c1cn(C2CCOCC2)c2ncc(-c3c(C)noc3C)cc12] | 4-(5-(3,5-dimethylisoxazol-4-yl)-1-(tetrahydro-2H-pyran-4-yl)-1H-pyrrolo[2,3-b]pyridin-3-yl)-3,5-diethoxy-2-fluorobenzoic acid | 524.2 |
| P-0375 | 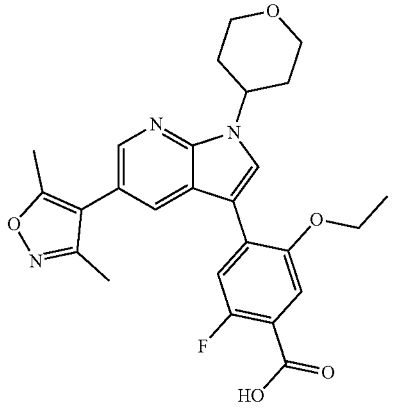 [SMILES: CCOc1cc(C(=O)O)c(F)cc1-c1cn(C2CCOCC2)c2ncc(-c3c(C)noc3C)cc12] | 4-(5-(3,5-dimethylisoxazol-4-yl)-1-(tetrahydro-2H-pyran-4-yl)-1H-pyrrolo[2,3-b]pyridin-3-yl)-5-ethoxy-2-fluorobenzoic acid | 480.2 |
| P-0376 | 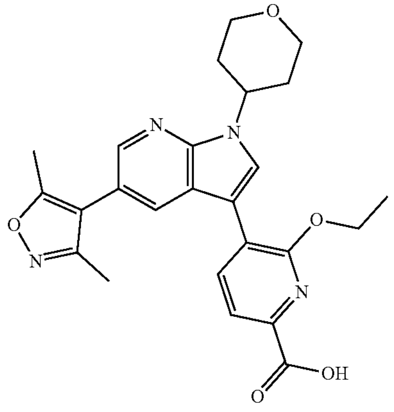 [SMILES: CCOc1nc(C(=O)O)ccc1-c1cn(C2CCOCC2)c2ncc(-c3c(C)noc3C)cc12] | 5-(5-(3,5-dimethylisoxazol-4-yl)-1-(tetrahydro-2H-pyran-4-yl)-1H-pyrrolo[2,3-b]pyridin-3-yl)-6-ethoxypicolinic acid | 463.2 |

TABLE 1-continued

| P# | Structure | Name | (MH)+ |
|---|---|---|---|
| P-0377 | 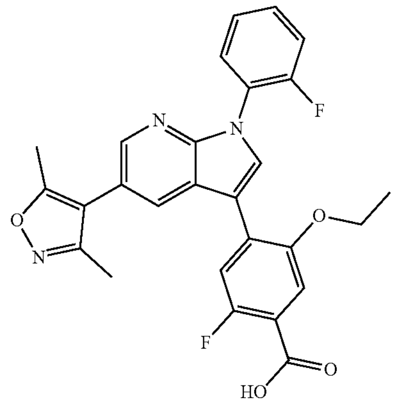 [SMILES: CCOc1cc(C(=O)O)c(F)cc1-c1cn(-c2ccccc2F)c2ncc(-c3c(C)noc3C)cc12] | 4-(5-(3,5-dimethylisoxazol-4-yl)-1-(2-fluorophenyl)-1H-pyrrolo[2,3-b]pyridin-3-yl)-5-ethoxy-2-fluorobenzoic acid | 490.1 |
| P-0378 | 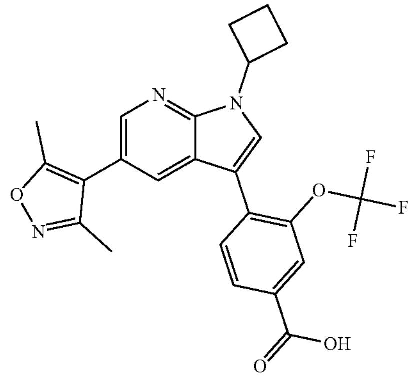 [SMILES: Cc1noc(C)c1-c1cnc2c(c1)c(-c1ccc(C(=O)O)cc1OC(F)(F)F)cn2C1CCC1] | 4-(1-cyclobutyl-5-(3,5-dimethylisoxazol-4-yl)-1H-pyrrolo[2,3-b]pyridin-3-yl)-3-(trifluoromethoxy)benzoic acid | 472.1 |
| P-0379 | 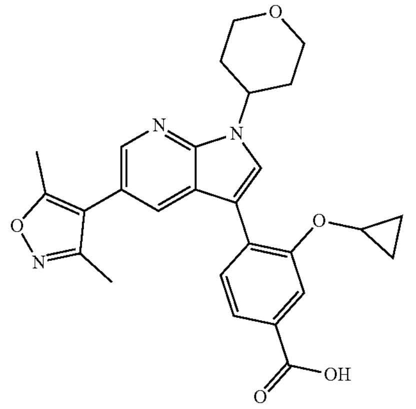 [SMILES: Cc1noc(C)c1-c1cnc2c(c1)c(-c1ccc(C(=O)O)cc1OC1CC1)cn2C1CCOCC1] | 3-cyclopropoxy-4-(5-(3,5-dimethylisoxazol-4-yl)-1-(tetrahydro-2H-pyran-4-yl)-1H-pyrrolo[2,3-b]pyridin-3-yl)benzoic acid | 474.5 |
| P-0380 | 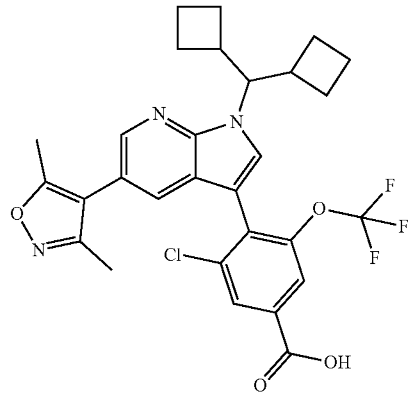 [SMILES: Cc1noc(C)c1-c1cnc2c(c1)c(-c1c(Cl)cc(C(=O)O)cc1OC(F)(F)F)cn2C(C1CCC1)C1CCC1] | 3-chloro-4-(1-(dicyclobutylmethyl)-5-(3,5-dimethylisoxazol-4-yl)-1H-pyrrolo[2,3-b]pyridin-3-yl)-5-(trifluoromethoxy)benzoic acid | 574.1 |

TABLE 1-continued
| P# | Structure | Name | (MH)+ |
|---|---|---|---|
| P-0381 | 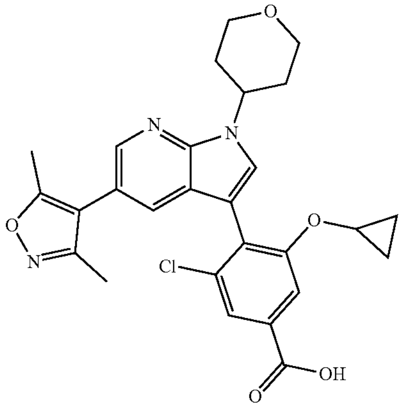 [SMILES: Cc1noc(C)c1-c1cnc2c(c1)c(-c1c(Cl)cc(C(=O)O)cc1OC1CC1)cn2C1CCOCC1] | 3-chloro-5-cyclopropoxy-4-(5-(3,5-dimethylisoxazol-4-yl)-1-(tetrahydro-2H-pyran-4-yl)-1H-pyrrolo[2,3-b]pyridin-3-yl)benzoic acid | 508.1 |
| P-0382 | 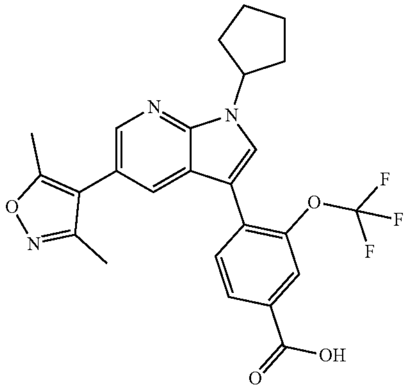 [SMILES: Cc1noc(C)c1-c1cnc2c(c1)c(-c1ccc(C(=O)O)cc1OC(F)(F)F)cn2C1CCCC1] | 4-(1-cyclopentyl-5-(3,5-dimethylisoxazol-4-yl)-1H-pyrrolo[2,3-b]pyridin-3-yl)-3-(trifluoromethoxy)benzoic acid | 486.1 |
| P-0383 | 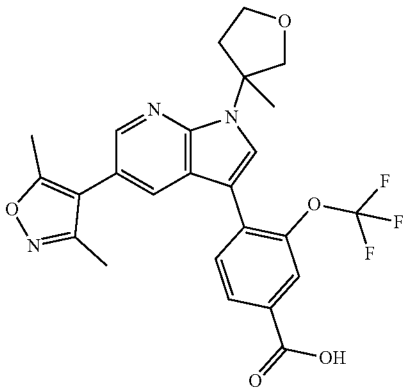 [SMILES: Cc1noc(C)c1-c1cnc2c(c1)c(-c1ccc(C(=O)O)cc1OC(F)(F)F)cn2C1(C)CCOC1] | 4-(5-(3,5-dimethylisoxazol-4-yl)-1-(3-methyltetrahydrofuran-3-yl)-1H-pyrrolo[2,3-b]pyridin-3-yl)-3-(trifluoromethoxy)benzoic acid | 502.0 |

TABLE 1-continued
| P# | Structure | Name | (MH)+ |
|---|---|---|---|
| P-0384 | 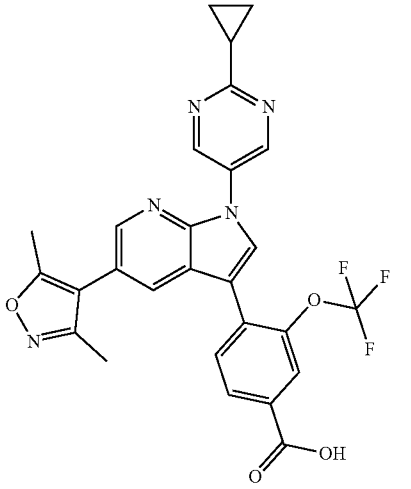 [SMILES: Cc1noc(C)c1-c1cnc2c(c1)c(-c1ccc(C(=O)O)cc1OC(F)(F)F)cn2-c1cnc(C2CC2)nc1] | 4-(1-(2-cyclopropylpyrimidin-5-yl)-5-(3,5-dimethylisoxazol-4-yl)-1H-pyrrolo[2,3-b]pyridin-3-yl)-3-(trifluoromethoxy)benzoic acid | 536.1 |
| P-0385 | 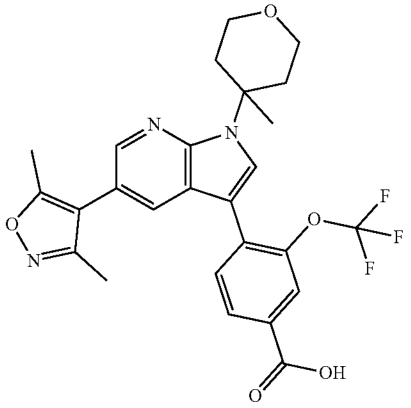 [SMILES: Cc1noc(C)c1-c1cnc2c(c1)c(-c1ccc(C(=O)O)cc1OC(F)(F)F)cn2C1(C)CCOCC1] | 4-(5-(3,5-dimethylisoxazol-4-yl)-1-(4-methyltetrahydro-2H-pyran-4-yl)-1H-pyrrolo[2,3-b]pyridin-3-yl)-3-(trifluoromethoxy)benzoic acid | 516.0 |
| P-0386 | 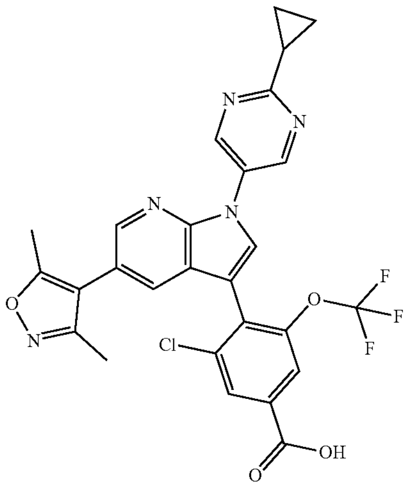 [SMILES: Cc1noc(C)c1-c1cnc2c(c1)c(-c1c(Cl)cc(C(=O)O)cc1OC(F)(F)F)cn2-c1cnc(C2CC2)nc1] | 3-chloro-4-(1-(2-cyclopropylpyrimidin-5-yl)-5-(3,5-dimethylisoxazol-4-yl)-1H-pyrrolo[2,3-b]pyridin-3-yl)-5-(trifluoromethoxy)benzoic acid | 570.1 |

TABLE 1-continued
| P# | Structure | Name | (MH)+ |
|---|---|---|---|
| P-0387 | 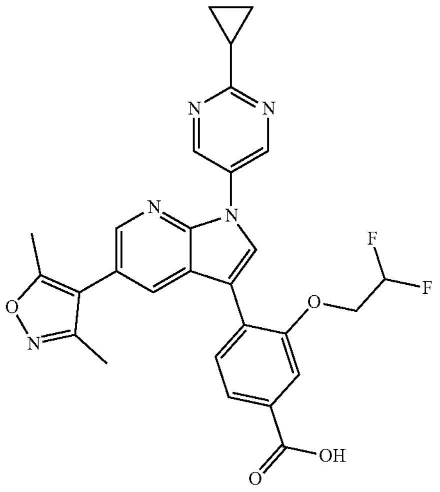 [SMILES: Cc1noc(C)c1-c1cnc2c(c1)c(-c1ccc(C(=O)O)cc1OCC(F)F)cn2-c1cnc(C2CC2)nc1] | 4-(1-(2-cyclopropylpyrimidin-5-yl)-5-(3,5-dimethylisoxazol-4-yl)-1H-pyrrolo[2,3-b]pyridin-3-yl)-3-(2,2-difluoroethoxy)benzoic acid | 532.2 |
| P-0388 | 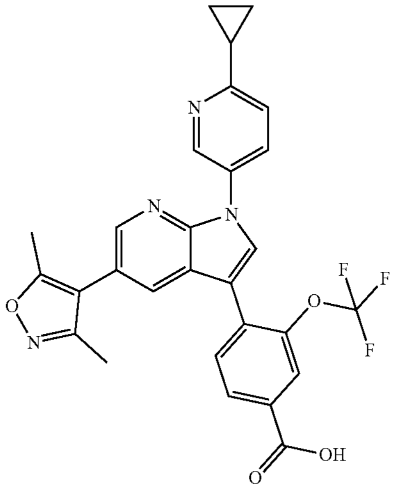 [SMILES: Cc1noc(C)c1-c1cnc2c(c1)c(-c1ccc(C(=O)O)cc1OC(F)(F)F)cn2-c1ccc(C2CC2)nc1] | 4-(1-(6-cyclopropylpyridin-3-yl)-5-(3,5-dimethylisoxazol-4-yl)-1H-pyrrolo[2,3-b]pyridin-3-yl)-3-(trifluoromethoxy)benzoic acid | 535.2 |
| P-0389 | 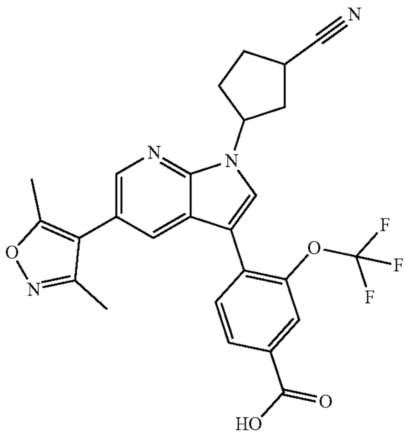 [SMILES: Cc1noc(C)c1-c1cnc2c(c1)c(-c1ccc(C(=O)O)cc1OC(F)(F)F)cn2C1CCC(C#N)C1] | 4-(1-(3-cyanocyclopentyl)-5-(3,5-dimethylisoxazol-4-yl)-1H-pyrrolo[2,3-b]pyridin-3-yl)-3-(trifluoromethoxy)benzoic acid | 511.1 |

TABLE 1-continued
| P# | Structure | Name | (MH)+ |
|---|---|---|---|
| P-0390 | 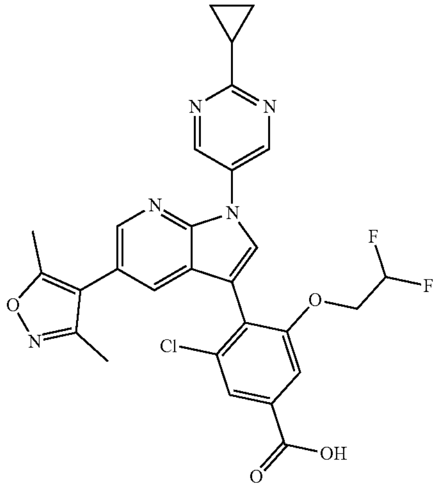 [SMILES: Cc1noc(C)c1-c1cnc2c(c1)c(-c1c(Cl)cc(C(=O)O)cc1OCC(F)F)cn2-c1cnc(C2CC2)nc1] | 3-chloro-4-(1-(2-cyclopropylpyrimidin-5-yl)-5-(3,5-dimethylisoxazol-4-yl)-1H-pyrrolo[2,3-b]pyridin-3-yl)-5-(2,2-difluoroethoxy)benzoic acid | 566.1 |
| P-0391 | 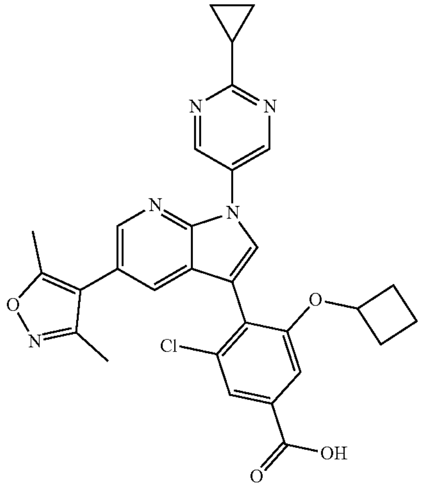 [SMILES: Cc1noc(C)c1-c1cnc2c(c1)c(-c1c(Cl)cc(C(=O)O)cc1OC1CCC1)cn2-c1cnc(C2CC2)nc1] | 3-chloro-5-cyclobutoxy-4-(1-(2-cyclopropylpyrimidin-5-yl)-5-(3,5-dimethylisoxazol-4-yl)-1H-pyrrolo[2,3-b]pyridin-3-yl)benzoic acid | 556.1 |
| P-0392 | 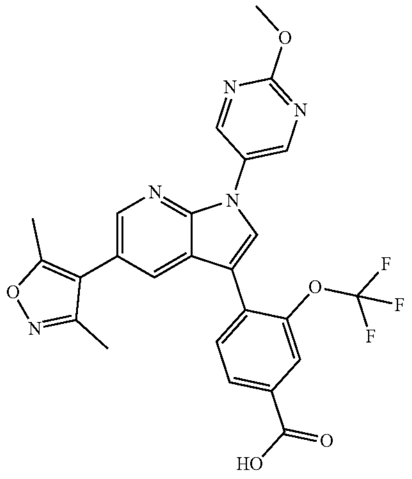 [SMILES: COc1ncc(-n2cc(-c3ccc(C(=O)O)cc3OC(F)(F)F)c3cc(-c4c(C)noc4C)cnc32)cn1] | 4-(5-(3,5-dimethylisoxazol-4-yl)-1-(2-methoxypyrimidin-5-yl)-1H-pyrrolo[2,3-b]pyridin-3-yl)-3-(trifluoromethoxy)benzoic acid | 526.1 |

TABLE 1-continued
| P# | Structure | Name | (MH)+ |
|---|---|---|---|
| P-0393 | 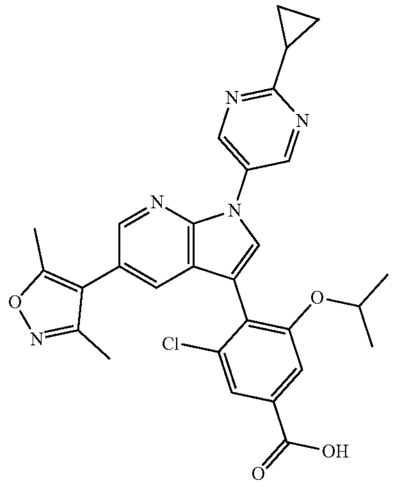 [SMILES: Cc1noc(C)c1-c1cnc2c(c1)c(-c1c(Cl)cc(C(=O)O)cc1OC(C)C)cn2-c1cnc(C2CC2)nc1] | 3-chloro-4-(1-(2-cyclopropylpyrimidin-5-yl)-5-(3,5-dimethylisoxazol-4-yl)-1H-pyrrolo[2,3-b]pyridin-3-yl)-5-isopropoxybenzoic acid | 544.1 |
| P-0394 | 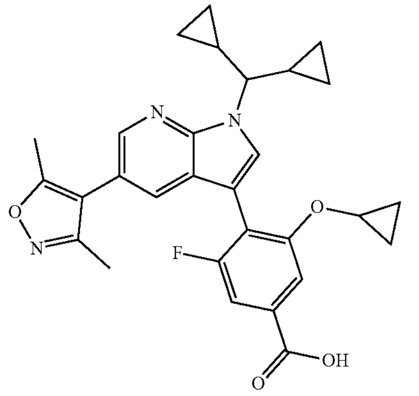 [SMILES: Cc1noc(C)c1-c1cnc2c(c1)c(-c1c(F)cc(C(=O)O)cc1OC1CC1)cn2C(C1CC1)C1CC1] | 3-cyclopropoxy-4-(1-(dicyclopropylmethyl)-5-(3,5-dimethylisoxazol-4-yl)-1H-pyrrolo[2,3-b]pyridin-3-yl)-5-fluorobenzoic acid | 502.2 |
| P-0395 | 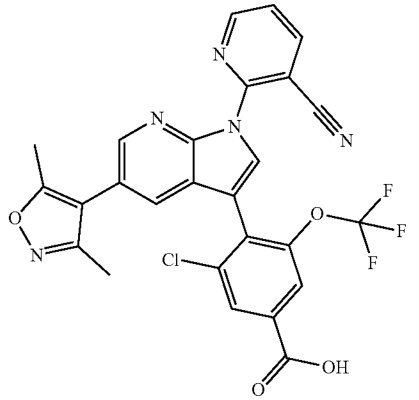 [SMILES: Cc1noc(C)c1-c1cnc2c(c1)c(-c1c(Cl)cc(C(=O)O)cc1OC(F)(F)F)cn2-c1ncccc1C#N] | 3-chloro-4-(1-(3-cyanopyridin-2-yl)-5-(3,5-dimethylisoxazol-4-yl)-1H-pyrrolo[2,3-b]pyridin-3-yl)-5-(trifluoromethoxy)benzoic acid | 554.1 |

TABLE 1-continued
| P# | Structure | Name | (MH)+ |
|---|---|---|---|
| P-0396 | 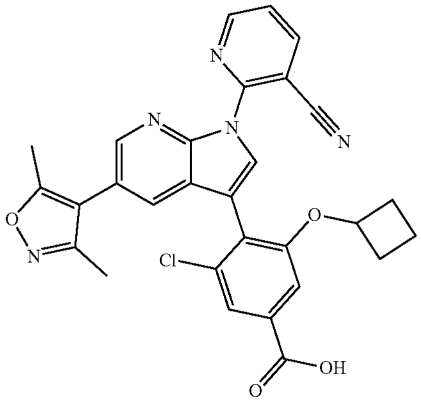 [SMILES: Cc1noc(C)c1-c1cnc2c(c1)c(-c1c(Cl)cc(C(=O)O)cc1OC1CCC1)cn2-c1ncccc1C#N] | 3-chloro-4-(1-(3-cyanopyridin-2-yl)-5-(3,5-dimethylisoxazol-4-yl)-1H-pyrrolo[2,3-b]pyridin-3-yl)-5-cyclobutoxybenzoic acid | 540.0 |
| P-0397 | 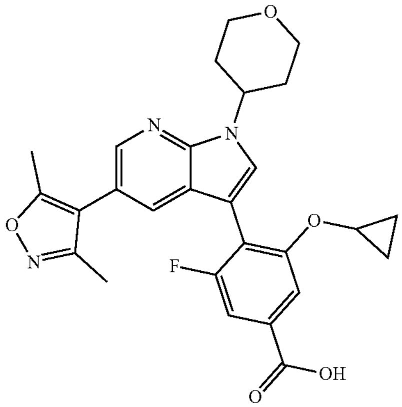 [SMILES: Cc1noc(C)c1-c1cnc2c(c1)c(-c1c(F)cc(C(=O)O)cc1OC1CC1)cn2C1CCOCC1] | 3-cyclopropoxy-4-(5-(3,5-dimethylisoxazol-4-yl)-1-(tetrahydro-2H-pyran-4-yl)-1H-pyrrolo[2,3-b]pyridin-3-yl)-5-fluorobenzoic acid | 492.2 |
| P-0398 | 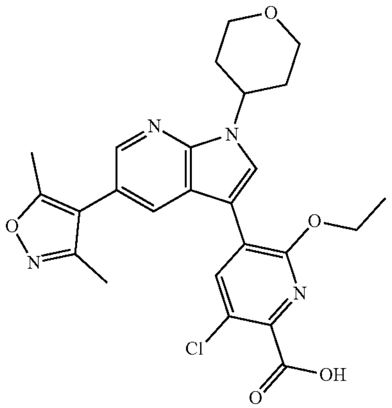 [SMILES: CCOc1nc(C(=O)O)c(Cl)cc1-c1cn(C2CCOCC2)c2ncc(-c3c(C)noc3C)cc12] | 3-chloro-5-(5-(3,5-dimethylisoxazol-4-yl)-1-(tetrahydro-2H-pyran-4-yl)-1H-pyrrolo[2,3-b]pyridin-3-yl)-6-ethoxypicolinic acid | 497.1 |

TABLE 1-continued
| P# | Structure | Name | (MH)+ |
|---|---|---|---|
| P-0399 | 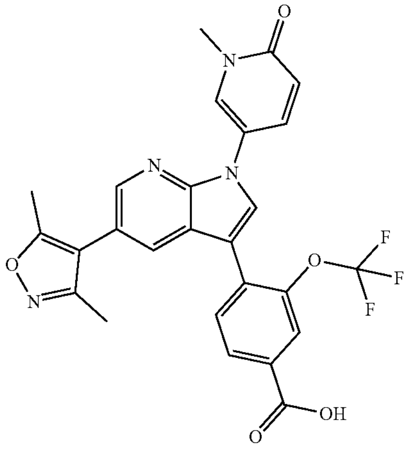 [SMILES: Cc1noc(C)c1-c1cnc2c(c1)c(-c1ccc(C(=O)O)cc1OC(F)(F)F)cn2-c1ccc(=O)n(C)c1] | 4-(5-(3,5-dimethylisoxazol-4-yl)-1-(1-methyl-6-oxo-1,6-dihydropyridin-3-yl)-1H-pyrrolo[2,3-b]pyridin-3-yl)-3-(trifluoromethoxy)benzoic acid | 525.1 |
| P-0400 | 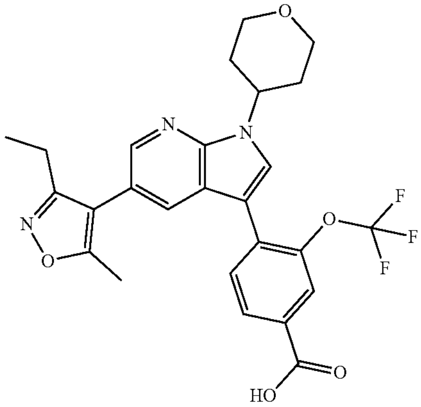 [SMILES: CCc1noc(C)c1-c1cnc2c(c1)c(-c1ccc(C(=O)O)cc1OC(F)(F)F)cn2C1CCOCC1] | 4-(5-(3-ethyl-5-methylisoxazol-4-yl)-1-(tetrahydro-2H-pyran-4-yl)-1H-pyrrolo[2,3-b]pyridin-3-yl)-3-(trifluoromethoxy)benzoic acid | 516.1 |
| P-0401 | 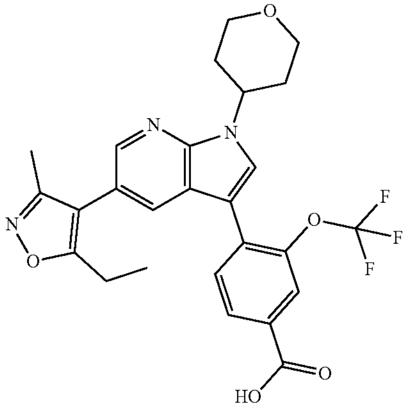 [SMILES: CCc1onc(C)c1-c1cnc2c(c1)c(-c1ccc(C(=O)O)cc1OC(F)(F)F)cn2C1CCOCC1] | 4-(5-(5-ethyl-3-methylisoxazol-4-yl)-1-(tetrahydro-2H-pyran-4-yl)-1H-pyrrolo[2,3-b]pyridin-3-yl)-3-(trifluoromethoxy)benzoic acid | 516.1 |

TABLE 1-continued
| P# | Structure | Name | (MH)+ |
|---|---|---|---|
| P-0402 | 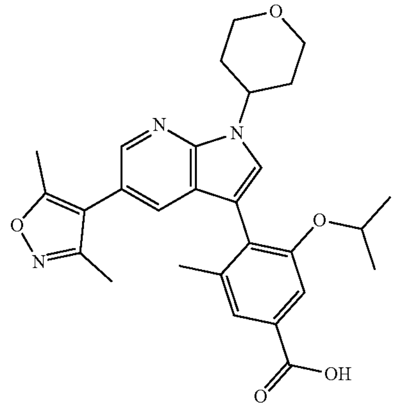 [SMILES: Cc1cc(C(=O)O)cc(OC(C)C)c1-c1cn(C2CCOCC2)c2ncc(-c3c(C)noc3C)cc12] | 4-(5-(3,5-dimethylisoxazol-4-yl)-1-(tetrahydro-2H-pyran-4-yl)-1H-pyrrolo[2,3-b]pyridin-3-yl)-3-isopropoxy-5-methylbenzoic acid | 490.1 |
| P-0403 | 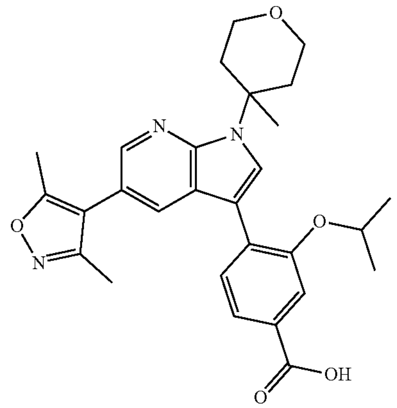 [SMILES: Cc1noc(C)c1-c1cnc2c(c1)c(-c1ccc(C(=O)O)cc1OC(C)C)cn2C1(C)CCOCC1] | 4-(5-(3,5-dimethylisoxazol-4-yl)-1-(4-methyltetrahydro-2H-pyran-4-yl)-1H-pyrrolo[2,3-b]pyridin-3-yl)-3-isopropoxybenzoic acid | 490.2 |
| P-0404 | 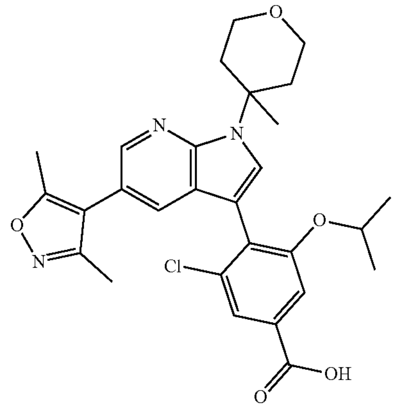 [SMILES: Cc1noc(C)c1-c1cnc2c(c1)c(-c1c(Cl)cc(C(=O)O)cc1OC(C)C)cn2C1(C)CCOCC1] | 3-chloro-4-(5-(3,5-dimethylisoxazol-4-yl)-1-(4-methyltetrahydro-2H-pyran-4-yl)-1H-pyrrolo[2,3-b]pyridin-3-yl)-5-isopropoxybenzoic acid | 524.2 |

TABLE 1-continued

| P# | Structure | Name | (MH)+ |
|---|---|---|---|
| P-0405 | 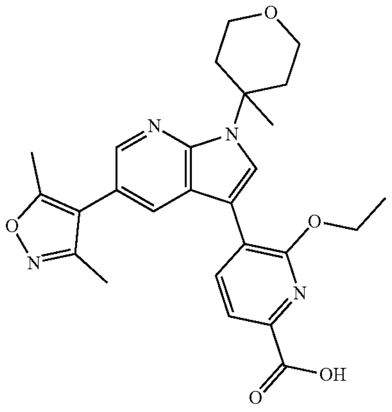 [SMILES: CCOc1nc(C(=O)O)ccc1-c1cn(C2(C)CCOCC2)c2ncc(-c3c(C)noc3C)cc12] | 5-(5-(3,5-dimethylisoxazol-4-yl)-1-(4-methyltetrahydro-2H-pyran-4-yl)-1H-pyrrolo[2,3-b]pyridin-3-yl)-6-ethoxypicolinic acid | 477.1 |
| P-0406 | 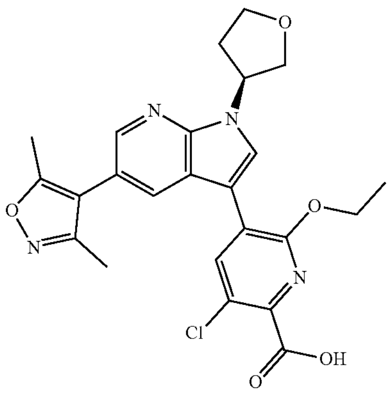 [SMILES: CCOc1nc(C(=O)O)c(Cl)cc1-c1cn([C@H]2CCOC2)c2ncc(-c3c(C)noc3C)cc12] | (S)-3-chloro-5-(5-(3,5-dimethylisoxazol-4-yl)-1-(tetrahydrofuran-3-yl)-1H-pyrrolo[2,3-b]pyridin-3-yl)-6-ethoxypicolinic acid | 483.1 |
| P-0407 | 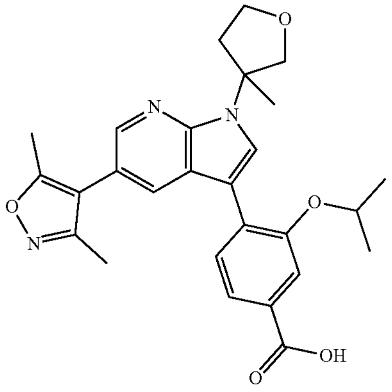 [SMILES: Cc1noc(C)c1-c1cnc2c(c1)c(-c1ccc(C(=O)O)cc1OC(C)C)cn2C1(C)CCOC1] | 4-(5-(3,5-dimethylisoxazol-4-yl)-1-(3-methyltetrahydrofuran-3-yl)-1H-pyrrolo[2,3-b]pyridin-3-yl)-3-isopropoxybenzoic acid | 476.1 |
| P-0408 | 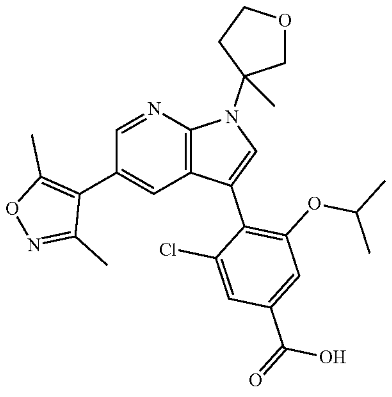 [SMILES: Cc1noc(C)c1-c1cnc2c(c1)c(-c1c(Cl)cc(C(=O)O)cc1OC(C)C)cn2C1(C)CCOC1] | 3-chloro-4-(5-(3,5-dimethylisoxazol-4-yl)-1-(3-methyltetrahydrofuran-3-yl)-1H-pyrrolo[2,3-b]pyridin-3-yl)-5-isopropoxybenzoic acid | 510.1 |

TABLE 1-continued
| P# | Structure | Name | (MH)+ |
|---|---|---|---|
| P-0409 | 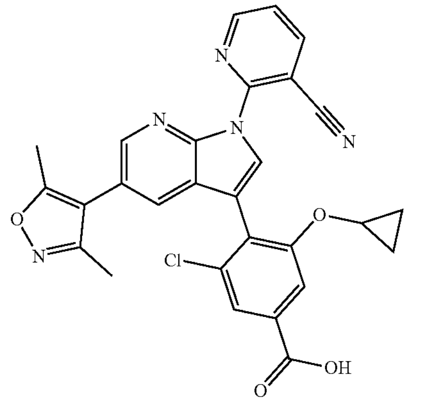 [SMILES: Cc1noc(C)c1-c1cnc2c(c1)c(-c1c(Cl)cc(C(=O)O)cc1OC1CC1)cn2-c1ncccc1C#N] | 3-chloro-4-(1-(3-cyanopyridin-2-yl)-5-(3,5-dimethylisoxazol-4-yl)-1H-pyrrolo[2,3-b]pyridin-3-yl)-5-cyclopropoxybenzoic acid | 526.1 |
| P-0410 | 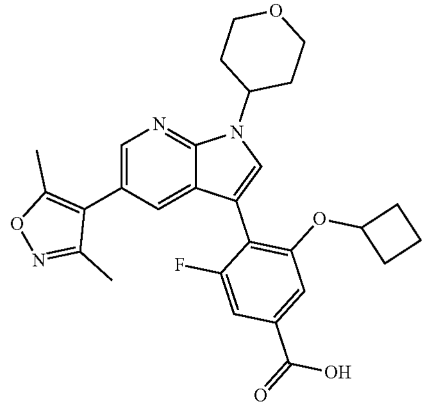 | 3-cyclobutoxy-4-(5-(3,5-dimethylisoxazol-4-yl)-1-(tetrahydro-2H-pyran-4-yl)-1H-pyrrolo[2,3-b]pyridin-3-yl)-5-fluorobenzoic acid | 506.2 |
| P-0411 | 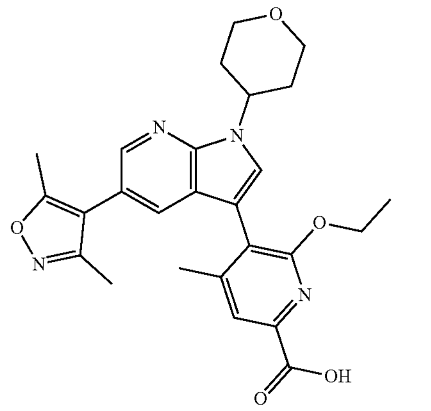 [SMILES: CCOc1nc(C(=O)O)cc(C)c1-c1cn(C2CCOCC2)c2ncc(-c3c(C)noc3C)cc12] | 5-(5-(3,5-dimethylisoxazol-4-yl)-1-(tetrahydro-2H-pyran-4-yl)-1H-pyrrolo[2,3-b]pyridin-3-yl)-6-ethoxy-4-methylpicolinic acid | 477.2 |

TABLE 1-continued
| P# | Structure | Name | (MH)+ |
|---|---|---|---|
| P-0412 | 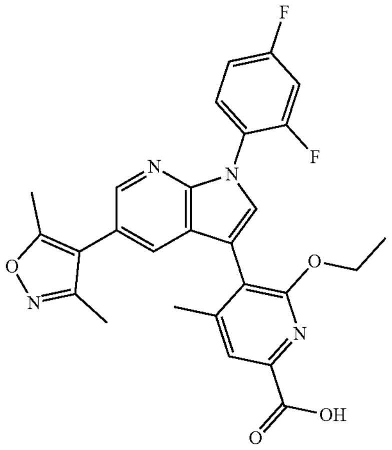 [SMILES: CCOc1nc(C(=O)O)cc(C)c1-c1cn(-c2ccc(F)cc2F)c2ncc(-c3c(C)noc3C)cc12] | 5-(1-(2,4-difluorophenyl)-5-(3,5-dimethylisoxazol-4-yl)-1H-pyrrolo[2,3-b]pyridin-3-yl)-6-ethoxy-4-methylpicolinic acid | 505.2 |
| P-0413 | 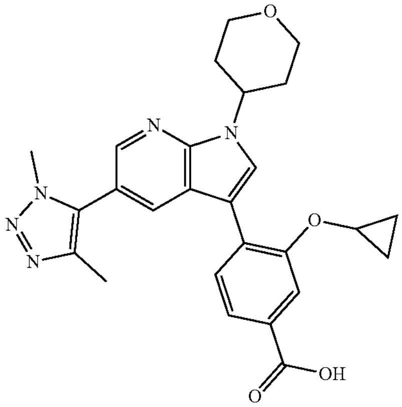 [SMILES: Cc1nnn(C)c1-c1cnc2c(c1)c(-c1ccc(C(=O)O)cc1OC1CC1)cn2C1CCOCC1] | 3-cyclopropoxy-4-(5-(1,4-dimethyl-1H-1,2,3-triazol-5-yl)-1-(tetrahydro-2H-pyran-4-yl)-1H-pyrrolo[2,3-b]pyridin-3-yl)benzoic acid | Insert |
| P-0414 | 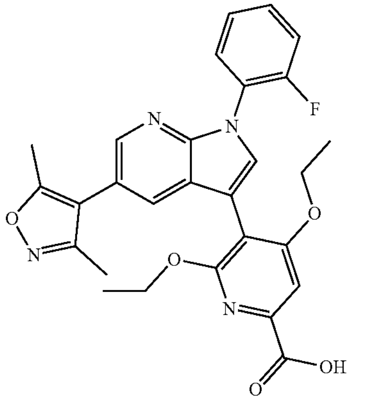 [SMILES: CCOc1cc(C(=O)O)nc(OCC)c1-c1cn(-c2ccccc2F)c2ncc(-c3c(C)noc3C)cc12] | 5-(5-(3,5-dimethylisoxazol-4-yl)-1-(2-fluorophenyl)-1H-pyrrolo[2,3-b]pyridin-3-yl)-4,6-diethoxypicolinic acid | 517.2 |

TABLE 1-continued

| P# | Structure | Name | (MH)+ |
| --- | --- | --- | --- |
| P-0415 | 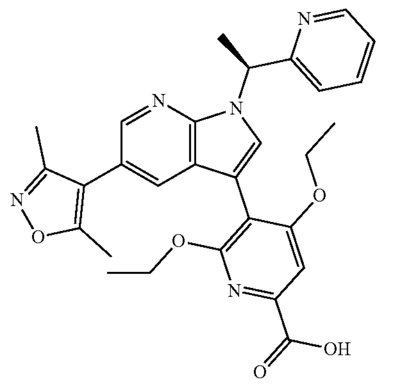 [SMILES: CCOc1cc(C(=O)O)nc(OCC)c1-c1cn([C@@H](C)c2ccccn2)c2ncc(-c3c(C)noc3C)cc12] | (S)-5-(5-(3,5-dimethylisoxazol-4-yl)-1-(1-(pyridin-2-yl)ethyl)-1H-pyrrolo[2,3-b]pyridin-3-yl)-4,6-diethoxypicolinic acid | 528.2 |
| P-0416 | 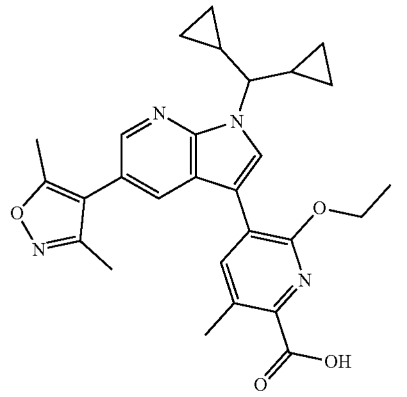 [SMILES: CCOc1nc(C(=O)O)c(C)cc1-c1cn(C(C2CC2)C2CC2)c2ncc(-c3c(C)noc3C)cc12] | 5-(1-(dicyclopropylmethyl)-5-(3,5-dimethylisoxazol-4-yl)-1H-pyrrolo[2,3-b]pyridin-3-yl)-6-ethoxy-3-methylpicolinic acid | 487.2 |
| P-0417 | 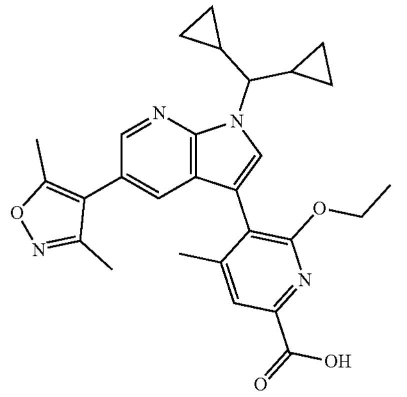 [SMILES: CCOc1nc(C(=O)O)cc(C)c1-c1cn(C(C2CC2)C2CC2)c2ncc(-c3c(C)noc3C)cc12] | 5-(1-(dicyclopropylmethyl)-5-(3,5-dimethylisoxazol-4-yl)-1H-pyrrolo[2,3-b]pyridin-3-yl)-6-ethoxy-4-methylpicolinic acid | 487.2 |
| P-0418 | 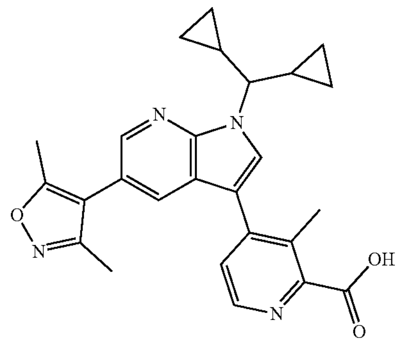 [SMILES: Cc1noc(C)c1-c1cnc2c(c1)c(-c1ccnc(C(=O)O)c1C)cn2C(C1CC1)C1CC1] | 4-(1-(dicyclopropylmethyl)-5-(3,5-dimethylisoxazol-4-yl)-1H-pyrrolo[2,3-b]pyridin-3-yl)-3-methylpicolinic acid | 443.2 |

TABLE 1-continued

| P# | Structure | Name | (MH)+ |
|---|---|---|---|
| P-0419 | 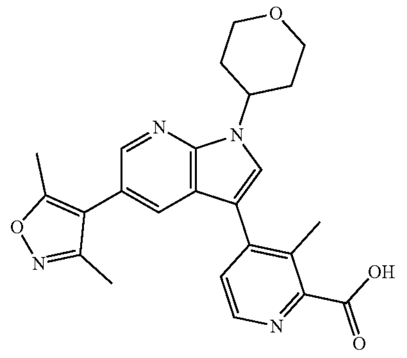 [SMILES: Cc1noc(C)c1-c1cnc2c(c1)c(-c1ccnc(C(=O)O)c1C)cn2C1CCOCC1] | 4-(5-(3,5-dimethylisoxazol-4-yl)-1-(tetrahydro-2H-pyran-4-yl)-1H-pyrrolo[2,3-b]pyridin-3-yl)-3-methylpicolinic acid | 433.2 |
| P-0420 | 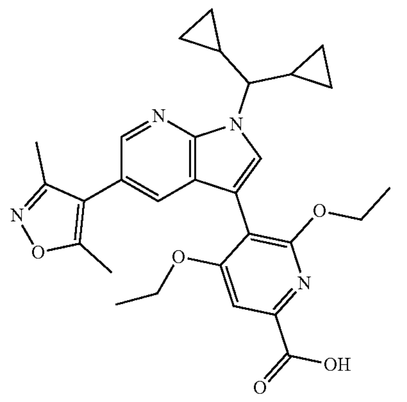 [SMILES: CCOc1cc(C(=O)O)nc(OCC)c1-c1cn(C(C2CC2)C2CC2)c2ncc(-c3c(C)noc3C)cc12] | 5-(1-(dicyclopropylmethyl)-5-(3,5-dimethylisoxazol-4-yl)-1H-pyrrolo[2,3-b]pyridin-3-yl)-4,6-diethoxypicolinic acid | 517.2 |
| P-0421 | 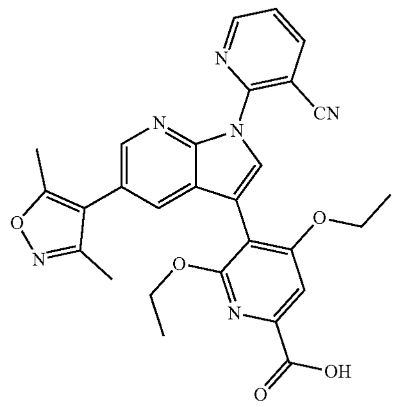 [SMILES: CCOc1cc(C(=O)O)nc(OCC)c1-c1cn(-c2ncccc2C#N)c2ncc(-c3c(C)noc3C)cc12] | 5-(1-(3-cyanopyridin-2-yl)-5-(3,5-dimethylisoxazol-4-yl)-1H-pyrrolo[2,3-b]pyridin-3-yl)-4,6-diethoxypicolinic acid | 525.1 |
| P-0422 | 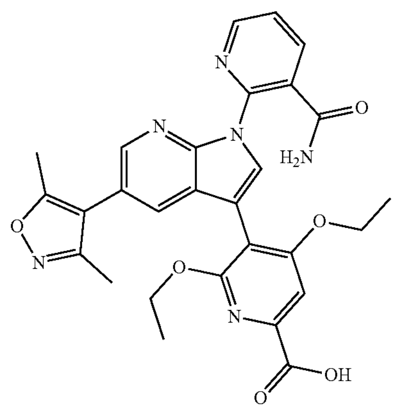 [SMILES: CCOc1cc(C(=O)O)nc(OCC)c1-c1cn(-c2ncccc2C(N)=O)c2ncc(-c3c(C)noc3C)cc12] | 5-(1-(3-carbamoylpyridin-2-yl)-5-(3,5-dimethylisoxazol-4-yl)-1H-pyrrolo[2,3-b]pyridin-3-yl)-4,6-diethoxypicolinic acid | 543.2 |

TABLE 1-continued
| P# | Structure | Name | (MH)+ |
|---|---|---|---|
| P-0423 | 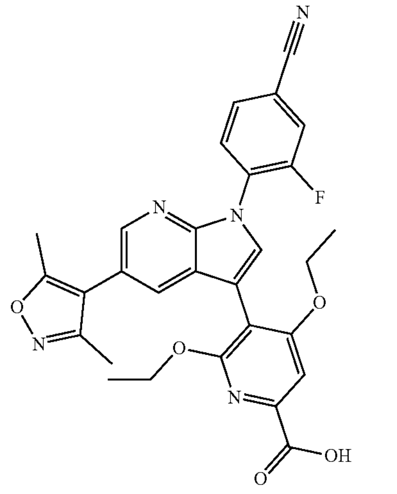 [SMILES: CCOc1cc(C(=O)O)nc(OCC)c1-c1cn(-c2ccc(C#N)cc2F)c2ncc(-c3c(C)noc3C)cc12] | 5-(1-(4-cyano-2-fluorophenyl)-5-(3,5-dimethylisoxazol-4-yl)-1H-pyrrolo[2,3-b]pyridin-3-yl)-4,6-diethoxypicolinic acid | 542.2 |
| P-0424 | 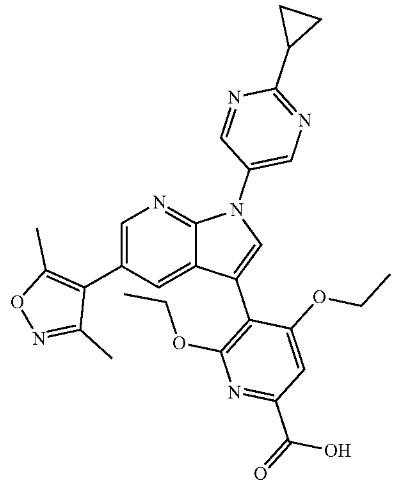 [SMILES: CCOc1cc(C(=O)O)nc(OCC)c1-c1cn(-c2cnc(C3CC3)nc2)c2ncc(-c3c(C)noc3C)cc12] | 5-(1-(2-cyclopropylpyrimidin-5-yl)-5-(3,5-dimethylisoxazol-4-yl)-1H-pyrrolo[2,3-b]pyridin-3-yl)-4,6-diethoxypicolinic acid | 541.2 |
| P-0425 | 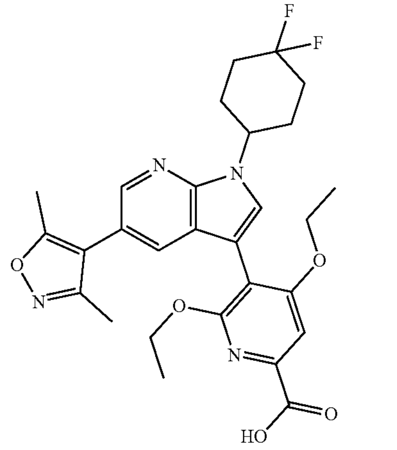 [SMILES: CCOc1cc(C(=O)O)nc(OCC)c1-c1cn(C2CCC(F)(F)CC2)c2ncc(-c3c(C)noc3C)cc12] | 5-(1-(4,4-difluorocyclohexyl)-5-(3,5-dimethylisoxazol-4-yl)-1H-pyrrolo[2,3-b]pyridin-3-yl)-4,6-diethoxypicolinic acid | 541.2 |

TABLE 1-continued
| P# | Structure | Name | (MH)+ |
| --- | --- | --- | --- |
| P-0426 | 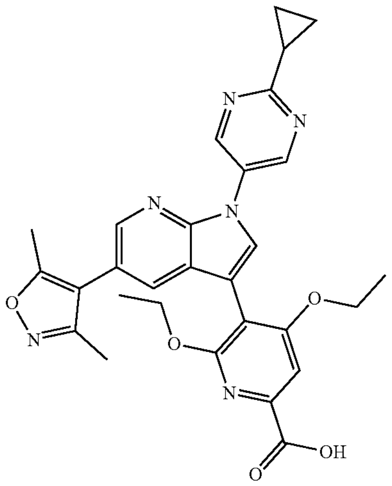 [SMILES: CCOc1cc(C(=O)O)nc(OCC)c1-c1cn(-c2cnc(C3CC3)nc2)c2ncc(-c3c(C)noc3C)cc12] | 5-(1-(6-cyclopropylpyridin-3-yl)-5-(3,5-dimethylisoxazol-4-yl)-1H-pyrrolo[2,3-b]pyridin-3-yl)-4,6-diethoxypicolinic acid | 540.2 |
| P-0427 | 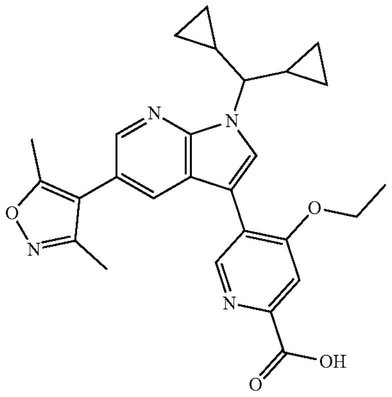 [SMILES: CCOc1cc(C(=O)O)ncc1-c1cn(C(C2CC2)C2CC2)c2ncc(-c3c(C)noc3C)cc12] | 5-(1-(dicyclopropylmethyl)-5-(3,5-dimethylisoxazol-4-yl)-1H-pyrrolo[2,3-b]pyridin-3-yl)-4-ethoxypicolinic acid | 473.2 |
| P-0428 | 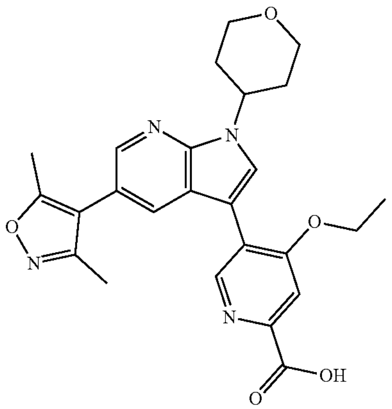 [SMILES: CCOc1cc(C(=O)O)ncc1-c1cn(C2CCOCC2)c2ncc(-c3c(C)noc3C)cc12] | 5-(5-(3,5-dimethylisoxazol-4-yl)-1-(tetrahydro-2H-pyran-4-yl)-1H-pyrrolo[2,3-b]pyridin-3-yl)-4-ethoxypicolinic acid | 463.2 |

TABLE 1-continued
| P# | Structure | Name | (MH)+ |
| --- | --- | --- | --- |
| P-0429 | 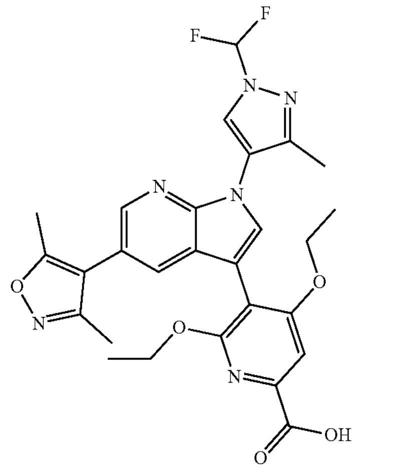 [SMILES: CCOc1cc(C(=O)O)nc(OCC)c1-c1cn(-c2cn(C(F)F)nc2C)c2ncc(-c3c(C)noc3C)cc12] | 5-(1-(1-(difluoromethyl)-3-methyl-1H-pyrazol-4-yl)-5-(3,5-dimethylisoxazol-4-yl)-1H-pyrrolo[2,3-b]pyridin-3-yl)-4,6-diethoxypicolinic acid | 553.2 |
| P-0430 | 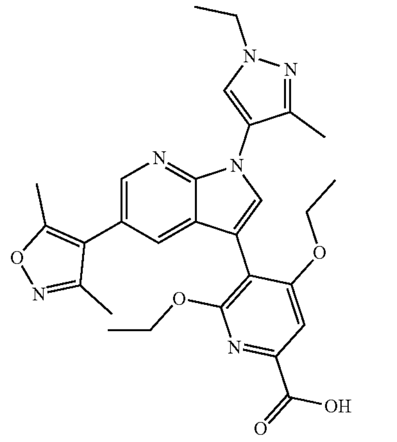 [SMILES: CCOc1cc(C(=O)O)nc(OCC)c1-c1cn(-c2cn(CC)nc2C)c2ncc(-c3c(C)noc3C)cc12] | 5-(5-(3,5-dimethylisoxazol-4-yl)-1-(1-ethyl-3-methyl-1H-pyrazol-4-yl)-1H-pyrrolo[2,3-b]pyridin-3-yl)-4,6-diethoxypicolinic acid | 531.2 |
| P-0431 | 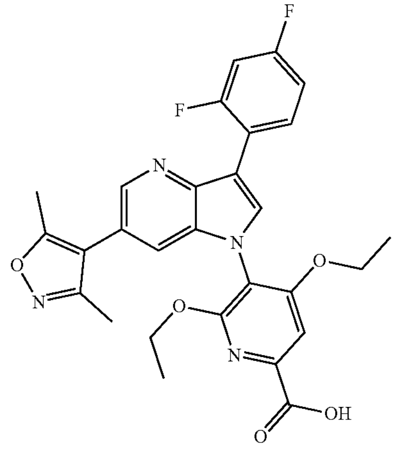 [SMILES: CCOc1cc(C(=O)O)nc(OCC)c1-n1cc(-c2ccc(F)cc2F)c2ncc(-c3c(C)noc3C)cc21] | 5-(3-(2,4-difluorophenyl)-6-(3,5-dimethylisoxazol-4-yl)-1H-pyrrolo[3,2-b]pyridin-1-yl)-4,6-diethoxypicolinic acid | 535.2 |

TABLE 1-continued
| P# | Structure | Name | (MH)+ |
|---|---|---|---|
| P-0432 | 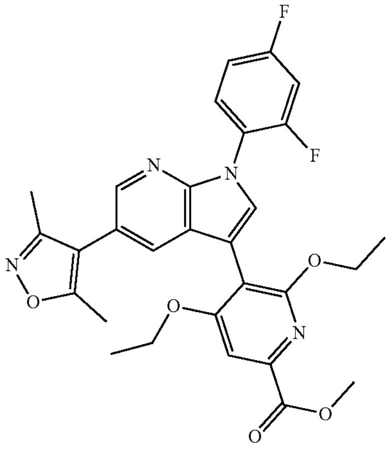 [SMILES: CCOc1cc(C(=O)OC)nc(OCC)c1-c1cn(-c2ccc(F)cc2F)c2ncc(-c3c(C)noc3C)cc12] | methyl 5-(1-(2,4-difluorophenyl)-5-(3,5-dimethylisoxazol-4-yl)-1H-pyrrolo[2,3-b]pyridin-3-yl)-4,6-diethoxypicolinate | 549.2 |
| P-0433 | 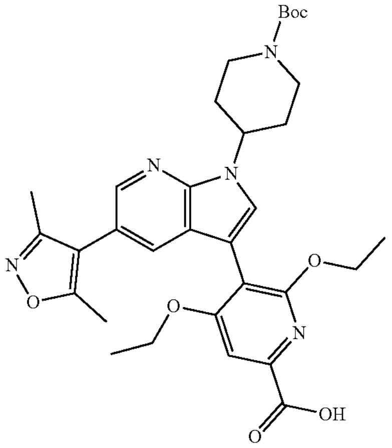 [SMILES: CCOc1cc(C(=O)O)nc(OCC)c1-c1cn(C2CCN(C(=O)OC(C)(C)C)CC2)c2ncc(-c3c(C)noc3C)cc12] | 5-(1-(1-(tert-butoxycarbonyl)piperidin-4-yl)-5-(3,5-dimethylisoxazol-4-yl)-1H-pyrrolo[2,3-b]pyridin-3-yl)-4,6-diethoxypicolinic acid | 606.3 |
| P-0434 | 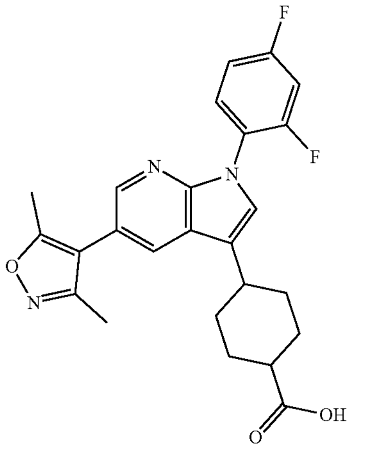 [SMILES: Cc1noc(C)c1-c1cnc2c(c1)c(C1CCC(C(=O)O)CC1)cn2-c1ccc(F)cc1F] | 4-(1-(2,4-difluorophenyl)-5-(3,5-dimethylisoxazol-4-yl)-1H-pyrrolo[2,3-b]pyridin-3-yl)cyclohexane-1-carboxylic acid | 452.2 |

TABLE 1-continued
| P# | Structure | Name | (MH)+ |
|---|---|---|---|
| P-0435 | 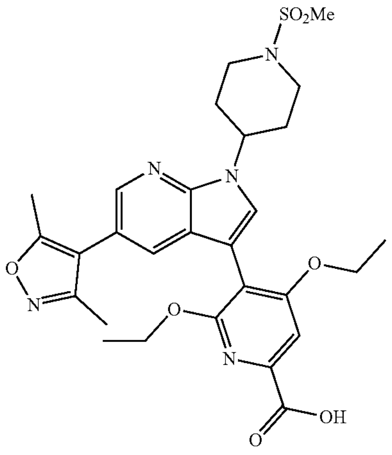 [SMILES: CCOc1cc(C(=O)O)nc(OCC)c1-c1cn(C2CCN(S(C)(=O)=O)CC2)c2ncc(-c3c(C)noc3C)cc12] | 5-(5-(3,5-dimethylisoxazol-4-yl)-1-(1-(methylsulfonyl)piperidin-4-yl)-1H-pyrrolo[2,3-b]pyridin-3-yl)-4,6-diethoxypicolinic acid | 584.2 |
| P-0436 | 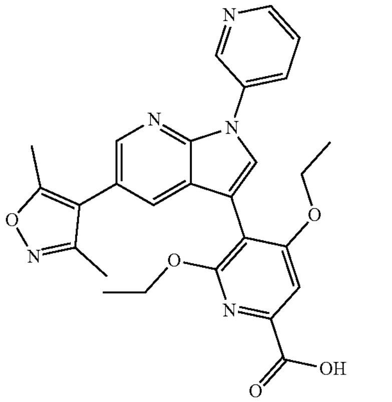 [SMILES: CCOc1cc(C(=O)O)nc(OCC)c1-c1cn(-c2cccnc2)c2ncc(-c3c(C)noc3C)cc12] | 5-(5-(3,5-dimethylisoxazol-4-yl)-1-(pyridin-3-yl)-1H-pyrrolo[2,3-b]pyridin-3-yl)-4,6-diethoxypicolinic acid | 500.0 |
| P-0437 | 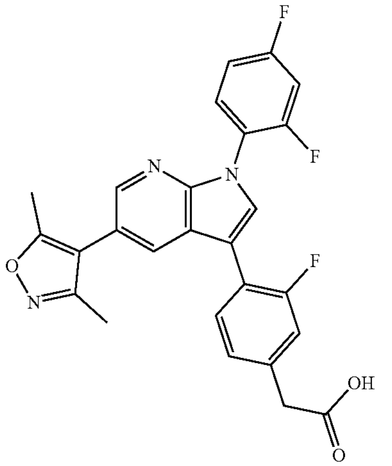 [SMILES: Cc1noc(C)c1-c1cnc2c(c1)c(-c1ccc(CC(=O)O)cc1F)cn2-c1ccc(F)cc1F] | 2-(4-(1-(2,4-difluorophenyl)-5-(3,5-dimethylisoxazol-4-yl)-1H-pyrrolo[2,3-b]pyridin-3-yl)-3-fluorophenypacetic acid | 478.1 |

TABLE 1-continued
| P# | Structure | Name | (MH)+ |
| --- | --- | --- | --- |
| P-0438 | 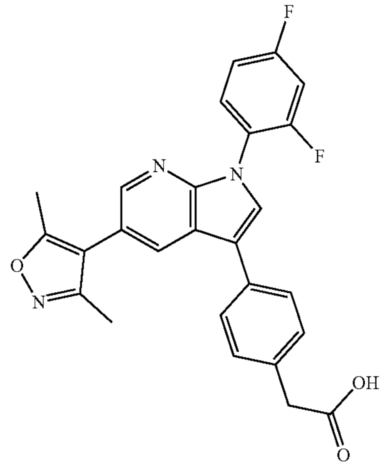 [SMILES: Cc1noc(C)c1-c1cnc2c(c1)c(-c1ccc(CC(=O)O)cc1)cn2-c1ccc(F)cc1F] | 2-(4-(1-(2,4-difluorophenyl)-5-(3,5-dimethylisoxazol-4-yl)-1H-pyrrolo[2,3-b]pyridin-3-yl)phenyl)acetic acid | 460.1 |
| P-0439 | 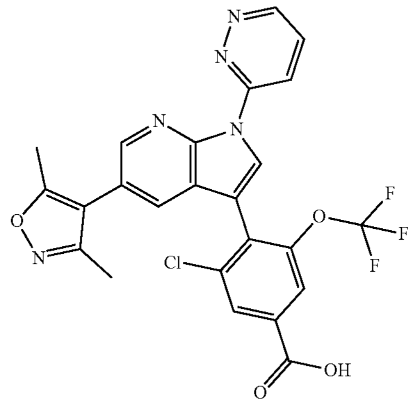 [SMILES: Cc1noc(C)c1-c1cnc2c(c1)c(-c1c(Cl)cc(C(=O)O)cc1OC(F)(F)F)cn2-c1cccnn1] | 3-chloro-4-(5-(3,5-dimethylisoxazol-4-yl)-1-(pyridazin-3-yl)-1H-pyrrolo[2,3-b]pyridin-3-yl)-5-(trifluoromethoxy)benzoic acid | 530.1 |
| P-0440 | 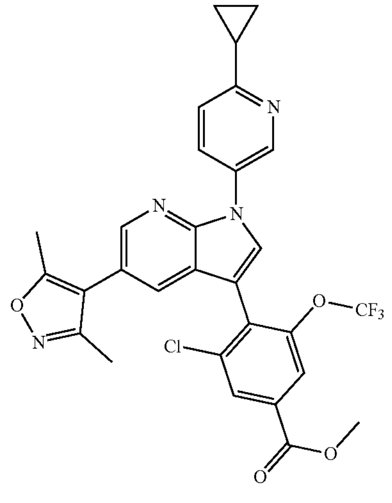 [SMILES: COC(=O)c1cc(Cl)c(-c2cn(-c3ccc(C4CC4)nc3)c3ncc(-c4c(C)noc4C)cc23)c(OC(F)(F)F)c1] | methyl 3-chloro-4-(1-(6-cyclopropylpyridin-3-yl)-5-(3,5-dimethylisoxazol-4-yl)-1H-pyrrolo[2,3-b]pyridin-3-yl)-5-(trifluoromethoxy)benzoate | 583.1 |

TABLE 1-continued
| P# | Structure | Name | (MH)+ |
| --- | --- | --- | --- |
| P-0441 | 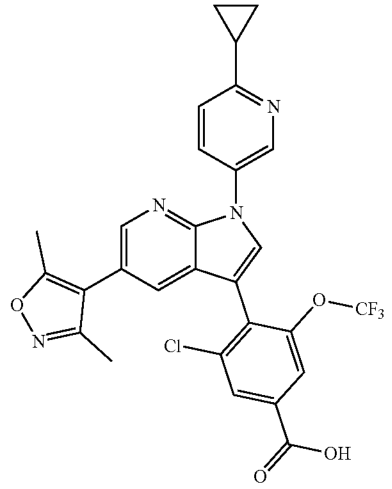 [SMILES: Cc1noc(C)c1-c1cnc2c(c1)c(-c1c(Cl)cc(C(=O)O)cc1OC(F)(F)F)cn2-c1ccc(C2CC2)nc1] | 3-chloro-4-(1-(6-cyclopropylpyridin-3-yl)-5-(3,5-dimethylisoxazol-4-yl)-1H-pyrrolo[2,3-b]pyridin-3-yl)-5-(trifluoromethoxy)benzoic acid | 569.1 |
| P-0442 | 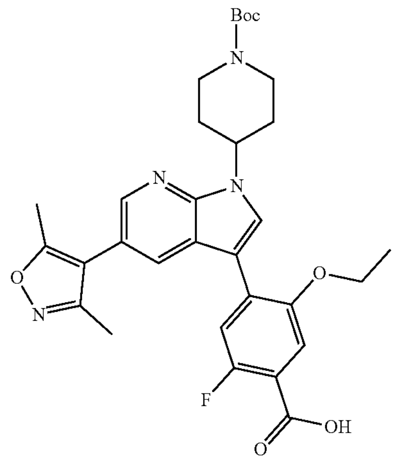 [SMILES: CCOc1cc(C(=O)O)c(F)cc1-c1cn(C2CCN(C(=O)OC(C)(C)C)CC2)c2ncc(-c3c(C)noc3C)cc12] | 4-(1-(1-(tert-butoxycarbonyl)piperidin-4-yl)-5-(3,5-dimethylisoxazol-4-yl)-1H-pyrrolo[2,3-b]pyridin-3-yl)-5-ethoxy-2-fluorobenzoic acid | 579.3 |
| P-0443 | 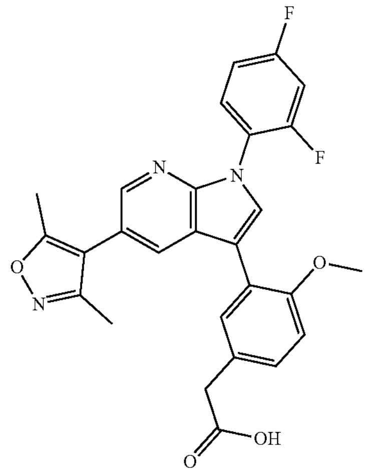 [SMILES: COc1ccc(CC(=O)O)cc1-c1cn(-c2ccc(F)cc2F)c2ncc(-c3c(C)noc3C)cc12] | 2-(3-(1-(2,4-difluorophenyl)-5-(3,5-dimethylisoxazol-4-yl)-1H-pyrrolo[2,3-b]pyridin-3-yl)-4-methoxyphenyl)acetic acid | 490.1 |

TABLE 1-continued
| P# | Structure | Name | (MH)+ |
|---|---|---|---|
| P-0444 | 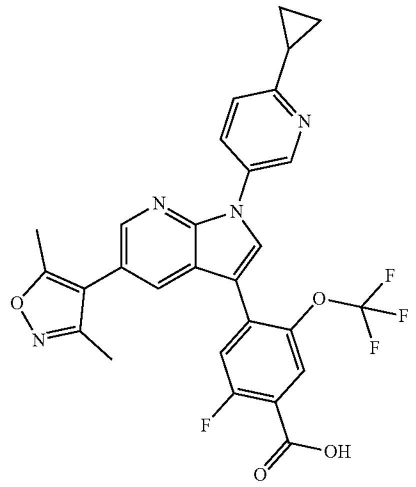 [SMILES: Cc1noc(C)c1-c1cnc2c(c1)c(-c1cc(F)c(C(=O)O)cc1OC(F)(F)F)cn2-c1ccc(C2CC2)nc1] | 4-(1-(6-cyclopropylpyridin-3-yl)-5-(3,5-dimethylisoxazol-4-yl)-1H-pyrrolo[2,3-b]pyridin-3-yl)-2-fluoro-5-(trifluoromethoxy)benzoic acid | 553.2 |
| P-0445 | 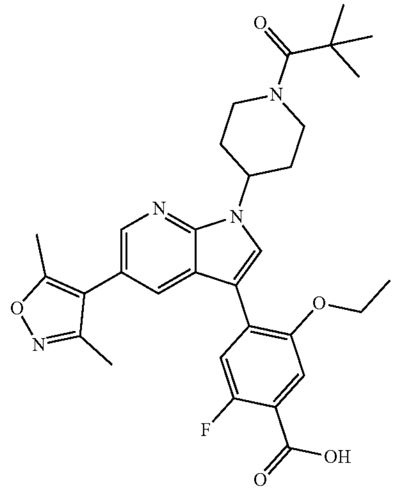 [SMILES: CCOc1cc(C(=O)O)c(F)cc1-c1cn(C2CCN(C(=O)C(C)(C)C)CC2)c2ncc(-c3c(C)noc3C)cc12] | 4-(5-(3,5-dimethylisoxazol-4-yl)-1-(1-pivaloylpiperidin-4-yl)-1H-pyrrolo[2,3-b]pyridin-3-yl)-5-ethoxy-2-fluorobenzoic acid | 563.3 |
| P-0446 | 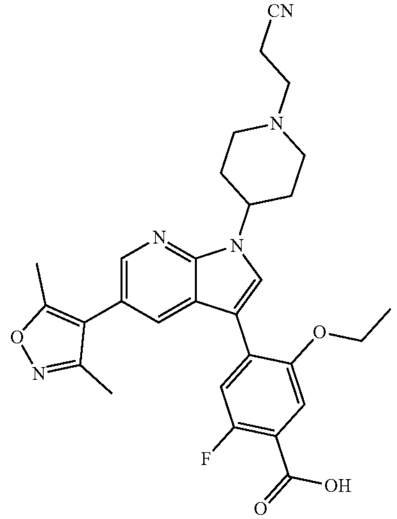 [SMILES: CCOc1cc(C(=O)O)c(F)cc1-c1cn(C2CCN(CCC#N)CC2)c2ncc(-c3c(C)noc3C)cc12] | 4-(1-(1-(2-cyanoethyl)piperidin-4-yl)-5-(3,5-dimethylisoxazol-4-yl)-1H-pyrrolo[2,3-b]pyridin-3-yl)-5-ethoxy-2-fluorobenzoic acid | 532.2 |

TABLE 1-continued

| P# | Structure | Name | (MH)+ |
|---|---|---|---|
| P-0447 | 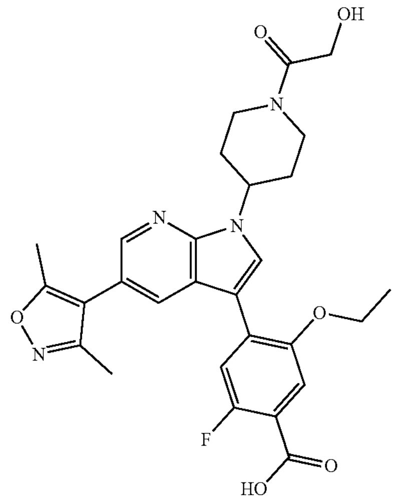 [SMILES: CCOc1cc(C(=O)O)c(F)cc1-c1cn(C2CCN(C(=O)CO)CC2)c2ncc(-c3c(C)noc3C)cc12] | 4-(5-(3,5-dimethylisoxazol-4-yl)-1-(1-(2-hydroxyacetyl)piperidin-4-yl)-1H-pyrrolo[2,3-b]pyridin-3-yl)-5-ethoxy-2-fluorobenzoic acid | 537.2 |
| P-0448 | 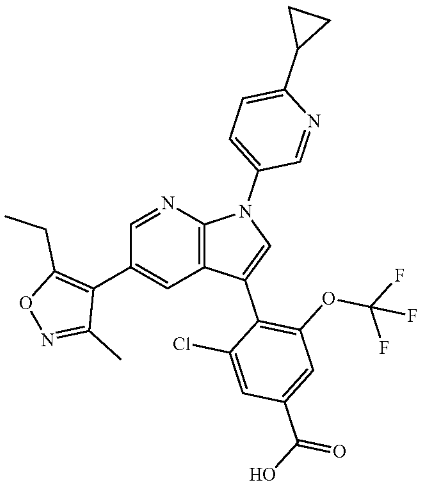 [SMILES: CCc1onc(C)c1-c1cnc2c(c1)c(-c1c(Cl)cc(C(=O)O)cc1OC(F)(F)F)cn2-c1ccc(C2CC2)nc1] | 3-chloro-4-(1-(6-cyclopropylpyridin-3-yl)-5-(5-ethyl-3-methylisoxazol-4-yl)-1H-pyrrolo[2,3-b]pyridin-3-yl)-5-(trifluoromethoxy)benzoic acid | 583.2 |
| P-0449 | 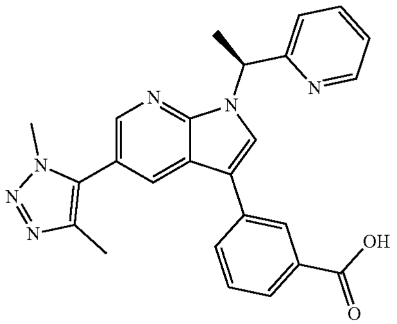 [SMILES: Cc1nnn(C)c1-c1cnc2c(c1)c(-c1cccc(C(=O)O)c1)cn2[C@@H](C)c1ccccn1] | (S)-3-(5-(1,4-dimethyl-1H-1,2,3-triazol-5-yl)-1-(1-(pyridin-2-yl)ethyl)-1H-pyrrolo[2,3-b]pyridin-3-yl)benzoic acid | 439.1 |

BIOLOGICAL EXAMPLES

Biological Test Methods

The compounds of disclosure were tested using the following assays:

EP300 Alphascreen Binding Assay

Binding of compounds of Formula (I) with EP300 was assessed using Alphascreen™ binding assay. The inhibition of the interaction between the EP300 bromodomain and its acetylated target protein was measured quantitatively using recombinant EP300 protein, an acetylated Histone 3 peptide and AlphaScreen™ technology. In absence of inhibition of the EP300 protein bound to AlphaScreen™ nickel chelate acceptor beads can interact with the acetylated Histone 3 peptide which is immobilized by the AlphaScreen™ Streptavidin coated beads. This interaction brings donor and acceptor beads in proximity. The close proximity allows the singlet oxygen produced by laser excitation of the donor beads to reach the acceptor beads and generate a luminescence signal. EP300 inhibitors result in a decrease in the proximity signal through an inhibition of the EP300—acetylated peptide interaction.

Recombinant human EP300 containing the bromodomain (EP300-BD (1040-1161)) was prepared and purified as described in protein expression and purification session. The peptide is human Histone $H3_{45-64}K56_{Ac}$-Biotin (Anaspec CA, USA).

Protocol for EP300 assay: All components were prepared in buffer composed of 50 mM HEPES pH 7.5, 50 mM NaCl, 0.01% BSA, 0.01% Triton X-100, 2 mM DTT. Test compounds and DMSO vehicle were diluted 1:50 in buffer and a 4 μL volume is transferred to an Alphaplate. 5.5 μL of EP300 protein and 5.5 μL of peptide were added to wells containing 4 μL of various concentrations of test compounds of Formula (I) or DMSO vehicle in an Alphaplate (PerkinElmer GA, USA) and incubated for 1 hour at room temperature. 5 μL donor and acceptor bead mixture was then added with final concentrations of 7.5 μg/ml. 60 minutes after bead addition, Alpha signal is read on the Envision spectrometer ($\lambda_{Ex}$ 680 nm, $\lambda_{Em}$ 520-620 nm). Final concentrations of bromodomain proteins and peptide are as shown below.

| Assay name | EP300 protein (nM) | Peptide (nM) |
|---|---|---|
| EP300-BD | 50 | 150 |

All data were normalized to the mean of 16 high and 16 low control wells on each plate. A four parameter curve fit of the following formula was then applied:

$$Y=A+((B-A)/(1+((C/x)^D)))$$

Where 'A' is the minimum, 'B' is the maximum, 'C' is the IC50 and 'D' is the Hill slope.

Protein Expression and Purification

Recombinant human EP300 bromodomain (EP300-BD (1040-1161)) was expressed in *E. coli* cells (in a modified pET vector) with an N-terminal six-His tag and purified using a combination of both IMAC (Ni-affinity) and size exclusion chromatography steps.

Recombinant EP300 protein was expressed using the *E. coli* strain BL21-CodonPlus (DE3) (Agilent Technologies CA, USA). Cells were grown in Terrific Broth (TB) media to an OD600 of 0.7 at 37° C. at which temperature was reduced to 18° C., protein was induced with 1.0 mM isopropyl-β-D-thiogalactopyranoside ("IPTG") for 20 hours and harvested by centrifugation at 8500×g for 20 minutes. Cells were re-suspended in 0.1M $K_2PO_4$ pH 8.0, 250 mM NaCl, 10% Glycerol, 0.75% NP-40, 25 mM Imidazole, with 0.2 mg/ml Lysozyme, 0.2 mM phenylmethanesulfonyl fluoride ("PMSF"), 25 μg/ml DNase I, incubated on ice for 30 minutes and lysed with a cell disruptor (MicroFluidics MA, USA). The lysate was clarified by centrifugation at 20,000×g for 1 hour. The protein was captured with Ni-NTA resin (Life Technologies, USA). Contaminating proteins were washed off with 50 mM HEPES pH 7.5, 500 mM NaCl, and 5% Glycerol. Following 3× wash steps, protein was eluted step wise using 10, 25, 50, 100, 150, and 250 mM Imidazole in 50 mM HEPES pH 7.5, 500 mM NaCl, and 5% glycerol. The protein was further purified using a size exclusion column (26/600 Superdex 200, GE Biosciences NJ, USA) in 10 mM HEPES pH 7.5, 500.

BRD4 Alphascreen Binding Assay

Binding of compounds of Formula (I) with BRD4 was assessed using Alphascreen binding assay. The inhibition of the interaction between BRD4 and its acetylated target protein was measured quantitatively using recombinant BRD4 protein, an acetylated Histone 4 peptide, and AlphaScreen™ technology. In absence of inhibition of the BRD4 protein bound to AlphaScreen™ nickel chelate acceptor beads can interact with the acetylated Histone 4 peptide which was immobilized by the AlphaScreen™ Streptavidin coated beads. This interaction brings donor and acceptor beads in proximity. The close proximity allows the singlet oxygen produced by laser excitation of the donor beads to reach the acceptor beads and generate a luminescence signal. BRD4 inhibitors result in a decrease in the proximity signal through an inhibition of the BRD4—acetylated peptide interaction.

Recombinant human BRD4 containing dual bromodomains (BRD4-BD12 (1-477)) was prepared and purified as described in protein expression and purification session. The peptide was human Histone $H4_{1-21}K5_{Ac}K8_{Ac}K12_{Ac}K16_{Ac}$-Biotin (Anaspec CA, USA).

Protocol for BRD4 assay: All components are prepared in buffer composed of 50 mM HEPES pH 7.5, 50 mM NaCl, 0.01% BSA, 0.01% Triton X-100, 2 mM DTT. Test compounds and DMSO vehicle are diluted 1:50 in buffer and a 4 μL volume was transferred to an Alphaplate. 5.5 μL of Bromodomain protein and 5.5 μL of peptide are added to wells containing 4 μL of various concentrations of test compounds of Formula (I) or DMSO vehicle in an Alphaplate (PerkinElmer GA, USA) and incubated for 1 hour at room temperature. 5 μL donor and acceptor bead mixture was then added with final concentrations of 7.5 μg/ml. 30 minutes after bead addition, Alpha signal was read on the Envision spectrometer ($\lambda_{Ex}$ 680 nm, $\lambda_{Em}$ 520-620 nm). Final concentrations of bromodomain proteins and peptide are as shown below.

| Assay name | BRD protein (nM) | Peptide (nM) |
|---|---|---|
| BRD4-BD12 | 3.6 | 36 |

All data were normalized to the mean of 16 high and 16 low control wells on each plate. A four parameter curve fit of the following formula was then applied:

$$Y=A+((B-A)/(1+((C/x)^D)))$$

Where 'A' is the minimum, 'B' is the maximum, 'C' is the IC50 and 'D' is the Hill slope.

Protein Expression and Purification

Recombinant human BRD4 containing dual bromodomains (BRD4-BD12 (1-477)) was expressed in *E. coli* cells (in a modified pET vector) with an N-terminal six-His tag and purified using a combination of both IMAC (Ni-affinity) and size exclusion chromatography steps.

Recombinant BRD4 was expressed using the *E. coli* strain BL21-CodonPlus (DE3) (Agilent Technologies CA, USA). Cells were grown in Terrific Broth (TB) media to an OD600 of 2.0 at 37° C. at which temperature was reduced to 18° C., protein was induced with 0.1 mM isopropyl-β-D-thiogalactopyranoside ("IPTG") for 12-18 hours and harvested by centrifugation at 8000×g for 20 minutes. Cells were re-suspended in 40 mM Tris-HCl pH 8.0, 0.5 M NaCl, 25 mM Imidazole, 5% glycerol, 1/200 vol. Protease Inhibitor Cocktail Set III (Calbiochem), 5 mM beta-mercaptoethanol ("BME"), 0.5 mg/mL Lysozyme, and 0.5 mg/mL DNaseI, incubated on ice for 30 minutes and lysed with a cell disruptor (MicroFluidics MA, USA). The lysate was clarified by centrifugation at 20,000×g for 2 hours. The protein was captured with Ni-NTA resin (Life Technologies, USA). Contaminating proteins were washed off with 40 mM Tris-HCl pH 8.0, 0.5 M NaCl, 25 mM Imidazole, 5% glycerol, and 5 mM BME. Following 3× wash steps, protein was eluted step wise into wash buffer containing 50, 100, 150, 500 mM Imidazole. The protein was further purified using Gel Filtration column 16/60 Superdex 200 (GE Biosciences NJ, USA) in 10 mM HEPES pH 8.0, 150 mM NaCl, and 5 mM DTT. Glycerol was added to a final concentration of 12% and the protein was aliquoted and flash-frozen in liquid Nitrogen.

CBP Alphascreen Binding Assay

Binding of compounds of Formula (I) with CBP was assessed using Alphascreen™ binding assay. The inhibition of the interaction between the CBP bromodomain and its acetylated target protein was measured quantitatively using recombinant CBP, an acetylated Histone 3 peptide and AlphaScreen™ technology. In absence of inhibition of the CBP protein bound to AlphaScreen™ nickel chelate acceptor beads can interact with the acetylated Histone 3 peptide which was immobilized by the AlphaScreen™ Streptavidin coated beads. This interaction brings donor and acceptor beads in proximity. The close proximity allows the singlet oxygen produced by laser excitation of the donor beads to reach the acceptor beads and generate a luminescence signal. CBP inhibitors result in a decrease in the proximity signal through an inhibition of the CBP—acetylated peptide interaction.

Recombinant human CBP containing the bromodomain (CBP-BD (1043-1159)) was prepared and purified as described in protein expression and purification session. The peptide was human Histone H345-64K56Ac-Biotin (Anaspec CA, USA).

Protocol for CBP assay: All components are prepared in buffer composed of 50 mM HEPES pH 7.5, 50 mM NaCl, 0.01% BSA, 0.01% Triton X-100, 2 mM DTT. Test compounds and DMSO vehicle are diluted 1:50 in buffer and a 4 μL volume was transferred to an Alphaplate. 5.5 μL of CBP protein and 5.5 μL of peptide are added to wells containing 4 μL of various concentrations of test compounds of Formula (I) or DMSO vehicle in an Alphaplate (PerkinElmer GA, USA) and incubated for 1 hour at room temperature. 5 μL donor and acceptor bead mixture was then added with final concentrations of 7.5 μg/ml. 60 minutes after bead addition, Alpha signal was read on the Envision spectrometer (λEx 680 nm, λEm 520-620 nm). Final concentrations of bromodomain proteins and peptide are as shown below.

| Assay name | CBP protein (nM) | Peptide (nM) |
|---|---|---|
| BD | 50 | 150 |

All data were normalized to the mean of 16 high and 16 low control wells on each plate. A four parameter curve fit of the following formula was then applied:

$$Y=A+((B-A)/(1+((C/x)^D)))$$

Where 'A' is the minimum, 'B' is the maximum, 'C' is the IC50 and 'D' is the Hill slope.

Protein Expression and Purification

Recombinant human CBP bromodomain (CBP-BD (1043-1159)) was expressed in *E. coli* cells (in a modified pET vector) with an N-terminal six-His tag and purified using a combination of both IMAC (Ni-affinity) and size exclusion chromatography steps.

Recombinant CBP protein was expressed using the *E. coli* strain BL21-CodonPlus (DE3) (Agilent Technologies CA, USA). Cells were grown in Terrific Broth (TB) media to an OD600 of 0.92 at 37° C. at which temperature was reduced to 20° C., protein was induced with 1.0 mM isopropyl-β-D-thiogalactopyranoside ("IPTG") for 20 hours and harvested by centrifugation at 8500×g for 20 minutes. Cells were re-suspended in 0.1M K2PO4 pH 8.0, 250 mM NaCl, 10% Glycerol, 0.75% NP-40, 25 mM Imidazole, with 0.2 mg/ml Lysozyme, 0.2 mM phenylmethanesulfonyl fluoride ("PMSF"), 0.5 beta-mercaptoethanol ("BME"), 25 μg/ml DNase I, incubated on ice for 30 minutes and lysed with a cell disruptor (MicroFluidics MA, USA). The lysate was clarified by centrifugation at 20,000×g for 1 hour. The protein was captured with Ni-NTA resin (Life Technologies, USA). Contaminating proteins were washed off with 40 mM HEPES pH 7.5, 500 mM NaCl, 5% Glycerol, 5 mM Imidazole, and 5 mM BME. Following 3× wash steps, protein was eluted using 400 mM Imidazole in 40 mM HEPES pH 7.5, 400 mM NaCl, and 5 mM BME. The protein was further purified using a size exclusion column (26/600 Superdex 200, GE Biosciences NJ, USA) in 40 mM HEPES pH 7.5, 250 mM NaCl, 5 mM BME. The protein was aliquoted and flash-frozen in liquid Nitrogen.

The following Table 2 provides data indicating biochemical and/or cell inhibitory activity for exemplary compounds as described herein in Table 1. In Table 2 below, activity is provided as follows: +++=0.0001 $\mu M<IC_{50}<1$ μM; ++=1 $\mu M<IC_{50}<8$ μM, +=8 $\mu M<IC_{50}<1000$ μM.

TABLE 2

| P # | EP300 $IC_{50}$ (μM) | BRD4 $IC_{50}$ (μM) | CREBBP (CBP) $IC_{50}$ (μM) |
|---|---|---|---|
| P-0001 | +++ | + | +++ |
| P-0002 | +++ | +++ | +++ |
| P-0003 | + | + | + |
| P-0004 | +++ | + | +++ |
| P-0005 | + | + | + |
| P-0006 | ++ | + | ++ |
| P-0007 | +++ | + | +++ |
| P-0008 | +++ | + | +++ |
| P-0009 | +++ | + | +++ |
| P-0010 | +++ | + | +++ |
| P-0011 | +++ | + | ++ |
| P-0012 | +++ | + | +++ |
| P-0013 | +++ | + | +++ |
| P-0014 | +++ | + | +++ |
| P-0015 | +++ | ++ | +++ |
| P-0016 | +++ | ++ | +++ |
| P-0017 | +++ | ++ | +++ |
| P-0018 | +++ | ++ | +++ |
| P-0019 | ++ | ++ | ++ |
| P-0020 | ++ | ++ | ++ |
| P-0021 | ++ | ++ | ++ |
| P-0022 | + | + | + |
| P-0023 | ++ | ++ | ++ |
| P-0024 | ++ | + | ++ |
| P-0025 | +++ | ++ | +++ |
| P-0026 | +++ | ++ | +++ |
| P-0027 | +++ | ++ | +++ |
| P-0028 | +++ | ++ | +++ |
| P-0029 | +++ | ++ | +++ |
| P-0030 | ++ | + | ++ |
| P-0031 | +++ | ++ | +++ |
| P-0032 | +++ | ++ | +++ |
| P-0033 | +++ | ++ | +++ |
| P-0034 | +++ | ++ | +++ |
| P-0035 | +++ | ++ | +++ |
| P-0036 | +++ | ++ | +++ |
| P-0037 | ++ | ++ | ++ |
| P-0038 | +++ | ++ | +++ |
| P-0040 | +++ | ++ | +++ |
| P-0041 | +++ | +++ | +++ |
| P-0042 | +++ | +++ | +++ |
| P-0043 | +++ | ++ | +++ |
| P-0044 | +++ | +++ | +++ |

TABLE 2-continued

| P # | EP300 $IC_{50}$ (μM) | BRD4 $IC_{50}$ (μM) | CREBBP (CBP) $IC_{50}$ (μM) |
|---|---|---|---|
| P-0045 | +++ | +++ | +++ |
| P-0046 | +++ | + | +++ |
| P-0047 | +++ | ++ | +++ |
| P-0048 | +++ | ++ | +++ |
| P-0049 | +++ | + | +++ |
| P-0050 | +++ | + | +++ |
| P-0051 | +++ | + | +++ |
| P-0052 | +++ | ++ | +++ |
| P-0053 | +++ | ++ | +++ |
| P-0054 | +++ | +++ | +++ |
| P-0055 | +++ | +++ | +++ |
| P-0056 | +++ | ++ | +++ |
| P-0057 | +++ | ++ | +++ |
| P-0058 | +++ | + | +++ |
| P-0059 | +++ | + | +++ |
| P-0060 | +++ | ++ | +++ |
| P-0061 | +++ | + | +++ |
| P-0062 | +++ | + | +++ |
| P-0063 | +++ | + | +++ |
| P-0064 | +++ | ++ | +++ |
| P-0065 | +++ | ++ | +++ |
| P-0066 | +++ | + | +++ |
| P-0067 | +++ | ++ | +++ |
| P-0068 | +++ | + | +++ |
| P-0069 | +++ | + | +++ |
| P-0070 | +++ | + | +++ |
| P-0071 | +++ | ++ | +++ |
| P-0072 | +++ | ++ | +++ |
| P-0073 | +++ | + | +++ |
| P-0074 | +++ | + | +++ |
| P-0075 | +++ | + | +++ |
| P-0076 | ++ | + | ++ |
| P-0077 | +++ | ++ | +++ |
| P-0078 | +++ | ++ | ++ |
| P-0079 | +++ | ++ | +++ |
| P-0080 | ++ | ++ | ++ |
| P-0081 | +++ | ++ | ++ |
| P-0082 | ++ | ++ | + |
| P-0083 | +++ | ++ | ++ |
| P-0084 | +++ | +++ | +++ |
| P-0085 | +++ | + | ++ |
| P-0086 | +++ | ++ | +++ |
| P-0087 | +++ | ++ | +++ |
| P-0088 | +++ | ++ | +++ |
| P-0089 | +++ | ++ | +++ |
| P-0090 | +++ | +++ | +++ |
| P-0091 | +++ | ++ | +++ |
| P-0092 | +++ | ++ | ++ |
| P-0093 | +++ | ++ | +++ |
| P-0094 | +++ | + | +++ |
| P-0095 | +++ | ++ | +++ |
| P-0096 | +++ | ++ | ++ |
| P-0097 | +++ | + | +++ |
| P-0098 | +++ | ++ | +++ |
| P-0099 | +++ | ++ | +++ |
| P-0100 | +++ | ++ | +++ |
| P-0101 | +++ | + | +++ |
| P-0102 | ++ | + | ++ |
| P-0103 | +++ | + | +++ |
| P-0104 | +++ | + | +++ |
| P-0105 | +++ | + | +++ |
| P-0106 | ++ | + | ++ |
| P-0107 | ++ | + | ++ |
| P-0108 | +++ | ++ | +++ |
| P-0109 | +++ | ++ | +++ |
| P-0110- | +++ | ++ | +++ |
| P-0111 | +++ | + | +++ |
| P-0112 | +++ | + | +++ |
| P-0113 | +++ | + | +++ |
| P-0114 | +++ | + | +++ |
| P-0115 | +++ | + | +++ |
| P-0116 | +++ | ++ | +++ |
| P-0117 | +++ | ++ | +++ |
| P-0118 | +++ | + | +++ |
| P-0119 | +++ | ++ | +++ |
| P-0120 | +++ | ++ | ++ |
| P-0121 | +++ | ++ | +++ |

TABLE 2-continued

| P # | EP300 $IC_{50}$ (μM) | BRD4 $IC_{50}$ (μM) | CREBBP (CBP) $IC_{50}$ (μM) |
|---|---|---|---|
| P-0122 | ++ | + | ++ |
| P-0123 | +++ | + | +++ |
| P-0124 | +++ | + | +++ |
| P-0125 | +++ | + | +++ |
| P-0126 | +++ | + | +++ |
| P-0127 | +++ | + | +++ |
| P-0128 | +++ | ++ | +++ |
| P-0129 | +++ | ++ | +++ |
| P-0130 | + | + | + |
| P-0131 | +++ | ++ | +++ |
| P-0132 | +++ | + | +++ |
| P-0133 | +++ | ++ | +++ |
| P-0134 | ++ | + | ++ |
| P-0135 | +++ | + | +++ |
| P-0136 | +++ | +++ | +++ |
| P-0137 | +++ | + | +++ |
| P-0138 | +++ | + | +++ |
| P-0139 | +++ | + | +++ |
| P-0140 | +++ | + | ++ |
| P-0141 | +++ | + | +++ |
| P-0142 | +++ | +++ | +++ |
| P-0143 | ++ | + | ++ |
| P-0144 | +++ | + | +++ |
| P-0145 | ++ | + | + |
| P-0146 | ++ | + | ++ |
| P-0147 | +++ | + | +++ |
| P-0148 | +++ | ++ | +++ |
| P-0149 | +++ | + | +++ |
| P-0150 | +++ | ++ | +++ |
| P-0151 | +++ | ++ | +++ |
| P-0152 | +++ | + | +++ |
| P-0153 | +++ | + | +++ |
| P-0154 | +++ | +++ | +++ |
| P-0155 | +++ | +++ | +++ |
| P-0156 | +++ | + | +++ |
| P-0157 | +++ | +++ | +++ |
| P-0158 | +++ | +++ | +++ |
| P-0159 | +++ | +++ | +++ |
| P-0160 | +++ | +++ | +++ |
| P-0161 | +++ | + | +++ |
| P-0162 | +++ | + | +++ |
| P-0163 | +++ | + | +++ |
| P-0164 | +++ | ++ | +++ |
| P-0165 | +++ | + | +++ |
| P-0166 | +++ | +++ | +++ |
| P-0167 | +++ | +++ | +++ |
| P-0168 | +++ | ++ | +++ |
| P-0169 | +++ | +++ | +++ |
| P-0170 | +++ | + | +++ |
| P-0171 | +++ | +++ | +++ |
| P-0172 | ++ | ++ | ++ |
| P-0173 | +++ | ++ | +++ |
| P-0174 | +++ | + | +++ |
| P-0175 | +++ | ++ | +++ |
| P-0176 | +++ | ++ | +++ |
| P-0177 | +++ | + | +++ |
| P-0178 | ++ | + | ++ |
| P-0179 | +++ | + | +++ |
| P-0180 | +++ | + | +++ |
| P-0181 | +++ | + | +++ |
| P-0182 | +++ | ++ | +++ |
| P-0183 | +++ | + | +++ |
| P-0184 | +++ | ++ | +++ |
| P-0185 | +++ | ++ | +++ |
| P-0186 | +++ | + | +++ |
| P-0187 | +++ | + | +++ |
| P-0188 | +++ | ++ | +++ |
| P-0189 | +++ | + | +++ |
| P-0190 | +++ | ++ | +++ |
| P-0191 | +++ | + | +++ |
| P-0192 | +++ | ++ | +++ |
| P-0193 | +++ | ++ | +++ |
| P-0194 | +++ | ++ | +++ |
| P-0195 | +++ | ++ | +++ |
| P-0196 | +++ | ++ | +++ |
| P-0197 | +++ | + | +++ |
| P-0198 | +++ | + | +++ |

TABLE 2-continued

| P # | EP300 $IC_{50}$ (μM) | BRD4 $IC_{50}$ (μM) | CREBBP (CBP) $IC_{50}$ (μM) |
|---|---|---|---|
| P-0199 | +++ | + | +++ |
| P-0200 | +++ | + | +++ |
| P-0201 | +++ | ++ | +++ |
| P-0202 | +++ | ++ | +++ |
| P-0203 | +++ | ++ | +++ |
| P-0204 | +++ | + | +++ |
| P-0205 | +++ | ++ | +++ |
| P-0206 | +++ | + | +++ |
| P-0207 | ++ | ++ | ++ |
| P-0208 | +++ | ++ | +++ |
| P-0209 | +++ | ++ | +++ |
| P-0210 | +++ | + | +++ |
| P-0211 | +++ | ++ | +++ |
| P-0212 | +++ | + | +++ |
| P-0213 | +++ | + | +++ |
| P-0214 | +++ | + | +++ |
| P-0215 | +++ | ++ | +++ |
| P-0216 | +++ | + | +++ |
| P-0217 | +++ | ++ | +++ |
| P-0218 | +++ | ++ | +++ |
| P-0219 | +++ | ++ | +++ |
| P-0220 | +++ | +++ | +++ |
| P-0221 | +++ | + | ++ |
| P-0222 | +++ | ++ | +++ |
| P-0223 | +++ | ++ | +++ |
| P-0224 | ++ | ++ | ++ |
| P-0225 | +++ | ++ | +++ |
| P-0226 | +++ | ++ | +++ |
| P-0227 | +++ | ++ | +++ |
| P-0228 | +++ | ++ | +++ |
| P-0229 | +++ | ++ | +++ |
| P-0230 | +++ | ++ | +++ |
| P-0231 | +++ | + | +++ |
| P-0232 | +++ | ++ | +++ |
| P-0233 | +++ | ++ | +++ |
| P-0234 | +++ | ++ | +++ |
| P-0235 | +++ | + | +++ |
| P-0236 | +++ | ++ | +++ |
| P-0237 | +++ | ++ | +++ |
| P-0238 | +++ | ++ | +++ |
| P-0239 | +++ | + | ++ |
| P-0240 | +++ | + | +++ |
| P-0241 | +++ | + | +++ |
| P-0242 | ++ | + | ++ |
| P-0243 | ++ | ++ | ++ |
| P-0244 | ++ | ++ | ++ |
| P-0245 | +++ | + | +++ |
| P-0246 | ++ | + | ++ |
| P-0247 | +++ | + | +++ |
| P-0248 | + | + | + |
| P-0249 | +++ | + | +++ |
| P-0250 | +++ | + | +++ |
| P-0251 | +++ | + | +++ |
| P-0252 | +++ | + | +++ |
| P-0253 | +++ | + | +++ |
| P-0254 | +++ | ++ | +++ |
| P-0255 | +++ | ++ | +++ |
| P-0256 | +++ | + | +++ |
| P-0257 | +++ | + | +++ |
| P-0258 | +++ | ++ | +++ |
| P-0259 | +++ | ++ | +++ |
| P-0260 | +++ | ++ | +++ |
| P-0261 | +++ | ++ | +++ |
| P-0262 | +++ | ++ | +++ |
| P-0263 | +++ | ++ | +++ |
| P-0264 | +++ | ++ | +++ |
| P-0265 | +++ | ++ | +++ |
| P-0266 | +++ | ++ | +++ |
| P-0267 | +++ | ++ | +++ |
| P-0268 | +++ | ++ | +++ |
| P-0269 | +++ | ++ | +++ |
| P-0270 | ++ | + | ++ |
| P-0271 | +++ | + | +++ |
| P-0272 | +++ | + | +++ |
| P-0273 | +++ | ++ | +++ |
| P-0274 | +++ | ++ | +++ |
| P-0275 | +++ | ++ | +++ |

TABLE 2-continued

| P # | EP300 $IC_{50}$ (μM) | BRD4 $IC_{50}$ (μM) | CREBBP (CBP) $IC_{50}$ (μM) |
|---|---|---|---|
| P-0276 | +++ | ++ | +++ |
| P-0277 | +++ | ++ | +++ |
| P-0278 | +++ | ++ | +++ |
| P-0279 | +++ | ++ | +++ |
| P-0280 | +++ | + | +++ |
| P-0281 | +++ | ++ | +++ |
| P-0282 | +++ | +++ | +++ |
| P-0283 | +++ | ++ | +++ |
| P-0284 | +++ | + | +++ |
| P-0285 | +++ | + | +++ |
| P-0286 | +++ | + | +++ |
| P-0287 | +++ | ++ | +++ |
| P-0288 | +++ | ++ | +++ |
| P-0289 | +++ | ++ | +++ |
| P-0290 | +++ | + | +++ |
| P-0291 | +++ | + | +++ |
| P-0292 | +++ | ++ | +++ |
| P-0293 | +++ | ++ | +++ |
| P-0294 | +++ | +++ | +++ |
| P-0295 | +++ | ++ | +++ |
| P-0296 | +++ | + | +++ |
| P-0297 | +++ | + | +++ |
| P-0298 | +++ | ++ | +++ |
| P-0299 | +++ | ++ | +++ |
| P-0300 | +++ | + | +++ |
| P-0301 | +++ | + | +++ |
| P-0302 | +++ | + | +++ |
| P-0303 | +++ | + | +++ |
| P-0304 | +++ | ++ | +++ |
| P-0305 | +++ | + | +++ |
| P-0306 | +++ | + | +++ |
| P-0307 | +++ | ++ | +++ |
| P-0308 | +++ | ++ | +++ |
| P-0309 | +++ | + | +++ |
| P-0310 | +++ | ++ | +++ |
| P-0311 | +++ | ++ | +++ |
| P-0312 | +++ | + | +++ |
| P-0313 | +++ | ++ | +++ |
| P-0314 | +++ | +++ | +++ |
| P-0315 | +++ | +++ | +++ |
| P-0316 | +++ | ++ | +++ |
| P-0317 | +++ | + | +++ |
| P-0318 | +++ | +++ | +++ |
| P-0319 | +++ | ++ | +++ |
| P-0320 | +++ | ++ | +++ |
| P-0321 | +++ | ++ | +++ |
| P-0322 | +++ | ++ | +++ |
| P-0323 | +++ | ++ | +++ |
| P-0324 | +++ | ++ | +++ |
| P-0325 | +++ | + | +++ |
| P-0326 | +++ | + | +++ |
| P-0327 | +++ | ++ | +++ |
| P-0328 | +++ | + | +++ |
| P-0329 | +++ | ++ | +++ |
| P-0330 | +++ | ++ | +++ |
| P-0331 | +++ | +++ | +++ |
| P-0332 | +++ | ++ | +++ |
| P-0333 | +++ | + | +++ |
| P-0334 | +++ | + | +++ |
| P-0335 | +++ | + | +++ |
| P-0336 | +++ | + | +++ |
| P-0337 | +++ | + | +++ |
| P-0338 | +++ | + | +++ |
| P-0339 | +++ | ++ | +++ |
| P-0340 | +++ | + | +++ |
| P-0341 | +++ | + | +++ |
| P-0342 | +++ | + | +++ |
| P-0343 | +++ | + | +++ |
| P-0344 | +++ | + | +++ |
| P-0345 | +++ | + | +++ |
| P-0346 | +++ | + | +++ |
| P-0347 | +++ | + | +++ |
| P-0348 | +++ | + | +++ |
| P-0349 | +++ | + | +++ |
| P-0350 | +++ | + | +++ |
| P-0351 | +++ | + | +++ |
| P-0352 | +++ | ++ | +++ |

TABLE 2-continued

| P # | EP300 $IC_{50}$ (μM) | BRD4 $IC_{50}$ (μM) | CREBBP (CBP) $IC_{50}$ (μM) |
|---|---|---|---|
| P-0353 | +++ | + | +++ |
| P-0354 | +++ | + | +++ |
| P-0355 | +++ | ++ | +++ |
| P-0356 | +++ | ++ | +++ |
| P-0357 | +++ | + | +++ |
| P-0358 | +++ | ++ | +++ |
| P-0359 | +++ | + | +++ |
| P-0360 | +++ | + | +++ |
| P-0361 | +++ | + | +++ |
| P-0362 | +++ | +++ | +++ |
| P-0363 | +++ | ++ | +++ |
| P-0364 | +++ | ++ | +++ |
| P-0365 | +++ | ++ | +++ |
| P-0366 | +++ | + | +++ |
| P-0367 | +++ | ++ | +++ |
| P-0368 | +++ | + | +++ |
| P-0369 | +++ | ++ | +++ |
| P-0370 | +++ | ++ | +++ |
| P-0371 | +++ | ++ | +++ |
| P-0372 | +++ | ++ | +++ |
| P-0373 | +++ | + | +++ |
| P-0374 | +++ | + | +++ |
| P-0375 | +++ | + | +++ |
| P-0376 | +++ | + | +++ |
| P-0377 | +++ | ++ | +++ |
| P-0378 | +++ | +++ | +++ |
| P-0379 | +++ | + | +++ |
| P-0380 | +++ | + | +++ |
| P-0381 | +++ | ++ | +++ |
| P-0382 | +++ | ++ | +++ |
| P-0383 | +++ | + | +++ |
| P-0384 | +++ | ++ | +++ |
| P-0385 | +++ | + | +++ |
| P-0386 | +++ | ++ | +++ |
| P-0387 | +++ | + | +++ |
| P-0388 | +++ | ++ | +++ |
| P-0389 | +++ | ++ | +++ |
| P-0390 | +++ | ++ | +++ |
| P-0391 | +++ | ++ | +++ |
| P-0392 | +++ | ++ | +++ |
| P-0393 | +++ | ++ | +++ |
| P-0394 | +++ | ++ | +++ |
| P-0395 | +++ | ++ | +++ |
| P-0396 | +++ | ++ | +++ |
| P-0397 | +++ | + | +++ |
| P-0398 | +++ | + | +++ |
| P-0399 | +++ | ++ | +++ |
| P-0400 | +++ | ++ | +++ |
| P-0401 | +++ | ++ | +++ |
| P-0402 | +++ | ++ | +++ |
| P-0403 | +++ | + | +++ |
| P-0404 | +++ | + | +++ |
| P-0405 | +++ | ++ | +++ |
| P-0406 | +++ | + | +++ |
| P-0407 | +++ | + | +++ |
| P-0408 | +++ | + | +++ |
| P-0409 | +++ | ++ | +++ |
| P-0410 | +++ | + | +++ |
| P-0411 | +++ | + | +++ |
| P-0412 | +++ | ++ | +++ |
| P-0413 | +++ | ++ | +++ |
| P-0414 | +++ | ++ | +++ |
| P-0415 | +++ | + | +++ |
| P-0416 | +++ | + | +++ |
| P-0417 | +++ | + | +++ |
| P-0418 | +++ | +++ | +++ |
| P-0419 | +++ | +++ | +++ |
| P-0420 | +++ | + | +++ |
| P-0421 | +++ | + | +++ |
| P-0422 | +++ | + | +++ |
| P-0423 | +++ | ++ | +++ |
| P-0424 | +++ | ++ | +++ |
| P-0425 | +++ | + | +++ |
| P-0426 | +++ | ++ | +++ |
| P-0427 | +++ | ++ | +++ |
| P-0428 | +++ | +++ | +++ |
| P-0429 | +++ | + | +++ |

TABLE 2-continued

| P # | EP300 $IC_{50}$ (μM) | BRD4 $IC_{50}$ (μM) | CREBBP (CBP) $IC_{50}$ (μM) |
|---|---|---|---|
| P-0430 | +++ | ++ | +++ |
| P-0431 | +++ | ++ | +++ |
| P-0432 | +++ | + | +++ |
| P-0433 | +++ | + | +++ |
| P-0434 | +++ | ++ | +++ |
| P-0435 | +++ | + | +++ |
| P-0436 | +++ | ++ | +++ |
| P-0437 | +++ | ++ | +++ |
| P-0438 | +++ | + | +++ |
| P-0439 | +++ | +++ | +++ |
| P-0440 | ++ | + | ++ |
| P-0441 | +++ | +++ | +++ |
| P-0442 | +++ | + | +++ |
| P-0443 | +++ | ++ | +++ |
| P-0444 | +++ | ++ | +++ |
| P-0445 | +++ | + | +++ |
| P-0446 | +++ | + | +++ |
| P-0447 | +++ | + | +++ |
| P-0448 | +++ | ++ | +++ |
| P-0449 | +++ | ++ | +++ |

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of the embodiments described herein are exemplary and are not intended as limitations on the scope of the disclosure. Changes therein and other uses will occur to those skilled in the art, which are encompassed within the spirit of the disclosure, are defined by the scope of the claims.

It will be readily apparent to one skilled in the art that varying substitutions and modifications may be made to the present disclosure described herein without departing from the scope and spirit of the disclosure. For example, variations can be made to provide additional compounds of the compounds of this disclosure and/or various methods of administration can be used. Thus, such additional embodiments are within the scope of the present disclosure and the following claims.

The present disclosure illustratively described herein suitably may be practiced in the absence of any element or elements, limitation or limitations which is not specifically described herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or aspects of the disclosure are described in terms grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure.

Thus, additional embodiments are within the scope of the disclosure and within the following claims.

What is claimed is:

1. A compound of Formula I:

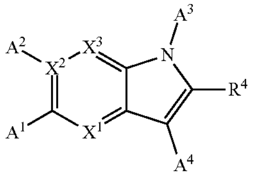

I or a pharmaceutically acceptable salt, a solvate, a tautomer, a stereoisomer, or a deuterated analog thereof, wherein:

$A^1$ is $R^6$, $A^2$ is $R^7$, $A^3$ is -L-$R^1$, $A^4$ is $R^5$, $X^1$ is CH, $X^2$ is C, and $X^3$ is N; or $A^1$ is $R^6$, $A^2$ is absent, $A^3$ is -$L^1$-$R^1$, $A^4$ is $R^5$, $X^1$ is CH, $X^2$ is N, and $X^3$ is CH; or $A^1$ is $R^7$, $A^2$ is $R^6$, $A^3$ is -L-$R^1$, $A^4$ is $R^5$, $X^1$ is N, $X^2$ is C, and $X^3$ is CH; or $A^1$ is $R^7$, $A^2$ is $R^6$, $A^3$ is $R^5$, $A^4$ is -L-$R^1$, $X^1$ is N, $X^2$ is C, and $X^3$ is CH;

L is a bond, $—CH_2—CH_2—$, $—(CH_2)_{1-2}—CH═CH—(CH_2)_{0-1}—$, $—CR^2R^3—$, or —C(O)—; provided that when $A^1$ is $R^7$, $A^2$ is $R^6$, $A^3$ is $A^4$ is $R^5$, $X^1$ is N, $X^2$ is C, and $X^3$ is C, then L is a bond;

$L^2$ is a bond or $—C(R^{13})_2—$;

$R^1$ is phenyl, 5-9 membered heteroaryl, $C_3$-$C_6$cycloalkyl, $C_5$-$C_6$cycloalkenyl, 4-9 membered heterocycloalkyl, or 5-6 membered heterocycloalkenyl, wherein $R^1$ is optionally substituted with 1 $G^1$ group and 1-3 $G^2$ groups;

$R^2$ is H, $C_1$-$C_6$alkyl, or OH;

$R^3$ is H, $C_1$-$C_6$alkyl, $C_1$-$C_6$cyanoalkyl, $C_1$-$C_6$haloalkyl, $C_3$-$C_6$cycloalkyl, or 5-6 membered heteroaryl;

$R^4$ is H, OH, $C_1$-$C_6$alkyl, or $C_1$-$C_6$haloalkyl;

$R^5$, when attached to carbon, is 4-6 membered cycloalkyl, 5-6 membered cycloalkenyl, phenyl, 5-9 membered heteroaryl, 5-6-membered heterocycloalkyl,

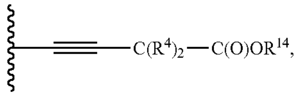

or

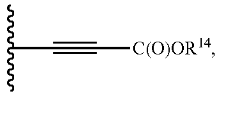

wherein the 4-6 membered cycloalkyl, 5-6 membered cycloalkenyl, phenyl, or 5-9-membered heteroaryl are each optionally substituted with one -$L^2$-$J^1$ group and 0-4 $J^2$ groups, provided that $J^1$ is directly bonded to a carbon atom;

or $R^5$, when attached to nitrogen, is 4-6 membered cycloalkyl, 5-6 membered cycloalkenyl, phenyl, or 5-9 membered heteroaryl, wherein the 4-6 membered cycloalkyl, 5-6 membered cycloalkenyl, phenyl, or 5-9-membered heteroaryl are each optionally substituted with 1-$L^2$-$J^1$ group and 1-4 $J^2$ groups, provided that $J^1$ is directly bonded to a carbon atom;

$R^6$ is a five membered heteroaryl containing at least one nitrogen atom, wherein the 5-membered heteroaryl is optionally substituted with 0-2 $R^8$ groups;

$R^7$ is H, halo, or $C_1$-$C_6$alkyl;

$R^8$ is $C_1$-$C_6$alkyl or $C_1$-$C_3$alkoxy$C_1$-$C_3$alkylene;

each $R^{10}$ is independently H, $C_1$-$C_6$alkyl, $C_1$-$C_6$haloalkyl, or cyclopropyl;

each $R^{11}$ is independently H, $C_1$-$C_6$alkyl, or $C_1$-$C_6$haloalkyl, or two $R^{11}$ groups, together with the carbon atom to which both $R^{11}$ groups are attached, join to form a cyclopropyl group;

each $R^{12}$ is independently H, $C_1$-$C_6$alkyl, $C_1$-$C_6$hydroxyalkyl, or $C_1$-$C_6$haloalkyl;

each $R^{13}$ is independently H, $CH_3$, or F, or each $R^{13}$ join, together with the carbon atom to which they are both attached, to form a $C_3$-$C_6$ cycloalkyl group;

$R^{14}$ is H, $C_1$-$C_6$alkyl, or $C_1$-$C_3$alkoxy$C_1$-$C_3$alkylene;

$G^1$ is CN, $C_2$-$C_6$ alkenyl, $C_1$-$C_6$cyanoalkyl, $C_1$-$C_6$cyanoalkylethynylene, $C_2$-$C_6$alkenyl$C_1$-$C_6$alkylene, $C_1$-$C_6$alkylsulfonyl, $C_1$-$C_6$alkylsulfonyl$C_1$-$C_6$alkylene, $—N(R^{10})_2$, di-$C_1$-$C_6$alkylamino$C_1$-$C_6$alkylene, $C_1$-$C_6$alkylamino$C_1$-$C_6$alkylene, amino$C_1$-$C_6$alkylene, —C(O)—$C_1$-$C_6$alkyl, —C(O)—$C_1$-$C_6$hydroxyalkyl, —C(O)—$C_1$-$C_6$haloalkyl, $—C(O)OR^{12}$, —$C_1$-$C_3$alkylene-C(O)$OR^{12}$, —C(O)—N(H)—$C_3$-$C_6$cycloalkyl, $C_3$-$C_6$cycloalkyl, $C_3$-$C_6$cycloalkyl$C_1$-$C_6$alkylene, $C_3$-$C_6$cycloalkyl$C_2$-$C_6$alkynylene, 4-6 membered heterocycloalkyl, $—C(O)—N(R^{10})_2$, —$C_1$-$C_6$alkylene-C(O)$—N(R^{10})_2$ or phenyl-$C_1$-$C_6$alkoxy, provided that when $G^1$ is attached to a nitrogen atom, $G^1$ is not CN;

each $G^2$ is independently CN, halo, $C_1$-$C_6$alkyl, $C_1$-$C_6$haloalkyl, $C_1$-$C_6$alkoxy, $C_1$-$C_6$haloalkoxy, OH, oxo, $C_1$-$C_6$hydroxyalkyl, provided that when $G^2$ is attached to a nitrogen atom, $G^2$ is not CN, halo, $C_1$-$C_6$alkoxy, $C_1$-$C_6$haloalkoxy, or OH;

$J^1$ is $—C(R^{11})_2—C(O)OH$, —C(O)OH, —C(O)O—$C_1$-$C_6$alkyl, $—CH_2—C(O)O—$$C_1$-$C_6$alkyl, $—C(O)N(R^{10})_2$, —C(O)N(H)—CN, —C(O)N(H)OH, $—C(O)N(H)—SO_2—$$C_1$-$C_6$alkyl, $—N(H)—SO_2—$$C_1$-$C_6$alkyl, $C_1$-$C_6$alkylsulfonyl, tetrazolyl, or)-$S(O)_2—N(R^{10})_2$; and each $J^2$ is independently 4-6 membered heterocycloalkyl, —O-(4-6 membered heterocycloalkyl), —O—$C_3$-$C_6$cycloalkyl, $C_3$-$C_6$cycloalkylalkoxy, phenyl-$C_1$-$C_6$alkoxy, $C_1$-$C_6$alkyl, $C_1$-$C_6$alkoxy, halo, $C_1$-$C_6$haloalkyl, $C_1$-$C_6$haloalkoxy, OH, $C_1$-$C_6$hydroxyalkyl, CN, $C_1$-$C_6$cyanoalkyl, $C_2$-$C_6$alkynyl, $C_3$-$C_6$cycloalkylethynylene, $C_3$-$C_6$cycloalkyl, 4-6 membered heterocycloalkyl, $NO_2$, or $—N(R^{10})_2$, provided that when $J^2$ is attached to nitrogen, $J^2$ is not —O-(4-6 membered heterocycloalkyl), —O—$C_3$-$C_6$cycloalkyl, $C_3$-$C_6$cycloalkylalkoxy, phenyl-$C_1$-$C_6$alkoxy, $C_1$-$C_6$alkoxy, halo, $C_1$-$C_6$haloalkoxy, OH, CN, $C_2$-$C_6$alkynyl, $C_3$-$C_6$cycloalkylethynylene, or $—N(R^{10})_2$.

2. The compound according to claim 1, wherein:

$R^1$ is phenyl, 5-6 membered heteroaryl, $C_3$-$C_6$cycloalkyl, $C_5$-$C_6$cycloalkenyl, 4-6 membered heterocycloalkyl, or 5-6 membered heterocycloalkenyl, wherein $R^1$ is optionally substituted with 1 $G^1$ group and 1-3 $G^2$ groups;

$R^3$ is H, $C_1$-$C_6$alkyl, $C_1$-$C_6$cyanoalkyl, $C_1$-$C_6$haloalkyl, $C_3$-$C_6$cycloalkyl, or 5-6 membered heteroaryl;

$R^4$ is H, OH, $C_1$-$C_2$alkyl, or $C_1$-$C_2$haloalkyl;

$R^5$, when attached to carbon, is 4-6 membered cycloalkyl, cyclohexenyl, phenyl, 5-6 membered heteroaryl, 5-6-membered heterocycloalkyl,

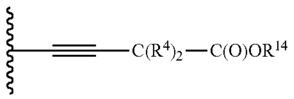

, or

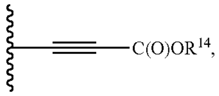

wherein the 4-6 membered cycloalkyl, cyclohexenyl, phenyl, 5-6-membered heteroaryl, or 5-6-membered heterocycloalkyl are each optionally substituted with one $J^1$ group and 0-4 $J^2$ groups, provided that $J^1$ is directly bonded to a carbon atom;

or $R^5$, when attached to nitrogen, is 4-6 membered cycloalkyl, cyclohexenyl, phenyl, or 5-6 membered heteroaryl, wherein the 4-6 membered cycloalkyl, cyclohexenyl, phenyl, or 5-6-membered heteroaryl are each optionally substituted with 1-$L^2$-$J^1$ group and 1-4 $J^2$ groups, provided that $J^1$ is directly bonded to a carbon atom;

$R^6$ is a five membered heteroaryl containing at least one nitrogen atom, wherein the heteroaryl is optionally substituted with 1-2 $R^8$ groups;

$R^7$ is H, halo or $C_1$-$C_5$alkyl;

$R^8$ is $C_1$-$C_4$alkyl or $C_1$-$C_2$alkoxy$C_1$-$C_2$alkylene;

each $R^{10}$ is independently H, $C_1$-$C_5$alkyl, $C_1$-$C_5$haloalkyl or cyclopropyl;

each $R^{11}$ is independently H, $C_1$-$C_5$alkyl, or $C_1$-$C_5$haloalkyl, or two $R^{11}$ groups, together with the carbon atom to which both $R^{11}$ groups are attached, join to form a cyclopropyl group;

each $R^{12}$ is H;

$R^{14}$ is H, $C_1$-$C_5$alkyl or $C_1$-$C_3$alkoxy$C_1$-$C_3$alkylene;

$G^1$ is CN, $C_1$-$C_6$cyanoalkyl, $C_1$-$C_5$cyanoalkylethynylene, $C_2$-$C_5$alkenyl$C_1$-$C_5$alkylene, $C_1$-$C_5$alkylsulfonyl, $C_1$-$C_5$alkylsulfonyl$C_1$-$C_5$alkylene, —$N(R^{10})_2$, di-$C_1$-$C_5$alkylamino-$C_1$-$C_5$alkylene, $C_1$-$C_5$alkylamino-$C_1$-$C_5$alkylene, amino$C_1$-$C_5$alkylene, —C(O)—$C_1$-$C_5$alkyl, —C(O)—$C_1$-$C_5$hydroxyalkyl, —C(O)—$C_1$-$C_5$haloalkyl, —C(O)$OR^{12}$, —$C_1$-$C_3$alkylene-C(O)$OR^{12}$, —C(O)—N(H)—$C_3$-$C_6$cycloalkyl, $C_3$-$C_6$cycloalkyl, $C_3$-$C_6$cycloalkyl$C_1$-$C_5$alkylene, $C_3$-$C_6$cycloalkyl$C_2$-$C_5$alkynylene, 4-6 membered heterocycloalkyl, —C(O)—$N(R^{10})_2$, —$C_1$-$C_5$alkylene-C(O)—$N(R^{10})_2$ or phenyl-$C_1$-$C_5$alkoxy, provided that when $G^1$ is attached to a nitrogen atom, $G^1$ is not CN;

each $G^2$ is independently halo, $C_1$-$C_5$alkyl, $C_1$-$C_5$haloalkyl, $C_1$-$C_5$alkoxy, $C_1$-$C_5$haloalkoxy, OH, oxo, $C_1$-$C_5$hydroxyalkyl, provided that when $G^2$ is attached to a nitrogen atom, $G^2$ is not halo, $C_1$-$C_5$alkoxy, $C_1$-$C_5$haloalkoxy, or OH;

$J^1$ is —$C(R^{11})_2$—C(O)OH, —C(O)OH, —C(O)O—$C_1$-$C_5$alkyl, —$CH_2$—C(O)O—$C_1$-$C_5$alkyl, —C(O)$N(R^{10})_2$, —C(O)N(H)—CN, —C(O)N(H)OH, —C(O)N(H)—$SO_2$—$C_1$-$C_5$alkyl, —N(H)—$SO_2$—$C_1$-$C_5$alkyl, $C_1$-$C_5$alkylsulfonyl, tetrazolyl, or —$S(O)_2$—$N(R^{10})_2$; and each $J^2$ is independently 4-6 membered heterocycloalkyl, —O-(4-6 membered heterocycloalkyl), —O—$C_3$-$C_6$cycloalkyl, $C_3$-$C_6$cycloalkylalkoxy, phenyl-$C_1$-$C_5$alkoxy, $C_1$-$C_5$alkyl, $C_1$-$C_5$alkoxy, halo, $C_1$-$C_5$haloalkyl, $C_1$-$C_5$haloalkoxy, OH, $C_1$-$C_5$hydroxyalkyl, CN, $C_1$-$C_5$cyanoalkyl, $C_2$-$C_5$alkynyl, $C_3$-$C_6$cycloalkylethynylene, $C_3$-$C_6$cycloalkyl, 4-6 membered heterocycloalkyl, or —$N(R^{10})_2$, provided that when $J^2$ is attached to nitrogen, $J^2$ is not —O-(4-6 membered heterocycloalkyl), —O—$C_3$-$C_6$cycloalkyl, $C_3$-$C_6$cycloalkylalkoxy, phenyl-$C_1$-$C_5$alkoxy, $C_1$-$C_5$alkoxy, halo, $C_1$-$C_5$haloalkoxy, OH, CN, $C_2$-$C_6$alkynyl, $C_3$-$C_6$cycloalkylethynylene, or —$N(R^{10})_2$.

3. The compound according to claim 1 having Formula II(a), II(b) or II(c)

II(a)

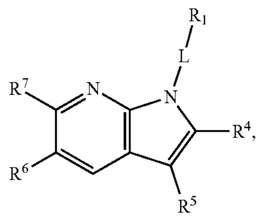

II(b)

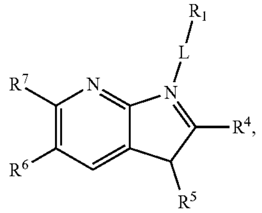

II(c)

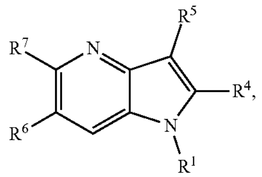

or a pharmaceutically acceptable salt, a solvate, a tautomer, a stereoisomer, or a deuterated analog thereof.

4. The compound according to claim 1 having any one of Formulae III(a), III(c), III(d), III(e), or III(f):

III(a)

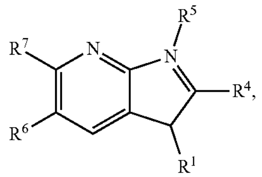

III(c)

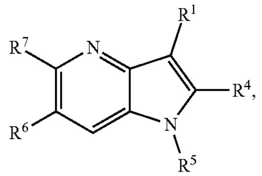

-continued

III(d)

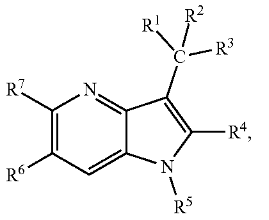

III(e)

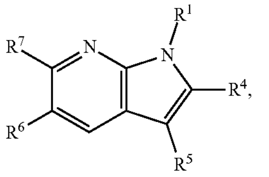

III(f)

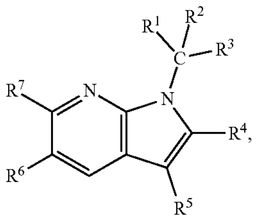

or a pharmaceutically acceptable salt, a solvate, a tautomer, a stereoisomer, or a deuterated analog thereof.

5. The compound according to claim 1, wherein $R^6$ is:

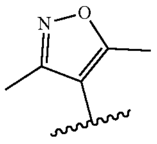 , 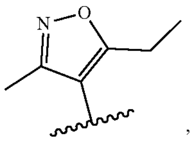 ,

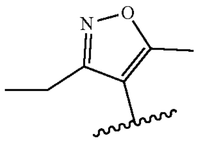 , 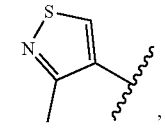 , 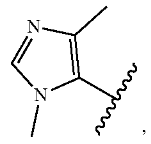 ,

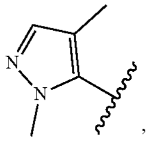 , 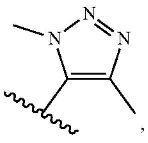 , 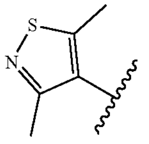 or

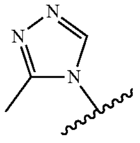 .

6. The compound according to claim 1 wherein $R^6$ is:

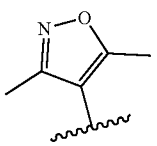 , 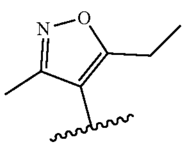 or

-continued

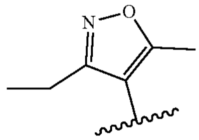 .

7. The compound according to claim 1, wherein $R^4$ is H, OH, $CF_3$, or $CH_3$.

8. The compound according to claim 1, wherein L is a bond, —$CH_2$—, —$(CH_2)_2$—, $CH(CH_3)$—, $CH(CH_2CH_3)$—, —C(O)—, —$CH(C_3$-$C_6$cycloalkyl)-, —CH(pyridyl)-, —$C(CH_3)$(pyridyl)-, or —C(H)($CH_2CN$)—.

9. The compound according to claim 1, wherein $R^1$ is phenyl, pyridyl, pyrimidinyl, pyridazinyl, pyrazolyl, $C_3$-$C_6$ cycloalkyl, cyclohexenyl, morpholinyl, piperazinyl, piperidinyl, pyrrolidinyl, tetrahydro-2H-furanyl, oxetanyl, azetidine, tetrahydro-2H-pyranyl, tetrahydro-2H-thiopyranyl 1,1-dioxide, tetrahydro-2H-thiopyranyl 1-oxide, tetrahydro-2H-thiopyranyl, tetrahydrothienyl, or thienyl, wherein $R^1$ is optionally substituted with 1 $G^1$ group and 1-3 $G^2$ groups.

10. The compound according to claim 1, wherein:

$R^1$ is one of (a), (b), (c), (d), (e), (f), (g), (h), (i), (j), (k), (l), or (m):

(a) $C_3$-$C_6$ cycloalkyl optionally substituted with 1 $G^1$ group and 1-3 $G^2$ groups, wherein
$G^1$ is —$CH_2CN$ and
$G^2$ is F or CN;

(b) phenyl optionally substituted with 1 $G^1$ group and 1-3 $G^2$ groups, wherein $G^1$ is benzyloxy, —C(=$CH_2$)$CH_3$, —C(O)OH, —C(O)$NH_2$, —C(O)N(H)-cyclopropyl, cyclopropyl, CN, or —$SO_2CH_3$; and each $G^2$ is independently —$OCHF_2$, Cl, F, —$OCH_3$, —$OCF_3$, $CH_3$, $CF_3$, and —$C(CH_3)_2$—OH;

(c) pyridyl optionally substituted with 1 $G^1$ group and 1-2 $G^2$ groups, wherein $G^1$ is —C(O)OH, —C(O)$NH_2$, cyclopropyl, or cyclopropylalkynylene; and each $G^2$ is independently F, CN, $OCH_3$, $CF_3$, $CH_3$, OH, —CH$(CH_3)_2$, and $C_1$;

(d) pyrazolyl optionally substituted with 1 $G^1$ group and 1-2 $G^2$ groups, provided that L is a bond when $R^1$ is pyrazolyl, wherein $G^1$, which can substitute a hydrogen atom of —NH— or =CH—, is —$CH_2$—$SO_2$—$CH_3$, —$(CH_2)_2$—$N(CH_3)_2$, cyclopropyl, —$CH_2$-cyclopropyl, —$(CH_2)_2$—CN, or —$CH_2C(O)N(CH_3)_2$; and each $G^2$, which can substitute a hydrogen atom of —NH— or =CH—, is independently $C_1$-$C_6$alkyl, $C_1$-$C_6$haloalkyl, and hydroxy$C_1$-$C_6$alkyl;

(e) pyrimidinyl optionally substituted with —$NH_2$, —$N(CH_3)_2$, $OCH_3$, N-azetidinyl or cyclopropyl;

(f) pyridazinyl;

(g) tetrahydro-2H-pyranyl optionally substituted with 1-2 groups each independently $C_1$-$C_6$alkyl, $C_1$-$C_6$haloalkyl, hydroxy$C_1$-$C_6$alkyl, Cl and F;

(h) tetrahydro-2H-furanyl optionally substituted with 1-2 groups each independently $C_1$-$C_6$alkyl, $C_1$-$C_6$haloalkyl, hydroxy$C_1$-$C_6$alkyl, Cl and F;

(i) morpholinyl optionally substituted with 1-2 groups each independently $C_1$-$C_6$alkyl, $C_1$-$C_6$haloalkyl, and hydroxy$C_1$-$C_6$alkyl;

(j) oxetanyl;

(k) piperidinyl optionally substituted with 1-2 groups each independently $C_1$-$C_6$alkyl, $C_1$-$C_6$haloalkyl, and hydroxy$C_1$-$C_6$alkyl;

(l) cyclohexenyl optionally substituted with 1-2 groups each independently $C_1$-$C_6$alkyl, $C_1$-$C_6$haloalkyl, hydroxy$C_1$-$C_6$alkyl, Cl and F; or
(m) thienyl.
11. The compound according to claim 1, wherein -L-$R^1$ is:
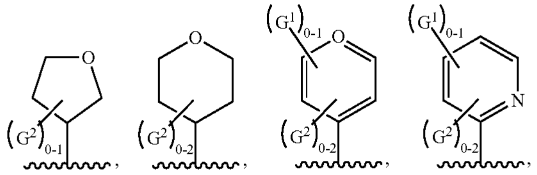
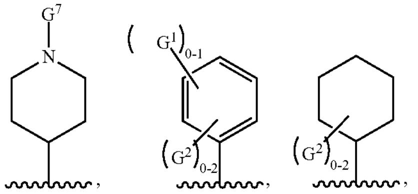
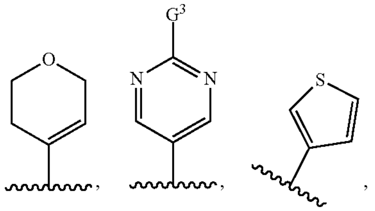
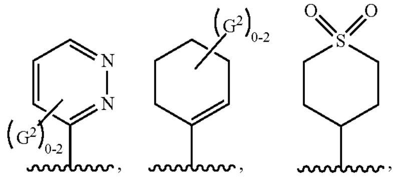
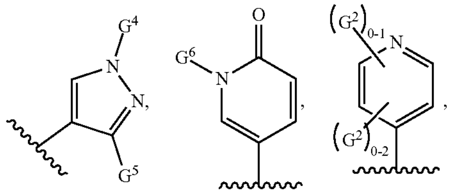
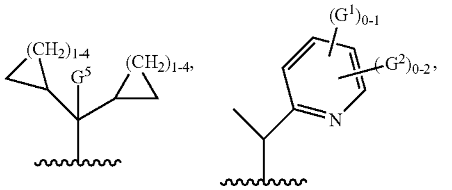
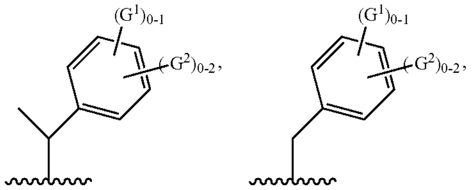
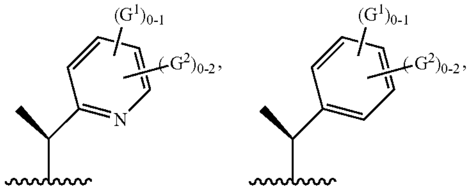
-continued
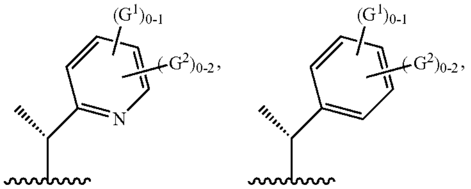
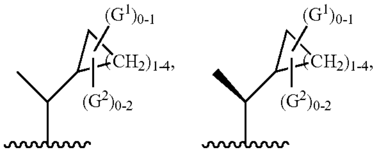
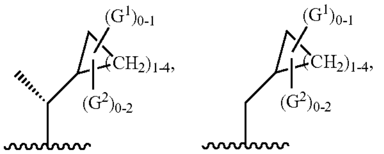
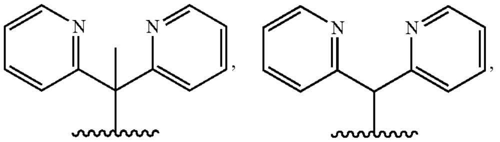
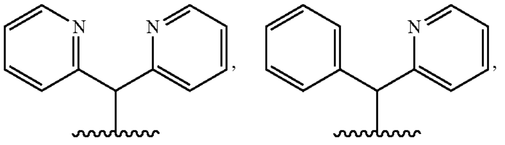
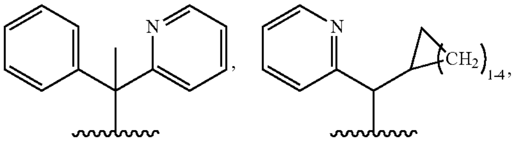
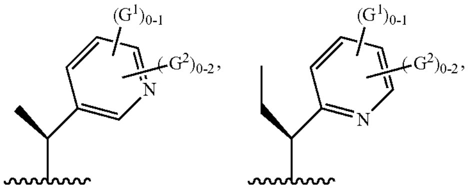
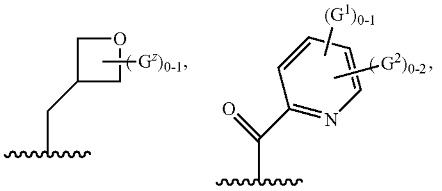
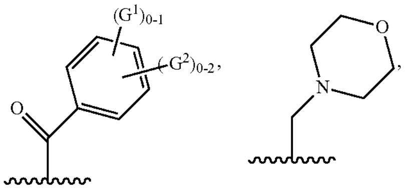
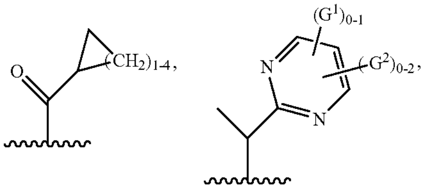

-continued

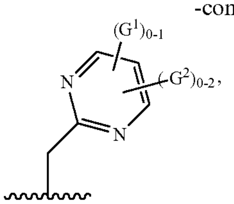

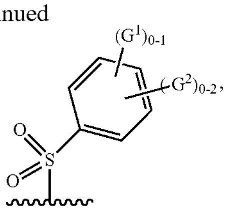

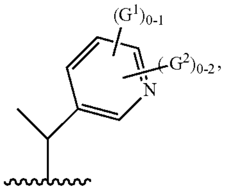

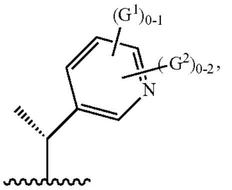

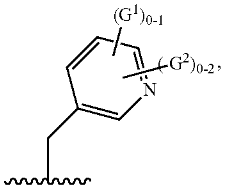

or

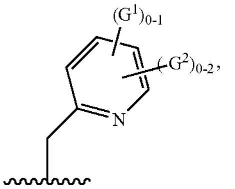

wherein:

$G^3$ is H, $OCH_3$, N-azetidinyl, $NH_2$, $—N(CH_3)_2$, or cyclopropyl;

$G^4$ is H, $CH_3$, $—CH_2CH_3$, $—(CH_2)N(CH_3)_2$, $—CH_2—SO_2—CH_3$, $—CH(CH_3)_2$, $—CH_2C(CH_3)_2(OH)$, cyclopropyl, $—CH_2$-cyclopropyl, $—(CH_2)_2—CN$, or $—CH_2C(O)N(CH_3)_2$;

$G^5$ is H or OH;

$G^6$ is H or $CH_3$, and $G^7$ is H, $CH_3$, $—(CH_2)N(CH_3)_2$, $—SO_2—CH_3$, $—CH_2—SO_2—CH_3$, $—CH(CH_3)_2$, $—CH_2C(CH_3)_2(OH)$, cyclopropyl, $—CH_2$-cyclopropyl, $—(CH_2)_2—CN$, $—CH_2C(O)N(CH_3)_2$, $—C(O)OC(CH_3)_3$, $—C(O)CH_3$, or $—C(O)C(CH_3)_3$.

12. The compound according to claim 11, wherein:

$G^1$ is $—CH_2CN$, benzyloxy, $—C(=CH_2)CH_3$, $—C(O)OH$, $—C(O)NH_2$, $—C(O)N(H)$-cyclopropyl, cyclopropyl, $—CH_2$-cyclopropyl, cyclopropylalkynylene, $—CH_2—SO_2—CH_3$, $—SO_2—CH_3$, $—(CH_2)N(CH_3)_2$, $—(CH_2)_2—N(CH_3)_2$, $—CH_2$-cyclopropyl, $—(CH_2)_2—CN$, $—C(O)OC(CH_3)_3$, $—C(O)CH_3$, and $—C(O)C(CH_3)_3$, $—CH_2C(O)N(CH_3)_2$, CN, or $—SO_2CH_3$; and each $G^2$ is independently $—OCHF_2$, $—OCH_2F$, Cl, F, $—OCH_3$, OH, $—OCF_3$, $CH_3$, $—CH(CH_3)_2$, $CF_3$, $CH_2C(CH_3)_2(OH)$, and $—C(CH_3)_2—OH$.

13. The compound according to claim 1, wherein -L-$R^1$ is:

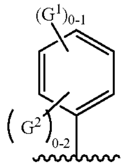
,
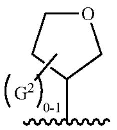
,
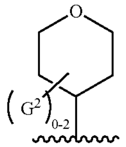
,
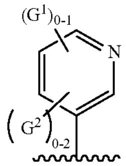
,
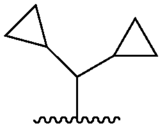
,

-continued

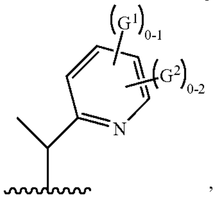
,
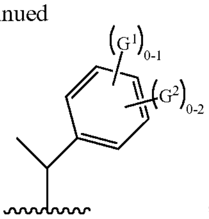
,
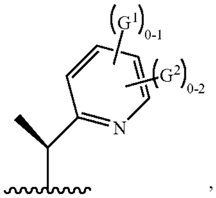
,
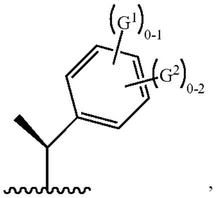
,
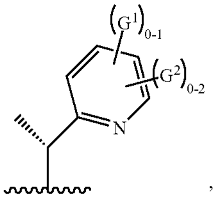
,
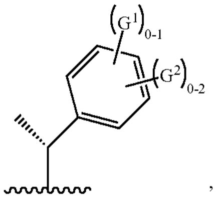
,
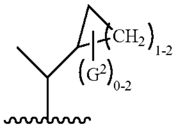
,
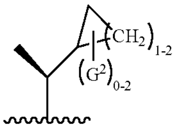
,
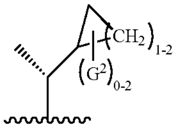
,
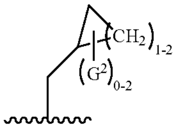
,
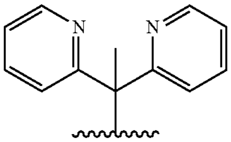
,
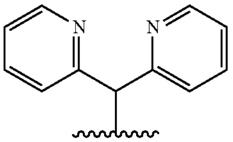
,
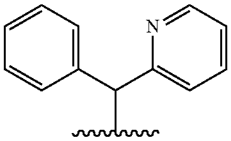
,
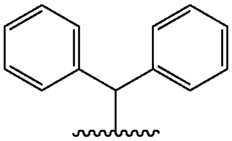
,
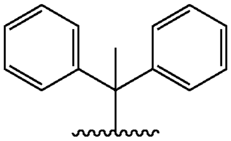

or

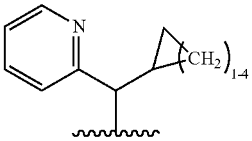
.

14. The compound according to claim 13, wherein $G^1$ is $—CH_2CN$, benzyloxy, $—C(=CH_2)CH_3$, $—C(O)OH$, $—C(O)NH_2$, $—C(O)N(H)$-cyclopropyl, cyclopropyl, $—CH_2$-cyclopropyl, cyclopropylalkynylene, $—CH_2—SO_2—CH_3$, $—SO_2—CH_3$, $—(CH_2)N(CH_3)_2$, $—(CH_2)_2—N(CH_3)_2$, $—CH_2$-cyclopropyl, $—(CH_2)_2—CN$, $—C(O)OC(CH_3)_3$, $—C(O)CH_3$, $—C(O)C(CH_3)_3$, $—CH_2C(O)N(CH_3)_2$, CN, or $—SO_2CH_3$; and each $G^2$ is independently $—OCHF_2$, $—OCH_2F$, Cl, F, $—OCH_3$, OH, $—OCF_3$, $CH_3$, $—CH(CH_3)_2$, $CF_3$, $CH_2C(CH_3)_2(OH)$, and $—C(CH_3)_2—OH$.

15. The compound according to claim 1, wherein $R^5$, when attached to carbon, is:
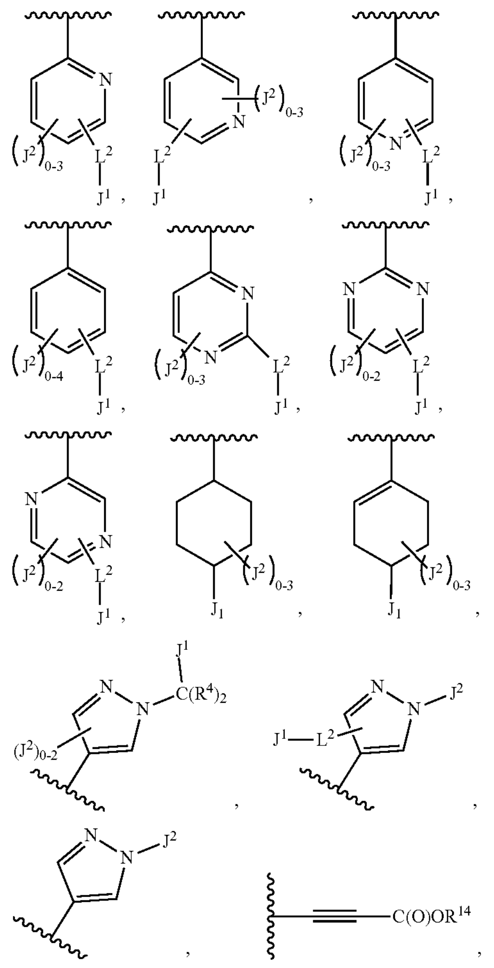
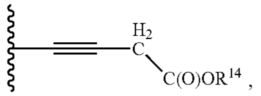
or
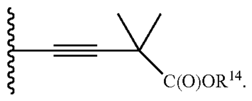
-continued
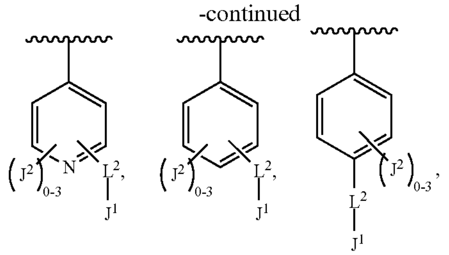
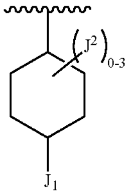
or
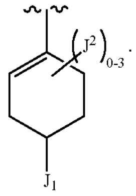
16. The compound according to claim 1, wherein $R^5$ is:
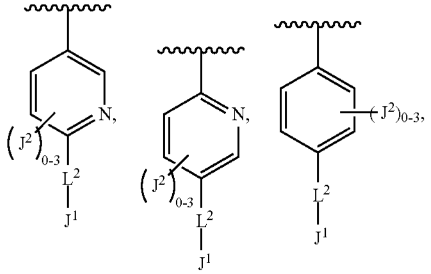
17. The compound according to claim 1, wherein $R^5$ is:
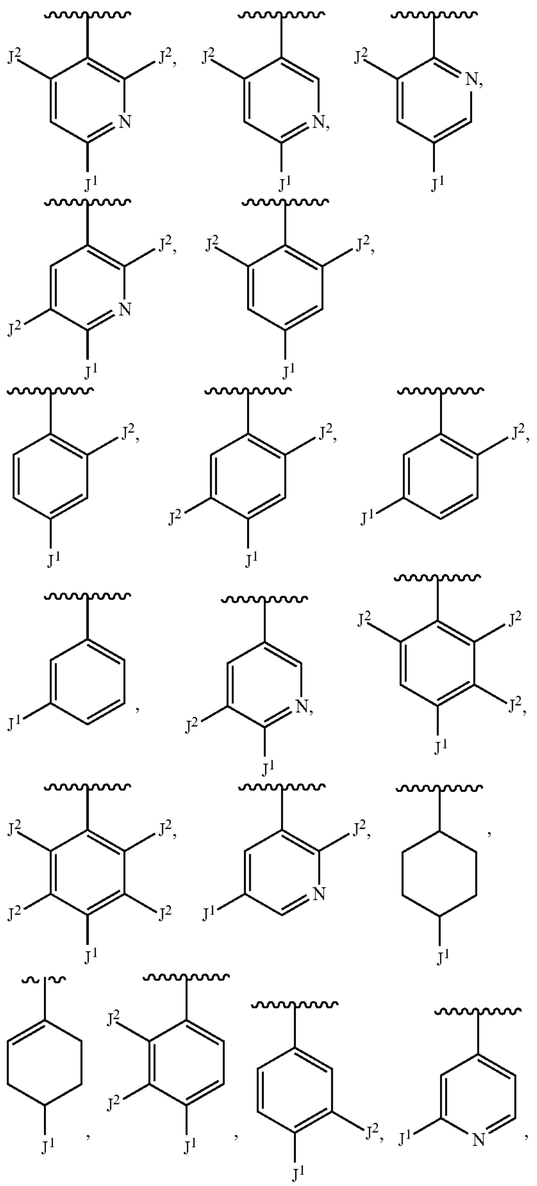

-continued

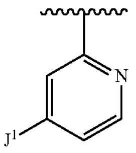
or
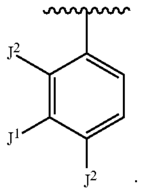
.

18. The compound according to claim 1, wherein $R^5$ is:

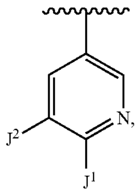
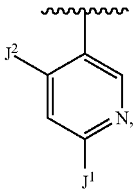
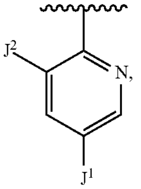
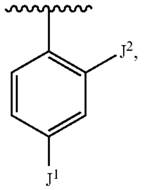
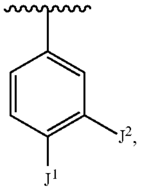
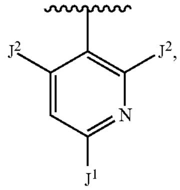
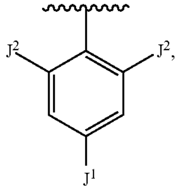
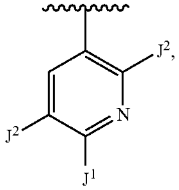
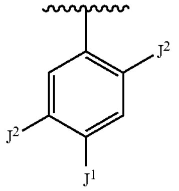
or
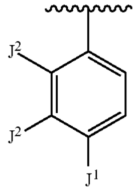
.

19. The compound according to claim 1, wherein:

$J^1$ is —C(O)OH, —C(O)OCH$_3$, —CH$_2$C(O)OH, —C(O)N(H)CH$_3$, —C(O)NH$_2$, tetrazolyl, —SO$_2$CH$_3$, —C(O)N(H)CN, C(O)N(H)OH, —SO$_2$NH$_2$, —SO$_2$NH-cyclopropyl, —C(O)N(H)SO$_2$CH$_3$; and each $J^2$ is independently —O-cyclobutyl, —OCH$_2$-phenyl, —O-cyclopropyl, —O—CH$_2$-cyclopropyl, cyclopropylethynylene, CN, OH, cyclopropyl, F, Cl, —OCH$_3$, —OCHF$_2$, OCF$_3$, —OCH$_2$CF$_3$, —OCH$_2$CHF$_2$, —OCH(CH$_3$)$_2$, —CH$_2$CH$_3$, —OCH$_2$CH$_3$, —OCH$_2$CH$_2$CH$_3$, and CH$_3$.

20. The compound according to claim 19, wherein:

$J^1$ is —C(O)OH or —C(O)OCH$_3$; and each $J^2$ is independently F, $C_1$, —OCH$_3$, —OCHF$_2$, OCF$_3$, —OCH$_2$CF$_3$, —OCH$_2$CHF$_2$, —OCH(CH$_3$)$_2$, —CH$_2$CH$_3$, —OCH$_2$CH$_3$, —OCH$_2$CH$_2$CH$_3$, and CH$_3$.

21. The compound according to claim 1 having Formulae IV(a) or IV(c):

IV(a)

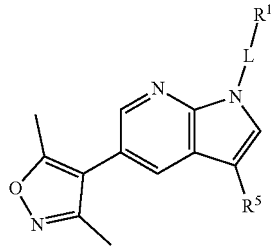
or

IV(c)

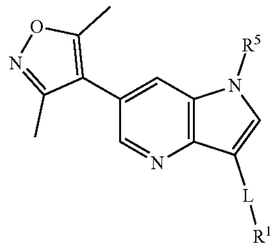

or a pharmaceutically acceptable salt, a solvate, a tautomer, a stereoisomer, or a deuterated analog thereof, wherein:

$R^5$ is:

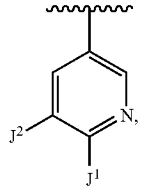
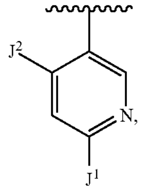
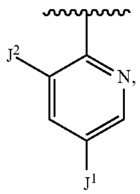
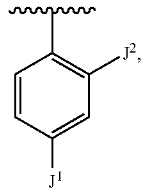
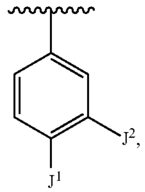
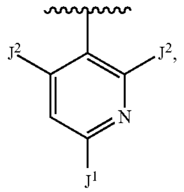
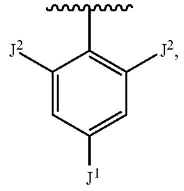
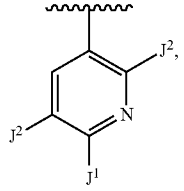
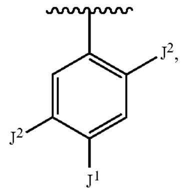
or
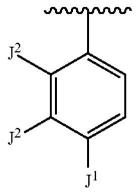
;

$J^1$ is —C(O)OH or —C(O)OCH$_3$;

each $J^2$ is independently F, $C_1$, —OCH$_3$, —OCHF$_2$, OCF$_3$, —OCH$_2$CF$_3$, —OCH$_2$CHF$_2$, —OCH(CH$_3$)$_2$, —CH$_2$CH$_3$, —OCH$_2$CH$_3$, —OCH$_2$CH$_2$CH$_3$, and CH$_3$;

-L-$R^1$ is:

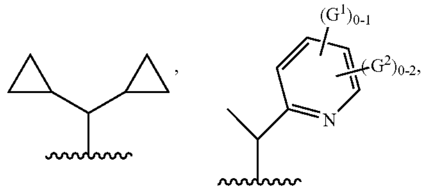

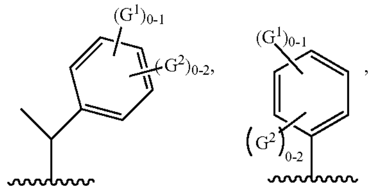

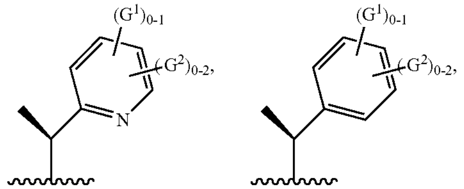

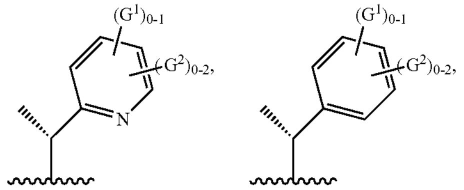

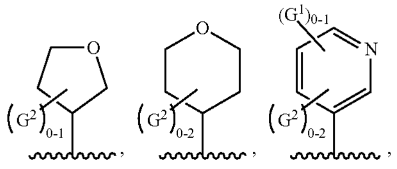

or

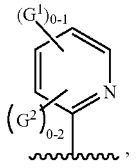

wherein $G^1$ is —$CH_2CN$, benzyloxy, —$C(=CH_2)CH_3$, —C(O)OH, —$C(O)NH_2$, —C(O)N(H)-cyclopropyl, cyclopropyl, —$CH_2$-cyclopropyl, cyclopropylalkynylene, —$CH_2$—$SO_2$—$CH_3$, —$SO_2$—$CH_3$, —$(CH_2)N(CH_3)_2$, —$(CH_2)_2$—$N(CH_3)_2$, —$CH_2$-cyclopropyl, —$(CH_2)_2$—CN, —$C(O)OC(CH_3)_3$, —$C(O)CH_3$, —$C(O)C(CH_3)_3$, —$CH_2C(O)N(CH_3)_2$, CN, or —$SO_2CH_3$; and each $G^2$ is independently —$OCHF_2$, —$OCH_2F$, Cl, F, —$OCH_3$, OH, —$OCF_3$, $CH_3$, —$CH(CH_3)_2$, $CF_3$, CN, $CH_2C(CH_3)_2(OH)$, and —$C(CH_3)_2$—OH.

22. A compound selected from

| P# | Structure |
| --- | --- |
| P-0001 | 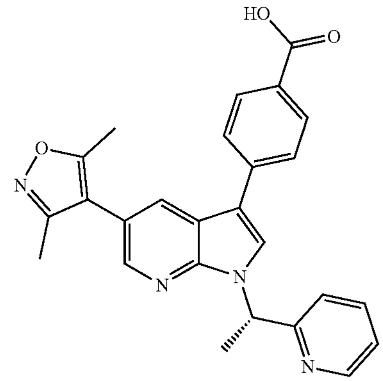 [SMILES: Cc1noc(C)c1-c1cnc2c(c1)c(-c1ccc(C(=O)O)cc1)cn2[C@@H](C)c1ccccn1] |
| P-0002 | 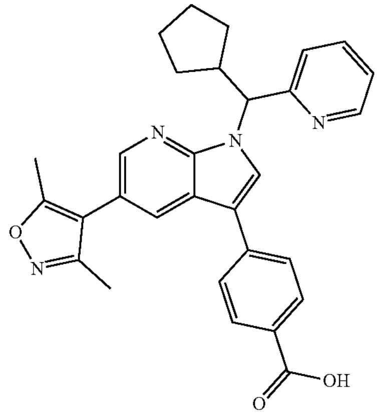 [SMILES: Cc1noc(C)c1-c1cnc2c(c1)c(-c1ccc(C(=O)O)cc1)cn2C(c1ccccn1)C1CCCC1] |
| P-0003 | 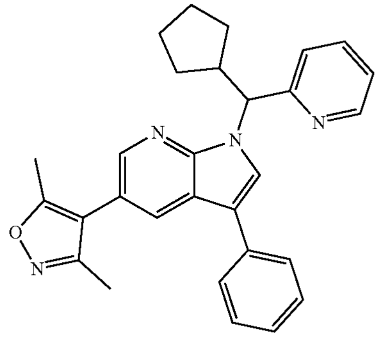 [SMILES: Cc1noc(C)c1-c1cnc2c(c1)c(-c1ccccc1)cn2C(c1ccccn1)C1CCCC1] |
| P-0004 | 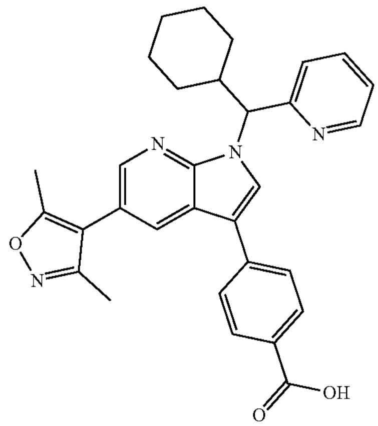 [SMILES: Cc1noc(C)c1-c1cnc2c(c1)c(-c1ccc(C(=O)O)cc1)cn2C(c1ccccn1)C1CCCCC1] |

-continued
| P# | Structure |
|---|---|
| P-0005 | 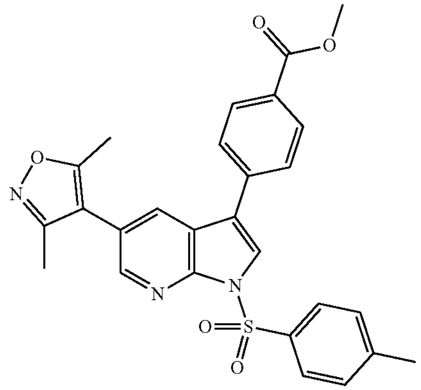 [SMILES: COC(=O)c1ccc(-c2cn(S(=O)(=O)c3ccc(C)cc3)c3ncc(-c4c(C)noc4C)cc23)cc1] |
| P-0006 | 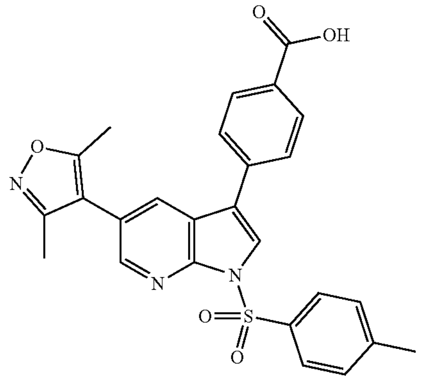 [SMILES: Cc1ccc(S(=O)(=O)n2cc(-c3ccc(C(=O)O)cc3)c3cc(-c4c(C)noc4C)cnc32)cc1] |
| P-0007 | 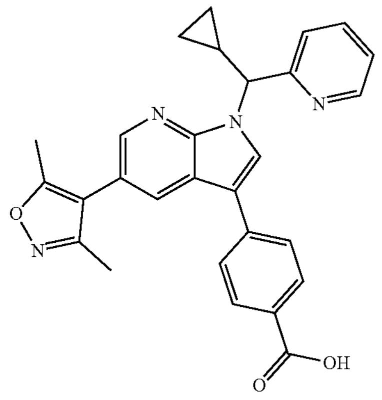 [SMILES: Cc1noc(C)c1-c1cnc2c(c1)c(-c1ccc(C(=O)O)cc1)cn2C(c1ccccn1)C1CC1] |
| P-0008 | 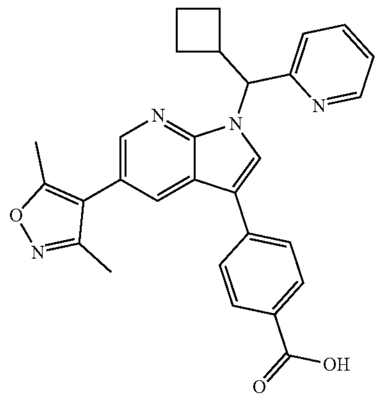 [SMILES: Cc1noc(C)c1-c1cnc2c(c1)c(-c1ccc(C(=O)O)cc1)cn2C(c1ccccn1)C1CCC1] |
-continued
| P# | Structure |
|---|---|
| P-0009 | 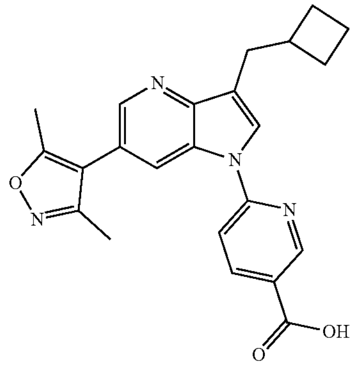 [SMILES: Cc1noc(C)c1-c1cnc2c(CC3CCC3)cn(-c3ccc(C(=O)O)cn3)c2c1] |
| P-0010 | 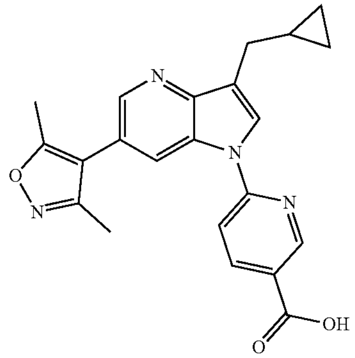 [SMILES: Cc1noc(C)c1-c1cnc2c(CC3CC3)cn(-c3ccc(C(=O)O)cn3)c2c1] |
| P-0011 | 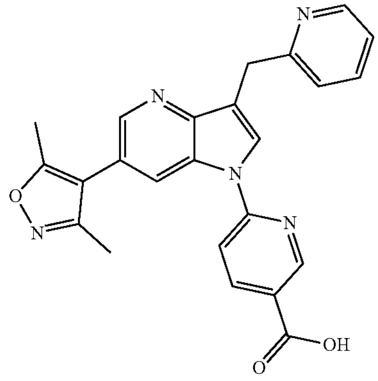 [SMILES: Cc1noc(C)c1-c1cnc2c(Cc3ccccn3)cn(-c3ccc(C(=O)O)cn3)c2c1] |
| P-0012 | 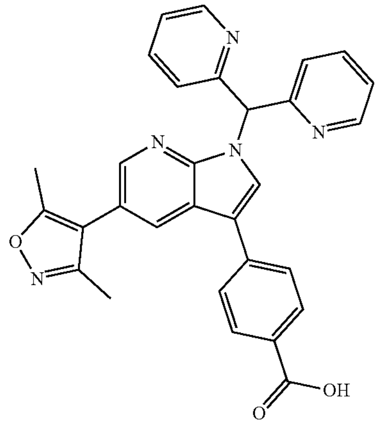 [SMILES: Cc1noc(C)c1-c1cnc2c(c1)c(-c1ccc(C(=O)O)cc1)cn2C(c1ccccn1)c1ccccn1] |

-continued
| P# | Structure |
|---|---|
| P-0013 | 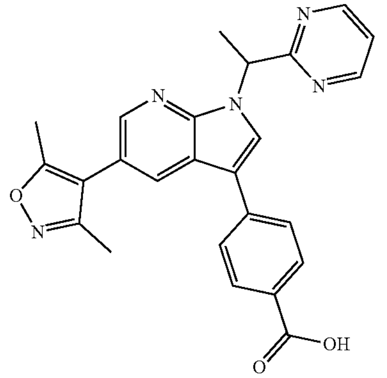 [SMILES: Cc1noc(C)c1-c1cnc2c(c1)c(-c1ccc(C(=O)O)cc1)cn2C(C)c1ncccn1] |
| P-0014 | 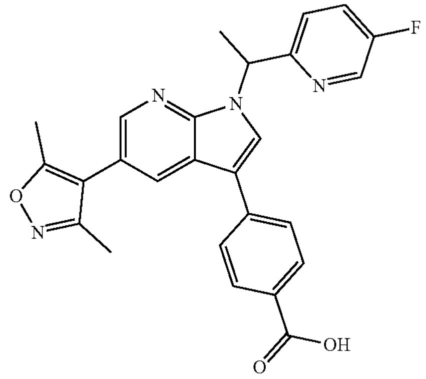 [SMILES: Cc1noc(C)c1-c1cnc2c(c1)c(-c1ccc(C(=O)O)cc1)cn2C(C)c1ccc(F)cn1] |
| P-0015 | 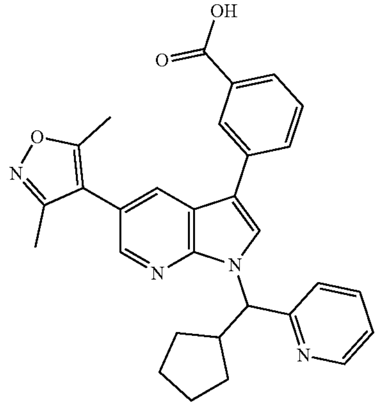 [SMILES: Cc1noc(C)c1-c1cnc2c(c1)c(-c1cccc(C(=O)O)c1)cn2C(c1ccccn1)C1CCCC1] |
| P-0016 | 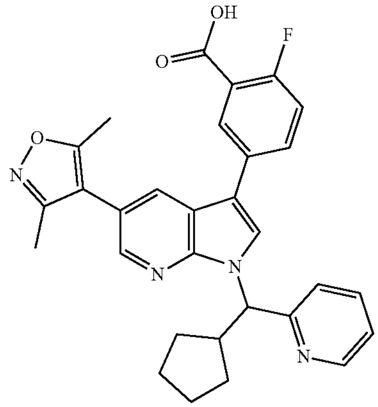 [SMILES: Cc1noc(C)c1-c1cnc2c(c1)c(-c1ccc(F)c(C(=O)O)c1)cn2C(c1ccccn1)C1CCCC1] |
-continued
| P# | Structure |
|---|---|
| P-0017 | 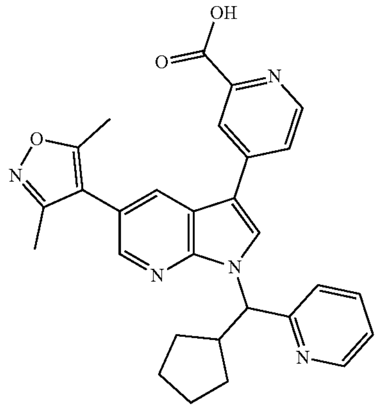 [SMILES: Cc1noc(C)c1-c1cnc2c(c1)c(-c1ccnc(C(=O)O)c1)cn2C(c1ccccn1)C1CCCC1] |
| P-0018 | 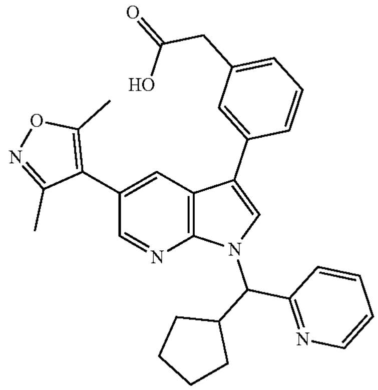 [SMILES: Cc1noc(C)c1-c1cnc2c(c1)c(-c1cccc(CC(=O)O)c1)cn2C(c1ccccn1)C1CCCC1] |
| P-0019 | 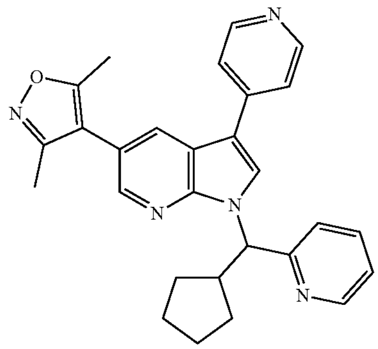 [SMILES: Cc1noc(C)c1-c1cnc2c(c1)c(-c1ccncc1)cn2C(c1ccccn1)C1CCCC1] |
| P-0020 | 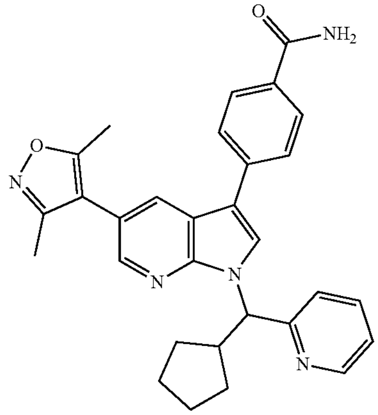 [SMILES: Cc1noc(C)c1-c1cnc2c(c1)c(-c1ccc(C(N)=O)cc1)cn2C(c1ccccn1)C1CCCC1] |

-continued
| P# | Structure |
| --- | --- |
| P-0021 | 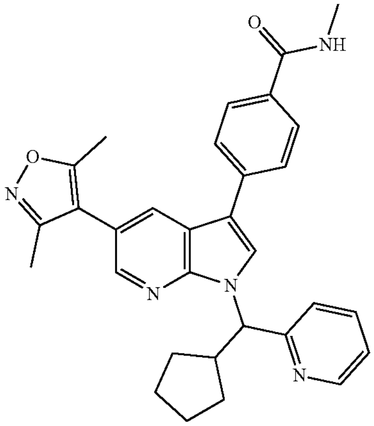 [SMILES: CNC(=O)c1ccc(-c2cn(C(c3ccccn3)C3CCCC3)c3ncc(-c4c(C)noc4C)cc23)cc1] |
| P-0022 | 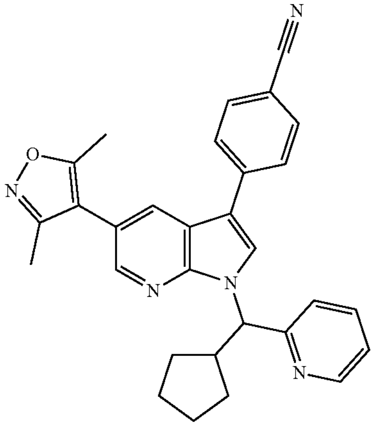 [SMILES: Cc1noc(C)c1-c1cnc2c(c1)c(-c1ccc(C#N)cc1)cn2C(c1ccccn1)C1CCCC1] |
| P-0023 | 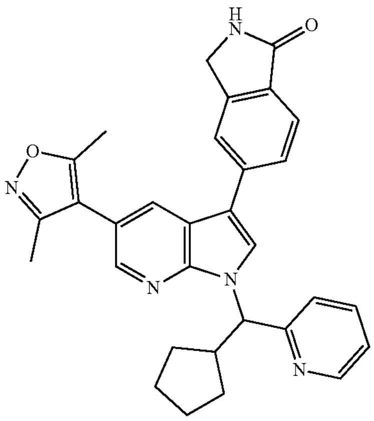 [SMILES: Cc1noc(C)c1-c1cnc2c(c1)c(-c1ccc3c(c1)CNC3=O)cn2C(c1ccccn1)C1CCCC1] |
-continued
| P# | Structure |
| --- | --- |
| P-0024 | 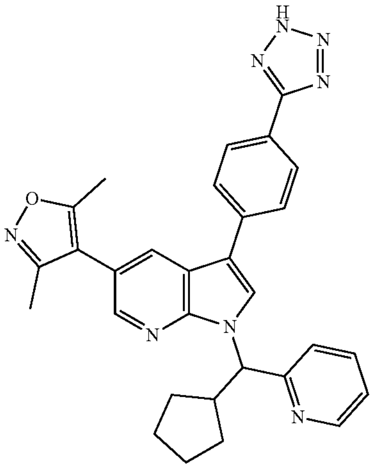 [SMILES: Cc1noc(C)c1-c1cnc2c(c1)c(-c1ccc(-c3nn[nH]n3)cc1)cn2C(c1ccccn1)C1CCCC1] |
| P-0025 | 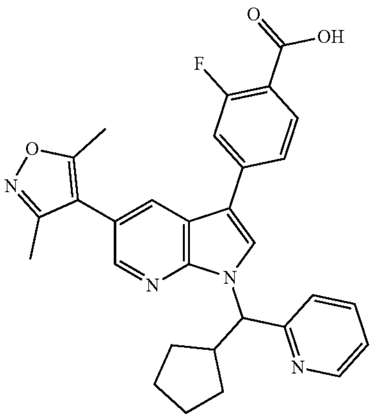 |
| P-0026 | 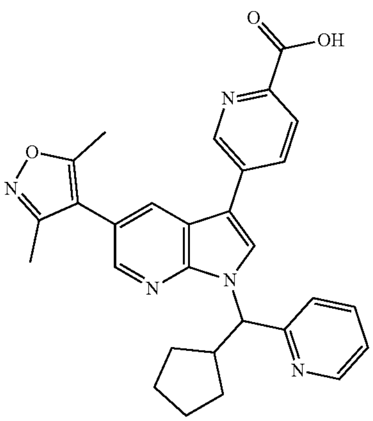 [SMILES: Cc1noc(C)c1-c1cnc2c(c1)c(-c1ccc(C(=O)O)nc1)cn2C(c1ccccn1)C1CCCC1] |

-continued
| P# | Structure |
|---|---|
| P-0027 | 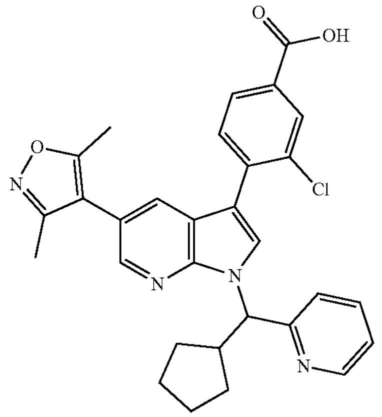 [SMILES: Cc1noc(C)c1-c1cnc2c(c1)c(-c1ccc(C(=O)O)cc1Cl)cn2C(c1ccccn1)C1CCCC1] |
| P-0028 | 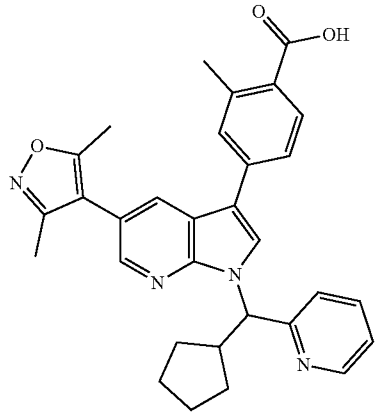 [SMILES: Cc1cc(-c2cn(C(c3ccccn3)C3CCCC3)c3ncc(-c4c(C)noc4C)cc23)ccc1C(=O)O] |
| P-0029 | 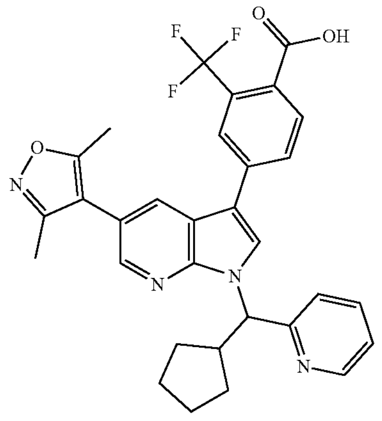 [SMILES: Cc1noc(C)c1-c1cnc2c(c1)c(-c1ccc(C(=O)O)c(C(F)(F)F)c1)cn2C(c1ccccn1)C1CCCC1] |
-continued
| P# | Structure |
|---|---|
| P-0030 | 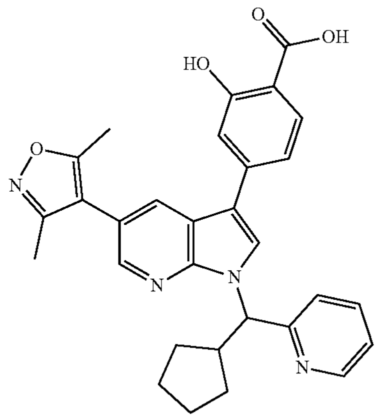 [SMILES: Cc1noc(C)c1-c1cnc2c(c1)c(-c1ccc(C(=O)O)c(O)c1)cn2C(c1ccccn1)C1CCCC1] |
| P-0031 | 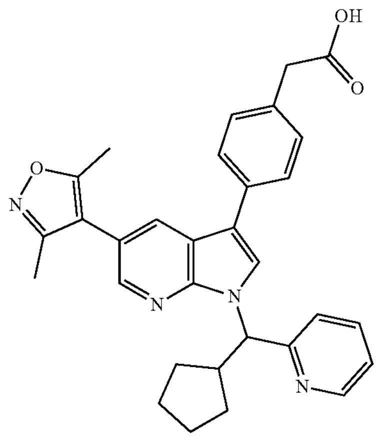 [SMILES: Cc1noc(C)c1-c1cnc2c(c1)c(-c1ccc(CC(=O)O)cc1)cn2C(c1ccccn1)C1CCCC1] |
| P-0032 | 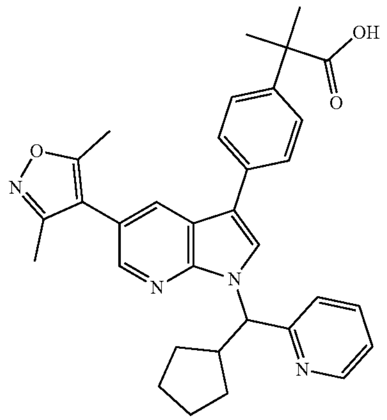 [SMILES: Cc1noc(C)c1-c1cnc2c(c1)c(-c1ccc(C(C)(C)C(=O)O)cc1)cn2C(c1ccccn1)C1CCCC1] |

-continued
| P# | Structure |
|---|---|
| P-0033 | 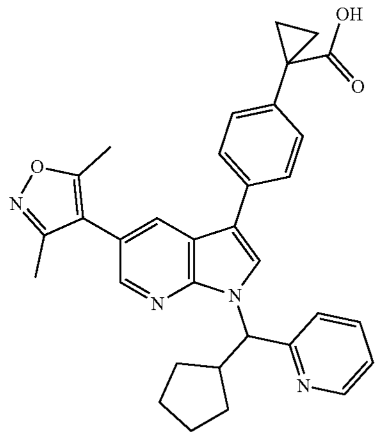 [SMILES: Cc1noc(C)c1-c1cnc2c(c1)c(-c1ccc(C3(C(=O)O)CC3)cc1)cn2C(c1ccccn1)C1CCCC1] |
| P-0034 | 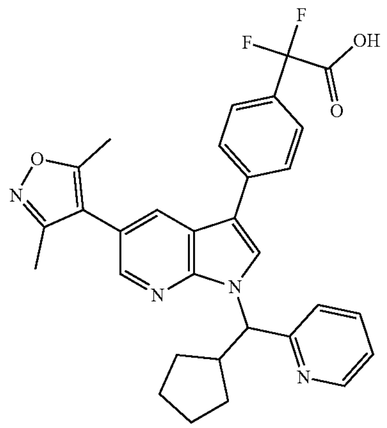 [SMILES: Cc1noc(C)c1-c1cnc2c(c1)c(-c1ccc(C(F)(F)C(=O)O)cc1)cn2C(c1ccccn1)C1CCCC1] |
| P-0035 | 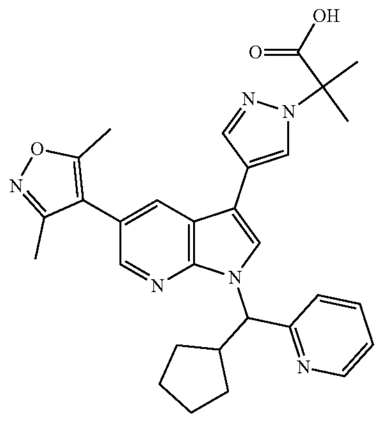 [SMILES: Cc1noc(C)c1-c1cnc2c(c1)c(-c1cnn(C(C)(C)C(=O)O)c1)cn2C(c1ccccn1)C1CCCC1] |
-continued
| P# | Structure |
|---|---|
| P-0036 | 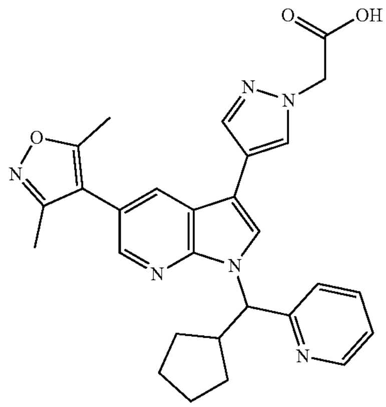 [SMILES: Cc1noc(C)c1-c1cnc2c(c1)c(-c1cnn(CC(=O)O)c1)cn2C(c1ccccn1)C1CCCC1] |
| P-0037 | 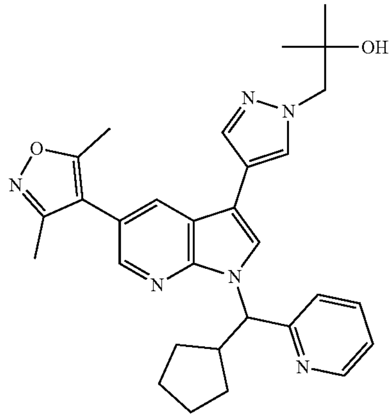 [SMILES: Cc1noc(C)c1-c1cnc2c(c1)c(-c1cnn(CC(C)(C)O)c1)cn2C(c1ccccn1)C1CCCC1] |
| P-0038 | 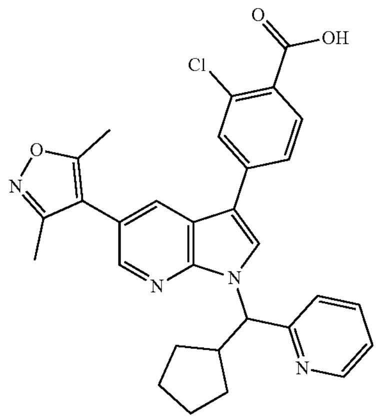 [SMILES: Cc1noc(C)c1-c1cnc2c(c1)c(-c1ccc(C(=O)O)c(Cl)c1)cn2C(c1ccccn1)C1CCCC1] |
| P-0040 | 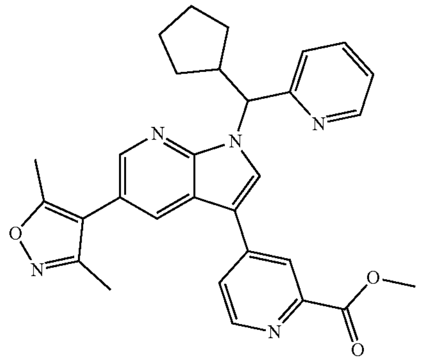 [SMILES: COC(=O)c1cc(-c2cn(C(c3ccccn3)C3CCCC3)c3ncc(-c4c(C)noc4C)cc23)ccn1] |

-continued
| P# | Structure |
|---|---|
| P-0041 | 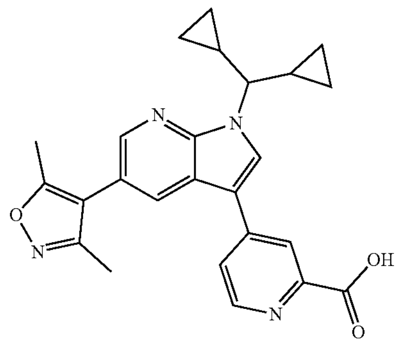 [SMILES: Cc1noc(C)c1-c1cnc2c(c1)c(-c1ccnc(C(=O)O)c1)cn2C(C1CC1)C1CC1] |
| P-0042 | 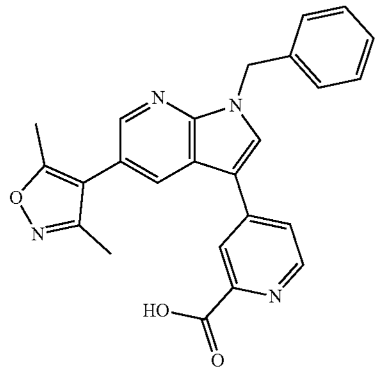 [SMILES: Cc1noc(C)c1-c1cnc2c(c1)c(-c1ccnc(C(=O)O)c1)cn2Cc1ccccc1] |
| P-0043 | 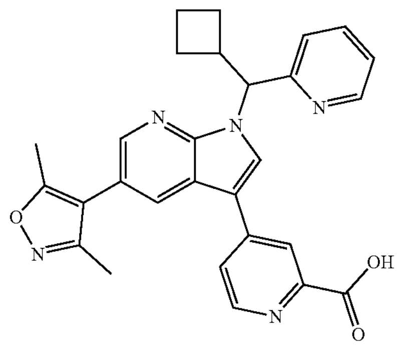 [SMILES: Cc1noc(C)c1-c1cnc2c(c1)c(-c1ccnc(C(=O)O)c1)cn2C(c1ccccn1)C1CCC1] |
| P-0044 | 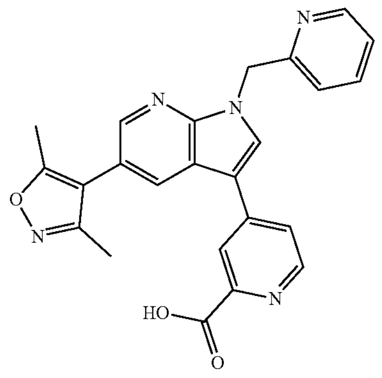 [SMILES: Cc1noc(C)c1-c1cnc2c(c1)c(-c1ccnc(C(=O)O)c1)cn2Cc1ccccn1] |
-continued
| P# | Structure |
|---|---|
| P-0045 | 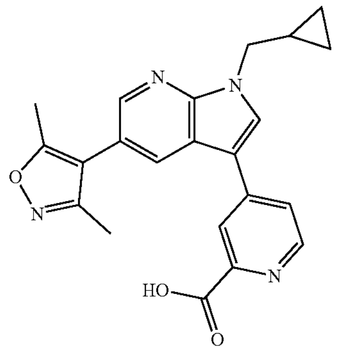 [SMILES: Cc1noc(C)c1-c1cnc2c(c1)c(-c1ccnc(C(=O)O)c1)cn2CC1CC1] |
| P-0046 | 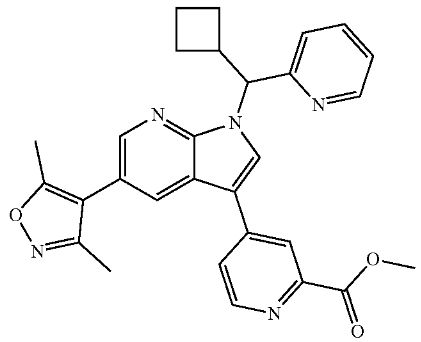 [SMILES: COC(=O)c1cc(-c2cn(C(c3ccccn3)C3CCC3)c3ncc(-c4c(C)noc4C)cc23)ccn1] |
| P-0047 | 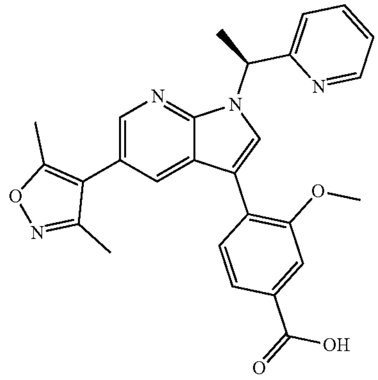 [SMILES: COc1cc(C(=O)O)ccc1-c1cn([C@@H](C)c2ccccn2)c2ncc(-c3c(C)noc3C)cc12] |
| P-0048 | 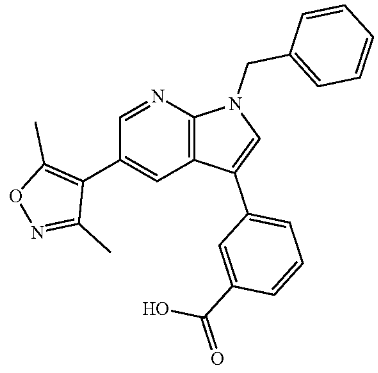 [SMILES: Cc1noc(C)c1-c1cnc2c(c1)c(-c1cccc(C(=O)O)c1)cn2Cc1ccccc1] |

-continued
| P# | Structure |
|---|---|
| P-0049 | 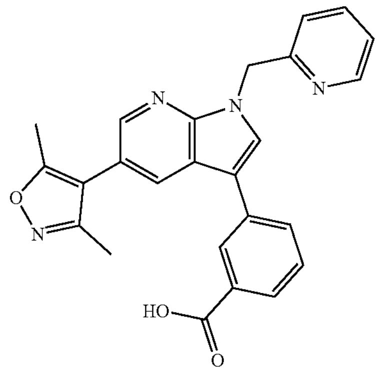 [SMILES: Cc1noc(C)c1-c1cnc2c(c1)c(-c1cccc(C(=O)O)c1)cn2Cc1ccccn1] |
| P-0050 | 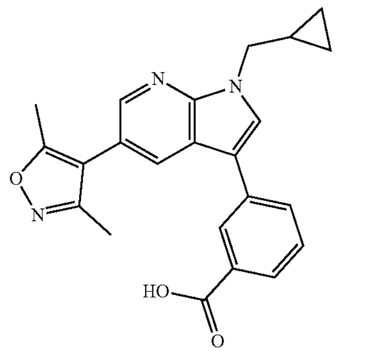 [SMILES: Cc1noc(C)c1-c1cnc2c(c1)c(-c1cccc(C(=O)O)c1)cn2CC1CC1] |
| P-0051 | 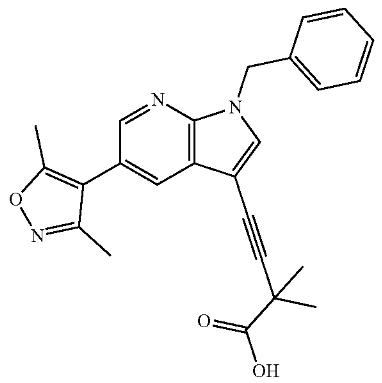 [SMILES: Cc1noc(C)c1-c1cnc2c(c1)c(C#CC(C)(C)C(=O)O)cn2Cc1ccccc1] |
| P-0052 | 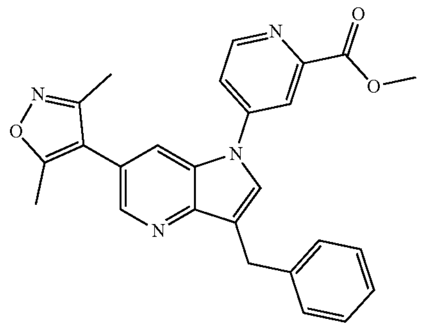 [SMILES: COC(=O)c1cc(-n2cc(Cc3ccccc3)c3ncc(-c4c(C)noc4C)cc32)ccn1] |
-continued
| P# | Structure |
|---|---|
| P-0053 | 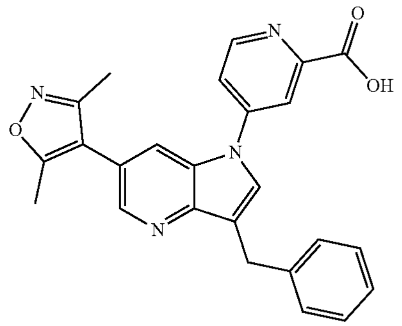 [SMILES: Cc1noc(C)c1-c1cnc2c(Cc3ccccc3)cn(-c3ccnc(C(=O)O)c3)c2c1] |
| P-0054 | 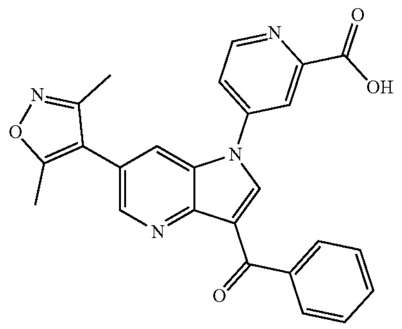 [SMILES: Cc1noc(C)c1-c1cnc2c(C(=O)c3ccccc3)cn(-c3ccnc(C(=O)O)c3)c2c1] |
| P-0055 | 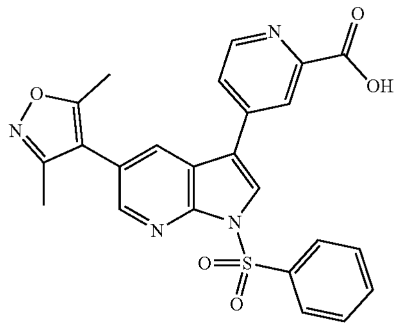 [SMILES: Cc1noc(C)c1-c1cnc2c(c1)c(-c1ccnc(C(=O)O)c1)cn2S(=O)(=O)c1ccccc1] |
| P-0056 | 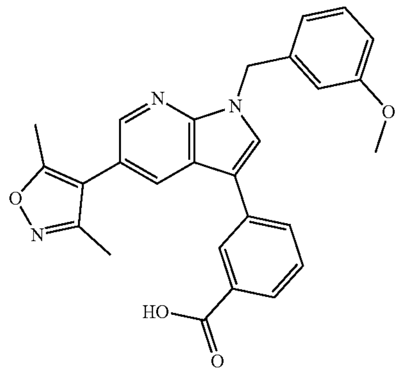 [SMILES: COc1cccc(Cn2cc(-c3cccc(C(=O)O)c3)c3cc(-c4c(C)noc4C)cnc32)c1] |

-continued
| P# | Structure |
|---|---|
| P-0057 | 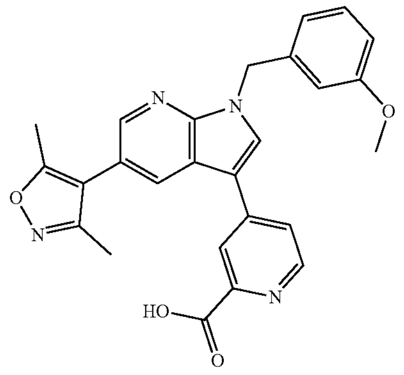 [SMILES: COc1cccc(Cn2cc(-c3ccnc(C(=O)O)c3)c3cc(-c4c(C)noc4C)cnc32)c1] |
| P-0058 | 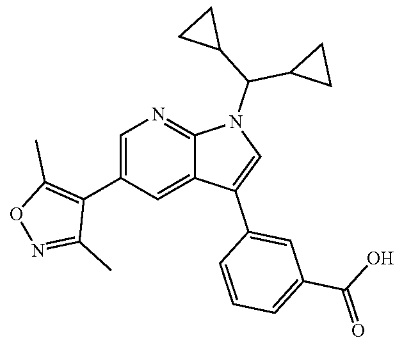 [SMILES: Cc1noc(C)c1-c1cnc2c(c1)c(-c1cccc(C(=O)O)c1)cn2C(C1CC1)C1CC1] |
| P-0059 | 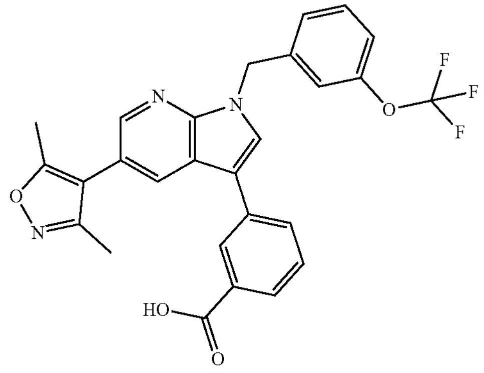 [SMILES: Cc1noc(C)c1-c1cnc2c(c1)c(-c1cccc(C(=O)O)c1)cn2Cc1cccc(OC(F)(F)F)c1] |
| P-0060 | 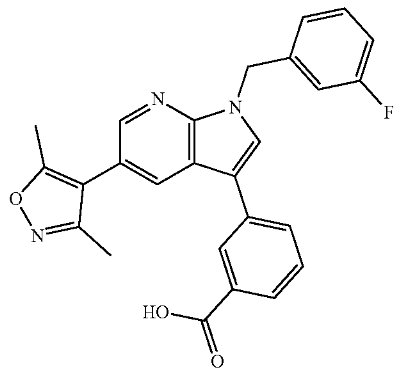 [SMILES: Cc1noc(C)c1-c1cnc2c(c1)c(-c1cccc(C(=O)O)c1)cn2Cc1cccc(F)c1] |
-continued
| P# | Structure |
|---|---|
| P-0061 | 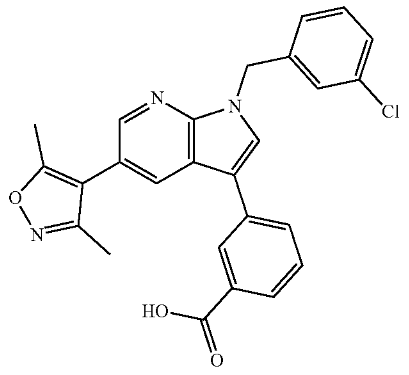 [SMILES: Cc1noc(C)c1-c1cnc2c(c1)c(-c1cccc(C(=O)O)c1)cn2Cc1cccc(Cl)c1] |
| P-0062 | 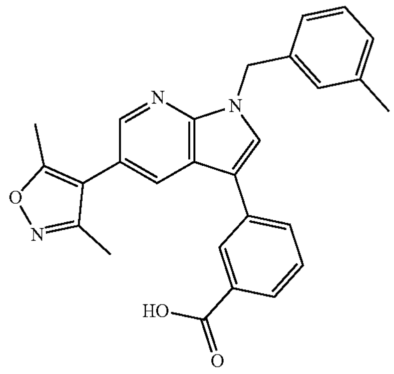 [SMILES: Cc1cccc(Cn2cc(-c3cccc(C(=O)O)c3)c3cc(-c4c(C)noc4C)cnc32)c1] |
| P-0063 | 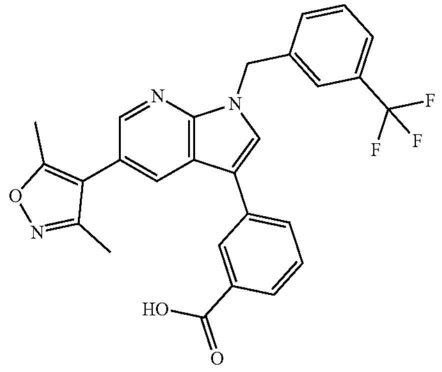 [SMILES: Cc1noc(C)c1-c1cnc2c(c1)c(-c1cccc(C(=O)O)c1)cn2Cc1cccc(C(F)(F)F)c1] |
| P-0064 | 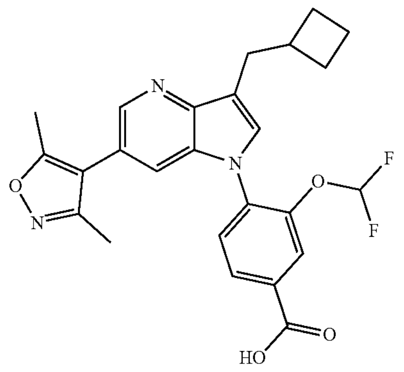 [SMILES: Cc1noc(C)c1-c1cnc2c(CC3CCC3)cn(-c3ccc(C(=O)O)cc3OC(F)F)c2c1] |

-continued
| P# | Structure |
|---|---|
| P-0065 | 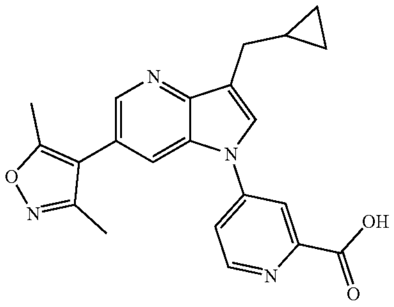 [SMILES: Cc1noc(C)c1-c1cnc2c(CC3CC3)cn(-c3ccnc(C(=O)O)c3)c2c1] |
| P-0066 | 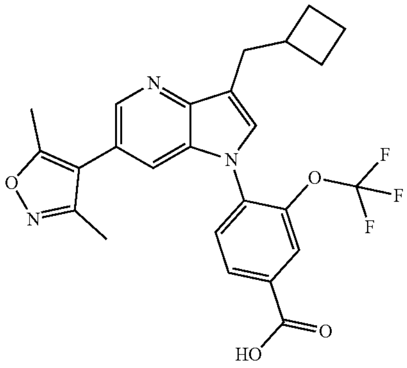 [SMILES: Cc1noc(C)c1-c1cnc2c(CC3CCC3)cn(-c3ccc(C(=O)O)cc3OC(F)(F)F)c2c1] |
| P-0067 | 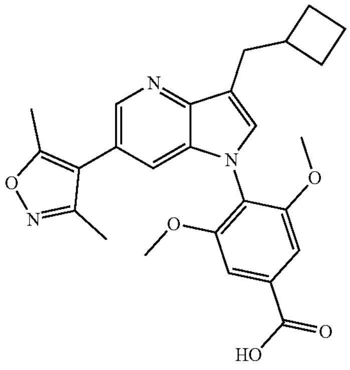 [SMILES: COc1cc(C(=O)O)cc(OC)c1-n1cc(CC2CCC2)c2ncc(-c3c(C)noc3C)cc21] |
| P-0068 | 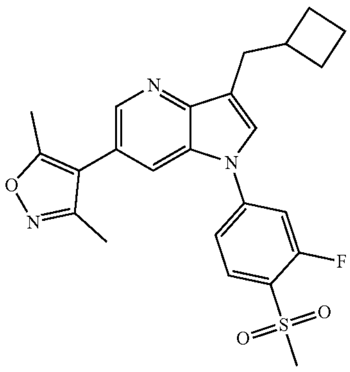 [SMILES: Cc1noc(C)c1-c1cnc2c(CC3CCC3)cn(-c3ccc(S(C)(=O)=O)c(F)c3)c2c1] |
-continued
| P# | Structure |
|---|---|
| P-0069 | 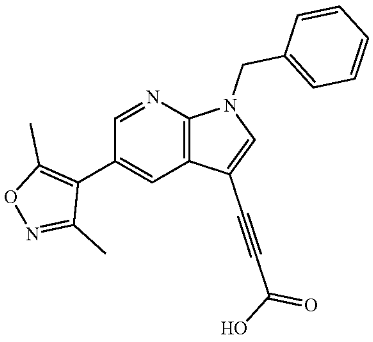 [SMILES: Cc1noc(C)c1-c1cnc2c(c1)c(C#CC(=O)O)cn2Cc1ccccc1] |
| P-0070 | 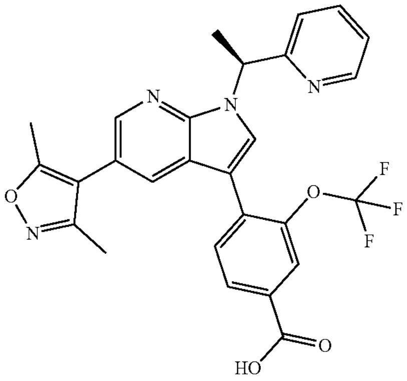 [SMILES: Cc1noc(C)c1-c1cnc2c(c1)c(-c1ccc(C(=O)O)cc1OC(F)(F)F)cn2[C@@H](C)c1ccccn1] |
| P-0071 | 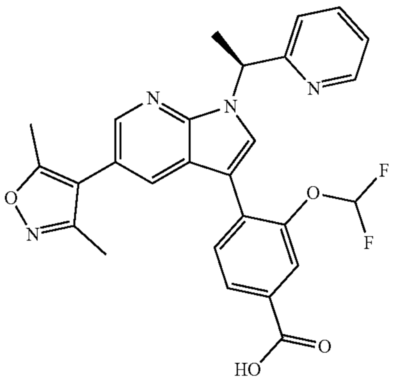 [SMILES: Cc1noc(C)c1-c1cnc2c(c1)c(-c1ccc(C(=O)O)cc1OC(F)F)cn2[C@@H](C)c1ccccn1] |
| P-0072 | 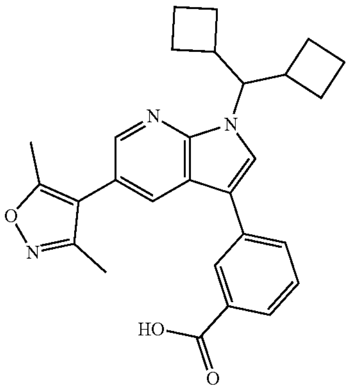 [SMILES: Cc1noc(C)c1-c1cnc2c(c1)c(-c1cccc(C(=O)O)c1)cn2C(C1CCC1)C1CCC1] |

-continued
| P# | Structure |
|---|---|
| P-0073 | 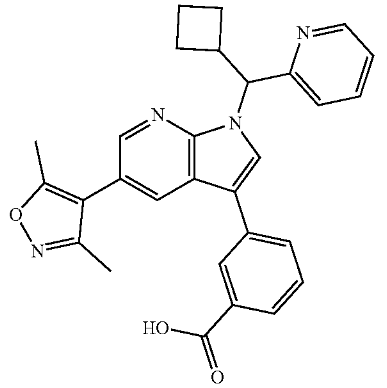 [SMILES: Cc1noc(C)c1-c1cnc2c(c1)c(-c1cccc(C(=O)O)c1)cn2C(c1ccccn1)C1CCC1] |
| P-0074 | 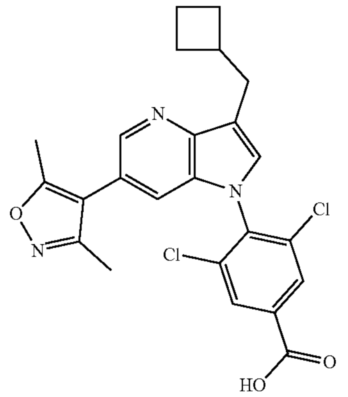 [SMILES: Cc1noc(C)c1-c1cnc2c(CC3CCC3)cn(-c3c(Cl)cc(C(=O)O)cc3Cl)c2c1] |
| P-0075 | 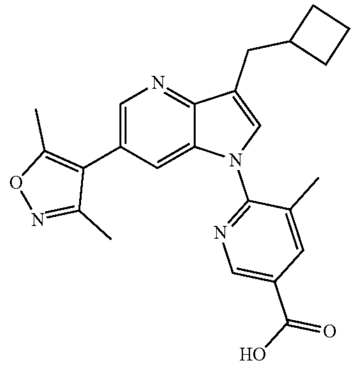 [SMILES: Cc1cc(C(=O)O)cnc1-n1cc(CC2CCC2)c2ncc(-c3c(C)noc3C)cc21] |
| P-0076 | 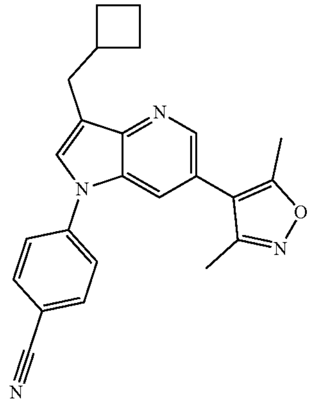 [SMILES: Cc1noc(C)c1-c1cnc2c(CC3CCC3)cn(-c3ccc(C#N)cc3)c2c1] |
-continued
| P# | Structure |
|---|---|
| P-0077 | 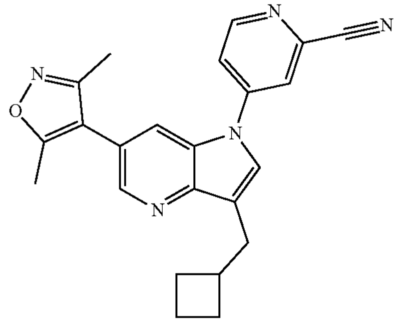 [SMILES: Cc1noc(C)c1-c1cnc2c(CC3CCC3)cn(-c3ccnc(C#N)c3)c2c1] |
| P-0078 | 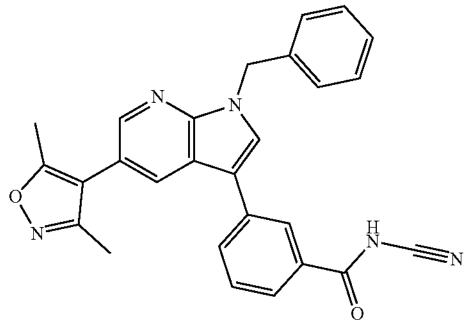 [SMILES: Cc1noc(C)c1-c1cnc2c(c1)c(-c1cccc(C(=O)NC#N)c1)cn2Cc1ccccc1] |
| P-0079 | 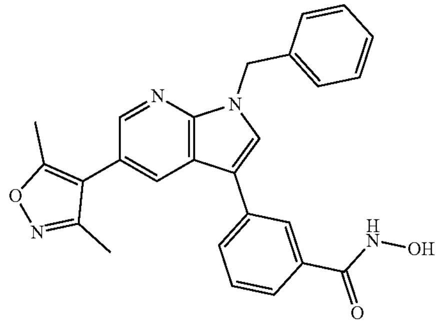 [SMILES: Cc1noc(C)c1-c1cnc2c(c1)c(-c1cccc(C(=O)NO)c1)cn2Cc1ccccc1] |
| P-0080 | 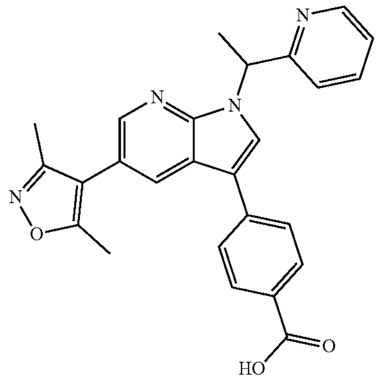 [SMILES: Cc1noc(C)c1-c1cnc2c(c1)c(-c1ccc(C(=O)O)cc1)cn2C(C)c1ccccn1] |

-continued
| P# | Structure |
| --- | --- |
| P-0081 | 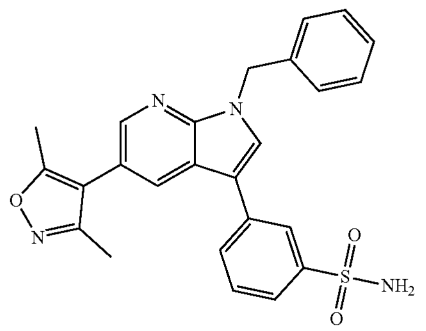 [SMILES: Cc1noc(C)c1-c1cnc2c(c1)c(-c1cccc(S(N)(=O)=O)c1)cn2Cc1ccccc1] |
| P-0082 | 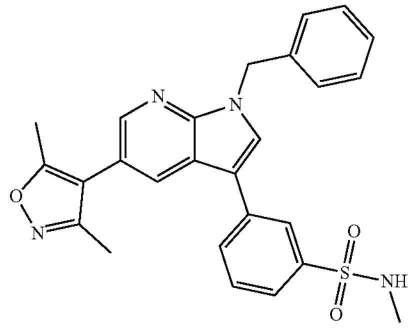 [SMILES: CNS(=O)(=O)c1cccc(-c2cn(Cc3ccccc3)c3ncc(-c4c(C)noc4C)cc23)c1] |
| P-0083 | 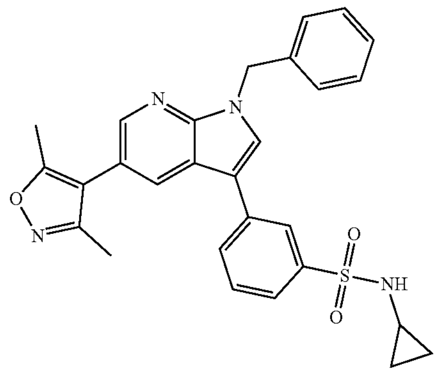 [SMILES: Cc1noc(C)c1-c1cnc2c(c1)c(-c1cccc(S(=O)(=O)NC3CC3)c1)cn2Cc1ccccc1] |
| P-0084 | 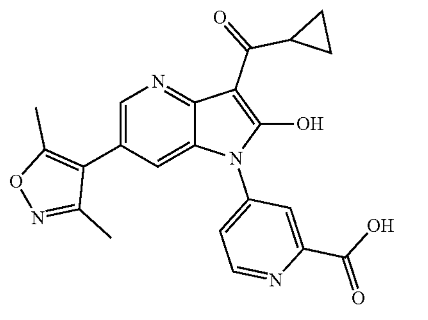 [SMILES: Cc1noc(C)c1-c1cnc2c(C(=O)C3CC3)c(O)n(-c3ccnc(C(=O)O)c3)c2c1] |
-continued
| P# | Structure |
| --- | --- |
| P-0085 | 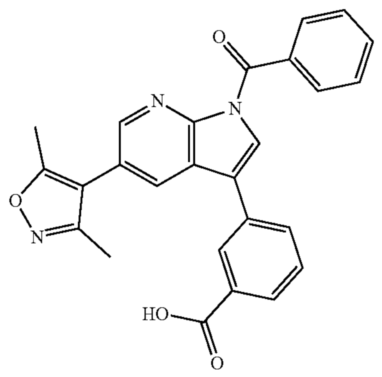 [SMILES: Cc1noc(C)c1-c1cnc2c(c1)c(-c1cccc(C(=O)O)c1)cn2C(=O)c1ccccc1] |
| P-0086 | 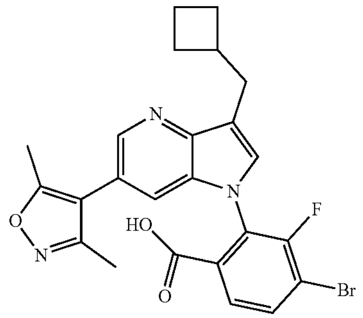 [SMILES: Cc1noc(C)c1-c1cnc2c(CC3CCC3)cn(-c3c(C(=O)O)ccc(Br)c3F)c2c1] |
| P-0087 | 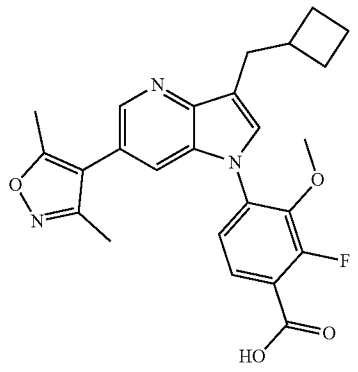 [SMILES: COc1c(-n2cc(CC3CCC3)c3ncc(-c4c(C)noc4C)cc32)ccc(C(=O)O)c1F] |
| P-0088 | 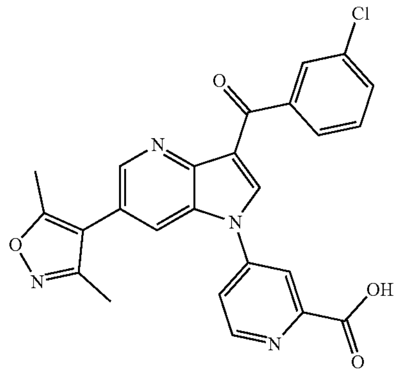 [SMILES: Cc1noc(C)c1-c1cnc2c(C(=O)c3cccc(Cl)c3)cn(-c3ccnc(C(=O)O)c3)c2c1] |

-continued
| P# | Structure |
|---|---|
| P-0089 | 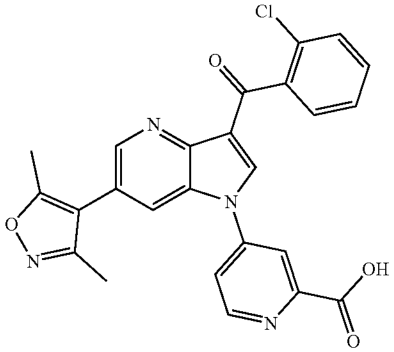 [SMILES: Cc1noc(C)c1-c1cnc2c(C(=O)c3ccccc3Cl)cn(-c3ccnc(C(=O)O)c3)c2c1] |
| P-0090 | 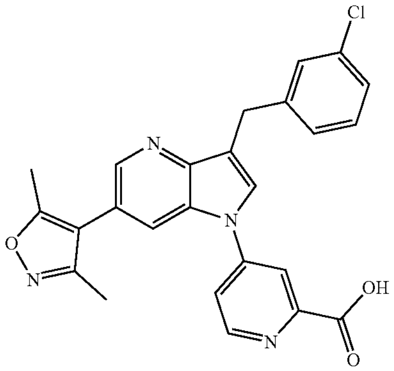 [SMILES: Cc1noc(C)c1-c1cnc2c(Cc3cccc(Cl)c3)cn(-c3ccnc(C(=O)O)c3)c2c1] |
| P-0091 | 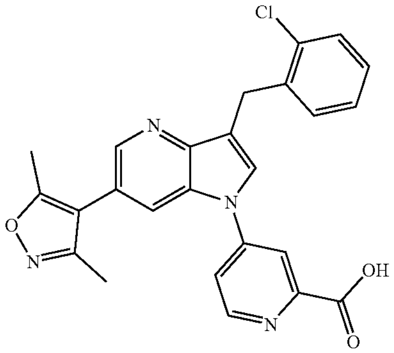 [SMILES: Cc1noc(C)c1-c1cnc2c(Cc3ccccc3Cl)cn(-c3ccnc(C(=O)O)c3)c2c1] |
| P-0092 | 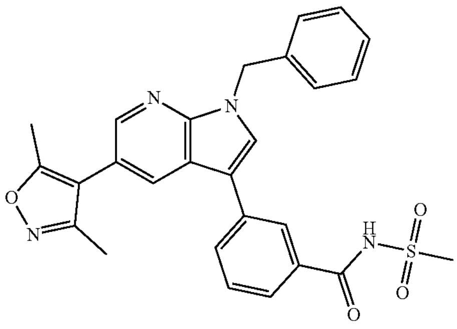 [SMILES: Cc1noc(C)c1-c1cnc2c(c1)c(-c1cccc(C(=O)NS(C)(=O)=O)c1)cn2Cc1ccccc1] |
-continued
| P# | Structure |
|---|---|
| P-0093 | 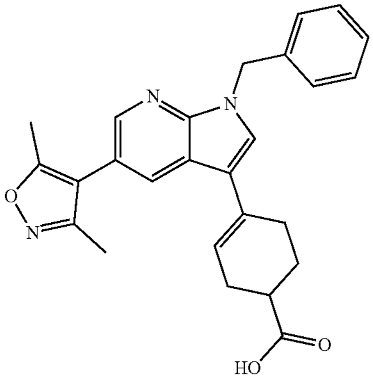 [SMILES: Cc1noc(C)c1-c1cnc2c(c1)c(C1=CCC(C(=O)O)CC1)cn2Cc1ccccc1] |
| P-0094 | 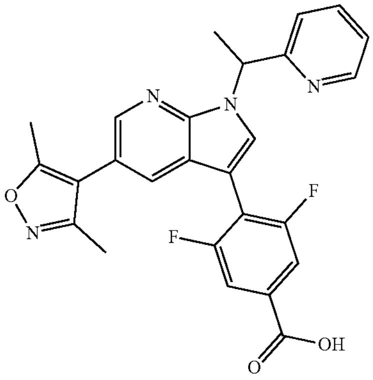 [SMILES: Cc1noc(C)c1-c1cnc2c(c1)c(-c1c(F)cc(C(=O)O)cc1F)cn2C(C)c1ccccn1] |
| P-0095 | 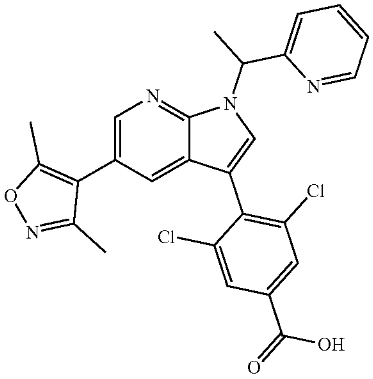 [SMILES: Cc1noc(C)c1-c1cnc2c(c1)c(-c1c(Cl)cc(C(=O)O)cc1Cl)cn2C(C)c1ccccn1] |
| P-0096 | 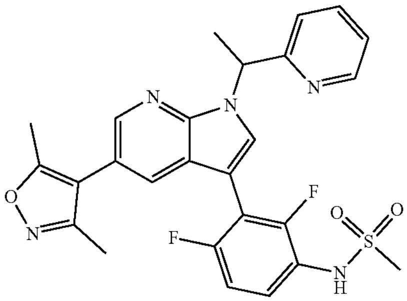 [SMILES: Cc1noc(C)c1-c1cnc2c(c1)c(-c1c(F)ccc(NS(C)(=O)=O)c1F)cn2C(C)c1ccccn1] |

-continued
| P# | Structure |
|---|---|
| P-0097 | 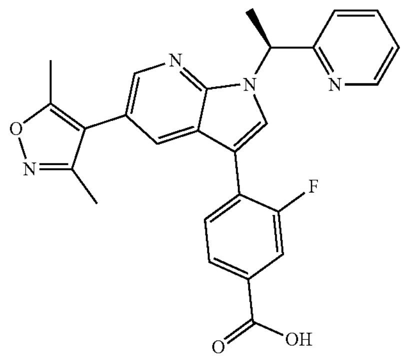 [SMILES: Cc1noc(C)c1-c1cnc2c(c1)c(-c1ccc(C(=O)O)cc1F)cn2[C@@H](C)c1ccccn1] |
| P-0098 | 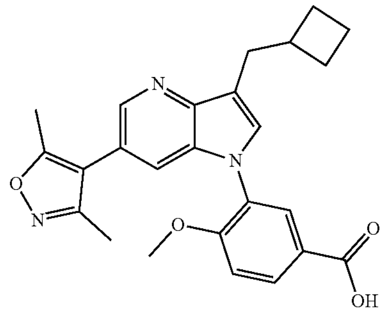 [SMILES: COc1ccc(C(=O)O)cc1-n1cc(CC2CCC2)c2ncc(-c3c(C)noc3C)cc21] |
| P-0099 | 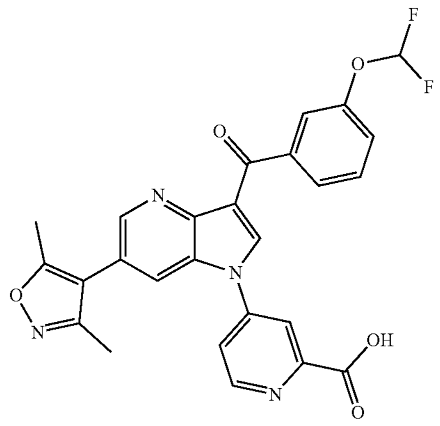 [SMILES: Cc1noc(C)c1-c1cnc2c(C(=O)c3cccc(OC(F)F)c3)cn(-c3ccnc(C(=O)O)c3)c2c1] |
| P-0100 | 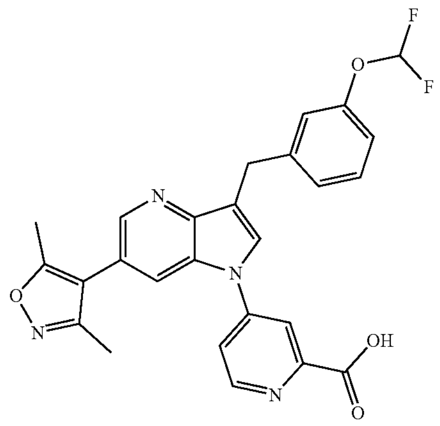 [SMILES: Cc1noc(C)c1-c1cnc2c(Cc3cccc(OC(F)F)c3)cn(-c3ccnc(C(=O)O)c3)c2c1] |
-continued
| P# | Structure |
|---|---|
| P-0101 | 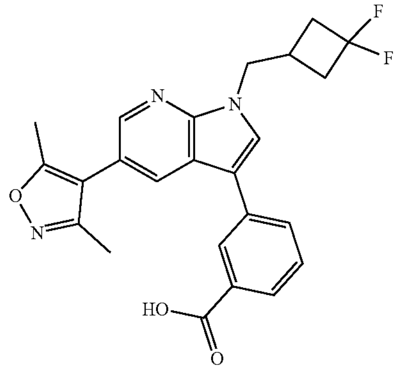 [SMILES: Cc1noc(C)c1-c1cnc2c(c1)c(-c1cccc(C(=O)O)c1)cn2CC1CC(F)(F)C1] |
| P-0102 | 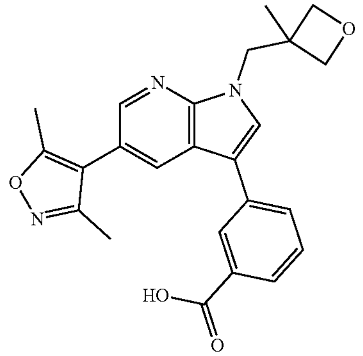 [SMILES: Cc1noc(C)c1-c1cnc2c(c1)c(-c1cccc(C(=O)O)c1)cn2CC1(C)COC1] |
| P-0103 | 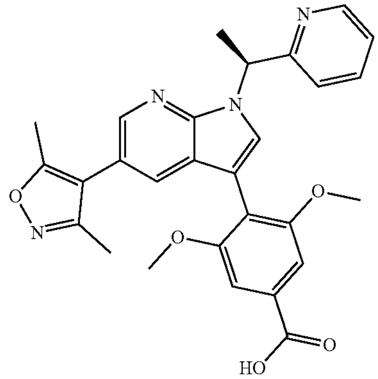 [SMILES: COc1cc(C(=O)O)cc(OC)c1-c1cn([C@@H](C)c2ccccn2)c2ncc(-c3c(C)noc3C)cc12] |
| P-0104 | 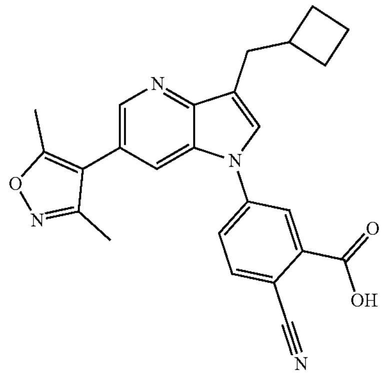 [SMILES: Cc1noc(C)c1-c1cnc2c(CC3CCC3)cn(-c3ccc(C#N)c(C(=O)O)c3)c2c1] |

| P# | Structure |
|---|---|
| P-0105 | 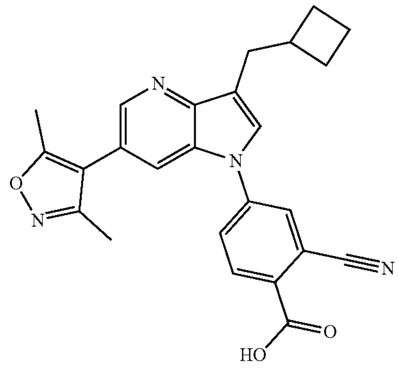 [SMILES: Cc1noc(C)c1-c1cnc2c(CC3CCC3)cn(-c3ccc(C(=O)O)c(C#N)c3)c2c1] |
| P-0106 | 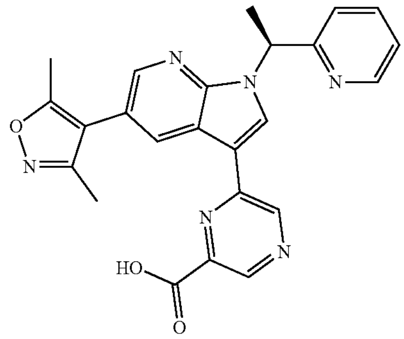 [SMILES: Cc1noc(C)c1-c1cnc2c(c1)c(-c1cncc(C(=O)O)n1)cn2[C@@H](C)c1ccccn1] |
| P-0107 | 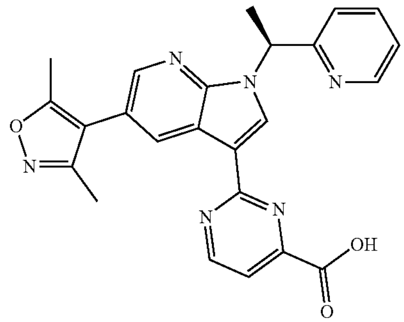 [SMILES: Cc1noc(C)c1-c1cnc2c(c1)c(-c1nccc(C(=O)O)n1)cn2[C@@H](C)c1ccccn1] |
| P-0108 | 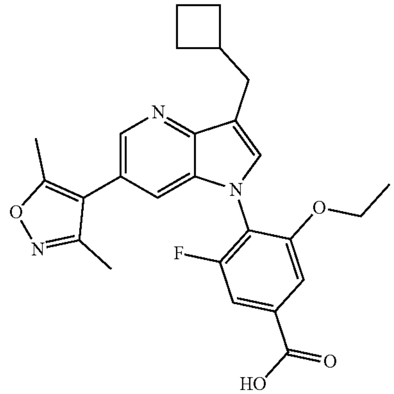 [SMILES: CCOc1cc(C(=O)O)cc(F)c1-n1cc(CC2CCC2)c2ncc(-c3c(C)noc3C)cc21] |
| P# | Structure |
|---|---|
| P-0109 | 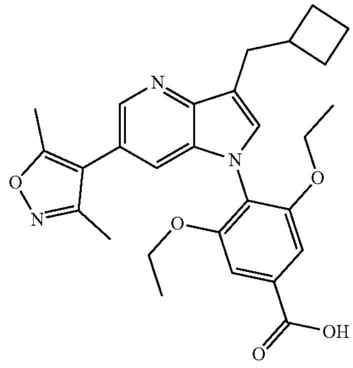 [SMILES: CCOc1cc(C(=O)O)cc(OCC)c1-n1cc(CC2CCC2)c2ncc(-c3c(C)noc3C)cc21] |
| P-0110 | 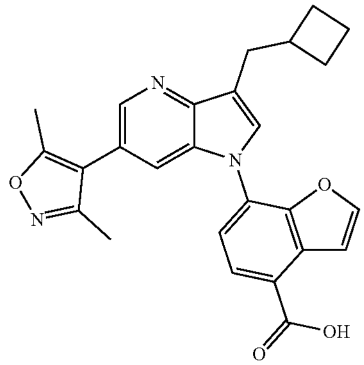 [SMILES: Cc1noc(C)c1-c1cnc2c(CC3CCC3)cn(-c3ccc(C(=O)O)c4ccoc34)c2c1] |
| P-0111 | 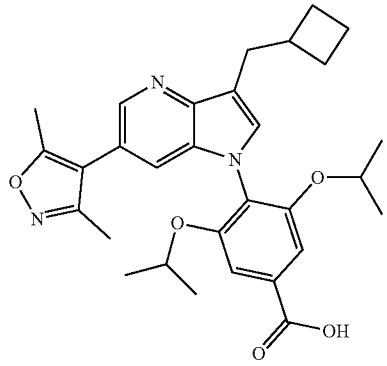 [SMILES: Cc1noc(C)c1-c1cnc2c(CC3CCC3)cn(-c3c(OC(C)C)cc(C(=O)O)cc3OC(C)C)c2c1] |
| P-0112 | 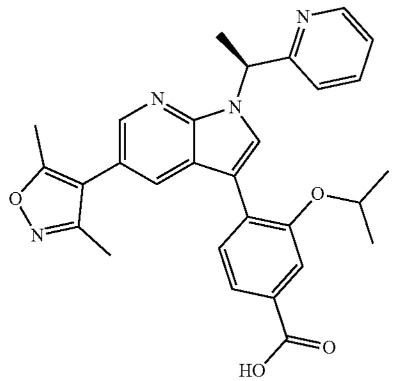 [SMILES: Cc1noc(C)c1-c1cnc2c(c1)c(-c1ccc(C(=O)O)cc1OC(C)C)cn2[C@@H](C)c1ccccn1] |

-continued
| P# | Structure |
|---|---|
| P-0113 | 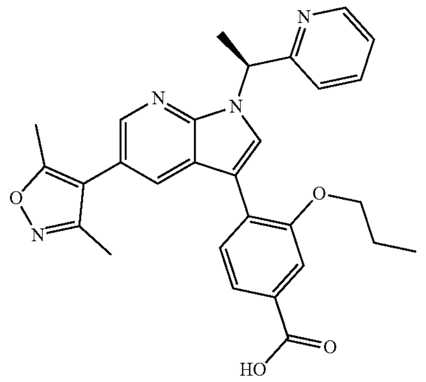 [SMILES: CCCOc1cc(C(=O)O)ccc1-c1cn([C@@H](C)c2ccccn2)c2ncc(-c3c(C)noc3C)cc12] |
| P-0114 | 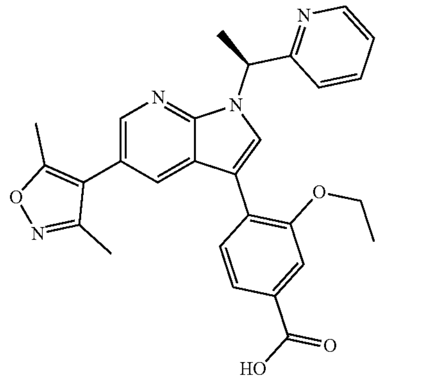 [SMILES: CCOc1cc(C(=O)O)ccc1-c1cn([C@@H](C)c2ccccn2)c2ncc(-c3c(C)noc3C)cc12] |
| P-0115 | 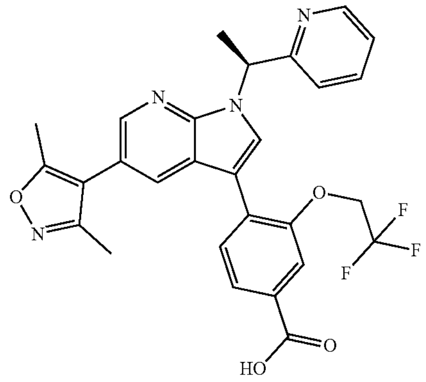 [SMILES: Cc1noc(C)c1-c1cnc2c(c1)c(-c1ccc(C(=O)O)cc1OCC(F)(F)F)cn2[C@@H](C)c1ccccn1] |
| P-0116 | 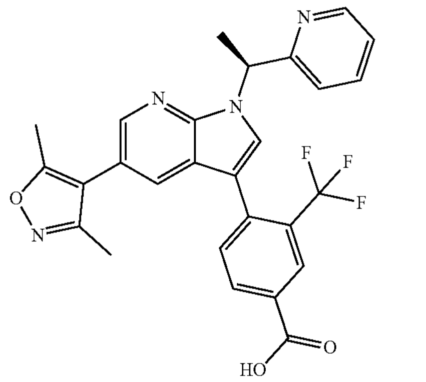 [SMILES: Cc1noc(C)c1-c1cnc2c(c1)c(-c1ccc(C(=O)O)cc1C(F)(F)F)cn2[C@@H](C)c1ccccn1] |
-continued
| P# | Structure |
|---|---|
| P-0117 | 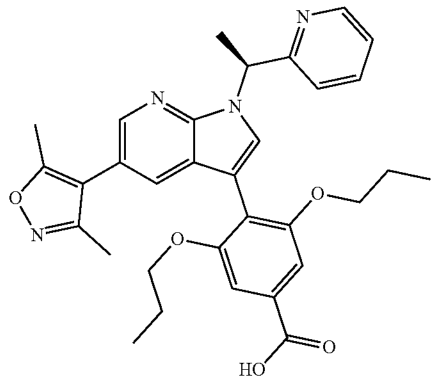 [SMILES: CCCOc1cc(C(=O)O)cc(OCCC)c1-c1cn([C@@H](C)c2ccccn2)c2ncc(-c3c(C)noc3C)cc12] |
| P-0118 | 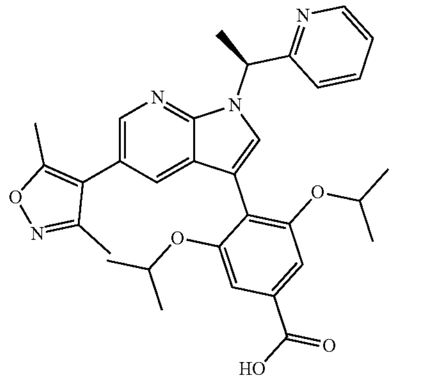 [SMILES: Cc1noc(C)c1-c1cnc2c(c1)c(-c1c(OC(C)C)cc(C(=O)O)cc1OC(C)C)cn2[C@@H](C)c1ccccn1] |
| P-0119 | 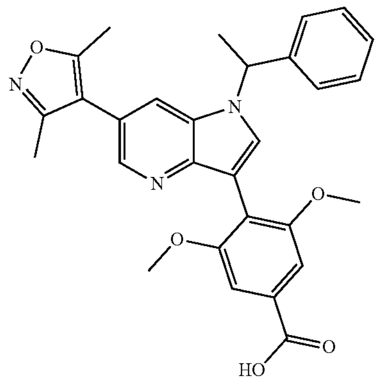 [SMILES: COc1cc(C(=O)O)cc(OC)c1-c1cn(C(C)c2ccccc2)c2cc(-c3c(C)noc3C)cnc12] |
| P-0120 | 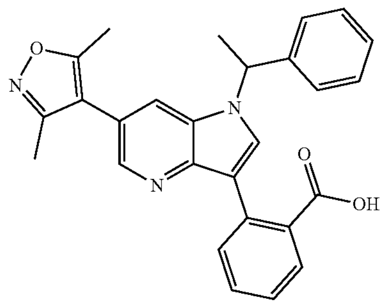 [SMILES: Cc1noc(C)c1-c1cnc2c(-c3ccccc3C(=O)O)cn(C(C)c3ccccc3)c2c1] |

-continued
| P# | Structure |
|---|---|
| P-0121 | 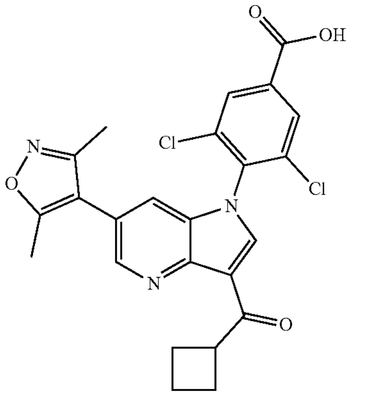 [SMILES: Cc1noc(C)c1-c1cnc2c(C(=O)C3CCC3)cn(-c3c(Cl)cc(C(=O)O)cc3Cl)c2c1] |
| P-0122 | 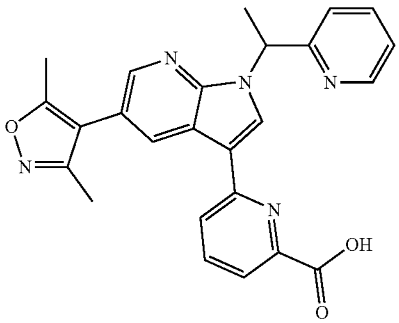 [SMILES: Cc1noc(C)c1-c1cnc2c(c1)c(-c1cccc(C(=O)O)n1)cn2C(C)c1ccccn1] |
| P-0123 | 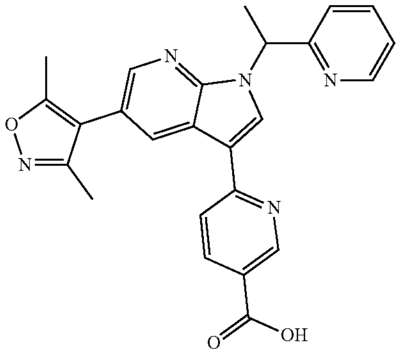 [SMILES: Cc1noc(C)c1-c1cnc2c(c1)c(-c1ccc(C(=O)O)cn1)cn2C(C)c1ccccn1] |
| P-0124 | 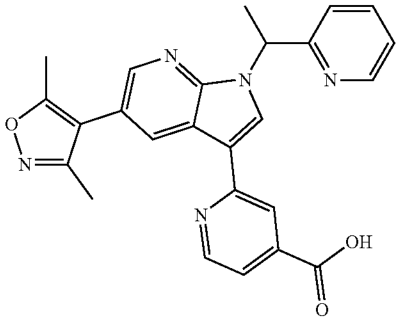 [SMILES: Cc1noc(C)c1-c1cnc2c(c1)c(-c1cc(C(=O)O)ccn1)cn2C(C)c1ccccn1] |
-continued
| P# | Structure |
|---|---|
| P-0125 | 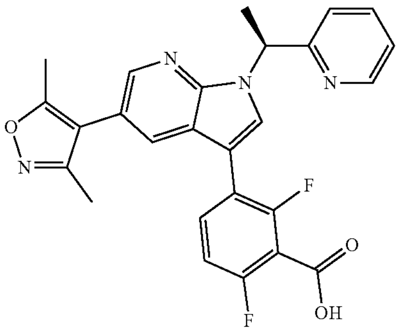 [SMILES: Cc1noc(C)c1-c1cnc2c(c1)c(-c1ccc(F)c(C(=O)O)c1F)cn2[C@@H](C)c1ccccn1] |
| P-0126 | 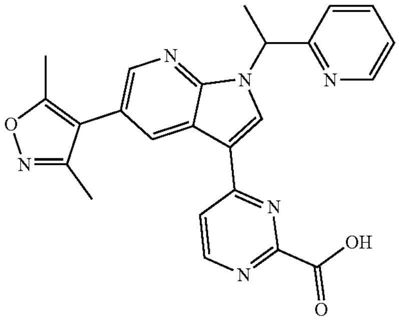 [SMILES: Cc1noc(C)c1-c1cnc2c(c1)c(-c1ccnc(C(=O)O)n1)cn2C(C)c1ccccn1] |
| P-0127 | 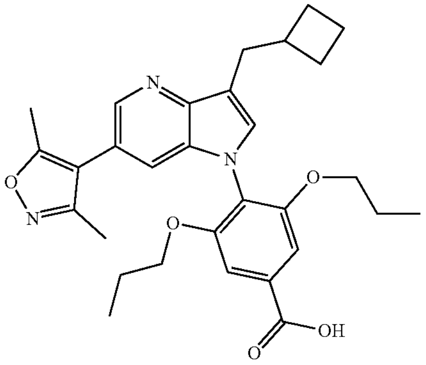 [SMILES: CCCOc1cc(C(=O)O)cc(OCCC)c1-n1cc(CC2CCC2)c2ncc(-c3c(C)noc3C)cc21] |
| P-0128 | 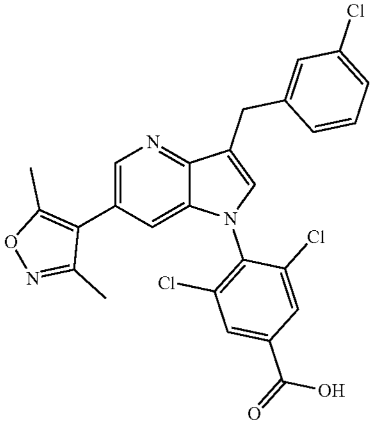 [SMILES: Cc1noc(C)c1-c1cnc2c(Cc3cccc(Cl)c3)cn(-c3c(Cl)cc(C(=O)O)cc3Cl)c2c1] |

-continued
| P# | Structure |
|---|---|
| P-0129 | 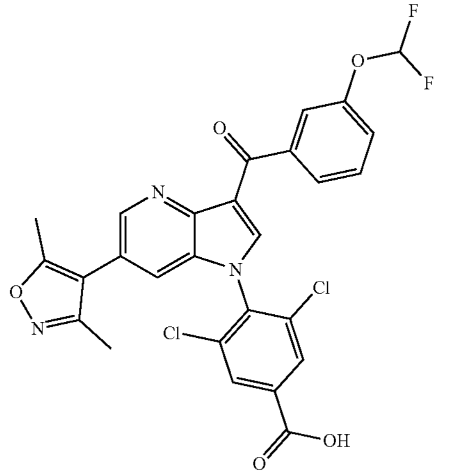 [SMILES: Cc1noc(C)c1-c1cnc2c(C(=O)c3cccc(OC(F)F)c3)cn(-c3c(Cl)cc(C(=O)O)cc3Cl)c2c1] |
| P-0130 | 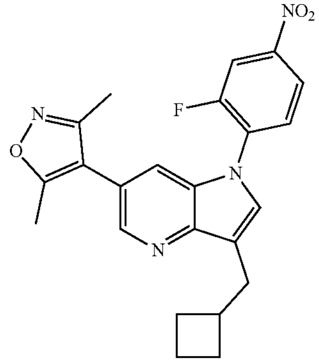 [SMILES: Cc1noc(C)c1-c1cnc2c(CC3CCC3)cn(-c3ccc([N+](=O)[O-])cc3F)c2c1] |
| P-0131 | 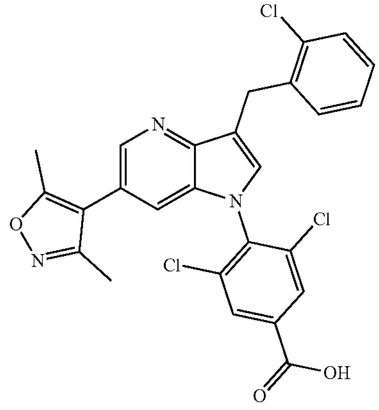 [SMILES: Cc1noc(C)c1-c1cnc2c(Cc3ccccc3Cl)cn(-c3c(Cl)cc(C(=O)O)cc3Cl)c2c1] |
-continued
| P# | Structure |
|---|---|
| P-0132 | 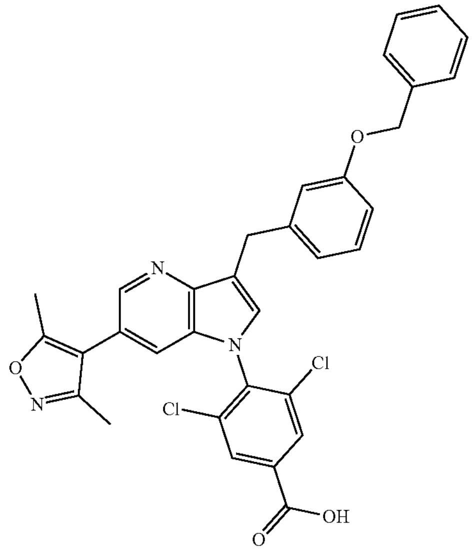 [SMILES: Cc1noc(C)c1-c1cnc2c(Cc3cccc(OCc4ccccc4)c3)cn(-c3c(Cl)cc(C(=O)O)cc3Cl)c2c1] |
| P-0133 | 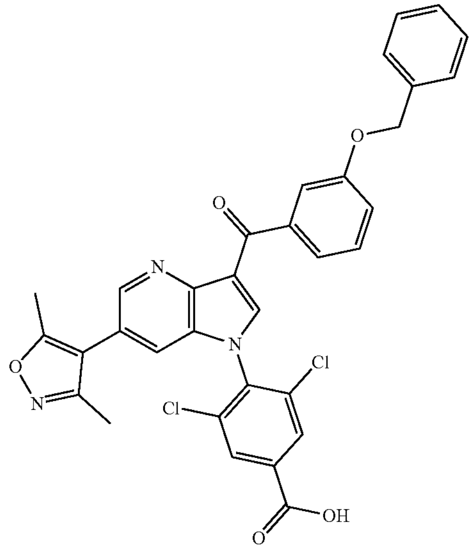 [SMILES: Cc1noc(C)c1-c1cnc2c(C(=O)c3cccc(OCc4ccccc4)c3)cn(-c3c(Cl)cc(C(=O)O)cc3Cl)c2c1] |
| P-0134 | 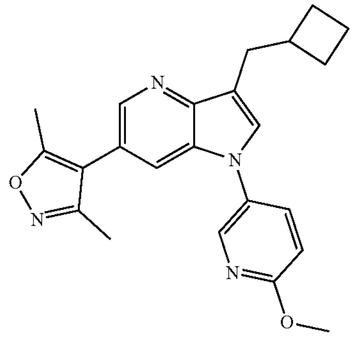 [SMILES: COc1ccc(-n2cc(CC3CCC3)c3ncc(-c4c(C)noc4C)cc32)cn1] |

-continued
| P# | Structure |
|---|---|
| P-0135 | 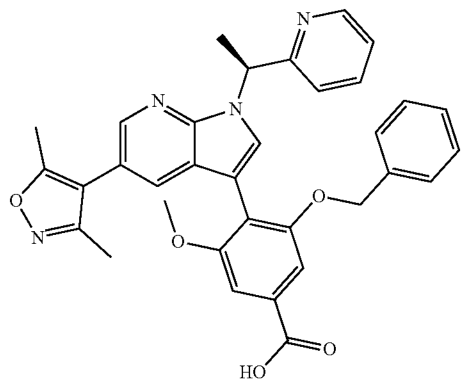 [SMILES: COc1cc(C(=O)O)cc(OCc2ccccc2)c1-c1cn([C@@H](C)c2ccccn2)c2ncc(-c3c(C)noc3C)cc12] |
| P-0136 | 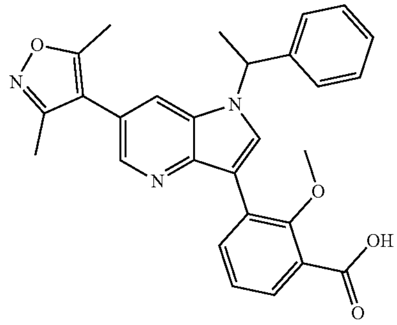 [SMILES: COc1c(C(=O)O)cccc1-c1cn(C(C)c2ccccc2)c2cc(-c3c(C)noc3C)cnc12] |
| P-0137 | 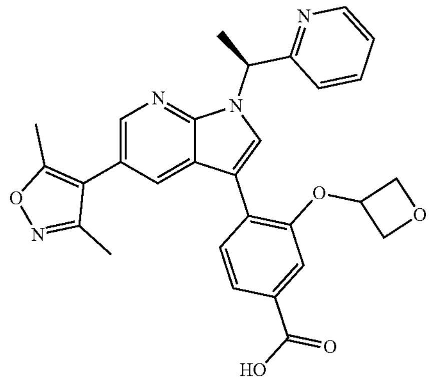 [SMILES: Cc1noc(C)c1-c1cnc2c(c1)c(-c1ccc(C(=O)O)cc1OC1COC1)cn2[C@@H](C)c1ccccn1] |
| P-0138 | 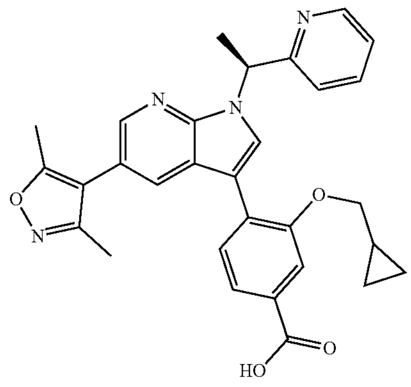 [SMILES: Cc1noc(C)c1-c1cnc2c(c1)c(-c1ccc(C(=O)O)cc1OCC1CC1)cn2[C@@H](C)c1ccccn1] |
-continued
| P# | Structure |
|---|---|
| P-0139 | 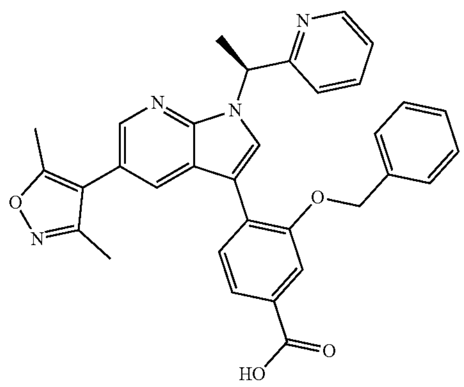 [SMILES: Cc1noc(C)c1-c1cnc2c(c1)c(-c1ccc(C(=O)O)cc1OCc1ccccc1)cn2[C@@H](C)c1ccccn1] |
| P-0140 | 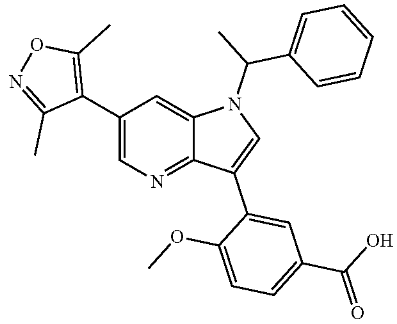 [SMILES: COc1ccc(C(=O)O)cc1-c1cn(C(C)c2ccccc2)c2cc(-c3c(C)noc3C)cnc12] |
| P-0141 | 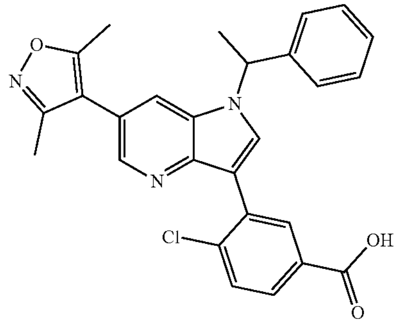 [SMILES: Cc1noc(C)c1-c1cnc2c(-c3cc(C(=O)O)ccc3Cl)cn(C(C)c3ccccc3)c2c1] |
| P-0142 | 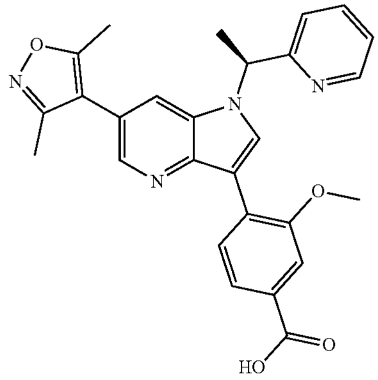 [SMILES: COc1cc(C(=O)O)ccc1-c1cn([C@@H](C)c2ccccn2)c2cc(-c3c(C)noc3C)cnc12] |

-continued
| P# | Structure |
|---|---|
| P-0143 | 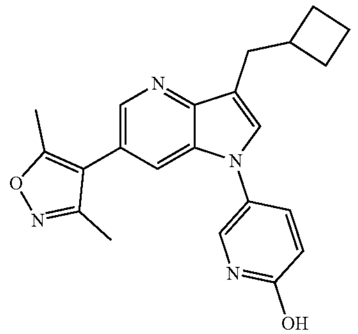 [SMILES: Cc1noc(C)c1-c1cnc2c(CC3CCC3)cn(-c3ccc(O)nc3)c2c1] |
| P-0144 | 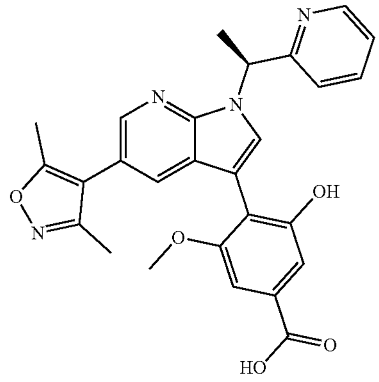 [SMILES: COc1cc(C(=O)O)cc(O)c1-c1cn([C@@H](C)c2ccccn2)c2ncc(-c3c(C)noc3C)cc12] |
| P-0145 | 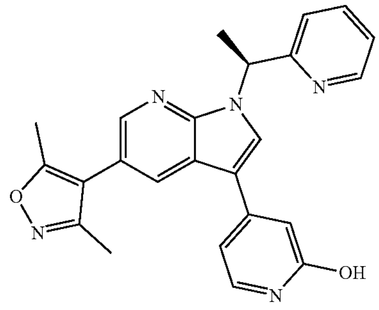 [SMILES: Cc1noc(C)c1-c1cnc2c(c1)c(-c1ccnc(O)c1)cn2[C@@H](C)c1ccccn1] |
| P-0146 | 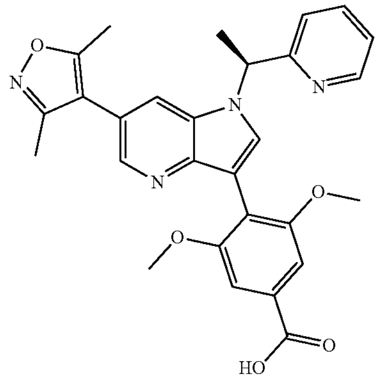 [SMILES: COc1cc(C(=O)O)cc(OC)c1-c1cn([C@@H](C)c2ccccn2)c2cc(-c3c(C)noc3C)cnc12] |
-continued
| P# | Structure |
|---|---|
| P-0147 | 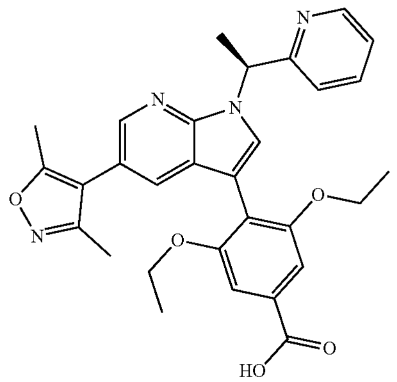 [SMILES: CCOc1cc(C(=O)O)cc(OCC)c1-c1cn([C@@H](C)c2ccccn2)c2ncc(-c3c(C)noc3C)cc12] |
| P-0148 | 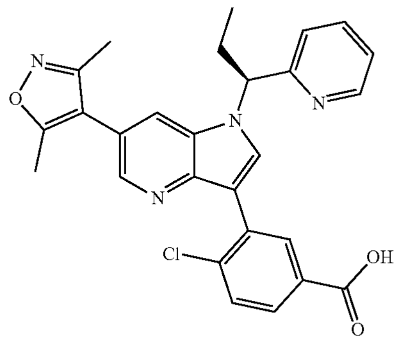 [SMILES: CC[C@@H](c1ccccn1)n1cc(-c2cc(C(=O)O)ccc2Cl)c2ncc(-c3c(C)noc3C)cc21] |
| P-0149 | 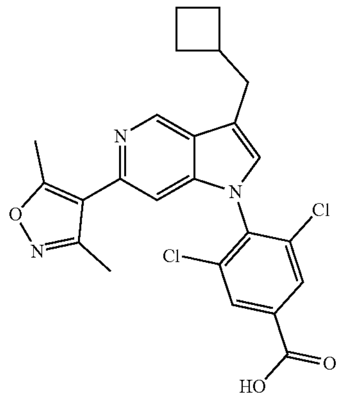 [SMILES: Cc1noc(C)c1-c1cc2c(cn1)c(CC1CCC1)cn2-c1c(Cl)cc(C(=O)O)cc1Cl] |
| P-0150 | 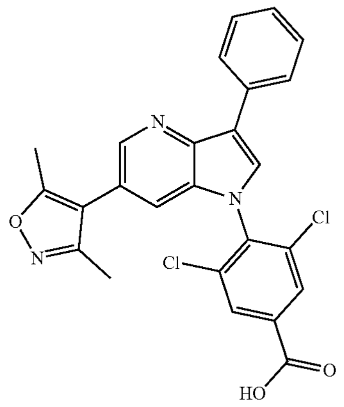 [SMILES: Cc1noc(C)c1-c1cnc2c(-c3ccccc3)cn(-c3c(Cl)cc(C(=O)O)cc3Cl)c2c1] |

-continued
| P# | Structure |
|---|---|
| P-0151 | 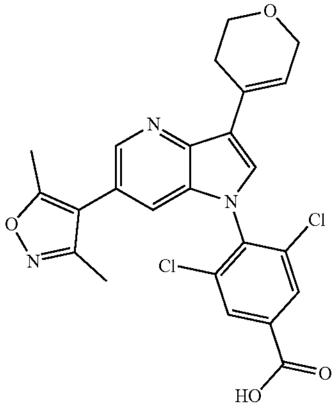 [SMILES: Cc1noc(C)c1-c1cnc2c(C3=CCOCC3)cn(-c3c(Cl)cc(C(=O)O)cc3Cl)c2c1] |
| P-0152 | 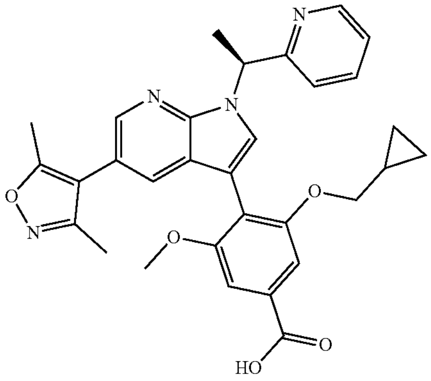 [SMILES: COc1cc(C(=O)O)cc(OCC2CC2)c1-c1cn([C@@H](C)c2ccccn2)c2ncc(-c3c(C)noc3C)cc12] |
| P-0153 | 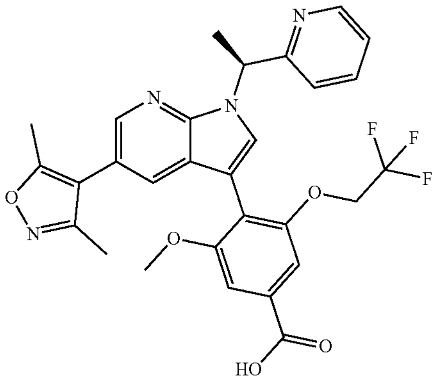 [SMILES: COc1cc(C(=O)O)cc(OCC(F)(F)F)c1-c1cn([C@@H](C)c2ccccn2)c2ncc(-c3c(C)noc3C)cc12] |
| P-0154 | 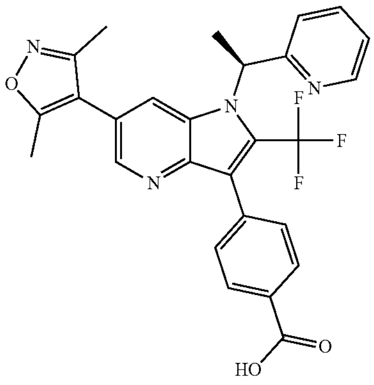 [SMILES: Cc1noc(C)c1-c1cnc2c(-c3ccc(C(=O)O)cc3)c(C(F)(F)F)n([C@@H](C)c3ccccn3)c2c1] |
-continued
| P# | Structure |
|---|---|
| P-0155 | 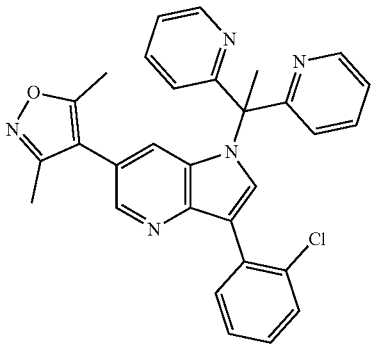 [SMILES: Cc1noc(C)c1-c1cnc2c(-c3ccccc3Cl)cn(C(C)(c3ccccn3)c3ccccn3)c2c1] |
| P-0156 | 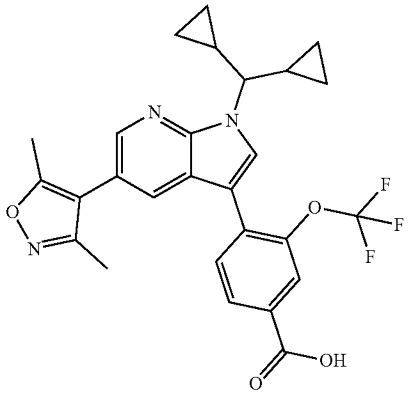 [SMILES: Cc1noc(C)c1-c1cnc2c(c1)c(-c1ccc(C(=O)O)cc1OC(F)(F)F)cn2C(C1CC1)C1CC1] |
| P-0157 | 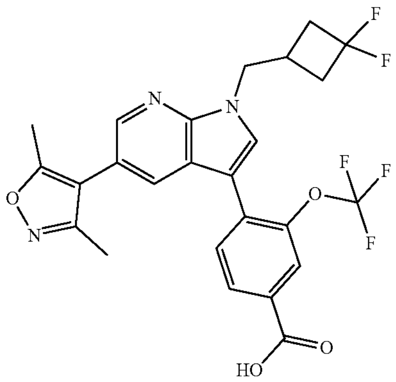 [SMILES: Cc1noc(C)c1-c1cnc2c(c1)c(-c1ccc(C(=O)O)cc1OC(F)(F)F)cn2CC1CC(F)(F)C1] |
| P-0158 | 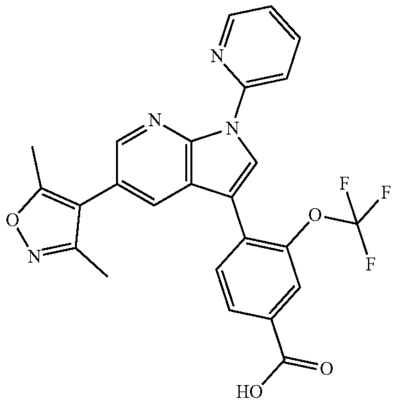 [SMILES: Cc1noc(C)c1-c1cnc2c(c1)c(-c1ccc(C(=O)O)cc1OC(F)(F)F)cn2-c1ccccn1] |

-continued
| P# | Structure |
|---|---|
| P-0159 | 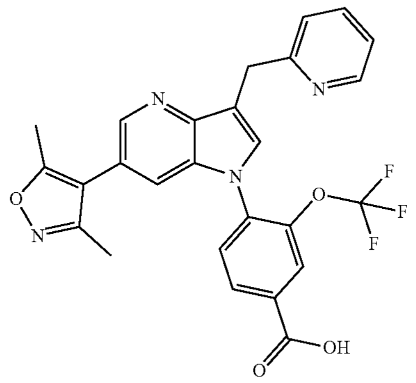 [SMILES: Cc1noc(C)c1-c1cnc2c(Cc3ccccn3)cn(-c3ccc(C(=O)O)cc3OC(F)(F)F)c2c1] |
| P-0160 | 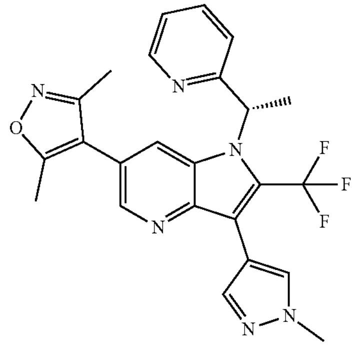 [SMILES: Cc1noc(C)c1-c1cnc2c(-c3cnn(C)c3)c(C(F)(F)F)n([C@@H](C)c3ccccn3)c2c1] |
| P-0161 | 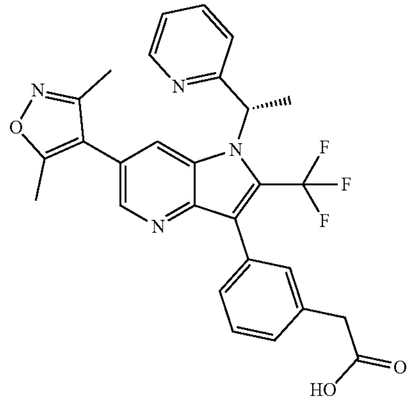 [SMILES: Cc1noc(C)c1-c1cnc2c(-c3cccc(CC(=O)O)c3)c(C(F)(F)F)n([C@@H](C)c3ccccn3)c2c1] |
| P-0162 | 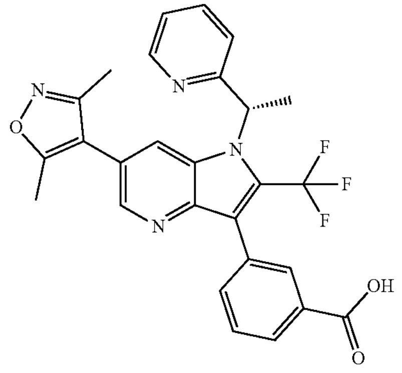 [SMILES: Cc1noc(C)c1-c1cnc2c(-c3cccc(C(=O)O)c3)c(C(F)(F)F)n([C@@H](C)c3ccccn3)c2c1] |
-continued
| P# | Structure |
|---|---|
| P-0163 | 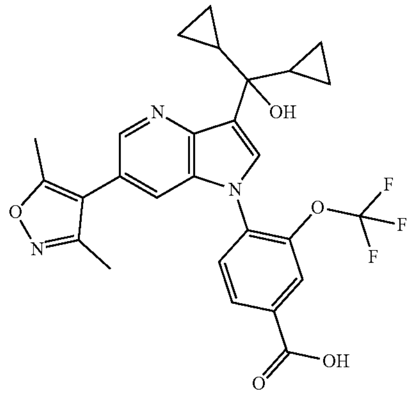 [SMILES: Cc1noc(C)c1-c1cnc2c(C(O)(C3CC3)C3CC3)cn(-c3ccc(C(=O)O)cc3OC(F)(F)F)c2c1] |
| P-0164 | 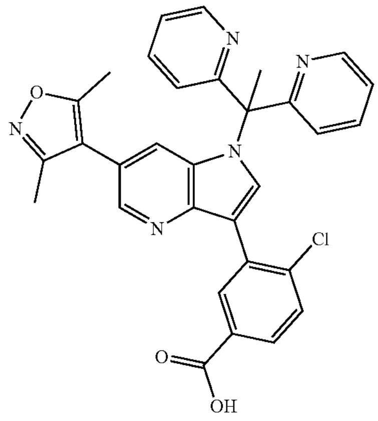 [SMILES: Cc1noc(C)c1-c1cnc2c(-c3cc(C(=O)O)ccc3Cl)cn(C(C)(c3ccccn3)c3ccccn3)c2c1] |
| P-0165 | 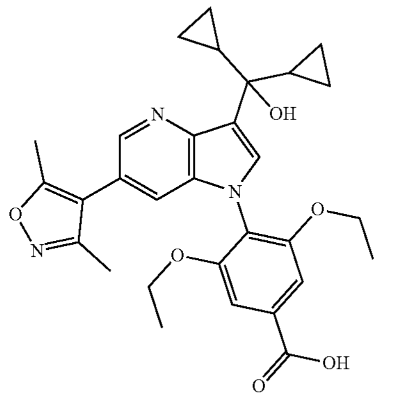 [SMILES: CCOc1cc(C(=O)O)cc(OCC)c1-n1cc(C(O)(C2CC2)C2CC2)c2ncc(-c3c(C)noc3C)cc21] |

-continued
| P# | Structure |
| --- | --- |
| P-0166 | 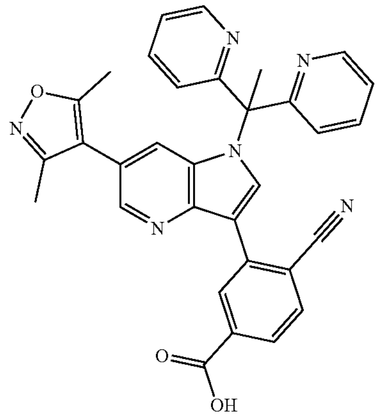 [SMILES: Cc1noc(C)c1-c1cnc2c(-c3cc(C(=O)O)ccc3C#N)cn(C(C)(c3ccccn3)c3ccccn3)c2c1] |
| P-0167 | 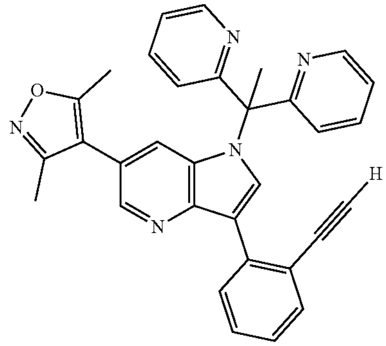 [SMILES: C#Cc1ccccc1-c1cn(C(C)(c2ccccn2)c2ccccn2)c2cc(-c3c(C)noc3C)cnc12] |
| P-0168 | 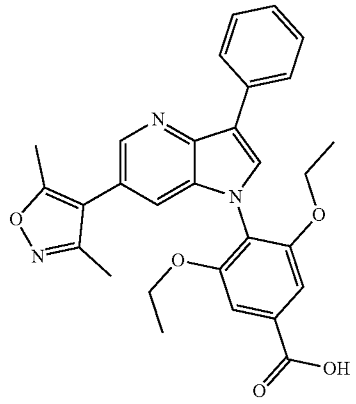 [SMILES: CCOc1cc(C(=O)O)cc(OCC)c1-n1cc(-c2ccccc2)c2ncc(-c3c(C)noc3C)cc21] |
| P-0169 | 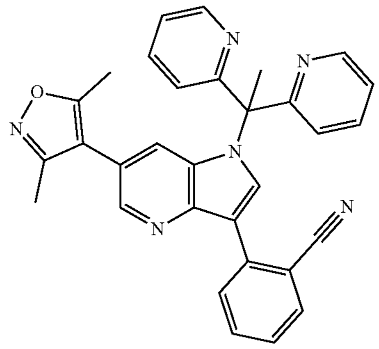 [SMILES: Cc1noc(C)c1-c1cnc2c(-c3ccccc3C#N)cn(C(C)(c3ccccn3)c3ccccn3)c2c1] |
-continued
| P# | Structure |
| --- | --- |
| P-0170 | 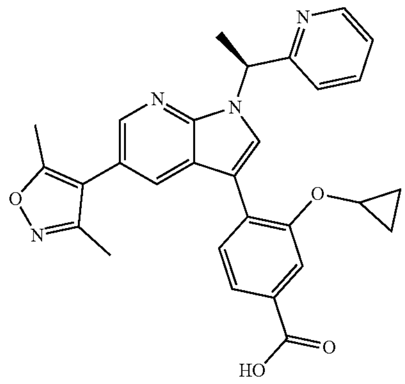 [SMILES: Cc1noc(C)c1-c1cnc2c(c1)c(-c1ccc(C(=O)O)cc1OC1CC1)cn2[C@@H](C)c1ccccn1] |
| P-0171 | 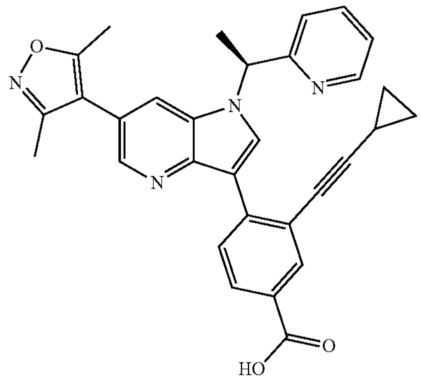 [SMILES: Cc1noc(C)c1-c1cnc2c(-c3ccc(C(=O)O)cc3C#CC3CC3)cn([C@@H](C)c3ccccn3)c2c1] |
| P-0172 | 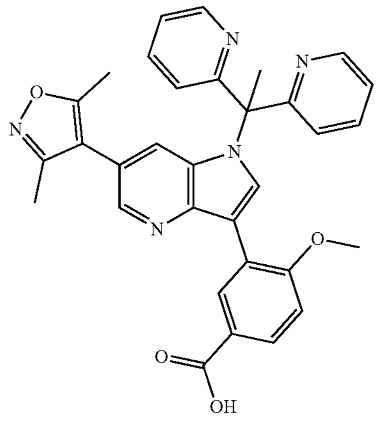 [SMILES: COc1ccc(C(=O)O)cc1-c1cn(C(C)(c2ccccn2)c2ccccn2)c2cc(-c3c(C)noc3C)cnc12] |
| P-0173 | 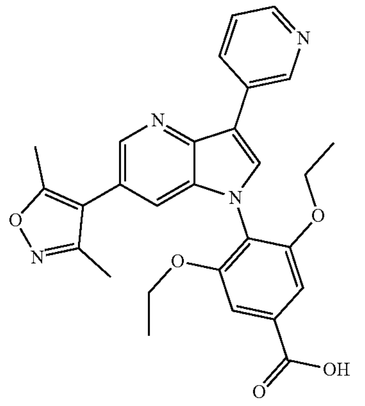 [SMILES: CCOc1cc(C(=O)O)cc(OCC)c1-n1cc(-c2cccnc2)c2ncc(-c3c(C)noc3C)cc21] |

-continued
| P# | Structure |
|---|---|
| P-0174 | 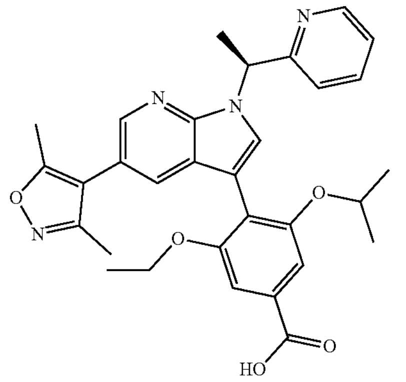 [SMILES: CCOc1cc(C(=O)O)cc(OC(C)C)c1-c1cn([C@@H](C)c2ccccn2)c2ncc(-c3c(C)noc3C)cc12] |
| P-0175 | 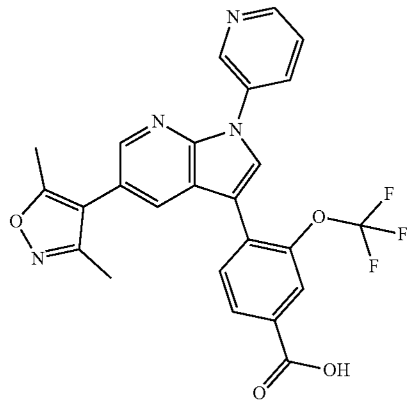 [SMILES: Cc1noc(C)c1-c1cnc2c(c1)c(-c1ccc(C(=O)O)cc1OC(F)(F)F)cn2-c1cccnc1] |
| P-0176 | 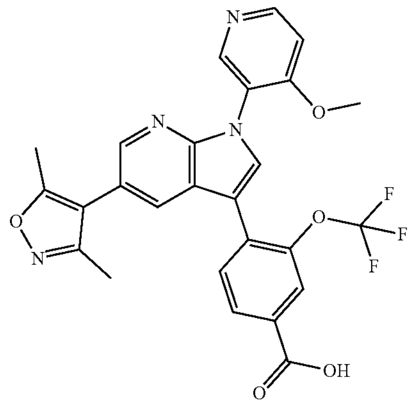 [SMILES: COc1ccncc1-n1cc(-c2ccc(C(=O)O)cc2OC(F)(F)F)c2cc(-c3c(C)noc3C)cnc21] |
| P-0177 | 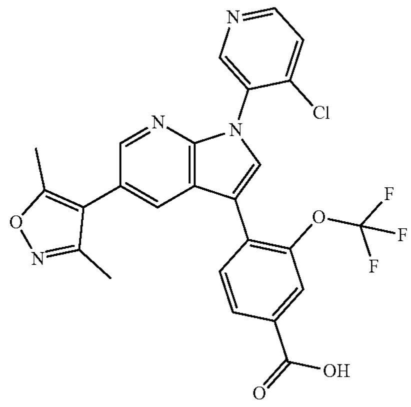 |
-continued
| P# | Structure |
|---|---|
| P-0178 | 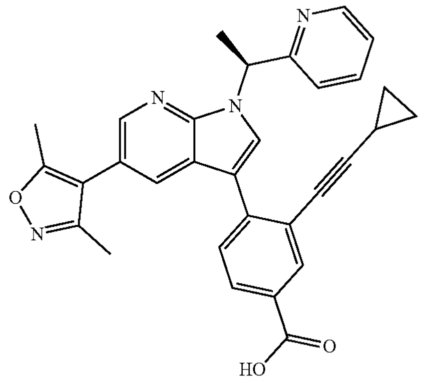 [SMILES: Cc1noc(C)c1-c1cnc2c(c1)c(-c1ccc(C(=O)O)cc1C#CC1CC1)cn2[C@@H](C)c1ccccn1] |
| P-0179 | 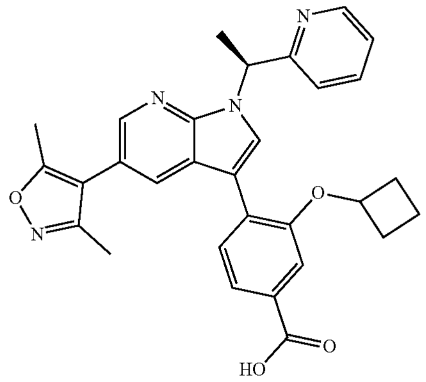 [SMILES: Cc1noc(C)c1-c1cnc2c(c1)c(-c1ccc(C(=O)O)cc1OC1CCC1)cn2[C@@H](C)c1ccccn1] |
| P-0180 | 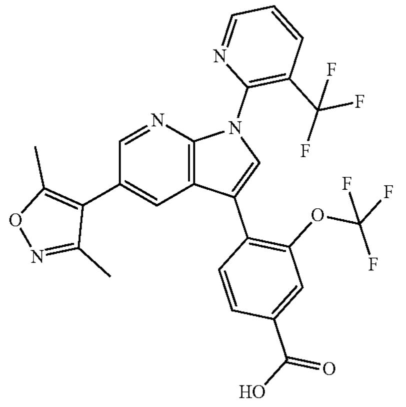 [SMILES: Cc1noc(C)c1-c1cnc2c(c1)c(-c1ccc(C(=O)O)cc1OC(F)(F)F)cn2-c1ncccc1C(F)(F)F] |
| P-0181 | 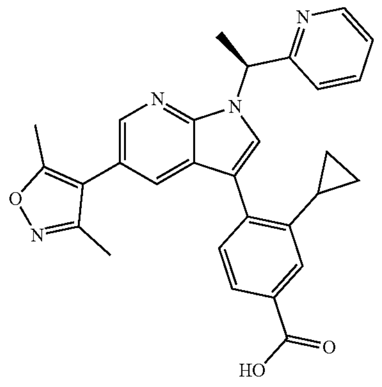 [SMILES: Cc1noc(C)c1-c1cnc2c(c1)c(-c1ccc(C(=O)O)cc1C1CC1)cn2[C@@H](C)c1ccccn1] |

-continued
| P# | Structure |
|---|---|
| P-0182 | 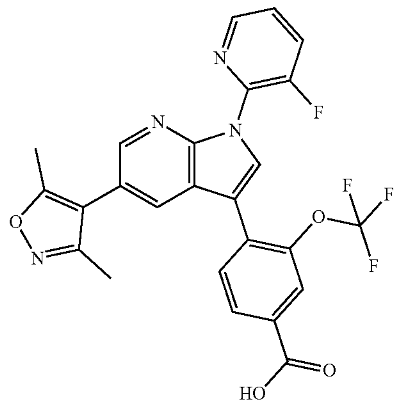 [SMILES: Cc1noc(C)c1-c1cnc2c(c1)c(-c1ccc(C(=O)O)cc1OC(F)(F)F)cn2-c1ncccc1F] |
| P-0183 | 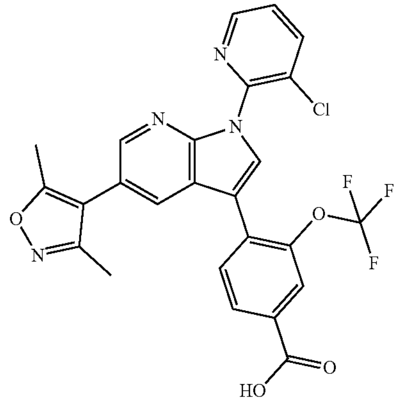 [SMILES: Cc1noc(C)c1-c1cnc2c(c1)c(-c1ccc(C(=O)O)cc1OC(F)(F)F)cn2-c1ncccc1Cl] |
| P-0184 | 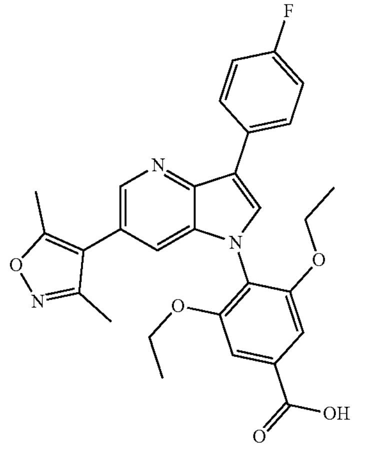 [SMILES: CCOc1cc(C(=O)O)cc(OCC)c1-n1cc(-c2ccc(F)cc2)c2ncc(-c3c(C)noc3C)cc21] |
-continued
| P# | Structure |
|---|---|
| P-0185 | 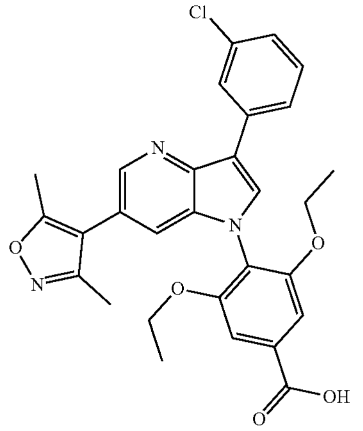 [SMILES: CCOc1cc(C(=O)O)cc(OCC)c1-n1cc(-c2cccc(Cl)c2)c2ncc(-c3c(C)noc3C)cc21] |
| P-0186 | 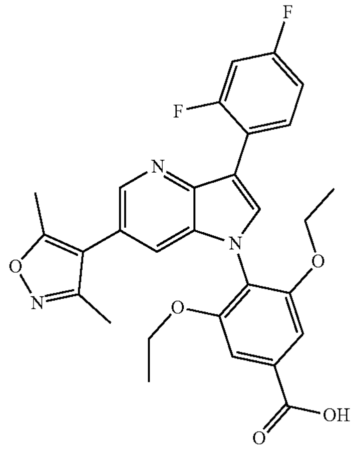 [SMILES: CCOc1cc(C(=O)O)cc(OCC)c1-n1cc(-c2ccc(F)cc2F)c2ncc(-c3c(C)noc3C)cc21] |
| P-0187 | 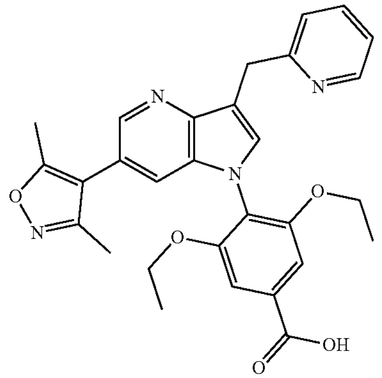 [SMILES: CCOc1cc(C(=O)O)cc(OCC)c1-n1cc(Cc2ccccn2)c2ncc(-c3c(C)noc3C)cc21] |

-continued
| P# | Structure |
|---|---|
| P-0188 | 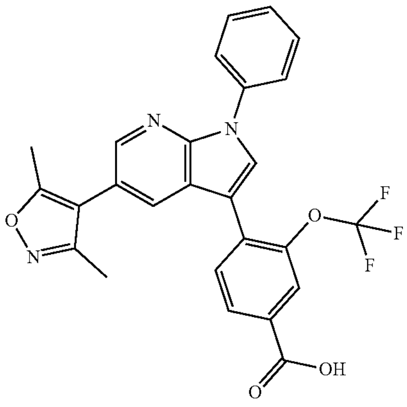 [SMILES: Cc1noc(C)c1-c1cnc2c(c1)c(-c1ccc(C(=O)O)cc1OC(F)(F)F)cn2-c1ccccc1] |
| P-0189 | 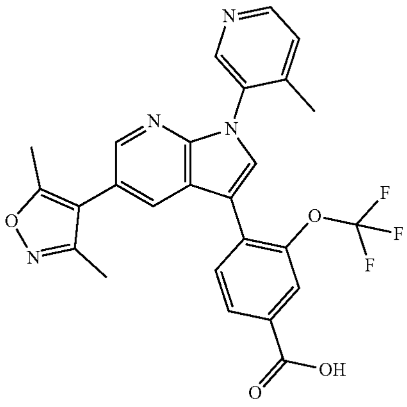 [SMILES: Cc1ccncc1-n1cc(-c2ccc(C(=O)O)cc2OC(F)(F)F)c2cc(-c3c(C)noc3C)cnc21] |
| P-0190 | 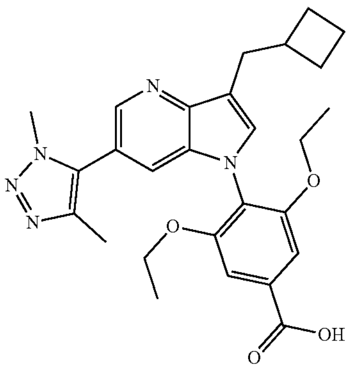 [SMILES: CCOc1cc(C(=O)O)cc(OCC)c1-n1cc(CC2CCC2)c2ncc(-c3c(C)nnn3C)cc21] |
-continued
| P# | Structure |
|---|---|
| P-0191 | 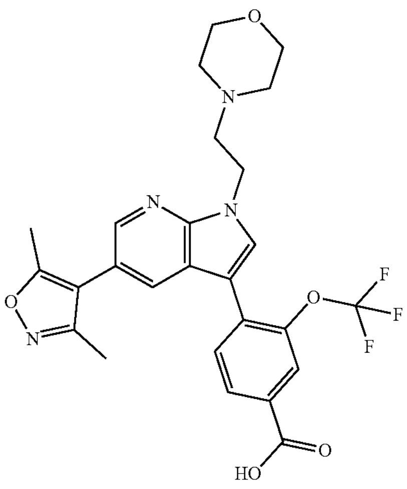 [SMILES: Cc1noc(C)c1-c1cnc2c(c1)c(-c1ccc(C(=O)O)cc1OC(F)(F)F)cn2CCN1CCOCC1] |
| P-0192 | 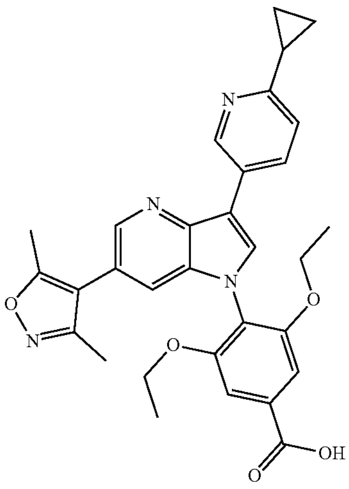 [SMILES: CCOc1cc(C(=O)O)cc(OCC)c1-n1cc(-c2ccc(C3CC3)nc2)c2ncc(-c3c(C)noc3C)cc21] |
| P-0193 | 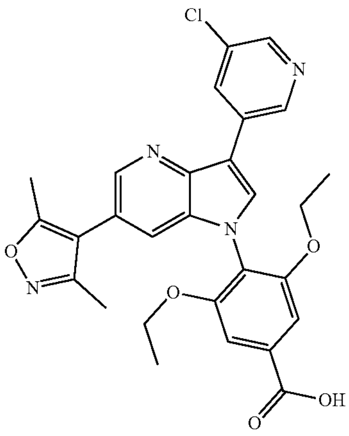 [SMILES: CCOc1cc(C(=O)O)cc(OCC)c1-n1cc(-c2cncc(Cl)c2)c2ncc(-c3c(C)noc3C)cc21] |

-continued
| P# | Structure |
|---|---|
| P-0194 | 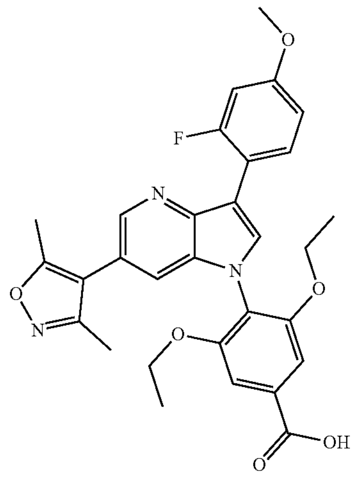 [SMILES: CCOc1cc(C(=O)O)cc(OCC)c1-n1cc(-c2ccc(OC)cc2F)c2ncc(-c3c(C)noc3C)cc21] |
| P-0195 | 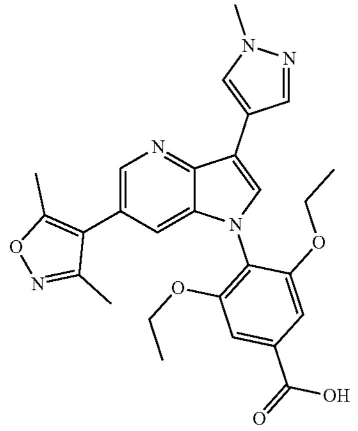 [SMILES: CCOc1cc(C(=O)O)cc(OCC)c1-n1cc(-c2cnn(C)c2)c2ncc(-c3c(C)noc3C)cc21] |
| P-0196 | 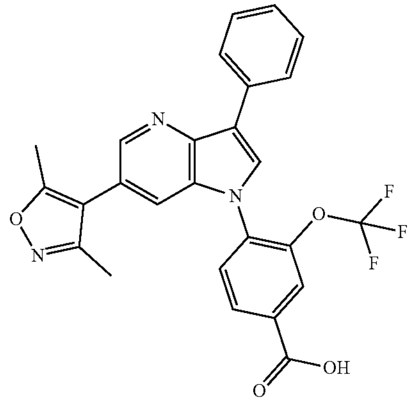 [SMILES: Cc1noc(C)c1-c1cnc2c(-c3ccccc3)cn(-c3ccc(C(=O)O)cc3OC(F)(F)F)c2c1] |
-continued
| P# | Structure |
|---|---|
| P-0197 | 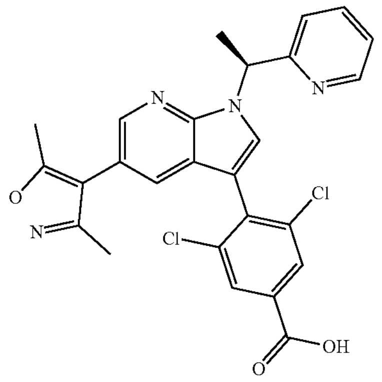 [SMILES: CC(=N)/C(=C(/C)O)c1cnc2c(c1)c(-c1c(Cl)cc(C(=O)O)cc1Cl)cn2[C@@H](C)c1ccccn1] |
| P-0198 | 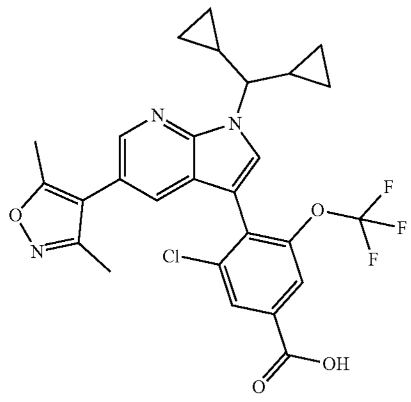 [SMILES: Cc1noc(C)c1-c1cnc2c(c1)c(-c1c(Cl)cc(C(=O)O)cc1OC(F)(F)F)cn2C(C1CC1)C1CC1] |
| P-0199 | 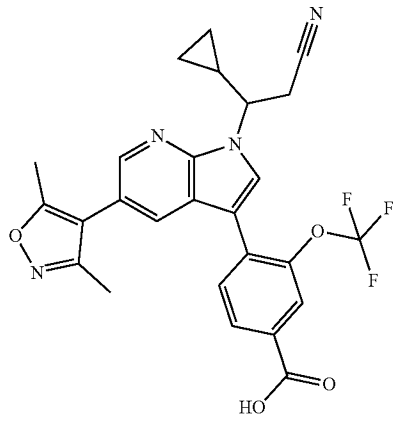 [SMILES: Cc1noc(C)c1-c1cnc2c(c1)c(-c1ccc(C(=O)O)cc1OC(F)(F)F)cn2C(CC#N)C1CC1] |

-continued
| P# | Structure |
|---|---|
| P-0200 | 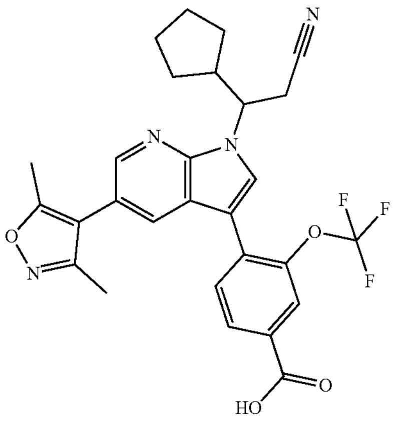 [SMILES: Cc1noc(C)c1-c1cnc2c(c1)c(-c1ccc(C(=O)O)cc1OC(F)(F)F)cn2C(CC#N)C1CCCC1] |
| P-0201 | 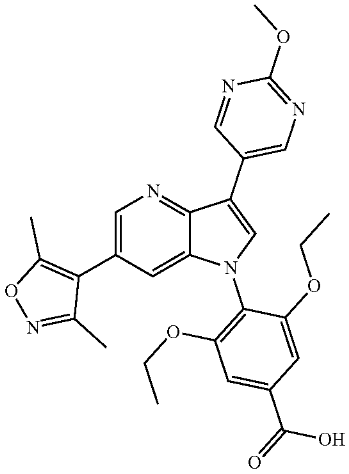 [SMILES: CCOc1cc(C(=O)O)cc(OCC)c1-n1cc(-c2cnc(OC)nc2)c2ncc(-c3c(C)noc3C)cc21] |
| P-0202 | 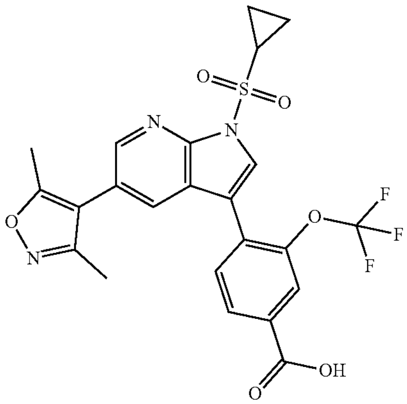 [SMILES: Cc1noc(C)c1-c1cnc2c(c1)c(-c1ccc(C(=O)O)cc1OC(F)(F)F)cn2S(=O)(=O)C1CC1] |
| P-0203 | 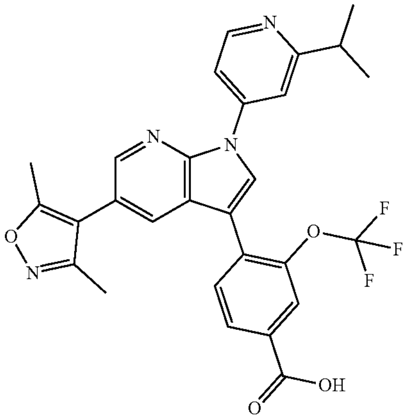 [SMILES: Cc1noc(C)c1-c1cnc2c(c1)c(-c1ccc(C(=O)O)cc1OC(F)(F)F)cn2-c1ccnc(C(C)C)c1] |
| P-0204 | 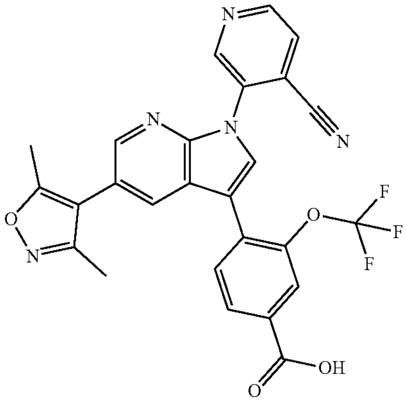 [SMILES: Cc1noc(C)c1-c1cnc2c(c1)c(-c1ccc(C(=O)O)cc1OC(F)(F)F)cn2-c1cnccc1C#N] |
| P-0205 | 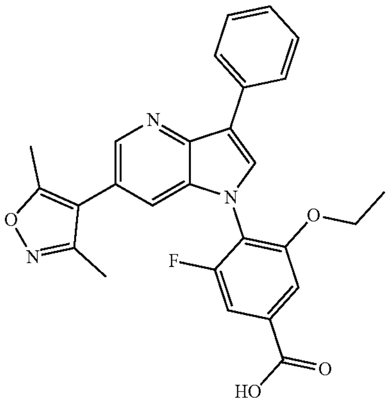 [SMILES: CCOc1cc(C(=O)O)cc(F)c1-n1cc(-c2ccccc2)c2ncc(-c3c(C)noc3C)cc21] |
| P-0206 | 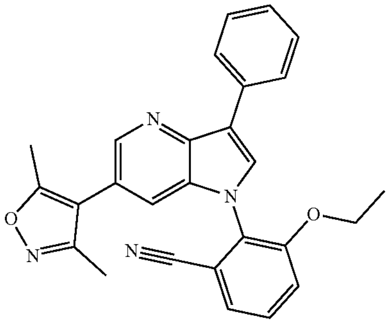 [SMILES: CCOc1cccc(C#N)c1-n1cc(-c2ccccc2)c2ncc(-c3c(C)noc3C)cc21] |

-continued
| P# | Structure |
|---|---|
| P-0207 | 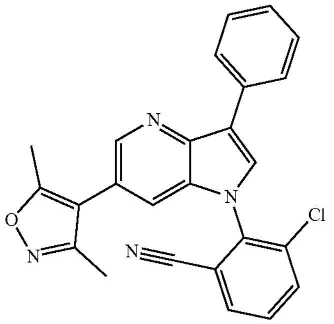 [SMILES: Cc1noc(C)c1-c1cnc2c(-c3ccccc3)cn(-c3c(Cl)cccc3C#N)c2c1] |
| P-0208 | 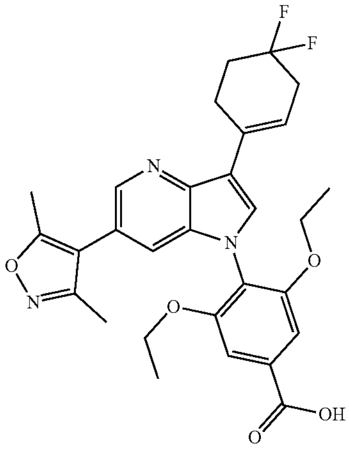 [SMILES: CCOc1cc(C(=O)O)cc(OCC)c1-n1cc(C2=CCC(F)(F)CC2)c2ncc(-c3c(C)noc3C)cc21] |
| P-0209 | 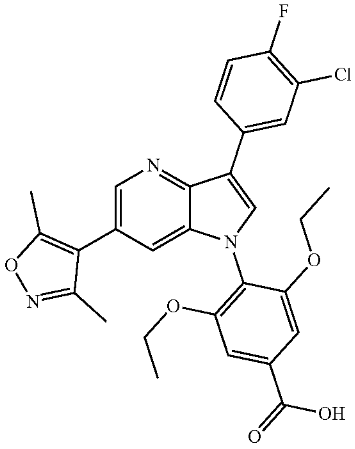 [SMILES: CCOc1cc(C(=O)O)cc(OCC)c1-n1cc(-c2ccc(F)c(Cl)c2)c2ncc(-c3c(C)noc3C)cc21] |
| P-0210 | 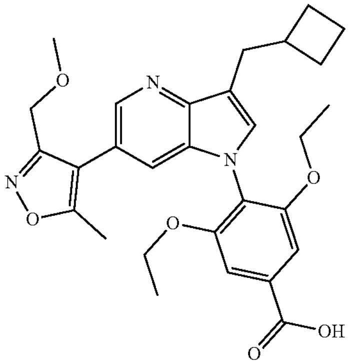 [SMILES: CCOc1cc(C(=O)O)cc(OCC)c1-n1cc(CC2CCC2)c2ncc(-c3c(COC)noc3C)cc21] |
-continued
| P# | Structure |
|---|---|
| P-0211 | 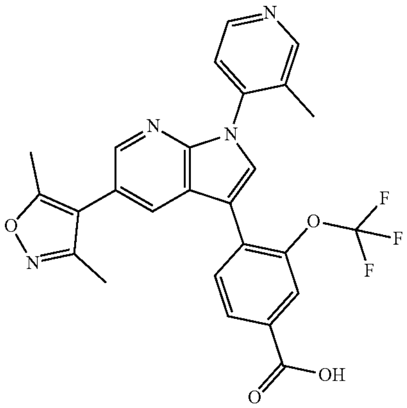 [SMILES: Cc1cnccc1-n1cc(-c2ccc(C(=O)O)cc2OC(F)(F)F)c2cc(-c3c(C)noc3C)cnc21] |
| P-0212 | 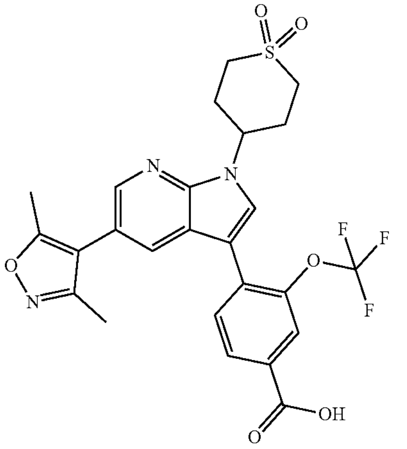 [SMILES: Cc1noc(C)c1-c1cnc2c(c1)c(-c1ccc(C(=O)O)cc1OC(F)(F)F)cn2C1CCS(=O)(=O)CC1] |
| P-0213 | 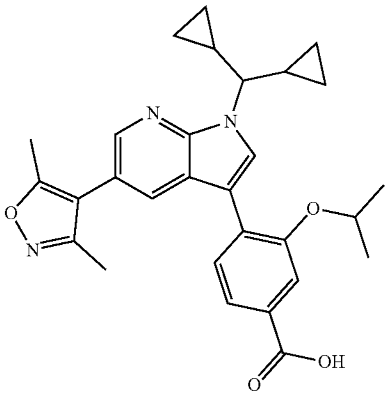 [SMILES: Cc1noc(C)c1-c1cnc2c(c1)c(-c1ccc(C(=O)O)cc1OC(C)C)cn2C(C1CC1)C1CC1] |

-continued
| P# | Structure |
|---|---|
| P-0214 | 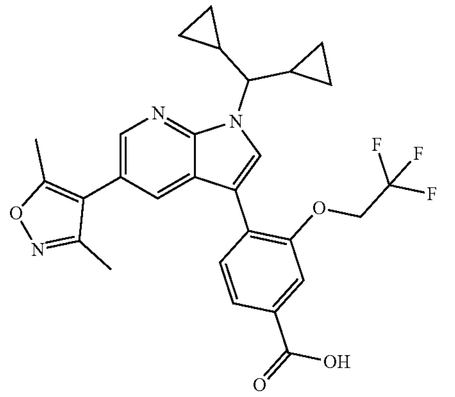 [SMILES: Cc1noc(C)c1-c1cnc2c(c1)c(-c1ccc(C(=O)O)cc1OCC(F)(F)F)cn2C(C1CC1)C1CC1] |
| P-0215 | 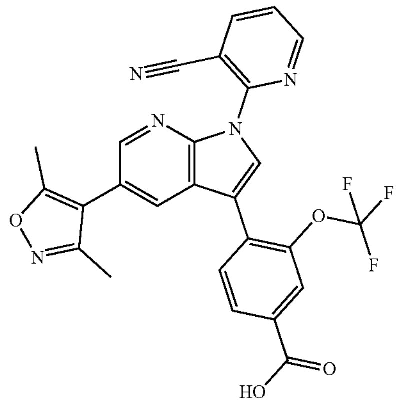 [SMILES: Cc1noc(C)c1-c1cnc2c(c1)c(-c1ccc(C(=O)O)cc1OC(F)(F)F)cn2-c1ncccc1C#N] |
| P-0216 | 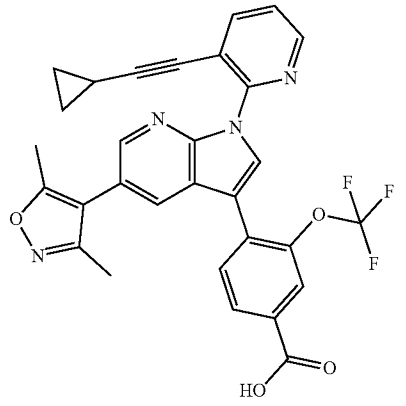 [SMILES: Cc1noc(C)c1-c1cnc2c(c1)c(-c1ccc(C(=O)O)cc1OC(F)(F)F)cn2-c1ncccc1C#CC1CC1] |
-continued
| P# | Structure |
|---|---|
| P-0217 | 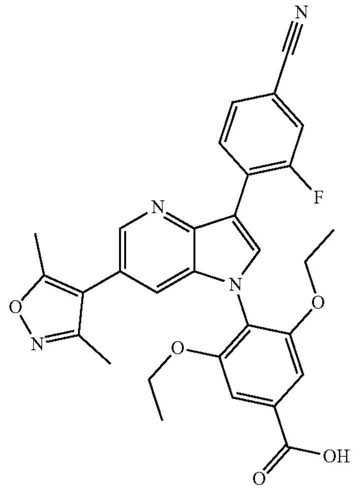 [SMILES: CCOc1cc(C(=O)O)cc(OCC)c1-n1cc(-c2ccc(C#N)cc2F)c2ncc(-c3c(C)noc3C)cc21] |
| P-0218 | 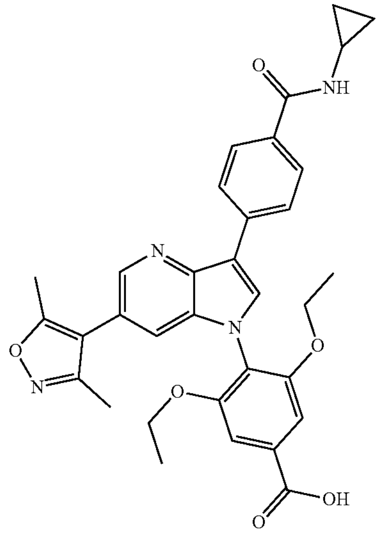 [SMILES: CCOc1cc(C(=O)O)cc(OCC)c1-n1cc(-c2ccc(C(=O)NC3CC3)cc2)c2ncc(-c3c(C)noc3C)cc21] |
| P-0219 | 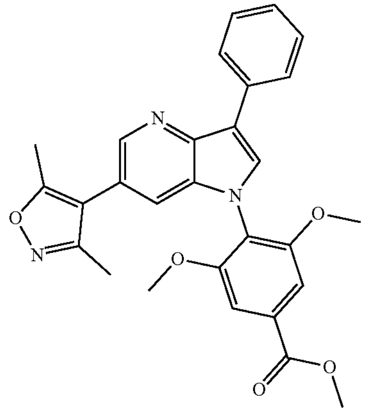 [SMILES: COC(=O)c1cc(OC)c(-n2cc(-c3ccccc3)c3ncc(-c4c(C)noc4C)cc32)c(OC)c1] |

-continued
| P# | Structure |
|---|---|
| P-0220 | 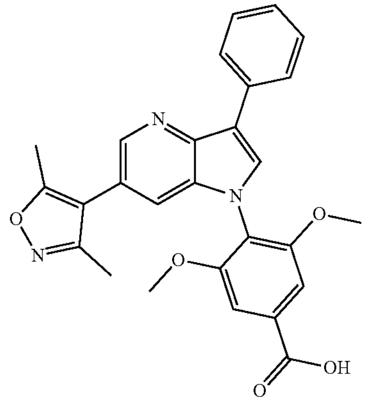 [SMILES: COc1cc(C(=O)O)cc(OC)c1-n1cc(-c2ccccc2)c2ncc(-c3c(C)noc3C)cc21] |
| P-0221 | 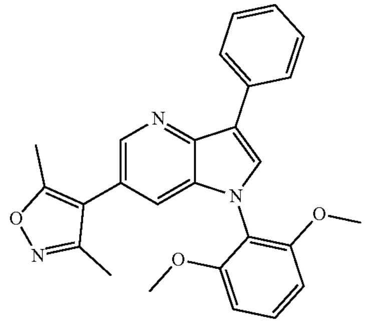 [SMILES: COc1cccc(OC)c1-n1cc(-c2ccccc2)c2ncc(-c3c(C)noc3C)cc21] |
| P-0222 | 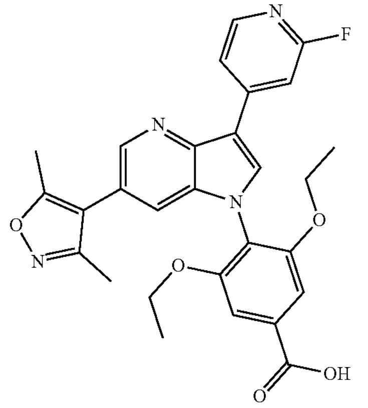 [SMILES: CCOc1cc(C(=O)O)cc(OCC)c1-n1cc(-c2ccnc(F)c2)c2ncc(-c3c(C)noc3C)cc21] |
| P-0223 | 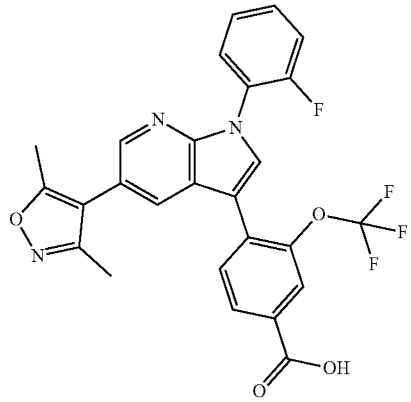 |
-continued
| P# | Structure |
|---|---|
| P-0224 | 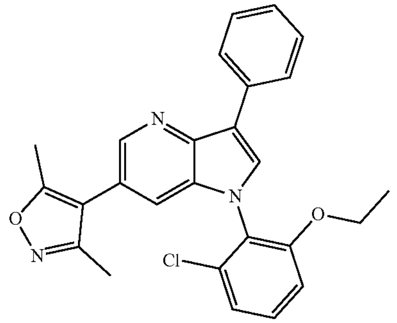 [SMILES: CCOc1cccc(Cl)c1-n1cc(-c2ccccc2)c2ncc(-c3c(C)noc3C)cc21] |
| P-0225 | 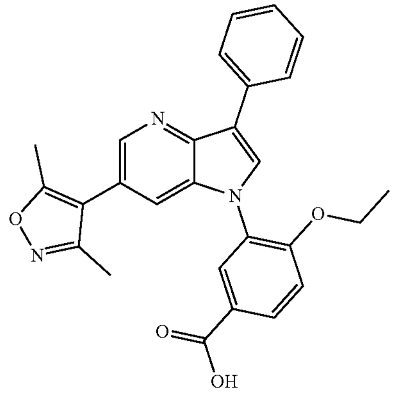 [SMILES: CCOc1ccc(C(=O)O)cc1-n1cc(-c2ccccc2)c2ncc(-c3c(C)noc3C)cc21] |
| P-0226 | 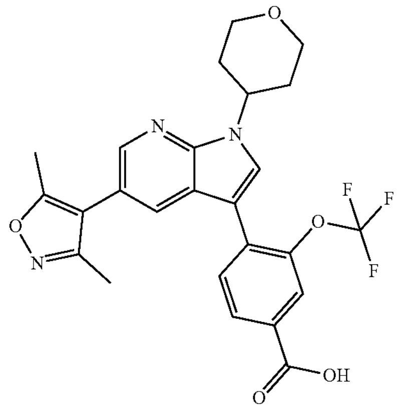 [SMILES: Cc1noc(C)c1-c1cnc2c(c1)c(-c1ccc(C(=O)O)cc1OC(F)(F)F)cn2C1CCOCC1] |
| P-0227 | 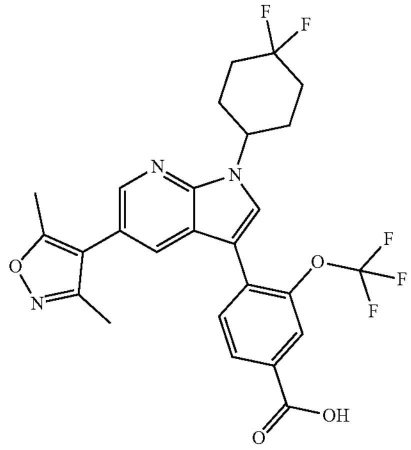 [SMILES: Cc1noc(C)c1-c1cnc2c(c1)c(-c1ccc(C(=O)O)cc1OC(F)(F)F)cn2C1CCC(F)(F)CC1] |

-continued
| P# | Structure |
|---|---|
| P-0228 | 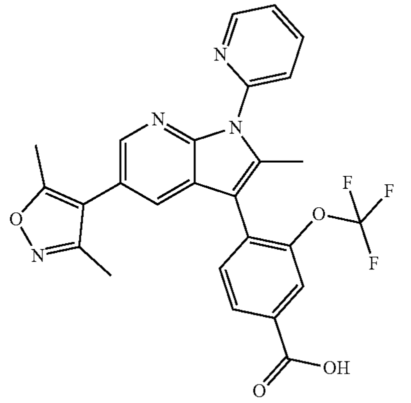 [SMILES: Cc1noc(C)c1-c1cnc2c(c1)c(-c1ccc(C(=O)O)cc1OC(F)(F)F)c(C)n2-c1ccccn1] |
| P-0229 | 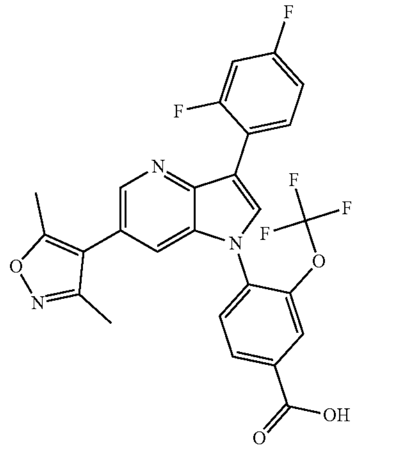 [SMILES: Cc1noc(C)c1-c1cnc2c(-c3ccc(F)cc3F)cn(-c3ccc(C(=O)O)cc3OC(F)(F)F)c2c1] |
| P-0230 | 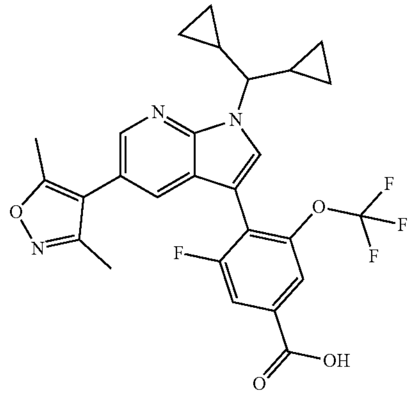 [SMILES: Cc1noc(C)c1-c1cnc2c(c1)c(-c1c(F)cc(C(=O)O)cc1OC(F)(F)F)cn2C(C1CC1)C1CC1] |
-continued
| P# | Structure |
|---|---|
| P-0231 | 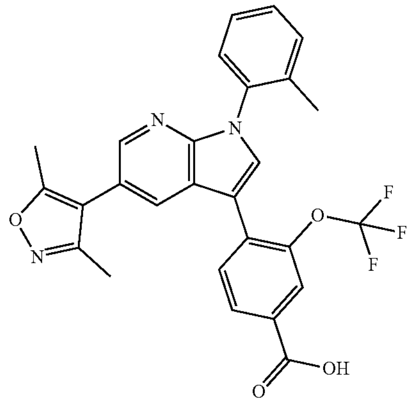 [SMILES: Cc1ccccc1-n1cc(-c2ccc(C(=O)O)cc2OC(F)(F)F)c2cc(-c3c(C)noc3C)cnc21] |
| P-0232 | 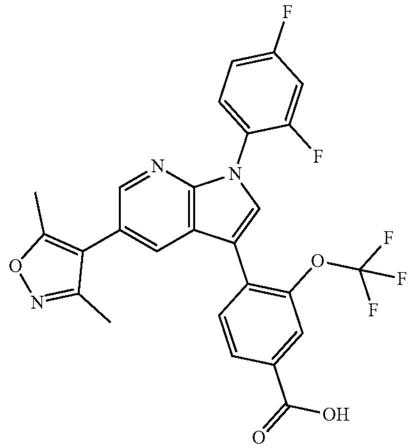 [SMILES: Cc1noc(C)c1-c1cnc2c(c1)c(-c1ccc(C(=O)O)cc1OC(F)(F)F)cn2-c1ccc(F)cc1F] |
| P-0233 | 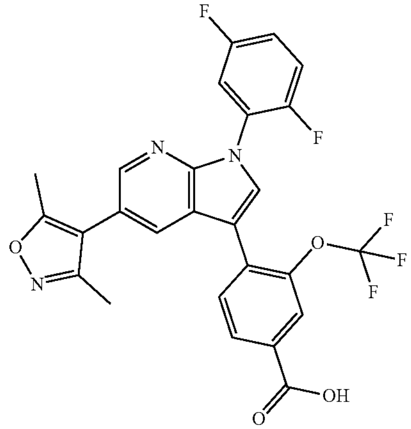 [SMILES: Cc1noc(C)c1-c1cnc2c(c1)c(-c1ccc(C(=O)O)cc1OC(F)(F)F)cn2-c1cc(F)ccc1F] |

-continued
| P# | Structure |
|---|---|
| P-0234 | 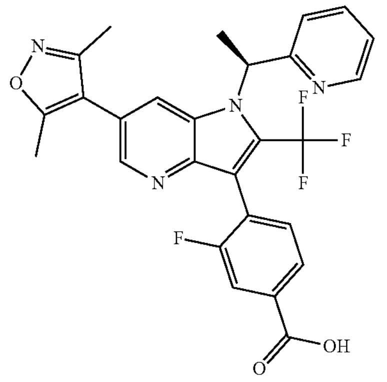 [SMILES: Cc1noc(C)c1-c1cnc2c(-c3ccc(C(=O)O)cc3F)c(C(F)(F)F)n([C@@H](C)c3ccccn3)c2c1] |
| P-0235 | 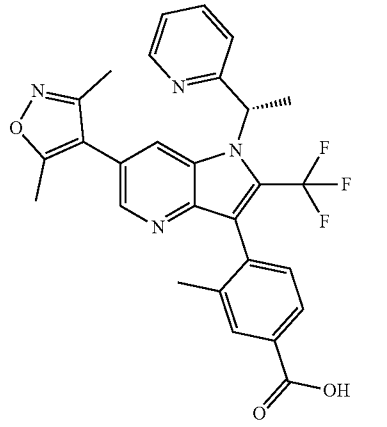 [SMILES: Cc1cc(C(=O)O)ccc1-c1c(C(F)(F)F)n([C@@H](C)c2ccccn2)c2cc(-c3c(C)noc3C)cnc12] |
| P-0236 | 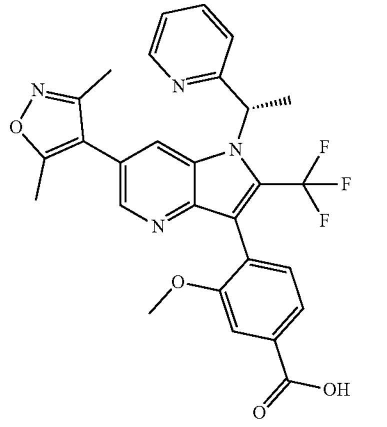 [SMILES: COc1cc(C(=O)O)ccc1-c1c(C(F)(F)F)n([C@@H](C)c2ccccn2)c2cc(-c3c(C)noc3C)cnc12] |
| P-0237 | 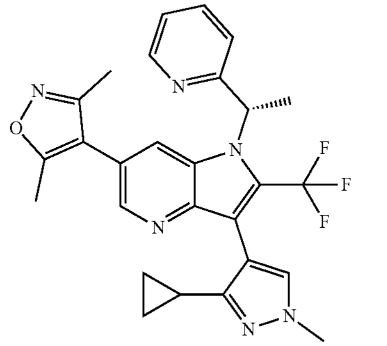 [SMILES: Cc1noc(C)c1-c1cnc2c(-c3cn(C)nc3C3CC3)c(C(F)(F)F)n([C@@H](C)c3ccccn3)c2c1] |
-continued
| P# | Structure |
|---|---|
| P-0238 | 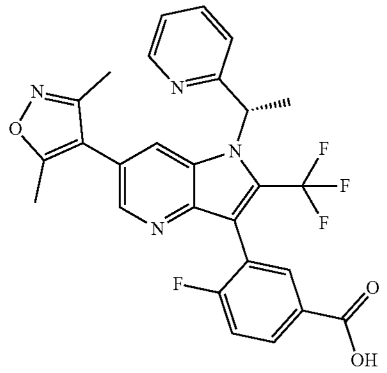 [SMILES: Cc1noc(C)c1-c1cnc2c(-c3cc(C(=O)O)ccc3F)c(C(F)(F)F)n([C@@H](C)c3ccccn3)c2c1] |
| P-0239 | 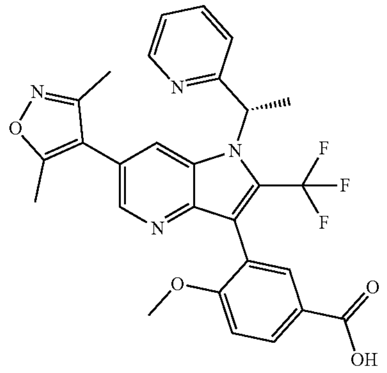 [SMILES: COc1ccc(C(=O)O)cc1-c1c(C(F)(F)F)n([C@@H](C)c2ccccn2)c2cc(-c3c(C)noc3C)cnc12] |
| P-0240 | 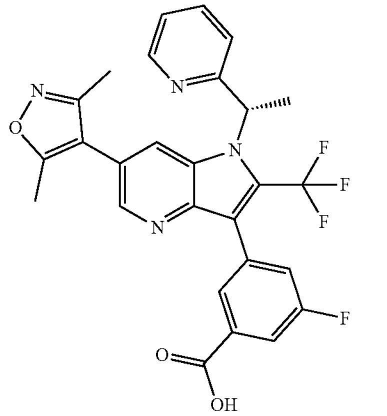 [SMILES: Cc1noc(C)c1-c1cnc2c(-c3cc(F)cc(C(=O)O)c3)c(C(F)(F)F)n([C@@H](C)c3ccccn3)c2c1] |
| P-0241 | 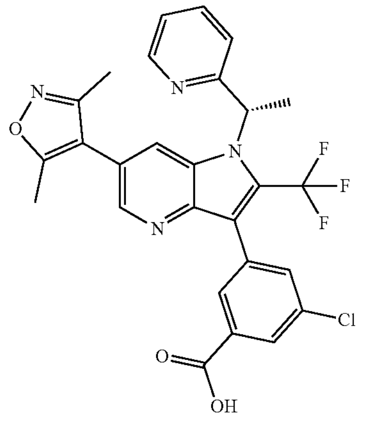 [SMILES: Cc1noc(C)c1-c1cnc2c(-c3cc(Cl)cc(C(=O)O)c3)c(C(F)(F)F)n([C@@H](C)c3ccccn3)c2c1] |

-continued
| P# | Structure |
| --- | --- |
| P-0242 | 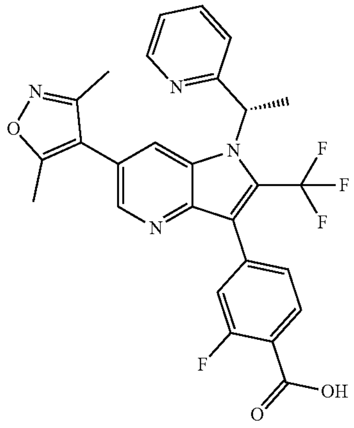 [SMILES: Cc1noc(C)c1-c1cnc2c(-c3ccc(C(=O)O)c(F)c3)c(C(F)(F)F)n([C@@H](C)c3ccccn3)c2c1] |
| P-0243 | 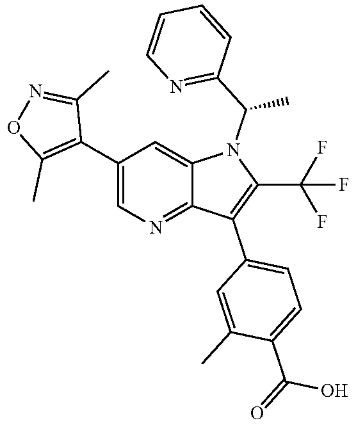 [SMILES: Cc1cc(-c2c(C(F)(F)F)n([C@@H](C)c3ccccn3)c3cc(-c4c(C)noc4C)cnc23)ccc1C(=O)O] |
| P-0244 | 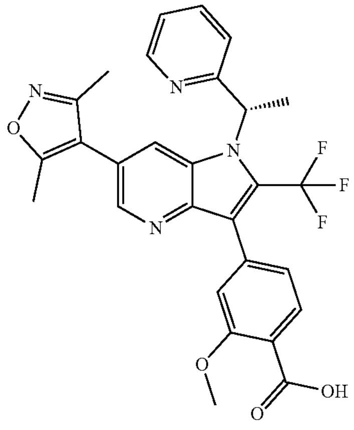 [SMILES: COc1cc(-c2c(C(F)(F)F)n([C@@H](C)c3ccccn3)c3cc(-c4c(C)noc4C)cnc23)ccc1C(=O)O] |
-continued
| P# | Structure |
| --- | --- |
| P-0245 | 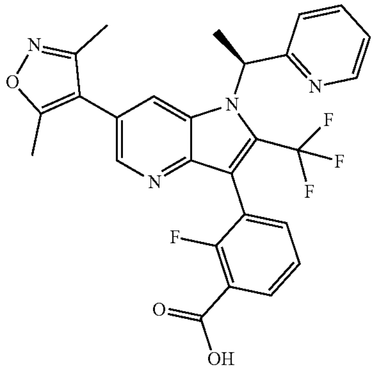 [SMILES: Cc1noc(C)c1-c1cnc2c(-c3cccc(C(=O)O)c3F)c(C(F)(F)F)n([C@@H](C)c3ccccn3)c2c1] |
| P-0246 | 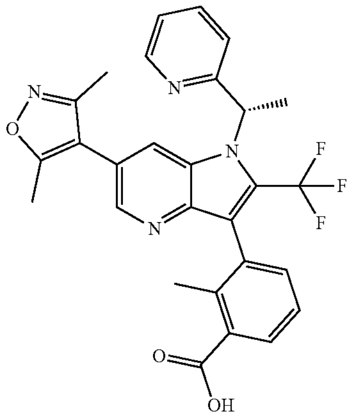 [SMILES: Cc1noc(C)c1-c1cnc2c(-c3cccc(C(=O)O)c3C)c(C(F)(F)F)n([C@@H](C)c3ccccn3)c2c1] |
| P-0247 | 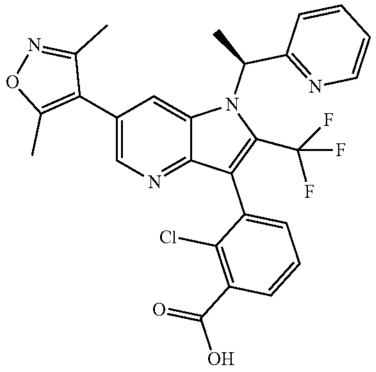 [SMILES: Cc1noc(C)c1-c1cnc2c(-c3cccc(C(=O)O)c3Cl)c(C(F)(F)F)n([C@@H](C)c3ccccn3)c2c1] |
| P-0248 | 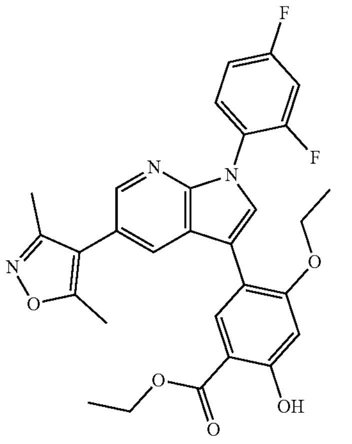 [SMILES: CCOC(=O)c1cc(-c2cn(-c3ccc(F)cc3F)c3ncc(-c4c(C)noc4C)cc23)c(OCC)cc1O] |

| P# | Structure |
|---|---|
| P-0249 | 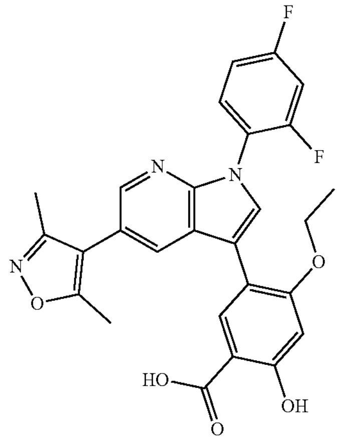 [SMILES: CCOc1cc(O)c(C(=O)O)cc1-c1cn(-c2ccc(F)cc2F)c2ncc(-c3c(C)noc3C)cc12] |
| P-0250 | 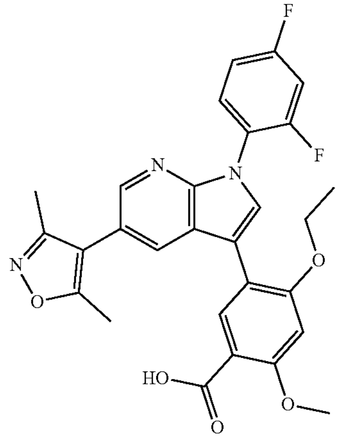 [SMILES: CCOc1cc(OC)c(C(=O)O)cc1-c1cn(-c2ccc(F)cc2F)c2ncc(-c3c(C)noc3C)cc12] |
| P-0251 | 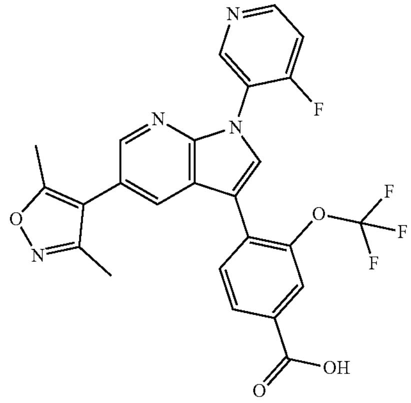 |
| P# | Structure |
|---|---|
| P-0252 | 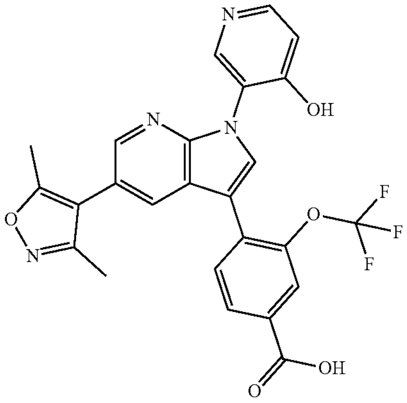 [SMILES: Cc1noc(C)c1-c1cnc2c(c1)c(-c1ccc(C(=O)O)cc1OC(F)(F)F)cn2-c1cnccc1O] |
| P-0253 | 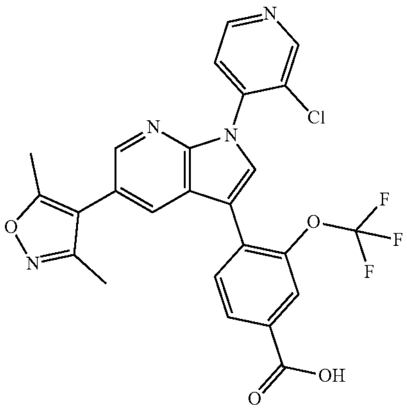 |
| P-0254 | 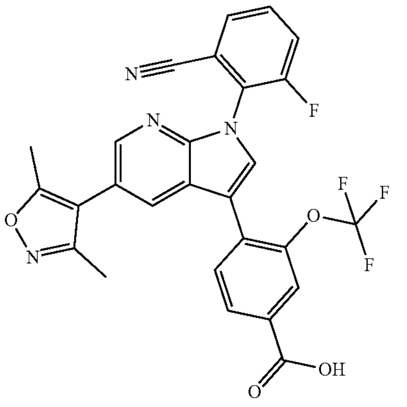 [SMILES: Cc1noc(C)c1-c1cnc2c(c1)c(-c1ccc(C(=O)O)cc1OC(F)(F)F)cn2-c1c(F)cccc1C#N] |

-continued
| P# | Structure |
|---|---|
| P-0255 | 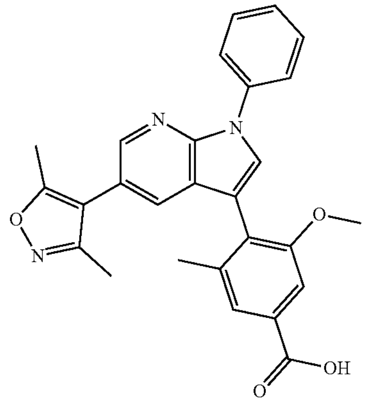 [SMILES: COc1cc(C(=O)O)cc(C)c1-c1cn(-c2ccccc2)c2ncc(-c3c(C)noc3C)cc12] |
| P-0256 | 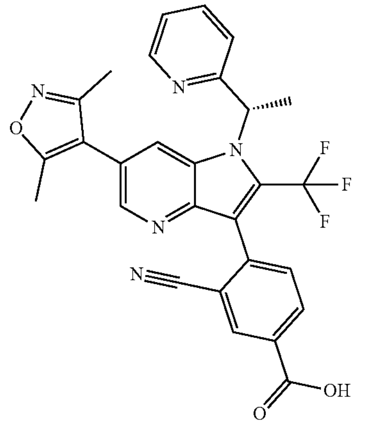 [SMILES: Cc1noc(C)c1-c1cnc2c(-c3ccc(C(=O)O)cc3C#N)c(C(F)(F)F)n([C@@H](C)c3ccccn3)c2c1] |
| P-0257 | 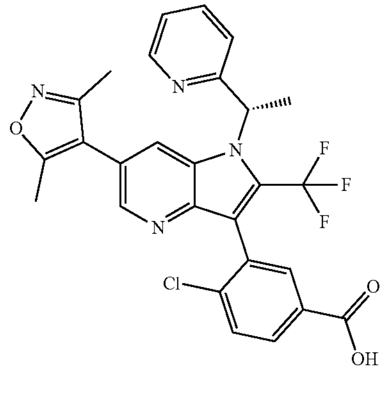 [SMILES: Cc1noc(C)c1-c1cnc2c(-c3cc(C(=O)O)ccc3Cl)c(C(F)(F)F)n([C@@H](C)c3ccccn3)c2c1] |
-continued
| P# | Structure |
|---|---|
| P-0258 | 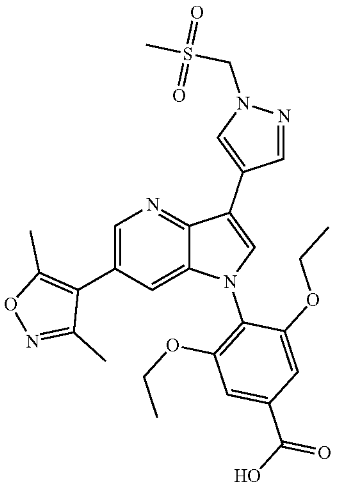 [SMILES: CCOc1cc(C(=O)O)cc(OCC)c1-n1cc(-c2cnn(CS(C)(=O)=O)c2)c2ncc(-c3c(C)noc3C)cc21] |
| P-0259 | 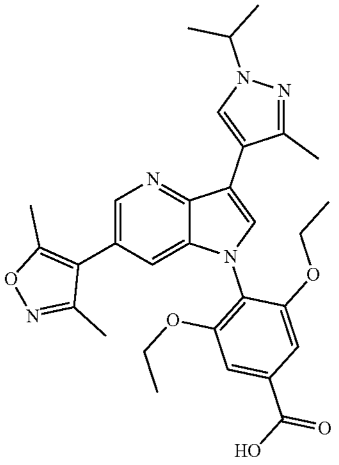 [SMILES: CCOc1cc(C(=O)O)cc(OCC)c1-n1cc(-c2cn(C(C)C)nc2C)c2ncc(-c3c(C)noc3C)cc21] |
| P-0260 | 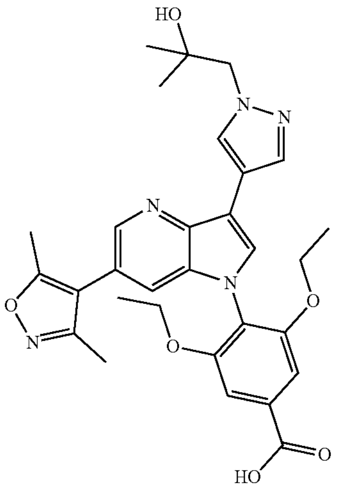 [SMILES: CCOc1cc(C(=O)O)cc(OCC)c1-n1cc(-c2cnn(CC(C)(C)O)c2)c2ncc(-c3c(C)noc3C)cc21] |

-continued
| P# | Structure |
|---|---|
| P-0261 | 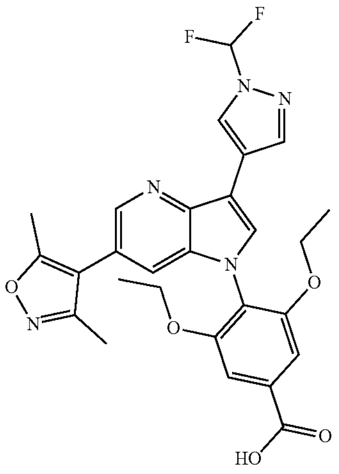 [SMILES: CCOc1cc(C(=O)O)cc(OCC)c1-n1cc(-c2cnn(C(F)F)c2)c2ncc(-c3c(C)noc3C)cc21] |
| P-0262 | 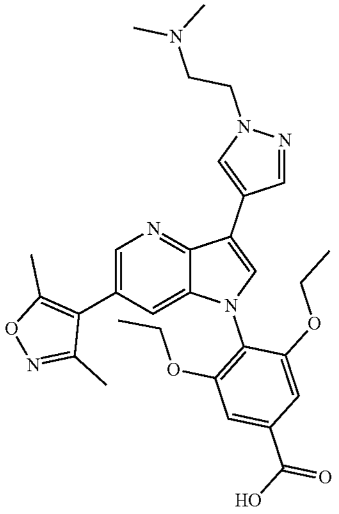 [SMILES: CCOc1cc(C(=O)O)cc(OCC)c1-n1cc(-c2cnn(CCN(C)C)c2)c2ncc(-c3c(C)noc3C)cc21] |
| P-0263 | 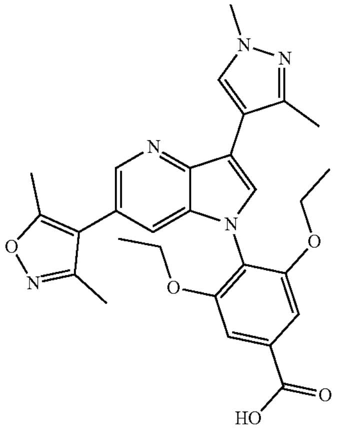 [SMILES: CCOc1cc(C(=O)O)cc(OCC)c1-n1cc(-c2cn(C)nc2C)c2ncc(-c3c(C)noc3C)cc21] |
-continued
| P# | Structure |
|---|---|
| P-0264 | 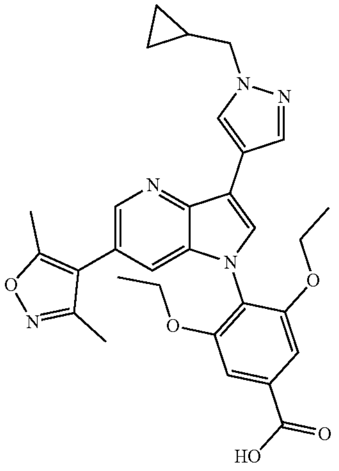 [SMILES: CCOc1cc(C(=O)O)cc(OCC)c1-n1cc(-c2cnn(CC3CC3)c2)c2ncc(-c3c(C)noc3C)cc21] |
| P-0265 | 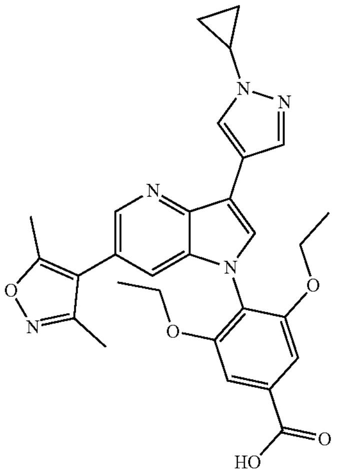 [SMILES: CCOc1cc(C(=O)O)cc(OCC)c1-n1cc(-c2cnn(C3CC3)c2)c2ncc(-c3c(C)noc3C)cc21] |
| P-0266 | 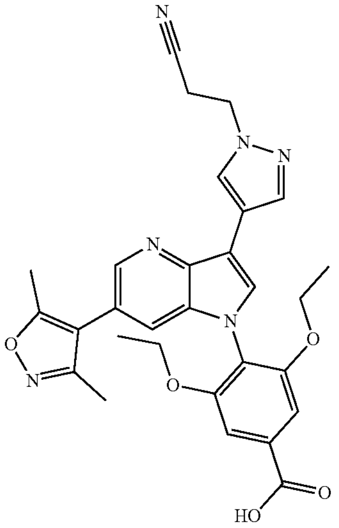 [SMILES: CCOc1cc(C(=O)O)cc(OCC)c1-n1cc(-c2cnn(CCC#N)c2)c2ncc(-c3c(C)noc3C)cc21] |

-continued
| P# | Structure |
|---|---|
| P-0267 | 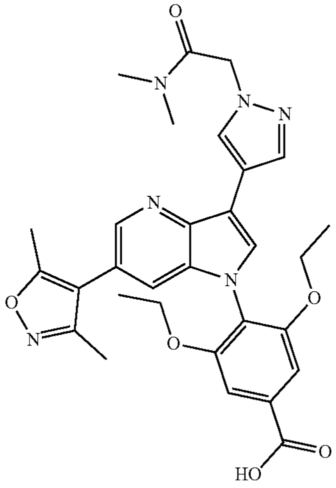 [SMILES: CCOc1cc(C(=O)O)cc(OCC)c1-n1cc(-c2cnn(CC(=O)N(C)C)c2)c2ncc(-c3c(C)noc3C)cc21] |
| P-0268 | 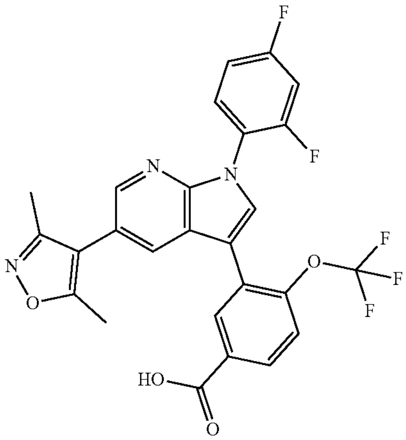 [SMILES: Cc1noc(C)c1-c1cnc2c(c1)c(-c1cc(C(=O)O)ccc1OC(F)(F)F)cn2-c1ccc(F)cc1F] |
| P-0269 | 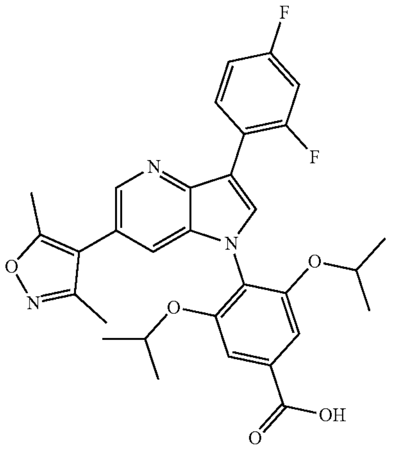 [SMILES: Cc1noc(C)c1-c1cnc2c(-c3ccc(F)cc3F)cn(-c3c(OC(C)C)cc(C(=O)O)cc3OC(C)C)c2c1] |
-continued
| P# | Structure |
|---|---|
| P-0270 | 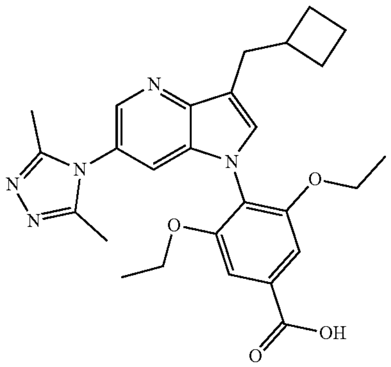 [SMILES: CCOc1cc(C(=O)O)cc(OCC)c1-n1cc(CC2CCC2)c2ncc(-n3c(C)nnc3C)cc21] |
| P-0271 | 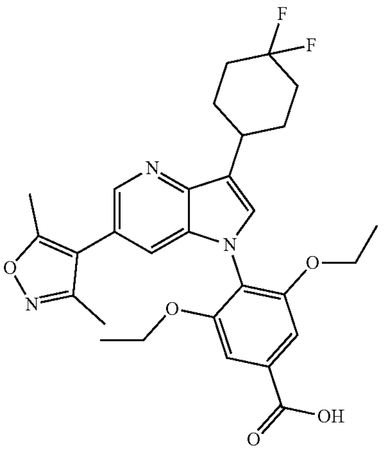 [SMILES: CCOc1cc(C(=O)O)cc(OCC)c1-n1cc(C2CCC(F)(F)CC2)c2ncc(-c3c(C)noc3C)cc21] |
| P-0272 | 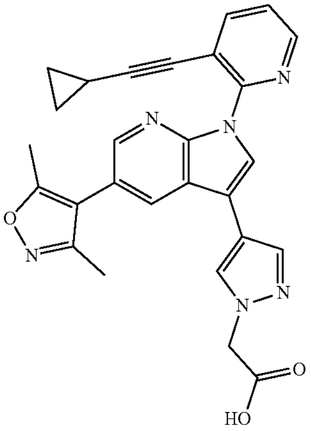 [SMILES: Cc1noc(C)c1-c1cnc2c(c1)c(-c1cnn(CC(=O)O)c1)cn2-c1ncccc1C#CC1CC1] |

-continued
| P# | Structure |
|---|---|
| P-0273 | 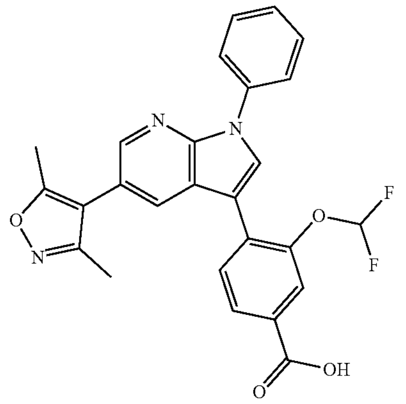 [SMILES: Cc1noc(C)c1-c1cnc2c(c1)c(-c1ccc(C(=O)O)cc1OC(F)F)cn2-c1ccccc1] |
| P-0274 | 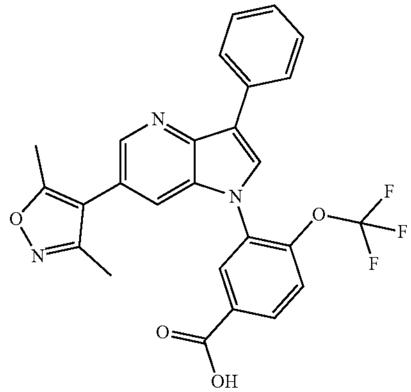 [SMILES: Cc1noc(C)c1-c1cnc2c(-c3ccccc3)cn(-c3cc(C(=O)O)ccc3OC(F)(F)F)c2c1] |
| P-0275 | 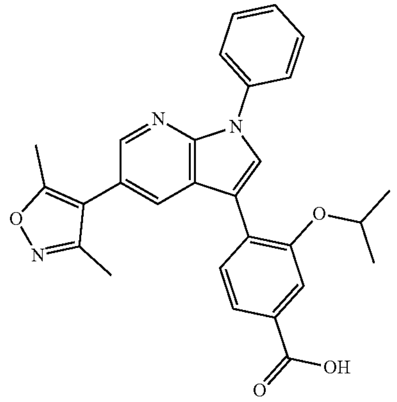 [SMILES: Cc1noc(C)c1-c1cnc2c(c1)c(-c1ccc(C(=O)O)cc1OC(C)C)cn2-c1ccccc1] |
| P-0276 | 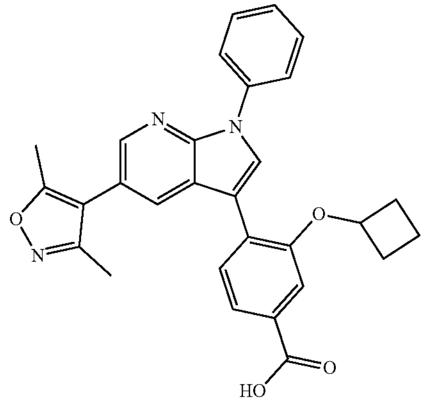 [SMILES: Cc1noc(C)c1-c1cnc2c(c1)c(-c1ccc(C(=O)O)cc1OC1CCC1)cn2-c1ccccc1] |
-continued
| P# | Structure |
|---|---|
| P-0277 | 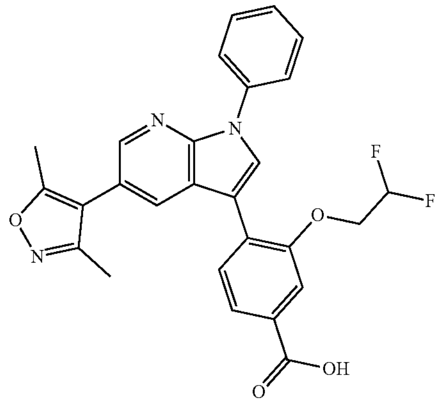 [SMILES: Cc1noc(C)c1-c1cnc2c(c1)c(-c1ccc(C(=O)O)cc1OCC(F)F)cn2-c1ccccc1] |
| P-0278 | 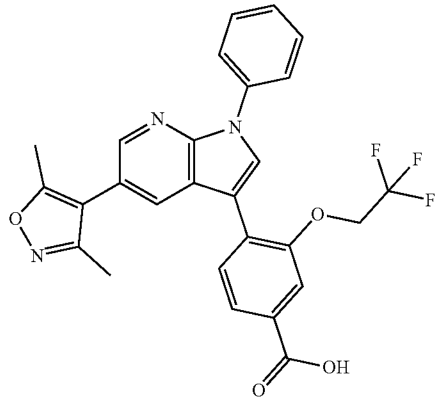 [SMILES: Cc1noc(C)c1-c1cnc2c(c1)c(-c1ccc(C(=O)O)cc1OCC(F)(F)F)cn2-c1ccccc1] |
| P-0279 | 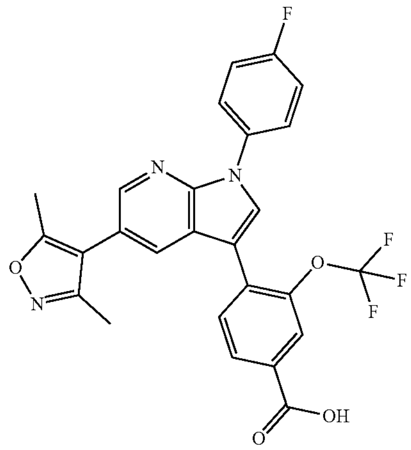 [SMILES: Cc1noc(C)c1-c1cnc2c(c1)c(-c1ccc(C(=O)O)cc1OC(F)(F)F)cn2-c1ccc(F)cc1] |

-continued
| P# | Structure |
|---|---|
| P-0280 | 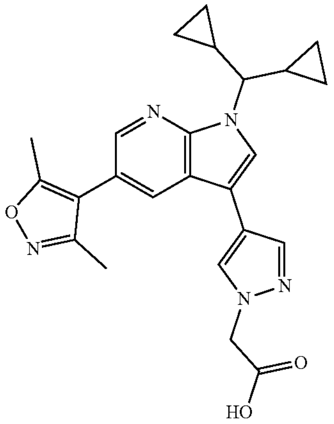 [SMILES: Cc1noc(C)c1-c1cnc2c(c1)c(-c1cnn(CC(=O)O)c1)cn2C(C1CC1)C1CC1] |
| P-0281 | 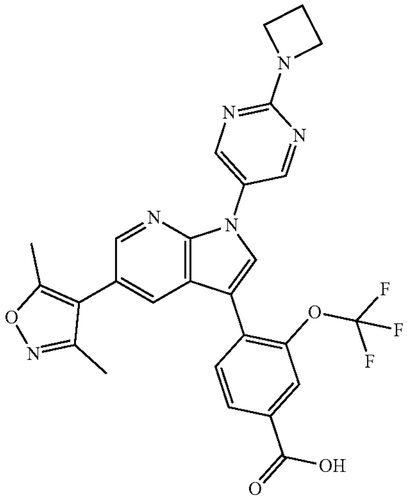 [SMILES: Cc1noc(C)c1-c1cnc2c(c1)c(-c1ccc(C(=O)O)cc1OC(F)(F)F)cn2-c1cnc(N2CCC2)nc1] |
| P-0282 | 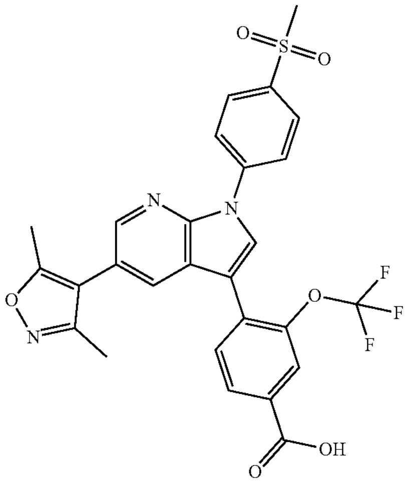 [SMILES: Cc1noc(C)c1-c1cnc2c(c1)c(-c1ccc(C(=O)O)cc1OC(F)(F)F)cn2-c1ccc(S(C)(=O)=O)cc1] |
-continued
| P# | Structure |
|---|---|
| P-0283 | 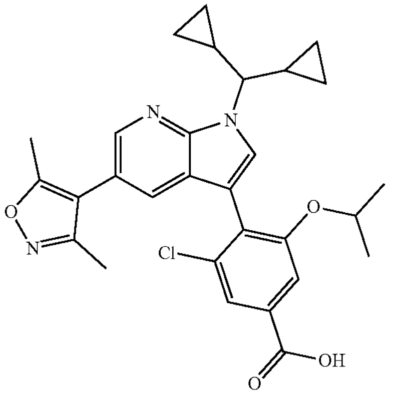 [SMILES: Cc1noc(C)c1-c1cnc2c(c1)c(-c1c(Cl)cc(C(=O)O)cc1OC(C)C)cn2C(C1CC1)C1CC1] |
| P-0284 | 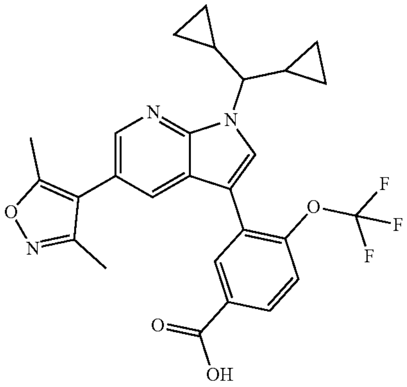 [SMILES: Cc1noc(C)c1-c1cnc2c(c1)c(-c1cc(C(=O)O)ccc1OC(F)(F)F)cn2C(C1CC1)C1CC1] |
| P-0285 | 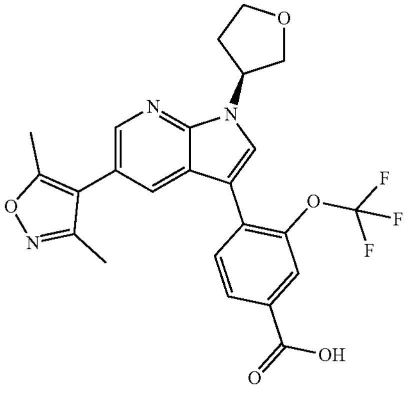 [SMILES: Cc1noc(C)c1-c1cnc2c(c1)c(-c1ccc(C(=O)O)cc1OC(F)(F)F)cn2[C@H]1CCOC1] |
| P-0286 | 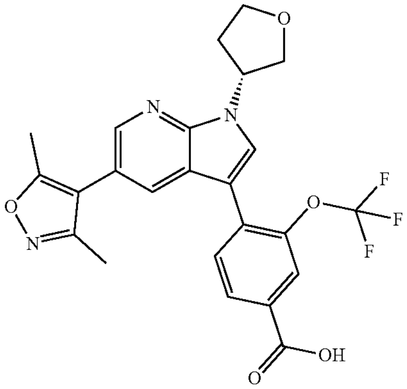 [SMILES: Cc1noc(C)c1-c1cnc2c(c1)c(-c1ccc(C(=O)O)cc1OC(F)(F)F)cn2[C@@H]1CCOC1] |

-continued
| P# | Structure |
|---|---|
| P-0287 | 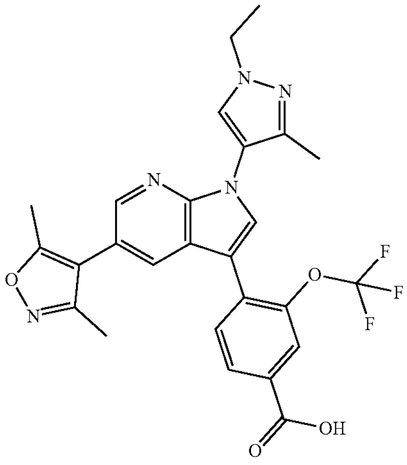 [SMILES: CCn1cc(-n2cc(-c3ccc(C(=O)O)cc3OC(F)(F)F)c3cc(-c4c(C)noc4C)cnc32)c(C)n1] |
| P-0288 | 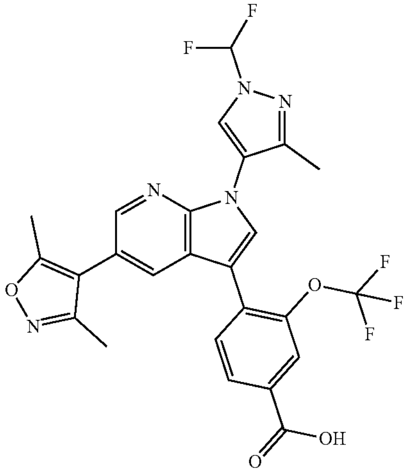 [SMILES: Cc1nn(C(F)F)cc1-n1cc(-c2ccc(C(=O)O)cc2OC(F)(F)F)c2cc(-c3c(C)noc3C)cnc21] |
| P-0289 | 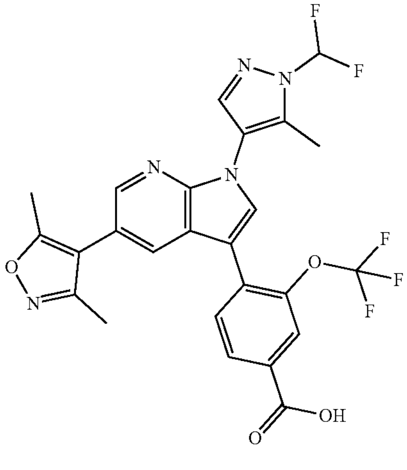 [SMILES: Cc1noc(C)c1-c1cnc2c(c1)c(-c1ccc(C(=O)O)cc1OC(F)(F)F)cn2-c1cnn(C(F)F)c1C] |
-continued
| P# | Structure |
|---|---|
| P-0290 | 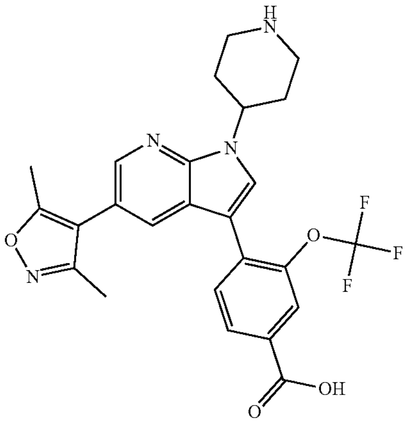 [SMILES: Cc1noc(C)c1-c1cnc2c(c1)c(-c1ccc(C(=O)O)cc1OC(F)(F)F)cn2C1CCNCC1] |
| P-0291 | 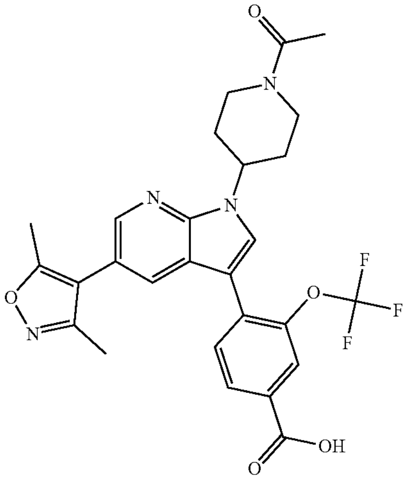 [SMILES: CC(=O)N1CCC(n2cc(-c3ccc(C(=O)O)cc3OC(F)(F)F)c3cc(-c4c(C)noc4C)cnc32)CC1] |
| P-0292 | 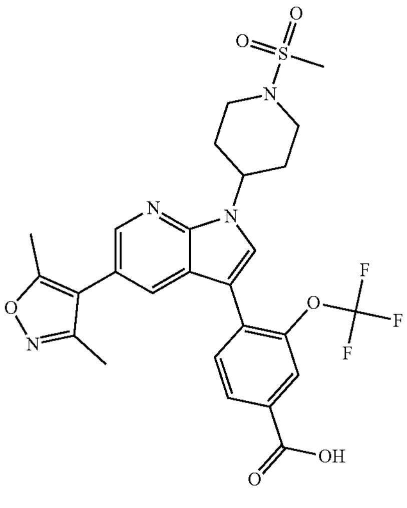 [SMILES: Cc1noc(C)c1-c1cnc2c(c1)c(-c1ccc(C(=O)O)cc1OC(F)(F)F)cn2C1CCN(S(C)(=O)=O)CC1] |

-continued
| P# | Structure |
|---|---|
| P-0293 | 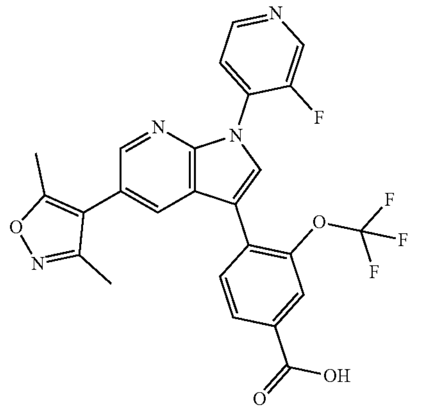 [SMILES: Cc1noc(C)c1-c1cnc2c(c1)c(-c1ccc(C(=O)O)cc1OC(F)(F)F)cn2-c1ccncc1F] |
| P-0294 | 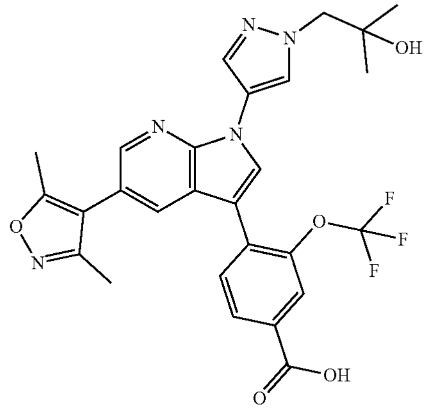 [SMILES: Cc1noc(C)c1-c1cnc2c(c1)c(-c1ccc(C(=O)O)cc1OC(F)(F)F)cn2-c1cnn(CC(C)(C)O)c1] |
| P-0295 | 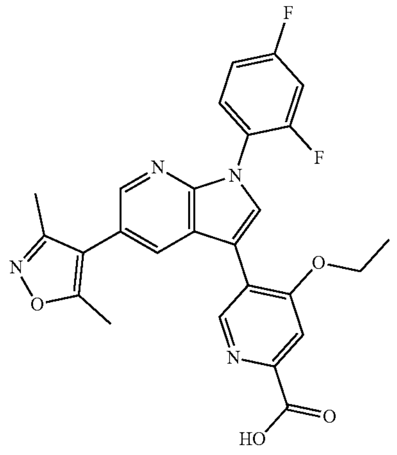 [SMILES: CCOc1cc(C(=O)O)ncc1-c1cn(-c2ccc(F)cc2F)c2ncc(-c3c(C)noc3C)cc12] |
-continued
| P# | Structure |
|---|---|
| P-0296 | 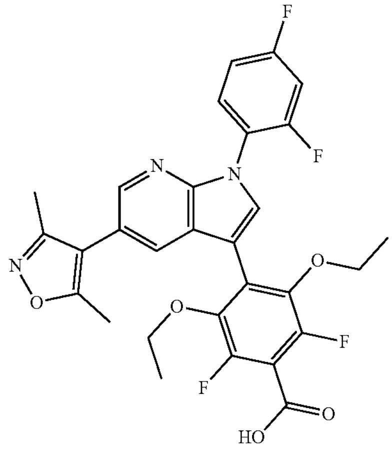 [SMILES: CCOc1c(F)c(C(=O)O)c(F)c(OCC)c1-c1cn(-c2ccc(F)cc2F)c2ncc(-c3c(C)noc3C)cc12] |
| P-0297 | 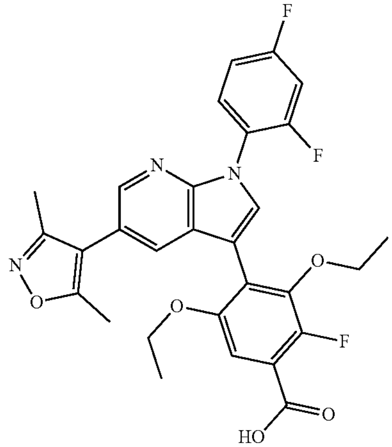 [SMILES: CCOc1cc(C(=O)O)c(F)c(OCC)c1-c1cn(-c2ccc(F)cc2F)c2ncc(-c3c(C)noc3C)cc12] |
| P-0298 | 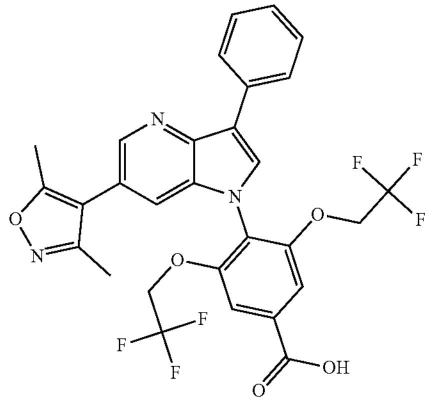 [SMILES: Cc1noc(C)c1-c1cnc2c(-c3ccccc3)cn(-c3c(OCC(F)(F)F)cc(C(=O)O)cc3OCC(F)(F)F)c2c1] |

-continued
| P# | Structure |
|---|---|
| P-0299 | 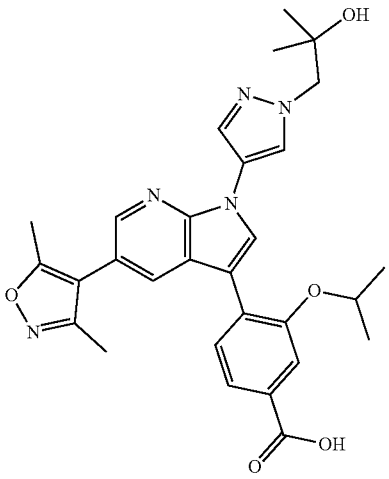 [SMILES: Cc1noc(C)c1-c1cnc2c(c1)c(-c1ccc(C(=O)O)cc1OC(C)C)cn2-c1cnn(CC(C)(C)O)c1] |
| P-0300 | 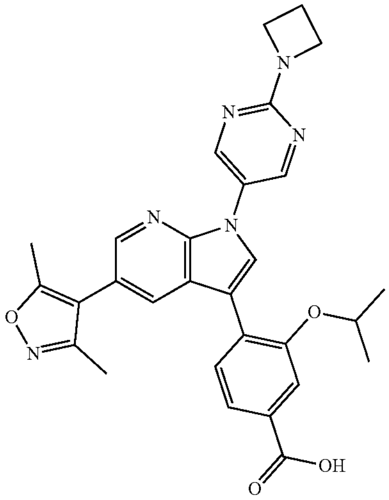 [SMILES: Cc1noc(C)c1-c1cnc2c(c1)c(-c1ccc(C(=O)O)cc1OC(C)C)cn2-c1cnc(N2CCC2)nc1] |
| P-0301 | 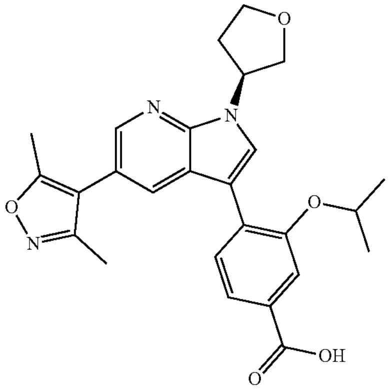 [SMILES: Cc1noc(C)c1-c1cnc2c(c1)c(-c1ccc(C(=O)O)cc1OC(C)C)cn2[C@H]1CCOC1] |
-continued
| P# | Structure |
|---|---|
| P-0302 | 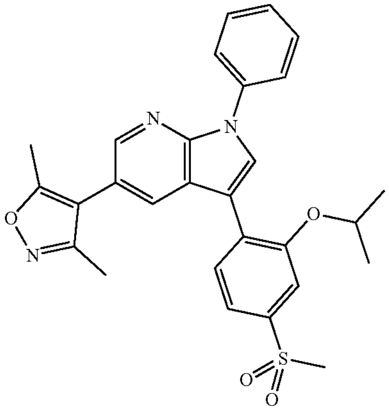 [SMILES: Cc1noc(C)c1-c1cnc2c(c1)c(-c1ccc(S(C)(=O)=O)cc1OC(C)C)cn2-c1ccccc1] |
| P-0303 | 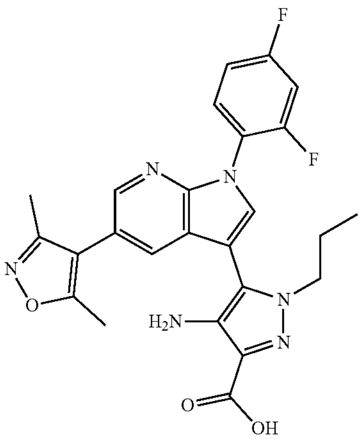 [SMILES: CCCn1nc(C(=O)O)c(N)c1-c1cn(-c2ccc(F)cc2F)c2ncc(-c3c(C)noc3C)cc12] |
| P-0304 | 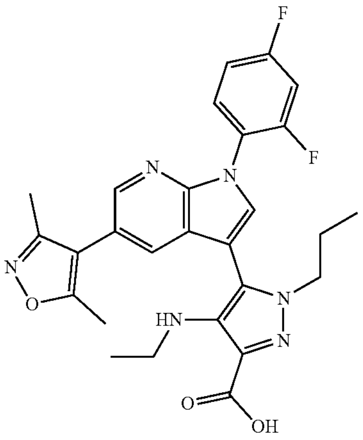 [SMILES: CCCn1nc(C(=O)O)c(NCC)c1-c1cn(-c2ccc(F)cc2F)c2ncc(-c3c(C)noc3C)cc12] |

-continued
| P# | Structure |
|---|---|
| P-0305 | 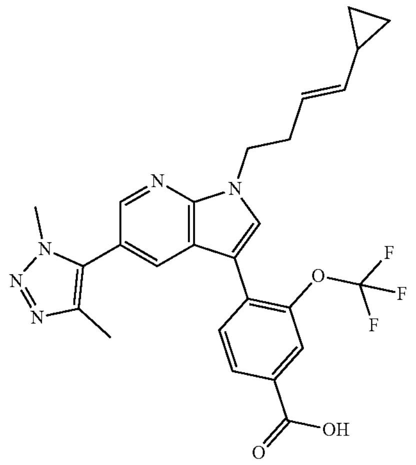 [SMILES: Cc1nnn(C)c1-c1cnc2c(c1)c(-c1ccc(C(=O)O)cc1OC(F)(F)F)cn2CC/C=C/C1CC1] |
| P-0306 | 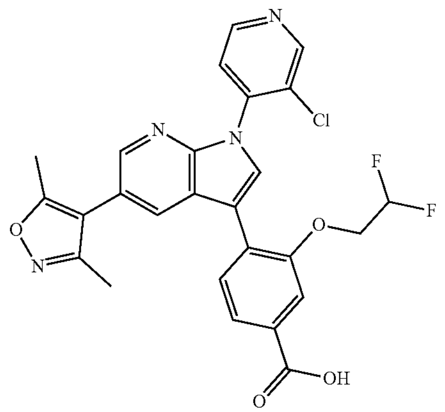 [SMILES: Cc1noc(C)c1-c1cnc2c(c1)c(-c1ccc(C(=O)O)cc1OCC(F)F)cn2-c1ccncc1Cl] |
| P-0307 | 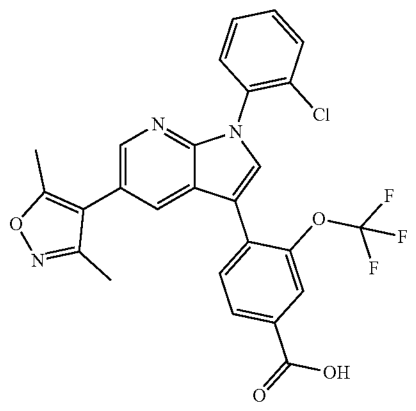 [SMILES: Cc1noc(C)c1-c1cnc2c(c1)c(-c1ccc(C(=O)O)cc1OC(F)(F)F)cn2-c1ccccc1Cl] |
-continued
| P# | Structure |
|---|---|
| P-0308 | 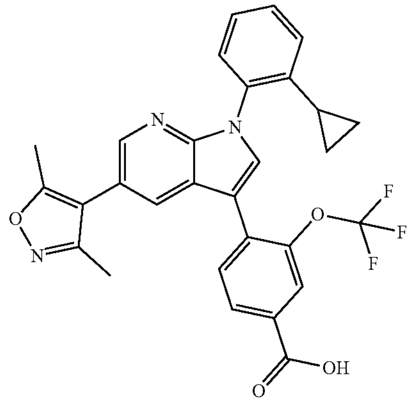 [SMILES: Cc1noc(C)c1-c1cnc2c(c1)c(-c1ccc(C(=O)O)cc1OC(F)(F)F)cn2-c1ccccc1C1CC1] |
| P-0309 | 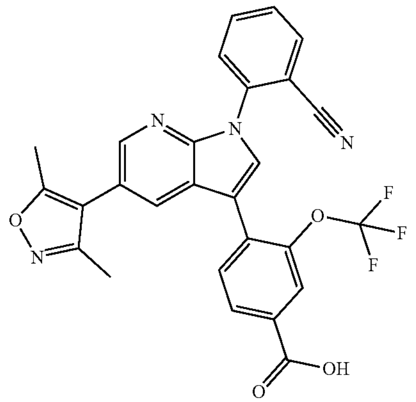 [SMILES: Cc1noc(C)c1-c1cnc2c(c1)c(-c1ccc(C(=O)O)cc1OC(F)(F)F)cn2-c1ccccc1C#N] |
| P-0310 | 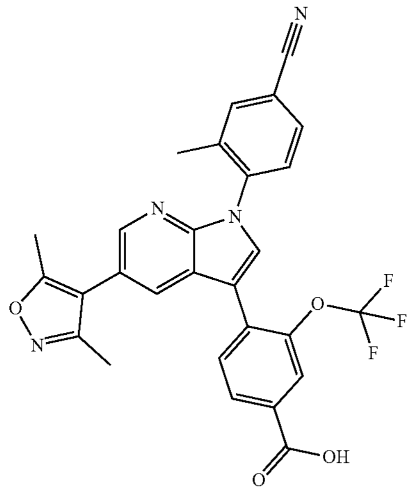 [SMILES: Cc1cc(C#N)ccc1-n1cc(-c2ccc(C(=O)O)cc2OC(F)(F)F)c2cc(-c3c(C)noc3C)cnc21] |

-continued
| P# | Structure |
| --- | --- |
| P-0311 | 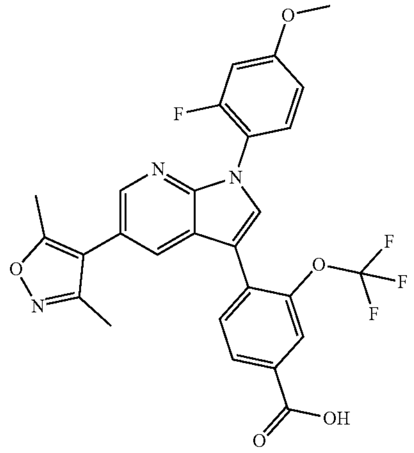 [SMILES: COc1ccc(-n2cc(-c3ccc(C(=O)O)cc3OC(F)(F)F)c3cc(-c4c(C)noc4C)cnc32)c(F)c1] |
| P-0312 | 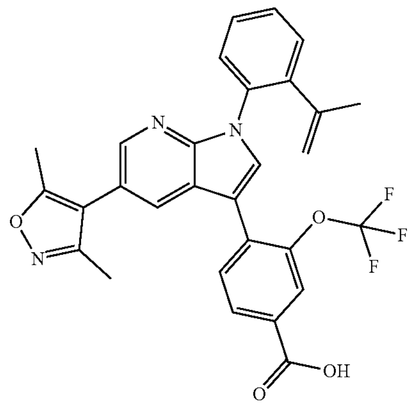 [SMILES: C=C(C)c1ccccc1-n1cc(-c2ccc(C(=O)O)cc2OC(F)(F)F)c2cc(-c3c(C)noc3C)cnc21] |
| P-0313 | 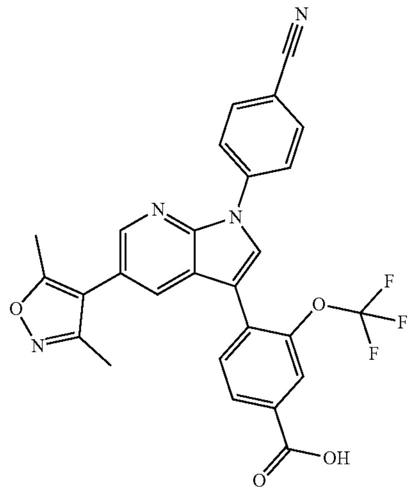 [SMILES: Cc1noc(C)c1-c1cnc2c(c1)c(-c1ccc(C(=O)O)cc1OC(F)(F)F)cn2-c1ccc(C#N)cc1] |
-continued
| P# | Structure |
| --- | --- |
| P-0314 | 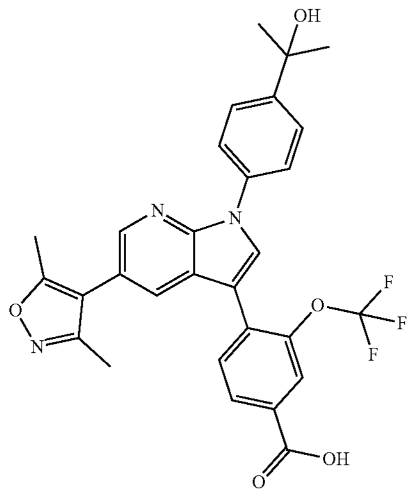 [SMILES: Cc1noc(C)c1-c1cnc2c(c1)c(-c1ccc(C(=O)O)cc1OC(F)(F)F)cn2-c1ccc(C(C)(C)O)cc1] |
| P-0315 | 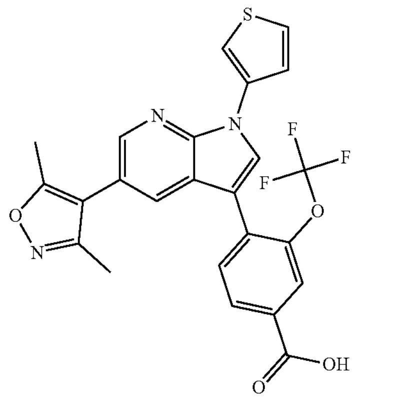 [SMILES: Cc1noc(C)c1-c1cnc2c(c1)c(-c1ccc(C(=O)O)cc1OC(F)(F)F)cn2-c1ccsc1] |
| P-0316 | 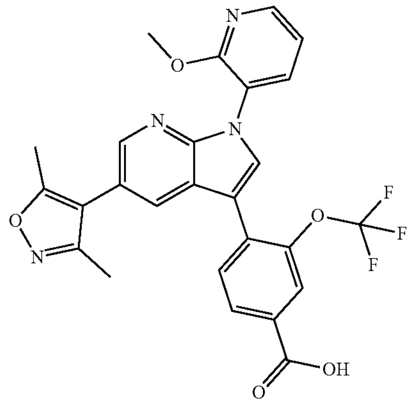 [SMILES: COc1ncccc1-n1cc(-c2ccc(C(=O)O)cc2OC(F)(F)F)c2cc(-c3c(C)noc3C)cnc21]

-continued
| P# | Structure |
|---|---|
| P-0317 | 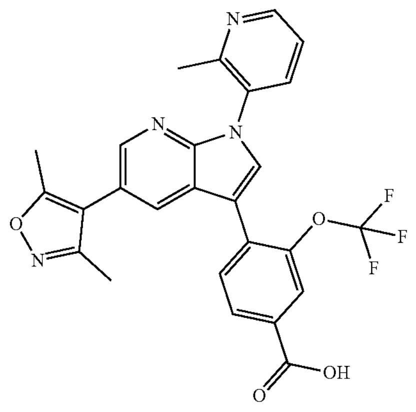 [SMILES: Cc1ncccc1-n1cc(-c2ccc(C(=O)O)cc2OC(F)(F)F)c2cc(-c3c(C)noc3C)cnc21] |
| P-0318 | 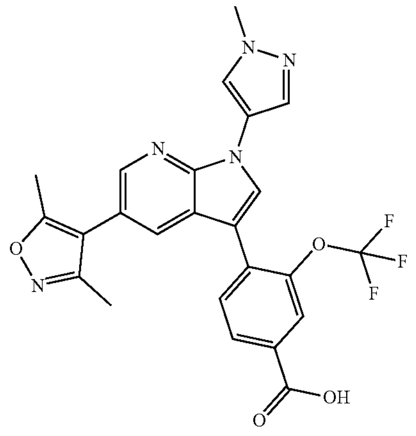 [SMILES: Cc1noc(C)c1-c1cnc2c(c1)c(-c1ccc(C(=O)O)cc1OC(F)(F)F)cn2-c1cnn(C)c1] |
| P-0319 | 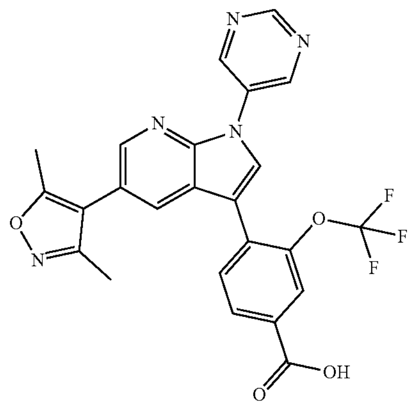 [SMILES: Cc1noc(C)c1-c1cnc2c(c1)c(-c1ccc(C(=O)O)cc1OC(F)(F)F)cn2-c1cncnc1] |
-continued
| P# | Structure |
|---|---|
| P-0320 | 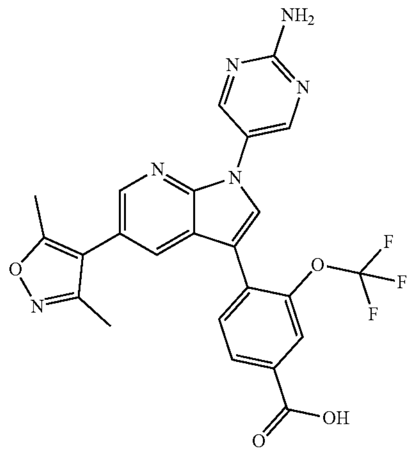 [SMILES: Cc1noc(C)c1-c1cnc2c(c1)c(-c1ccc(C(=O)O)cc1OC(F)(F)F)cn2-c1cnc(N)nc1] |
| P-0321 | 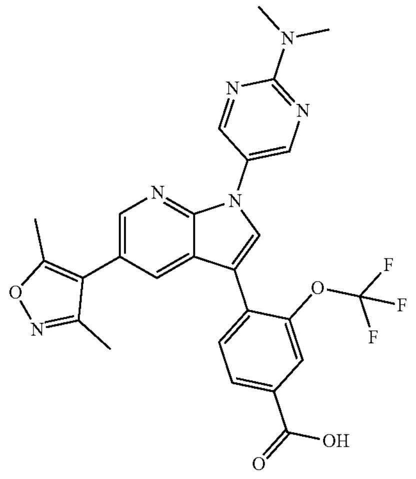 [SMILES: Cc1noc(C)c1-c1cnc2c(c1)c(-c1ccc(C(=O)O)cc1OC(F)(F)F)cn2-c1cnc(N(C)C)nc1] |
| P-0322 | 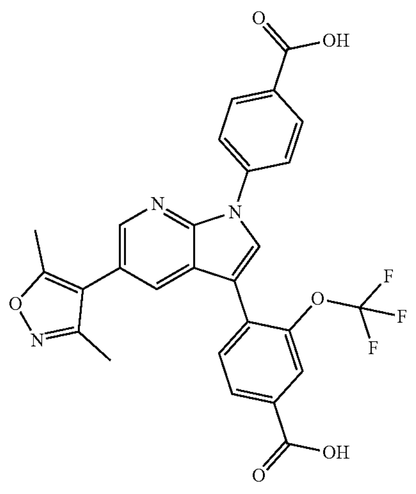 [SMILES: Cc1noc(C)c1-c1cnc2c(c1)c(-c1ccc(C(=O)O)cc1OC(F)(F)F)cn2-c1ccc(C(=O)O)cc1] |

-continued
| P# | Structure |
|---|---|
| P-0323 | 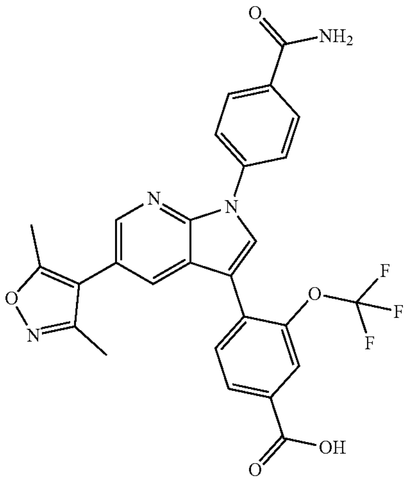 [SMILES: Cc1noc(C)c1-c1cnc2c(c1)c(-c1ccc(C(=O)O)cc1OC(F)(F)F)cn2-c1ccc(C(N)=O)cc1] |
| P-0324 | 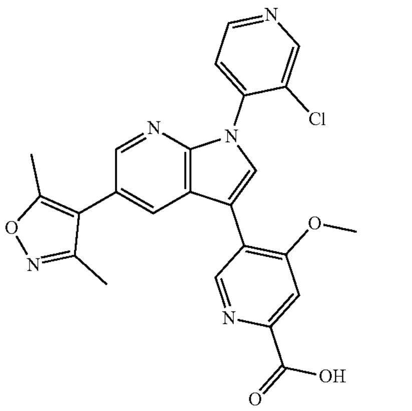 [SMILES: COc1cc(C(=O)O)ncc1-c1cn(-c2ccncc2Cl)c2ncc(-c3c(C)noc3C)cc12] |
| P-0325 | 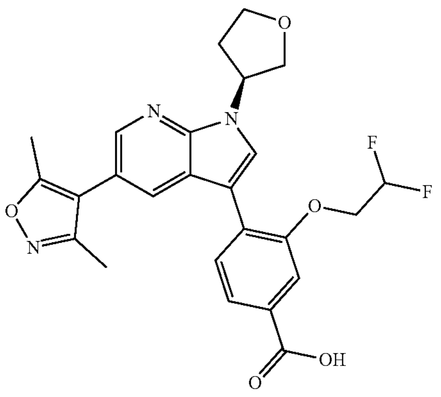 [SMILES: Cc1noc(C)c1-c1cnc2c(c1)c(-c1ccc(C(=O)O)cc1OCC(F)F)cn2[C@H]1CCOC1] |
-continued
| P# | Structure |
|---|---|
| P-0326 | 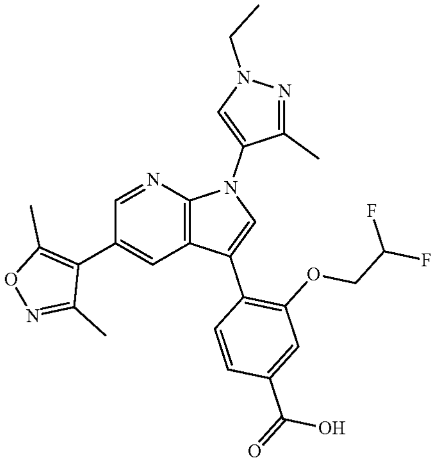 [SMILES: CCn1cc(-n2cc(-c3ccc(C(=O)O)cc3OCC(F)F)c3cc(-c4c(C)noc4C)cnc32)c(C)n1] |
| P-0327 | 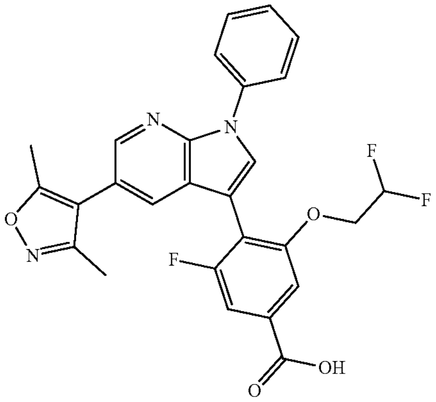 [SMILES: Cc1noc(C)c1-c1cnc2c(c1)c(-c1c(F)cc(C(=O)O)cc1OCC(F)F)cn2-c1ccccc1] |
| P-0328 | 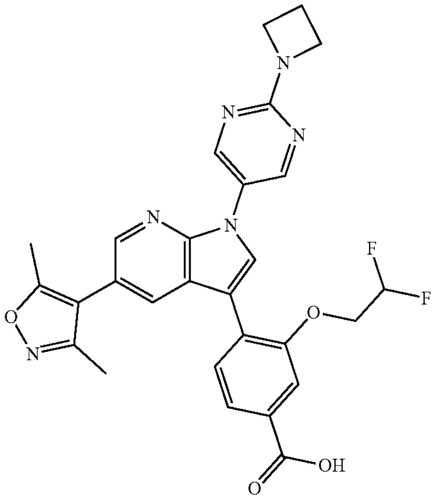 [SMILES: Cc1noc(C)c1-c1cnc2c(c1)c(-c1ccc(C(=O)O)cc1OCC(F)F)cn2-c1cnc(N2CCC2)nc1] |

-continued
| P# | Structure |
|---|---|
| P-0329 | 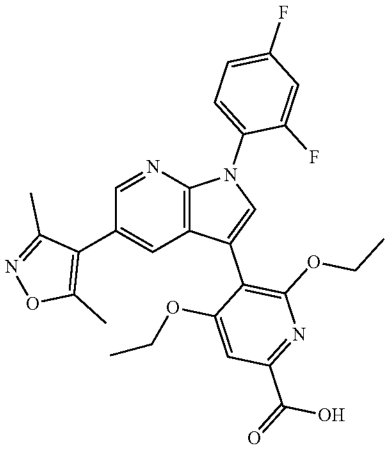 [SMILES: CCOc1cc(C(=O)O)nc(OCC)c1-c1cn(-c2ccc(F)cc2F)c2ncc(-c3c(C)noc3C)cc12] |
| P-0330 | 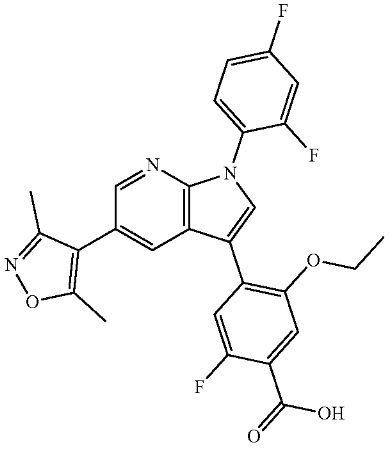 [SMILES: CCOc1cc(C(=O)O)c(F)cc1-c1cn(-c2ccc(F)cc2F)c2ncc(-c3c(C)noc3C)cc12] |
| P-0331 | 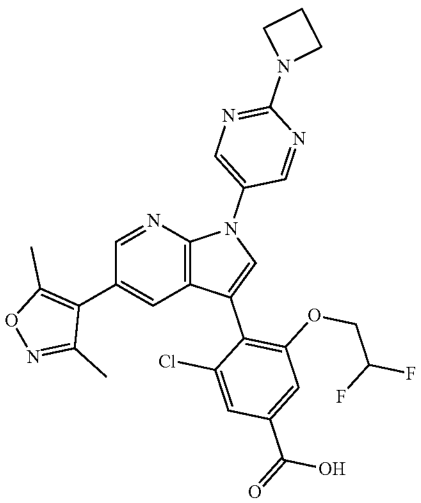 [SMILES: Cc1noc(C)c1-c1cnc2c(c1)c(-c1c(Cl)cc(C(=O)O)cc1OCC(F)F)cn2-c1cnc(N2CCC2)nc1] |
-continued
| P# | Structure |
|---|---|
| P-0332 | 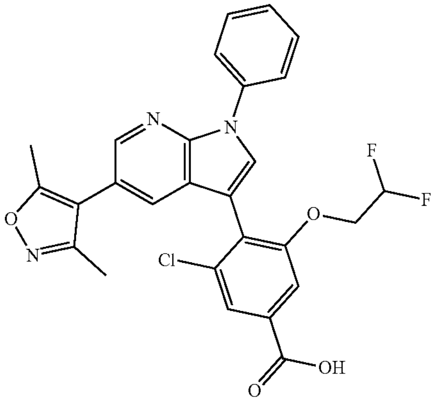 [SMILES: Cc1noc(C)c1-c1cnc2c(c1)c(-c1c(Cl)cc(C(=O)O)cc1OCC(F)F)cn2-c1ccccc1] |
| P-0333 | 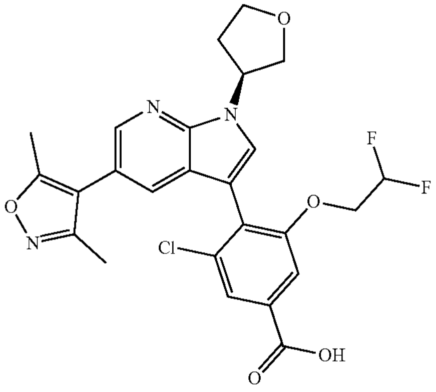 [SMILES: Cc1noc(C)c1-c1cnc2c(c1)c(-c1c(Cl)cc(C(=O)O)cc1OCC(F)F)cn2[C@H]1CCOC1] |
| P-0334 | 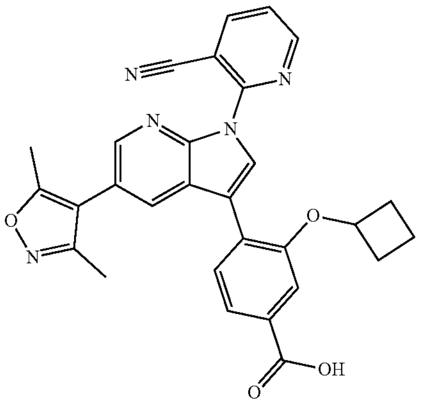 [SMILES: Cc1noc(C)c1-c1cnc2c(c1)c(-c1ccc(C(=O)O)cc1OC1CCC1)cn2-c1ncccc1C#N] |

-continued
| P# | Structure |
|---|---|
| P-0335 | 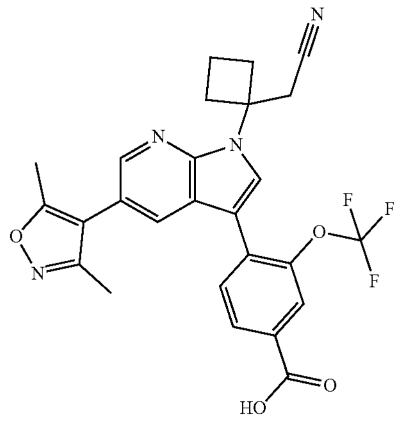 [SMILES: Cc1noc(C)c1-c1cnc2c(c1)c(-c1ccc(C(=O)O)cc1OC(F)(F)F)cn2C1(CC#N)CCC1] |
| P-0336 | 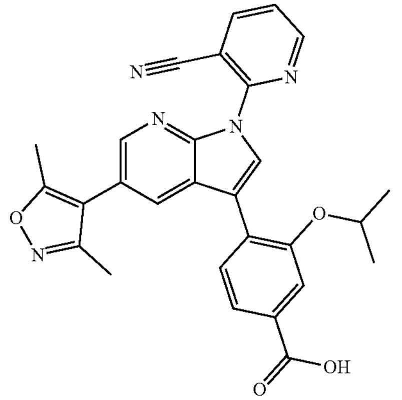 [SMILES: Cc1noc(C)c1-c1cnc2c(c1)c(-c1ccc(C(=O)O)cc1OC(C)C)cn2-c1ncccc1C#N] |
| P-0337 | 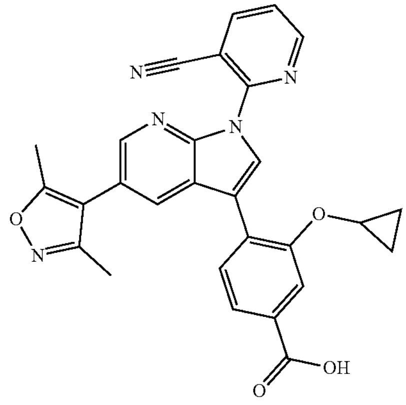 [SMILES: Cc1noc(C)c1-c1cnc2c(c1)c(-c1ccc(C(=O)O)cc1OC1CC1)cn2-c1ncccc1C#N] |
-continued
| P# | Structure |
|---|---|
| P-0338 | 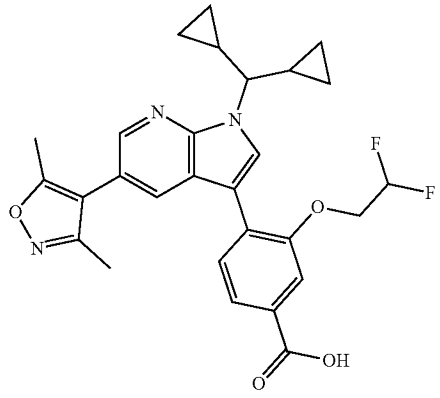 [SMILES: Cc1noc(C)c1-c1cnc2c(c1)c(-c1ccc(C(=O)O)cc1OCC(F)F)cn2C(C1CC1)C1CC1] |
| P-0339 | 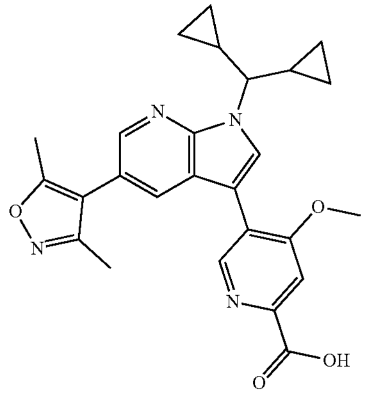 [SMILES: COc1cc(C(=O)O)ncc1-c1cn(C(C2CC2)C2CC2)c2ncc(-c3c(C)noc3C)cc12] |
| P-0340 | 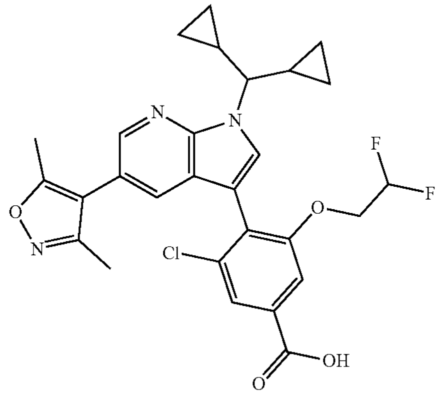 [SMILES: Cc1noc(C)c1-c1cnc2c(c1)c(-c1c(Cl)cc(C(=O)O)cc1OCC(F)F)cn2C(C1CC1)C1CC1] |
| P-0341 | 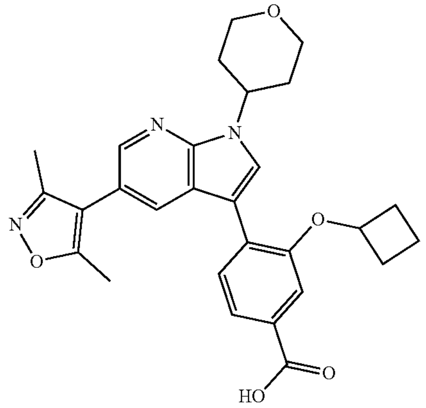 [SMILES: Cc1noc(C)c1-c1cnc2c(c1)c(-c1ccc(C(=O)O)cc1OC1CCC1)cn2C1CCOCC1] |

-continued
| P# | Structure |
|---|---|
| P-0342 | 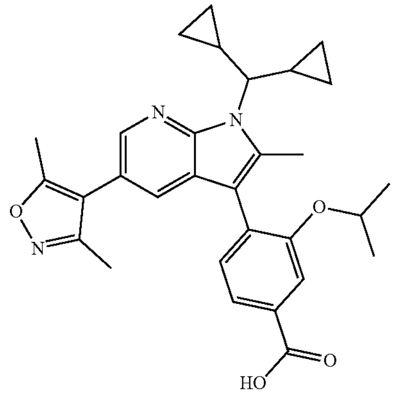 [SMILES: Cc1noc(C)c1-c1cnc2c(c1)c(-c1ccc(C(=O)O)cc1OC(C)C)c(C)n2C(C1CC1)C1CC1] |
| P-0343 | 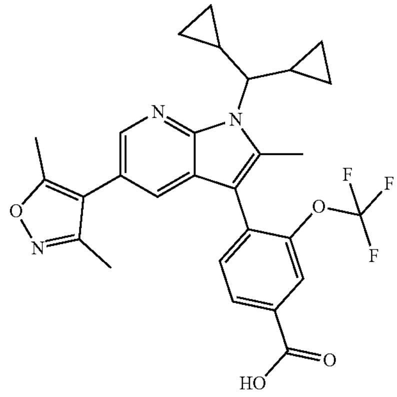 [SMILES: Cc1noc(C)c1-c1cnc2c(c1)c(-c1ccc(C(=O)O)cc1OC(F)(F)F)c(C)n2C(C1CC1)C1CC1] |
| P-0344 | 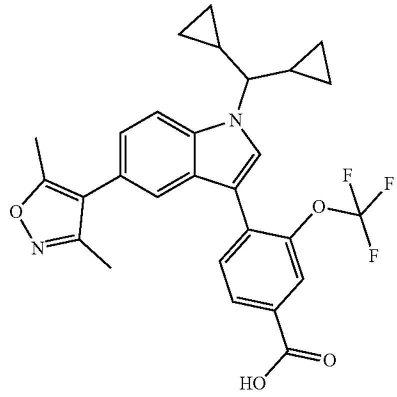 [SMILES: Cc1noc(C)c1-c1ccc2c(c1)c(-c1ccc(C(=O)O)cc1OC(F)(F)F)cn2C(C1CC1)C1CC1] |
-continued
| P# | Structure |
|---|---|
| P-0345 | 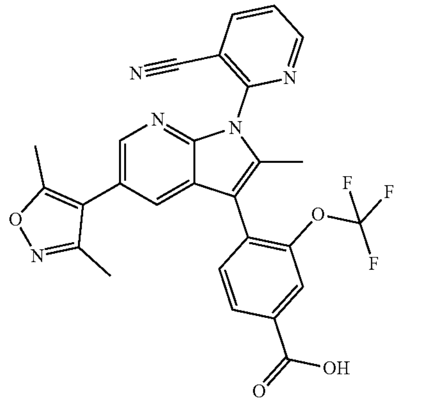 [SMILES: Cc1noc(C)c1-c1cnc2c(c1)c(-c1ccc(C(=O)O)cc1OC(F)(F)F)c(C)n2-c1ncccc1C#N] |
| P-0346 | 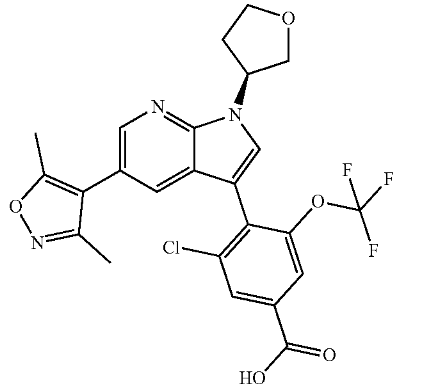 [SMILES: Cc1noc(C)c1-c1cnc2c(c1)c(-c1c(Cl)cc(C(=O)O)cc1OC(F)(F)F)cn2[C@H]1CCOC1] |
| P-0347 | 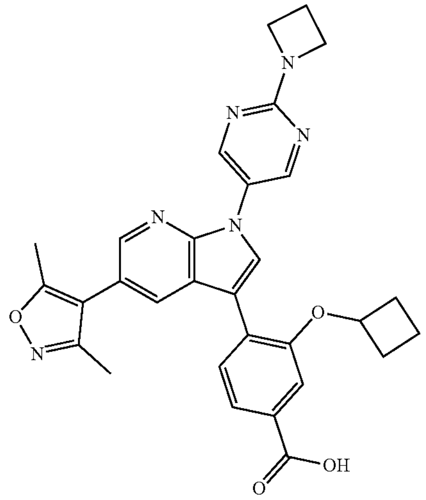 [SMILES: Cc1noc(C)c1-c1cnc2c(c1)c(-c1ccc(C(=O)O)cc1OC1CCC1)cn2-c1cnc(N2CCC2)nc1] |

-continued
| P# | Structure |
|---|---|
| P-0348 | 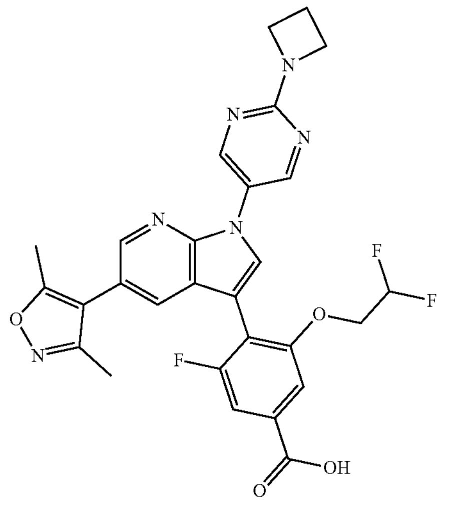 [SMILES: Cc1noc(C)c1-c1cnc2c(c1)c(-c1c(F)cc(C(=O)O)cc1OCC(F)F)cn2-c1cnc(N2CCC2)nc1] |
| P-0349 | 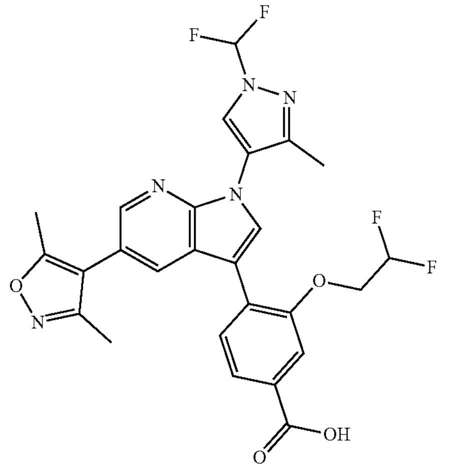 [SMILES: Cc1nn(C(F)F)cc1-n1cc(-c2ccc(C(=O)O)cc2OCC(F)F)c2cc(-c3c(C)noc3C)cnc21] |
| P-0350 | 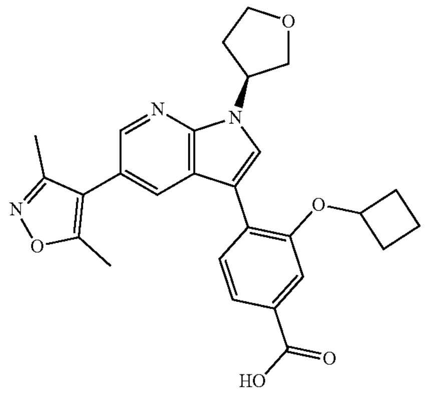 [SMILES: Cc1noc(C)c1-c1cnc2c(c1)c(-c1ccc(C(=O)O)cc1OC1CCC1)cn2[C@H]1CCOC1] |
-continued
| P# | Structure |
|---|---|
| P-0351 | 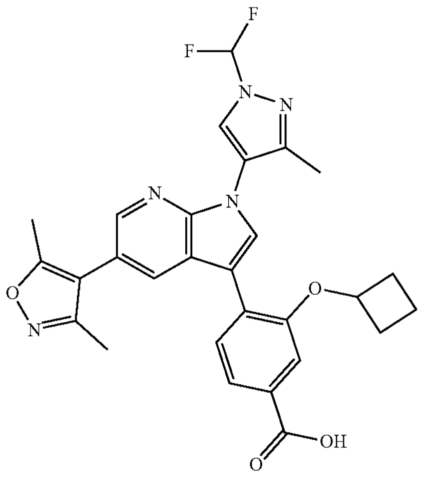 [SMILES: Cc1nn(C(F)F)cc1-n1cc(-c2ccc(C(=O)O)cc2OC2CCC2)c2cc(-c3c(C)noc3C)cnc21] |
| P-0352 | 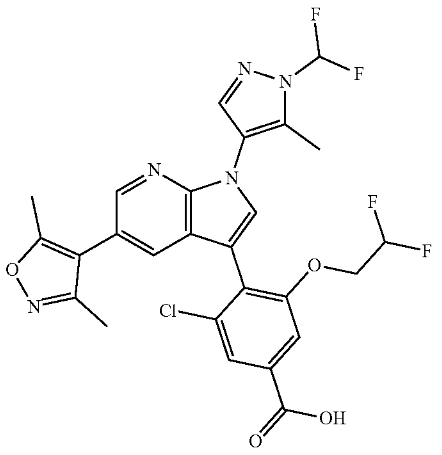 [SMILES: Cc1noc(C)c1-c1cnc2c(c1)c(-c1c(Cl)cc(C(=O)O)cc1OCC(F)F)cn2-c1cnn(C(F)F)c1C] |
| P-0353 | 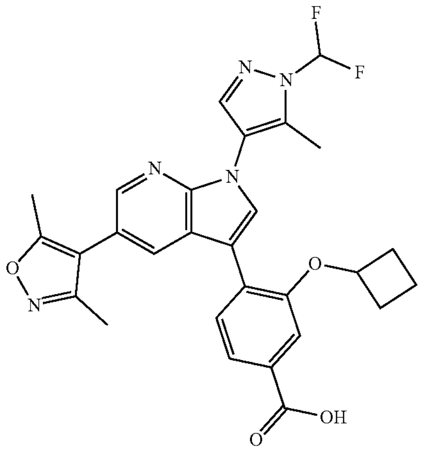 [SMILES: Cc1noc(C)c1-c1cnc2c(c1)c(-c1ccc(C(=O)O)cc1OC1CCC1)cn2-c1cnn(C(F)F)c1C] |

-continued
| P# | Structure |
|---|---|
| P-0354 | 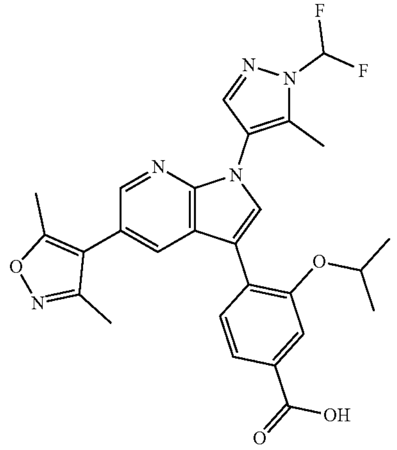 [SMILES: Cc1noc(C)c1-c1cnc2c(c1)c(-c1ccc(C(=O)O)cc1OC(C)C)cn2-c1cnn(C(F)F)c1C] |
| P-0355 | 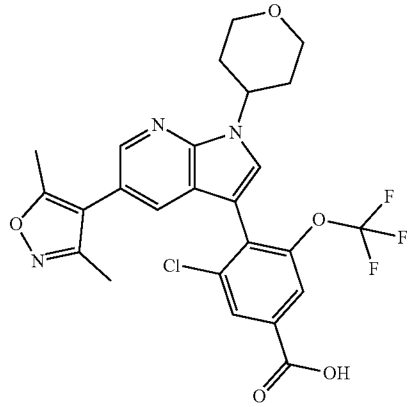 [SMILES: Cc1noc(C)c1-c1cnc2c(c1)c(-c1c(Cl)cc(C(=O)O)cc1OC(F)(F)F)cn2C1CCOCC1] |
| P-0356 | 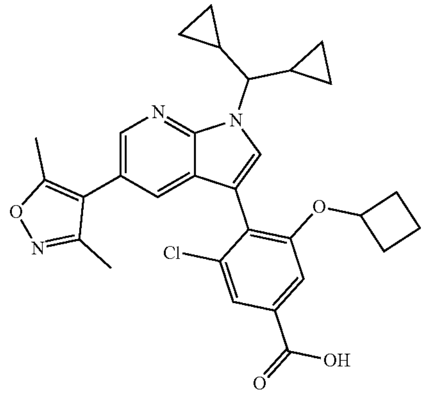 [SMILES: Cc1noc(C)c1-c1cnc2c(c1)c(-c1c(Cl)cc(C(=O)O)cc1OC1CCC1)cn2C(C1CC1)C1CC1] |
| P-0357 | 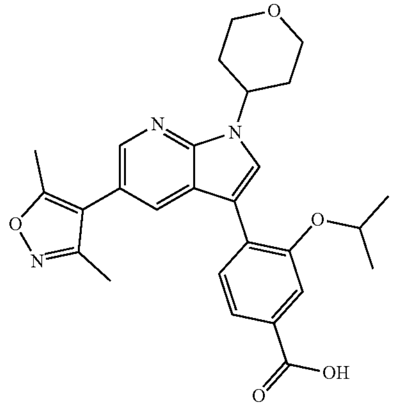 [SMILES: Cc1noc(C)c1-c1cnc2c(c1)c(-c1ccc(C(=O)O)cc1OC(C)C)cn2C1CCOCC1] |
| P-0358 | 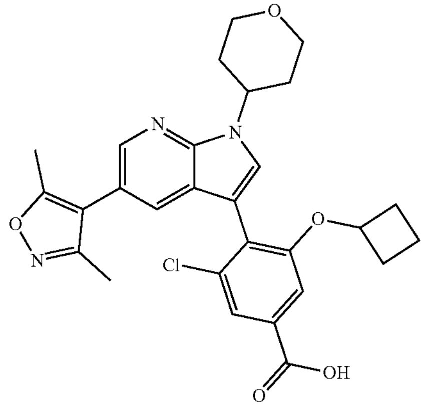 [SMILES: Cc1noc(C)c1-c1cnc2c(c1)c(-c1c(Cl)cc(C(=O)O)cc1OC1CCC1)cn2C1CCOCC1] |
| P-0359 | 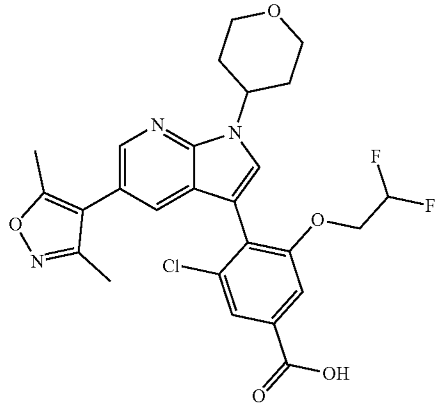 [SMILES: Cc1noc(C)c1-c1cnc2c(c1)c(-c1c(Cl)cc(C(=O)O)cc1OCC(F)F)cn2C1CCOCC1] |

-continued
| P# | Structure |
|---|---|
| P-0360 | 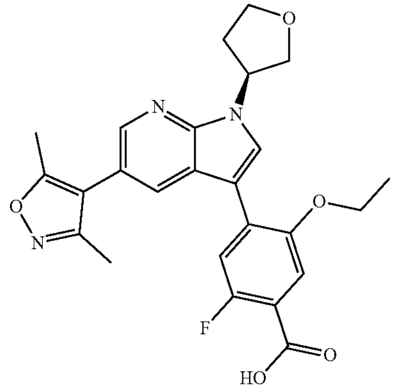 [SMILES: CCOc1cc(C(=O)O)c(F)cc1-c1cn([C@H]2CCOC2)c2ncc(-c3c(C)noc3C)cc12] |
| P-0361 | 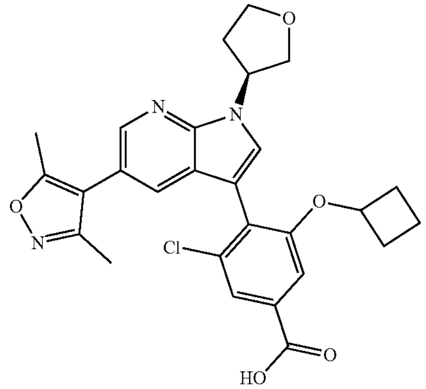 [SMILES: Cc1noc(C)c1-c1cnc2c(c1)c(-c1c(Cl)cc(C(=O)O)cc1OC1CCC1)cn2[C@H]1CCOC1] |
| P-0362 | 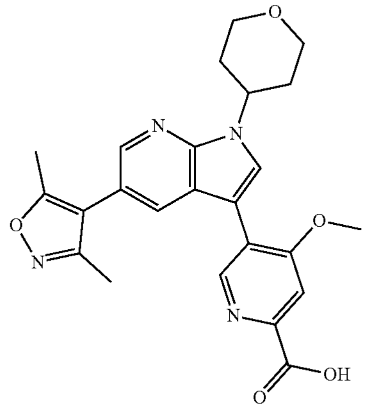 [SMILES: COc1cc(C(=O)O)ncc1-c1cn(C2CCOCC2)c2ncc(-c3c(C)noc3C)cc12] |
| P-0363 | 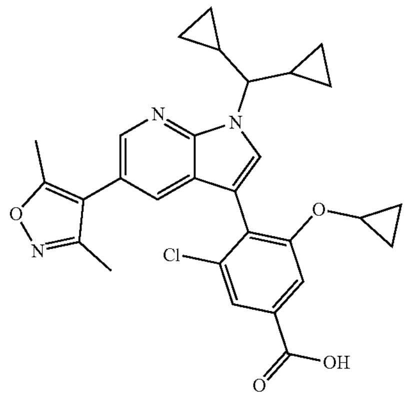 [SMILES: Cc1noc(C)c1-c1cnc2c(c1)c(-c1c(Cl)cc(C(=O)O)cc1OC1CC1)cn2C(C1CC1)C1CC1] |
-continued
| P# | Structure |
|---|---|
| P-0364 | 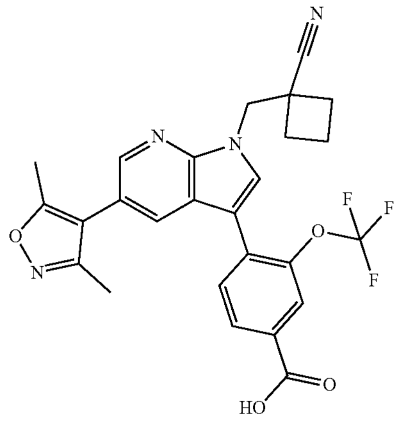 [SMILES: Cc1noc(C)c1-c1cnc2c(c1)c(-c1ccc(C(=O)O)cc1OC(F)(F)F)cn2CC1(C#N)CCC1] |
| P-0365 | 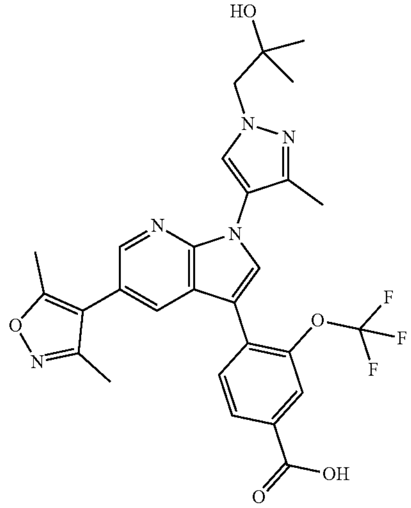 [SMILES: Cc1nn(CC(C)(C)O)cc1-n1cc(-c2ccc(C(=O)O)cc2OC(F)(F)F)c2cc(-c3c(C)noc3C)cnc21] |
| P-0366 | 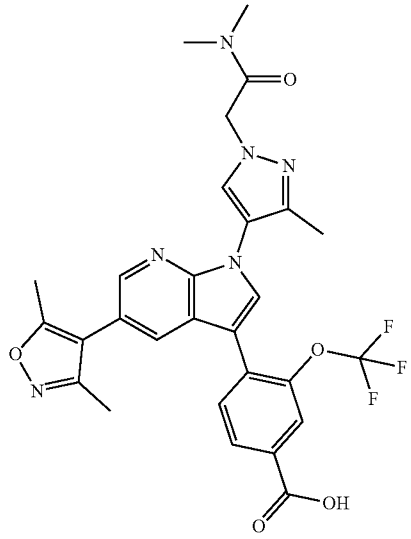 [SMILES: Cc1nn(CC(=O)N(C)C)cc1-n1cc(-c2ccc(C(=O)O)cc2OC(F)(F)F)c2cc(-c3c(C)noc3C)cnc21] |

| P# | Structure |
|---|---|
| P-0367 | 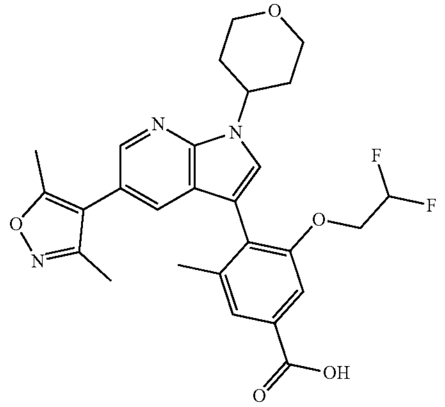 [SMILES: Cc1cc(C(=O)O)cc(OCC(F)F)c1-c1cn(C2CCOCC2)c2ncc(-c3c(C)noc3C)cc12] |
| P-0368 | 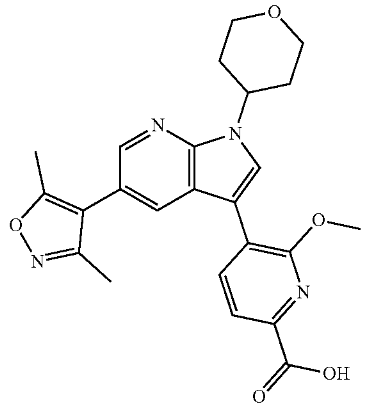 [SMILES: COc1nc(C(=O)O)ccc1-c1cn(C2CCOCC2)c2ncc(-c3c(C)noc3C)cc12] |
| P-0369 | 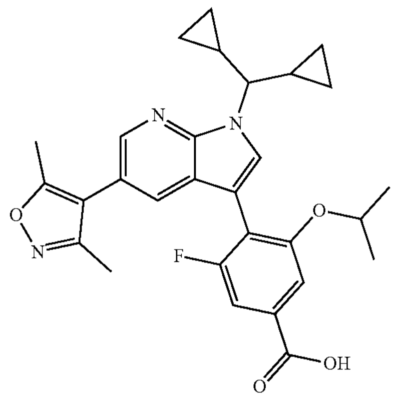 [SMILES: Cc1noc(C)c1-c1cnc2c(c1)c(-c1c(F)cc(C(=O)O)cc1OC(C)C)cn2C(C1CC1)C1CC1] |
| P# | Structure |
|---|---|
| P-0370 | 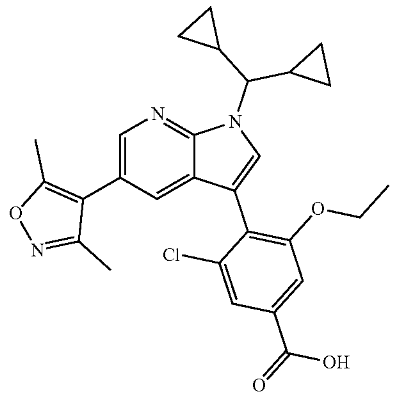 [SMILES: CCOc1cc(C(=O)O)cc(Cl)c1-c1cn(C(C2CC2)C2CC2)c2ncc(-c3c(C)noc3C)cc12] |
| P-0371 | 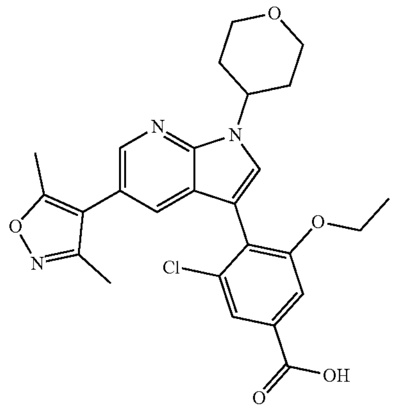 [SMILES: CCOc1cc(C(=O)O)cc(Cl)c1-c1cn(C2CCOCC2)c2ncc(-c3c(C)noc3C)cc12] |
| P-0372 | 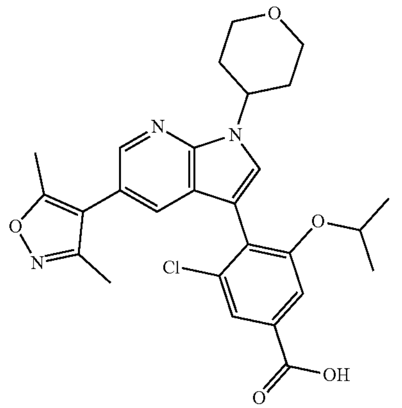 [SMILES: Cc1noc(C)c1-c1cnc2c(c1)c(-c1c(Cl)cc(C(=O)O)cc1OC(C)C)cn2C1CCOCC1] |

-continued
| P# | Structure |
|---|---|
| P-0373 | 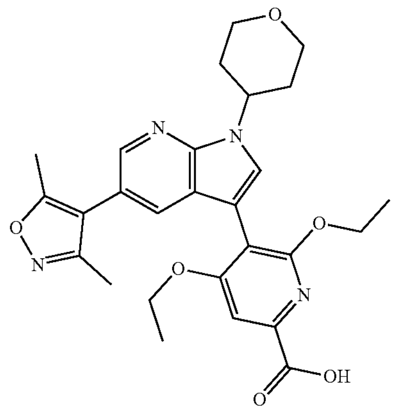 [SMILES: CCOc1cc(C(=O)O)nc(OCC)c1-c1cn(C2CCOCC2)c2ncc(-c3c(C)noc3C)cc12] |
| P-0374 | 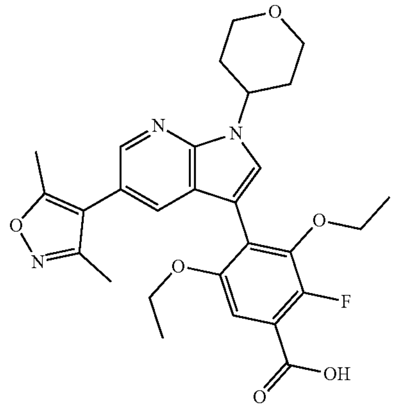 [SMILES: CCOc1cc(C(=O)O)c(F)c(OCC)c1-c1cn(C2CCOCC2)c2ncc(-c3c(C)noc3C)cc12] |
| P-0375 | 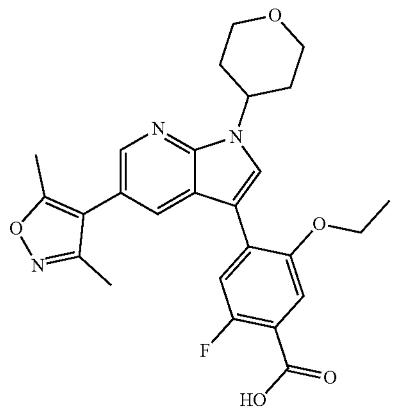 [SMILES: CCOc1cc(C(=O)O)c(F)cc1-c1cn(C2CCOCC2)c2ncc(-c3c(C)noc3C)cc12] |
-continued
| P# | Structure |
|---|---|
| P-0376 | 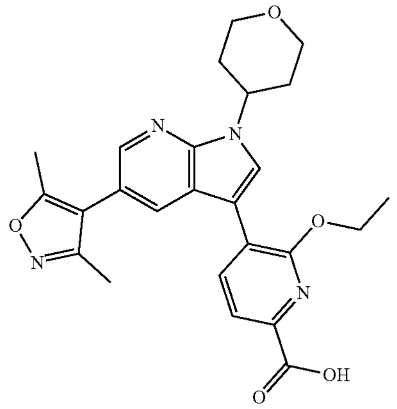 [SMILES: CCOc1nc(C(=O)O)ccc1-c1cn(C2CCOCC2)c2ncc(-c3c(C)noc3C)cc12] |
| P-0377 | 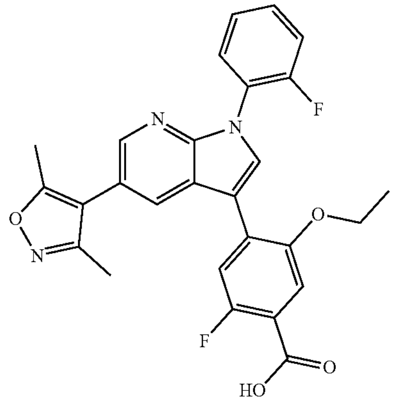 [SMILES: CCOc1cc(C(=O)O)c(F)cc1-c1cn(-c2ccccc2F)c2ncc(-c3c(C)noc3C)cc12] |
| P-0378 | 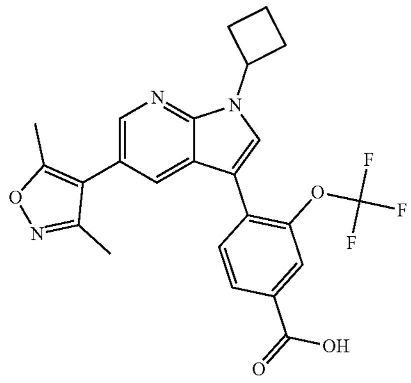 [SMILES: Cc1noc(C)c1-c1cnc2c(c1)c(-c1ccc(C(=O)O)cc1OC(F)(F)F)cn2C1CCC1] |
| P-0379 | 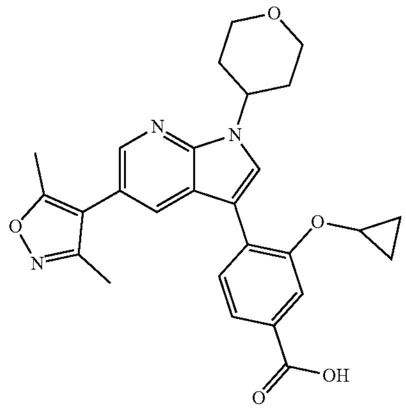 [SMILES: Cc1noc(C)c1-c1cnc2c(c1)c(-c1ccc(C(=O)O)cc1OC1CC1)cn2C1CCOCC1] |

-continued
| P# | Structure |
|---|---|
| P-0380 | 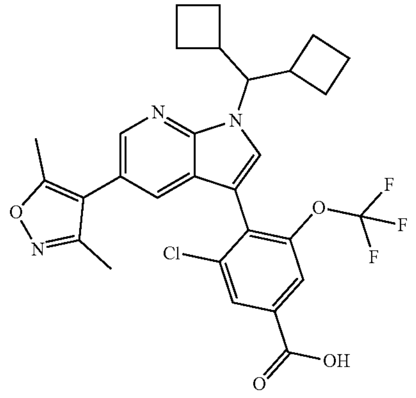 [SMILES: Cc1noc(C)c1-c1cnc2c(c1)c(-c1c(Cl)cc(C(=O)O)cc1OC(F)(F)F)cn2C(C1CCC1)C1CCC1] |
| P-0381 | 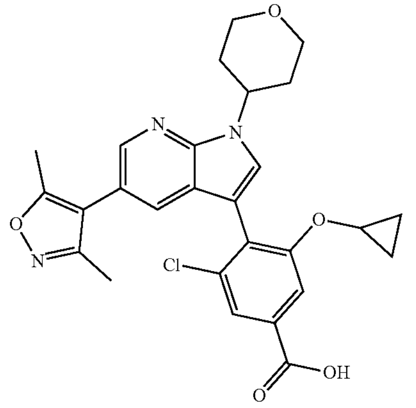 [SMILES: Cc1noc(C)c1-c1cnc2c(c1)c(-c1c(Cl)cc(C(=O)O)cc1OC1CC1)cn2C1CCOCC1] |
| P-0382 | 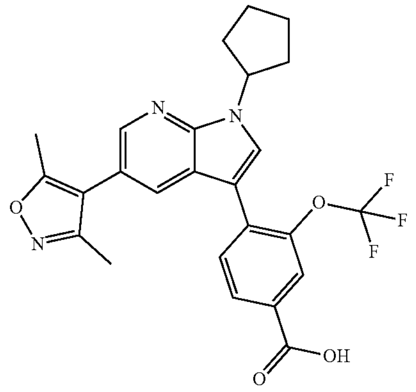 [SMILES: Cc1noc(C)c1-c1cnc2c(c1)c(-c1ccc(C(=O)O)cc1OC(F)(F)F)cn2C1CCCC1] |
-continued
| P# | Structure |
|---|---|
| P-0383 | 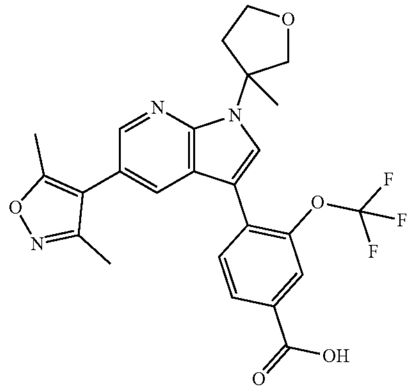 [SMILES: Cc1noc(C)c1-c1cnc2c(c1)c(-c1ccc(C(=O)O)cc1OC(F)(F)F)cn2C1(C)CCOC1] |
| P-0384 | 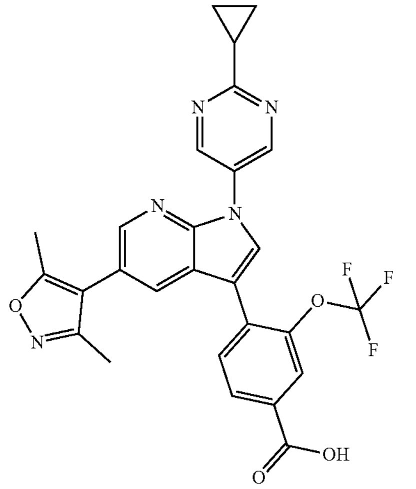 [SMILES: Cc1noc(C)c1-c1cnc2c(c1)c(-c1ccc(C(=O)O)cc1OC(F)(F)F)cn2-c1cnc(C2CC2)nc1] |
| P-0385 | 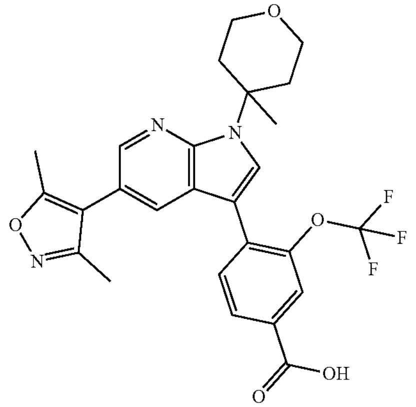 [SMILES: Cc1noc(C)c1-c1cnc2c(c1)c(-c1ccc(C(=O)O)cc1OC(F)(F)F)cn2C1(C)CCOCC1] |

-continued
| P# | Structure |
| --- | --- |
| P-0386 | 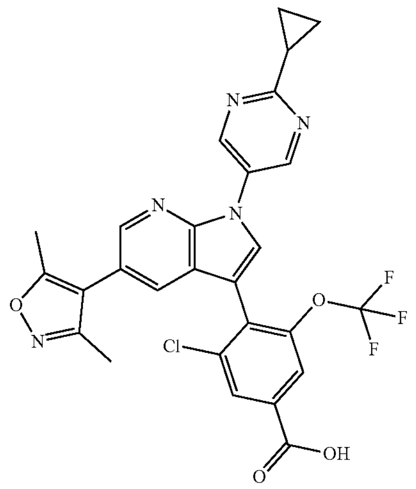 [SMILES: Cc1noc(C)c1-c1cnc2c(c1)c(-c1c(Cl)cc(C(=O)O)cc1OC(F)(F)F)cn2-c1cnc(C2CC2)nc1] |
| P-0387 | 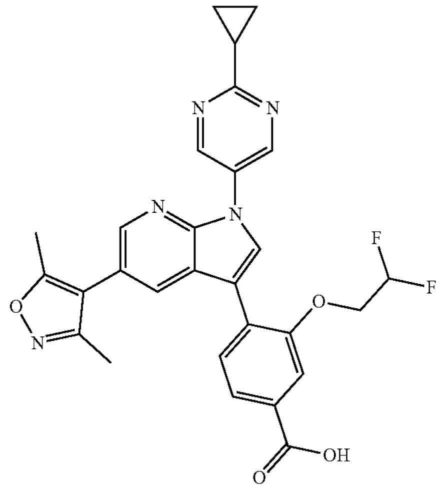 [SMILES: Cc1noc(C)c1-c1cnc2c(c1)c(-c1ccc(C(=O)O)cc1OCC(F)F)cn2-c1cnc(C2CC2)nc1] |
| P-0388 | 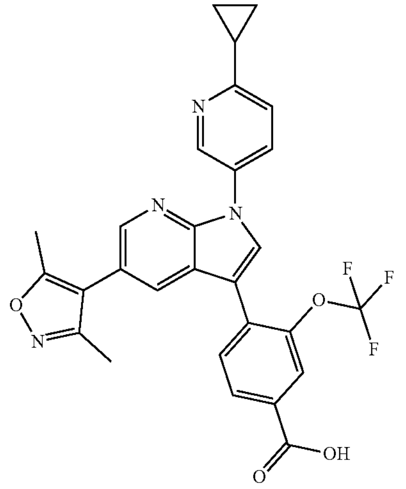 [SMILES: Cc1noc(C)c1-c1cnc2c(c1)c(-c1ccc(C(=O)O)cc1OC(F)(F)F)cn2-c1ccc(C2CC2)nc1] |
-continued
| P# | Structure |
| --- | --- |
| P-0389 | 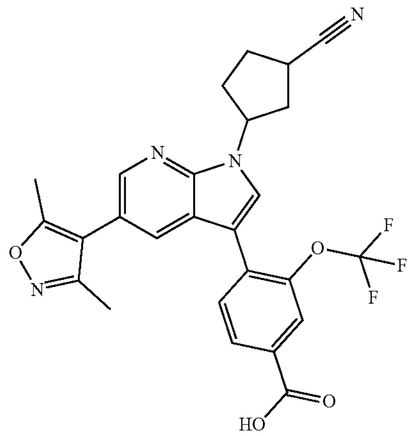 [SMILES: Cc1noc(C)c1-c1cnc2c(c1)c(-c1ccc(C(=O)O)cc1OC(F)(F)F)cn2C1CCC(C#N)C1] |
| P-0390 | 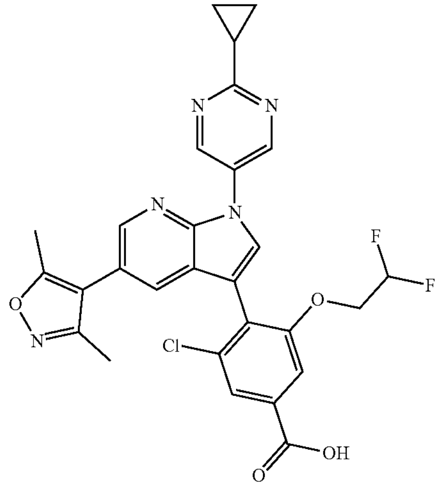 [SMILES: Cc1noc(C)c1-c1cnc2c(c1)c(-c1c(Cl)cc(C(=O)O)cc1OCC(F)F)cn2-c1cnc(C2CC2)nc1] |
| P-0391 | 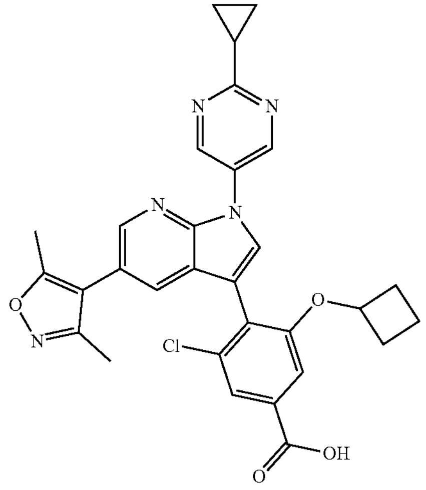 [SMILES: Cc1noc(C)c1-c1cnc2c(c1)c(-c1c(Cl)cc(C(=O)O)cc1OC1CCC1)cn2-c1cnc(C2CC2)nc1] |

-continued
| P# | Structure |
|---|---|
| P-0392 | 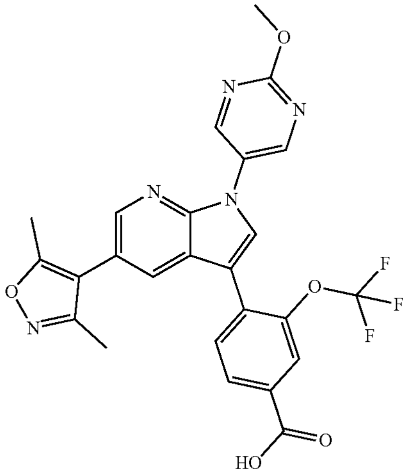 [SMILES: COc1ncc(-n2cc(-c3ccc(C(=O)O)cc3OC(F)(F)F)c3cc(-c4c(C)noc4C)cnc32)cn1] |
| P-0393 | 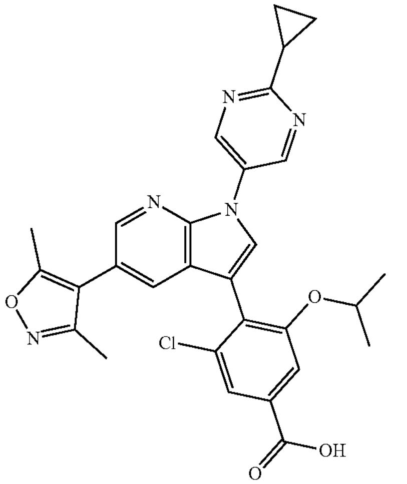 [SMILES: Cc1noc(C)c1-c1cnc2c(c1)c(-c1c(Cl)cc(C(=O)O)cc1OC(C)C)cn2-c1cnc(C2CC2)nc1] |
| P-0394 | 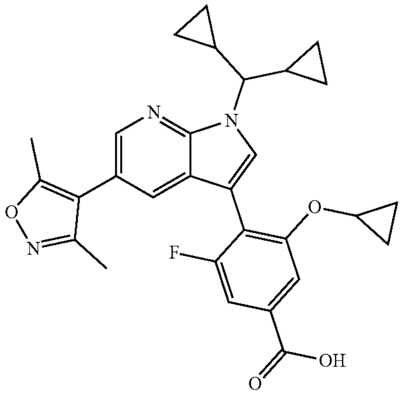 [SMILES: Cc1noc(C)c1-c1cnc2c(c1)c(-c1c(F)cc(C(=O)O)cc1OC1CC1)cn2C(C1CC1)C1CC1] |
| P-0395 | 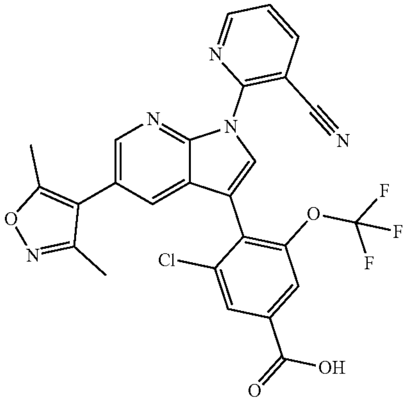 [SMILES: Cc1noc(C)c1-c1cnc2c(c1)c(-c1c(Cl)cc(C(=O)O)cc1OC(F)(F)F)cn2-c1ncccc1C#N] |
| P-0396 | 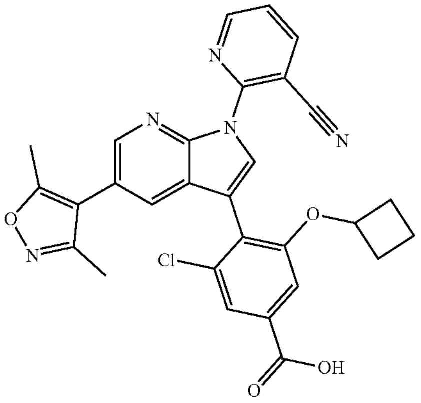 [SMILES: Cc1noc(C)c1-c1cnc2c(c1)c(-c1c(Cl)cc(C(=O)O)cc1OC1CCC1)cn2-c1ncccc1C#N] |
| P-0397 | 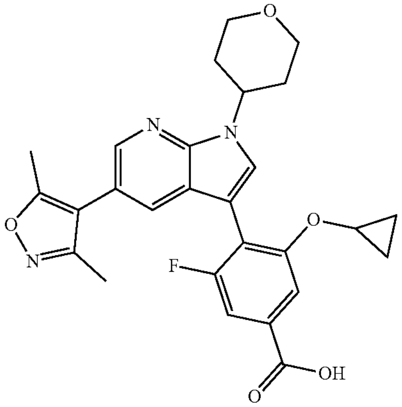 [SMILES: Cc1noc(C)c1-c1cnc2c(c1)c(-c1c(F)cc(C(=O)O)cc1OC1CC1)cn2C1CCOCC1] |

-continued
| P# | Structure |
|---|---|
| P-0398 | 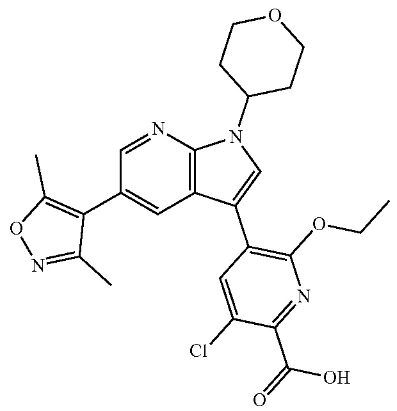 [SMILES: CCOc1nc(C(=O)O)c(Cl)cc1-c1cn(C2CCOCC2)c2ncc(-c3c(C)noc3C)cc12] |
| P-0399 | 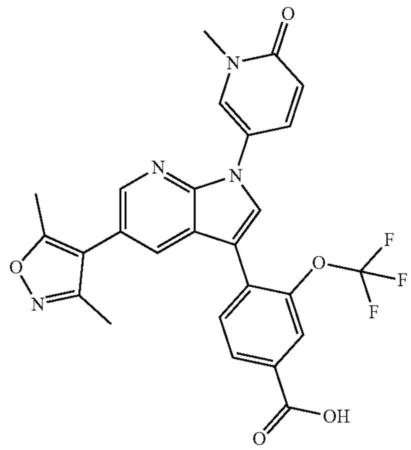 [SMILES: Cc1noc(C)c1-c1cnc2c(c1)c(-c1ccc(C(=O)O)cc1OC(F)(F)F)cn2-c1ccc(=O)n(C)c1] |
| P-0400 | 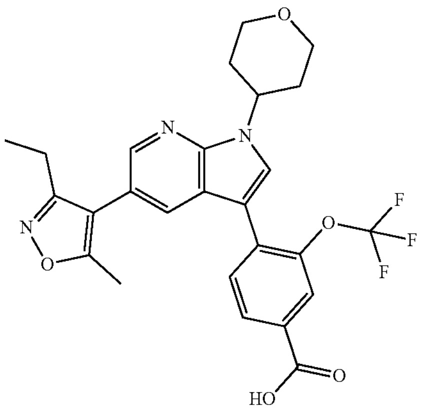 [SMILES: CCc1noc(C)c1-c1cnc2c(c1)c(-c1ccc(C(=O)O)cc1OC(F)(F)F)cn2C1CCOCC1] |
-continued
| P# | Structure |
|---|---|
| P-0401 | 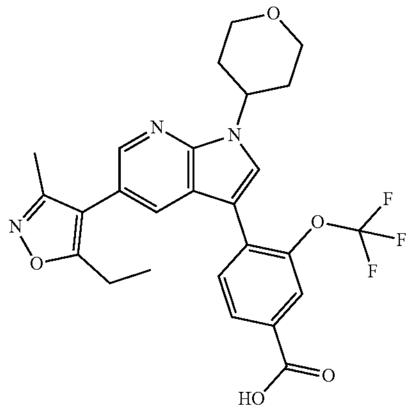 [SMILES: CCc1onc(C)c1-c1cnc2c(c1)c(-c1ccc(C(=O)O)cc1OC(F)(F)F)cn2C1CCOCC1] |
| P-0402 | 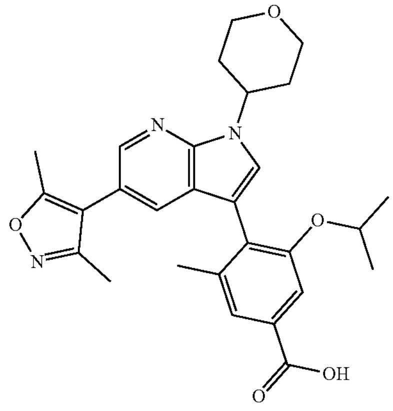 [SMILES: Cc1cc(C(=O)O)cc(OC(C)C)c1-c1cn(C2CCOCC2)c2ncc(-c3c(C)noc3C)cc12] |
| P-0403 | 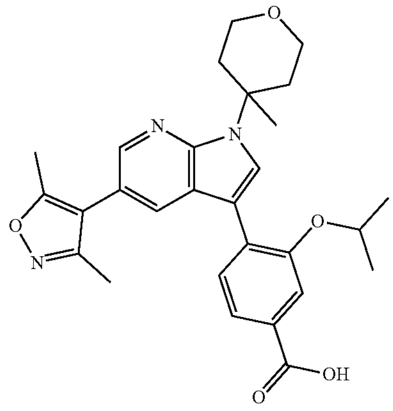 [SMILES: Cc1noc(C)c1-c1cnc2c(c1)c(-c1ccc(C(=O)O)cc1OC(C)C)cn2C1(C)CCOCC1] |

-continued
| P# | Structure |
|---|---|
| P-0404 | 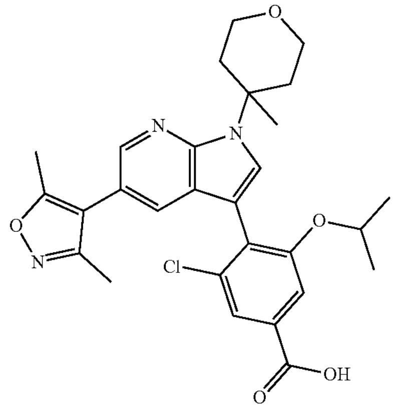 [SMILES: Cc1noc(C)c1-c1cnc2c(c1)c(-c1c(Cl)cc(C(=O)O)cc1OC(C)C)cn2C1(C)CCOCC1] |
| P-0405 | 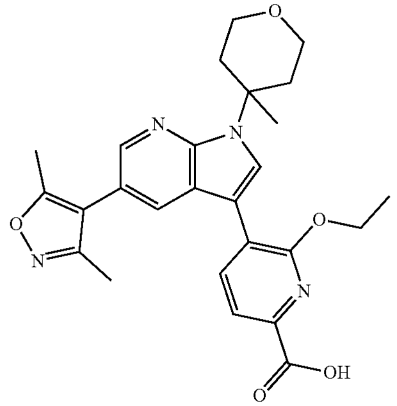 [SMILES: CCOc1nc(C(=O)O)ccc1-c1cn(C2(C)CCOCC2)c2ncc(-c3c(C)noc3C)cc12] |
| P-0406 | 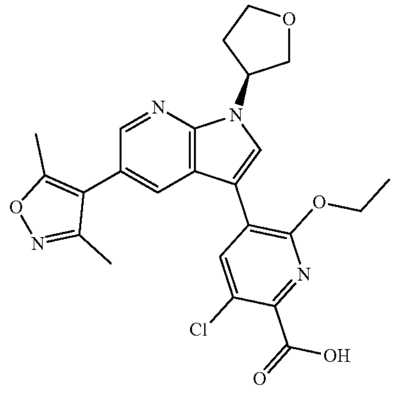 [SMILES: CCOc1nc(C(=O)O)c(Cl)cc1-c1cn([C@H]2CCOC2)c2ncc(-c3c(C)noc3C)cc12] |
| P-0407 | 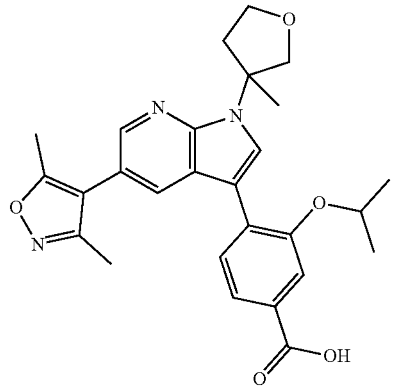 [SMILES: Cc1noc(C)c1-c1cnc2c(c1)c(-c1ccc(C(=O)O)cc1OC(C)C)cn2C1(C)CCOC1] |
-continued
| P# | Structure |
|---|---|
| P-0408 | 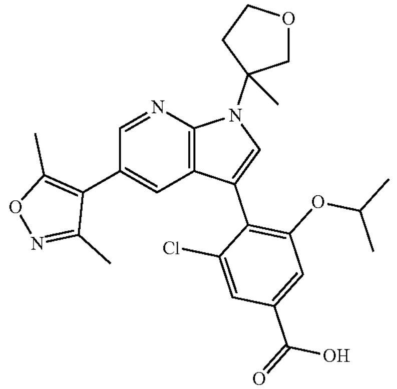 [SMILES: Cc1noc(C)c1-c1cnc2c(c1)c(-c1c(Cl)cc(C(=O)O)cc1OC(C)C)cn2C1(C)CCOC1] |
| P-0409 | 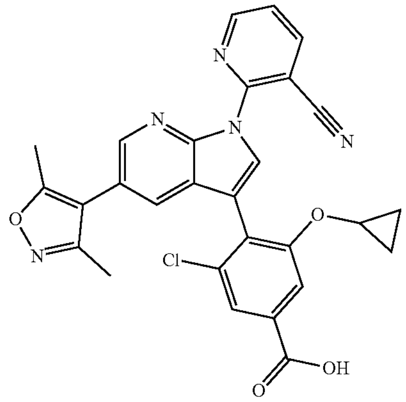 [SMILES: Cc1noc(C)c1-c1cnc2c(c1)c(-c1c(Cl)cc(C(=O)O)cc1OC1CC1)cn2-c1ncccc1C#N] |
| P-0410 | 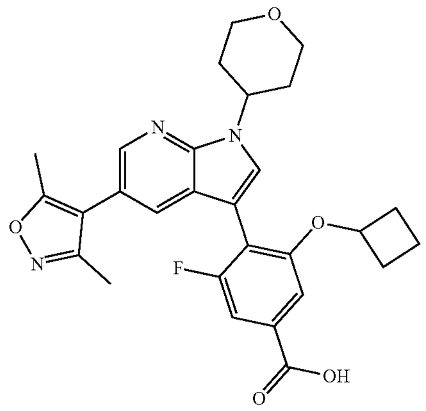 [SMILES: Cc1noc(C)c1-c1cnc2c(c1)c(-c1c(F)cc(C(=O)O)cc1OC1CCC1)cn2C1CCOCC1] |

-continued
| P# | Structure |
|---|---|
| P-0411 | 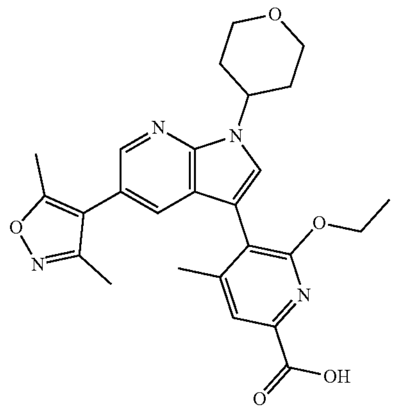 [SMILES: CCOc1nc(C(=O)O)cc(C)c1-c1cn(C2CCOCC2)c2ncc(-c3c(C)noc3C)cc12] |
| P-0412 | 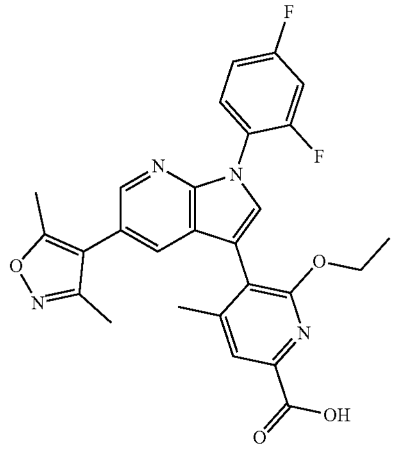 [SMILES: CCOc1nc(C(=O)O)cc(C)c1-c1cn(-c2ccc(F)cc2F)c2ncc(-c3c(C)noc3C)cc12] |
| P-0413 | 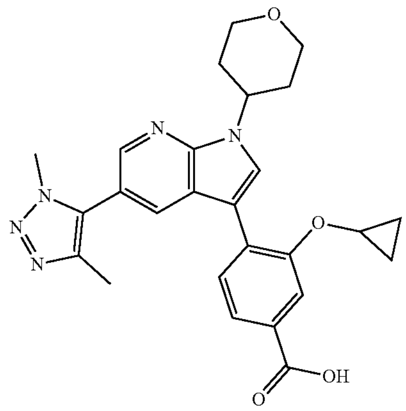 [SMILES: Cc1nnn(C)c1-c1cnc2c(c1)c(-c1ccc(C(=O)O)cc1OC1CC1)cn2C1CCOCC1] |
-continued
| P# | Structure |
|---|---|
| P-0414 | 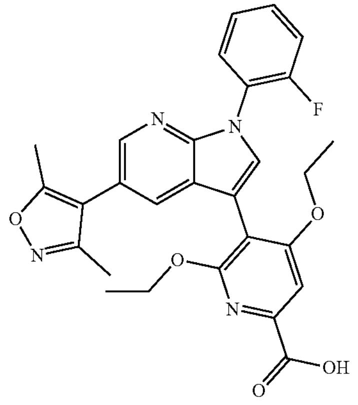 [SMILES: CCOc1cc(C(=O)O)nc(OCC)c1-c1cn(-c2ccccc2F)c2ncc(-c3c(C)noc3C)cc12] |
| P-0415 | 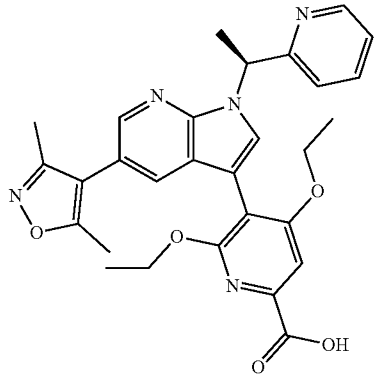 [SMILES: CCOc1cc(C(=O)O)nc(OCC)c1-c1cn([C@@H](C)c2ccccn2)c2ncc(-c3c(C)noc3C)cc12] |
| P-0416 | 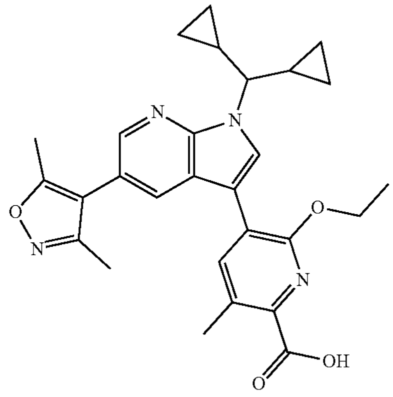 [SMILES: CCOc1nc(C(=O)O)c(C)cc1-c1cn(C(C2CC2)C2CC2)c2ncc(-c3c(C)noc3C)cc12] |
| P-0417 | 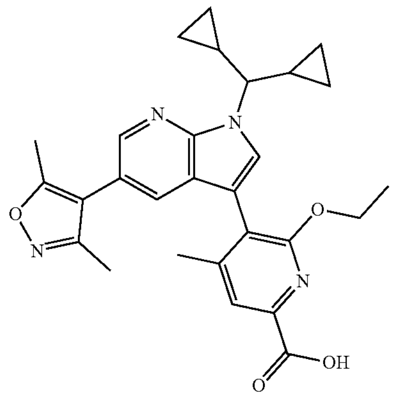 [SMILES: CCOc1nc(C(=O)O)cc(C)c1-c1cn(C(C2CC2)C2CC2)c2ncc(-c3c(C)noc3C)cc12] |

-continued
| P# | Structure |
|---|---|
| P-0418 | 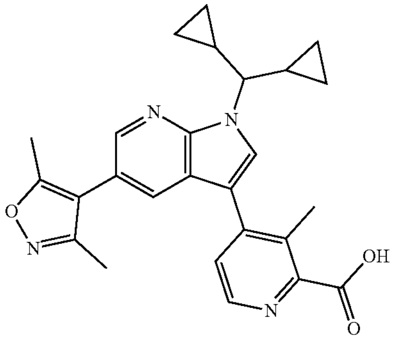 [SMILES: Cc1noc(C)c1-c1cnc2c(c1)c(-c1ccnc(C(=O)O)c1C)cn2C(C1CC1)C1CC1] |
| P-0419 | 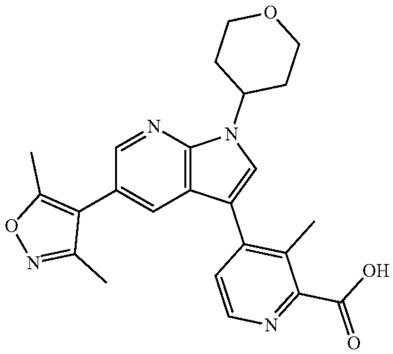 [SMILES: Cc1noc(C)c1-c1cnc2c(c1)c(-c1ccnc(C(=O)O)c1C)cn2C1CCOCC1] |
| P-0420 | 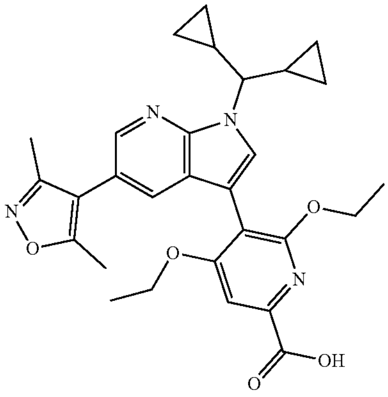 [SMILES: CCOc1cc(C(=O)O)nc(OCC)c1-c1cn(C(C2CC2)C2CC2)c2ncc(-c3c(C)noc3C)cc12] |
| P-0421 | 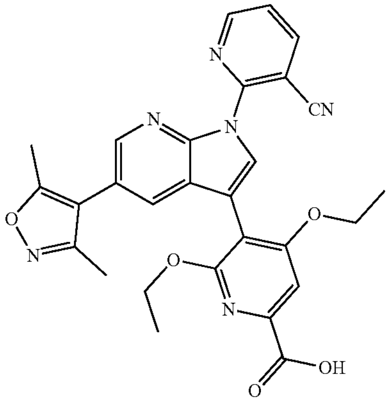 [SMILES: CCOc1cc(C(=O)O)nc(OCC)c1-c1cn(-c2ncccc2C#N)c2ncc(-c3c(C)noc3C)cc12] |
-continued
| P# | Structure |
|---|---|
| P-0422 | 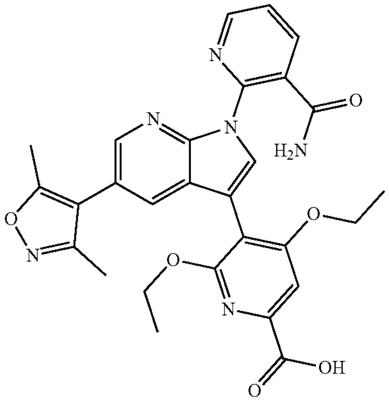 [SMILES: CCOc1cc(C(=O)O)nc(OCC)c1-c1cn(-c2ncccc2C(N)=O)c2ncc(-c3c(C)noc3C)cc12] |
| P-0423 | 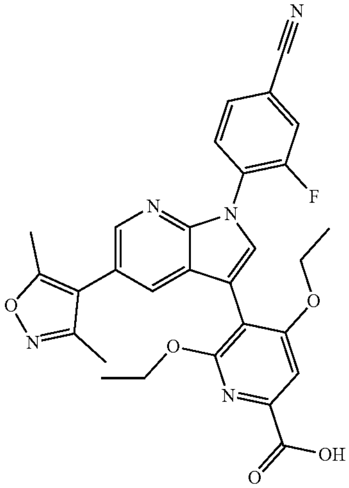 [SMILES: CCOc1cc(C(=O)O)nc(OCC)c1-c1cn(-c2ccc(C#N)cc2F)c2ncc(-c3c(C)noc3C)cc12] |
| P-0424 | 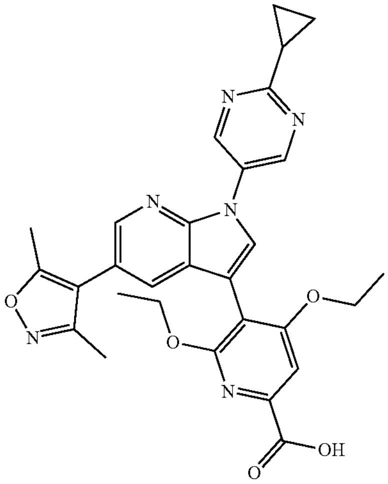 [SMILES: CCOc1cc(C(=O)O)nc(OCC)c1-c1cn(-c2cnc(C3CC3)nc2)c2ncc(-c3c(C)noc3C)cc12] |

-continued
| P# | Structure |
|---|---|
| P-0425 | 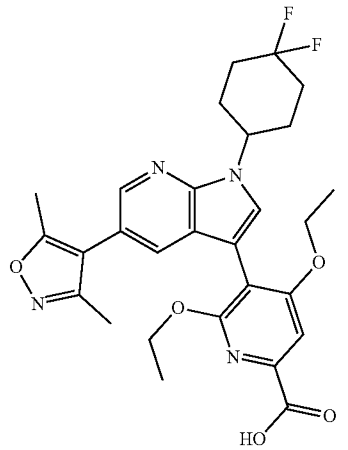 [SMILES: CCOc1cc(C(=O)O)nc(OCC)c1-c1cn(C2CCC(F)(F)CC2)c2ncc(-c3c(C)noc3C)cc12] |
| P-0426 | 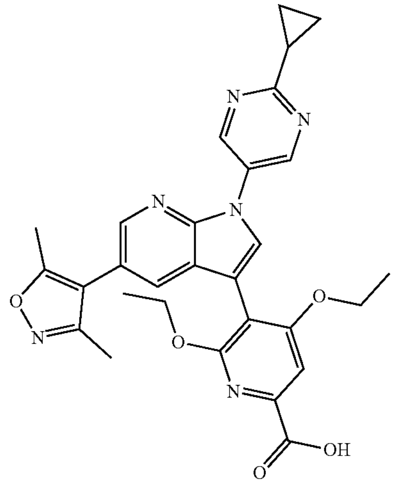 [SMILES: CCOc1cc(C(=O)O)nc(OCC)c1-c1cn(-c2cnc(C3CC3)nc2)c2ncc(-c3c(C)noc3C)cc12] |
| P-0427 | 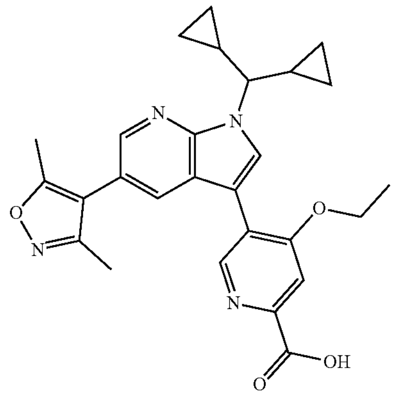 [SMILES: CCOc1cc(C(=O)O)ncc1-c1cn(C(C2CC2)C2CC2)c2ncc(-c3c(C)noc3C)cc12] |
-continued
| P# | Structure |
|---|---|
| P-0428 | 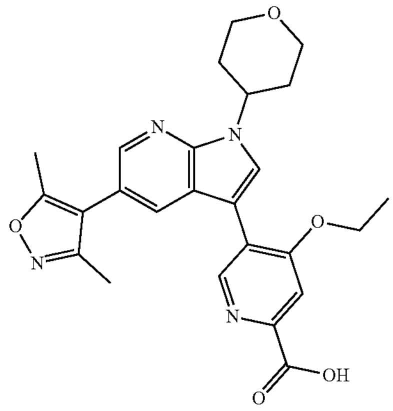 [SMILES: CCOc1cc(C(=O)O)ncc1-c1cn(C2CCOCC2)c2ncc(-c3c(C)noc3C)cc12] |
| P-0429 | 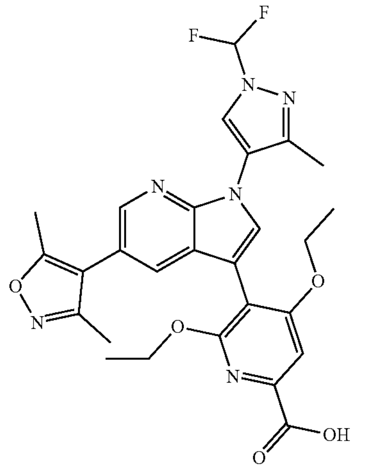 [SMILES: CCOc1cc(C(=O)O)nc(OCC)c1-c1cn(-c2cn(C(F)F)nc2C)c2ncc(-c3c(C)noc3C)cc12] |
| P-0430 | 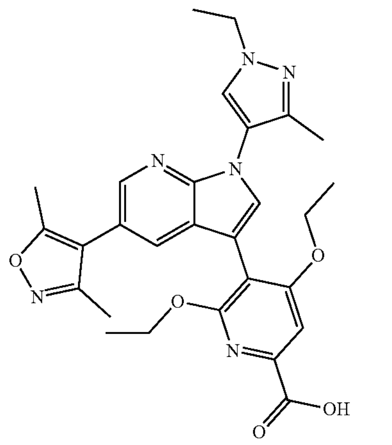 [SMILES: CCOc1cc(C(=O)O)nc(OCC)c1-c1cn(-c2cn(CC)nc2C)c2ncc(-c3c(C)noc3C)cc12] |

-continued
| P# | Structure |
|---|---|
| P-0431 | 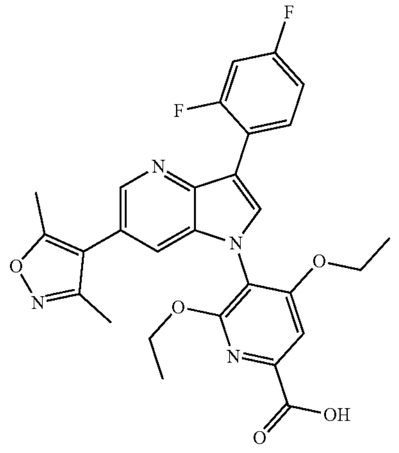 [SMILES: CCOc1cc(C(=O)O)nc(OCC)c1-n1cc(-c2ccc(F)cc2F)c2ncc(-c3c(C)noc3C)cc21] |
| P-0432 | 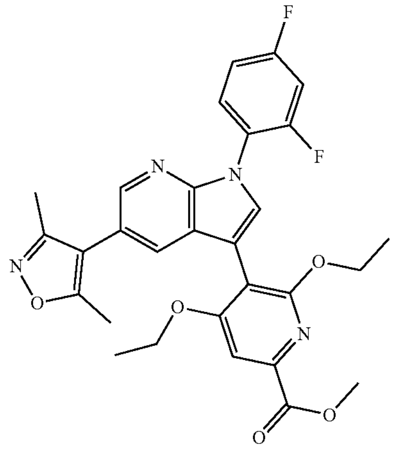 [SMILES: CCOc1cc(C(=O)OC)nc(OCC)c1-c1cn(-c2ccc(F)cc2F)c2ncc(-c3c(C)noc3C)cc12] |
| P-0433 | 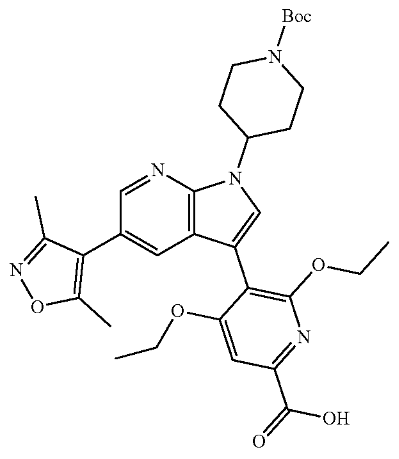 [SMILES: CCOc1cc(C(=O)O)nc(OCC)c1-c1cn(C2CCN(C(=O)OC(C)(C)C)CC2)c2ncc(-c3c(C)noc3C)cc12] |
-continued
| P# | Structure |
|---|---|
| P-0434 | 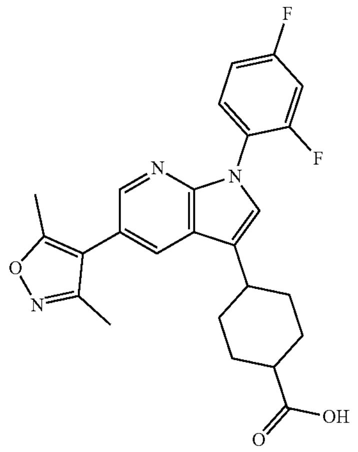 [SMILES: Cc1noc(C)c1-c1cnc2c(c1)c(C1CCC(C(=O)O)CC1)cn2-c1ccc(F)cc1F] |
| P-0435 | 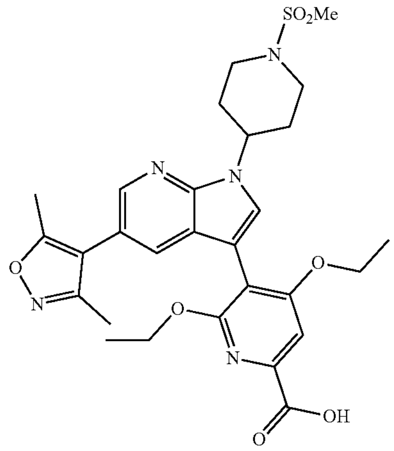 [SMILES: CCOc1cc(C(=O)O)nc(OCC)c1-c1cn(C2CCN(S(C)(=O)=O)CC2)c2ncc(-c3c(C)noc3C)cc12] |
| P-0436 | 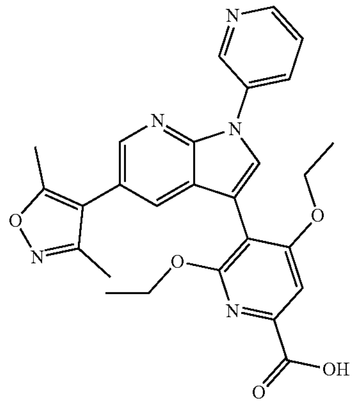 [SMILES: CCOc1cc(C(=O)O)nc(OCC)c1-c1cn(-c2cccnc2)c2ncc(-c3c(C)noc3C)cc12] |

| P# | Structure |
|---|---|
| P-0437 | 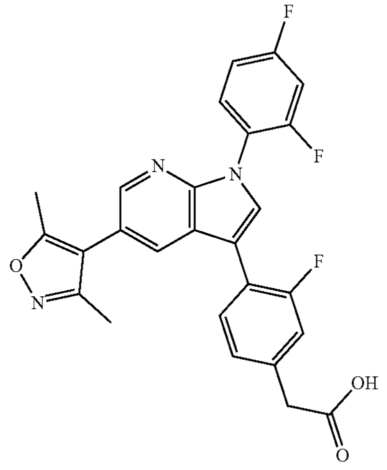 [SMILES: Cc1noc(C)c1-c1cnc2c(c1)c(-c1ccc(CC(=O)O)cc1F)cn2-c1ccc(F)cc1F] |
| P-0438 | 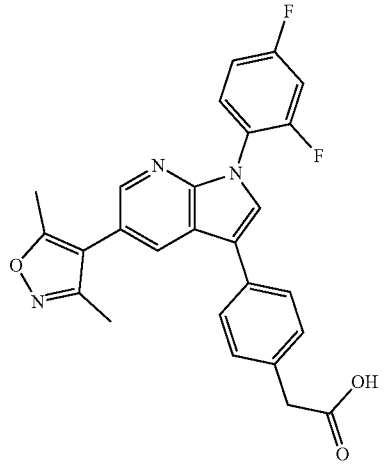 [SMILES: Cc1noc(C)c1-c1cnc2c(c1)c(-c1ccc(CC(=O)O)cc1)cn2-c1ccc(F)cc1F] |
| P-0439 | 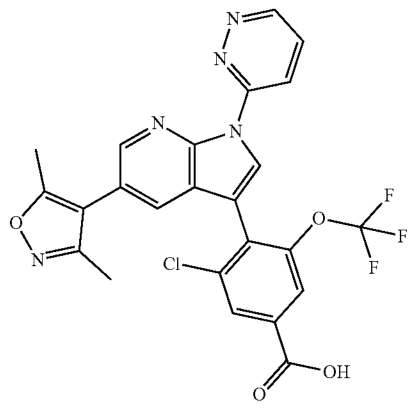 [SMILES: Cc1noc(C)c1-c1cnc2c(c1)c(-c1c(Cl)cc(C(=O)O)cc1OC(F)(F)F)cn2-c1cccnn1] |
| P# | Structure |
|---|---|
| P-0440 | 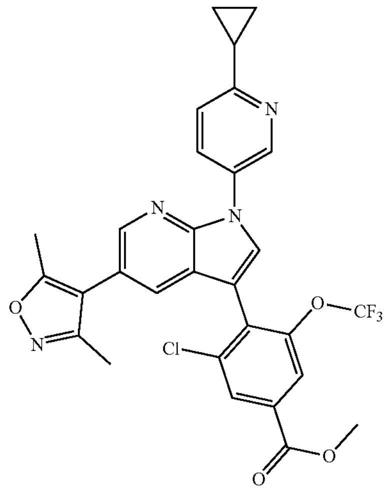 [SMILES: COC(=O)c1cc(Cl)c(-c2cn(-c3ccc(C4CC4)nc3)c3ncc(-c4c(C)noc4C)cc23)c(OC(F)(F)F)c1] |
| P-0441 | 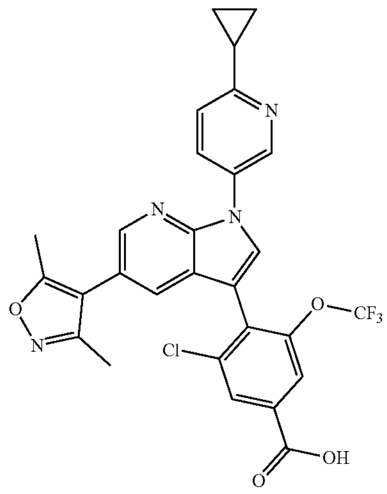 [SMILES: Cc1noc(C)c1-c1cnc2c(c1)c(-c1c(Cl)cc(C(=O)O)cc1OC(F)(F)F)cn2-c1ccc(C2CC2)nc1] |
| P-0442 | 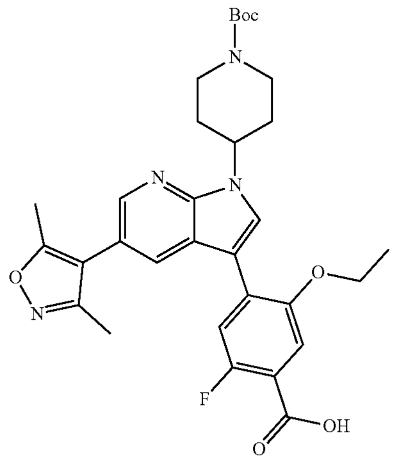 [SMILES: CCOc1cc(C(=O)O)c(F)cc1-c1cn(C2CCN(C(=O)OC(C)(C)C)CC2)c2ncc(-c3c(C)noc3C)cc12] |

-continued
| P# | Structure |
|---|---|
| P-0443 | 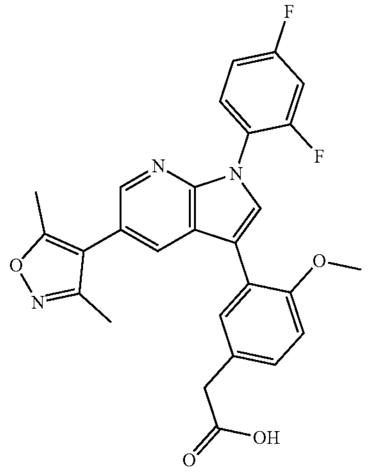 [SMILES: COc1ccc(CC(=O)O)cc1-c1cn(-c2ccc(F)cc2F)c2ncc(-c3c(C)noc3C)cc12] |
| P-0444 | 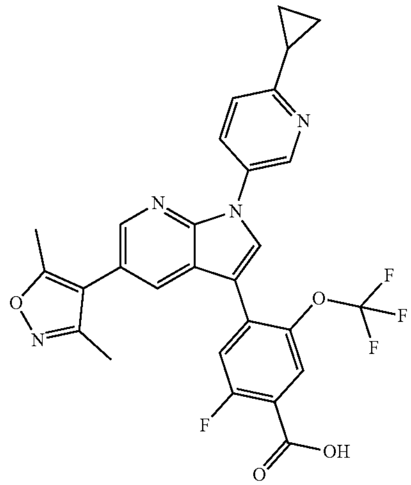 [SMILES: Cc1noc(C)c1-c1cnc2c(c1)c(-c1cc(F)c(C(=O)O)cc1OC(F)(F)F)cn2-c1ccc(C2CC2)nc1] |
| P-0445 | 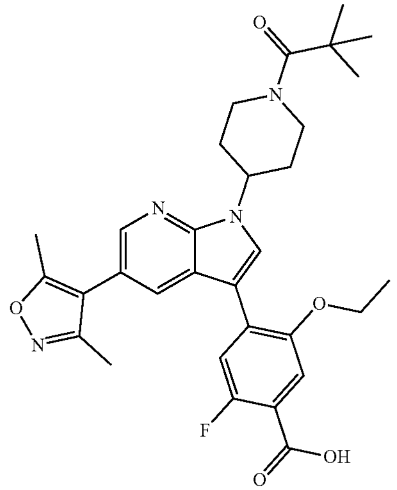 [SMILES: CCOc1cc(C(=O)O)c(F)cc1-c1cn(C2CCN(C(=O)C(C)(C)C)CC2)c2ncc(-c3c(C)noc3C)cc12] |
-continued
| P# | Structure |
|---|---|
| P-0446 | 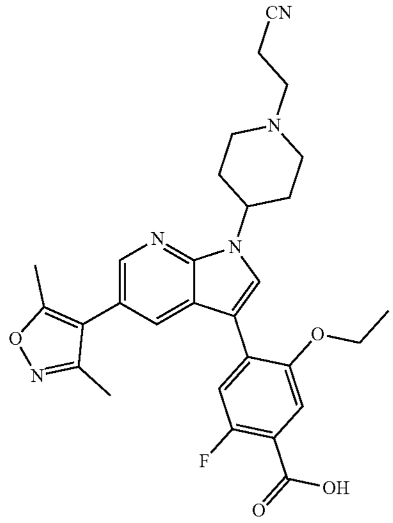 [SMILES: CCOc1cc(C(=O)O)c(F)cc1-c1cn(C2CCN(CCC#N)CC2)c2ncc(-c3c(C)noc3C)cc12] |
| P-0447 | 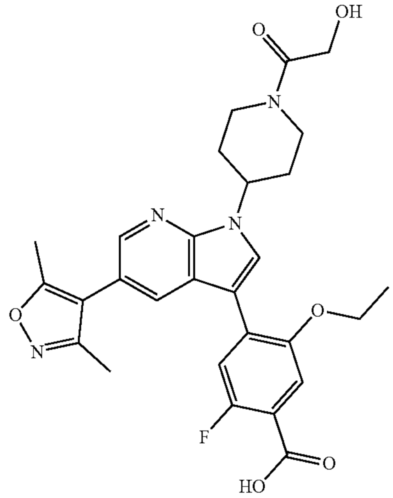 [SMILES: CCOc1cc(C(=O)O)c(F)cc1-c1cn(C2CCN(C(=O)CO)CC2)c2ncc(-c3c(C)noc3C)cc12] |
| P-0448 | 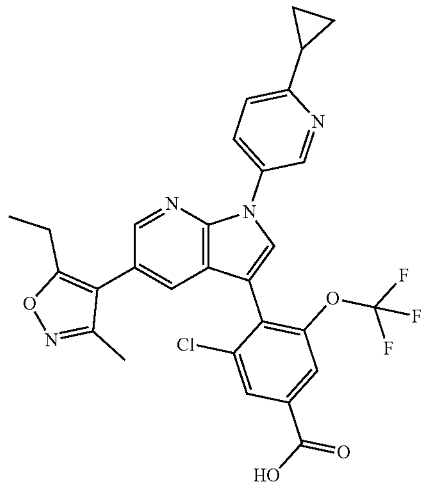 [SMILES: CCc1onc(C)c1-c1cnc2c(c1)c(-c1c(Cl)cc(C(=O)O)cc1OC(F)(F)F)cn2-c1ccc(C2CC2)nc1] |

-continued

| P# | Structure |
| --- | --- |
| P-0449 | 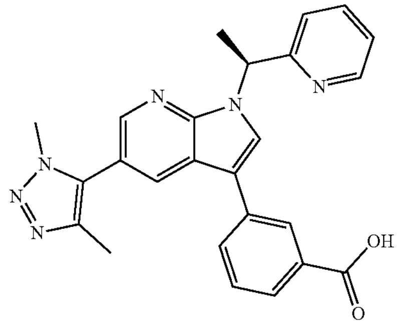 [SMILES: Cc1nnn(C)c1-c1cnc2c(c1)c(-c1cccc(C(=O)O)c1)cn2[C@@H](C)c1ccccn1] |

or a pharmaceutically acceptable salt thereof.

23. A pharmaceutical composition comprising a compound according to claim 1, and a pharmaceutically acceptable carrier.

24. The pharmaceutical composition of claim 23, further comprising a second pharmaceutical agent.

25. A method for treating a subject with a disease or condition mediated by EP300 or CBP, said method comprising administering to the subject an effective amount of a compound according to claim 1.

26. A method for treatment of a disease or condition according to claim 25, wherein the disease or condition is a cancer that harbors inactivating mutations in CBP or EP300, or a cancer where there is activation of EP300 or CBP.

27. A method for treatment of a disease or condition according to claim 25, wherein the disease or condition is a cancer that expresses the androgen receptor.

28. A method for treatment of a disease or condition according to claim 25, wherein the disease or condition is a neoplastic disorder, a cancer, an age-related disease, an inflammatory disorder, a cognitive disorder and or a neurodegenerative disease.

29. A method for treatment of a disease or condition according to claim 25, wherein the disease or condition is acral lentiginous melanoma, acute eosinophilic leukemia, acute erythroid leukemia, acute lymphoblastic leukemia, acute megakaryoblastic leukemia, acute monocytic leukemia, acute promyelocytic leukemia, bladder cancer, adenocarcinoma, adult T-cell leukemia/lymphoma, aggressive NK-cell leukemia, AIDS-related lymphoma, anaplastic large cell lymphoma, angioimmunoblastic T-cell lymphoma, B-cell chronic lymphocytic leukemia, B-cell prolymphocytic leukemia, B-cell lymphoma, bone cancer, Burkitt's lymphoma, cutaneous T-cell lymphoma, colorectal cancer, diffuse large B-cell lymphoma, enteropathy-associated T-cell lymphoma, follicular lymphoma,-glioblastoma multiforme, glioma, gastric cancer, hepatosplenic T-cell lymphoma, Hodgkin's lymphoma, non-Hodgkin's lymphoma, leukemia, lymphoma, acute lymphocytic leukemia, acute myeloid leukemia, chronic lymphocytic leukemia, small cell lung cancer, non-small cell lung cancer, MALT lymphoma, malignant peripheral nerve sheath tumor, mantle cell lymphoma, marginal zone B-cell lymphoma, mast cell leukemia, breast cancer, medulloblastoma, melanoma, merkel cell cancer, mesothelioma, multiple myeloma, neuroblastoma, neurofibroma, nodular melanoma, osteosarcoma, ovarian cancer, precursor T-lymphoblastic lymphoma, primary central nervous system lymphoma, primary effusion lymphoma, prostate cancer, pancreatic cancer, skin cancer, T-cell lymphoma, uveal melanoma, Alzheimer's disease, Parkinson's disease, or colorectal cancer.

30. The method of claim 29, wherein the disease or condition is small-cell lung cancer, non-small cell lung cancer, bladder cancer, non-Hodgkin's lymphoma, acute myeloid leukemia, multiple myeloma, diffuse large B-cell lymphoma, breast cancer or prostate cancer.

31. The method of claim 29, wherein the disease or condition is Alzheimer's disease or Parkinson's disease.

32. The method according to claim 25, further comprising administering one or more additional therapeutic agents.

33. The method according to claim 32, wherein the one or more additional therapeutic agents is one or more of:

i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an immunotherapy agent selected from a PD-1 or PD-L1 inhibitor; v) a hormone or hormone antagonist selected from the group consisting of enzalutamide, abiraterone, anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib, quizartinib, selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, a PD-1 inhibitor, or xx) an epigenetic modulator.

34. The method of claim 33, wherein the one or more additional therapeutic agents is an epigenetic modulator selected from the group consisting of:

(a) a DNA methyltransferase;
(b) a histone or protein methyltransferase;
(c) a histone demethylase;
(d) a histone deacetylase inhibitor;
(e) histone acetyltransferase;
(f) other chromatin remodelers; and
(g) a BRD4 inhibitor.

35. The method of claim 34, wherein the epigenetic modulator is a histone deacetylase inhibitor selected from the group consisting of: vorinostat, romidepsin, chidamide, panobinostat, belinostat, valproic acid, mocetinostat, abexinostat, entinostat, resminostat, givinostat, and quisinostat.

36. The method of claim 34, wherein the epigenetic modulator is a BRD4 inhibitor.

37. The method of claim 33, wherein the one or more additional therapeutic agents is a PD-1 inhibitor, quizartinib, enzalutamide, abiraterone, or a BRD4 inhibitor.

* * * * *

UNITED STATES PATENT AND TRADEMARK OFFICE

CERTIFICATE OF CORRECTION

PATENT NO. : 11,446,287 B2
APPLICATION NO. : 16/843700
DATED : September 20, 2022
INVENTOR(S) : Wayne Spevak et al.

It is certified that error appears in the above-identified patent and that said Letters Patent is hereby corrected as shown below:

In the Claims

Column 401, Claim 1, Line 37: after "$A^3$ is" please insert -- L-$R^1$, --;

Column 402, Claim 1, Line 46: please delete ")" after "or";

Column 404, Claim 3: please replace Formula II(b) " 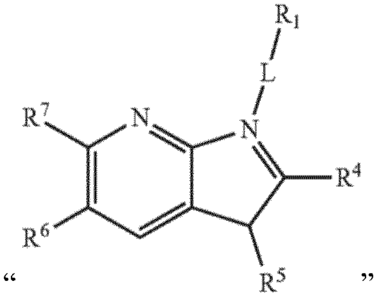 " with

-- 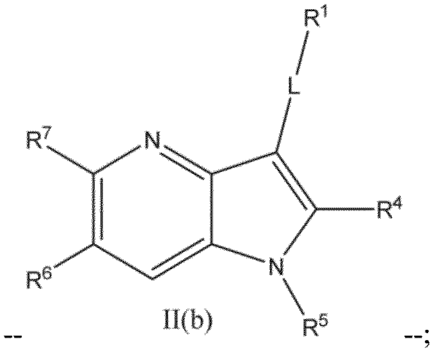
II(b) --;

Signed and Sealed this
Tenth Day of January, 2023

Katherine Kelly Vidal
*Director of the United States Patent and Trademark Office*

Column 404, Claim 4: please replace Formula III(a) " 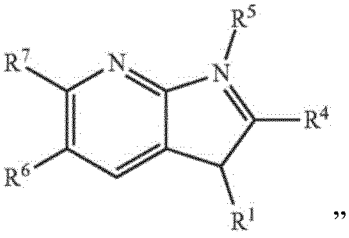 " with
-- 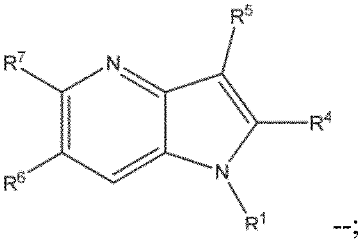 --;
Column 407, Claim 11, Lines 9-14: please replace " 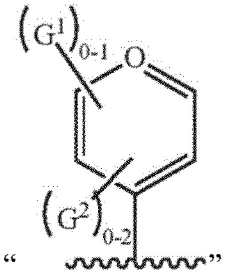 " with -- 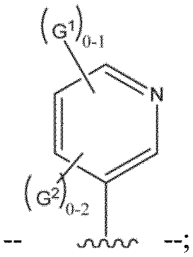 --;
Column 407, Claim 11, Lines 38-44: please replace " 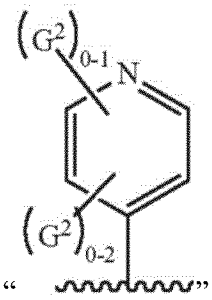 " with
-- 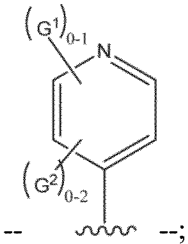 --;
Column 414, Claim 21, Line 65: please replace "$C_1$," with -- Cl, --;

Column 513, Claim 22, Lines 50-65: please delete "P-0344 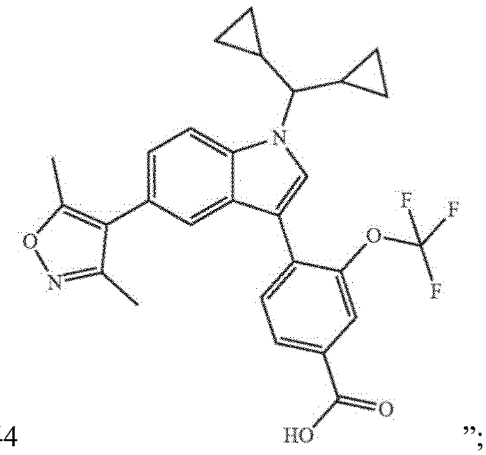 ";
Column 529, Claim 22, Lines 5-24: please replace " 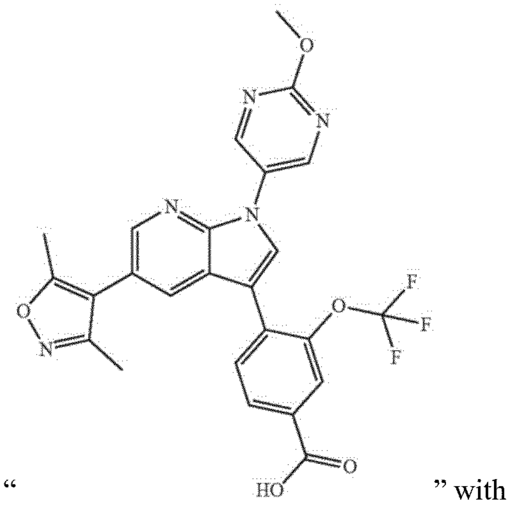 " with
-- 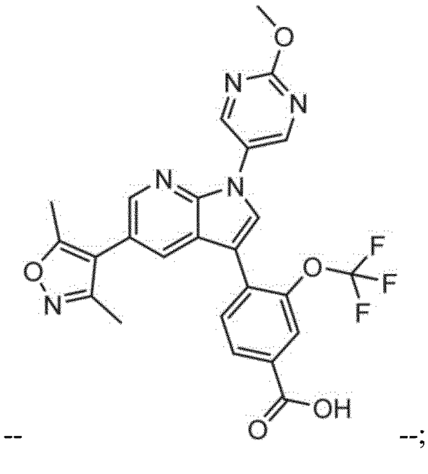 --;

Column 539, Claim 22, Lines 27-45: please replace " 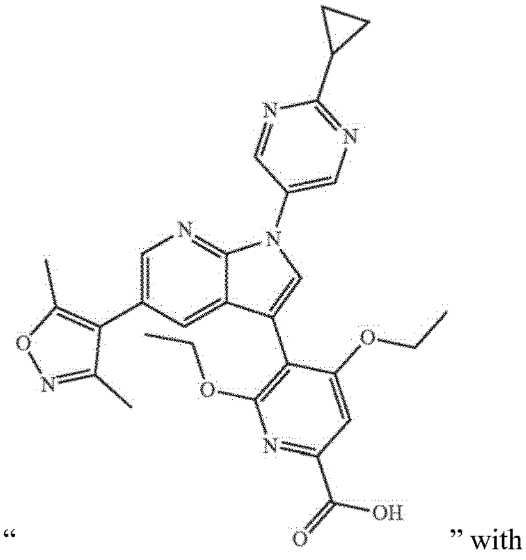 " with
-- 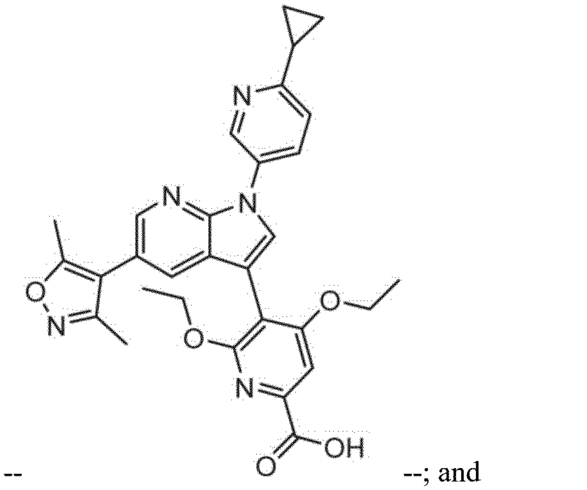 --; and
Column 547, Claim 29, Line 55: please delete "-" before "gliobastoma".